US012643926B2

(12) United States Patent
Radutoiu et al.

(10) Patent No.: US 12,643,926 B2
(45) Date of Patent: Jun. 2, 2026

(54) LysM RECEPTOR MOTIFS

(71) Applicant: Aarhus Universitet, Aarhus (DK)

(72) Inventors: Elena Simona Radutoiu, Aarhus (DK); Kasper Røjkjær Andersen, Aarhus (DK); Jens Stougaard Jensen, Aarhus (DK); Damiano Lironi, Aarhus (DK); Christina Krönauer, Aarhus (DK); Mette Laursen, Aarhus (DK)

(73) Assignee: Aarhus Universitet, Aarhus (DK)

( * ) Notice: Subject to any disclaimer, the term of this patent is extended or adjusted under 35 U.S.C. 154(b) by 0 days.

(21) Appl. No.: 17/324,354

(22) Filed: May 19, 2021

(65) Prior Publication Data

US 2021/0363200 A1 Nov. 25, 2021

Related U.S. Application Data

(60) Provisional application No. 63/027,151, filed on May 19, 2020.

(51) Int. Cl.
C07K 14/415 (2006.01)
A01H 1/00 (2006.01)
(Continued)

(52) U.S. Cl.
CPC .......... *C07K 14/415* (2013.01); *A01H 1/102* (2021.01); *C07K 1/107* (2013.01); *C12N 15/8213* (2013.01); *C12N 15/8262* (2013.01)

(58) Field of Classification Search
CPC ....... C07K 14/415; C07K 1/107; A01H 1/102
See application file for complete search history.

(56) References Cited

U.S. PATENT DOCUMENTS 4,407,956 A 10/1983 Howell
4,536,475 A 8/1985 Anderson
(Continued)

FOREIGN PATENT DOCUMENTS

AR 105982 A1 11/2017
CN 109136243 A 1/2019
(Continued)

OTHER PUBLICATIONS

Bensmihen et al. "Contribution of NFP LysM Domains to the Recognition of Nod Factors during the Medicago truncatula/ Sinorhizobium meliloti Symbiosis" 2011 PLoS ONE 6(11):e26114, 11 total pages. (Year: 2011).*
(Continued)

*Primary Examiner* — Matthew R Keogh
*Assistant Examiner* — Rebecca Stephens
(74) *Attorney, Agent, or Firm* — Morrison & Foerster LLP

(57) ABSTRACT

Aspects of the present disclosure relate to genetically altered LysM receptors. In particular, the present disclosure relates replacement of part or all of motifs in the LysM1 domain with the corresponding motifs of the LysM1 domain from a donor LysM receptor that can alter the affinity, selectivity, and/or specificity for an oligosaccharide, particularly for Nod factors (lipochitooligosaccharides (LCOs)). The present disclosure also relates to genetically altering LysM receptors in plants to include a modified LysM1 domain and to genetically altering LysM receptors in plants by replacement of part or all of motifs in the LysM1 domain. The present disclosure further relates to combining LysM1 domain modifications with modifications of LysM2 domains to include a hydrophobic patch or alter the hydrophobic patch, whereby the LysM2 domain modifications can alter the affinity, selectivity, and/or specificity for an oligosaccha-
(Continued)

ride, particularly for Nod factors (lipochitooligosaccharide (LCOs)).

10 Claims, 69 Drawing Sheets
(62 of 69 Drawing Sheet(s) Filed in Color)

Specification includes a Sequence Listing.

(51) Int. Cl.
| | |
|---|---|
| *C07K 1/107* | (2006.01) |
| *C12N 15/82* | (2006.01) |

(56) References Cited

U.S. PATENT DOCUMENTS

| | | |
|---|---|---|
| 4,676,980 A | 6/1987 | Segal et al. |
| 4,683,195 A | 7/1987 | Mullis et al. |
| 4,683,202 A | 7/1987 | Mullis |
| 4,684,611 A | 8/1987 | Schilperoort et al. |
| 4,800,159 A | 1/1989 | Mullis et al. |
| 5,633,363 A | 5/1997 | Colbert et al. |
| 5,679,558 A | 10/1997 | Gobel et al. |
| 5,759,808 A | 6/1998 | Casterman et al. |
| 6,140,553 A | 10/2000 | D'Halluin |
| 7,842,144 B1 | 11/2010 | Stiles et al. |
| 7,915,485 B2 | 3/2011 | Jensen et al. |
| 7,956,240 B2 | 6/2011 | Reuzeau |
| 8,034,344 B2 | 10/2011 | Ferlin et al. |
| 8,361,462 B2 | 1/2013 | Pandey et al. |
| 8,440,196 B1 | 5/2013 | Funakoshi et al. |
| 8,529,895 B2 | 9/2013 | Mihara et al. |
| 10,167,482 B2 | 1/2019 | Coffin |
| 12,190,997 B2 | 1/2025 | Andersen et al. |
| 2006/0005275 A1 | 1/2006 | Diehn et al. |
| 2006/0150283 A1 | 7/2006 | Alexandrov et al. |
| 2009/0113572 A1 | 4/2009 | Song et al. |
| 2012/0159672 A1 | 6/2012 | Alexandrov et al. |
| 2013/0097725 A1 | 4/2013 | Indrasumunar et al. |
| 2013/0317203 A1 | 11/2013 | Igawa et al. |
| 2014/0090106 A1 | 3/2014 | Wan et al. |
| 2014/0322239 A1 | 10/2014 | Lee et al. |
| 2015/0166666 A1 | 6/2015 | Igawa et al. |
| 2015/0232876 A1 | 8/2015 | Bono et al. |
| 2015/0368342 A1 | 12/2015 | Wu et al. |
| 2016/0152714 A1 | 6/2016 | Kano et al. |
| 2016/0244777 A1 | 8/2016 | Coffin et al. |
| 2017/0002082 A1 | 1/2017 | West et al. |
| 2018/0237793 A1 | 8/2018 | Aasen et al. |
| 2020/0096507 A1 | 3/2020 | Bonnet et al. |
| 2021/0163574 A1 | 6/2021 | Schneider et al. |
| 2021/0163974 A1 | 6/2021 | Batoko et al. |
| 2021/0163976 A1 | 6/2021 | Andersen et al. |
| 2021/0233608 A1* | 7/2021 | Andersen ............ C12N 9/1205 |
| 2021/0363217 A1 | 11/2021 | Pule et al. |
| 2022/0135630 A1 | 5/2022 | Zhou et al. |
| 2023/0078124 A1 | 3/2023 | Coruzzi et al. |
| 2024/0200085 A1 | 6/2024 | Andersen |
| 2024/0344077 A1 | 10/2024 | Radutoiu et al. |
| 2024/0344078 A1 | 10/2024 | Radutoiu et al. |
| 2025/0140337 A1 | 5/2025 | Andersen et al. |

FOREIGN PATENT DOCUMENTS

| | | |
|---|---|---|
| CN | 109734785 A | 5/2019 |
| CN | 112739820 A | 4/2021 |
| CN | 108728425 B | 12/2021 |
| EP | 67553 A2 | 12/1982 |
| EP | 116718 B2 | 8/1984 |
| EP | 223247 A2 | 11/1986 |
| EP | 242246 B1 | 10/1987 |
| EP | 270356 B1 | 6/1988 |
| EP | 270822 A1 | 6/1988 |
| EP | 452269 B1 | 10/1991 |
| EP | 1134231 A1 | 9/2001 |
| EP | 3837357 | 6/2021 |
| IN | 144268 A1 | 4/1978 |
| JP | 5229783 B2 | 7/2013 |
| KR | 20200085159 A | 7/2020 |
| WO | WO-1984002913 A1 | 8/1984 |
| WO | WO-1985001856 A1 | 5/1985 |
| WO | WO-1992009696 A1 | 6/1992 |
| WO | WO-1994004678 A1 | 3/1994 |
| WO | WO-1994025591 A1 | 11/1994 |
| WO | WO-1995004079 A1 | 2/1995 |
| WO | WO-1996006932 A1 | 3/1996 |
| WO | WO-1996034103 A1 | 10/1996 |
| WO | WO-1997048819 A1 | 12/1997 |
| WO | WO-1997049805 A2 | 12/1997 |
| WO | WO-1999037681 A2 | 7/1999 |
| WO | WO-2000040968 A1 | 7/2000 |
| WO | WO-2000042207 A2 | 7/2000 |
| WO | WO-2000043507 A1 | 7/2000 |
| WO | WO-2000065057 A1 | 11/2000 |
| WO | WO-2000071733 A1 | 11/2000 |
| WO | WO-2001021817 A1 | 3/2001 |
| WO | WO-2001040310 A2 | 6/2001 |
| WO | WO-2001044301 A1 | 6/2001 |
| WO | WO-2001090190 A2 | 11/2001 |
| WO | WO-2002046439 A2 | 6/2002 |
| WO | WO-2002048193 A2 | 6/2002 |
| WO | WO-2003025020 A1 | 3/2003 |
| WO | WO-2003035694 A2 | 5/2003 |
| WO | WO-2003050531 A2 | 6/2003 |
| WO | WO-2003054016 A2 | 7/2003 |
| WO | WO-2003055527 A2 | 7/2003 |
| WO | WO-2004041862 A2 | 5/2004 |
| WO | WO-2004041863 A2 | 5/2004 |
| WO | WO-2004041865 A2 | 5/2004 |
| WO | WO-2004041867 A2 | 5/2004 |
| WO | WO-2004062551 A2 | 7/2004 |
| WO | WO-2005003338 A1 | 1/2005 |
| WO | WO-2005044858 A1 | 5/2005 |
| WO | WO-2006040153 A2 | 4/2006 |
| WO | WO-2006079372 A1 | 8/2006 |
| WO | WO-2006122786 A2 | 11/2006 |
| WO | WO-2006122787 A1 | 11/2006 |
| WO | WO-2006122825 A2 | 11/2006 |
| WO | WO-2007024715 A2 | 3/2007 |
| WO | WO-2007076115 A2 | 7/2007 |
| WO | WO-2008024188 A2 | 2/2008 |
| WO | WO-2008101985 A2 | 8/2008 |
| WO | WO-2008142164 A2 | 11/2008 |
| WO | WO-2009016104 A1 | 2/2009 |
| WO | WO-2014033672 A1 | 3/2014 |
| WO | WO-2015103072 A1 | 7/2015 |
| WO | WO-2017103582 A1 | 6/2017 |
| WO | WO-2020035488 A1 | 2/2020 |
| WO | WO-2020104524 A1 | 5/2020 |
| WO | WO-2022026618 A2 | 2/2022 |

OTHER PUBLICATIONS

Luyten and Vanderleyden "Survey of genes identified in *Sinorhizobium meliloti* spp., necessary for the development of an efficient symbiosis" Eur. J. Soil Biol. 36:1-26. (Year: 2000).*

Adams et al., (2010). "Phenix: a comprehensive Python-based system for macromolecular structure solution. Acta crystallographica," Section D, Biological crystallography, 66(2):213-221.

Altschul et al., (1997). "Gapped BLAST and PSI-BLAST: a new generation of protein database search programs," Nucleic acids research, 25(17):3389-3402.

Altschul et al., (1990). "Basic local alignment search tool," Journal of molecular biology, 215(3):403-410.

An et al., (1996). "Strong, constitutive expression of the *Arabidopsis* ACT2/ACT8 actin subclass in vegetative tissues," The Plant Journal, 10(1):107-121.

Ardourel et al., (1994). "Rhizobium meliloti lipooligosaccharide nodulation factors: different structural requirements for bacterial entry into target root hair cells and induction of plant symbiotic developmental responses," The Plant Cell, 6(10):1357-1374.

(56) References Cited

OTHER PUBLICATIONS

Arrighi et al., (2006). "The Medicago truncatula Lysine Motif-Receptor-Like Kinase Gene Family Includes NFP and New Nodule-Expressed Genes," Plant Physiology, 142:265-279, 19 pages.

Bensmihen et al., (2011). "Contribution of NFP LysM Domains to the Recognition of Nod Factors during the Medicago truncatula/Sinorhizobium meliloti Symbiosis," PLOS ONE, 6:e26114, 11 pages.

Biasini et al., (2014). "Swiss-Model: modelling protein tertiary and quaternary structure using evolutionary information," Nucleic acids research, 42(W1):W252-W258.

Bozsoki et al., (2017). "Receptor-mediated chitin perception in legume roots is functionally separable from Nod factor perception," Proceedings of the National Academy of Sciences, 114(38):E8118-E8127.

Bucher et al., (2002). "The expression of an extensin-like protein correlates with cellular tip growth in tomato," Plant Physiology, 128(3):911-923.

Christensen et al., (1992). "Maize polyubiquitin genes: structure, thermal perturbation of expression and transcript splicing, and promoter activity following transfer to protoplasts by electroporation," Plant molecular biology, 18(4):675-689.

Christensen et al., (1996). "Ubiquitin promoter-based vectors for high-level expression of selectable and/or screenable marker genes in monocotyledonous plants," Transgenic research, 5(3):213-218.

Christou et al., (1990). "Soybean genetic engineering-commercial production of transgenic plants," Trends in Biotechnology, 8:145-151.

Datta et al., (1990). "Genetically engineered fertile indica-rice recovered from protoplasts," Bio/technology, 8(8):736-740.

De Framond, (1991). "A metallothionein-like gene from maize (*Zea mays*) Cloning and characterization," FEBS letters, 290(1-2):103-106.

De Lorenzo et al., (2011). "Engineering plant resistance by constructing chimeric receptors that recognize damage-associated molecular patterns (DAMPs)," FEBS Letters, 585:1521-1528.

De Pater et al., (1992). "The promoter of the rice gene GOS2 is active in various different monocot tissues and binds rice nuclear factor ASF-1," The Plant Journal, 2(6):837-844.

DeLano, (2002). "Pymol: An open-source molecular graphics tool," CCP4 Newsletter on protein crystallography, 10 pages.

Depicker et al., (1982). "Nopaline synthase: transcript mapping and DNA sequence," Journal of molecular and applied genetics, 1(6):561-573.

Emsley et al., (2010). "Features and development of Coot," Acta Crystallographica Section D: Biological Crystallography, D66(4):486-501.

Engler et al., (2008). "A one pot, one step, precision cloning method with high throughput capability," PloS one, 3(11):e3647, 7 pages.

Franck et al., (1980). "Nucleotide sequence of cauliflower mosaic virus DNA," Cell, 21(1):285-294.

Franke et al., (2009). "DAMMIF, a program for rapid ab-initio shape determination in small-angle scattering," Journal of applied crystallography, 42(2):342-346.

Fromm et al., (1990). "Inheritance and expression of chimeric genes in the progeny of transgenic maize plants," Bio/technology, 8(9):833-839.

Gardner et al., (1981). "The complete nucleotide sequence of an infectious clone of cauliflower mosaic virus by M13mp7 shotgun sequencing," Nucleic acids research, 9(12):2871-2888.

GenBank Accession No. X04049, "Maize alcohol dehydrogenase 1 gene (Adh1-1S)," Nov. 14, 2006, 4 pages.

GenBank Accession No. XM 004511944, "Predicted: Cicer arietinum protein LYK5-like (LOC101515074), transcript variant X2, mRNA," Jun. 8, 2015, 2 pages.

GenBank Accession No. XM 012719006, "Predicted: Cicer arietinum protein LYK5-like (LOC101515074), transcript variant X1, mRNA," Jun. 8, 2015, 2 pages.

Gielen et al., (1984). "The complete nucleotide sequence of the TL-DNA of the Agrobacterium tumefaciens plasmid pTiAch5," The EMBO Journal, 3(4):835-846.

Gomez et al., (2009). "Medicago truncatula and Glomus intraradices gene expression in cortical cells harboring arbuscules in the arbuscular mycorrhizal symbiosis," BMC Plant Biology, 9(10):1-19.

Gordon-Kamm et al., (1990). "Transformation of Maize Cells and Regeneration of Fertile Transgenic Plants," The Plant cell, 2(7):603-618.

Gough et al., (2018). "Evolutionary History of Plant LysM Receptor Proteins Related to Root Endosymbiosis," Frontiers in Plant Science, 9:923, 9 pages.

Gust et al., (2012). "Plant LysM proteins: modules mediating symbiosis and immunity," Trends in Plant Science, 17:495-502.

Hansen et al., (1989). "Hairy roots—a short cut to transgenic root nodules," Plant Cell Reports, 8(1):12-15.

Heidstra et al., (2004). "Mosaic analyses using marked activation and deletion clones dissect *Arabidopsis* Scarecrow action in asymmetric cell division," Genes & Development, 18(16):1964-1969.

Hinchee et al., (1988). "Production of transgenic soybean plants using Agrobacterium-mediated DNA transfer," Bio/technology, 6.8:915-922.

Hirel et al., (1992). "Forcing expression of a soybean root glutamine synthetase gene in tobacco leaves induces a native gene encoding cytosolic enzyme," Plant molecular biology, 20(2):207-218.

Hopkins et al., (2017). "BioXTAS RAW: improvements to a free open-source program for small-angle X-ray scattering data reduction and analysis," Journal of applied crystallography, 50(5):1545-1553.

Hull et al., (1978). "Structure of the cauliflower mosaic virus genome. II. Variation in DNA structure and sequence between isolates," Virology, 86(2):482-493.

Indrasumunar et al., (2010). "Inactivation of duplicated nod factor receptor 5 (NFR5) genes in recessive loss-of-function non-nodulation mutants of allotetraploid soybean (*Glycine max* L. Merr.)," Plant and cell physiology, 51(2):201-214.

Irvine, (2016). "A Receptor for All Occasions," Cell, 164:599-600.

Kabsch, (2010). "Integration, scaling, space-group assignment and post-refinement," Acta Crystallographica Section D: Biological Crystallography, 66(2):133-144.

Karlin et al., (1990). "Methods for assessing the statistical significance of molecular sequence features by using general scoring schemes," Proceedings of the National Academy of Sciences, 87(6):2264-2268.

Karlin et al., (1993). "Applications and statistics for multiple high-scoring segments in molecular sequences," Proceedings of the National Academy of Sciences, 90(12):5873-5877.

Kay et al., (1987). "Duplication of CaMV 35S Promoter Sequences Creates a Strong Enhancer for Plant Genes," Science, 236(4806):1299-1302.

Kelly et al., (2013). "Conditional requirement for exopolysaccharide in the Mesorhizobium-Lotus symbiosis," Molecular plant-microbe interactions, 26(3):319-329.

Konarev et al., (2003). "Primus: a Windows PC-based system for small-angle scattering data analysis," Journal of applied crystallography, 36(5):1277-1282.

Last et al., (1991). "pEmu: an improved promoter for gene expression in cereal cells." TAG. Theoretical and applied genetics, 81(5):581-588.

Lerouge et al., (1990). "Symbiotic host-specificity of Rhizobium meliloti is determined by a sulphated and acylated glucosamine oligosaccharide signal," Nature, 344(6268):781-784.

Li et al., (2016). "Plant pattern-recognition receptors controlling innate immunity," Science China Life Sciences, 59:878-888.

Liu et al., (2012). "Chitin-induced dimerization activates a plant immune receptor," Science, 336(6085):1160-1164.

Madsen et al., (2003). "A receptor kinase gene of the LysM type is involved in legume perception of rhizobial signals," Nature, 425:637-640.

Maekawa et al., (2008). "Polyubiquitin promoter-based binary vectors for overexpression and gene silencing in Lotus japonicus," Molecular Plant-Microbe Interactions, 21(4):375-382.

(56) References Cited

OTHER PUBLICATIONS

McCoy et al., (2007). "Phaser crystallographic software," Journal of applied crystallography, 40(4):658-674.

Mulder et al., (2006). "LysM domains of Medicago truncatula NFP protein involved in Nod factor perception. Glycosylation state, molecular modeling and docking of chitooligosaccharides and Nod factors," Glycobiology, 16(9):801-809.

Murakami et al., (2018). "Epidermal LysM receptor ensures robust symbiotic signalling in Lotus japonicus," Elife, 7:e33506, 21 pages.

Nakagawa et al., (2011). From defense to symbiosis: limited alterations in the kinase domain of LysM receptor-like kinases are crucial for evolution of legume-Rhizobium symbiosis, The Plant Journal, 65(2):169-180.

Norris et al., (1993). "The intron of *Arabidopsis thaliana* polyubiquitin genes is conserved in location and is a quantitative determinant of chimeric gene expression," Plant molecular biology, 21(5):895-906.

Oldroyd et al., (2001). "Evidence for structurally specific negative feedback in the Nod factor signal transduction pathway," The Plant Journal, 28(2):191-199.

Oldroyd et al., (2011). "The rules of engagement in the legume—rhizobial symbiosis," Annual review of genetics, 45:119-144.

Radutoiu et al., (2003). "Plant recognition of symbiotic bacteria requires two LysM receptor-like kinases," Nature, 425(6958):585-592.

Radutoiu et al., (2007). "LysM domains mediate lipochitin-oligosaccharide recognition and Nfr genes extend the symbiotic host range," The EMBO Journal, 26:3923-3935.

Rasmussen et al., (2016). "Intraradical colonization by arbuscular mycorrhizal fungi triggers induction of a lipochitooligosaccharide receptor," Scientific reports, 6:29733, 12 pages.

Rodpothong et al., (2009). "Nodulation Gene Mutants of Mesorhizobium loti R7A—nodZ and noIL Mutants Have Host-Specific Phenotypes on *Lotus* spp.," Molecular plant-microbe interactions, 22(12):1546-1554.

Saiki et al., (1985). "Enzymatic amplification of beta-globin genomic sequences and restriction site analysis for diagnosis of sickle cell anemia," Science, 230(4732):1350-1354.

Samac et al., (1990). "Isolation and characterization of the genes encoding basic and acidic chitinase in *Arabidopsis thaliana*," Plant physiology, 93(3):907-914.

Schindelin et al., (2012). "Fiji: an open-source platform for biological-image analysis," Nature methods, 9(7):676-682.

Schünmann et al., (2003). "A suite of novel promoters and terminators for plant biotechnology. II. The pPLEX series for use in monocots," Functional plant biology, 30(4):453-460.

Shimamoto et al., (1989). "Fertile transgenic rice plants regenerated from transformed protoplasts," Nature, 338(6212):274-276.

Smit et al., (2007). "Medicago LYK3, an entry receptor in rhizobial nodulation factor signaling," Plant physiology, 145(1):183-191.

Stougaard, (1995). "Agrobacterium rhizogenes as a vector for transforming higher plants, application in Lotus corniculatus transformation," Plant gene transfer and expression protocols, 49-61.

Svergun et al., (1995). "Crysol—a program to evaluate X-ray solution scattering of biological macromolecules from atomic coordinates," Journal of applied crystallography, 28(6):768-773.

Svergun, (1992). "Determination of the regularization parameter in indirect-transform methods using perceptual criteria," Journal of applied crystallography, 25(4):495-503.

Svergun, (1999). "Restoring low resolution structure of biological macromolecules from solution scattering using simulated annealing," Biophysical journal, 76(6):2879-2886.

Trinick, (1973). "Symbiosis between Rhizobium and the non-legume, Trema aspera," Nature, 244(5416):459-460.

Unni et al., (2011). "Web servers and services for electrostatics calculations with APBS and PDB2PQR," Journal of computational chemistry, 32(7):1488-1491, 6 pages.

Velten et al., (1984). "Isolation of a dual plant promoter fragment from the Ti plasmid of Agrobacterium tumefaciens," The EMBO Journal, 3(12):2723-2730.

Velten et al., (1985). "Selection-expression plasmid vectors for use in genetic transformation of higher plants," Nucleic Acids Research, 13(19):6981-6998.

Verdaguer et al., (1998). "Functional organization of the cassava vein mosaic virus (CsVMV) promoter," Plant molecular biology, 37(6):1055-1067.

Wang et al., (1997). "Improved vectors for Agrobacterium tumefaciens-mediated transformation of monocot plants," ISHS Acta Horticulturae 461: International Symposium on Biotechnology of Tropical and Subtropical Species Part 2, 461 (pp. 401-408).

Wang et al., (2014). "Functional analysis of chimeric lysin motif domain receptors mediating Nod factor-induced defense signaling in *Arabidopsis thaliana* and chitin-induced nodulation signaling in Lotus japonicus," The Plant Journal, 78(1):56-69.

Weber et al., (2011). "A modular cloning system for standardized assembly of multigene constructs," PloS one, 6(2):e16765, 11 pages.

Weising et al., (1988). "Foreign genes in plants: transfer, structure, expression, and applications," Annual review of genetics, 22(1):421-477.

Wheeler et al., (2014). "Skylign: a tool for creating informative, interactive logos representing sequence alignments and profile hidden Markov models," BMC bioinformatics, 15:7, 9 pages.

Wriggers et al., (2001). "Using Situs for the registration of protein structures with low-resolution bead models from X-ray solution scattering," Journal of applied crystallography, 34(6):773-776.

Zhang et al., (1991). "Analysis of rice Act1 5' region activity in transgenic rice plants," The Plant Cell, 3(11):1155-1165.

Zhang et al., (2007). "Molecular evolution of lysin motif-type receptor-like kinases in plants," Plant physiology, 144(2):623-636.

Zhukov et al., (2008). "The pea Sym37 receptor kinase gene controls infection-thread initiation and nodule development," Molecular Plant-Microbe Interactions, 21(12):1600-1608.

Cao et al., (2014). "The kinase LYK5 is a major chitin receptor in *Arabidopsis* and forms a chitin-induced complex with related kinase CERK1," Elife, 3:E03766, 19 pages.

Knox et al., (2018). "The Challenges of Analysing Highly Diverse Picobirnavirus Sequence Data," Viruses, 10:685, 13 pages.

Malkov et al., (2016). "Molecular basis of lipo-chitooligosaccharide recognition by the lysin motif receptor-like kinase LYR3 in legumes," Biochem. J., 473:1369-1378.

Rouge et al., (2011). "Chapter 27 Docking of Chitin Oligomers and Nod Factors on Lectin Domains of the LysM-RLK Receptors in the Medicago-Rhizobium Symbiosis," The Mol. Immunol. Complex Carbohydrates-3, pp. 511-521.

Uniprot, (2018). "EBI accession No. A0A2SOBYZ2: Nod-factor receptor 5," available online at <https://rest.uniprot.org/uniprotkb/A0A2S0BYZ2/txt>, 2 pages.

Waterhouse et al., (2018). "Swiss-Model: homology modelling of protein structures and complexes," Nuc. Acids Res., 46:W296-W303.

Abel et al., (2024). "Phosphorylation of the alpha-I motif in SYMRK drives root nodule organogenesis," PNAS USA, 121:e2311522121, 7 pages.

Aledo, (2019). "Methionine in proteins: The Cinderella of the proteinogenic amino acids," Protein Science, 28(10):1785-1796.

Amor et al., (2003). "The NFP locus of Medicago truncatula controls an early step of Nod factor signal transduction upstream of a rapid calcium flux and root hair deformation," The Plant Journal, 34:495-506.

Appleby, (1984). "Leghemoglobin and Rhizobium Respiration," Annual Review of Plant Physiology, 35(1):443-478.

Bahr, "Memorandum: Clarification of Written Description Guidance For Claims Drawn to Antibodies and Status of 2008 Training Materials," dated Feb. 22, 2018, 2 pages.

Bai et al., (2022). "Engineering Chimeras by Fusing Plant Receptor-like Kinase EMS1 and BRI1 Reveals the Two Receptors' Structural Specificity and Molecular Mechanisms," Int. J. Mol. Sci., 23:2155, 18 pages.

Benfey et al., (1990). "The Cauliflower Mosaic Virus 35S Promoter: Combinatorial Regulation of Transcription in Plants," Science, 250:959-966.

(56) References Cited

OTHER PUBLICATIONS

Beringer et al., (1979). "The Rhizobium-Legume Symbiosis," Proceedings of the Royal Society of London, 204(1155):219-233, 17 pages.

Binz et al., (2003). "Designing repeat proteins: well-expressed, soluble and stable proteins from combinatorial libraries of consensus ankyrin repeat proteins," J Mol Biol., 332(2):489-503.

Boran, (2012). "The regulatory role of the juxtamembrane region in the activity of the epidermal growth factor receptor," Biochemical Society Transactions, 40(1):195-199.

Bozsoki et al., (2020). "Ligand-recognizing motifs in plant LysM receptors are major determinants of specificity," Science, 369:663-670.

Brinkmann et al., (2017). "The making of bispecific antibodies," MABS, 9(2):182-212.

Broghammer et al., (2012). "Legume receptors perceive the rhizobial lipochitin oligosaccharide signal molecules by direct binding," PNAS, 109(34):13859-13864.

Broothaerts et al., (2005). "Gene transfer to plants by diverse species of bacteria," Nature, 433:629-633.

Broughton et al., (1971). "Control of leghaemoglobin synthesis in snake beans," Biochem J, 125:1075-1080.

Buendia et al., (2016). "The LysM receptor-like kinase SILYK10 regulates the arbuscular mycorrhizal symbiosis in tomato," New Phytol, 210:184-195.

Cheal et al., (2014). "Preclinical Evaluation of Multistep Targeting of Diasialoganglioside GD2 Using an IgG-scFv Bispecific Antibody with High Affinity for GD2 and DOTA Metal Complex," Mol. Cancer Ther., 13(7):1803-1812.

Chelius et al., (2010). "Structural and functional characterization of the trifunctional antibody catumaxomab," Mabs, 2(3):309-319.

Chen et al., (2021). "A Promising Intracellular Protein-Degradation Strategy: TRIMbody—Away Technique Based on Nanobody Fragment," Biomolecules, 11:1512, 15 pages.

Cuesta et al., (2010). "Multivalent antibodies: when design surpasses evolution," Trends in Biotechnol, 28(7):355-362.

Cummings et al., (2009). "Nodulation of *Sesbania* species by Rhizobium (Agrobacterium) strain IRBG74 and other rhizobia," Environmental Microbiology, 11:2510-2525.

Desaki et al., (2018). "MAMP-triggered plant immunity mediated by the LysM-receptor kinase CERK1," Journal of General Plant Pathology, 85, 11 pages.

Doyle, (2011). "Phylogenetic perspectives on the origins of nodulation," Mol Plant Microbe Interact, 24(11):1289-95.

Dumoulin et al., (2003). "A camelid antibody fragment inhibits the formation of amyloid fibrils by human lysozyme," Nature, 424:783-788.

Dunn, (1964). "Multiple Comparisons Using Rank Sums," Technometrics, 6:241-252.

Ekerljung et al., (2012). "Generation and Evaluation of Bispecific Affibody Molecules for Simultaneous Targeting of EGFR and HER2," Bioconjugate Chemistry, 23(9):1802-1811.

Endres et al., (2013). "Conformational Coupling across the Plasma Membrane in Activation of the EGF Receptor," Cell, 152:543-556.

Feng et al., (2019). "A combination of chitooligosaccharide and lipochitooligosaccharide recognition promotes arbuscular mycorrhizal associations in Medicago truncatula," Nature Communications, 10:5047, 12 pages.

Frank et al., (2023). "Single-cell analysis identifies genes facilitating rhizobium infection in Lotus japonicus," Nat Commun, 14:7171, 11 pages.

GenBank Accession No. ANS10208.1, "Nod-factor receptor 5 [*Arachis hypogaea* subsp. *hypogaea*]," Apr. 26, 2017, 2 pages.

GenBank Accession No. XP_020148045.1, "serine/threonine receptor-like kinase NFP [*Aegilops tauschii* subsp. *strangulata*]," Dec. 2, 2021, 2 pages.

GenBank Accession No. XP_020399958.1, "serine/threonine receptor-like kinase NFP [*Zea mays*]," Sep. 1, 2020, 2 pages.

Gil et al., (2020). "Optogenetic control of protein binding using light-switchable nanobodies," Nature Communications, 11:4044, 12 pages.

Guo et al., (2004). "Protein tolerance to random amino acid change," PNAS USA, 101:9205-9210.

Gysel et al., (2021). "Kinetic proofreading of lipochitooligosaccharides determines signal activation of symbiotic plant receptors," PNAS USA, 118(44):e2111031118, 10 pages.

Hamers-Casterman et al., (1993). "Naturally occurring antibodies devoid of light chains," Nature, 363:446-448.

Handberg et al., (1992). "Lotus japonicus, an autogamous, *diploid legume* species for classical and molecular genetics," Plant Journal, 2(4):487-496.

Häsler et al., (2016). "VNAR single-domain antibodies specific for BAFF inhibit B cell development by molecular mimicry," Mol. Immunol., 75:28-37, 20 pages.

He et al., (2019). "A LysM Receptor Heteromer Mediates Perception of Arbuscular Mycorrhizal Symbiotic Signal in Rice," Molecular Plant, 12(12):1561-1576.

Heo et al., (2016). "Potential therapeutic implications of IL-6/IL-6R/gp130-targeting agents in breast cancer," Oncotarget, 7(13):15460-15473.

Hohmann et al., (2017). "The Structural Basis of Ligand Perception and Signal Activation by Receptor Kinases," Annu. Rev. Plant Biol., 68:109-137.

Holt et al., (2003). "Domain antibodies: proteins for therapy," Trends Biotechnol, 21(11):484-490.

Hu et al., (2021). "Lysin Motif (LysM) Proteins: Interlinking Manipulation of Plant Immunity and Fungi," Int. J. Mol. Sci., 22:3114, 12 pages.

Hudson et al., (1999). "High avidity scFv multimers; diabodies and triabodies," J. Immunol. Methods, 23(1-2):177-189.

Hunter et al., (2015). "IL-6 as a keystone cytokine in health and disease," Nat. Immunol., 16:448-457.

Huston et al., (2001). "Engineered antibodies take center stage," Human Antibodies, 10(3-4):127-142.

Ingram et al., (2018). "Exploiting Nanobodies' Singular Traits," Annual Review of Immunology, 36:695-715.

International Search Report and Written Opinion for International Patent Application No. PCT/EP2023/086097 mailed on Apr. 8, 2024, 18 pages.

International Search Report and Written Opinion for International Patent Application No. PCT/EP2024/056882 mailed on Jun. 25, 2024, 17 pages.

International Search Report and Written Opinion for International Patent Application No. PCT/EP2024/056884 mailed on Jun. 26, 2024, 19 pages.

Jeffrey et al., (1995). "Mechanism of CDK activation revealed by the structure of a cyclinA-CDK2 complex," Nature, 376(6538):313-320.

Jumper et al., (2021). "Highly accurate protein structure prediction with AlphaFold," Nature, 596:583-589.

Kaku et al., (2006). "Plant cells recognize chitin fragments for defense signaling through a plasma membrane receptor," PNAS, 103:11086-11091.

Keller et al., (2019). "Selection and Characterization of a Nanobody Biosensor of GTP-Bound RHO Activities," Antibodies, 8:8, 17 pages.

Kistner et al., (2002). "Evolution of signal transduction in intracellular symbiosis," Trends in Plant Science, 7(11):511-518.

Kistner et al., (2005). "Seven Lotus japonicus genes required for transcriptional reprogramming of the root during fungal and bacterial symbiosis," Plant Cell, 17:2217-2229.

Kontermann et al., (2015). "Bispecific antibodies," Drug Discovery Today, 20(7):838-847, 12 pages.

Kruskal et al., (1952). "Use of Ranks in One-Criterion Variance Analysis," J Am Stat Assoc, 47:583-621.

Kwon et al., (2018). "Coupled regulation by the juxtamembrane and sterile a motif (SAM) linker is a hallmark of ephrin tyrosine kinase evolution," J Biol Chem, 293(14):5102-5116.

Levinson et al., (2006). "A Src-Like Inactive Conformation in the Abl Tyrosine Kinase Domain," PLOS Biology, 4(5):e144, 753-767.

(56)     References Cited

OTHER PUBLICATIONS

Lewis et al., (2016). "Oxidation increases the strength of the methionine-aromatic interaction," Nature Chemical Biology, 12(10):860-866, 20 pages.

Igolkina et al., (2018). "Structural Insight Into the Role of Mutual Polymorphism and Conservatism in the Contact Zone of the NFR5-K1 Heterodimer With the Nod Factor," Frontiers in Plant Sci., 9:344, 14 pages.

Li et al., (2017). "Selection of similar single domain antibodies from two immune VHH libraries obtained from two alpacas by using different selection methods," Immunol. Lett., 188:89-95, 23 pages.

Liebschner et al., (2019). "Macromolecular structure determination using X-rays, neutrons and electrons: recent developments in Phenix," Acta Cryst., 75:861-877.

Limpens et al., (2003). "LysM domain receptor kinases regulating rhizobial Nod factor-induced infection," Science, 302:630-633.

Liu et al., (2016). "Intracellularly expressed nanobodies against non-structural protein 4 of porcine reproductive and respiratory syndrome virus inhibit virus replication," Biotechnol Lett, 38:1081-1088.

Lohmann et al., (2010). "Evolution and regulation of the Lotus japonicus LysM receptor gene family," Mol Plant Microbe Interact, 23(4):510-521.

Lomize et al., (2018). "Membranome 2.0: database for proteome-wide profiling of bitopic proteins and their dimers," Bioinformatics, 34(6):1061-1062.

Madsen et al., (2011). "Autophosphorylation is essential for the in vivo function of the Lotus japonicus Nod factor receptor 1 and receptor-mediated signalling in cooperation with Nod factor receptor 5," Plant Journal, 65:404-417.

Maeda et al., (2018). "Lipid-Protein Interplay in Dimerization of Juxtamembrane Domains of Epidermal Growth Factor Receptor," Biophys. J., 114(4):893-903.

Mbengue et al., (2010). "The Medicago truncatula E3 Ubiquitin Ligase PUB1 Interacts with the LYK3 Symbiotic Receptor and Negatively Regulates Infection and Nodulation," Plant Cell, 22(10):3474-3488.

McMahon et al., (2018). "Yeast surface display platform for rapid discovery of conformationally selective nanobodies," Nat Struct Mol Biol., 25(3):289-296, 26 pages.

Miri et al., (2019). "Inside out: root cortex-localized LHK1 cytokinin receptor limits epidermal infection of Lotus japonicus roots by Mesorhizobium loti," New Phytologist, 222(3):1523-1537.

Miwa et al. (2006). "Analysis of Nod-factor-induced calcium signaling in root hairs of symbiotically defective mutants of Lotus japonicus," Mol. Plant-Microbe Interact, 19:914-923.

Miyata et al., (2016). "Evaluation of the Role of the LysM Receptor-Like Kinase, OsNFR5/OsRLK2 for AM Symbiosis in Rice," Plant Cell Physiol, 57:2283-2290.

Montiel et al., (2021). "Distinct signaling routes mediate intercellular and intracellular rhizobial infection in Lotus japonicus," Plant Physiology, 185:1131-1147.

Mossner et al., (2020). "Multimerization strategies for efficient production and purification of highly active synthetic cytokine receptor ligands," PLoS ONE, 15(4):e0230804, 19 pages.

Murray et al., (2007). "A cytokinin perception mutant colonized by Rhizobium in the absence of nodule organogenesis," Science, 315:101-104.

Muthuswamy et al., (1999). "Controlled Dimerization of ErbB Receptors Provides Evidence for Differential Signaling by *Homo*- and Heterodimers," Molecular And Cellular Biology, 19(10):6845-6857.

Muyldermans, (2001). "Single domain camel antibodies: current status," J. Biotechnol., 74:277-302.

Natsume et al., (2006). "Fucose removal from complex-type oligosaccharide enhances the antibody-dependent cellular cytotoxicity of single-gene-encoded bispecific antibody comprising of two single-chain antibodies linked to the antibody constant region," J. Biochem., 140(3):359-368.

Ochoa-Fernandez et al., (2020). "Optogenetic control of gene expression in plants in the presence of ambient white light," Nature Methods, 17:717-725.

Op Den Camp et al., (2011). "LysM-Type Mycorrhizal Receptor Recruited for Rhizobium Symbiosis in Nonlegume Parasponia," Science, 331:909-912.

Ott et al., (2005). "Symbiotic leghemoglobins are crucial for nitrogen fixation in legume root nodules but not for general plant growth and development," Current Biology, 15(6):531-535.

Parat et al., (2010). "Role of juxtamembrane and transmembrane domains in the mechanism of natriuretic peptide receptor A activation," Biochemistry, 49(22):4601-4610.

Petutschnig et al., (2010). "The lysin motif receptor-like kinase (LysM-RLK) CERK1 is a major chitin-binding protein in *Arabidopsis thaliana* and subject to chitin-induced phosphorylation," JBC, 285(37):28902-28911.

Pietraszewska-Bogiel et al., (2013). "Interaction of Medicago truncatula Lysin Motif Receptor-Like Kinases, NFP and LYK3, Produced in Nicotiana benthamiana Induces Defence-Like Responses," PLoS One, 8:e65055, 13 pages.

Pleschberger et al., (2003). "Generation of a Functional Monomolecular Protein Lattice Consisting of an S-Layer Fusion Protein Comprising the Variable Domain of a Camel Heavy Chain Antibody," Bioconjugate Chem, 14:440-448.

Pogozheva et al., (2018). "Evolution and adaptation of single-pass transmembrane proteins," Biochim Biophys Acta Biomembr, 1860(2):364-377.

Poljak, (1994). "Production and structure of diabodies," Structure, 2(12):1121-1123.

Prole et al., (2019). "A genetically encoded toolkit of functionalized nanobodies against fluorescent proteins for visualizing and manipulating intracellular signalling," BMC Biology, 17:41, 24 pages.

Radhakrishnan et al., (2020). "An ancestral signalling pathway is conserved in intracellular symbioses-forming plant lineages," Nature Plants, 6(3):280-289, 23 pages.

Regula et al., (2016). "Targeting key angiogenic pathways with a bispecific CrossMAb optimized for neovascular eye diseases," EMBO Mol. Med., 8(11):1265-1288.

Reid et al., (1985). "Sulphur-aromatic interactions in proteins," FEBS Letters, 190(2):209-213.

Reusch et al., (2014). "A novel tetravalent bispecific TandAb (CD30/CD16A) efficiently recruits NK cells for the lysis of CD30+ tumor cells," mAbs, 6(3):727-738.

Rhoads et al., (1998). "Regulation of the cyanide-resistant alternative oxidase of plant mitochondria. Identification of the cysteine residue involved in alpha-keto acid stimulation and intersubunit disulfide bond formation," J Biol Chem, 273(46):30750-30756.

Richins et al., (1987). "Sequence of figwort mosaic virus DNA (Caulimovirus group)," Nucleic Acids Res., 15:8451-8466.

Ried et al., (2014). "Spontaneous symbiotic reprogramming of plant roots triggered by receptor-like kinases," eLife, 3:e03891, 17 pages.

Rübsam et al., (2023). "Nanobody-driven signaling reveals the core receptor complex in root nodule symbiosis," Science, 379(6629):272-277.

Rohl et al., (1999). "Alanine is helix-stabilizing in both template-nucleated and standard peptide helices," PNAS, 96(7):3682-3687.

Sanz et al., (2004). "Antibodies and gene therapy: teaching old 'magic bullets' new tricks," Trends in Immunol, 25(2):85-91.

Schauser et al., (1999). "A plant regulator controlling development of symbiotic root nodules," Nature, 402:191-195.

Schneider et al., (2012). "NIH Image to ImageJ: 25 years of image analysis," Nature Methods, 9:671-675, 12 pages.

Schoonooghe et al., (2009). "Efficient production of human bivalent and trivalent anti-MUC1 Fab-scFv antibodies in Pichia pastoris," BMC Biotechnol, 9:70, 14 pages.

Shiu et al., (2001). "Receptor-like kinases from *Arabidopsis* form a monophyletic gene family related to animal receptor kinases," PNAS USA, 98:10763-10768.

Salmon et al., (2018). "The Mechanism of HdeA Unfolding and Chaperone Activation," Biochemistry, 37(1):33-40, 15 pages.

Søgaard et al., (2023). "Transmembrane signaling by a synthetic receptor in artificial cells," Nature Communications, 14:1646, 10 pages.

(56)  References Cited

OTHER PUBLICATIONS

Sokolowska-Wedzina et al., (2017). "High-Affinity Internalizing Human scFv-Fc Antibody for Targeting FGFR1-Overexpressing Lung Cancer," Mol. Cancer Res., 15(8):1040-1050.

Soltis et al., (1995). "Chloroplast gene sequence data suggest a single origin of the predisposition for symbiotic nitrogen fixation in angiosperms," PNAS, 92:2647-2651.

Stijlemans et al., (2004). "Efficient targeting of conserved cryptic epitopes of infectious agents by single domain antibodies. African trypanosomes as paradigm," J. Biol. Chem, 279:1256-1261.

Stocks, (2004). "Intrabodies: production and promise," Drug Discov. Today, 9(22):960-966.

Stracke et al., (2002). "A plant receptor-like kinase required for both bacterial and fungal symbiosis," Nature, 417:959-962.

Strong et al., (2006). "Toward the structural genomics of complexes: Crystal structure of a PE/PPE protein complex from *Mycobacterium tuberculosis*," PNAS, 103(21):8060-8065.

Sun et al., (2004). "Xa26, a gene conferring resistance to *Xanthomonas oryzae* pv. *Oryzae* in rice, encodes an LRR receptor kinase-like protein," Plant J, 37:517-527.

Suthaus et al., (2010). "Forced *Homo-* and Heterodimerization of All gp130-Type Receptor Complexes Leads to Constitutive Ligand-independent Signaling and Cytokine-independent Growth," Molecular Biology of the Cell, 21:2797-2807.

Tian et al., (2013). "Progress and Perspectives in Research of Chitin Triggered Immunity in Plant," Scientia Agricultura Sinica, 46(15):3115-3124. English abstract.

Tirichine et al., (2007). "A gain-of-function mutation in a cytokinin receptor triggers spontaneous root nodule organogenesis," Science, 315:104-107.

Tsai et al., (2016). "CD19xCD3 DART protein mediates human B-cell depletion in vivo in humanized BLT mice," Mol. Ther. Oncolytics, 3:15024, 9 pages.

Tutt et al., (1991). "Trispecific F(ab')3 derivatives that use cooperative signaling via the TCR/CD3 complex and CD2 to activate and redirect resting cytotoxic T cells," J. Immunol., 147:60-69.

Valley et al., (2012). "The Methionine-aromatic Motif Plays a Unique Role in Stabilizing Protein Structure," JBC, 287(42):34979-34991.

Varadi et al., (2022). "AlphaFold Protein Structure Database: massively expanding the structural coverage of protein-sequence space with high-accuracy models," Nucleic Acids Research, 50:D439-D444.

Veredas et al., (2017). "Methionine residues around phosphorylation sites are preferentially oxidized in vivo under stress conditions," Scientific Reports, 7(1):40403, 14 pages.

Wallin et al., (1998). "Genome-wide analysis of integral membrane proteins from eubacterial, archaean, and eukaryotic organisms," Protein Sci, 7(4):1029-1038.

Wan et al., (1989). "Efficient production of doubled haploid plants through colchicine treatment of anther-derived maize callus," Theor. Appl Genet., 77:889-892.

Wang et al., (2015). "Progress and Prospects in the Research on Wheat Receptor-like Kinases and Derivative Proteins," Chinese Bulletin of Botany, 50(2):255-262. English abstract on the last page.

Wang et al., (2006). "Crystal structures of IRAK-4 kinase in complex with inhibitors: a serine/threonine kinase with tyrosine as a gatekeeper," Structure, 14:1835-1844.

Wang et al., (2014). "Structural insights into the negative regulation of BRI1 signaling by BRI1-interacting protein BKI1," Cell Res, 24:1328-1341.

Wang et al., (2019). "Conformational flexibility and inhibitor binding to unphosphorylated interleukin-1 receptor-associated kinase 4 (IRAK4)," JBC, 294(12):4511-4519.

Watson et al., (2023). "De novo design of protein structure and function with RFdiffusion," Nature, 620(7976):1089-1100.

Wheeler et al., (2003). "Intrabody and intrakine strategies for molecular therapy," Mol. Ther., 8(3):355-366.

Williams et al., (2018). "MolProbity: More and better reference data for improved all-atom structure validation," Protein Sci, 27:293-315.

Willmann et al., (2011). "*Arabidopsis* lysin-motif proteins LYM1 LYM3 CERK1 mediate bacterial peptidoglycan sensing and immunity to bacterial infection," PNAS, 108:19824-19829.

Wolfe et al., (1989). "Date of the monocot-dicot divergence estimated from chloroplast DNA sequence data," PNAS, 86:6201-6205.

Wouters et al., (2019). "Luminescence- and Fluorescence-Based Complementation Assays to Screen for GPCR Oligomerization: Current State of the Art," International Journal of Molecular Sciences, 20:2958; 35 pages.

Wu et al., (2007). "Simultaneous targeting of multiple disease mediators by a dual-variable-domain immunoglobulin," Nat. Biotechnolg., 25(11):1290-1297.

Yamada et al., (2016). "The *Arabidopsis* CERK1-associated kinase PBL27 connects chitin perception to MAPK activation," EMBO J, 35(22):2468-2483.

Yan et al., (2012). "Structural basis for the impact of phosphorylation on the activation of plant receptor-like kinase BAK1," Cell Res, 22:1304-1308.

Yano et al., (2008). "Cyclops, a mediator of symbiotic intracellular accommodation," PNAS, 105(51):20540-20545.

Young et al., (2009). "Translating Medicago truncatula genomics to crop legumes," Curr Opin Plant Biol, 12:193-201.

Yu et al., (2019). "Optogenetic activation of intracellular antibodies for direct modulation of endogenous proteins," Nature Methods, 16:1095-1100.

Zapata et al., (1995). "Engineering linear F(ab')2 fragments for efficient production in *Escherichia coli* and enhanced antiproliferative activity," Protein Eng, 8(10):1057-1062.

Zheng et al., (1993). "Crystal structure of the catalytic subunit of cAMP-dependent protein kinase complexed with MgATP and peptide inhibitor," Biochemistry, 32:2154-2161.

Zhou et al., (2019). "The juxtamembrane domains of *Arabidopsis* CERK1, BAK1, and FLS2 play a conserved role in chitin-induced signaling," JIPB, 62(5):556-562.

Lomize et al., (2007). "The role of hydrophobic interactions in positioning of peripheral proteins in membranes," BMC Struct Biol, 7:44, 30 pages.

Zhang, (2003). "Overexpression analysis of plant transcription factors," Curr Opin Plant Biol, 6:430-440.

DeLano, (2002). "Pymol: An open-source molecular graphics tool," CCP4 Newsletter on protein crystallography, 161 pages.

Wang et al., (1998). "Improved vectors for Agrobacterium tumefaciens-mediated transformation of monocot plants," ISHS Acta Horticulturae 461: International Symposium on Biotechnology of Tropical and Subtropical Species Part 2, 461 (pp. 401-408).

* cited by examiner

*M. loti* Nod factor V (Cb,C18:1,Me,AcFuc)

R = H, Ac

*S. meliloti* Nod factor IV (Ac,C16:2,S)

FIG. 8C

LysM2

LysM3

Region IV

NNLDYVV

HvRLK4

Region II

NQNVTY

Region IV

LDYVAA

Region II

TPNVNV

HvRLK5

Region II

DDTLL

Region IV

PDSVEA

Marpol_Mapoly0080s0051.1

Region II    Region IV

GSNLTL    KDSVLA

Prupe.3G213100

Region II    Region IV

RGSNLT    QDSVIA

Solyc07g049180

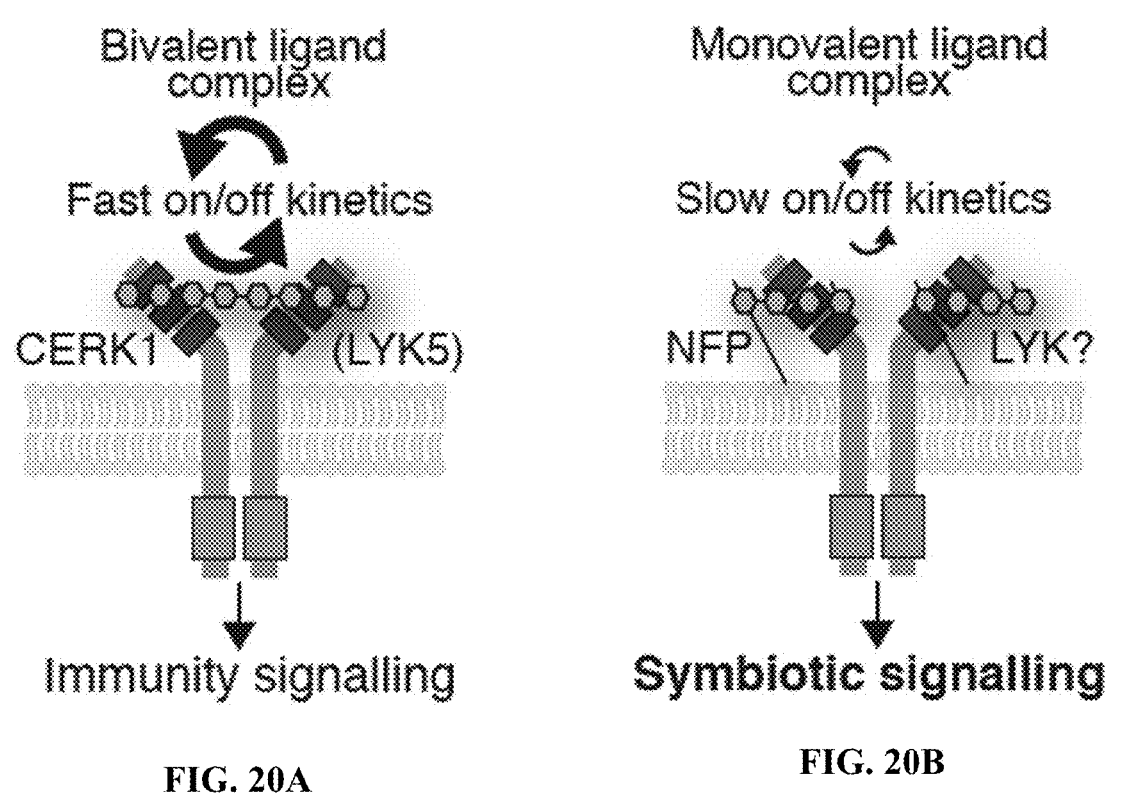
FIG. 20A
FIG. 20B
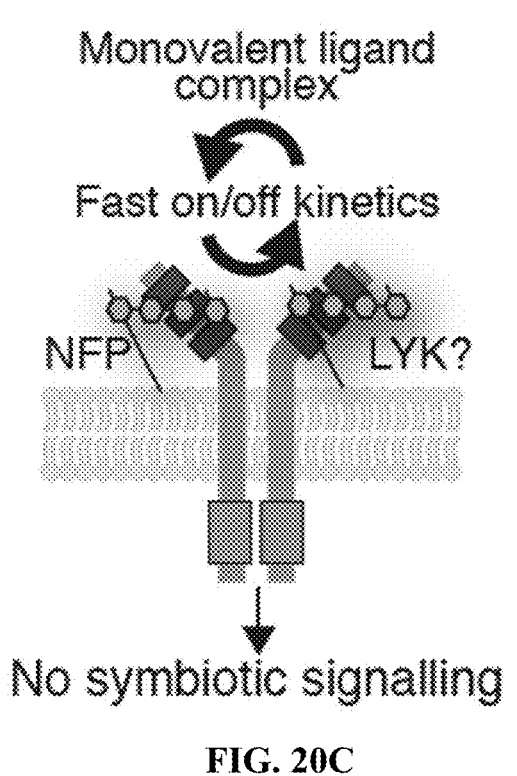
FIG. 20C

LysM RECEPTOR MOTIFS

CROSS-REFERENCE TO RELATED APPLICATION

This application claims the benefit of U.S. Provisional Application No. 63/027,151, filed May 19, 2020, which is hereby incorporated by reference in its entirety.

SUBMISSION OF SEQUENCE LISTING AS ASCII TEXT FILE

The content of the following submission on ASCII text file is incorporated herein by reference in its entirety: a computer readable form (CRF) of the Sequence Listing (file name: 794542001200SUBSEQLIST.TXT, date recorded: Jun. 28, 2021, size: 593 KB).

TECHNICAL FIELD

The present disclosure relates to genetically altered LysM receptors. In particular, the present disclosure relates replacement of part or all of motifs in the LysM1 domain with the corresponding motifs of the LysM1 domain from a donor LysM receptor that can alter the affinity, selectivity, and/or specificity for an oligosaccharide, particularly for Nod factors (lipochitooligosaccharides (LCOs)). The present disclosure also relates to genetically altering LysM receptors in plants to include a modified LysM1 domain and to genetically altering LysM receptors in plants by replacement of part or all of motifs in the LysM1 domain. The present disclosure further relates to combining LysM1 domain modifications with modifications of LysM2 domains to include a hydrophobic patch or alter the hydrophobic patch, whereby the LysM2 domain modifications can alter the affinity, selectivity, and/or specificity for an oligosaccharide, particularly for Nod factors (lipochitooligosaccharides (LCOs)).

BACKGROUND

Plants are exposed to a wide variety of microbes in their environment, both benign and pathogenic. To protect against the pathogenic microbes, plants have the ability to recognize specific molecular signals of the microbes through an array of receptors and, depending upon the pattern of the signals, can initiate an appropriate immune response. The molecular signals are derived from secreted materials, cell-wall components, and even cytosolic proteins of the microbes. Chitins (chitooligosaccharides (COs)) are an important fungal molecular signal that plants recognize through the chitin receptors such as CERK6, which are found on the plasma membrane. These receptors are in the LysM class of receptors and recognize the size and the acetylation of chitins from fungi. Nod factors (lipochitooligosaccharides (LCOs)) are another important molecular signal that can be found on both bacteria and fungi that are recognized by other LysM receptors.

In addition to benign and pathogenic microbes, some microbes can be beneficial to plants through association or symbiosis. Plants that enter into symbiotic relationships with certain nitrogen fixing bacteria and fungi need to be able to recognize the specific bacterial or fungal species to initiate the symbiosis while still being able to activate their immune systems to respond to other bacteria and fungi. One important mechanism that allows plants to recognize these specific bacteria or fungi is through specialized LysM Nod factor receptors that have high affinity, high selectivity, and/or high specificity for the form of Nod factors produced by the specific bacteria or fungi while Nod factors from other bacteria and fungi are not recognized by these specialized LysM receptors.

Experimental and computational approaches have been used to identify a number of these specialized LysM Nod factor receptors. As these receptors are required for recognizing symbiotic bacterial and fungal species, and for initiating symbiosis, these receptors represent an important component of any plant engineering strategy. Using these receptors, however, will not be particularly straightforward; transferring a specialized LysM Nod factor receptor into a plant that does not currently have one may require codon optimization, the identification of suitable promoters, the use of targeting signals, and further engineering approaches needed to adapt exogenous sequences for optimal expression. Further, the number of these receptors that have been identified is currently limited.

Moreover, species that already have specialized LysM Nod factor receptors, e.g., legumes, cannot be easily engineered with new specialized LysM receptors. Currently, legumes are limited to the specific bacterial or fungal species with which they form symbiotic associations. While legumes may have the benefit of existing symbiotic associations, their agricultural potential is limited. For example, legumes cannot currently be easily engineered to have different specificity for different symbiotic microbial species, which would allow legumes to better form associations with the bacterial or fungal species in different soils. Moreover, legumes cannot be easily engineered to have improved specialized LysM Nod factor receptors. Further, legumes cannot currently be engineered to have synergistic symbiotic requirements with other crops grown in rotation with them. Editing approaches are needed for both the modification of endogenous LysM receptors into specialized LysM Nod factor receptors able to perceive symbiotic bacterial and fungal species, and the modification of specialized LysM Nod factor receptors into specialized LysM Nod factor receptors with different specific recognition of symbiotic bacterial and fungal species. In particular, minimal editing approaches are needed, in which a small number of changes can be made to alter or improve the properties of existing LysM receptors.

BRIEF SUMMARY

In order to meet these needs, the present disclosure provides means of modifying LysM receptors by replacement of part or all of minimal motifs in the LysM1 domain with the corresponding motifs of the LysM1 domain from a donor LysM receptor that can alter or improve the affinity, selectivity, and/or specificity for an oligosaccharide, particularly for Nod factors (LCOs). In addition, the present disclosure provides complementary means of modifying LysM receptors by introduction of a hydrophobic patch into the LysM2 domain which can alter or improve affinity, selectivity, and/or specificity for Nod factors.

An aspect of the disclosure includes a modified plant LysM receptor polypeptide including a LysM1 domain including a first motif and a second motif, wherein the first motif and/or the second motif are modified as compared to the amino acid sequences of the corresponding wild-type plant LysM receptor polypeptide. An additional embodiment of this aspect includes the first motif corresponding to amino acids 42-48 of SEQ ID NO: 162 when the receptor polypeptide amino acid sequence is aligned to SEQ ID NO: 162 and the second motif corresponding to amino acids 75-80 of SEQ ID NO: 162 when the receptor polypeptide amino acid sequence is aligned to SEQ ID NO: 162. A further embodiment of this aspect includes the first motif corresponding to amino acids 44-49 of SEQ ID NO: 164 when the receptor polypeptide amino acid sequence is aligned to SEQ ID NO: 164 and the second motif corresponding to amino acids 76-81 of SEQ ID NO: 164 when the receptor polypeptide amino acid sequence is aligned to SEQ ID NO: 164. In yet another embodiment of this aspect, which may be combined with any of the preceding embodiments, the first motif is modified by substituting at least one, at least two, or at least three amino acid residues in the first motif with corresponding amino acid residues that are different in a third motif, and/or the second motif is modified by substituting at least one, at least two, or at least three amino acid residues in the second motif with corresponding amino acid residues that are different in a fourth motif. In still another embodiment of this aspect, which may be combined with any of the preceding embodiments, the first motif is modified by substituting the first motif with a third motif, and/or wherein the second motif is modified by substituting the second motif with a fourth motif. An additional embodiment of this aspect, which may be combined with any of the preceding embodiments that has the third motif and the fourth motif, includes the third motif and the fourth motif having different affinities, selectivities, and/or specificities for oligosaccharides than the first motif and the second motif. A further embodiment of this aspect includes the third motif and the fourth motif have different affinities for oligosaccharides than the first motif and the second motif. Yet another embodiment of this aspect includes the third motif and the fourth motif having different selectivities for oligosaccharides than the first motif and the second motif. Still another embodiment of this aspect includes the third motif and the fourth motif having different specificities for oligosaccharides than the first motif and the second motif. In a further embodiment of this aspect, which may be combined with any of the preceding embodiments that has the third motif and the fourth motif, the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM polypeptide amino acid sequence is aligned to SEQ ID NO: 162 and the fourth motif corresponds to amino acids 75-80 of SEQ ID NO: 162 when the second plant LysM polypeptide amino acid sequence is aligned to SEQ ID NO: 162. In an additional embodiment of this aspect, which may be combined with any of the preceding embodiments that has the third motif and the fourth motif, the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM polypeptide amino acid sequence is aligned to SEQ ID NO: 164 and the fourth motif corresponds to amino acids 76-81 of SEQ ID NO: 164 when the second plant LysM polypeptide amino acid sequence is aligned to SEQ ID NO: 164. In yet another embodiment of this aspect, which may be combined with any of the preceding embodiments that has the third motif and the fourth motif being from a second plant LysM receptor polypeptide having the different affinity, selectivity and/or specificity for oligosaccharides, at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

In an additional embodiment of this aspect, which may be combined with any of the preceding embodiments, the first motif includes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341. In a further embodiment of this aspect, which may be combined with any of the preceding embodiments, the first motif includes SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142. In yet another embodiment of this aspect, the third motif includes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and the first motif and the third motif are different. In still another embodiment of this aspect, the fourth motif includes SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID
NO: 34, SEQ ID NO: 35, SEQ ID NO: 36, SEQ ID NO: 37,
SEQ ID NO: 38, SEQ ID NO: 39, SEQ ID NO: 40, SEQ ID
NO: 41, SEQ ID NO: 42, SEQ ID NO: 43, SEQ ID NO: 44,
SEQ ID NO: 45, SEQ ID NO: 46, SEQ ID NO: 47, SEQ ID
NO: 48, SEQ ID NO: 49, SEQ ID NO: 50, SEQ ID NO: 51,
SEQ ID NO: 52, SEQ ID NO: 56, SEQ ID NO: 57, SEQ ID
NO: 58, SEQ ID NO: 69, SEQ ID NO: 70, SEQ ID NO: 71,
SEQ ID NO: 72, SEQ ID NO: 73, SEQ ID NO: 74, SEQ ID
NO: 75, SEQ ID NO: 76, SEQ ID NO: 77, SEQ ID NO: 78,
SEQ ID NO: 121, SEQ ID NO: 122, SEQ ID NO: 123, SEQ
ID NO: 124, SEQ ID NO: 125, SEQ ID NO: 126, SEQ ID
NO: 127, SEQ ID NO: 128, SEQ ID NO: 129, SEQ ID NO:
130, SEQ ID NO: 131, SEQ ID NO: 132, SEQ ID NO: 133,
SEQ ID NO: 134, SEQ ID NO: 135, SEQ ID NO: 136, SEQ
ID NO: 137, SEQ ID NO: 138, SEQ ID NO: 139, SEQ ID
NO: 140, SEQ ID NO: 141, or SEQ ID NO: 142, and the
second motif and the fourth motif are different.

Yet another embodiment of this aspect, which may be
combined with any of the preceding embodiments, further
includes a fifth motif in the LysM1 domain, wherein the fifth
motif is modified. An additional embodiment of this aspect
includes the fifth motif corresponding to amino acids 56-65
of SEQ ID NO: 162 when the receptor polypeptide amino
acid sequence is aligned to SEQ ID NO: 162. In still another
embodiment of this aspect, which may be combined with
any of the preceding embodiments that has a fifth motif, the
fifth motif is modified by substituting at least one, at least
two, or at least three amino acid residues in the fifth motif
with corresponding amino acid residues that are different in
a sixth motif. In yet another embodiment of this aspect,
which may be combined with any of the preceding embodi-
ments that has a fifth motif, the fifth motif is substituted with
a sixth motif. A further embodiment of this aspect, which
may be combined with any of the preceding embodiments
that has a sixth motif, includes the sixth motif being from a
second plant LysM receptor polypeptide having the different
specificity for oligosaccharides and the sixth motif corre-
sponding to amino acids 56-65 of SEQ ID NO: 162 when the
second plant LysM polypeptide amino acid sequence is
aligned to SEQ ID NO: 162. In still another embodiment of
this aspect, which may be combined with any of the pre-
ceding embodiments that has a fifth motif, the fifth motif
includes SEQ ID NO: 100, SEQ ID NO: 101, SEQ ID NO:
102, SEQ ID NO: 103, SEQ ID NO: 104, SEQ ID NO: 105,
SEQ ID NO: 106, SEQ ID NO: 107, SEQ ID NO: 108, SEQ
ID NO: 109, SEQ ID NO: 110, SEQ ID NO: 111, SEQ ID
NO: 112, SEQ ID NO: 113, SEQ ID NO: 114, SEQ ID NO:
115, SEQ ID NO: 116, SEQ ID NO: 117, SEQ ID NO: 118,
SEQ ID NO: 119, or SEQ ID NO: 120. In yet another
embodiment of this aspect, which may be combined with
any of the preceding embodiments that has a sixth motif, the
sixth motif includes SEQ ID NO: 100, SEQ ID NO: 101,
SEQ ID NO: 102, SEQ ID NO: 103, SEQ ID NO: 104, SEQ
ID NO: 105, SEQ ID NO: 106, SEQ ID NO: 107, SEQ ID
NO: 108, SEQ ID NO: 109, SEQ ID NO: 110, SEQ ID NO:
111, SEQ ID NO: 112, SEQ ID NO: 113, SEQ ID NO: 114,
SEQ ID NO: 115, SEQ ID NO: 116, SEQ ID NO: 117, SEQ
ID NO: 118, SEQ ID NO: 119, or SEQ ID NO: 120, and the
fifth motif and the sixth motif are different.

Still another embodiment of this aspect, which may be
combined with any of the preceding embodiments, includes
the modified receptor polypeptide binding one or more Nod
factors produced by nitrogen-fixing bacteria or by mycor-
rhizal fungi. An additional embodiment of this aspect,
includes the one or more Nod factors being produced by
nitrogen-fixing bacteria selected from the group of

*Mesorhizobium loti, Mesorhizobium huakuii, Mesorhizo-
bium mediterraneum, Mesorhizobium ciceri, Mesorhizo-
bium* spp., *Rhizobium mongolense, Rhizobium tropici,
Rhizobium etli phaseoli, Rhizobium giardinii, Rhizobium
leguminosarum* optionally *R. leguminosarum trifolii, R.
leguminosarum viciae,* and *R. leguminosarum phaseoli,*
Burkholderiales optionally symbionts of *Mimosa,
Sinorhizobium meliloti, Sinorhizobium medicae, Sinorhizo-
bium fredii, Sinorhizobium* NGR234, *Azorhizobium caulino-
dans, Bradyrhizobium japonicum, Bradyrhizobium elkanii,
Bradyrhizobium liaonginense, Frankia* spp., or any combi-
nation thereof, or by mycorrhizal fungi selected from the
group of *Acaulosporaceae* spp., *Diversisporaceae* spp.,
*Gigasporaceae* spp., *Pacisporaceae* spp., *Funneliformis*
spp., *Glomus* spp., *Rhizophagus* spp., *Sclerocystis* spp.,
*Septoglomus* spp., *Claroideoglomus* spp., *Ambispora* spp.,
*Archaeospora* spp., *Geosiphon pyriformis, Paraglomus*
spp., other species in the division Glomeromycota, or any
combination thereof. A further embodiment of this aspect,
which may be combined with any preceding embodiment
that has one or more Nod factors produced by nitrogen-
fixing bacteria or by mycorrhizal fungi, includes the modi-
fied receptor polypeptide binding one or more Nod factors
with higher affinity than an unmodified receptor polypep-
tide. Yet another embodiment of this aspect, which may be
combined with any preceding embodiment that has one or
more Nod factors produced by nitrogen-fixing bacteria or by
mycorrhizal fungi, includes the modified receptor polypep-
tide binding one or more Nod factors with higher selectivity
than an unmodified receptor polypeptide. Still another
embodiment of this aspect, which may be combined with
any preceding embodiment that has one or more Nod factors
produced by nitrogen-fixing bacteria or by mycorrhizal
fungi, includes the modified receptor polypeptide binding
one or more Nod factors with altered specificity as compared
to an unmodified receptor polypeptide.

Yet another embodiment of this aspect, which may be
combined with any of the preceding embodiments, further
includes a LysM2 domain modified to include a hydrophobic
patch on the surface of the LysM2 domain, wherein the
modified plant LysM receptor polypeptide has enhanced
affinity, selectivity, and/or specificity for one or more one or
more Nod factors as compared to the unmodified plant LysM
receptor polypeptide. An additional embodiment of this
aspect includes the hydrophobic patch being within 30 Å, 20
Å, 10 Å, 7.5 Å, 5 Å, 4 Å, 3 Å, 2 Å, 1.5 Å, or 1 Å of a chitin
binding motif. In a further embodiment of this aspect, which
may be combined with any preceding embodiment that has
a modified LysM2 domain, the LysM2 domain includes SEQ
ID NO: 278, SEQ ID NO: 279, SEQ ID NO: 280, SEQ ID
NO: 281, SEQ ID NO: 282, SEQ ID NO: 283, SEQ ID NO:
284, SEQ ID NO: 285, SEQ ID NO: 286, SEQ ID NO: 287,
SEQ ID NO: 288, SEQ ID NO: 289, SEQ ID NO: 290, SEQ
ID NO: 291, SEQ ID NO: 292, SEQ ID NO: 293, SEQ ID
NO: 294, SEQ ID NO: 295, SEQ ID NO: 296, SEQ ID NO:
297, SEQ ID NO: 298, SEQ ID NO: 299, or SEQ ID NO:
300. In yet another embodiment of this aspect, which may be
combined with any preceding embodiment that has a modi-
fied LysM2 domain, the hydrophobic patch was generated
by deleting at least one non-hydrophobic amino acid resi-
due, substituting at least one amino acid residue with a more
hydrophobic amino acid, or combinations thereof. Still
another embodiment of this aspect, which may be combined
with any preceding embodiment that has a LysM2 domain,
includes the at least one amino acid being identified by an
amino acid sequence alignment with a LysM2 domain from
a LysM high affinity Nod factor receptor that naturally has a hydrophobic patch that interacts with a Nod factor. In an additional embodiment of this aspect, the LysM2 domain from a LysM high affinity Nod factor receptor includes SEQ ID NO: 271, SEQ ID NO: 272, SEQ ID NO: 273, SEQ ID NO: 274, SEQ ID NO: 275, SEQ ID NO: 276, or SEQ ID NO: 277. In a further embodiment of this aspect, which may be combined with any preceding embodiment that has a LysM2 domain from a LysM high affinity Nod factor receptor, the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

Yet another embodiment of this aspect, which may be combined with any preceding embodiment where the hydrophobic patch was generated by deleting at least one non-hydrophobic amino acid residue, includes the at least one amino acid being identified by structural modeling to identify a region in LysM2 where the hydrophobic patch can be engineered. A further embodiment of this aspect includes the structural modeling using the unmodified plant LysM amino acid sequence and a LysM domain three dimensional structure that has a known hydrophobic patch. An additional embodiment of this aspect includes the LysM domain three dimensional structure being a *Medicago truncatula* NFP ectodomain. Still another embodiment of this aspect, which may be combined with any preceding embodiment that has a LysM domain three dimensional structure that has a known hydrophobic patch, includes the known hydrophobic patch amino acid residues of the LysM domain three dimensional structure being or correspond to L147, L151, L152, L154, T156, K157 and V158 of the *Medicago truncatula* NFP ectodomain. A further embodiment of this aspect includes the alpha carbon of at least one amino acid being within 3 Å of an alpha carbon of a known hydrophobic patch amino acid residue in the structural alignment. Yet another embodiment of this aspect, which may be combined with any preceding embodiment that has structural modeling, includes the structural modeling being performed using SWISS-MODEL, PDB2PQR, APBS, PyMol, and APBS tools 2.1. Still another embodiment of this aspect, which may be combined with any preceding embodiment that has a modified LysM2 domain, includes the modified receptor polypeptide binding one or more Nod factors produced by nitrogen-fixing bacteria or by mycorrhizal fungi. A further embodiment of this aspect includes the one or more Nod factors being produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli*, Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. An additional embodiment of this aspect, which may be combined with any preceding embodiment that has one or more Nod factors produced by nitrogen-fixing bacteria or by mycorrhizal fungi, includes the modified receptor polypeptide binding one or more Nod factors with higher affinity than an unmodified receptor polypeptide. In yet another embodiment of this aspect, which may be combined with any preceding embodiment that has one or more Nod factors produced by nitrogen-fixing bacteria or by mycorrhizal fungi, the modified receptor polypeptide binds one or more Nod factors with higher selectivity than an unmodified receptor polypeptide. In still another embodiment of this aspect, which may be combined with any preceding embodiment that has one or more Nod factors produced by nitrogen-fixing bacteria or by mycorrhizal fungi, the modified receptor polypeptide binds one or more Nod factors with altered specificity as compared to an unmodified receptor polypeptide.

A further aspect of the present disclosure includes a genetically altered plant or part thereof including the modified LysM receptor polypeptide of any one of the preceding embodiments. An additional embodiment of this aspect includes the modified LysM receptor polypeptide having higher affinity, higher selectivity, and/or altered specificity for one or more Nod factors than an unmodified LysM receptor polypeptide and the expression of the modified LysM receptor polypeptide allowing the plant or part thereof to recognize one or more Nod factors with high affinity, high selectivity, and/or altered specificity. Yet another embodiment of this aspect, which may be combined with any one of the preceding embodiments, includes the one or more Nod factors are produced by nitrogen-fixing bacteria or by mycorrhizal fungi. A further embodiment of this aspect includes the one or more Nod factors produced by nitrogen-fixing bacteria being selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli*, Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. Still another embodiment of this aspect, which may be combined with any one of the preceding embodiments, includes the modified LysM receptor polypeptide being localized to a plant cell plasma membrane. Yet another embodiment of this aspect includes the plant cell being a root cell. An additional embodiment of this aspect includes the root cell being a root epidermal cell. A further embodiment of this aspect, which may be combined with any of the preceding embodiments includes the modified LysM receptor polypeptide being expressed in a developing plant root system. An additional embodiment of this aspect, which may be combined with any of the preceding embodiments, includes a nucleic acid sequence encoding the modified LysM receptor polypeptide, wherein the nucleic acid sequence is operably linked to a promoter. Still another embodiment of this aspect includes the promoter being a root specific promoter, a constitutive promoter, or a combination thereof. In yet another embodiment of this aspect, which may be combined with any preceding embodiment that has a promoter, the promoter is selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. In an additional embodiment of this aspect, which may be combined with any preceding embodiment that has a promoter, the promoter is selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter.

An additional aspect of the present disclosure includes a genetically altered plant or part thereof including a first modified LysM receptor polypeptide of any one of the preceding embodiments and a second modified LysM receptor polypeptide including a LysM2 domain modified to include a hydrophobic patch on the surface of the LysM2 domain, wherein the second modified plant LysM receptor polypeptide has enhanced affinity, selectivity, and/or specificity for one or more Nod factors as compared to a second unmodified plant LysM receptor polypeptide. An additional embodiment of this aspect includes the hydrophobic patch being within 30 Å, 20 Å, 10 Å, 7.5 Å, 5 Å, 4 Å, 3 Å, 2 Å, 1.5 Å, or 1 Å of a chitin binding motif. In a further embodiment of this aspect, which may be combined with any of the preceding embodiments, the LysM2 domain includes SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300. In yet another embodiment of this aspect, which may be combined with any one of the preceding embodiments, the hydrophobic patch was generated by deleting at least one non-hydrophobic amino acid residue, substituting at least one amino acid residue with a more hydrophobic amino acid, or combinations thereof. Still another embodiment of this aspect, which may be combined with any one of the preceding embodiments, includes the at least one amino acid being identified by an amino acid sequence alignment with a LysM2 domain from a LysM high affinity Nod factor receptor that naturally has a hydrophobic patch that interacts with a Nod factor. In an additional embodiment of this aspect, the LysM2 domain from a LysM high affinity Nod factor receptor includes SEQ ID NO: 271, SEQ ID NO: 272, SEQ ID NO: 273, SEQ ID NO: 274, SEQ ID NO: 275, SEQ ID NO: 276, or SEQ ID NO: 277. In a further embodiment of this aspect, which may be combined with any preceding embodiment that has a LysM2 domain from a LysM high affinity Nod factor receptor, the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258. Yet another embodiment of this aspect, which may be combined with any preceding embodiment where the hydrophobic patch was generated by deleting at least one non-hydrophobic amino acid residue, includes the at least one amino acid being identified by structural modeling to identify a region in LysM2 where the hydrophobic patch can be engineered. A further embodiment of this aspect includes the structural modeling using the unmodified plant LysM amino acid sequence and a LysM domain three dimensional structure that has a known hydrophobic patch. An additional embodiment of this aspect includes the LysM domain three dimensional structure being a *Medicago truncatula* NFP ectodomain. Still another embodiment of this aspect, which may be combined with any preceding embodiment that has a LysM domain three dimensional structure that has a known hydrophobic patch, includes the known hydrophobic patch amino acid residues of the LysM domain three dimensional structure being or correspond to L147, L151, L152, L154, T156, K157 and V158 of the *Medicago truncatula* NFP ectodomain. A further embodiment of this aspect includes the alpha carbon of at least one amino acid being within 3 Å of an alpha carbon of a known hydrophobic patch amino acid residue in the structural alignment. Yet another embodiment of this aspect, which may be combined with any preceding embodiment that has structural modeling, includes the structural modeling being performed using SWISS-MODEL, PDB2PQR, APBS, PyMol, and APBS tools 2.1. Still another embodiment of this aspect, which may be combined with any of the preceding embodiments, includes the modified receptor polypeptide binding one or more Nod factors produced by nitrogen-fixing bacteria or by mycorrhizal fungi. A further embodiment of this aspect includes the one or more Nod factors being produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. An additional embodiment of this aspect, which may be combined with any preceding embodiment that has one or more Nod factors produced by nitrogen-fixing bacteria or by mycorrhizal fungi, includes the second modified receptor polypeptide binding one or more Nod factors with higher affinity than a second unmodified receptor polypeptide. In yet another embodiment of this aspect, which may be combined with any preceding embodiment that has one or more Nod factors produced by nitrogen-fixing bacteria or by mycorrhizal fungi, the second modified receptor polypeptide binds one or more Nod factors with higher selectivity than a second unmodified receptor polypeptide. In still another embodiment of this aspect, which may be combined with any preceding embodiment that has one or more Nod factors produced by nitrogen-fixing bacteria or by mycorrhizal fungi, the second modified receptor polypeptide binds one or more Nod factors with altered specificity as compared to a second unmodified receptor polypeptide. Still another embodiment of this aspect, which may be combined with any one of the preceding embodiments, includes the modified LysM receptor polypeptides being localized to a plant cell plasma membrane. Yet another embodiment of this aspect includes the plant cell being a root cell. An additional embodiment of this aspect includes the root cell being a root epidermal cell. A further embodiment of this aspect, which may be combined with any of the preceding embodiments, includes the modified LysM receptor polypeptides being expressed in a developing plant root system. An additional embodiment of this aspect, which may be combined with any of the preceding embodiments, includes a first nucleic acid sequence encoding the first modified plant LysM receptor polypeptide and a second nucleic acid sequence encoding the second modified plant LysM receptor polypeptide, wherein the first nucleic acid sequence is operably linked to a first promoter, and wherein the second nucleic acid sequence is operably linked to a second promoter. Still another embodiment of this aspect includes the first and second promoters being root specific promoters, constitutive promoters, or a combination thereof. In yet another embodiment of this aspect, which may be combined with any preceding embodiment that has a promoter, the first and/or second promoters are selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. In an additional embodiment of this aspect, which may be combined with any preceding embodiment that has a promoter, the first and/or second promoters are selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter.

In an additional embodiment of this aspect, which may be combined with any of the preceding embodiments, the plant is selected from the group of cassava, corn, cowpea, rice, barley, wheat, *Trema* spp., apple, pear, plum, apricot, peach, almond, walnut, strawberry, raspberry, blackberry, red currant, black currant, melon, cucumber, pumpkin, squash, grape, bean, soybean, pea, chickpea, cowpea, pigeon pea, lentil, Bambara groundnut, lupin, pulses, *Medicago* spp., *Lotus* spp., forage legumes, indigo, legume trees, or hemp. In a further embodiment of this aspect, which may be combined with any of the preceding embodiments, the plant part is a leaf, a stem, a root, a root primordia, a flower, a seed, a fruit, a kernel, a grain, a cell, or a portion thereof. An additional embodiment of this aspect includes the plant part being a fruit, a kernel, or a grain.

In some aspects, the present disclosure relates to a pollen grain or an ovule of the genetically altered plant of any of the above embodiments.

In some aspects, the present disclosure relates to a protoplast produced from the plant of any of the above embodiments.

In some aspects, the present disclosure relates to a tissue culture produced from protoplasts or cells from the plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell.

A further aspect of the present disclosure relates to methods of producing the genetically altered plant of the preceding embodiments including the modified LysM receptor polypeptide, including introducing a genetic alteration to the plant including a nucleic acid sequence encoding the modified LysM receptor polypeptide. An additional embodiment of this aspect includes the nucleic acid sequence being operably linked to a promoter. Yet another embodiment of this aspect includes the promoter being a root specific promoter, a constitutive promoters, or a combination thereof. Still another embodiment of this aspect, which may be combined with any preceding embodiment that has a promoter, includes the promoter being selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. Still another embodiment of this aspect, which may be combined with any preceding embodiment that has a promoter, includes the promoter is selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter. An additional embodiment of this aspect, which may be combined with any of the preceding embodiments, includes the nucleic acid sequence being inserted into the genome of the plant so that the nucleic acid sequence is operably linked to an endogenous promoter. A further embodiment of this aspect includes the endogenous promoter being a root specific promoter.

A further aspect of the present disclosure relates to methods of producing the genetically altered plant of the preceding embodiments including a first modified LysM receptor polypeptide and a second LysM receptor polypeptide, including introducing a genetic alteration to the plant including a first nucleic acid sequence encoding the first modified LysM receptor polypeptide and introducing a genetic alteration to the plant including a second nucleic acid sequence encoding the second modified LysM receptor polypeptide. An additional embodiment of this aspect includes the first nucleic acid sequence being operably linked to a first promoter, and the second nucleic acid sequence being operably linked to a second promoter. Yet another embodiment of this aspect includes the first and second promoters being root specific promoters, constitutive promoters, or a combination thereof. Still another embodiment of this aspect, which may be combined with any preceding embodiment that has a promoter, includes the first and/or second promoters are selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. An additional embodiment of this aspect, which may be combined with any preceding embodiment that has a promoter, includes the first and/or second promoters are selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter. Yet another embodiment of this aspect, which may be combined with any of the preceding embodiments, includes the first nucleic acid sequence being inserted into the genome of the plant so that the first nucleic acid sequence is operably linked to a first endogenous promoter, and/or the second nucleic acid sequence being inserted into the genome of the plant so that the second nucleic acid sequence is operably linked to a second endogenous promoter. A further embodiment of this aspect includes the first and second endogenous promoters being root specific promoters.

A further aspect of the present disclosure relates to methods of producing the genetically altered plant of any one of the preceding embodiments, including genetically editing a gene encoding an endogenous LysM receptor polypeptide in the plant to include the modified LysM1 domain. An additional embodiment of this aspect includes the endogenous LysM receptor polypeptide being an endogenous chitin LysM receptor polypeptide or an endogenous Nod factor LysM receptor polypeptide. Yet another embodiment of this aspect, which may be combined with any one of the preceding embodiments, includes the modified LysM receptor polypeptide being generated by: (a) providing a heterologous Nod factor LysM receptor polypeptide model including a structural model, a molecular model, a surface characteristics model, and/or an electrostatic potential model of a LysM1 domain, a LysM2 domain, a LysM3 domain, any combination thereof, or the ectodomain of the heterologous Nod factor LysM receptor polypeptide having selectivity for a beneficial nitrogen-fixing bacteria or a beneficial mycorrhizal fungus and an unmodified endogenous LysM receptor polypeptide; (b) identifying a first motif, a second motif, and/or optionally a fifth motif for modification in the unmodified endogenous LysM receptor polypeptide by comparing a LysM1 domain of the unmodified endogenous LysM receptor polypeptide with the corresponding LysM1 domain of the heterologous Nod factor LysM receptor polypeptide model; (c) modifying the first motif by substituting at least one, at least two, or at least three amino acid residues in the first motif with corresponding amino acid residues that are different in a third motif, modifying the second motif by substituting at least one, at least two, or at least three amino acid residues in the second motif with corresponding amino acid residues that are different in a fourth motif, and/or optionally modifying the fifth motif by substituting at least one, at least two, or at least three amino acid residues in the fifth motif with corresponding amino acid residues that are different in a sixth motif, wherein the third motif, the fourth motif, and the sixth motif have different affinities, selectivities, and/or specificities for oligosaccharides than the first motif, the second motif, and the fifth motif; and (d) generating the modified endogenous LysM receptor polypeptide wherein the first motif, the second motif, and/or optionally the fifth motif have been substituted with corresponding amino acid residues from the third motif, the fourth motif, and/or optionally the sixth motif.

Still another aspect of the present disclosure relates to methods of cultivating the genetically altered plant of any one of the preceding embodiments, including the steps of: (a) planting a genetically altered seedling, a genetically altered plantlet, a genetically altered cutting, a genetically altered tuber, a genetically altered root, or a genetically altered seed in soil to produce the genetically altered plant or grafting the genetically altered seedling, the genetically altered plantlet, or the genetically altered cutting to a root stock or a second plant grown in soil to produce the genetically altered plant; (b) cultivating the plant to produce harvestable seed, harvestable leaves, harvestable roots, harvestable cuttings, harvestable wood, harvestable fruit, harvestable kernels, harvestable tubers, and/or harvestable grain; and (c) harvesting the harvestable seed, harvestable leaves, harvestable roots, harvestable cuttings, harvestable wood, harvestable fruit, harvestable kernels, harvestable tubers, and/or harvestable grain.

ENUMERATED EMBODIMENTS

1. A modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide.

2. The receptor polypeptide of embodiment 1, wherein the first motif corresponds to amino acids 42-48 of SEQ ID NO: 162 when the receptor polypeptide amino acid sequence is aligned to SEQ ID NO: 162 and the second motif corresponds to amino acids 75-80 of SEQ ID NO: 162 when the receptor polypeptide amino acid sequence is aligned to SEQ ID NO: 162.

3. The receptor polypeptide of embodiment 1, wherein the first motif corresponds to amino acids 44-49 of SEQ ID NO: 164 when the receptor polypeptide amino acid sequence is aligned to SEQ ID NO: 164 and the second motif corresponds to amino acids 76-81 of SEQ ID NO: 164 when the receptor polypeptide amino acid sequence is aligned to SEQ ID NO: 164.

4. The receptor polypeptide of any one of embodiments 1-3, wherein the first motif is modified by substituting at least one, at least two, or at least three amino acid residues in the first motif with corresponding amino acid residues that are different in a third motif, and/or wherein the second motif is modified by substituting at least one, at least two, or at least three amino acid residues in the second motif with corresponding amino acid residues that are different in a fourth motif.

5. The receptor polypeptide of any one of embodiments 1-3, wherein the first motif is modified by substituting the first motif with a third motif, and/or wherein the second motif is modified by substituting the second motif with a fourth motif.

6. The receptor polypeptide of embodiment 4 or embodiment 5, wherein the third motif and the fourth motif have different affinities, selectivities, and/or specificities for oligosaccharides than the first motif and the second motif.

7. The receptor polypeptide of embodiment 6, wherein the third motif and the fourth motif have different affinities for oligosaccharides than the first motif and the second motif.

8. The receptor polypeptide of embodiment 6, wherein the third motif and the fourth motif have different selectivities for oligosaccharides than the first motif and the second motif.

9. The receptor polypeptide of embodiment 6, wherein the third motif and the fourth motif have different specificities for oligosaccharides than the first motif and the second motif.

10. The receptor polypeptide of any one of embodiments 4-9, wherein the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM polypeptide amino acid sequence is aligned to SEQ ID NO: 162 and the fourth motif corresponds to amino acids 75-80 of SEQ ID NO: 162 when the second plant LysM polypeptide amino acid sequence is aligned to SEQ ID NO: 162.

11. The receptor polypeptide of any one of embodiments 4-9, wherein the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM polypeptide amino acid sequence is aligned to SEQ ID NO: 164 and the fourth motif corresponds to amino acids 76-81 of SEQ ID NO: 164 when the second plant LysM polypeptide amino acid sequence is aligned to SEQ ID NO: 164.

12. The receptor polypeptide of embodiment 10 or embodiment 11, wherein at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

13. The receptor polypeptide of any one of embodiments 1-12, wherein the first motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341.

14. The receptor polypeptide of any one of embodiments 1-13, wherein the second motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142.

15. The receptor polypeptide of any one of embodiments 4-14, wherein the third motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and wherein the first motif and the third motif are different.

16. The receptor polypeptide of any one of embodiments 4-15, wherein the fourth motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142, and wherein the second motif and the fourth motif are different.

17. The receptor polypeptide of any one of embodiments 1-16, further comprising a fifth motif in the LysM1 domain, wherein the fifth motif is modified.

18. The receptor polypeptide of embodiment 17, wherein the fifth motif corresponds to amino acids 56-65 of SEQ ID NO: 162 when the receptor polypeptide amino acid sequence is aligned to SEQ ID NO: 162.

19. The receptor polypeptide of embodiment 17 or embodiment 18, wherein the fifth motif is modified by substituting at least one, at least two, or at least three amino acid residues in the fifth motif with corresponding amino acid residues that are different in a sixth motif.

20. The receptor polypeptide of any one of embodiments 17-19, wherein the fifth motif is substituted with a sixth motif.

21. The receptor polypeptide of embodiment 19 or embodiment 20, wherein the sixth motif has a different specificity for oligosaccharides than the fifth motif.

22. The receptor polypeptide of any one of embodiments 20-21, wherein the sixth motif is from a second plant LysM receptor polypeptide having the different specificity for oligosaccharides and the sixth motif corresponds to amino acids 56-65 of SEQ ID NO: 162 when the second plant LysM polypeptide amino acid sequence is aligned to SEQ ID NO: 162.

23. The receptor polypeptide of any one of embodiments 17-22, wherein the fifth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

24. The receptor polypeptide of any one of embodiments 19-23, wherein the sixth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120, and wherein the fifth motif and the sixth motif are different.

25. The receptor polypeptide of any one of embodiments 1-24, wherein the modified receptor polypeptide binds one or more Nod factors produced by nitrogen-fixing bacteria or by mycorrhizal fungi.

26. The receptor of embodiment 25, wherein the one or more Nod factors are produced by nitrogen-fixing bacteria selected from the group consisting of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaoninense, Frankia* spp., and any combination thereof, or by mycorrhizal fungi selected from the group consisting of *Acaulosporaceae* spp., *Diversisporaceae* spp., *Gigasporaceae* spp., *Pacispo-*

*raceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

27. The receptor polypeptide of embodiment 25 or embodiment 26, wherein the modified receptor polypeptide binds one or more Nod factors with higher affinity than an unmodified receptor polypeptide.

28. The receptor polypeptide of any one of embodiments 25-27, wherein the modified receptor polypeptide binds one or more Nod factors with higher selectivity than an unmodified receptor polypeptide.

29. The receptor polypeptide of any one of embodiments 25-28, wherein the modified receptor polypeptide binds one or more Nod factors with altered specificity as compared to an unmodified receptor polypeptide.

30. The modified plant LysM receptor polypeptide of any one of embodiments 1-29, further comprising a LysM2 domain modified to comprise a hydrophobic patch on the surface of the LysM2 domain, wherein the modified plant LysM receptor polypeptide has enhanced affinity, selectivity, and/or specificity for one or more Nod factors as compared to the unmodified plant LysM receptor polypeptide.

31. The receptor polypeptide of embodiment 30, wherein the hydrophobic patch is within 30 Å, 20 Å, 10 Å, 7.5 Å, 5 Å, 4 Å, 3 Å, 2 Å, 1.5 Å, or 1 Å of a chitin binding motif.

32. The receptor polypeptide of embodiment 30 or embodiment 31, wherein the LysM2 domain comprises SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

33. The receptor polypeptide of any one of embodiments 30-32, wherein the hydrophobic patch was generated by deleting at least one non-hydrophobic amino acid residue, substituting at least one amino acid residue with a more hydrophobic amino acid, or combinations thereof.

34. The receptor polypeptide of embodiment 33, wherein the at least one amino acid was identified by an amino acid sequence alignment with a LysM2 domain from a LysM high affinity Nod factor receptor that naturally has a hydrophobic patch that interacts with a Nod factor.

35. The receptor polypeptide of embodiment 34, wherein the LysM2 domain from a LysM high affinity Nod factor receptor comprises SEQ ID NO: 271, SEQ ID NO: 272, SEQ ID NO: 273, SEQ ID NO: 274, SEQ ID NO: 275, SEQ ID NO: 276, or SEQ ID NO: 277.

36. The receptor polypeptide of embodiment 34 or embodiment 35, wherein the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

37. The receptor polypeptide of any one of embodiments 33-36, wherein the at least one amino acid was identified by structural modeling to identify a region in LysM2 where the hydrophobic patch can be engineered.

38. The receptor polypeptide of embodiment 37, wherein the structural modeling used the unmodified plant LysM amino acid sequence and a LysM domain three dimensional structure that has a known hydrophobic patch.

39. The receptor polypeptide of embodiment 38, wherein the LysM domain three dimensional structure is a *Medicago truncatula* NFP ectodomain.

40. The receptor polypeptide of embodiment 38 or embodiment 39, wherein the known hydrophobic patch amino acid residues of the LysM domain three dimensional structure are or correspond to L147, L151, L152, L154, T156, K157 and V158 of the *Medicago truncatula* NFP ectodomain.

41. The receptor polypeptide of embodiment 40, wherein the alpha carbon of at least one amino acid was within 3 Å of an alpha carbon of a known hydrophobic patch amino acid residue in the structural alignment.

42. The receptor polypeptide of any one of embodiments 37-41, wherein the structural modeling was performed using SWISS-MODEL, PDB2PQR, APBS, PyMol, and APBS tools 2.1.

43. The receptor polypeptide of any one of embodiments 30-42, wherein the modified receptor polypeptide binds one or more Nod factors produced by nitrogen-fixing bacteria or by mycorrhizal fungi.

44. The receptor of embodiment 43, wherein the one or more Nod factors is produced by nitrogen-fixing bacteria selected from the group consisting of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

45. The receptor polypeptide of embodiment 43 or embodiment 44, wherein the modified receptor polypeptide binds the one or more Nod factors with higher affinity than an unmodified receptor polypeptide.

46. The receptor polypeptide of any one of embodiments 43-45, wherein the modified receptor polypeptide binds the one or more Nod factors with higher selectivity than an unmodified receptor polypeptide.

47. The receptor polypeptide of any one of embodiments 43-46, wherein the modified receptor polypeptide binds the one or more Nod factors with altered specificity as compared to an unmodified receptor polypeptide.

48. A genetically altered plant or part thereof comprising the modified LysM receptor polypeptide of any one of embodiments 1-47.

49. The genetically altered plant or part thereof of embodiment 48, wherein the modified LysM receptor polypeptide has higher affinity, higher selectivity, and/or altered specificity for one or more Nod factors than an unmodified LysM receptor polypeptide and the expression of the modified LysM receptor polypeptide allows the plant or part thereof to recognize one or more Nod factors with high affinity, high selectivity, and/or altered specificity.

50. The genetically altered plant or part thereof of embodiment 48 or embodiment 49, wherein the one or more Nod factors are produced by nitrogen-fixing bacteria or by mycorrhizal fungi.

51. The genetically altered plant or part thereof of embodiment 50, wherein the one or more Nod factors are produced by nitrogen-fixing bacteria selected from the group consisting of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., and any combination thereof, or by or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

52. The genetically altered plant or part thereof of any one of embodiments 48-51, wherein the modified LysM receptor polypeptide is localized to a plant cell plasma membrane.

53. The genetically altered plant or part thereof of embodiment 52, wherein the plant cell is a root cell.

54. The genetically altered plant or part thereof of embodiment 53, wherein the root cell is a root epidermal cell.

55. The genetically altered plant or part thereof of any one of embodiments 48-54, wherein the modified LysM receptor polypeptide is expressed in a developing plant root system.

56. The genetically altered plant or part thereof of any one of embodiments 48-55, comprising a nucleic acid sequence encoding the modified LysM receptor polypeptide, wherein the nucleic acid sequence is operably linked to a promoter.

57. The genetically altered plant or part thereof of embodiment 56, wherein the promoter is a root specific promoter, a constitutive promoter, or a combination thereof.

58. The genetically altered plant or part thereof of embodiment 56 or embodiment 57, wherein the promoter is selected from the group consisting of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a

*Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, and an *Arabidopsis* pCO2 promoter.

59. The genetically altered plant or part thereof of embodiment 56 or embodiment 57, wherein the promoter is selected from the group consisting of a CaMV35S promoter, a derivative of the CaMV35S promoter, a maize ubiquitin promoter, a trefoil promoter, a vein mosaic cassava virus promoter, and an *Arabidopsis* UBQ10 promoter.

60. A genetically altered plant or part thereof comprising a first modified LysM receptor polypeptide comprising the modified LysM receptor polypeptide of embodiments 1-29 and a second modified LysM receptor polypeptide comprising a LysM2 domain modified to comprise a hydrophobic patch on the surface of the LysM2 domain, wherein the second modified plant LysM receptor polypeptide has enhanced affinity, selectivity, and/or specificity for one or more Nod factors as compared to a second unmodified plant LysM receptor polypeptide.

61. The genetically altered plant or part thereof of embodiment 60, wherein the hydrophobic patch is within 30 Å, 20 Å, 10 Å, 7.5 Å, 5 Å, 4 Å, 3 Å, 2 Å, 1.5 Å, or 1 Å of a chitin binding motif.

62. The genetically altered plant or part thereof of embodiment 60 or embodiment 61, wherein the LysM2 domain comprises SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

63. The genetically altered plant or part thereof of any one of embodiments 60-62, wherein the hydrophobic patch was generated by deleting at least one non-hydrophobic amino acid residue, substituting at least one amino acid residue with a more hydrophobic amino acid, or combinations thereof.

64. The genetically altered plant or part thereof of embodiment 63, wherein the at least one amino acid was identified by an amino acid sequence alignment with a LysM2 domain from a LysM high affinity Nod factor receptor that naturally has a hydrophobic patch that interacts with a Nod factor.

65. The genetically altered plant or part thereof of embodiment 64, wherein the LysM2 domain from a LysM high affinity Nod factor receptor comprises SEQ ID NO: 271, SEQ ID NO: 272, SEQ ID NO: 273, SEQ ID NO: 274, SEQ ID NO: 275, SEQ ID NO: 276, or SEQ ID NO: 277.

66. The genetically altered plant or part thereof of embodiment 64 or embodiment 65, wherein the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

67. The genetically altered plant or part thereof of embodiments 63-66, wherein the at least one amino acid was identified by structural modeling to identify a region in LysM2 where the hydrophobic patch can be engineered.

68. The genetically altered plant or part thereof of embodiment 67, wherein the structural modeling used the second unmodified plant LysM amino acid sequence and a LysM domain three dimensional structure that has a known hydrophobic patch.

69. The genetically altered plant or part thereof of embodiment 68, wherein the LysM domain three dimensional structure is a *Medicago truncatula* NFP ectodomain.

70. The genetically altered plant or part thereof of embodiment 68 or embodiment 69, wherein the known hydrophobic patch amino acid residues of the LysM domain three dimensional structure are or correspond to L147, L151, L152, L154, T156, K157 and V158 of the *Medicago truncatula* NFP ectodomain.

71. The genetically altered plant or part thereof of embodiment 70, wherein the alpha carbon of at least one amino acid was within 3 Å of an alpha carbon of a known hydrophobic patch amino acid residue in the structural alignment.

72. The genetically altered plant or part thereof of any one of embodiments 67-71, wherein the structural modeling was performed using SWISS-MODEL, PDB2PQR, APBS, PyMol, and APBS tools 2.1.

73. The genetically altered plant or part thereof of any one of embodiments 60-72, wherein the second modified receptor polypeptide binds one or more Nod factors produced by nitrogen-fixing bacteria or by mycorrhizal fungi.

74. The genetically altered plant or part thereof of embodiment 73, wherein the one or more Nod factors is produced by nitrogen-fixing bacteria selected from the group consisting of *Mesorhizobium loti*, *Mesorhizobium huakuii*, *Mesorhizobium mediterraneum*, *Mesorhizobium ciceri*, *Mesorhizobium* spp., *Rhizobium mongolense*, *Rhizobium tropici*, *Rhizobium etli phaseoli*, *Rhizobium giardinii*, *Rhizobium leguminosarum* optionally *R. leguminosarum trifolii*, *R. leguminosarum viciae*, and *R. leguminosarum phaseoli*, Burkholderiales optionally symbionts of *Mimosa*, *Sinorhizobium meliloti*, *Sinorhizobium medicae*, *Sinorhizobium fredii*, *Sinorhizobium* NGR234, *Azorhizobium caulinodans*, *Bradyrhizobium japonicum*, *Bradyrhizobium elkanii*, *Bradyrhizobium liaonginense*, *Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis*, *Paraglomus* spp., other species in the division Glomeromycota, and any combination thereof.

75. The genetically altered plant or part thereof of embodiment 73 or embodiment 74, wherein the second modified receptor polypeptide binds one or more Nod factors with higher affinity than a second unmodified receptor polypeptide.

76. The genetically altered plant or part thereof of any one of embodiments 73-75, wherein the second modified receptor polypeptide binds one or more Nod factors with higher selectivity than a second unmodified receptor polypeptide. 77. The genetically altered plant or part thereof of any one of embodiments 73-76, wherein the second modified receptor polypeptide binds one or more Nod factors with altered specificity as compared to the second unmodified receptor polypeptide.

78. The genetically altered plant or part thereof of any one of embodiments 60-77, wherein the modified LysM receptor polypeptides are localized to a plant cell plasma membrane.

79. The genetically altered plant or part thereof of embodiment 78, wherein the plant cell is a root cell.

80. The genetically altered plant or part thereof of embodiment 79, wherein the root cell is a root epidermal cell.

81. The genetically altered plant or part thereof of any one of embodiments 60-80, wherein the modified LysM receptor polypeptides are expressed in a developing plant root system.

82. The genetically altered plant or part thereof of any one of embodiments 60-81, comprising a first nucleic acid sequence encoding the first modified plant LysM receptor polypeptide and a second nucleic acid sequence encoding the second modified plant LysM receptor polypeptide, wherein the first nucleic acid sequence is operably linked to a first promoter, and wherein the second nucleic acid sequence is operably linked to a second promoter.

83. The genetically altered plant or part thereof of embodiment 82, wherein the first and second promoters are root specific promoters, constitutive promoters, or a combination thereof.

84. The genetically altered plant or part thereof of embodiment 82 or embodiment 83, wherein the first and/or second promoters are selected from the group consisting of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, and an *Arabidopsis* pCO2 promoter.

85. The genetically altered plant or part thereof of embodiment 83 or embodiment 84, wherein the first and/or second promoters are selected from the group consisting of a CaMV35S promoter, a derivative of the CaMV35S promoter, a maize ubiquitin promoter, a trefoil promoter, a vein mosaic cassava virus promoter, and an *Arabidopsis* UBQ10 promoter.

86. The genetically altered plant or part thereof of any one of embodiments 48-85, wherein the plant is selected from the group consisting of cassava, corn, cowpea, rice, barley, wheat, *Trema* spp., apple, pear, plum, apricot, peach, almond, walnut, strawberry, raspberry, blackberry, red currant, black currant, melon, cucumber, pumpkin, squash, grape, bean, soybean, pea, chickpea, cowpea, pigeon pea, lentil, Bambara groundnut, lupin, pulses, *Medicago* spp., Lotus spp., forage legumes, indigo, legume trees, and hemp.

87. The genetically altered plant part of the plant of any one of embodiments 48-85, wherein the plant part is a leaf, a stem, a root, a root primordia, a flower, a seed, a fruit, a kernel, a grain, a cell, or a portion thereof.

88. The genetically altered plant part of embodiment 87, wherein the part is a fruit, a kernel, or a grain.

89. A pollen grain or an ovule of the genetically altered plant of any one of embodiments 48-85.

90. A protoplast produced from the plant of any one of embodiments 48-85.

91. A tissue culture produced from protoplasts or cells from the plant of any one of embodiments 48-85, wherein the cells or protoplasts are produced from a plant part selected from the group consisting of leaf, anther, pistil, stem, petiole, root, root primordia, root tip, fruit, seed, flower, cotyledon, hypocotyl, embryo, and meristematic cell.

92. A method of producing the genetically altered plant of any one of embodiments 48-59 and 86-91, comprising introducing a genetic alteration to the plant comprising a nucleic acid sequence encoding the modified LysM receptor polypeptide.

93. The method of embodiment 92, wherein the nucleic acid sequence is operably linked to a promoter.

94. The method of embodiment 93, wherein the promoter is a root specific promoter, a constitutive promoters, or a combination thereof.

95. The method of embodiment 93 or embodiment 94, wherein the promoter is selected from the group consisting of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, and an *Arabidopsis* pCO2 promoter.

96. The method of embodiment 94 or embodiment 95, wherein the promoter is selected from the group consisting of a CaMV35S promoter, a derivative of the CaMV35S promoter, a maize ubiquitin promoter, a trefoil promoter, a vein mosaic cassava virus promoter, and an *Arabidopsis* UBQ10 promoter.

97. The method of any one of embodiments 92-96, wherein the nucleic acid sequence is inserted into the genome of the plant so that the nucleic acid sequence is operably linked to an endogenous promoter.

98. The method of embodiment 97, wherein the endogenous promoter is a root specific promoter.

99. A method of producing the genetically altered plant of any one of embodiments 60-91, comprising introducing a genetic alteration to the plant comprising a first nucleic acid sequence encoding the first modified LysM receptor polypeptide and introducing a genetic alteration to the plant comprising a second nucleic acid sequence encoding the second modified LysM receptor polypeptide.

100. The method of embodiment 99, wherein the first nucleic acid sequence is operably linked to a first promoter, and wherein the second nucleic acid sequence is operably linked to a second promoter.

101. The method of embodiment 100, wherein the first and second promoters are root specific promoters, constitutive promoters, or a combination thereof.

102. The method of embodiment 100 or embodiment 101, wherein the first and/or second promoters are selected from the group consisting of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, and an *Arabidopsis* pCO2 promoter.

103. The method of embodiment 100 or embodiment 101, wherein the first and/or second promoters are selected from the group consisting of a CaMV35S promoter, a derivative of the CaMV35S promoter, a maize ubiquitin promoter, a trefoil promoter, a vein mosaic cassava virus promoter, and an *Arabidopsis* UBQ10 promoter.

104. The method of any one of embodiments 99-103, wherein the first nucleic acid sequence is inserted into the genome of the plant so that the first nucleic acid sequence is operably linked to a first endogenous promoter, and/or wherein the second nucleic acid sequence is inserted into the genome of the plant so that the second nucleic acid sequence is operably linked to a second endogenous promoter.

105. The method of embodiment 104, wherein the first and second endogenous promoters are root specific promoters.

106. A method of producing the genetically altered plant of any one of embodiments 50-93, comprising genetically editing a gene encoding an endogenous LysM receptor polypeptide in the plant to comprise the modified LysM1 domain.

107. The method of embodiment 106, wherein the endogenous LysM receptor polypeptide is an endogenous chitin LysM receptor polypeptide or an endogenous Nod factor LysM receptor polypeptide.

108. The method of embodiment 106 or embodiment 107, wherein the modified LysM receptor polypeptide was generated by:
(a) providing a heterologous Nod factor LysM receptor polypeptide model comprising a structural model, a molecular model, a surface characteristics model, and/or an electrostatic potential model of a LysM1 domain, a LysM2 domain, a LysM3 domain, any combination thereof, or the ectodomain of the heterologous Nod factor LysM receptor polypeptide having selectivity for a beneficial nitrogen-fixing bacteria or a beneficial mycorrhizal fungus and an unmodified endogenous LysM receptor polypeptide;
(b) identifying a first motif, a second motif, and/or optionally a fifth motif for modification in the unmodified endogenous LysM receptor polypeptide by comparing a LysM1 domain of the unmodified endogenous LysM receptor polypeptide with the corresponding LysM1 domain of the heterologous Nod factor LysM receptor polypeptide model;
(c) modifying the first motif by substituting at least one, at least two, or at least three amino acid residues in the first motif with corresponding amino acid residues that are different in a third motif, modifying the second motif by substituting at least one, at least two, or at least three amino acid residues in the second motif with corresponding amino acid residues that are different in a fourth motif, and/or optionally modifying the fifth motif by substituting at least one, at least two, or at least three amino acid residues in the fifth motif with corresponding amino acid residues that are different in a sixth motif, wherein the third motif, the fourth motif, and the sixth motif have different affinities, selectivities, and/or specificities for oligosaccharides than the first motif, the second motif, and the fifth motif; and
(d) generating the modified endogenous LysM receptor polypeptide wherein the first motif, the second motif, and/or optionally the fifth motif have been substituted with corresponding amino acid residues from the third motif, the fourth motif, and/or optionally the sixth motif.

109. A method of cultivating the genetically altered plant of any one of embodiments 48-91, comprising the steps of:
(a) planting a genetically altered seedling, a genetically altered plantlet, a genetically altered cutting, a genetically altered tuber, a genetically altered root, or a genetically altered seed in soil to produce the genetically altered plant or grafting the genetically altered seedling, the genetically altered plantlet, or the genetically altered cutting to a root stock or a second plant grown in soil to produce the genetically altered plant;
(b) cultivating the plant to produce harvestable seed, harvestable leaves, harvestable roots, harvestable cuttings, harvestable wood, harvestable fruit, harvestable kernels, harvestable tubers, and/or harvestable grain; and
(c) harvesting the harvestable seed, harvestable leaves, harvestable roots, harvestable cuttings, harvestable wood, harvestable fruit, harvestable kernels, harvestable tubers, and/or harvestable grain.

110. An isolated DNA molecule encoding a modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide.

111. The isolated DNA molecule of embodiment 110, wherein the first motif corresponds to amino acids 42-48 of SEQ ID NO: 162 when the receptor polypeptide amino acid sequence is aligned to SEQ ID NO: 162 and the second motif corresponds to amino acids 75-80 of SEQ ID NO: 162 when the receptor polypeptide amino acid sequence is aligned to SEQ ID NO: 162.

112. The isolated DNA molecule of embodiment 110, wherein the first motif corresponds to amino acids 44-49 of SEQ ID NO: 164 when the receptor polypeptide amino acid sequence is aligned to SEQ ID NO: 164 and the second motif corresponds to amino acids 76-81 of SEQ ID NO: 164 when the receptor polypeptide amino acid sequence is aligned to SEQ ID NO: 164.

113. The isolated DNA molecule of any one of embodiments 110-112, wherein the first motif is modified by substituting at least one, at least two, or at least three amino acid residues in the first motif with corresponding amino acid residues that are different in a third motif, and/or wherein the second motif is modified by substituting at least one, at least two, or at least three amino acid residues in the second motif with corresponding amino acid residues that are different in a fourth motif.

114. The isolated DNA molecule of any one of embodiments 110-112, wherein the first motif is modified by substituting the first motif with a third motif, and/or wherein the second motif is modified by substituting the second motif with a fourth motif.

115. The isolated DNA molecule of embodiment 113 or embodiment 114, wherein the third motif and the fourth motif have different affinities, selectivities, and/or specificities for oligosaccharides than the first motif and the second motif.

116. The isolated DNA molecule of embodiment 115, wherein the third motif and the fourth motif have different affinities for oligosaccharides than the first motif and the second motif.

117. The isolated DNA molecule of embodiment 115, wherein the third motif and the fourth motif have different selectivities for oligosaccharides than the first motif and the second motif.

118. The isolated DNA molecule of embodiment 115, wherein the third motif and the fourth motif have different specificities for oligosaccharides than the first motif and the second motif.

119. The isolated DNA molecule of any one of embodiments 113-118, wherein the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM polypeptide amino acid sequence is aligned to SEQ ID NO: 162 and the fourth motif corresponds to amino acids 75-80 of SEQ ID NO: 162 when the second plant LysM polypeptide amino acid sequence is aligned to SEQ ID NO: 162.

120. The isolated DNA molecule of any one of embodiments 113-118, wherein the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM polypeptide amino acid sequence is aligned to SEQ ID NO: 164 and the fourth motif corresponds to amino acids 76-81 of SEQ ID NO: 164 when the second plant LysM polypeptide amino acid sequence is aligned to SEQ ID NO: 164.

121. The isolated DNA molecule of embodiment 119 or embodiment 120, wherein at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

122. The isolated DNA molecule of any one of embodiments 110-121, wherein the first motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341.

123. The isolated DNA molecule of any one of embodiments 110-122, wherein the second motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142.

124. The isolated DNA molecule of any one of embodiments 113-123, wherein the third motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and wherein the first motif and the third motif are different.

125. The isolated DNA molecule of any one of embodiments 113-124, wherein the fourth motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142, and wherein the second motif and the fourth motif are different.

126. The isolated DNA molecule of any one of embodiments 110-125, further comprising a fifth motif in the LysM1 domain, wherein the fifth motif is modified.

127. The isolated DNA molecule of embodiment 126, wherein the fifth motif corresponds to amino acids 56-65 of SEQ ID NO: 162 when the receptor polypeptide amino acid sequence is aligned to SEQ ID NO: 162.

128. The isolated DNA molecule of embodiment 126 or embodiment 127, wherein the fifth motif is modified by substituting at least one, at least two, or at least three amino acid residues in the fifth motif with corresponding amino acid residues that are different in a sixth motif.

129. The isolated DNA molecule of any one of embodiments 126-128, wherein the fifth motif is substituted with a sixth motif.

130. The isolated DNA molecule of embodiment 128 or embodiment 129, wherein the sixth motif has a different specificity for oligosaccharides than the fifth motif.

131. The isolated DNA molecule of any one of embodiments 128-130, wherein the sixth motif is from a second plant LysM receptor polypeptide having the different specificity for oligosaccharides and the sixth motif corresponds to amino acids 56-65 of SEQ ID NO: 162 when the second plant LysM polypeptide amino acid sequence is aligned to SEQ ID NO: 162.

132. The isolated DNA molecule of any one of embodiments 126-131, wherein the fifth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

133. The isolated DNA molecule of any one of embodiments 128-132, wherein the sixth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120, and wherein the fifth motif and the sixth motif are different.

134. The isolated DNA molecule of any one of embodiments 110-133, wherein the modified receptor polypeptide binds one or more Nod factors produced by nitrogen-fixing bacteria or by mycorrhizal fungi.

135. The isolated DNA molecule of embodiment 134, wherein the one or more Nod factors are produced by nitrogen-fixing bacteria selected from the group consisting of Mesorhizobium loti, Mesorhizobium huakuii, Mesorhizobium mediterraneum, Mesorhizobium ciceri, Mesorhizobium spp., Rhizobium mongolense, Rhizobium tropici, Rhizobium etli phaseoli, Rhizobium giardinii, Rhizobium leguminosarum optionally R. leguminosarum trifolii, R. leguminosarum viciae, and R. leguminosarum phaseoli, Burkholderiales optionally symbionts of Mimosa, Sinorhizobium meliloti, Sinorhizobium medicae, Sinorhizobium fredii, Sinorhizobium NGR234, Azorhizobium caulinodans, Bradyrhizobium japonicum, Bradyrhizobium elkanii, Bradyrhizobium liaonginense, Frankia spp., and any combination thereof, or by mycorrhizal fungi selected from the group consisting of Acaulosporaceae spp., Diversisporaceae spp., Gigasporaceae spp., Pacisporaceae spp., Funneliformis spp., Glomus spp., Rhizophagus spp., Sclerocystis spp., Septoglomus spp., Claroideoglomus spp., Ambispora spp., Archaeospora spp., Geosiphon pyriformis, Paraglomus spp., other species in the division Glomeromycota, and any combination thereof.

136. The isolated DNA molecule of embodiment 134 or embodiment 135, wherein the modified receptor polypeptide binds one or more Nod factors with higher affinity than an unmodified receptor polypeptide.

137. The isolated DNA molecule of any one of embodiments 134-136, wherein the modified receptor polypeptide binds one or more Nod factors with higher selectivity than an unmodified receptor polypeptide.

138. The isolated DNA molecule of any one of embodiments 134-137, wherein the modified receptor polypeptide binds one or more Nod factors with altered specificity as compared to an unmodified receptor polypeptide.

139. The isolated DNA molecule of any one of embodiments 110-138, further comprising a LysM2 domain modified to comprise a hydrophobic patch on the surface of the LysM2 domain, wherein the modified plant LysM receptor polypeptide has enhanced affinity, selectivity, and/or specificity for one or more Nod factors as compared to the unmodified plant LysM receptor polypeptide.

140. The isolated DNA molecule of embodiment 139, wherein the hydrophobic patch is within 30 Å, 20 Å, 10 Å, 7.5 Å, 5 Å, 4 Å, 3 Å, 2 Å, 1.5 Å, or 1 Å of a chitin binding motif.

141. The isolated DNA molecule of embodiment 139 or embodiment 140, wherein the LysM2 domain comprises SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

142. The isolated DNA molecule of any one of embodiments 139-141, wherein the hydrophobic patch was generated by deleting at least one non-hydrophobic amino acid residue, substituting at least one amino acid residue with a more hydrophobic amino acid, or combinations thereof.

143. The isolated DNA molecule of embodiment 142, wherein the at least one amino acid was identified by an amino acid sequence alignment with a LysM2 domain from a LysM high affinity Nod factor receptor that naturally has a hydrophobic patch that interacts with a Nod factor.

144. The isolated DNA molecule of embodiment 143, wherein the LysM2 domain from a LysM high affinity Nod factor receptor comprises SEQ ID NO: 271, SEQ ID NO: 272, SEQ ID NO: 273, SEQ ID NO: 274, SEQ ID NO: 275, SEQ ID NO: 276, or SEQ ID NO: 277.

145. The isolated DNA molecule of embodiment 143 or embodiment 144, wherein the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

146. The isolated DNA molecule of any one of embodiments 142-145, wherein the at least one amino acid was identified by structural modeling to identify a region in LysM2 where the hydrophobic patch can be engineered.

147. The isolated DNA molecule of embodiment 146, wherein the structural modeling used the unmodified plant LysM amino acid sequence and a LysM domain three dimensional structure that has a known hydrophobic patch.

148. The isolated DNA molecule of embodiment 147, wherein the LysM domain three dimensional structure is a *Medicago truncatula* NFP ectodomain.

149. The isolated DNA molecule of embodiment 147 or embodiment 148, wherein the known hydrophobic patch amino acid residues of the LysM domain three dimensional structure are or correspond to L147, L151, L152, L154, T156, K157 and V158 of the *Medicago truncatula* NFP ectodomain.

150. The isolated DNA molecule of embodiment 149, wherein the alpha carbon of at least one amino acid was within 3 Å of an alpha carbon of a known hydrophobic patch amino acid residue in the structural alignment.

151. The isolated DNA molecule of any one of embodiments 146-150, wherein the structural modeling was performed using SWISS-MODEL, PDB2PQR, APBS, PyMol, and APBS tools 2.1.

152. The isolated DNA molecule of any one of embodiments 139-151, wherein the modified receptor polypeptide binds one or more Nod factors produced by nitrogen-fixing bacteria or by mycorrhizal fungi.

153. The isolated DNA molecule of embodiment 152, wherein the one or more Nod factors is produced by nitrogen-fixing bacteria selected from the group consisting of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

154. The isolated DNA molecule of embodiment 152 or embodiment 153, wherein the modified receptor polypeptide binds the one or more Nod factors with higher affinity than an unmodified receptor polypeptide.

155. The isolated DNA molecule of any one of embodiments 152-154, wherein the modified receptor polypeptide binds the one or more Nod factors with higher selectivity than an unmodified receptor polypeptide.

156. The isolated DNA molecule of any one of embodiments 152-156, wherein the modified receptor polypeptide binds the one or more Nod factors with altered specificity as compared to an unmodified receptor polypeptide.

157. A method of producing a genetically altered plant comprising introducing a genetic alteration to the plant comprising a DNA molecule encoding a modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide, wherein the encoded modified LysM receptor polypeptide has higher affinity, higher selectivity, and/ or altered specificity for one or more Nod factors produced by nitrogen-fixing bacteria or by mycorrhizal fungi than an unmodified LysM receptor polypeptide and the expression of the modified LysM receptor polypeptide allows the plant or part thereof to recognize one or more Nod factors with high affinity, high selectivity, and/or altered specificity.

158. A method of producing a genetically altered plant comprising genetically editing a gene encoding an endogenous LysM receptor polypeptide in the plant to comprise a DNA molecule encoding a modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide.

159. The method of embodiment 157 or embodiment 158, wherein the plant is selected from the group consisting of cassava, corn, cowpea, rice, barley, wheat, *Trema* spp., apple, pear, plum, apricot, peach, almond, walnut, strawberry, raspberry, blackberry, red currant, black currant, melon, cucumber, pumpkin, squash, grape, bean, soybean, pea, chickpea, cowpea, pigeon pea, lentil, Bambara groundnut, lupin, pulses, *Medicago* spp., *Lotus* spp., forage legumes, indigo, legume trees, and hemp.

160. The method of any one of embodiments 157-159, wherein the first motif corresponds to amino acids 42-48 of SEQ ID NO: 162 when the receptor polypeptide amino acid sequence is aligned to SEQ ID NO: 162 and the second motif corresponds to amino acids 75-80 of SEQ ID NO: 162 when the receptor polypeptide amino acid sequence is aligned to SEQ ID NO: 162.

161. The method of any one of embodiments 157-159, wherein the first motif corresponds to amino acids 44-49 of SEQ ID NO: 164 when the receptor polypeptide amino acid sequence is aligned to SEQ ID NO: 164 and the second motif corresponds to amino acids 76-81 of SEQ ID NO: 164 when the receptor polypeptide amino acid sequence is aligned to SEQ ID NO: 164.

162. The method of any one of embodiments 157-161, wherein the first motif is modified by substituting at least one, at least two, or at least three amino acid residues in the first motif with corresponding amino acid residues that are different in a third motif; wherein the second motif is modified by substituting at least one, at least two, or at least three amino acid residues in the second motif with corresponding amino acid residues that are different in a fourth motif.

163. The method of any one of embodiments 157-161, wherein the first motif is modified by substituting the first motif with a third motif, and/or wherein the second motif is modified by substituting the second motif with a fourth motif.

164. The method of embodiment 162 or embodiment 163, wherein the third motif and the fourth motif have different affinities, selectivities, and/or specificities for oligosaccharides than the first motif and the second motif.

165. The method of embodiment 164, wherein the third motif and the fourth motif have different affinities for oligosaccharides than the first motif and the second motif.

166. The method of embodiment 164, wherein the third motif and the fourth motif have different selectivities for oligosaccharides than the first motif and the second motif.

167. The method of embodiment 164, wherein the third motif and the fourth motif have different specificities for oligosaccharides than the first motif and the second motif.

168. The method of any one of embodiments 164-167, wherein the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM polypeptide amino acid sequence is aligned to SEQ ID NO: 162 and the fourth motif corresponds to amino acids 75-80 of SEQ ID NO: 162 when the second plant LysM polypeptide amino acid sequence is aligned to SEQ ID NO: 162.

169. The method of any one of embodiments 164-167, wherein the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM polypeptide amino acid sequence is aligned to SEQ ID NO: 164 and the fourth motif corresponds to amino acids 76-81 of SEQ ID NO: 164 when the second plant LysM polypeptide amino acid sequence is aligned to SEQ ID NO: 164.

170. The method of embodiment 168 or embodiment 169, wherein at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

171. The method of any one of embodiments 157-170, wherein the first motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341.

172. The method of any one of embodiments 157-171, wherein the second motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142.

173. The method of any one of embodiments 164-172, wherein the third motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and wherein the first motif and the third motif are different.

174. The method of any one of embodiments 163-173, wherein the fourth motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45,
SEQ ID NO: 46, SEQ ID NO: 47, SEQ ID NO: 48,
SEQ ID NO: 49, SEQ ID NO: 50, SEQ ID NO: 51,
SEQ ID NO: 52, SEQ ID NO: 56, SEQ ID NO: 57,
SEQ ID NO: 58, SEQ ID NO: 69, SEQ ID NO: 70,
SEQ ID NO: 71, SEQ ID NO: 72, SEQ ID NO: 73,
SEQ ID NO: 74, SEQ ID NO: 75, SEQ ID NO: 76,
SEQ ID NO: 77, SEQ ID NO: 78, SEQ ID NO: 121,
SEQ ID NO: 122, SEQ ID NO: 123, SEQ ID NO: 124,
SEQ ID NO: 125, SEQ ID NO: 126, SEQ ID NO: 127,
SEQ ID NO: 128, SEQ ID NO: 129, SEQ ID NO: 130,
SEQ ID NO: 131, SEQ ID NO: 132, SEQ ID NO: 133,
SEQ ID NO: 134, SEQ ID NO: 135, SEQ ID NO: 136,
SEQ ID NO: 137, SEQ ID NO: 138, SEQ ID NO: 139,
SEQ ID NO: 140, SEQ ID NO: 141, or SEQ ID NO:
142, and wherein the second motif and the fourth motif
are different.

175. The method of any one of embodiments 157-174,
wherein the modified plant LysM receptor polypeptide
further comprises a fifth motif in the LysM1 domain,
wherein the fifth motif is modified.

176. The method of embodiment 175, wherein the fifth
motif corresponds to amino acids 56-65 of SEQ ID NO:
162 when the receptor polypeptide amino acid
sequence is aligned to SEQ ID NO: 162.

177. The method of embodiment 175 or embodiment 176,
wherein the fifth motif is modified by substituting at
least one, at least two, or at least three amino acid
residues in the fifth motif with corresponding amino
acid residues that are different in a sixth motif.

178. The method of embodiment 177, wherein the fifth
motif is substituted with a sixth motif.

179. The method of embodiment 177 or embodiment 178,
wherein the sixth motif has a different specificity for
oligosaccharides than the fifth motif.

180. The method of any one of embodiments 177-179,
wherein the sixth motif is from a second plant LysM
receptor polypeptide having the different specificity for
oligosaccharides and the sixth motif corresponds to
amino acids 56-65 of SEQ ID NO: 162 when the
second plant LysM polypeptide amino acid sequence is
aligned to SEQ ID NO: 162.

181. The method of any one of embodiments 175-180,
wherein the fifth motif comprises SEQ ID NO: 100,
SEQ ID NO: 101, SEQ ID NO: 102, SEQ ID NO: 103,
SEQ ID NO: 104, SEQ ID NO: 105, SEQ ID NO: 106,
SEQ ID NO: 107, SEQ ID NO: 108, SEQ ID NO: 109,
SEQ ID NO: 110, SEQ ID NO: 111, SEQ ID NO: 112,
SEQ ID NO: 113, SEQ ID NO: 114, SEQ ID NO: 115,
SEQ ID NO: 116, SEQ ID NO: 117, SEQ ID NO: 118,
SEQ ID NO: 119, or SEQ ID NO: 120.

182. The method of any one of embodiment 177-181,
wherein the sixth motif comprises SEQ ID NO: 100,
SEQ ID NO: 101, SEQ ID NO: 102, SEQ ID NO: 103,
SEQ ID NO: 104, SEQ ID NO: 105, SEQ ID NO: 106,
SEQ ID NO: 107, SEQ ID NO: 108, SEQ ID NO: 109,
SEQ ID NO: 110, SEQ ID NO: 111, SEQ ID NO: 112,
SEQ ID NO: 113, SEQ ID NO: 114, SEQ ID NO: 115,
SEQ ID NO: 116, SEQ ID NO: 117, SEQ ID NO: 118,
SEQ ID NO: 119, or SEQ ID NO: 120, and wherein the
fifth motif and the sixth motif are different.

183. The method of any one of embodiments 157-182,
wherein the modified receptor polypeptide binds one or
more Nod factors produced by nitrogen-fixing bacteria
or by mycorrhizal fungi with higher affinity, higher
selectivity, and/or altered specificity than an unmodi-
fied receptor polypeptide.

184. The method of embodiment 183, wherein the one or
more Nod factors are produced by nitrogen-fixing
bacteria selected from the group consisting of
*Mesorhizobium loti, Mesorhizobium huakuii,
Mesorhizobium mediterraneum, Mesorhizobium ciceri,
Mesorhizobium* spp., *Rhizobium mongolense, Rhizo-
bium tropici, Rhizobium etli phaseoli, Rhizobium gia-
rdinii, Rhizobium leguminosarum* optionally *R. legu-
minosarum trifolii, R. leguminosarum viciae,* and *R.
leguminosarum phaseoli,* Burkholderiales optionally
symbionts of *Mimosa, Sinorhizobium meliloti,
Sinorhizobium medicae, Sinorhizobium fredii,
Sinorhizobium* NGR234, *Azorhizobium caulinodans,
Bradyrhizobium japonicum, Bradyrhizobium elkanii,
Bradyrhizobium liaonginense, Frankia* spp., and any
combination thereof, or by mycorrhizal fungi selected
from the group consisting of *Acaulosporaceae* spp.,
*Diversisporaceae* spp., *Gigasporaceae* spp., *Pacispo-
raceae* spp., *Funneliformis* spp., *Glomus* spp.,
*Rhizophagus* spp., *Sclerocystis* spp., *Septoglomus* spp.,
*Claroideoglomus* spp., *Ambispora* spp., *Archaeospora*
spp., *Geosiphon pyriformis, Paraglomus* spp., other
species in the division Glomeromycota, and any com-
bination thereof.

185. The method of embodiment 183 or embodiment 184,
wherein the modified LysM receptor polypeptide is
localized to a plant cell plasma membrane.

186. The method of any one of embodiments 183-185,
wherein the modified receptor polypeptide binds one or
more Nod factors with higher affinity than an unmodi-
fied receptor polypeptide.

187. The method of any one of embodiments 183-186,
wherein the modified receptor polypeptide binds one or
more Nod factors with higher selectivity than an
unmodified receptor polypeptide.

188. The method of any one of embodiments 183-187,
wherein the modified receptor polypeptide binds one or
more Nod factors with altered specificity as compared
to an unmodified receptor polypeptide.

189. The method of any one of embodiments 157-188,
wherein the modified plant LysM receptor polypeptide
further comprises a LysM2 domain modified to com-
prise a hydrophobic patch on the surface of the LysM2
domain, wherein the modified plant LysM receptor
polypeptide has enhanced affinity, selectivity, and/or
specificity for one or more Nod factors as compared to
the unmodified plant LysM receptor polypeptide.

190. The method of embodiment 189, wherein the hydro-
phobic patch is within 30 Å, 20 Å, 10 Å, 7.5 Å, 5 Å,
4 Å, 3 Å, 2 Å, 1.5 Å, or 1 Å of a chitin binding motif.

191. The method of embodiment 189 or embodiment 190,
wherein the LysM2 domain comprises SEQ ID NO:
278, SEQ ID NO: 279, SEQ ID NO: 280, SEQ ID NO:
281, SEQ ID NO: 282, SEQ ID NO: 283, SEQ ID NO:
284, SEQ ID NO: 285, SEQ ID NO: 286, SEQ ID NO:
287, SEQ ID NO: 288, SEQ ID NO: 289, SEQ ID NO:
290, SEQ ID NO: 291, SEQ ID NO: 292, SEQ ID NO:
293, SEQ ID NO: 294, SEQ ID NO: 295, SEQ ID NO:
296, SEQ ID NO: 297, SEQ ID NO: 298, SEQ ID NO:
299, or SEQ ID NO: 300.

192. The method of any one of embodiments 189-191,
wherein the hydrophobic patch was generated by delet-
ing at least one non-hydrophobic amino acid residue,
substituting at least one amino acid residue with a more
hydrophobic amino acid, or combinations thereof.

193. The method of embodiment 192, wherein the at least
one amino acid was identified by an amino acid sequence alignment with a LysM2 domain from a LysM high affinity Nod factor receptor that naturally has a hydrophobic patch that interacts with a Nod factor.

194. The method of embodiment 193, wherein the LysM2 domain from a LysM high affinity Nod factor receptor comprises SEQ ID NO: 271, SEQ ID NO: 272, SEQ ID NO: 273, SEQ ID NO: 274, SEQ ID NO: 275, SEQ ID NO: 276, or SEQ ID NO: 277.

195. The method of embodiment 193 or embodiment 194, wherein the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

196. The method of any one of embodiments 193-195, wherein the at least one amino acid was identified by structural modeling to identify a region in LysM2 where the hydrophobic patch can be engineered.

197. The method of embodiment 196, wherein the structural modeling used the unmodified plant LysM amino acid sequence and a LysM domain three dimensional structure that has a known hydrophobic patch.

198. The method of embodiment 197, wherein the LysM domain three dimensional structure is a *Medicago truncatula* NFP ectodomain.

199. The method of embodiment 197 or embodiment 198, wherein the known hydrophobic patch amino acid residues of the LysM domain three dimensional structure are or correspond to L147, L151, L152, L154, T156, K157 and V158 of the *Medicago truncatula* NFP ectodomain.

200. The method of embodiment 199, wherein the alpha carbon of at least one amino acid was within 3 Å of an alpha carbon of a known hydrophobic patch amino acid residue in the structural alignment.

201. The method of any one of embodiments 196-200, wherein the structural modeling was performed using SWISS-MODEL, PDB2PQR, APBS, PyMol, and APBS tools 2.1.

202. The method of any one of embodiments 189-201, wherein the modified receptor polypeptide binds one or more Nod factors produced by nitrogen-fixing bacteria or by mycorrhizal fungi.

203. The method of embodiment 202, wherein the one or more Nod factors is produced by nitrogen-fixing bacteria selected from the group consisting of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium lia-onginense, Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

204. The method of embodiment 202 or embodiment 203, wherein the modified receptor polypeptide binds the one or more Nod factors with higher affinity than an unmodified receptor polypeptide.

205. The method of any one of embodiments 202-204, wherein the modified receptor polypeptide binds the one or more Nod factors with higher selectivity than an unmodified receptor polypeptide.

206. The method of any one of embodiments 202-205, wherein the modified receptor polypeptide binds the one or more Nod factors with altered specificity as compared to an unmodified receptor polypeptide.

207. A genetically altered plant or part thereof produced by the method of any one of embodiments 157-206.

208. The genetically altered plant or part thereof of embodiment 207, wherein the modified LysM receptor polypeptide is localized to a plant cell plasma membrane.

209. The genetically altered plant or part thereof of embodiment 208, wherein the plant cell is a root cell.

210. The genetically altered plant or part thereof of embodiment 209, wherein the root cell is a root epidermal cell.

211. The genetically altered plant or part thereof of any one of embodiments 207-210, wherein the modified LysM receptor polypeptide is expressed in a developing plant root system.

212. The genetically altered plant part of any one of embodiments 207-211, wherein the plant part is a leaf, a stem, a root, a root primordia, a flower, a seed, a fruit, a kernel, a grain, a cell, or a portion thereof.

213. A pollen grain or an ovule of the genetically altered plant of any one of embodiments 207-211.

214. A protoplast produced from the genetically altered plant of any one of embodiments 207-211.

215. A tissue culture produced from protoplasts or cells from the plant of any one of embodiments 207-211, wherein the cells or protoplasts are produced from a plant part selected from the group consisting of leaf, anther, pistil, stem, petiole, root, root primordia, root tip, fruit, seed, flower, cotyledon, hypocotyl, embryo, and meristematic cell.

216. A method of making a modified plant LysM receptor polypeptide comprising generating a nucleic acid encoding a wild-type plant LysM receptor polypeptide that comprises a DNA molecule encoding a modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide, and wherein the encoded modified plant LysM receptor polypeptide has higher affinity, higher selectivity, and/or altered specificity for one or more Nod factors produced by nitrogen-fixing bacteria or by mycorrhizal fungi than an unmodified plant LysM receptor polypeptide.

217. The method of embodiment 216, wherein the first motif corresponds to amino acids 42-48 of SEQ ID NO: 162 when the plant LysM receptor polypeptide amino acid sequence is aligned to SEQ ID NO: 162 and the second motif corresponds to amino acids 75-80 of SEQ ID NO: 162 when the plant LysM receptor polypeptide amino acid sequence is aligned to SEQ ID NO: 162.

218. The method of embodiment 216, wherein the first motif corresponds to amino acids 44-49 of SEQ ID NO: 164 when the plant LysM receptor polypeptide amino acid sequence is aligned to SEQ ID NO: 164 and the second motif corresponds to amino acids 76-81 of SEQ ID NO: 164 when the plant LysM receptor polypeptide amino acid sequence is aligned to SEQ ID NO: 164.

219. The method of any one of embodiments 216-218, wherein the first motif is modified by substituting at least one, at least two, or at least three amino acid residues in the first motif with corresponding amino acid residues that are different in a third motif; wherein the second motif is modified by substituting at least one, at least two, or at least three amino acid residues in the second motif with corresponding amino acid residues that are different in a fourth motif.

220. The method of any one of embodiments 216-218, wherein the first motif is modified by substituting the first motif with a third motif, and/or wherein the second motif is modified by substituting the second motif with a fourth motif.

221. The method of embodiment 219 or embodiment 220, wherein the third motif and the fourth motif have different affinities, selectivities, and/or specificities for oligosaccharides than the first motif and the second motif.

222. The method of embodiment 221, wherein the third motif and the fourth motif have different affinities for oligosaccharides than the first motif and the second motif.

223. The method of embodiment 221, wherein the third motif and the fourth motif have different selectivities for oligosaccharides than the first motif and the second motif.

224. The method of embodiment 221, wherein the third motif and the fourth motif have different specificities for oligosaccharides than the first motif and the second motif.

225. The method of any one of embodiments 221-224, wherein the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM receptor polypeptide amino acid sequence is aligned to SEQ ID NO: 162 and the fourth motif corresponds to amino acids 75-80 of SEQ ID NO: 162 when the second plant LysM receptor polypeptide amino acid sequence is aligned to SEQ ID NO: 162.

226. The method of any one of embodiments 221-224, wherein the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM receptor polypeptide amino acid sequence is aligned to SEQ ID NO: 164 and the fourth motif corresponds to amino acids 76-81 of SEQ ID NO: 164 when the second plant LysM receptor polypeptide amino acid sequence is aligned to SEQ ID NO: 164.

227. The method of embodiment 225 or embodiment 226, wherein at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

228. The method of any one of embodiments 216-227, wherein the first motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341.

229. The method of any one of embodiments 216-228, wherein the second motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142.

230. The method of any one of embodiments 219-229, wherein the third motif comprises SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and wherein the first motif and the third motif are different.

231. The method of any one of embodiments 219-230, wherein the fourth motif comprises SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142, and wherein the second motif and the fourth motif are different.

232. The method of any one of embodiments 216-231, wherein the modified plant LysM receptor polypeptide further comprises a fifth motif in the LysM1 domain, wherein the fifth motif is modified.

233. The method of embodiment 232, wherein the fifth motif corresponds to amino acids 56-65 of SEQ ID NO: 162 when the plant LysM receptor polypeptide amino acid sequence is aligned to SEQ ID NO: 162.

234. The method of embodiment 232 or embodiment 233, wherein the fifth motif is modified by substituting at least one, at least two, or at least three amino acid residues in the fifth motif with corresponding amino acid residues that are different in a sixth motif.

235. The method of embodiment 234, wherein the fifth motif is substituted with a sixth motif.

236. The method of embodiment 234 or embodiment 235, wherein the sixth motif has a different specificity for oligosaccharides than the fifth motif.

237. The method of any one of embodiments 234-236, wherein the sixth motif is from a second plant LysM receptor polypeptide having the different specificity for oligosaccharides and the sixth motif corresponds to amino acids 56-65 of SEQ ID NO: 162 when the second plant LysM polypeptide amino acid sequence is aligned to SEQ ID NO: 162.

238. The method of any one of embodiments 232-237, wherein the fifth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

239. The method of any one of embodiment 232-238, wherein the sixth motif comprises SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120, and wherein the fifth motif and the sixth motif are different.

240. The method of any one of embodiments 216-239, wherein the modified plant LysM receptor polypeptide binds one or more Nod factors produced by nitrogen-fixing bacteria or by mycorrhizal fungi with higher affinity, higher selectivity, and/or altered specificity than an unmodified plant LysM receptor polypeptide.

241. The method of embodiment 240, wherein the one or more Nod factors are produced by nitrogen-fixing bacteria selected from the group consisting of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli*, Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

242. The method of embodiment 240 or embodiment 241, wherein the modified receptor polypeptide binds one or more Nod factors with higher affinity than an unmodified receptor polypeptide.

243. The method of any one of embodiments 240-242, wherein the modified receptor polypeptide binds one or more Nod factors with higher selectivity than an unmodified receptor polypeptide.

244. The method of any one of embodiments 240-243, wherein the modified receptor polypeptide binds one or more Nod factors with altered specificity as compared to an unmodified receptor polypeptide.

245. The method of any one of embodiments 216-244, wherein the modified plant LysM receptor polypeptide further comprises a LysM2 domain modified to comprise a hydrophobic patch on the surface of the LysM2 domain, wherein the modified plant LysM receptor polypeptide has enhanced affinity, selectivity, and/or specificity for one or more Nod factors as compared to the unmodified plant LysM receptor polypeptide.

246. The method of embodiment 245, wherein the hydrophobic patch is within 30 Å, 20 Å, 10 Å, 7.5 Å, 5 Å, 4 Å, 3 Å, 2 Å, 1.5 Å, or 1 Å of a chitin binding motif.

247. The method of embodiment 245 or embodiment 246, wherein the LysM2 domain comprises SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300.

248. The method of any one of embodiments 245-247, wherein the hydrophobic patch was generated by deleting at least one non-hydrophobic amino acid residue, substituting at least one amino acid residue with a more hydrophobic amino acid, or combinations thereof.

249. The method of embodiment 248, wherein the at least one amino acid was identified by an amino acid sequence alignment with a LysM2 domain from a LysM high affinity Nod factor receptor that naturally has a hydrophobic patch that interacts with a Nod factor.

250. The method of embodiment 249, wherein the LysM2 domain from a LysM high affinity Nod factor receptor comprises SEQ ID NO: 271, SEQ ID NO: 272, SEQ ID NO: 273, SEQ ID NO: 274, SEQ ID NO: 275, SEQ ID NO: 276, or SEQ ID NO: 277.

251. The method of embodiment 249 or embodiment 250, wherein the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258.

252. The method of any one of embodiments 249-251, wherein the at least one amino acid was identified by structural modeling to identify a region in LysM2 where the hydrophobic patch can be engineered.

253. The method of embodiment 252, wherein the structural modeling used the unmodified plant LysM amino acid sequence and a LysM domain three dimensional structure that has a known hydrophobic patch.

254. The method of embodiment 253, wherein the LysM domain three dimensional structure is a *Medicago truncatula* NFP ectodomain.

255. The method of embodiment 253 or embodiment 254, wherein the known hydrophobic patch amino acid residues of the LysM domain three dimensional structure are or correspond to L147, L151, L152, L154, T156, K157 and V158 of the *Medicago truncatula* NFP ectodomain.

256. The method of embodiment 255, wherein the alpha carbon of at least one amino acid was within 3 Å of an alpha carbon of a known hydrophobic patch amino acid residue in the structural alignment.

257. The method of any one of embodiments 252-256, wherein the structural modeling was performed using SWISS-MODEL, PDB2PQR, APBS, PyMol, and APBS tools 2.1.

258. The method of any one of embodiments 245-257, wherein the modified receptor polypeptide binds one or more Nod factors produced by nitrogen-fixing bacteria or by mycorrhizal fungi.

259. The method of embodiment 258, wherein the one or more Nod factors is produced by nitrogen-fixing bacteria selected from the group consisting of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., and any combination thereof, or by mycorrhizal fungi selected from the group consisting of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, and any combination thereof.

260. The method of embodiment 258 or embodiment 259, wherein the modified receptor polypeptide binds the one or more Nod factors with higher affinity than an unmodified receptor polypeptide.

261. The method of any one of embodiments 258-260, wherein the modified receptor polypeptide binds the one or more Nod factors with higher selectivity than an unmodified receptor polypeptide.

262. The method of any one of embodiments 258-261, wherein the modified receptor polypeptide binds the one or more Nod factors with altered specificity as compared to an unmodified receptor polypeptide.

263. The method of any one of embodiments 216-262, wherein the nucleic acid is generated by site-directed mutagenesis, by chemical synthesis, by genetic editing, or by genetic engineering.

264. The method of any one of embodiments 216-263, wherein the nucleic acid is an endogenous plant gene in a plant cell.

265. The method of any one of embodiments 216-264, wherein the nucleic acid sequence is operably linked to a promoter.

266. The method of embodiment 265, wherein the promoter is a root specific promoter, a constitutive promoters, or a combination thereof.

267. The method of embodiment 265 or embodiment 266, wherein the promoter is selected from the group consisting of a NFR1 promoter, a NFR5NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, and an *Arabidopsis* pCO2 promoter.

268. The method of any one of embodiments 265-267, wherein the nucleic acid sequence is inserted into the genome of the plant so that the nucleic acid sequence is operably linked to an endogenous promoter.

269. The method of embodiment 268, wherein the endogenous promoter is a root specific promoter.

270. A genetically altered plant comprising the modified plant LysM receptor polypeptide encoded by the nucleic acid of any one of embodiments 216-269.

271. The plant of embodiment 270, wherein the plant is selected from the group consisting of cassava, corn, cowpea, rice, barley, wheat, *Trema* spp., apple, pear, plum, apricot, peach, almond, walnut, strawberry, raspberry, blackberry, red currant, black currant, melon, cucumber, pumpkin, squash, grape, bean, soybean, pea, chickpea, cowpea, pigeon pea, lentil, Bambara groundnut, lupin, pulses, *Medicago* spp., *Lotus* spp., forage legumes, indigo, legume trees, and hemp.

272. The genetically altered plant of embodiment 270 or embodiment 271, wherein the nucleic acid is a transgene.

273. The genetically altered plant of embodiment 270 or embodiment 271, wherein the nucleic acid is an endogenous plant LysM receptor gene.

274. A method of making a modified plant LysM receptor polypeptide comprising generating a nucleic acid encoding a wild-type plant LysM receptor polypeptide that comprises a DNA molecule encoding a modified plant LysM receptor polypeptide comprising a LysM1 domain comprising a first motif and a second motif, wherein the first motif and/or the second motif are modified as compared to the amino acid sequences of the corresponding wild-type plant LysM receptor polypeptide, and wherein the encoded modified plant LysM receptor polypeptide has higher affinity, higher selectivity, and/or altered specificity for one or more Nod factors produced by nitrogen-fixing bacteria or by mycorrhizal fungi than an unmodified plant LysM receptor polypeptide.

275. The method of embodiment 274, wherein the first motif corresponds to amino acids 42-48 of SEQ ID NO: 162 when the plant LysM receptor polypeptide amino acid sequence is aligned to SEQ ID NO: 162 and the second motif corresponds to amino acids 75-80 of SEQ ID NO: 162 when the plant LysM receptor polypeptide amino acid sequence is aligned to SEQ ID NO: 162; or wherein the first motif corresponds to amino acids 44-49 of SEQ ID NO: 164 when the plant LysM receptor polypeptide amino acid sequence is aligned to SEQ ID NO: 164 and the second motif corresponds to amino acids 76-81 of SEQ ID NO: 164 when the plant LysM receptor polypeptide amino acid sequence is aligned to SEQ ID NO: 164.

276. The method of embodiment 274 or embodiment 275, wherein the first motif is modified by substituting at least one, at least two, or at least three amino acid residues in the first motif with corresponding amino acid residues that are different in a third motif; wherein the second motif is modified by substituting at least one, at least two, or at least three amino acid residues in the second motif with corresponding amino acid residues that are different in a fourth motif; and/or wherein the first motif is modified by substituting the first motif with a third motif, and/or wherein the second motif is modified by substituting the second motif with a fourth motif.

277. The method of embodiment 276, wherein the third motif and the fourth motif have different affinities, selectivities, and/or specificities for oligosaccharides than the first motif and the second motif.

278. The method of embodiment 277, wherein the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM receptor polypeptide amino acid sequence is aligned to SEQ ID NO: 162 and the fourth motif corresponds to amino acids 75-80 of SEQ ID NO: 162 when the second plant LysM receptor polypeptide amino acid sequence is aligned to SEQ ID NO: 162; or wherein the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM receptor polypeptide amino acid sequence is aligned to SEQ ID NO: 164 and the fourth motif corresponds to amino acids 76-81 of SEQ ID NO: 164 when the second plant LysM receptor polypeptide amino acid sequence is aligned to SEQ ID NO: 164.

279. The method of any one of embodiments 274-278, wherein the modified plant LysM receptor polypeptide further comprises a fifth motif in the LysM1 domain, wherein the fifth motif is modified.

280. The method of embodiment 279, wherein the fifth motif corresponds to amino acids 56-65 of SEQ ID NO: 162 when the plant LysM receptor polypeptide amino acid sequence is aligned to SEQ ID NO: 162.

281. The method of embodiment 279 or embodiment 280, wherein the fifth motif is modified by substituting at least one, at least two, or at least three amino acid residues in the fifth motif with corresponding amino acid residues that are different in a sixth motif; and/or wherein the fifth motif is substituted with a sixth motif.

282. The method of embodiment 281, wherein the sixth motif has a different specificity for oligosaccharides than the fifth motif.

283. The method of embodiment 281 or embodiment 282, wherein the sixth motif is from a second plant LysM receptor polypeptide having the different specificity for oligosaccharides and the sixth motif corresponds to amino acids 56-65 of SEQ ID NO: 162 when the second plant LysM polypeptide amino acid sequence is aligned to SEQ ID NO: 162.

284. The method of any one of embodiments 274-283, wherein the modified plant LysM receptor polypeptide binds one or more Nod factors produced by nitrogen-fixing bacteria or by mycorrhizal fungi with higher affinity, higher selectivity, and/or altered specificity than an unmodified plant LysM receptor polypeptide.

285. The method of any one of embodiments 274-284, wherein the modified plant LysM receptor polypeptide further comprises a LysM2 domain modified to comprise a hydrophobic patch on the surface of the LysM2 domain, wherein the modified plant LysM receptor polypeptide has enhanced affinity, selectivity, and/or specificity for one or more Nod factors as compared to the unmodified plant LysM receptor polypeptide.

286. The method of embodiment 285, wherein the hydrophobic patch was generated by deleting at least one non-hydrophobic amino acid residue, substituting at least one amino acid residue with a more hydrophobic amino acid, or combinations thereof.

287. The method of any one of embodiments 274-286, wherein the nucleic acid is generated by site-directed mutagenesis, by chemical synthesis, by genetic editing, or by genetic engineering.

288. The method of any one of embodiments 274-287, wherein the nucleic acid is an endogenous plant gene in a plant cell.

289. A method of generating a modified plant LysM receptor polypeptide comprising:
    (a) providing a heterologous Nod factor LysM receptor polypeptide model comprising a structural model, a molecular model, a surface characteristics model, and/or an electrostatic potential model of a LysM1 domain, a LysM2 domain, a LysM3 domain, any combination thereof, or the ectodomain of the heterologous Nod factor LysM receptor polypeptide having selectivity for a beneficial nitrogen-fixing bacteria or a beneficial mycorrhizal fungus and an unmodified endogenous LysM receptor polypeptide;

(b) identifying a first motif, a second motif, and/or optionally a fifth motif for modification in the unmodified endogenous LysM receptor polypeptide by comparing a LysM1 domain of the unmodified endogenous LysM receptor polypeptide with the corresponding LysM1 domain of the heterologous Nod factor LysM receptor polypeptide model;

(c) modifying the first motif by substituting at least one, at least two, or at least three amino acid residues in the first motif with corresponding amino acid residues that are different in a third motif, modifying the second motif by substituting at least one, at least two, or at least three amino acid residues in the second motif with corresponding amino acid residues that are different in a fourth motif, and/or optionally modifying the fifth motif by substituting at least one, at least two, or at least three amino acid residues in the fifth motif with corresponding amino acid residues that are different in a sixth motif, wherein the third motif, the fourth motif, and the sixth motif have different affinities, selectivities, and/or specificities for oligosaccharides than the first motif, the second motif, and the fifth motif; and (d) generating the modified endogenous LysM receptor polypeptide wherein the first motif, the second motif, and/or optionally the fifth motif have been substituted with corresponding amino acid residues from the third motif, the fourth motif, and/or optionally the sixth motif.

290. A genetically altered plant comprising the modified plant LysM receptor polypeptide encoded by the nucleic acid of any one of embodiments 274-286.

291. The plant of embodiment 290, wherein the plant is selected from the group consisting of cassava, corn, cowpea, rice, barley, wheat, *Trema* spp., apple, pear, plum, apricot, peach, almond, walnut, strawberry, raspberry, blackberry, red currant, black currant, melon, cucumber, pumpkin, squash, grape, bean, soybean, pea, chickpea, cowpea, pigeon pea, lentil, Bambara groundnut, lupin, pulses, *Medicago* spp., *Lotus* spp., forage legumes, indigo, legume trees, and hemp.

292. The genetically altered plant of embodiment 290 or embodiment 291, wherein the nucleic acid is a transgene.

293. The genetically altered plant of embodiment 290 or embodiment 291, wherein the nucleic acid is an endogenous plant LysM receptor gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A shows schematic diagrams of NFR1 (top, white boxes) and CERK6 (bottom, green boxes). From N to C terminus, the boxes represent LysM domains of the ectodomain (LysM1, LysM2 and LysM3), transmembrane and juxtamembrane domains (TJ), and the kinase domain (KD). The dotted lines and indicated amino acids (A226 and L325 for NFR1; G226 and L325 for CERK6) specify boundaries between the analyzed domains. FIG. 1B shows schematic diagrams of gene structures of *Medicago truncatula* LYK3 (Lyk3, MTR_5g086130, top), *Lotus*

*japonicus* NFR1 (Nfr1, Lj2g3v2904690, middle), and *L. japonicus* CERK6 (Cerk6, Lj6g3v1055580, bottom). Exons are depicted as black boxes and introns are depicted as black lines. Numbers above the gene structure diagrams display the nucleotide count, and the overall length in kilobases (kb) is indicated below the gene structure diagrams. FIG. 1C shows a protein alignment of amino acid sequences of *L. japonicus* NFR1 (LjNFR1, top row, SEQ ID NO: 162), *M. truncatula* LYK3 (MtLYK3, middle row, SEQ ID NO: 163), and *L. japonicus* CERK6 (LjCERK6, bottom row, SEQ ID NO: 164). Above the alignment, conserved cysteine residues are indicated with red arrows, residues that were mutated to tryptophan in constructs 23, 24, 31, and 32 are indicated with blue circles, and brackets indicate the boundaries of the ectodomain (EC), transmembrane and juxtamembrane domains (TM+JM), and the intracellular (IC) region of the proteins. Within the EC, the dotted red lines indicate the boundaries between the LysM1, LysM2 and LysM3 domains. Regions I, II, III, and IV within the LysM1 domain are also indicated by brackets above the alignment. FIG. 1D shows schematics of LysM receptor kinase protein expression constructs. As shown at left in grey, each construct has an expression cassette encoding the transformation marker triple YFP (tYFP) with a nuclear localization signal (NLS) driven by the Ubiquitin promoter (pUbi) and nod terminator (tnos). As shown at right, each construct also has an expression cassette encoding a LysM receptor kinase protein, including, from top to bottom, *L. japonicus* Nfr1 (genomic Nfr1) fused to a 6×histidine tag (6×-his) under control of the *L. japonicus* Nfr1 promoter and terminator (pLjNfr1 and tLjNFR1, respectively) (expression cassette in white); *L. japonicus* Cerk6 (genomic Cerk6) fused to a 6×histidine tag (6×-his) under control of the *L. japonicus* Cerk6 promoter and terminator (pLjCerk6 and tLjCerk6, respectively) (expression cassette in green); and *M. truncatula* Lyk3 (genomic Lyk3) fused to a 6× histidine (6×-his) tag under control of the *M. truncatula* Lyk3 promoter and the 35S terminator (pMtLyk3 and t35S, respectively) (expression cassette in blue). While FIG. 1D shows expression constructs encoding the genomic coding sequences of Nfr1, Cerk6, and Lyk3, equivalent constructs were used to express chimeric alleles of LysM receptor kinase proteins under control of the different promoters. FIG. 1E shows a schematic of constructs for expression of receptors in *N. benthamiana* (tobacco) leaves. At left, the first expression cassette encodes the plasma membrane localization marker *A. thaliana* PIP2A (AtPIP2A) fused to mCherry, under control of the Ubiquitin promoter (pUbi) and nod terminator (tnos). At right, the second expression cassette encodes a LysM receptor kinase protein Nfr1/chimera (i.e., Nfr1 or a chimeric protein) fused to eYFP under control of the 35S promoter (p35S) and terminator (t35S). LB and RB indicate the T-DNA left border and right border, respectively.

FIG. 2A shows nodule formation observed on roots of *L. japonicus* nfr1-1 mutants tested with different protein constructs, including NFR1 (construct 1) or NFR1/CERK6 chimeras (constructs 2-8), under control of the Nfr1 promoter. The x-axis indicates the identity of the LysM receptor kinase construct, and the y-axis indicates the number of nodules formed per plant. FIG. 2B shows representative images of *L. japonicus* nfr1-1 roots expressing, from top to bottom, NFR1 (construct 1) or NFR1/CERK6 chimeras (constructs 2-8, one construct per row, construct schematic indicated). The ratio of plants with nodules observed over total plants tested is provided. From left to right columns, the images show nodule formation as inspected in bright field, root transformation as monitored by the expression of a YFP marker gene, nodule infection by *M. loti*-DsRed bacteria, and Nin promoter activation as analyzed by GUS staining. The scale bars indicate 5 mm. FIG. 2C shows the level of reactive oxygen species (ROS) produced by *L. japonicus* wild-type (WT) and cerk6-1 mutant roots tested with different protein constructs, including NFR1 (construct 9), CERK6 (construct 13), or NFR1/ CERK6 chimeras (constructs 11-16), under control of the Cerk6 promoter. The x-axis indicates the identity of the LysM receptor kinase construct, and the y-axis indicates the ratio between ROS peak values obtained after treatment with CO8 vs. flg22 elicitors, and normalized to WT values. Flg22 treatment was used as an internal control for root responsiveness to elicitors. In FIGS. 2A-2C schematic diagrams of LysM receptor kinase constructs are shown with NFR1 domains shown in white, and CERK6 domains shown in green. Chimeras were generated by exchanging the ectodomain (EC), transmembrane and juxtamembrane domains (TJ), and the kinase domain (KD). In FIG. 2A and FIG. 2C, n indicates the number of analyzed plants, dots represent values from individual plants, and different letter labels indicate significant differences between samples as determined by ANOVA with Tukey's multiple comparisons test, $P<0.05$. The box and whisker plots represent the interquartile range, where the middle line represents the median, and the lower and upper lines represent the first and third interquartile.

FIG. 3A provides results for NFR1 (corresponding to constructs 1 and 9), NFR1 with the CERK6 TJ and KD and a K351N point mutation, (corresponding to constructs 4 and 12), CERK6 with a K351N point mutation (corresponding to constructs 5 and 13), and CERK6 with the NFR1 KD (corresponding to constructs 7 and 15). FIG. 3B provides results for NFR1 with an I78W point mutation (corresponding to construct 23), CERK6 with V79W and K351N point mutations (corresponding to construct 31), and CERK6 with NFR1 LysM1 regions II and IV and a K351N point mutation (corresponding to construct 65).

FIG. 4A shows schematic diagrams of NFR1 and CERK6. From N to C terminus, the boxes represent LysM domains of the ectodomain (LysM1, LysM2 and LysM3), transmembrane and juxtamembrane domains (TJ), and the kinase domain (KD). The dotted lines and indicated amino acids (D91, C152, A226 and L325 for NFR1; and D92, C153, G226 and L325 for CERK6) specify boundaries between domains. Also indicated above the protein schematics with blue arrows are the positions of point mutations (I78W and I140W for NFR1; and V79W and I141W for CERK6). FIG. 4B shows nodule formation observed on roots of *L. japonicus* nfr1-1 mutants tested with different protein constructs, including NFR1 (construct 1), NFR1/CERK6 chimeras (constructs 17-22), or NFR1 with point mutations (constructs 23-24), under control of the Nfr1 promoter. The x-axis indicates the identity of the LysM receptor kinase construct, and the y-axis indicates the number of nodules formed per plant. Schematic diagrams of the LysM receptor kinase proteins are shown on the x-axis, with NFR1 domains shown in white, and CERK6 domains in green. Constructs 23 and 24 contain point mutations I78W and I140W, respectively, as indicated. n indicates the number of analyzed plants, dots represent values from individual plants, and different letters labels indicate significant differences between samples as determined by ANOVA with Tukey's multiple comparisons test, $P<0.05$. The box and whisker plots represent the interquartile range, where the middle line represents the median, and the lower and upper lines represent the first and third interquartile.

FIG. 5A shows results for constructs 17-22. FIG. 5B shows results for constructs 23-24 and 33-36. In FIGS. 5A-5B, from the left to right columns, the images show nodule formation as inspected in bright field, root transformation as monitored by the expression of a YFP marker gene, nodule infection by *M. loti*-DsRed bacteria, and Nin promoter activation as analyzed by GUS staining. The ratio of plants with nodules observed is indicated for each construct.

FIG. 6A shows the level of ROS produced by *L. japonicus* wild-type (WT) and cerk6-1 mutant roots tested with different protein constructs, including CERK6 (construct 13), NFR1/CERK6 chimeras (constructs 12 and 25-30), or CERK6 with point mutations (constructs 31-32), under control of the Cerk6 promoter. The x-axis indicates the identity of the LysM receptor kinase construct, and the y-axis indicates the ratio between ROS peak values obtained after treatment with CO8 vs. flg22 elicitors, and normalized to WT values. Flg22 treatment was used as an internal control for root responsiveness to elicitors. Schematic diagrams of the LysM receptor kinase protein constructs are shown on the x-axis, with NFR1 domains shown in white, and CERK6 domains in green. Constructs 31 and 32 contain CERK6 with point mutations V79W and I141W, respectively, as indicated. n indicates the number of analyzed plants, dots represent values from individual plants, and different letters labels indicate significant differences between samples as determined by ANOVA with Tukey's multiple comparisons test, $P<0.05$. The box and whisker plots represent the interquartile range, where the middle line represents the median, and the lower and upper lines represent the first and third interquartile. FIG. 6B shows a structural model of the predicted chitin (CO) binding grooves in the LysM1 (left) and LysM2 (right) domains of CERK6. The LysM1 and LysM2 structures are shown as green ribbon diagrams. Arrows indicate the location of the tryptophan (W) that was inserted to create constructs 31 and 32 at position V79W for LysM1 (construct 31), and I141W for LysM2 (construct 32). The tryptophan (W) residue is shown as a blue stick diagram, surrounded by a space-filling model shown as a grey cloud. The CO ligand is shown as a ball and stick model in red and blue.

FIG. 7A shows an alignment of the specified amino acid sequences of the LysM1 domains of NFR1 (top, SEQ ID NO: 165) and CERK6 (bottom, SEQ ID NO: 166). Identical amino acids are marked in grey. Regions I, II, III, and IV are indicated above the alignment, and beta sheet ($\beta$1, $\beta$2) and alpha helix ($\alpha$1, $\alpha$2) secondary structures based on the CERK6 crystal structure are indicated below the alignment. FIG. 7B shows nodule formation observed on roots of *L. japonicus* nfr1-1 mutants tested with different protein constructs, including NFR1 (construct 1), or NFR1/CERK6 chimeras (constructs 33-36), under control of the Nfr1 promoter. The x-axis indicates the identity of the LysM receptor kinase construct, and the y-axis indicates the number of nodules formed per plant. FIG. 7C shows the level of ROS produced by *L. japonicus* wild-type (WT) and cerk6-1 mutant roots tested with different protein constructs, including CERK6 (construct 13), or NFR1/CERK6 chimeras (constructs 37-40), under control of the Cerk6 promoter. The x-axis indicates the identity of the LysM receptor kinase construct, and the y-axis indicates the ratio between ROS peak values obtained after treatment with CO8 vs. flg22 elicitors, and normalized to WT values. Flg22 treatment was used as an internal control for root responsiveness to elicitors. In FIGS. 7A-7B, schematic diagrams of LysM receptor kinase protein constructs are shown on the x-axis, with NFR1 domains and regions shown in white, and CERK6 domains and regions in green. n indicates number of individual biological samples, dots represent values from individual plants, and different letters labels indicate significant differences between samples as determined by ANOVA with Tukey's multiple comparisons test, P<0.05. The box and whisker plots represent the interquartile range, where the middle line represents the median, and the lower and upper lines represent the first and third interquartile.

FIGS. 8A-8D show comparisons of LysM1 domains of different LysM receptors and Nod factors of different bacterial species. FIG. 8A shows an alignment of the specified amino acid sequences of the LysM1 domains of *L. japonicus* NFR1 (SEQ ID NO: 165) and *M. truncatula* LYK3 (SEQ ID NO: 167). Identical amino acids are marked in grey. Regions II, III, and IV are indicated above the alignment, and beta sheet ($\beta$1, $\beta$2) and alpha helix ($\alpha$1, $\alpha$2) secondary structures based on the LYK3 crystal structure are indicated below the alignment. FIG. 8B shows a schematic diagram showing NFR1 (top, white boxes) and LYK3 (bottom, blue boxes). From N to C terminus, the boxes represent LysM domains of the ectodomain (LysM1, LysM2 and LysM3), transmembrane and juxtamembrane domains (TJ), and the kinase domain (KD). The dotted lines and indicated amino acids (D91, G227, and L325 for NFR1; E91, G226 and L324 for LYK3) specify boundaries between the analyzed domains. FIG. 8C shows chemical structures of *M. loti* Nod factor V (Cb, $C_{18:1}$, Me, AcFuc; top) and *S. meliloti* Nod factor IV (Ac, $C_{16:2}$, S; bottom). FIG. 8D shows the structure of a generic Nod factor, with the locations of ten different moieties (R1 through R10) indicated. The number of N-Acetylglucosamine monomers (in square brackets) varies in number (n) between different Nod factors.

FIG. 9A shows nodule formation observed on roots of *L. japonicus* nfr1-1 mutants tested with different protein constructs, including NFR1 (construct 1), or NFR1/LYK3 chimeras (constructs 41-45), under control of the Nfr1 promoter. The x-axis indicates the identity of the LysM receptor kinase construct, and the y-axis indicates the number of nodules formed per plant. FIG. 9B shows nodule formation observed on roots of *M. truncatula* lyk3-1 mutant roots tested with different protein constructs, including NFR1 (construct 46), or NFR1/LYK3 chimeras (constructs 47-51), under control of the Lyk3 promoter. In FIGS. 9A-9B, the y-axis indicates the number of nodules formed per plant. Schematic diagrams of the LysM receptor kinase constructs are shown on the x-axis, with NFR1 domains and regions shown in white, and LYK3 domains and regions in blue. n indicates the number of analyzed plants, dots represent values from individual plants, and different letters labels indicate significant differences between samples as determined by ANOVA with Tukey's multiple comparisons test, P<0.05. The box and whisker plots represent the interquartile range, where the middle line represents the median, and the lower and upper lines represent the first and third interquartile.

FIG. 10A shows nodulation phenotypes and expression of pNin-GUS for *L. japonicus* nfr1-1 roots transformed with the indicated constructs 41-45. FIG. 10B shows nodulation phenotypes of *M. truncatula* lyk3-1 roots transformed with constructs 46-51. FIG. 10C shows nodulation phenotypes and expression of pNin-GUS for *L. japonicus* nfr1-1 roots transformed with constructs 52-65. FIG. 10D shows nodulation phenotypes of *M. truncatula* lyk3-1 roots transformed with constructs 54-58. In each of FIGS. 10A-10D, the ratios indicate the number of plants with nodules out the total number of analyzed plants. The schematic diagrams at left indicate the composition of the LysM receptor kinase constructs with NFR1 domains and regions in white, CERK6 domains and regions in green, and LYK3 domains and regions in blue. The scale bars indicate 3 mm.

FIGS. 11A-11E show size-exclusion chromatography (SEC) $A_{280}$ profiles of NFR1 (FIG. 11A), CERK6 (FIG. 11B), LYK3 (FIG. 11E), NFR1 with the LysM1 regions II and IV of CERK6 (FIG. 11C) and CERK6 with the LysM1 regions II and IV of NFR1 (FIG. 11D), as depicted in the schematic diagram insets. In FIGS. 11A-11E, NFR1 domains and sequences are shown in white, CERK6 domains and sequences are shown in green, and LYK3 is shown in blue. At right are coomassie-stained SDS-PAGE gels showing the purified proteins. Elution volumes ($V_e$) in ml are shown on the x-axis, and absorbance at 280 nm in milli-absorbance units (mAU) is shown on the y-axis. The inset elution volumes ($V_e$) correspond to monomeric ectodomains, with $V_e$=18.4 ml for NFR1 in FIG. 11A, $V_e$=72.2 ml for CERK6 in FIG. 11B, $V_e$=18.0 ml for NFR1 with CERK6 LysM1 regions II and IV in FIG. 11C, $V_e$=16.2 ml for CERK6 with NFR1 LysM1 regions II and IV in FIG. 11D, and $V_e$=16.3 ml for LYK3 in FIG. 11E. FIG. 11F shows an HPLC chromatogram (215 nm) of *S. meliloti* Nod factor IV (Ac, $C_{16:2}$, S) conjugated to biotin. Time in minutes is indicated on the x-axis, and mAU is indicated on the y-axis. FIG. 11G shows a mass spectrometric in-source fragmentation analysis performed at 75 eV (m/z±0.5 accuracy) using an MSQ Plus ESI mass spectrometer from ThermoFisher. FIG. 11H shows a structure and fragmentation analysis of *S. meliloti* Nod factor IV conjugated to biotin, with calculated masses indicated.

FIG. 12A shows BLI measurements of *M. loti* (left) and *S. meliloti* (right) Nod factors binding to LYK3 ectodomain. FIG. 12B shows BLI measurements of *M. loti* (left) and *S. meliloti* (right) Nod factors binding to NFR1 ectodomain. FIG. 12C shows BLI measurements of *M. loti* Nod factor binding to CERK6 ectodomain. FIG. 12D shows BLI measurements of *M. loti* Nod factor binding to chimeric NFR1 ectodomain with LysM1 regions II and IV from CERK6. In each of FIGS. 12A-12D, time in seconds is indicated on the x-axis, and the level of binding in nm is indicated on the y-axis. The schematic diagrams at right indicate the composition of the LysM receptor kinase ectodomains with NFR1 domains in white, CERK6 domains and regions in green, and LYK3 domains in blue.

FIG. 13A shows the *M. truncatula* LYK3 ectodomain with the three LysM domains labeled, with LysM1 in blue, LysM2 in light blue, and LysM3 in teal. Secondary structures (i. e., alpha helices and beta sheets) within the LysM domains are also labeled: LysM1 secondary structures=α1, α2, β1, and β2; LysM2 secondary structures=α3, α4, β3, and β4; and LysM2 secondary structures=α5, α6, β5, and β6. Glycosylations are shown as grey stick diagrams. The three conserved disulfide bridges are indicated in black, and labeled with arrows and the residue numbers (C29-C154, C90-C152, and C25-C92). The N- and C-termini of the ectodomain are also labeled. FIG. 13B shows a structural superposition of LYK3 (blue) and CERK6 (PDB: 5LS2; green). The three LysM domains are labeled, with LYK3 LysM1 in blue, LYK3 LysM2 in light blue, and LYK3 LysM3 in teal. The N- and C-termini of the ectodomains are also labeled. A dotted line box highlights the region of the LysM1 domain that possesses structural differences between LYK3 and CERK6. FIG. 13C shows a close-up of the LysM1 domain structural superposition of LYK3 (blue) and CERK6 (green), showing the structural differences between LYK3 (blue) and CERK6 (green). The LysM1 secondary structures α1, α2, β1, and β2 are labeled. The position of one region of the LysM1 backbone shows a distance of about 11 Å between the CERK6 and LYK3 structures, as indicated. FIG. 13D shows a superposition of chitotetraose ("CO ligand") from the *Arabidopsis thaliana* CERK1 crystal structure (PDB: 4EBZ) onto LysM1 from CERK6. CERK6 is shown in green, and the CO ligand is shown as a ball and stick model in red and blue. LysM1 alpha helices α1 and α2, and regions II and IV are indicated. FIG. 13E shows a superposition of chitotetraose ("Nod factor ligand") from the *A. thaliana* CERK1 crystal structure (PDB: 4EBZ) onto LysM1 from LYK3. LysM1 alpha helices α1 and α2, regions II and IV, and the position of the P87S mutation in *M. truncatula* lyk3-3 and L77P mutation in *Pisum sativum* SYM37 (RisNod4) mutants are indicated.

FIGS. 14A-14C show an amino acid sequence alignment of NFR1-type LysM Nod factor receptor ectodomain sequences from *Medicago truncatula* (Q6UD73.1|LYK3 (SEQ ID NO: 168)), *Phaseolus vulgaris* (XP_007141617.1 (SEQ ID NO: 169)), *Arachis hypogaea* (XP_029150476.1

(SEQ ID NO: 170) and XP_029144024.1 (SEQ ID NO: 171)), *Cajanus cajan* (XP_020213700.2 (SEQ ID NO: 172)), *Cicer arietinum* (XP_004491136.1 (SEQ ID NO: 173)), *Abrus precatorius* (XP_027332267.1 (SEQ ID NO: 174)), *Glycine max* (XP_006575588.1 (SEQ ID NO: 175) and XP_006595821.2 (SEQ ID NO: 176)), *Lupinus angustifolius* (XP_019434083.1 (SEQ ID NO: 177) and XP_019461629.1 (SEQ ID NO: 178)), *Lotus japonicus* (CAE02590.1|NFR1 (SEQ ID NO: 179)), *Pisum sativum* (ARX80051.1|Sym37 (SEQ ID NO: 180)), *Vigna angularis* (KOM46748.1 (SEQ ID NO: 181)), *Vigna radiata* var. *radiata* (XP_014504127.1 (SEQ ID NO: 182)), *Vigna unguiculata* (XP_027939826.1 (SEQ ID NO: 183)), *Arachis duranensis* (XP_020982945.1 (SEQ ID NO: 184)), *Arachis ipaensis* (XP_020962820.1 (SEQ ID NO: 185)), *Chamaecrista fasciculata* (2879S20281 (SEQ ID NO: 186)), *Mimosa pudica* (Scaffold15743 (SEQ ID NO: 187)), *Lupinus albus* (Chr04g0249871 (SEQ ID NO: 188)), *Spatholobus suberectus* (TKY57029.1 (SEQ ID NO: 189)), and *Prosopis alba* (XP_028753017.1 (SEQ ID NO: 190)). LysM1, LysM2 and LysM3 domains are indicated with labels above the alignment, and LysM1 domain regions II, III, and IV are indicated with labels above the alignment and dashed boxes. Conserved residues are highlighted blue. The conservation score of each residue is shown below the alignment as a histogram. FIG. 14A shows the alignment of the N-terminal portion of the NFR1-type LysM Nod factor receptor kinase ectodomains. FIG. 14B shows the alignment of the central portion of the NFR1-type LysM Nod factor receptor kinase ectodomains. FIG. 14C shows the alignment of the C-terminal portion of the NFR1-type LysM Nod factor receptor kinase ectodomains. FIG. 14D shows a model of the conservation of NFR1-type LysM Nod factor receptors mapped onto the structure of LYK3. The N-terminus (N), C-terminus (C), LysM domains (LysM1, LysM2, and LysM3), and LysM1 regions II, III and IV are labeled. LysM1 regions II, III and IV are highlighted in blue. Amino acid variations identified in the LYKX (LykX) protein from different cultivars of *P. sativum* (pea) known to correlate with ability to nodulate in the presence of *R. leguminosarum* producing acetylated Nod factors are also indicated on the model, including QN/RY, and RA/PA/RD. FIG. 14E shows a model of the conservation of NFR1-type LysM Nod factor receptor kinases mapped onto the structure of LYK3 LysM1. The N- and C-termini are labeled, and regions II, III and IV are labeled and highlighted in blue. The alignment logos of regions II, III and IV are shown in boxes. In FIGS. 14D-14E, the thickness of the backbone atoms signifies relative conservation, with a thin backbone indicating conserved regions, and a thick backbone indicating variable regions.

FIGS. 15A-15C show an amino acid sequence alignment of CERK6-type LysM chitin receptor ectodomains with sequences from *Lotus japonicus* (BAI79273.1|CERK6 (SEQ ID NO: 191)), *Phaseolus vulgaris* (XP_007146026.1 (SEQ ID NO: 192)), *Arachis ipaensis* (XP_016196976.1 (SEQ ID NO: 193)), *Arachis duranensis* (XP_015958400.1 (SEQ ID NO: 194)), *Cajanus cajan* (XP_020220445.1 (SEQ ID NO: 195)), *Cicer arietinum* (XP_004502028.1 (SEQ ID NO: 196)), *Abrus precatorius* (XP_027343427.1 (SEQ ID NO: 197)), *Medicago truncatula* (XP_003601376.2|LYK9 (SEQ ID NO: 198)), *Glycine max* (XP_003555584.1 (SEQ ID NO: 199) and XP_003518454.1 (SEQ ID NO: 200)), *Lupinus angustifolius* (XP_019425563.1 (SEQ ID NO: 201) and XP_019455825.1 (SEQ ID NO: 202)), *Vigna angularis* (XP_017436810.1 (SEQ ID NO: 203)), *Vigna radiata*

(XP_014509761.1 (SEQ ID NO: 204)), *Vigna unguiculata* (XP_027932400.1 (SEQ ID NO: 205)), *Arachis hypogaea* (XP_025693415.1 (SEQ ID NO: 206)), *Mimosa pudica* (Scaffold8584 (SEQ ID NO: 207)), *Chamaecrista fasciculata* (QANZ01053660 (SEQ ID NO: 208)), *Lupinus albus* (Chr04g0263521 (SEQ ID NO: 209)), *Pisum sativum* (LYK9 (SEQ ID NO: 210)), *Arachis hypogaea* (XP_025645378.1 (SEQ ID NO: 211)), *Spatholobus suberectus* (TKY72192.1 (SEQ ID NO: 212)), and *Prosopis alba* (XP_028758101.1 (SEQ ID NO: 213)). LysM1, LysM2 and LysM3 domains are indicated with labels above the alignment, and LysM1 domain regions II and IV are indicated with labels above the alignment and dashed boxes. The conservation score of each residue is shown below the alignment as a histogram. FIG. 15A shows the alignment of the N-terminal portion of the CERK6-type LysM chitin receptor kinase ectodomains. FIG. 15B shows the alignment of the central portion of the CERK6-type LysM chitin receptor kinase ectodomains. FIG. 15C shows the alignment of the C-terminal portion of the CERK6-type LysM chitin receptor kinase ectodomains. FIG. 15D shows a model of the conservation of CERK6-type LysM chitin receptors mapped onto the structure of CERK6. The N-terminus (N), C-terminus (C), LysM domains (LysM1, LysM2, and LysM3), and LysM1 regions II, III and IV are labeled. LysM1 regions II and IV are highlighted in green. FIG. 15E shows a model of the conservation of CERK6-type LysM chitin receptors mapped onto the structure of CERK6 LysM1. Regions II and IV are highlighted in green, and the CO ligand is shown as a ball and stick model in red and blue. The alignment logos of the chitooligosaccharide (CO) signature motifs in regions II and IV are shown in boxes. In FIGS. 15D-15E, the thickness of the backbone atoms signifies relative conservation, with a thin backbone indicating conserved regions, and a thick backbone indicating variable regions.

FIG. 16A shows nodule formation observed on roots of *L. japonicus* nfr1-1 mutants tested with different protein constructs, including NFR1 (construct 1), NFR1/LYK3 chimeras (constructs 52 and 53), or NFR1/CERK6 chimeras (constructs 59-65), under control of the Nfr1 promoter. FIG. 16B shows nodule formation observed on roots of *M. truncatula* lyk3-1 mutants tested with different protein constructs, including LYK3 (construct 47), or NFR1/LYK3 chimeras (constructs 54-58), under control of the Lyk3 promoter. In FIGS. 16A-16B, the x-axis indicates the identity of the LysM receptor kinase construct, and the y-axis indicates the number of nodules formed per plant. Schematic diagrams of the LysM receptor kinase protein constructs are shown on the x-axis, with NFR1 domains and regions shown in white, CERK6 domains and regions shown in green, and LYK3 domains and regions shown in blue. n indicates the number of analyzed plants, and the different letters indicate significant difference among samples as determined by ANOVA with Tukey's multiple comparisons test, P<0.05. FIG. 16C shows BLI measurements of *M. loti* Nod factor binding to chimeric ectodomains of CERK6 with LysM1 regions II and IV from NFR1. Time in seconds is on the x-axis, and binding in nm is on the y-axis. At right, a schematic diagram shows the ectodomain construct with CERK6 domains in green and NFR1 regions in white.

17A shows the structure of the LysM1 domain of *A. thaliana* CERK1 (AtCERK1), with motifs within regions II (amino acid residues GTTLSV (SEQ ID NO: 59)) and IV (amino acid residues KDRIQM (SEQ ID NO: 69)) indicated, and in yellow. FIG. 17B shows a superposition of the structures of the LysM1 domain of *A. thaliana* CERK1 (AtCERK1) and *L. japonicus* CERK6 (LjCERK6) with motifs within regions II and IV indicated. *A. thaliana* motifs within regions II and IV are in yellow, and *L. japonicus* motifs within regions II and IV are in red. For *A. thaliana* CERK1, the amino acid residues of motifs within regions II and IV are as shown in FIG. 17A. For *L. japonicus* CERK6, the region II motif is amino acid residues GSNLTY (SEQ ID NO: 14), and the region IV motif is amino acid residues KDSVQA (SEQ ID NO: 40). FIG. 17C shows the structure of the LysM1 domain of *Hordeum vulgare* (barley) RLK4 (HvRLK4), with motifs within regions II (amino acid residues NQNVTY (SEQ ID NO: 62)) and IV (amino acid residues NNLDYVV (SEQ ID NO: 142)) indicated and in green. FIG. 17D shows the structure of the LysM1 domain of *H. vulgare* RLK5 (HvRLK5), with motifs within regions II (amino acid residues TPNVNV (SEQ ID NO: 143)) and IV (amino acid residues LDYVAA (SEQ ID NO: 70)) indicated and in green. FIG. 17E shows the structure of the LysM1 domain of a *Marchantia polymorpha* homolog of CERK1 and NFR1 (Marpol Mapoly0080s0051.1), with motifs within regions II (amino acid residues DDTLL (SEQ ID NO: 67) and IV (amino acid residues PDSVEA (SEQ ID NO: 77)) indicated and in purple. FIG. 17F shows the structure of the LysM1 domain of a *Prunus persica* homolog of CERK1 and NFR1 (Prupe.3G213100), with motifs within regions II (amino acid residues GSNLTL (SEQ ID NO: 54)) and IV (amino acid residues KDSVLA (SEQ ID NO: 57)) indicated and in blue. FIG. 17G shows the structure of the LysM1 domain of a *Solanum lycopersicum* homolog of CERK1 and NFR1 (Solyc07g049180), with motifs within regions II (amino acid residues RGSNLT (SEQ ID NO: 341)) and IV (amino acid residues QDSVIA (SEQ ID NO: 56)) indicated and in purple. In FIGS. 17A-17G, chitin (C04) molecules are shown as stick models in orange, blue, and red.

FIG. 18A shows the structure of the NFP receptor ectodomain (NFP-ECD) with the three LysM domains labeled (LysM1, LysM2, and LysM3). Secondary structures (beta sheet and alpha helix) within the LysM domains are also labeled: LysM1 secondary structures=α1, α2, β1, and β2; LysM2 secondary structures=α3, α4, β3, and β4; and LysM3 secondary structures=α5, α6, β5, and β6. Glycosylations (di-GlcNAc cores are shown (projecting from α1 at upper; additional cores visible at center adjacent to β2 and β1 as well as at bottom left behind α4), and disulfide bridges are indicated with arrows and labeled with the residue numbers (C47-C166; C39-C104; and C102-C164). FIG. 18B shows *M. truncatula* NFP shaded with electrostatic surface potential with molecular docking of chitin (C04; designated as "Ligand"). The hydrophobic patch is circled by a dashed black line, and the locations of important residues L147 and L154 are shown using arrows. The position of the Nod factor fatty-acid is depicted with a dashed orange line. FIG. 18C shows BLI binding curves for WT *M. truncatula* NFP ectodomain binding to *S. meliloti* LCO-IV. FIG. 18D shows BLI binding curves for *M. truncatula* NFP ectodomain with the double mutation L147D L154D binding to *S. meliloti* LCO-IV. For FIGS. 18C-18D, seven 2-fold dilution series of analyte (1.56-100 μM) were used for each experiment; and experimental binding curves are represented in solid lines, fitting curves in dashed lines. FIG. 18E shows BLI binding curves for *A. thaliana* CERK1 binding to chitopentaose (chitin; CO5). FIG. 18F shows BLI binding curves for *A. thaliana* CERK1 binding to chitooctaose (chitin; CO8). For FIGS. 18E-18F, seven 2-fold dilution series of analyte (1.56-100 μM) were used for each experiment; experimental binding curves are represented in solid lines, fitting curves in dashed lines; goodness of fit is described by the global fit $R^2$ on the mean value of each point; number of replicates performed using independent protein preparations (n) indicated; and kinetic parameters ($k_{on}$ and $k_{off}$) are shown. FIG. 18G shows a schematic of the *M. truncatula* NFP receptor with LysM1 domain, LysM2 domain, LysM3 domain, stem, transmembrane (TM) domain, and kinase domains labeled, and the location of the hydrophobic patch in the LysM2 domain indicated by a grey bar. Numbers below the schematic provide the corresponding amino acid residues, and the locations of the CxC motifs flanking the LysM domains are shown. FIG. 18H shows the general schematic of the construct used for *M. truncatula* nfp mutant complementation experiments. Designations are as follows: T-DNA left border=LB, T-DNA right border=RB, nuclear localized triple yellow fluorescent protein=tYFPnls, buffer sequence=buffer, constitutive ubiquitin promoter=pUbi, Nfr1 promoter=pNfr1, Cerk6 promoter=pCerk6. The arrows indicate the directions of gene transcription. FIGS. 18I-18J show complementation assays of *M. truncatula* nfp mutants. FIG. 18I shows complementation tested by inoculation with *S. meliloti* strain 2011. FIG. 18J shows complementation tested by inoculation with *S. medicae*. Columns represent the mean nodule numbers, while circles represent the number of nodule counts on individual plants. Empty circles=*M. truncatula* A17 wild type; filled circles=*M. truncatula* nfp mutant; EVC=empty vector control; and WT=wild type. Error bars show the SEM. Different letters indicate significant differences between the samples (ANOVA, Tukey, P<0.05).

FIG. 19A shows a comparison of the *L. japonicus* LYS11 ectodomain model (LYS11—model; left) with the crystal structure of the *L. japonicus* LYS11 ectodomain (LYS11—crystal structure; right) shaded with electrostatic surface potential. The molecular docking of a CO4 ligand (orange stick diagram) is shown, and the hydrophobic patch is circled by a dashed black line. FIG. 19B shows schematics of modified *L. japonicus* LYS11 ectodomains (*L. japonicus* LYS11/NFR5 chimeras) used for testing. The top schematic shows an ectodomain with entirely *L. japonicus* LYS11 domains (black), the middle schematic shows an ectodomain where the LysM2 domain from *L. japonicus* LYS11 was replaced with the LysM2 domain from *L. japonicus* NFR5 (grey), and the bottom schematic shows an ectodomain where key residues from *L. japonicus* LYS11 were replaced with key residues from *L. japonicus* NFR5 (grey) (N-terminus=N'; LysM1=M1; LysM2=M2; LysM3=M3; 6×HIS tag used for purification=6×HIS; C-terminus=C'). FIG. 19C shows the results of binding assays with the ectodomain with entirely *L. japonicus* jLYS11 components (ectodomain schematic shown at top with *L. japonicus* jLYS11 domains in black; results of binding assays shown at bottom). The Kd is shown in the title of each graph (CO5 (Kd=11.4 *M. loti* LCO (Kd=38.6 and *S. meliloti* LCO (weak binding)). FIG. 19D shows the results of binding assays with the ectodomain where LysM2 from *L. japonicus* LYS11 was replaced with LysM2 from *L.*

*japonicus* NFR5 (ectodomain schematic shown at top with *L. japonicus* LYS11 domains in black and *L. japonicus* NFR5 domains in grey; results of binding assays shown at bottom). FIG. 19E shows the results of binding assays with the ectodomain where key residues from *L. japonicus* LYS11 were replaced with key residues from *L. japonicus* NFR5 (ectodomain schematic shown at top with *L. japonicus* LYS11 domains in black and *L. japonicus* NFR5 residues in grey; results of binding assays shown at bottom). For FIGS. 19C-19E, binding in nm is shown on the y-axes, time in seconds (s) is shown on the x-axes, and the tested molecules are shown in the titles of the graphs (CO5, *M. loti* LCO, and *S. meliloti* LCO). FIG. 19F shows complementation of *L. japonicus* nfr5 (Ljnfr5) mutants with *L. japonicus* NFR5/LYS11 chimeras depicted at the bottom of the graph. Complementation was assayed by counting nodules formed per plant, which is shown at the top of FIG. 19F. Black dots represent individual plants, columns indicate the mean values, and error bars show the SEM. Different letters indicate significant difference among the samples (ANOVA, Tukey, P<0.01). The schematics of the individual chimeric ectodomains tested are shown at the bottom of FIG. 19F, with light grey indicating *L. japonicus* NFR5 domains, dark grey indicating *L. japonicus* LYS11 domains, and empty vector denoted by a label (LysM1, LysM2 and LysM3 are shown as boxes; transmembrane domain is shown as a wavy shape; kinase domain is shown as an oval shape). Below the receptor schematics, the number of plants (Plant), the number of plants without nodules (neg), the number of plants with nodules (pos), and the frequency (freq) of plants forming nodules when transformed with the depicted vector is provided.

FIGS. 20A-20D show models of chitin and Nod factor perception, and structural alignment of the ectodomains of *M. truncatula* NFP, *A. thaliana* CERK1 and *L. japonicus* CERK6. FIG. 20A shows a model of chitin perception by chitin receptors (e.g., *A. thaliana* CERK1). FIG. 20B shows a model of Nod factor perception by Nod factor receptors (e.g., *M. truncatula* NFP). FIG. 20C shows a model of Nod factor perception by hydrophobic patch mutant Nod factor receptors (e.g., *M. truncatula* NFP L147D L154D). FIG. 20D shows structural alignment of the ectodomains of *M. truncatula* NFP (*Medicago* NFP), *A. thaliana* CERK1 (*Arabidopsis* CERK1) and *L. japonicus* CERK6 (Lotus CERK6). Molecular fits (RMSD values) based on structural superposition of the ectodomains are shown in A (Angstrom). The structures (above) are shaded according to the schematic representation of the ectodomain (below). The conserved disulfide connectivity pattern between *M. truncatula* NFP, *A. thaliana* CERK1 and *L. japonicus* CERK6 is highlighted.

FIG. 21A shows the PyMol visualization of the LysM1, LysM2, and LysM3 domains of the *H. vulgare* LysM receptor RLK2 ectodomain (residues 37-247) model with the LysM1 domain labeled and in blue, the LysM2 domain labeled and in green, and the LysM3 domain labeled and in light grey. FIG. 21B shows the electrostatic surface potential of the model with chitin modeled in the binding groove.

DETAILED DESCRIPTION

Figure 1A:
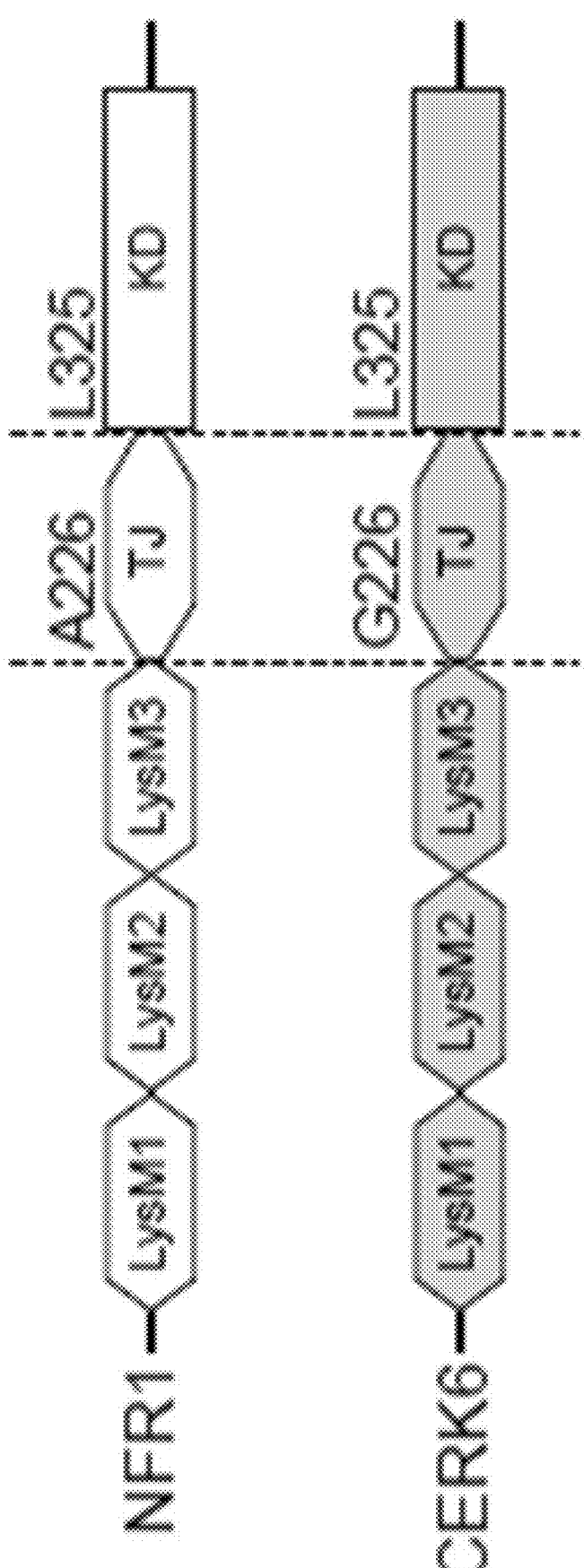
FIGS. 1A-1E show LysM receptor kinase proteins and expression constructs.
Figure 1B:
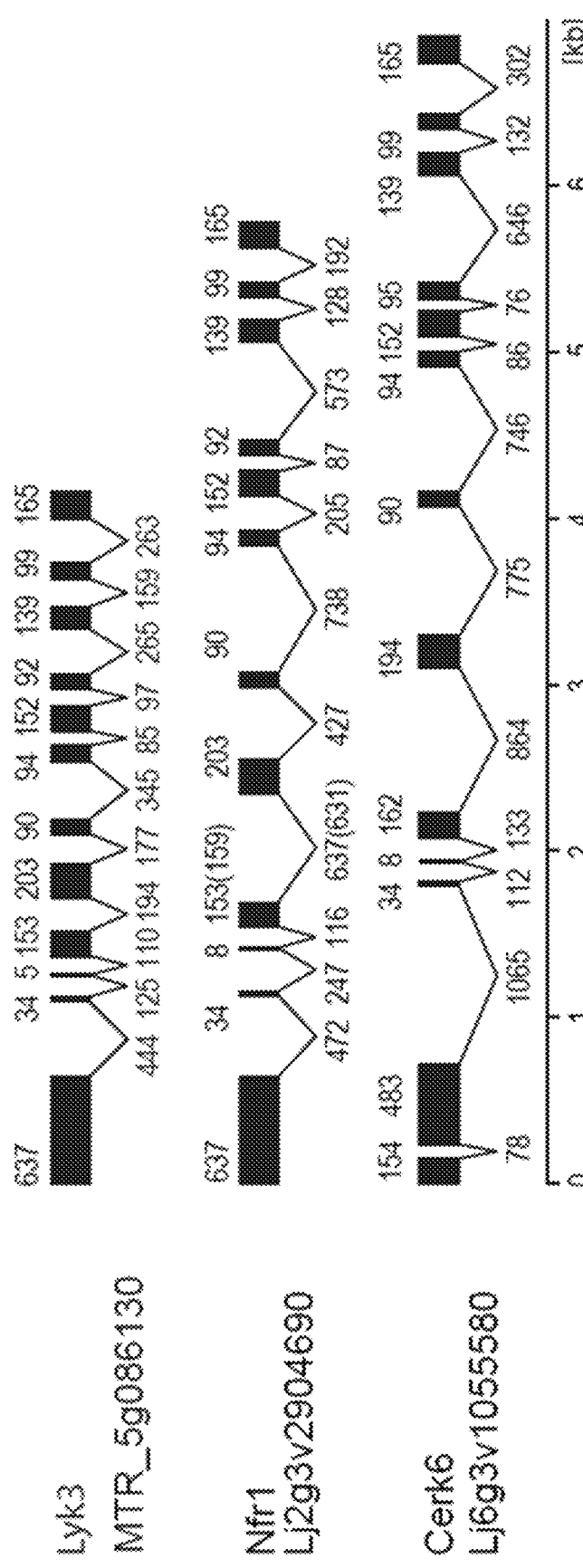
Figure 1C:
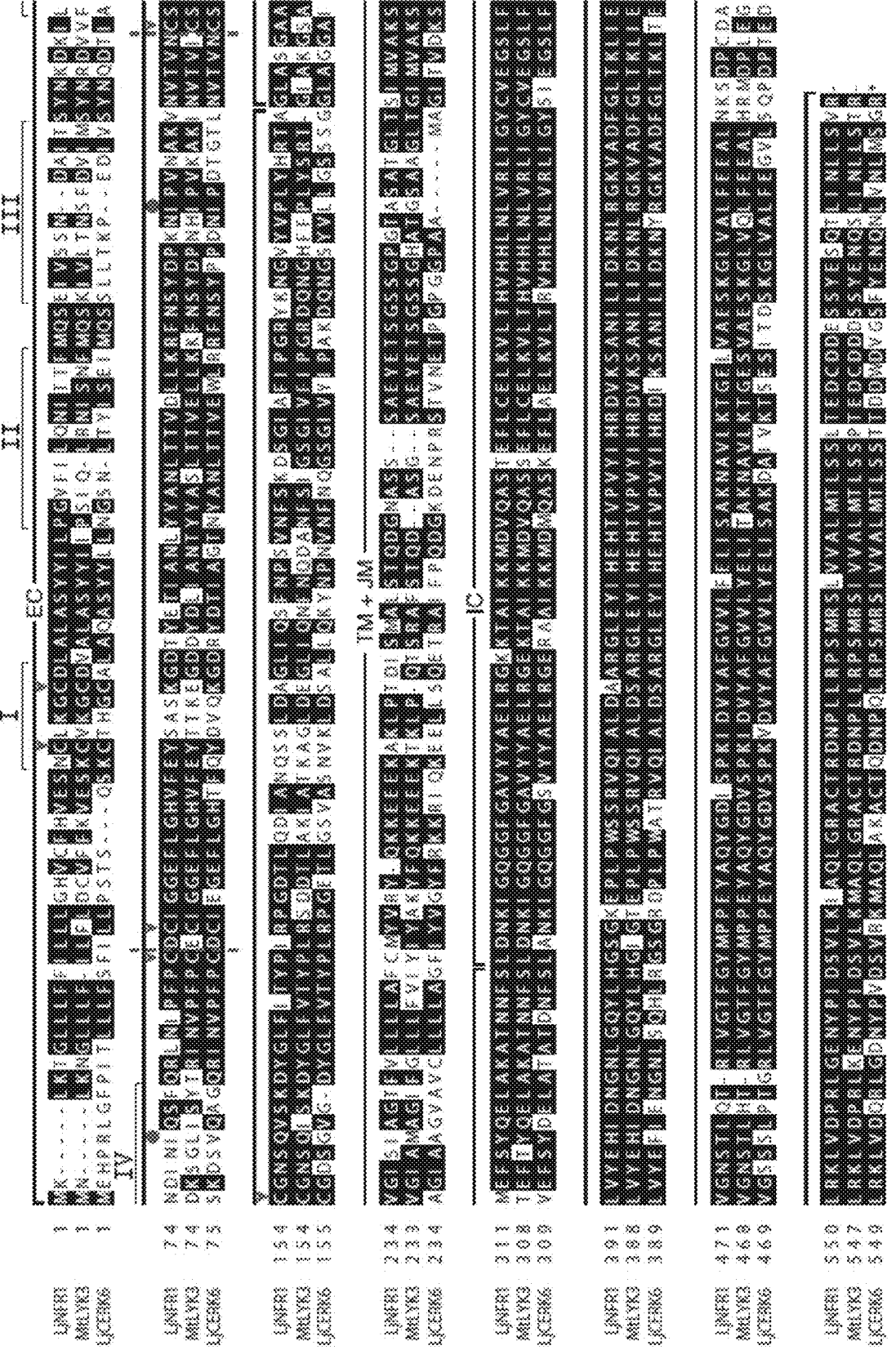

The following description sets forth exemplary methods, parameters, and the like. It should be recognized, however, that such description is not intended as a limitation on the scope of the present disclosure but is instead provided as a description of exemplary embodiments.

Modified Plant LysM Receptors

An aspect of the present disclosure includes a modified plant LysM receptor polypeptide including a LysM1 domain including a first motif and a second motif, wherein the first motif and/or the second motif are modified as compared to the amino acid sequences of the corresponding wild-type plant LysM receptor polypeptide. An additional embodiment of this aspect includes the first motif corresponding to amino acids 42-48 SEQ ID NO: 162 when the receptor polypeptide amino acid sequence is aligned to SEQ ID NO: 162 and the second motif corresponding to amino acids 75-80 of SEQ ID NO: 162 when the receptor polypeptide amino acid sequence is aligned to SEQ ID NO: 162. A further embodiment of this aspect includes the first motif corresponding to amino acids 44-49 of SEQ ID NO: 164 when the receptor polypeptide amino acid sequence is aligned to SEQ ID NO: 164 and the second motif corresponding to amino acids 76-81 of SEQ ID NO: 164 when the receptor polypeptide amino acid sequence is aligned to SEQ ID NO: 164. In yet another embodiment of this aspect, which may be combined with any of the preceding embodiments, the first motif is modified by substituting at least one, at least two, or at least three amino acid residues in the first motif with corresponding amino acid residues that are different in a third motif, and/or the second motif is modified by substituting at least one, at least two, or at least three amino acid residues in the second motif with corresponding amino acid residues that are different in a fourth motif. In still another embodiment of this aspect, which may be combined with any of the preceding embodiments, the first motif is modified by substituting the first motif with a third motif, and/or wherein the second motif is modified by substituting the second motif with a fourth motif. An additional embodiment of this aspect, which may be combined with any of the preceding embodiments that has the third motif and the fourth motif, includes the third motif and the fourth motif having different affinities, selectivities, and/or specificities for oligosaccharides than the first motif and the second motif. Oligosaccharides recognized by the first motif and the second motif may be chitins (chitooligosaccharides (COs)) or Nod factors (lipochitooligosaccharides (LCOs)), and oligosaccharides recognized by the third motif and the fourth motif may be Nod factors (lipochitooligosaccharides (LCOs)). A further embodiment of this aspect includes the third motif and the fourth motif have different affinities for oligosaccharides than the first motif and the second motif. Yet another embodiment of this aspect includes the third motif and the fourth motif having different selectivities for oligosaccharides than the first motif and the second motif. Still another embodiment of this aspect includes the third motif and the fourth motif having different specificities for oligosaccharides than the first motif and the second motif. In a further embodiment of this aspect, which may be combined with any of the preceding embodiments that has the third motif and the fourth motif, the third motif and the fourth motif are from a second plant LysM receptor polypeptide having the different affinity, selectivity and/or specificity for oligosaccharides and the third motif corresponds to amino acids 42-48 of SEQ ID NO: 162 when the second plant LysM polypeptide amino acid sequence is aligned to SEQ ID NO: 162 and the fourth motif corresponds to amino acids 75-80 of SEQ ID NO: 162 when the second plant LysM polypeptide amino acid sequence is aligned to SEQ ID NO: 162. The second plant LysM receptor may be a LysM Nod factor receptor, such as a LysM high affinity Nod factor receptor.

In an additional embodiment of this aspect, which may be combined with any of the preceding embodiments that has the third motif and the fourth motif, the third motif and the fourth motif are from a second plant LysM receptor polypeptide having the different affinity, selectivity and/or specificity for oligosaccharides and the third motif corresponds to amino acids 44-49 of SEQ ID NO: 164 when the second plant LysM polypeptide amino acid sequence is aligned to SEQ ID NO: 164 and the fourth motif corresponds to amino acids 76-81 of SEQ ID NO: 164 when the second plant LysM polypeptide amino acid sequence is aligned to SEQ ID NO: 164. In yet another embodiment of this aspect, which may be combined with any of the preceding embodiments that has the third motif and the fourth motif being from a second plant LysM receptor polypeptide having the different affinity, selectivity and/or specificity for oligosaccharides, at least one amino acid residue in flanking regions of the receptor polypeptide is different than the corresponding amino acid in the flanking regions of the second plant LysM receptor polypeptide and the flanking regions correspond to amino acids 41, 49-52, 73-74, and 81 of SEQ ID NO: 162, amino acids 47-53, 66-74, and 81-82 of SEQ ID NO: 163, and/or amino acids 43, 50-53, 74-75, and 82 of SEQ ID NO: 164.

In an additional embodiment of this aspect, which may be combined with any of the preceding embodiments, the first motif includes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341. In a further embodiment of this aspect, which may be combined with any of the preceding embodiments, the first motif includes SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142. In yet another embodiment of this aspect, the third motif includes SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341, and the first motif and the third motif are different. In still another embodiment of this aspect, the fourth motif includes SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142, and the second motif and the fourth motif are different.

Yet another embodiment of this aspect, which may be combined with any of the preceding embodiments, further includes a fifth motif in the LysM1 domain, wherein the fifth motif is modified. An additional embodiment of this aspect includes the fifth motif corresponding to amino acids 56-65 of SEQ ID NO: 162 when the receptor polypeptide amino acid sequence is aligned to SEQ ID NO: 162. In still another embodiment of this aspect, which may be combined with any of the preceding embodiments that has a fifth motif, the fifth motif is modified by substituting at least one, at least two, or at least three amino acid residues in the fifth motif with corresponding amino acid residues that are different in a sixth motif. In yet another embodiment of this aspect, which may be combined with any of the preceding embodiments that has a fifth motif, the fifth motif is substituted with a sixth motif. A further embodiment of this aspect, which may be combined with any of the preceding embodiments that has a sixth motif, includes the sixth motif being from a second plant LysM receptor polypeptide having the different specificity for oligosaccharides and the sixth motif corresponding to amino acids 56-65 of SEQ ID NO: 162 when the second plant LysM polypeptide amino acid sequence is aligned to SEQ ID NO: 162. Oligosaccharides recognized by the fifth motif and sixth motif may be Nod factors (lipochitooligosaccharides (LCOs)). In still another embodiment of this aspect, which may be combined with any of the preceding embodiments that has a fifth motif, the fifth motif includes SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120. In yet another embodiment of this aspect, which may be combined with any of the preceding embodiments that has a sixth motif, the sixth motif includes SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120, and the fifth motif and the sixth motif are different.

Still another embodiment of this aspect, which may be combined with any of the preceding embodiments, includes the modified receptor polypeptide binding one or more Nod factors (lipochitooligosaccharides (LCOs)) produced by nitrogen-fixing bacteria or by mycorrhizal fungi. An additional embodiment of this aspect, includes the one or more Nod factors being produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. In some embodiments, the Nod factors are *M. loti* LCO, *S. meliloti* LCO-IV, or *S. meliloti* LCO-V. A further embodiment of this aspect, which may be combined with any preceding embodiment that has one or more Nod factors produced by nitrogen-fixing bacteria or by mycorrhizal fungi, includes the modified receptor polypeptide binding one or more Nod factors with higher affinity than an unmodified receptor polypeptide. Yet another embodiment of this aspect, which may be combined with any preceding embodiment that has one or more Nod factors produced by nitrogen-fixing bacteria or by mycorrhizal fungi, includes the modified receptor polypeptide binding one or more Nod factors with higher selectivity than an unmodified receptor polypeptide. Still another embodiment of this aspect, which may be combined with any preceding embodiment that has one or more Nod factors produced by nitrogen-fixing bacteria or by mycorrhizal fungi, includes the modified receptor polypeptide binding one or more Nod factors with altered specificity as compared to an unmodified receptor polypeptide.

Yet another embodiment of this aspect, which may be combined with any of the preceding embodiments, further includes a LysM2 domain modified to include a hydrophobic patch on the surface of the LysM2 domain, wherein the modified plant LysM receptor polypeptide has enhanced affinity, selectivity, and/or specificity for one or more one or more Nod factors as compared to the unmodified plant LysM receptor polypeptide. An additional embodiment of this aspect includes the hydrophobic patch being within 30 Å, 20 Å, 10 Å, 7.5 Å, 5 Å, 4 Å, 3 Å, 2 Å, 1.5 Å, or 1 Å of a chitin binding motif. In a further embodiment of this aspect, which may be combined with any preceding embodiment that has a modified LysM2 domain, the LysM2 domain includes SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300. In yet another embodiment of this aspect, which may be combined with any preceding embodiment that has a modified LysM2 domain, the hydrophobic patch was generated by deleting at least one non-hydrophobic amino acid residue, substituting at least one amino acid residue with a more hydrophobic amino acid, or combinations thereof. Still another embodiment of this aspect, which may be combined with any preceding embodiment that has a LysM2 domain, includes the at least one amino acid being identified by an amino acid sequence alignment with a LysM2 domain from a LysM high affinity Nod factor receptor that naturally has a hydrophobic patch that interacts with a Nod factor. In an additional embodiment of this aspect, the LysM2 domain from a LysM high affinity Nod factor receptor includes SEQ ID NO: 271, SEQ ID NO: 272, SEQ ID NO: 273, SEQ ID NO: 274, SEQ ID NO: 275, SEQ ID NO: 276, or SEQ ID NO: 277. In a further embodiment of this aspect, which may be combined with any preceding embodiment that has a LysM2 domain from a LysM high affinity Nod factor receptor, the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258. In still another embodiment of this aspect, which may be combined with any preceding embodiment that has a LysM2 domain from a LysM high affinity Nod factor receptor, the at least one amino acid corresponds to residues immediately adjacent to hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258. In yet another embodiment of this aspect, which may be combined with any preceding embodiment that has a LysM2 domain from a LysM high affinity Nod factor receptor, the at least one amino acid corresponds to the hydrophobic patch residues from SEQ ID NO: 252, SEQ ID NO: 253, SEQ ID NO: 255, SEQ ID NO: 256, SEQ ID NO: 259, SEQ ID NO: 260, SEQ ID NO: 228, SEQ ID NO: 229, SEQ ID NO: 230, SEQ ID NO: 231, SEQ ID NO: 233, or SEQ ID NO: 234. In an additional embodiment of this aspect, which may be combined with any preceding embodiment that has a LysM2 domain from a LysM high affinity Nod factor receptor, the at least one amino acid corresponds to residues immediately adjacent to hydrophobic patch residues from SEQ ID NO: 252, SEQ ID NO: 253, SEQ ID NO: 255, SEQ ID NO: 256, SEQ ID NO: 259, SEQ ID NO: 260, SEQ ID NO: 228, SEQ ID NO: 229, SEQ ID NO: 230, SEQ ID NO: 231, SEQ ID NO: 233, or SEQ ID NO: 234.

Yet another embodiment of this aspect, which may be combined with any preceding embodiment where the hydrophobic patch was generated by deleting at least one non-hydrophobic amino acid residue, includes the at least one amino acid being identified by structural modeling to identify a region in LysM2 where the hydrophobic patch can be engineered. A further embodiment of this aspect includes the structural modeling using the unmodified plant LysM amino acid sequence and a LysM domain three dimensional structure that has a known hydrophobic patch. An additional embodiment of this aspect includes the LysM domain three dimensional structure being a *Medicago truncatula* NFP ectodomain. Still another embodiment of this aspect, which may be combined with any preceding embodiment that has a LysM domain three dimensional structure that has a known hydrophobic patch, includes the known hydrophobic patch amino acid residues of the LysM domain three dimensional structure being or correspond to L147, L151, L152, L154, T156, K157 and V158 of the *Medicago truncatula* NFP ectodomain. A further embodiment of this aspect includes the alpha carbon of at least one amino acid being within 3 Å of an alpha carbon of a known hydrophobic patch amino acid residue in the structural alignment. Yet another embodiment of this aspect, which may be combined with any preceding embodiment that has structural modeling, includes the structural modeling being performed using SWISS-MODEL, PDB2PQR, APBS, PyMol, and APBS tools 2.1. Still another embodiment of this aspect, which may be combined with any preceding embodiment that has a modified LysM2 domain, includes the modified receptor polypeptide binding one or more Nod factors (lipochitooligosaccharides (LCOs)) produced by nitrogen-fixing bacteria or by mycorrhizal fungi. A further embodiment of this aspect includes the one or more Nod factors being produced by nitrogen-fixing bacteria selected from the group of *Mesorhizobium loti, Mesorhizobium huakuii, Mesorhizobium mediterraneum, Mesorhizobium ciceri, Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae,* and *R. leguminosarum phaseoli,* Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. In some embodiments, the Nod factors are *M. loti* LCO, *S. meliloti* LCO-IV, or *S. meliloti* LCO-V. An additional embodiment of this aspect, which may be combined with any preceding embodiment that has one or more Nod factors produced by nitrogen-fixing bacteria or by mycorrhizal fungi, includes the modified receptor polypeptide binding one or more Nod factors with higher affinity than an unmodified receptor polypeptide. In yet another embodiment of this aspect, which may be combined with any preceding embodiment that has one or more Nod factors produced by nitrogen-fixing bacteria or by mycorrhizal fungi, the modified receptor polypeptide binds one or more Nod factors with higher selectivity than an unmodified receptor polypeptide. In still another embodiment of this aspect, which may be combined with any preceding embodiment that has one or more Nod factors produced by nitrogen-fixing bacteria or by mycorrhizal fungi, the modified receptor polypeptide binds one or more Nod factors with altered specificity as compared to an unmodified receptor polypeptide.

Figure 14A:
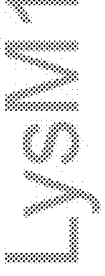
FIGS. 14A-14E show alignments and structural models of NFR1-type LysM Nod factor receptor kinase ectodomains.
Figure 14B:
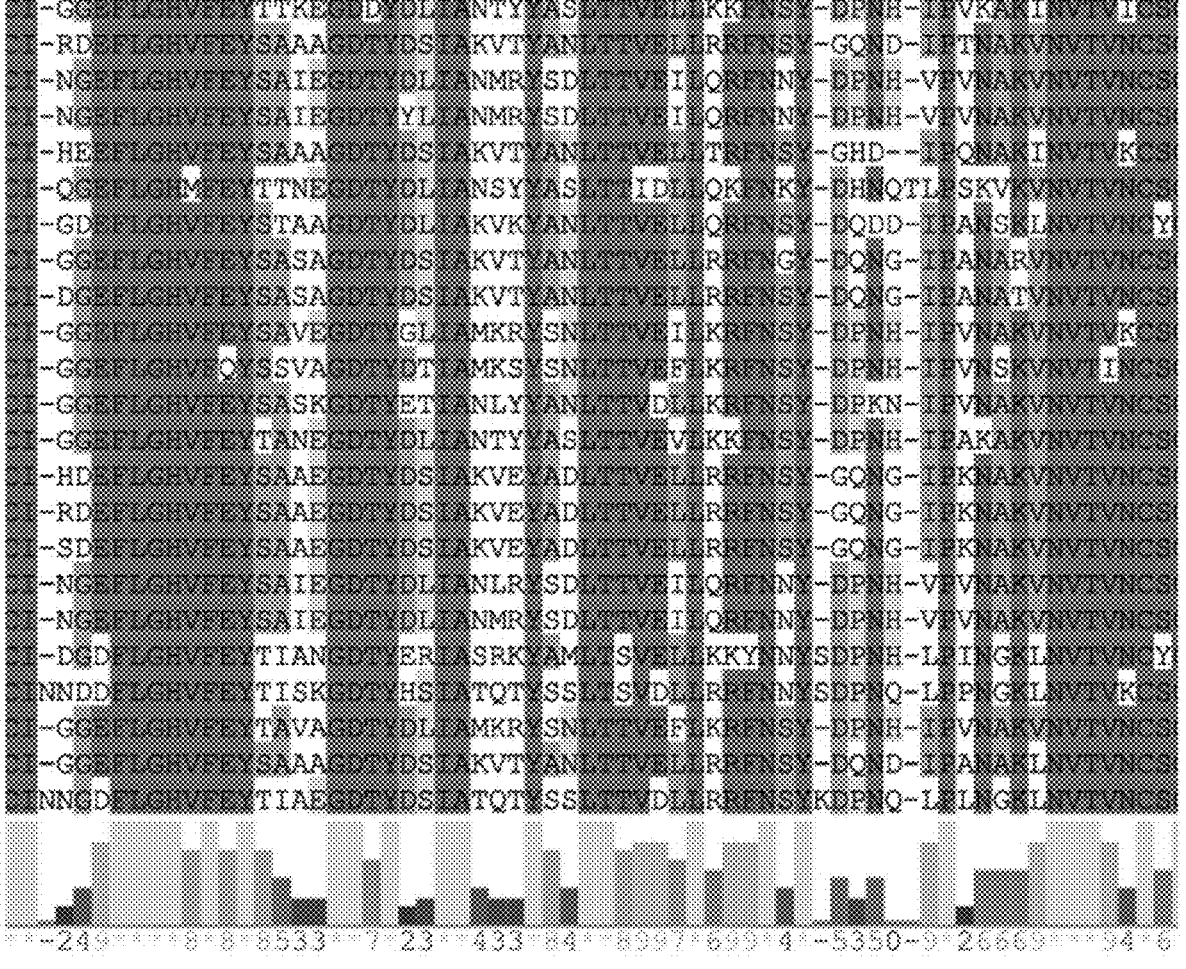
Figure 14C:
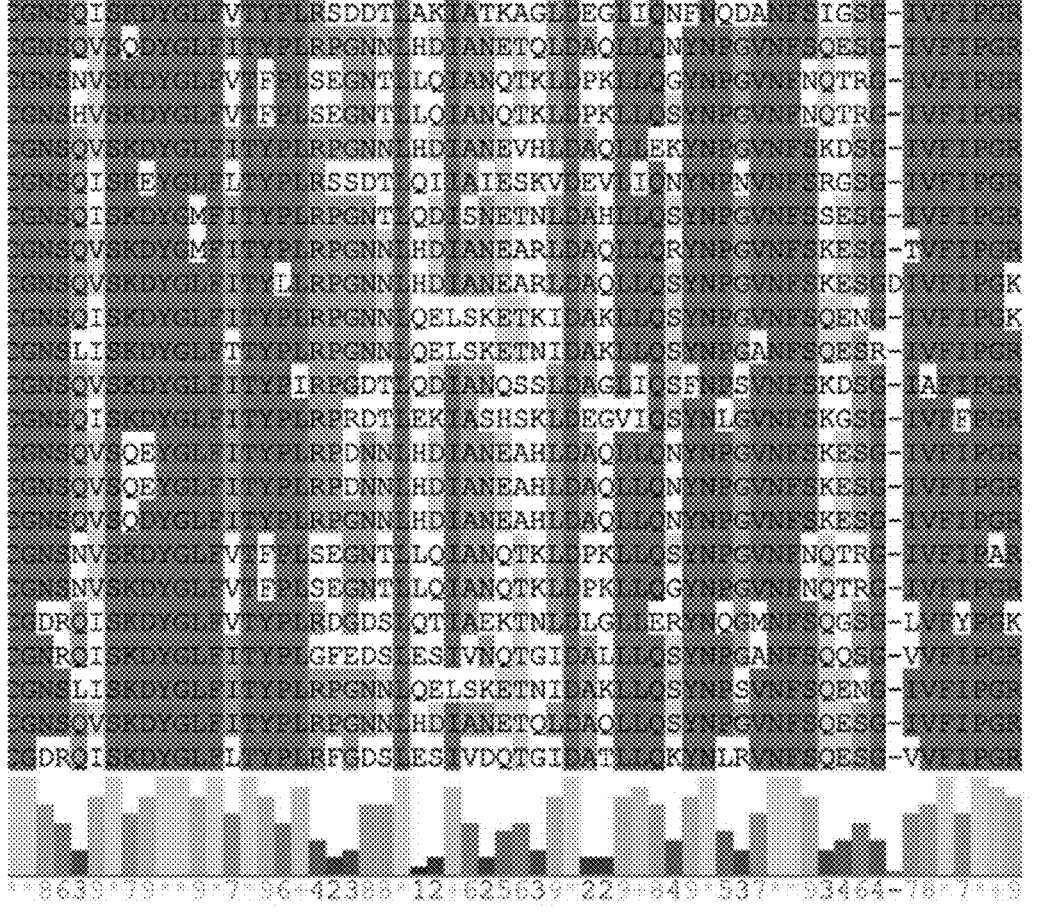
Figure 15A:
FIGS. 15A-15E show alignments and structural models of CERK6-type LysM chitin receptor kinase ectodomains.
Figure 15B:
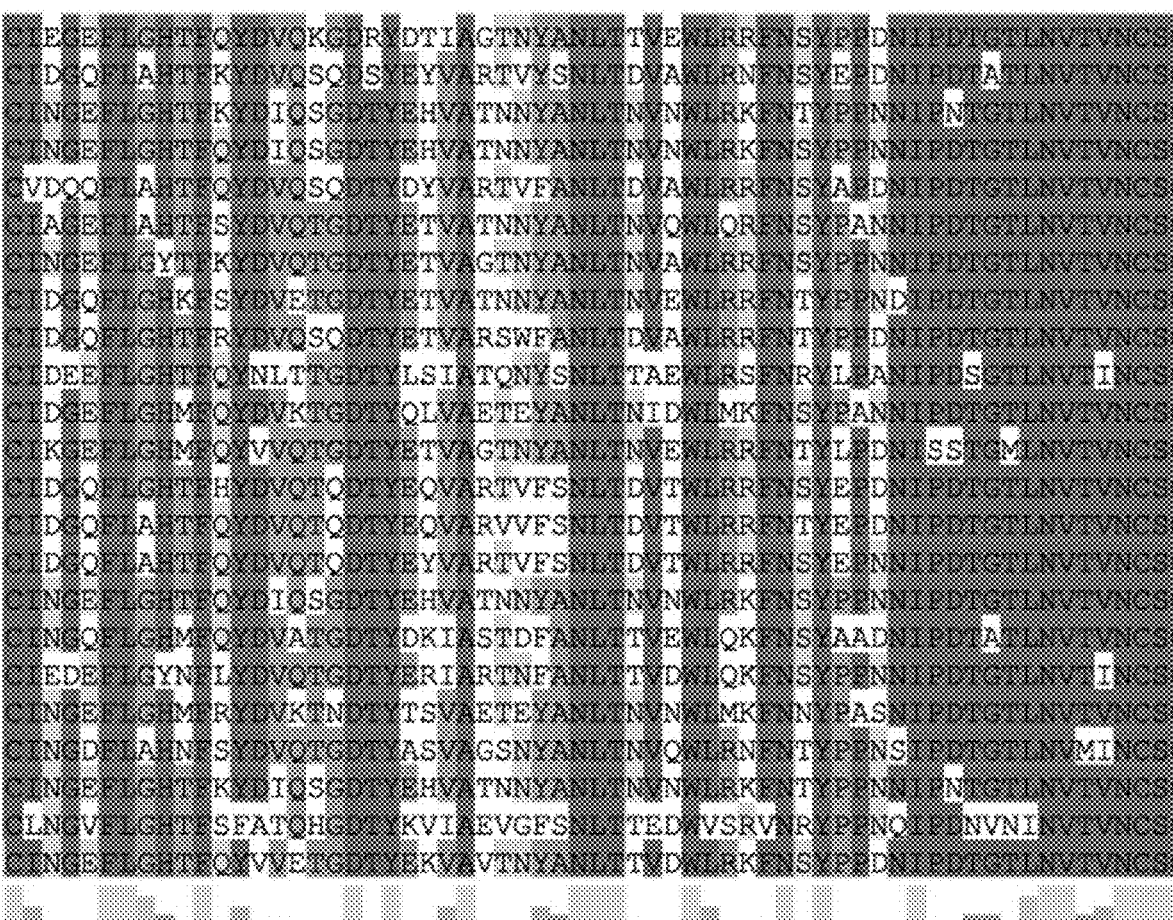
Figure 15C:
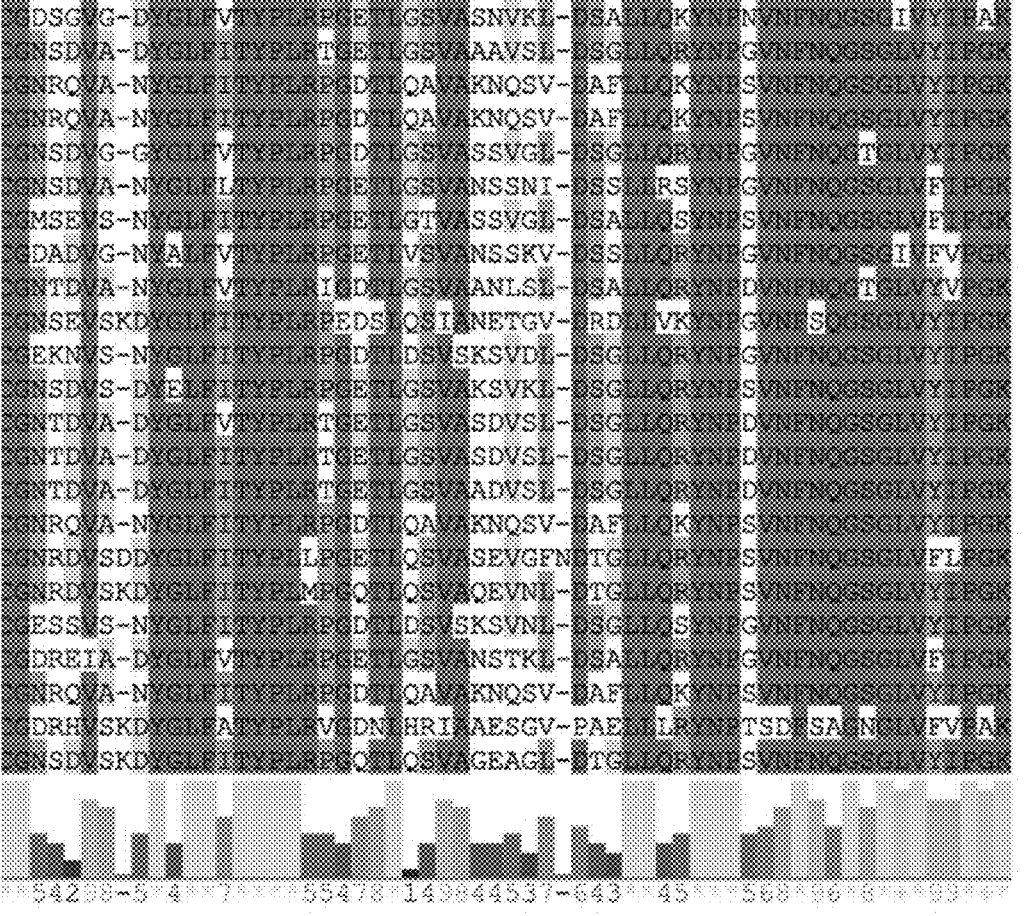

Plant LysM receptors are a well known and well understood type of receptor. LysM receptors have three characteristic domains located in the ectodomain of the protein: LysM1, LysM2, and LysM3, which are present in this order on the protein sequence and separated by CxC motifs (see FIG. 20D). The LysM1 domain is located toward the N-terminal end of the protein sequence, and is preceded by an N-terminal signal peptide. The three LysM domains are clearly shown in FIGS. 14A-14C and 15A-15C that show alignments of the ectodomains of NFR1-type LysM Nod factor receptors and CERK6-type LysM chitin receptors, respectively. FIGS. 14A-14C show an amino acid sequence alignment of NFR1-type LysM Nod factor receptor ectodomain sequences (FIG. 14A shows the LysM1 domain, FIG. 14B shows the LysM2 domain, and FIG. 14C shows the LysM3 domain). The ectodomain sequences and full length sequences of the aligned NFR1-type LysM Nod factor receptors are as follows: *Medicago truncatula* Q6UD73.1|LYK3 ectodomain=SEQ ID NO: 168, full length sequence=SEQ ID NO: 163; *Phaseolus vulgaris* XP_007141617.1 ectodomain=SEQ ID NO: 169, full length sequence=SEQ ID NO: 301; *Arachis hypogaea* XP_029150476.1 ectodomain=SEQ ID NO: 170, full length sequence=SEQ ID NO: 302; *Arachis hypogaea* XP_029144024.1 ectodomain=SEQ ID NO: 171, full length sequence=SEQ ID NO: 303; *Cajanus cajan* XP_020213700.2 ectodomain=SEQ ID NO: 172, full length sequence=SEQ ID NO: 304; *Cicer arietinum* XP_004491136.1 ectodomain=SEQ ID NO: 173, full length sequence=SEQ ID NO: 305; *Abrus precatorius* XP_027332267.1 ectodomain=SEQ ID NO: 174, full length sequence=SEQ ID NO: 306; *Glycine max* XP_006575588.1 ectodomain=SEQ ID NO: 175, full length sequence=SEQ ID NO: 307; *Glycine max* XP_006595821.2 ectodomain=SEQ ID NO: 176, full length sequence=SEQ ID NO: 308; *Lupinus angustifolius* XP_019434083.1 ectodomain=SEQ ID NO: 177, full length sequence=SEQ ID NO: 309; *Lupinus angustifolius* XP_019461629.1 ectodomain=SEQ ID NO: 178, full length sequence=SEQ ID NO: 310; *Lotus japonicus* CAE02590.1|NFR1 ectodomain=SEQ ID NO: 179, full length sequence=SEQ ID NO: 162; *Pisum sativum* ARX80051.1|Sym37 ectodomain=SEQ ID NO: 180, full length sequence=SEQ ID NO: 311; *Vigna angularis* KOM46748.1 ectodomain=SEQ ID NO: 181, full length sequence=SEQ ID NO: 312; *Vigna radiata* var. *radiata* XP_014504127.1 ectodomain=SEQ ID NO: 182, full length sequence=SEQ ID NO: 313; *Vigna unguiculata* XP_027939826.1 ectodomain=SEQ ID NO: 183, full length sequence=SEQ ID NO: 314; *Arachis duranensis* XP_020982945.1 ectodomain=SEQ ID NO: 184, full length sequence=SEQ ID NO: 315; *Arachis ipaensis* XP_020962820.1 ectodomain=SEQ ID NO: 185, full length sequence=SEQ ID NO: 316; *Chamaecrista fasciculata* 2879S20281 ectodomain=SEQ ID NO: 186, full length sequence=SEQ ID NO: 317; *Mimosa pudica* Scaffold15743 ectodomain=SEQ ID NO: 187, full length sequence=SEQ ID NO: 318; *Lupinus albus* Chr04g0249871 ectodomain=SEQ ID NO: 188, full length sequence=SEQ ID NO: 319; *Spatholobus suberectus* TKY57029.1 ectodomain=SEQ ID NO: 189, full length sequence=SEQ ID NO: 320; and *Prosopis alba* XP_028753017.1 ectodomain=SEQ ID NO: 190, full length sequence=SEQ ID NO: 321. FIGS. 15A-15C show an amino acid sequence alignment of CERK6-type LysM chitin receptor ectodomain sequences (FIG. 15A shows the LysM1 domain, FIG. 15B shows the LysM2 domain, and FIG. 15C shows the LysM3 domain). The ectodomain sequences and full length sequences of the aligned CERK6-type LysM chitin receptors are as follows: *Lotus japonicus* BAI79273.1|CERK6 ectodomain=SEQ ID NO: 191, full length sequence=SEQ ID NO: 164; *Phaseolus vulgaris* XP_007146026.1 ectodomain=SEQ ID NO: 192, full length sequence=SEQ ID NO: 322; *Arachis ipaensis* XP_016196976.1 ectodomain=SEQ ID NO: 193, full length sequence=SEQ ID NO: 323; *Arachis duranensis* XP_015958400.1 ectodomain=SEQ ID NO: 194, full length sequence=SEQ ID NO: 324; *Cajanus cajan* XP_020220445.1 ectodomain=SEQ ID NO: 195, full length sequence=SEQ ID NO: 325; *Cicer arietinum* XP_004502028.1 ectodomain=SEQ ID NO: 196, full length sequence=SEQ ID NO: 326; *Abrus precatorius* XP_027343427.1 ectodomain=SEQ ID NO: 197, full length sequence=SEQ ID NO: 327; *M. truncatula* XP_003601376.2|LYK9 ectodomain=SEQ ID NO: 198, full length sequence=SEQ ID NO: 216; *Glycine max* XP_003555584.1 ectodomain=SEQ ID NO: 199, full length sequence=SEQ ID NO: 328; *Glycine max* XP_003518454.1 ectodomain=SEQ ID NO: 200, full length sequence=SEQ ID NO: 329; *Lupinus angustifolius* XP_019425563.1 ectodomain=SEQ ID NO: 201, full length sequence=SEQ ID NO: 330; *Lupinus angustifolius* XP_019455825.1 ectodomain=SEQ ID NO: 202, full length sequence=SEQ ID NO: 331; *Vigna angularis* XP_017436810.1 ectodomain=SEQ ID NO: 203, full length sequence=SEQ ID NO: 332; *Vigna radiata* XP_014509761.1 ectodomain=SEQ ID NO: 204, full length sequence=SEQ ID NO: 333; *Vigna unguiculata* XP_027932400.1 ectodomain=SEQ ID NO: 205, full length sequence=SEQ ID NO: 334; *Arachis hypogaea* XP_025693415.1 ectodomain=SEQ ID NO: 206, full length sequence=SEQ ID NO: 334; *Mimosa pudica* Scaffold8584 ectodomain=SEQ ID NO: 207, full length sequence=SEQ ID NO: 335; *Chamaecrista fasciculata* QANZ01053660 ectodomain=SEQ ID NO: 208, full length sequence=SEQ ID NO: 336; *Lupinus albus* Chr04g0263521 ectodomain=SEQ ID NO: 209, full length sequence=SEQ ID NO: 337; *Pisum sativum* LYK9 ectodomain=SEQ ID NO: 210, full length sequence=SEQ ID NO: 338; *Arachis hypogaea* XP_025645378.1 ectodomain=SEQ ID NO: 211, full length sequence=SEQ ID NO: 323; *Spatholobus suberectus* TKY72192.1 ectodomain=SEQ ID NO: 212, full length sequence=SEQ ID NO: 339; and *Prosopis alba* XP_028758101.1 ectodomain=SEQ ID NO: 213, full length sequence=SEQ ID NO: 340. Additional LysM receptors include SEQ ID NO: 164, SEQ ID NO: 216, SEQ ID NO: 162, SEQ ID NO: 163, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, or SEQ ID NO: 248. The category of plant LysM receptors is therefore known by one of skill in the art.

As used in the present disclosure, the term "affinity" refers to affinity for Nod factors generally. The LysM receptors of the present disclosure may contain a modified motif in region II, a modified motif in region IV, and optionally a modified motif in region III of the LysM1 domain. The LysM1 domain is clearly shown in FIG. 14A that shows an alignment of NFR1-type LysM Nod factor receptors, and clearly designates region II, region III, and region IV within the LysM1 domain. Without wanting to be limited to theory, it is believed that LysM receptors with the modified motifs in regions of the LysM1 domain have higher affinity for Nod factors as compared to LysM receptors without the modified motifs, but LysM receptors with motif-swapped LysM1 domains would also provide higher affinity for Nod factors and other agonists. In addition, the LysM receptors of the present disclosure may contain a hydrophobic patch in their LysM2 domain. Without wanting to be limited to theory, it is believed that LysM receptors with the hydrophobic patch have higher affinity for LCOs as compared to LysM receptors without the hydrophobic patch, but LysM receptors with domain-swapped LysM1 domains would also provide higher affinity for LCOs and other agonists. Affinity can be measured using the methods described in the Examples below, and using other methods known in the art that measure binding kinetics, association, dissociation, and KD.

As used in the present disclosure, the term "selectivity" refers to the differentiation between different polysaccharide ligands, specifically between Nod factors (lipochitooligosaccharides (LCOs)) as a class and other polysaccharide ligands, preferably chitins (chitooligosaccharides (COs)). Without wanting to be limited to theory, it is believed that the modified motifs in regions of the LysM1 domain or motif-swapped LysM1 domains confer selective recognition of Nod factors over chitins, and that therefore LysM receptors with modified motifs have increased or altered selectivity as compared to LysM receptors without modified motifs. In addition, without wanting to be limited to theory, it is believed that the hydrophobic patch in LysM2 confers selective recognition of Nod factors over chitins, and that therefore LysM receptors with the hydrophobic patch have increased or altered selectivity as compared to LysM receptors without the hydrophobic patch.

As used in the present disclosure, the term "specificity" refers to the differentiation between different Nod factors (lipochitooligosaccharides (LCOs)) produced by different nitrogen-fixing bacterial species and/or mycorrhizal fungi. The LysM receptors of the present disclosure may contain a LysM1 domain where motifs in the LysM1 domain have been replaced with the corresponding motifs of the LysM1 domain from a donor LysM receptor. These motifs may be a motif in region II, a motif in region IV, and optionally a motif in region III. Without wanting to be limited to theory, it is believed that if the donor LysM receptor is a high affinity and specificity LysM Nod factor receptor such as a legume NFR1 LysM Nod factor receptor, this replacement can alter the specificity of the LysM receptor. LysM receptors with a hydrophobic patch in the LysM2 domain may also provide specificity for specific Nod factors. The LysM1 and LysM2 domains are clearly shown in FIGS. 14A-14C and 15A-15C that show alignments of the ectodomains of NFR1-type Nod factor receptors and CERK6-type chitin receptors, respectively. FIG. 14A clearly designates region II, region III, and region IV within the LysM1 domain. LysM1 motif modification and/or replacement can confer highly specific recognition of Nod factors produced by particular nitrogen-fixing bacterial species and/or mycorrhizal fungal species, and therefore LysM receptors with the modified and/or replaced domain can have altered specificity as compared to LysM receptors without the replaced domain, which allows the modified receptors to recognize different nitrogen-fixing bacterial species and/or mycorrhizal fungal species. For at least these reasons, the high affinity, high selectivity, and/or high specificity LysM receptors of the present disclosure will be readily understood by one of skill in the art.

Genetically Altered Plants and Plant Parts

A further aspect of the present disclosure includes a genetically altered plant or part thereof, including a modified plant LysM receptor of any one of the embodiments described in the section "Modified plant LysM receptors". An additional embodiment of this aspect includes the modified LysM receptor polypeptide having higher affinity, higher selectivity, and/or altered specificity for one or more Nod factors than an unmodified LysM receptor polypeptide and the expression of the modified LysM receptor polypeptide allowing the plant or part thereof to recognize one or more Nod factors with high affinity, high selectivity, and/or altered specificity. Yet another embodiment of this aspect, which may be combined with any one of the preceding embodiments, includes the one or more Nod factors (lipochitooligosaccharides (LCOs)) are produced by nitrogen-fixing bacteria or by mycorrhizal fungi. A further embodiment of this aspect includes the one or more Nod factors produced by nitrogen-fixing bacteria being selected from the group of Mesorhizobium loti, Mesorhizobium huakuii, Mesorhizobium mediterraneum, Mesorhizobium ciceri, Mesorhizobium spp., Rhizobium mongolense, Rhizobium tropici, Rhizobium etli phaseoli, Rhizobium giardinii, Rhizobium leguminosarum optionally R. leguminosarum trifolii, R. leguminosarum viciae, and R. leguminosarum phaseoli, Burkholderiales optionally symbionts of Mimosa, Sinorhizobium meliloti, Sinorhizobium medicae, Sinorhizobium fredii, Sinorhizobium NGR234, Azorhizobium caulinodans, Bradyrhizobium japonicum, Bradyrhizobium elkanii, Bradyrhizobium liaonginense, Frankia spp., or any combination thereof, or by mycorrhizal fungi selected from the group of Acaulosporaceae spp., Diversisporaceae spp., Gigasporaceae spp., Pacisporaceae spp., Funneliformis spp., Glomus spp., Rhizophagus spp., Sclerocystis spp., Septoglomus spp., Claroideoglomus spp., Ambispora spp., Archaeospora spp., Geosiphon pyriformis, Paraglomus spp., other species in the division Glomeromycota, or any combination thereof. In some embodiments, the Nod factors are M. loti LCO, S. meliloti LCO-IV, or S. meliloti LCO-V. Still another embodiment of this aspect, which may be combined with any one of the preceding embodiments, includes the modified LysM receptor polypeptide being localized to a plant cell plasma membrane. Yet another embodiment of this aspect includes the plant cell being a root cell. An additional embodiment of this aspect includes the root cell being a root epidermal cell. A further embodiment of this aspect, which may be combined with any of the preceding embodiments includes the modified LysM receptor polypeptide being expressed in a developing plant root system. An additional embodiment of this aspect, which may be combined with any of the preceding embodiments, includes a nucleic acid sequence encoding the modified LysM receptor polypeptide, wherein the nucleic acid sequence is operably linked to a promoter. Still another embodiment of this aspect includes the promoter being a root specific promoter, a constitutive promoter, or a combination thereof. In yet another embodiment of this aspect, which may be combined with any preceding embodiment that has a promoter, the promoter is selected from the group of a NFR1 promoter, a NFR5/NFP promoter, a LYK3 promoter, a CERK6 promoter, a NFR5/NFP promoter, a Lotus japonicus NFR5 promoter (SEQ ID NO: 261), a Lotus japonicus NFR1 promoter (SEQ ID NO: 261), a Lotus japonicus CERK6 promoter (SEQ ID NO: 264), a Medicago truncatula NFP promoter (SEQ ID NO: 263), a Medicago truncatula LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. In an additional embodiment of this aspect, which may be combined with any preceding embodiment that has a promoter, the promoter is selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter.

An additional aspect of the present disclosure includes a genetically altered plant or part thereof including a first modified LysM receptor polypeptide of any one of the preceding embodiments and a second modified LysM receptor polypeptide including a LysM2 domain modified to include a hydrophobic patch on the surface of the LysM2 domain, wherein the second modified plant LysM receptor polypeptide has enhanced affinity, selectivity, and/or specificity for one or more Nod factors as compared to a second unmodified plant LysM receptor polypeptide. An additional embodiment of this aspect includes the hydrophobic patch being within 30 Å, 20 Å, 10 Å, 7.5 Å, 5 Å, 4 Å, 3 Å, 2 Å, 1.5 Å, or 1 Å of a chitin binding motif. In a further embodiment of this aspect, which may be combined with any of the preceding embodiments, the LysM2 domain includes SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, or SEQ ID NO: 300. In yet another embodiment of this aspect, which may be combined with any one of the preceding embodiments, the hydrophobic patch was generated by deleting at least one non-hydrophobic amino acid residue, substituting at least one amino acid residue with a more hydrophobic amino acid, or combinations thereof. Still another embodiment of this aspect, which may be combined with any one of the preceding embodiments, includes the at least one amino acid being identified by an amino acid sequence alignment with a LysM2 domain from a LysM high affinity Nod factor receptor that naturally has a hydrophobic patch that interacts with a Nod factor. In an additional embodiment of this aspect, the LysM2 domain from a LysM high affinity Nod factor receptor includes SEQ ID NO: 271, SEQ ID NO: 272, SEQ ID NO: 273, SEQ ID NO: 274, SEQ ID NO: 275, SEQ ID NO: 276, or SEQ ID NO: 277. In a further embodiment of this aspect, which may be combined with any preceding embodiment that has a LysM2 domain from a LysM high affinity Nod factor receptor, the at least one amino acid corresponds to the hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258. In still another embodiment of this aspect, which may be combined with any preceding embodiment that has a LysM2 domain from a LysM high affinity Nod factor receptor, the at least one amino acid corresponds to residues immediately adjacent to hydrophobic patch residues from SEQ ID NO: 223, SEQ ID NO: 249, SEQ ID NO: 250, SEQ ID NO: 251, SEQ ID NO: 254, SEQ ID NO: 257, or SEQ ID NO: 258. In yet another embodiment of this aspect, which may be combined with any preceding embodiment that has a LysM2 domain from a LysM high affinity Nod factor receptor, the at least one amino acid corresponds to the hydrophobic patch residues from SEQ ID NO: 252, SEQ ID NO: 253, SEQ ID NO: 255, SEQ ID NO: 256, SEQ ID NO: 259, SEQ ID NO: 260, SEQ ID NO: 228, SEQ ID NO: 229, SEQ ID NO: 230, SEQ ID NO: 231, SEQ ID NO: 233, or SEQ ID NO: 234. In an additional embodiment of this aspect, which may be combined with any preceding embodiment that has a LysM2 domain from a LysM high affinity Nod factor receptor, the at least one amino acid corresponds to residues immediately adjacent to hydrophobic patch residues from SEQ ID NO: 252, SEQ ID NO: 253, SEQ ID NO: 255, SEQ ID NO: 256, SEQ ID NO: 259, SEQ ID NO: 260, SEQ ID NO: 228, SEQ ID NO: 229, SEQ ID NO: 230, SEQ ID NO: 231, SEQ ID NO: 233, or SEQ ID NO: 234. Yet another embodiment of this aspect, which may be combined with any preceding embodiment where the hydrophobic patch was generated by deleting at least one non-hydrophobic amino acid residue, includes the at least one amino acid being identified by structural modeling to identify a region in LysM2 where the hydrophobic patch can be engineered. A further embodiment of this aspect includes the structural modeling using the unmodified plant LysM amino acid sequence and a LysM domain three dimensional structure that has a known hydrophobic patch. An additional embodiment of this aspect includes the LysM domain three dimensional structure being a *Medicago truncatula* NFP ectodomain. Still another embodiment of this aspect, which may be combined with any preceding embodiment that has a LysM domain three dimensional structure that has a known hydrophobic patch, includes the known hydrophobic patch amino acid residues of the LysM domain three dimensional structure being or correspond to L147, L151, L152, L154, T156, K157 and V158 of the *Medicago truncatula* NFP ectodomain. A further embodiment of this aspect includes the alpha carbon of at least one amino acid being within 3 Å of an alpha carbon of a known hydrophobic patch amino acid residue in the structural alignment. Yet another embodiment of this aspect, which may be combined with any preceding embodiment that has structural modeling, includes the structural modeling being performed using SWISS-MODEL, PDB2PQR, APBS, PyMol, and APBS tools 2.1. Still another embodiment of this aspect, which may be combined with any of the preceding embodiments, includes the modified receptor polypeptide binding one or more Nod factors (lipochitooligosaccharides (LCOs)) produced by nitrogen-fixing bacteria or by mycorrhizal fungi. A further embodiment of this aspect includes the one or more Nod factors being produced by nitrogen-fixing bacteria selected from the group of *Mesorhizobium loti, Mesorhizobium huakuii, Mesorhizobium mediterraneum, Mesorhizobium* ciceri, *Mesorhizobium* spp., *Rhizobium mongolense, Rhizobium tropici, Rhizobium etli phaseoli, Rhizobium giardinii, Rhizobium leguminosarum* optionally *R. leguminosarum trifolii, R. leguminosarum viciae*, and *R. leguminosarum phaseoli*, Burkholderiales optionally symbionts of *Mimosa, Sinorhizobium meliloti, Sinorhizobium medicae, Sinorhizobium fredii, Sinorhizobium* NGR234, *Azorhizobium caulinodans, Bradyrhizobium japonicum, Bradyrhizobium elkanii, Bradyrhizobium liaonginense, Frankia* spp., or any combination thereof, or by mycorrhizal fungi selected from the group of *Acaulosporaceae* spp., *Diversisporaceae* spp., *Gigasporaceae* spp., *Pacisporaceae* spp., *Funneliformis* spp., *Glomus* spp., *Rhizophagus* spp., *Sclerocystis* spp., *Septoglomus* spp., *Claroideoglomus* spp., *Ambispora* spp., *Archaeospora* spp., *Geosiphon pyriformis, Paraglomus* spp., other species in the division Glomeromycota, or any combination thereof. In some embodiments, the Nod factors are *M. loti* LCO, *S. meliloti* LCO-IV, or *S. meliloti* LCO-V. An additional embodiment of this aspect, which may be combined with any preceding embodiment that has one or more Nod factors produced by nitrogen-fixing bacteria or by mycorrhizal fungi, includes the second modified receptor polypeptide binding one or more Nod factors with higher affinity than a second unmodified receptor polypeptide. In yet another embodiment of this aspect, which may be combined with any preceding embodiment that has one or more Nod factors produced by nitrogen-fixing bacteria or by mycorrhizal fungi, the second modified receptor polypeptide binds one or more Nod factors with higher selectivity than a second unmodified receptor polypeptide. In still another embodiment of this aspect, which may be combined with any preceding embodiment that has one or more Nod factors produced by nitrogen-fixing bacteria or by mycorrhizal fungi, the second modified receptor polypeptide binds one or more Nod factors with altered specificity as compared to a second unmodified receptor polypeptide. Still another embodiment of this aspect, which may be combined with any one of the preceding embodiments, includes the modified LysM receptor polypeptides being localized to a plant cell plasma membrane. Yet another embodiment of this aspect includes the plant cell being a root cell. An additional embodiment of this aspect includes the root cell being a root epidermal cell. A further embodiment of this aspect, which may be combined with any of the preceding embodiments, includes the modified LysM receptor polypeptides being expressed in a developing plant root system. An additional embodiment of this aspect, which may be combined with any of the preceding embodiments, includes a first nucleic acid sequence encoding the first modified plant LysM receptor polypeptide and a second nucleic acid sequence encoding the second modified plant LysM receptor polypeptide, wherein the first nucleic acid sequence is operably linked to a first promoter, and wherein the second nucleic acid sequence is operably linked to a second promoter. Still another embodiment of this aspect includes the first and second promoters being root specific promoters, constitutive promoters, or a combination thereof. In yet another embodiment of this aspect, which may be combined with any preceding embodiment that has a promoter, the first and/or second promoters are selected from the group of a NFR1 promoter, a NFR5/NFP promoter, a LYK3 promoter, a CERK6 promoter, a NFR5NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. In an additional embodiment of this aspect, which may be combined with any preceding embodiment that has a promoter, the first and/or second promoters are selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter.

In an additional embodiment of this aspect, which may be combined with any of the preceding embodiments, the plant is selected from the group of cassava (e.g., manioc, *yucca, Manihot esculenta*), corn (e.g., maize, *Zea mays*), rice (e.g., indica rice, *japonica* rice, aromatic rice, glutinous rice, *Oryza sativa, Oryza glaberrima*), wild rice (e.g., *Zizania* spp., *Porteresia* spp.), barley (e.g., *Hordeum vulgare*), sorghum (e.g., *Sorghum bicolor*), millet (e.g., finger millet, fonio millet, foxtail millet, pearl millet, barnyard millets,

*Eleusine coracana, Panicum sumatrense, Panicum milaceum, Setaria italica, Pennisetum glaucum, Digitaria* spp., *Echinocloa* spp.), teff (e.g., *Eragrostis tef*), oat (e.g., *Avena sativa*), triticale (e.g., X *Triticosecale* Wittmack, *Triticosecale schlanstedtense* Wittm., *Triticosecale neoblaringhemii* A. Camus, *Triticosecale neoblaringhemii* A. Camus), rye (e.g., *Secale cereale, Secale cereanum*), wheat (e.g., common wheat, spelt, durum, einkorn, emmer, kamut, *Triticum aestivum, Triticum spelta, Triticum durum, Triticum urartu, Triticum monococcum, Triticum turanicum, Triticum* spp.), *Trema* spp. (e.g., *Trema cannabina, Trema cubense, Trema discolor, Trema domingensis, Trema integerrima, Trema lamarckiana, Trema micrantha, Trema orientalis, Trema philippinensis, Trema strigilosa, Trema tomentosa, Trema levigata*), apple (e.g., *Malus domestica, Malus pumila, Pyrus malus*), pear (e.g., *Pyrus communis, Pyrus×bretschneideri, Pyrus pyrifolia, Pyrus sinkiangensis, Pyrus pashia, Pyrus* spp.), plum (e.g., Mirabelle, greengage, damson, *Prunus domestica, Prunus salicina, Prunus* mume), apricot (e.g., *Prunus armeniaca, Prunus brigantine, Prunus mandshurica*), peach (e.g., *Prunus persica*), almond (e.g., *Prunus dukis, Prunus amygdalus*), walnut (e.g., Persian walnut, English walnut, black walnut, *Juglans regia, Juglans nigra, Juglans cinerea, Juglans californica*), strawberry (e.g., *Fragaria×xananassa, Fragaria chiloensis, Fragaria virginiana, Fragaria vesca*), raspberry (e.g., European red raspberry, black raspberry, *Rubus idaeus* L., *Rubus occidentalis, Rubus strigosus*), blackberry (e.g., evergreen blackberry, Himalayan blackberry, *Rubus fruticosus, Rubus ursinus, Rubus laciniatus, Rubus argutus, Rubus armeniacus, Rubus plicatus, Rubus ulmifolius, Rubus allegheniensis, Rubus* subgenus *Eubatus* sect. Moriferi & Ursini), red currant (e.g., white currant, *Ribes rubrum*), black currant (e.g., cassis, *Ribes nigrum*), gooseberry (e.g., *Ribes uva-crispa, Ribes grossulari, Ribes hirtellum*), melon (e.g., watermelon, winter melon, casabas, cantaloupe, honeydew, muskmelon, *Citrullus lanatus, Benincasa hispida, Cucumis melo, Cucumis melo cantalupensis, Cucumis melo inodorus, Cucumis melo reticulatus*), cucumber (e.g., slicing cucumbers, pickling cucumbers, English cucumber, *Cucumis sativus*), pumpkin (e.g., *Cucurbita pepo, Cucurbita maxima*), squash (e.g., gourd, *Cucurbita argyrosperma, Cucurbita ficifolia, Cucurbita maxima, Cucurbita moschata*), grape (e.g., *Vitis vinifera, Vitis amurensis, Vitis labrusca, Vitis mustangensis, Vitis riparia, Vitis rotundifolia*), bean (e.g., *Phaseolus vulgaris, Phaseolus lunatus, Vigna angularis, Vigna radiate, Vigna mungo, Phaseolus coccineus, Vigna umbellate, Vigna acontifolia, Phaseolus acutifolius, Vicia faba, Vicia faba* equine, *Phaseolus* spp., *Vigna* spp.), soybean (e.g., soy, soya bean, *Glycine max, Glycine soja*), pea (e.g., *Pisum* spp., *Pisum sativum* var. *sativum, Pisum sativum* var. *arvense*), pea (e.g., *Pisum* spp., *Pisum sativum* var. *sativum, Pisum sativum* var. *arvense*), chickpea (e.g., garbanzo, Bengal gram, *Cicer arietinum*), cowpea (e.g., *Vigna unguiculata*), pigeon pea (e.g., Arhar/Toor, caj an pea, Congo bean, gandules, *Caganus cajan*), lentil (e.g., *Lens culinaris*), Bambara groundnut (e.g., earth pea, *Vigna subterranea*), lupin (e.g., *Lupinus* spp.), pulses (e.g., minor pulses, *Lablab purpureaus, Canavalia ensiformis, Canavalia gladiate, Psophocarpus tetragonolobus, Mucuna pruriens* var. *utilis, Pachyrhizus* erosus), *Medicago* spp. (e.g., *Medicago sativa, Medicago truncatula, Medicago arborea*), *Lotus* spp. (e.g., *Lotus japonicus*), forage legumes (e.g., *Leucaena* spp., *Albizia* spp., *Cyamopsis* spp., *Sesbania* spp., *Stylosanthes* spp., *Trifolium* spp., *Vicia* spp.), indigo (e.g., *Indigofera* spp., *Indigofera tinctoria, Indigofera suffruticosa, Indigofera articulata, Indigofera oblongifolia*,

*Indigofera aspalthoides, Indigofera suffruticosa, Indigofera arrecta*), legume trees (e.g., locust trees, *Gleditsia* spp., *Robinia* spp., Kentucky coffeetree, *Gymnocladus dioicus, Acacia* spp., *Laburnum* spp., *Wisteria* spp.), or hemp (e.g., *cannabis, Cannabis sativa*). In a further embodiment of this aspect, which may be combined with any of the preceding embodiments, the plant part is a leaf, a stem, a root, a root primordia, a flower, a seed, a fruit, a kernel, a grain, a cell, or a portion thereof. An additional embodiment of this aspect includes the plant part being a fruit, a kernel, or a grain.

In some aspects, the present disclosure relates to a pollen grain or an ovule of the genetically altered plant of any of the above embodiments.

In some aspects, the present disclosure relates to a protoplast produced from the plant of any of the above embodiments.

In some aspects, the present disclosure relates to a tissue culture produced from protoplasts or cells from the plant of any of the above embodiments, wherein the cells or protoplasts are produced from a plant part selected from the group of leaf, anther, pistil, stem, petiole, root, root primordia, root tip, fruit, seed, flower, cotyledon, hypocotyl, embryo, or meristematic cell.

An additional embodiment of any of the above genetically altered plants includes the genetic alteration allowing the genetically altered plant to recognize a different specific nitrogen-fixing bacterial species and/or specific mycorrhizal fungal species as compared to a plant without the genetic alteration. Still another embodiment of any of the above genetically altered plants includes the genetic alteration providing the plant with the ability to recognize one or more Nod factors produced by nitrogen-fixing bacteria and/or mycorrhizal fungi with high affinity, high selectivity, and/or high specificity. In an additional embodiment of this aspect, the plant is transplanted into conditions where the ability to recognize the one or more Nod factors produced by nitrogen-fixing bacteria and/or mycorrhizal fungi results in increased growth, yield, and/or biomass, as compared to a plant grown under the same conditions that lacks the one or more genetic alterations. In some embodiments, the plant is cultivated in nutrient-poor soil. A further embodiment of any of the above genetically altered plants includes the genetically altered plant being able to be grown in different agricultural conditions (e.g., different soils containing different symbiotic microbial species, etc.). Still another embodiment of this aspect includes the genetic alteration providing the plant with specific recognition of one or more Nod factors produced by a specific nitrogen-fixing bacterial species and/or specific mycorrhizal fungal species, whereby that species may already be present in the soil or may be provided (e.g., via seed treatment, spray application, soil inoculum, etc.). Yet another embodiment of any of the above genetically altered plants includes the genetically altered plant being able to be grown with different crop species (e.g., different crop rotations, etc.).

Methods of Producing and Cultivating Genetically Altered Plants

A further aspect of the present disclosure relates to methods of producing the genetically altered plant of the preceding embodiments including the modified LysM receptor polypeptide, including introducing a genetic alteration to the plant including a nucleic acid sequence encoding the modified LysM receptor polypeptide. An additional embodiment of this aspect includes the nucleic acid sequence being operably linked to a promoter. Yet another embodiment of this aspect includes the promoter being a root specific promoter, a constitutive promoters, or a combination thereof. Still another embodiment of this aspect, which may be combined with any preceding embodiment that has a promoter, includes the promoter being selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. Still another embodiment of this aspect, which may be combined with any preceding embodiment that has a promoter, includes the promoter is selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter. An additional embodiment of this aspect, which may be combined with any of the preceding embodiments, includes the nucleic acid sequence being inserted into the genome of the plant so that the nucleic acid sequence is operably linked to an endogenous promoter. A further embodiment of this aspect includes the endogenous promoter being a root specific promoter. A further embodiment of this aspect that can be combined with any of the preceding embodiments includes a plant or plant part produced by the method of any one of the preceding embodiments.

A further aspect of the present disclosure relates to methods of producing the genetically altered plant of the preceding embodiments including a first modified LysM receptor polypeptide and a second LysM receptor polypeptide, including introducing a genetic alteration to the plant including a first nucleic acid sequence encoding the first modified LysM receptor polypeptide and introducing a genetic alteration to the plant including a second nucleic acid sequence encoding the second modified LysM receptor polypeptide. An additional embodiment of this aspect includes the first nucleic acid sequence being operably linked to a first promoter, and the second nucleic acid sequence being operably linked to a second promoter. Yet another embodiment of this aspect includes the first and second promoters being root specific promoters, constitutive promoters, or a combination thereof. Still another embodiment of this aspect, which may be combined with any preceding embodiment that has a promoter, includes the first and/or second promoters are selected from the group of a NFR1 promoter, a NFR5/NFP promoter, a LYK3 promoter, a CERK6 promoter, a NFR5/NFP promoter, a *Lotus japonicus* NFR5 promoter (SEQ ID NO: 261), a *Lotus japonicus* NFR1 promoter (SEQ ID NO: 261), a *Lotus japonicus* CERK6 promoter (SEQ ID NO: 264), a *Medicago truncatula* NFP promoter (SEQ ID NO: 263), a *Medicago truncatula* LYK3 promoter (SEQ ID NO: 262), a maize allothioneine promoter, a chitinase promoter, a maize ZRP2 promoter, a tomato LeExtl promoter, a glutamine synthetase soybean root promoter, a RCC3 promoter, a rice antiquitine promoter, a LRR receptor kinase promoter, or an *Arabidopsis* pCO2 promoter. An additional embodiment of this aspect, which may be combined with any preceding embodiment that has a promoter, includes the first and/or second promoters are selected from the group of a CaMV35S promoter, a derivative of the CaMV35S promoter, a maize ubiquitin promoter, a trefoil promoter, a vein mosaic cassava virus promoter, or an *Arabidopsis* UBQ10 promoter. Yet another embodiment of this aspect, which may be combined with any of the preceding embodiments, includes the first nucleic acid sequence being inserted into the genome of the plant so that the first nucleic acid sequence is operably linked to a first endogenous promoter, and/or the second nucleic acid sequence being inserted into the genome of the plant so that the second nucleic acid sequence is operably linked to a second endogenous promoter. A further embodiment of this aspect includes the first and second endogenous promoters being root specific promoters. A further embodiment of this aspect that can be combined with any of the preceding embodiments includes a plant or plant part produced by the method of any one of the preceding embodiments.

A further aspect of the present disclosure relates to methods of producing the genetically altered plant of any one of the preceding embodiments, including genetically editing a gene encoding an endogenous LysM receptor polypeptide in the plant to include the modified LysM1 domain. An additional embodiment of this aspect includes the endogenous LysM receptor polypeptide being an endogenous chitin LysM receptor polypeptide or an endogenous Nod factor LysM receptor polypeptide. Yet another embodiment of this aspect, which may be combined with any one of the preceding embodiments, includes the modified LysM receptor polypeptide being generated by: (a) providing a heterologous Nod factor LysM receptor polypeptide model including a structural model, a molecular model, a surface characteristics model, and/or an electrostatic potential model of a LysM1 domain, a LysM2 domain, a LysM3 domain, any combination thereof, or the ectodomain of the heterologous Nod factor LysM receptor polypeptide having selectivity for a beneficial nitrogen-fixing bacteria or a beneficial mycorrhizal fungus and an unmodified endogenous LysM receptor polypeptide; (b) identifying a first motif, a second motif, and/or optionally a fifth motif for modification in the unmodified endogenous LysM receptor polypeptide by comparing a LysM1 domain of the unmodified endogenous LysM receptor polypeptide with the corresponding LysM1 domain of the heterologous Nod factor LysM receptor polypeptide model; (c) modifying the first motif by substituting at least one, at least two, or at least three amino acid residues in the first motif with corresponding amino acid residues that are different in a third motif, modifying the second motif by substituting at least one, at least two, or at least three amino acid residues in the second motif with corresponding amino acid residues that are different in a fourth motif, and/or optionally modifying the fifth motif by substituting at least one, at least two, or at least three amino acid residues in the fifth motif with corresponding amino acid residues that are different in a sixth motif, wherein the third motif, the fourth motif, and the sixth motif have different affinities, selectivities, and/or specificities for oligosaccharides than the first motif, the second motif, and the fifth motif; and (d) generating the modified endogenous LysM receptor polypeptide wherein the first motif, the second motif, and/or optionally the fifth motif have been substituted with corresponding amino acid residues from the third motif, the fourth motif, and/or optionally the sixth motif. Still another embodiment of this aspect includes genetically editing a gene encoding an endogenous LysM receptor polypeptide using one or more gene editing components being selected from the group of a ribonucleoprotein complex; a TALEN protein; a ZFN protein; an oligonucleotide donor (ODN); or a CRISPR/Cas enzyme and a targeting sequence. A further embodiment of this aspect that can be combined with any of the preceding embodiments includes a plant or plant part produced by the method of any one of the preceding embodiments.

In some aspects, the present disclosure relates to a method of producing a genetically altered plant of any one of the preceding embodiments, including the steps of: introducing a genetic alteration to the plant including the provision of an ability for Nod factors produced by nitrogen-fixing bacteria and/or mycorrhizal fungi to be recognized, thereby enabling the plant to recognize Nod factors. In yet another embodiment of this aspect, the provision of an ability for Nod factors produced by nitrogen-fixing bacteria and/or mycorrhizal fungi to be recognized results in Nod factors produced by nitrogen-fixing bacteria and/or mycorrhizal fungi being recognized with higher affinity, higher selectivity, and/or higher specificity as compared to an unmodified plant, thereby enabling the modified plant to recognize Nod factors with high affinity, high selectivity, and/or high specificity.

In some aspects, the present disclosure relates to methods of producing a genetically altered plant of any one of the preceding embodiments, including the steps of: introducing a genetic alteration to the plant including the provision of an ability for Nod factors produced by the specific nitrogen-fixing bacterial species and/or the specific mycorrhizal fungal species to be recognized with altered specificity, thereby enabling the plant to recognize Nod factors with altered specificity. In some embodiments, the genetic alteration allows the genetically altered plant to recognize a different specific nitrogen-fixing bacterial species and/or specific mycorrhizal fungal species as compared to a plant without the genetic alteration. An additional embodiment of this aspect includes the genetically altered plant being able to be grown in different agricultural conditions (e.g., different soils containing different symbiotic microbial species, etc.). Yet another embodiment of this aspect includes the genetic alteration allowing the genetically altered plant to be grown in different agricultural conditions containing specific bacterial strains producing Nod factors detected with high specificity, sensitivity, and/or selectivity by the genetically altered plant. A further embodiment of this aspect includes the bacterial strains being added as a seed coating, a soil inoculum, or applied as a spray. Still another embodiment of this aspect includes the genetically altered plant being able to be grown with different crop species (e.g., different crop rotations, etc.).

In some aspects, the present disclosure relates to methods of cultivating the genetically altered plant of any one of the preceding embodiments, including the steps of: cultivating the plant under conditions where the ability to recognize Nod factors produced by nitrogen-fixing bacteria and/or mycorrhizal fungi results with altered specificity, high affinity, high selectivity, and/or high specificity in increased growth, yield, and/or biomass, as compared to a plant grown under the same conditions that lacks the one or more genetic alterations. An additional embodiment of this aspect includes the plant being cultivated in nutrient-poor soil. In some embodiments, the genetic alteration allows the genetically altered plant to recognize a different specific nitrogen-fixing bacterial species and/or specific mycorrhizal fungal species as compared to a plant without the genetic alteration. Yet another embodiment of this aspect includes the genetically altered plant being able to be grown in different agricultural conditions (e.g., different soils containing different symbiotic microbial species, etc.). Still another embodiment of this aspect includes the genetically altered plant being able to be grown with different crop species (e.g., different crop rotations, etc.).

In additional embodiments of any of the above methods, the ability to recognize Nod factors is conferred by a modified plant LysM receptor of any one of the embodiments described in the section "Modified plant LysM receptors". In yet further embodiments of any of the above methods, the modified plant LysM receptor has altered specificity for Nod factors than the unmodified plant LysM receptor and the expression of the modified plant LysM receptor allows the plant or part thereof to recognize different Nod factors than a plant with an unmodified LysM receptor. In further embodiments of any of the above methods, the modified plant LysM receptor has higher affinity, selectivity, and/or specificity for Nod factors than the unmodified plant LysM receptor and the expression of the modified plant LysM receptor allows the plant or part thereof to recognize Nod factors with high affinity, selectivity, and/or specificity.

Still another aspect of the present disclosure relates to methods of cultivating the genetically altered plant of any one of the preceding embodiments, including the steps of: (a) planting a genetically altered seedling, a genetically altered plantlet, a genetically altered cutting, a genetically altered tuber, a genetically altered root, or a genetically altered seed in soil to produce the genetically altered plant or grafting the genetically altered seedling, the genetically altered plantlet, or the genetically altered cutting to a root stock or a second plant grown in soil to produce the genetically altered plant; (b) cultivating the plant to produce harvestable seed, harvestable leaves, harvestable roots, harvestable cuttings, harvestable wood, harvestable fruit, harvestable kernels, harvestable tubers, and/or harvestable grain; and (c) harvesting the harvestable seed, harvestable leaves, harvestable roots, harvestable cuttings, harvestable wood, harvestable fruit, harvestable kernels, harvestable tubers, and/or harvestable grain.

Molecular Biological Methods to Produce Genetically Altered Plants and Plant Cells One embodiment of the present invention provides a genetically altered plant or plant cell containing a modified plant LysM receptor. For example, the present disclosure provides a genetically altered plant or plant part with modified LysM receptors with modified and/or replaced motifs in region II, region IV, and optionally region III of the LysM1 domain. Another embodiment of the present disclosure provides a genetically altered plant or plant part with modified LysM receptors including LysM1 domain modifications as well as a LysM2 domain modified to include a hydrophobic patch or alter the hydrophobic patch in the LysM2 domain. An additional embodiment of the present disclosure provides a genetically altered plant or plant part with a first modified LysM receptor including LysM1 domain modifications and a second modified LysM receptor including LysM2 domain modifications. Plants with these modified receptors can have altered specificity for Nod factors, and/or increased affinity, selectivity, and/or specificity for Nod factors.

Figure 20D:
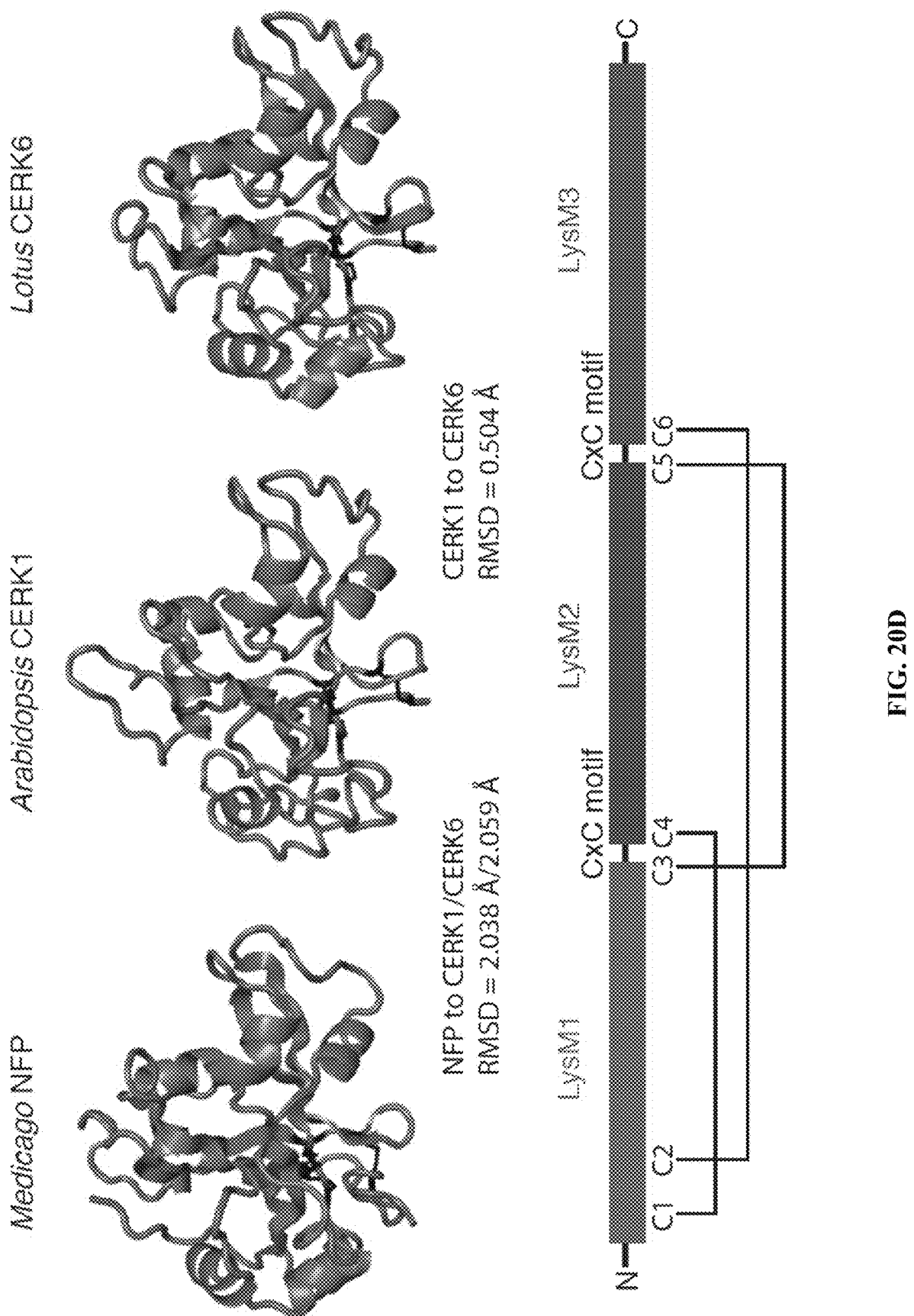

Certain aspects of the present disclosure relate to modified plant LysM receptors, including LysM chitin receptors (i.e., LysM CO receptors), modified LysM Nod factor receptors (i.e., LysM LCO receptors), and/or modified high affinity LysM Nod factor receptors (i.e., high affinity LysM Nod factor receptors). LysM receptors have an ectodomain, which contains three characteristic domains located in the ectodomain of the protein: LysM1, LysM2, and LysM3, which are present in this order on the protein sequence and separated by CxC motifs. The LysM1 domain is located toward the N-terminal end of the protein sequence, and is preceded by an N-terminal signal peptide. The three LysM domains are shown in FIGS. 14A and 15A that show alignments of the ectodomains of NFR1-type LysM Nod factor receptors and CERK6-type LysM chitin receptors, respectively. Moreover, as shown in FIG. 20D, the structure of different LysM receptor types is conserved. The category of plant LysM receptors is therefore known by one of skill in the art.

Figure 14D:
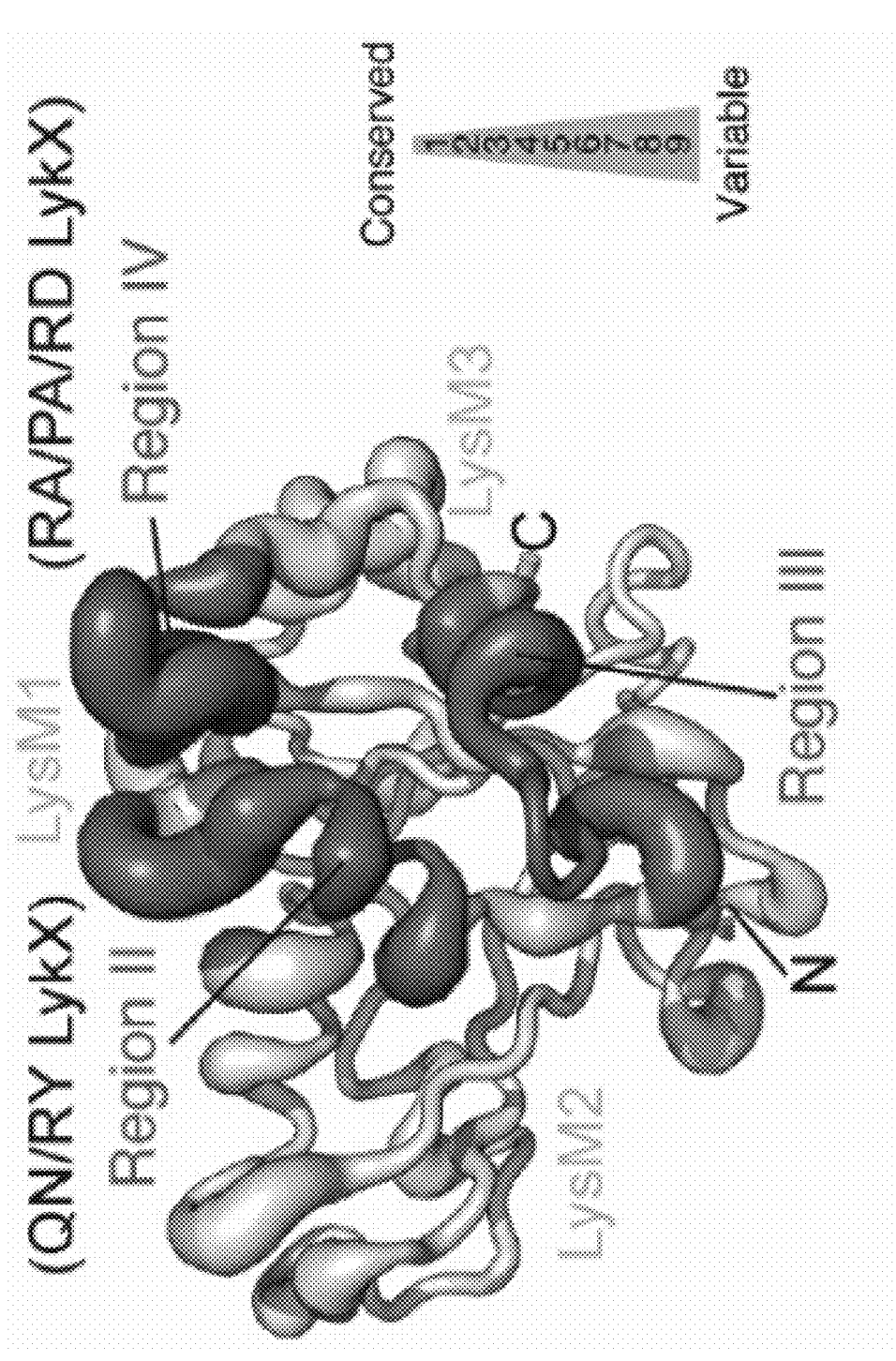
Figure 14E:
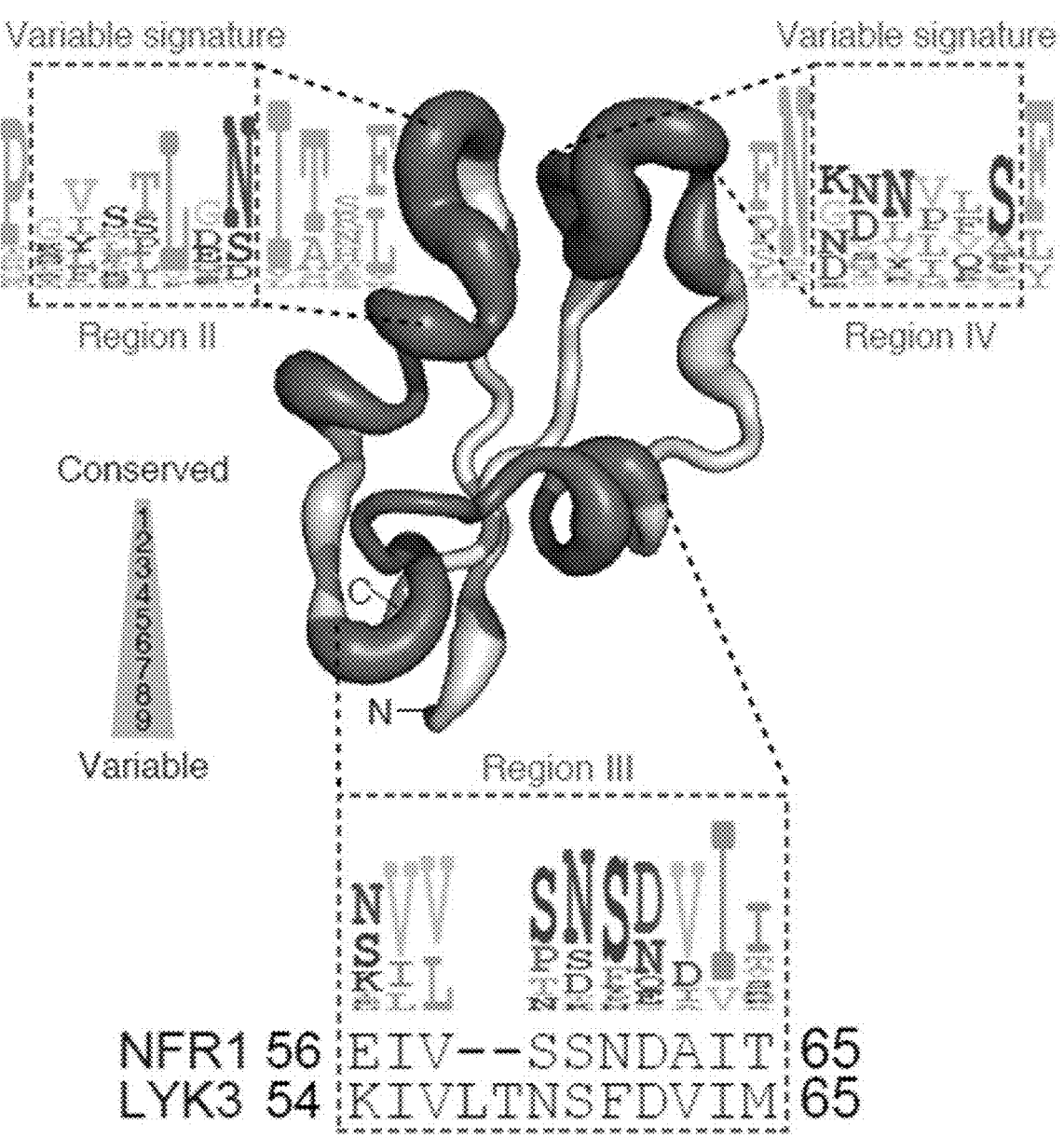
Figure 15D:
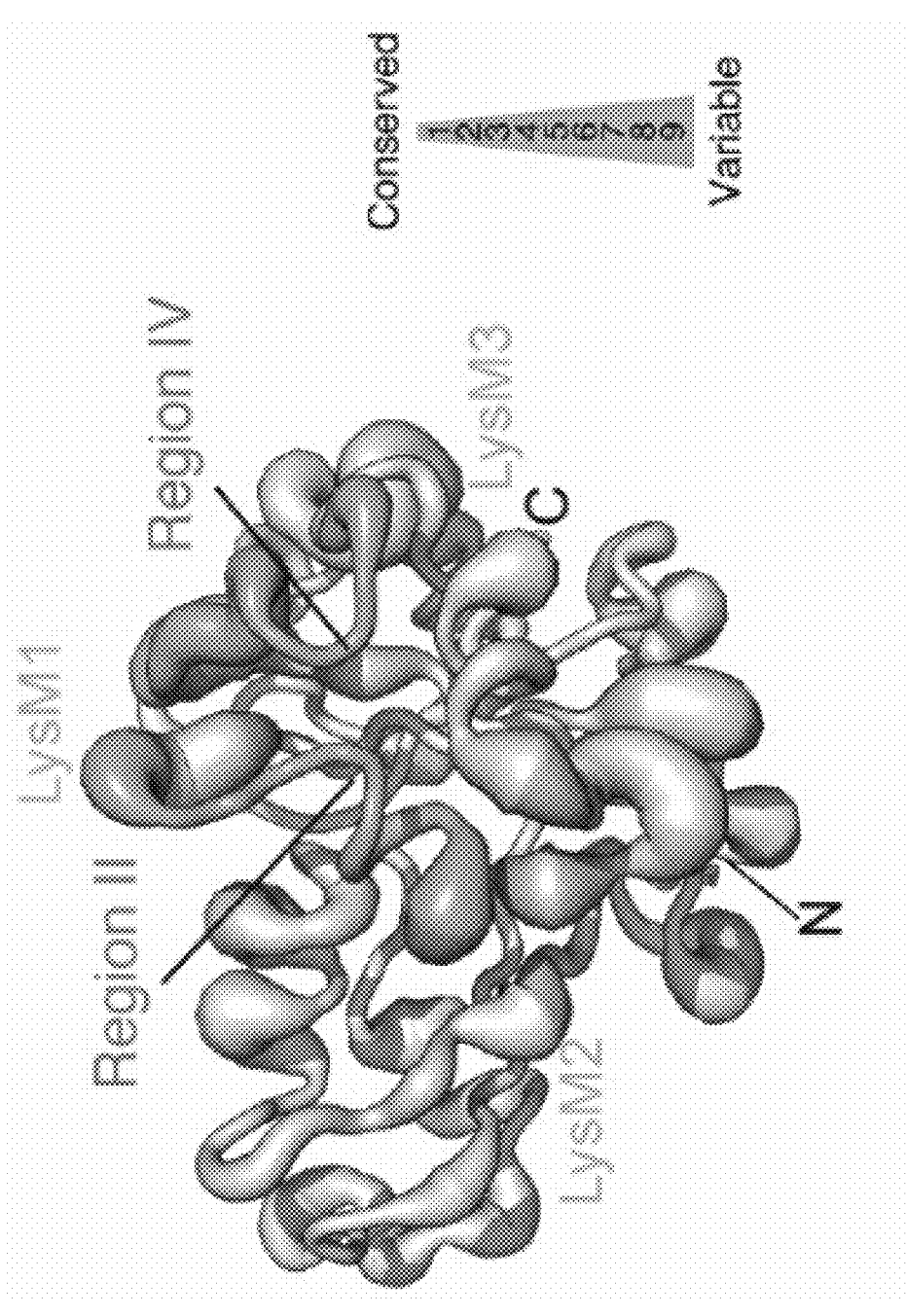
Figure 15E:
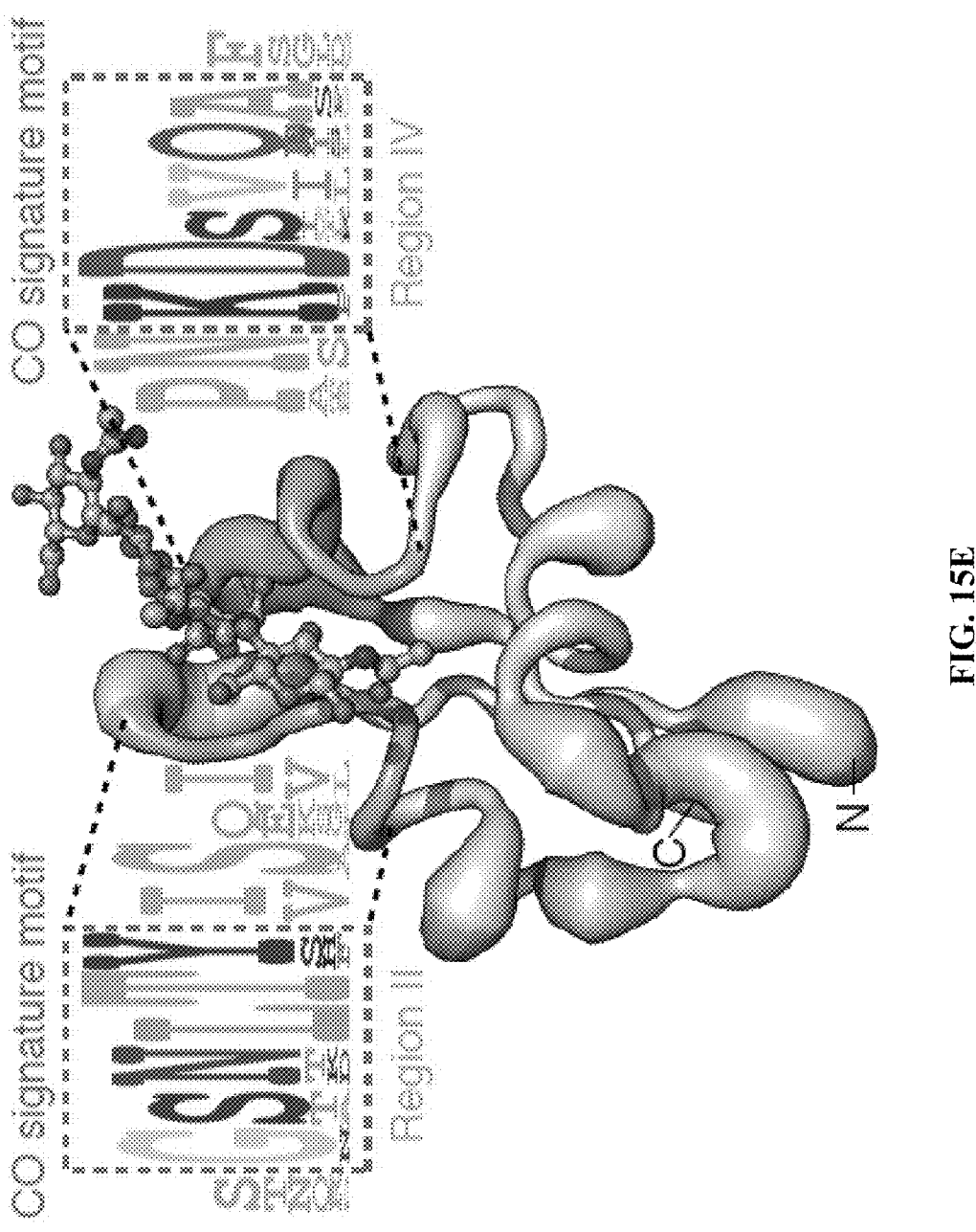

There are four regions within the LysM1 domain (I-IV), three of which (II-IV, shown in FIG. 14A) are important for oligosaccharide (e.g., chitin (CO), Nod factor (LCO), etc.) recognition. Each of these regions important for oligosaccharide recognition further contains specific minimal motifs. The motif in region II (motif II) corresponds to amino acids 42-48 of SEQ ID NO: 162 when aligned to SEQ ID NO: 162, amino acids 44-49 of SEQ ID NO: 164 when aligned to SEQ ID NO: 164, or amino acids 41-46 of SEQ ID NO: 163 when aligned to SEQ ID NO: 163. The motif in region IV (motif IV) corresponds to amino acids 75-80 of SEQ ID NO: 162 when aligned to SEQ ID NO: 162, amino acids 76-81 of SEQ ID NO: 164 when aligned to SEQ ID NO: 164, or amino acids 75-80 of SEQ ID NO: 163 when aligned to SEQ ID NO: 163. The motif in region III (motif III) corresponds to amino acids 56-65 of SEQ ID NO: 162 when aligned to SEQ ID NO: 162 or amino acids 54-65 of SEQ ID NO: 163 when aligned to SEQ ID NO: 163. In LysM chitin receptors (e.g., L. japonicus CERK6), the motifs in region II and region IV are conserved (FIGS. 15D-15E). The flanking regions in region II and region IV (i.e., amino acids within regions II and IV that are not in the motifs within regions II and IV (not in motifs II and IV)) correspond to amino acids 41, 49-52, 73-74, and 81 of SEQ ID NO: 162 when aligned to SEQ ID NO: 162, amino acids 47-53, 66-74, and 81-82 of SEQ ID NO: 163 when aligned to SEQ ID NO: 163, and/or amino acids 43, 50-53, 74-75, and 82 of SEQ ID NO: 164 when aligned to SEQ ID NO: 164. Without wishing to be bound by theory, it is thought that these motifs are characteristic of LysM chitin receptors. In LysM Nod factor receptors, the motifs in region II, region III, and region IV are variable (FIGS. 14D-14E). It is thought that this variability may be linked to the variability in Nod factor structure features recognized (see Tables 4-5). Further, and without wishing to be bound by theory, motifs in region III appear to confer Nod factor recognition specificity, but motifs in region III are not required for all LysM Nod factor receptors to specifically recognize their cognate Nod factors.

Figure 18A:
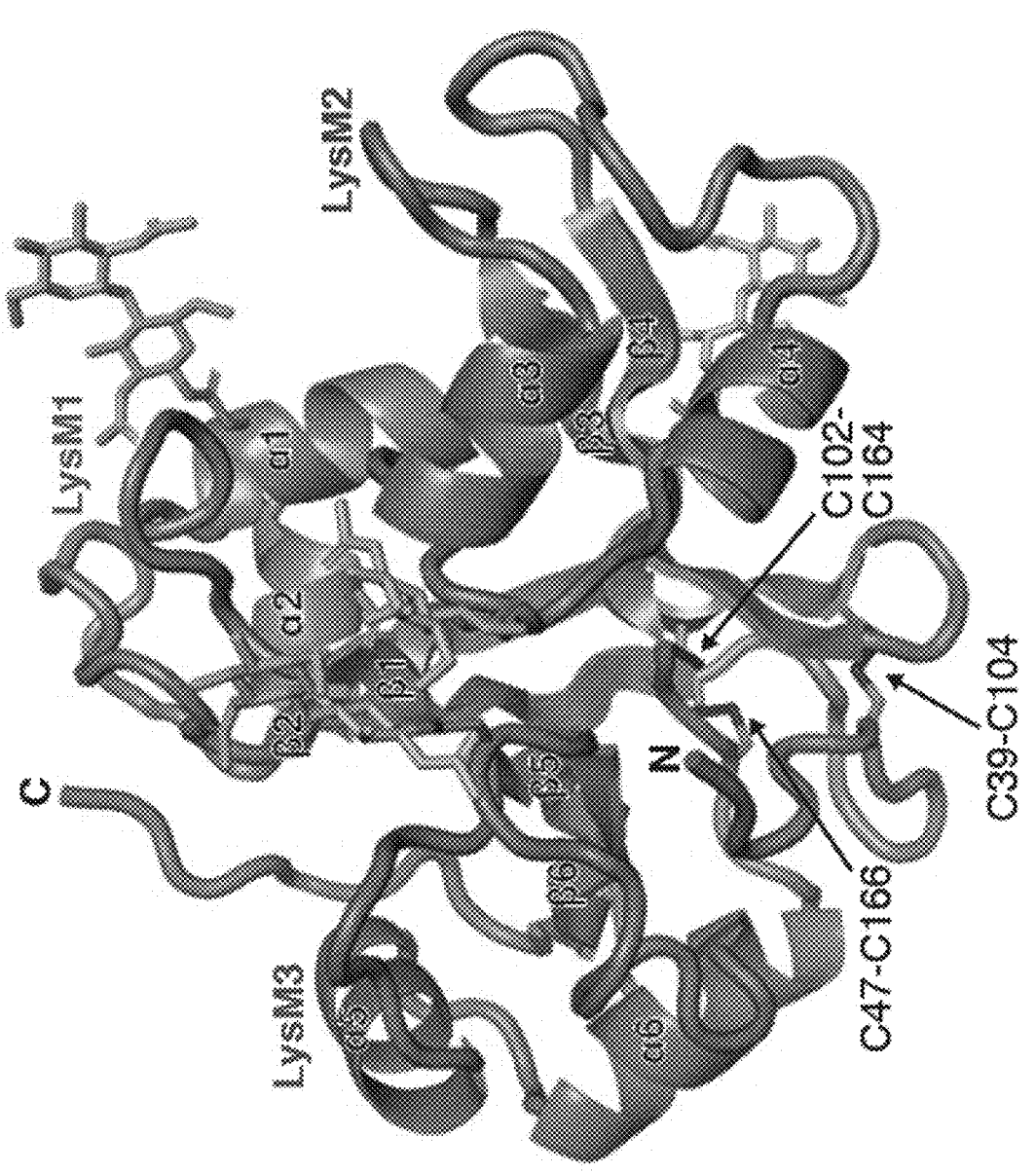
FIGS. 18A-18J show structural and experimental results characterizing important residues in the LysM2 domain for Nod factor perception.
Figure 18B:
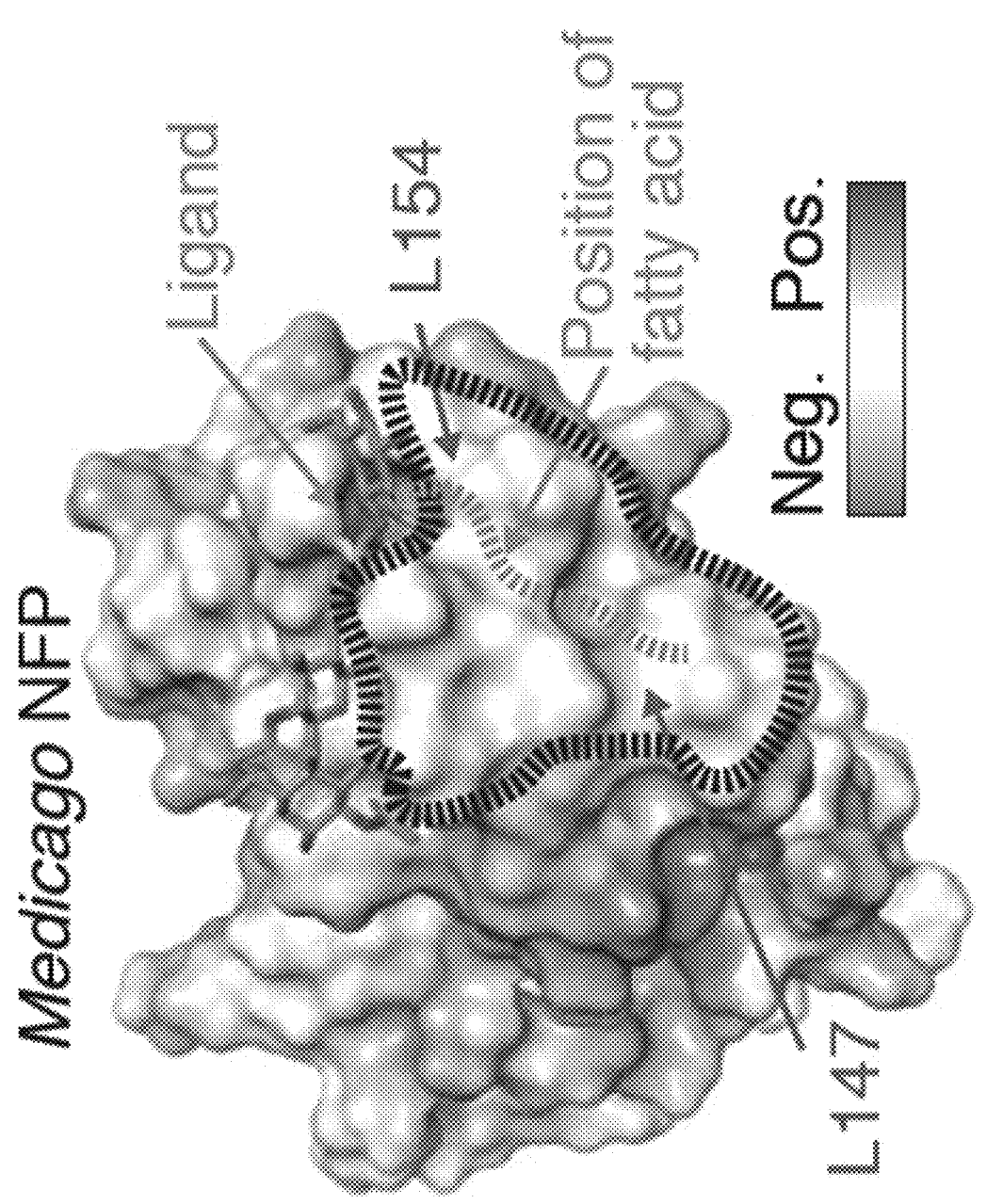
Figures 19A, 19B:
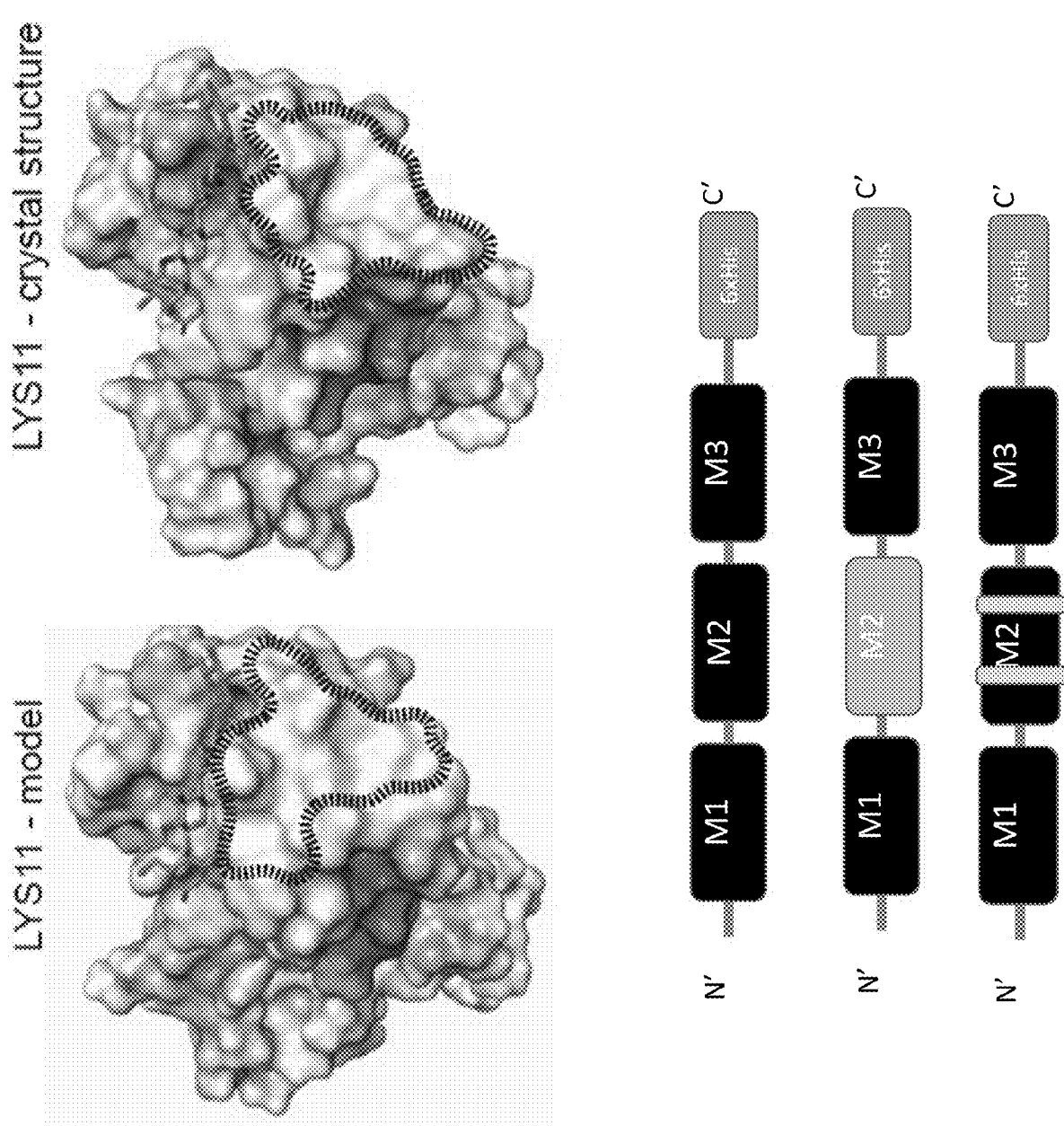
FIGS. 19A-19F show *L. japonicus* LYS11 ectodomain model and crystal structure, modified *L. japonicus* LYS11 ectodomains, and testing of modified *L. japonicus* LYS11 ectodomains.

In LysM Nod factor receptors, the LysM2 domain contains a hydrophobic patch. FIG. 18B shows *M. truncatula* NFP shaded with electrostatic surface potential, in which the hydrophobic patch in the LysM2 domain is circled by a dashed black line, and the locations of important residues L147 and L154 are shown using arrows. FIG. 19A shows the hydrophobic patch on *L. japonicus* LYS11 model and crystal structure. Without wanting to be limited to theory, it is believed that this hydrophobic patch confers selective recognition of Nod factors (LCOs) over chitins (COs), and that therefore LysM receptors with the hydrophobic patch have increased selectivity as compared to LysM receptors without the hydrophobic patch. LysM receptors with a hydrophobic patch in the LysM2 domain may also provide specificity for specific Nod factors.

A modified plant LysM receptor of the present disclosure includes a plant LysM receptor including a modified LysM1 domain in which at least one, at least two, or at least three amino acid residues motifs in region II, region IV, and optionally region III have been modified or in which the motifs in region II, region IV, and optionally region III have been substituted. Sequences of motifs in region II (motif II sequences) include SEQ ID NO: 1, SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 53, SEQ ID NO: 54, SEQ ID NO: 55, SEQ ID NO: 59, SEQ ID NO: 60, SEQ ID NO: 61, SEQ ID NO: 62, SEQ ID NO: 63, SEQ ID NO: 64, SEQ ID NO: 65, SEQ ID NO: 66, SEQ ID NO: 67, SEQ ID NO: 68, SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 143, or SEQ ID NO: 341. Sequences of motifs in region IV (motif IV sequences) include SEQ ID NO: 27, SEQ ID NO: 28, SEQ ID NO: 29, SEQ ID NO: 30, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 40, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 49, SEQ ID NO: 50, SEQ ID NO: 51, SEQ ID NO: 52, SEQ ID NO: 56, SEQ ID NO: 57, SEQ ID NO: 58, SEQ ID NO: 69, SEQ ID NO: 70, SEQ ID NO: 71, SEQ ID NO: 72, SEQ ID NO: 73, SEQ ID NO: 74, SEQ ID NO: 75, SEQ ID NO: 76, SEQ ID NO: 77, SEQ ID NO: 78, SEQ ID NO: 121, SEQ ID NO: 122, SEQ ID NO: 123, SEQ ID NO: 124, SEQ ID NO: 125, SEQ ID NO: 126, SEQ ID NO: 127, SEQ ID NO: 128, SEQ ID NO: 129, SEQ ID NO: 130, SEQ ID NO: 131, SEQ ID NO: 132, SEQ ID NO: 133, SEQ ID NO: 134, SEQ ID NO: 135, SEQ ID NO: 136, SEQ ID NO: 137, SEQ ID NO: 138, SEQ ID NO: 139, SEQ ID NO: 140, SEQ ID NO: 141, or SEQ ID NO: 142. Sequences of motifs in region III (motif III sequences) include SEQ ID NO: 100, SEQ ID NO: 101, SEQ ID NO: 102, SEQ ID NO: 103, SEQ ID NO: 104, SEQ ID NO: 105, SEQ ID NO: 106, SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117, SEQ ID NO: 118, SEQ ID NO: 119, or SEQ ID NO: 120.

Further, a modified plant LysM receptor of the present disclosure includes a plant LysM receptor including a LysM2 domain modified to comprise a hydrophobic patch on the surface of the LysM2 domain. Methods of selecting a target plant LysM receptor and modifying the LysM2 domain of the same are described in Example 9 below, and disclosed in U.S. Prov. App. No. 62/718,282 and PCT App. No. PCT/EP2019/071705, published as WO 2020/035488, both of which are hereby incorporated by reference. The modified plant LysM receptors of the present disclosure may be used to produce the genetically altered plant of any one of the above embodiments relating to plants as described in the section "Genetically altered plants and parts thereof".

Transformation and generation of genetically altered monocotyledonous and dicotyledonous plant cells is well known in the art. See, e.g., Weising, et al., Ann. Rev. Genet. 22:421-477 (1988); U.S. Pat. No. 5,679,558; *Agrobacterium* Protocols, ed: Gartland, Humana Press Inc. (1995); and Wang, et al. Acta Hort. 461:401-408 (1998). The choice of method varies with the type of plant to be transformed, the particular application and/or the desired result. The appropriate transformation technique is readily chosen by the skilled practitioner.

Any methodology known in the art to delete, insert or otherwise modify the cellular DNA (e.g., genomic DNA and organelle DNA) can be used in practicing the inventions disclosed herein. For example, a disarmed Ti plasmid, containing a genetic construct for deletion or insertion of a target gene, in *Agrobacterium tumefaciens* can be used to transform a plant cell, and thereafter, a transformed plant can be regenerated from the transformed plant cell using procedures described in the art, for example, in EP 0116718, EP 0270822, PCT publication WO 84/02913 and published European Patent application ("EP") 0242246. Ti-plasmid vectors each contain the gene between the border sequences, or at least located to the left of the right border sequence, of the T-DNA of the Ti-plasmid. Of course, other types of vectors can be used to transform the plant cell, using procedures such as direct gene transfer (as described, for example in EP 0233247), pollen mediated transformation (as described, for example in EP 0270356, PCT publication WO 85/01856, and U.S. Pat. No. 4,684,611), plant RNA virus-mediated transformation (as described, for example in EP 0 067 553 and U.S. Pat. No. 4,407,956), liposome-mediated transformation (as described, for example in U.S. Pat. No. 4,536,475), and other methods such as the methods for transforming certain lines of corn (e.g., U.S. Pat. No. 6,140, 553; Fromm et al., Bio/Technology (1990) 8, 833 839); Gordon-Kamm et al., The Plant Cell, (1990) 2, 603 618) and rice (Shimamoto et al., Nature, (1989) 338, 274 276; Datta et al., Bio/Technology, (1990) 8, 736 740) and the method for transforming monocots generally (PCT publication WO 92/09696). For cotton transformation, the method described in PCT patent publication WO 00/71733 can be used. For soybean transformation, reference is made to methods known in the art, e.g., Hinchee et al. (Bio/Technology, (1988) 6, 915) and Christou et al. (Trends Biotech, (1990) 8, 145) or the method of WO 00/42207.

Genetically altered plants of the present invention can be used in a conventional plant breeding scheme to produce more genetically altered plants with the same characteristics, or to introduce the genetic alteration(s) in other varieties of the same or related plant species. Seeds, which are obtained from the altered plants, preferably contain the genetic alteration(s) as a stable insert in chromosomal or organelle DNA or as modifications to an endogenous gene or promoter. Plants comprising the genetic alteration(s) in accordance with the invention include plants comprising, or derived from, root stocks of plants comprising the genetic alteration(s) of the invention, e.g., fruit trees or ornamental plants. Hence, any non-transgenic grafted plant parts inserted on a transformed plant or plant part are included in the invention.

Introduced genetic elements, whether in an expression vector or expression cassette, which result in the expression of an introduced gene will typically utilize a plant-express-ible promoter. A 'plant-expressible promoter' as used herein refers to a promoter that ensures expression of the genetic alteration(s) of the invention in a plant cell. Examples of promoters directing constitutive expression in plants are known in the art and include: the strong constitutive 35S promoters (the "35S promoters") of the cauliflower mosaic virus (CaMV), e.g., of isolates CM 1841 (Gardner et al., Nucleic Acids Res, (1981) 9, 2871 2887), CabbB S (Franck et al., Cell (1980) 21, 285 294) and CabbB JI (Hull and Howell, Virology, (1987) 86, 482 493); promoters from the ubiquitin family (e.g., the maize ubiquitin promoter of Christensen et al., Plant Mol Biol, (1992) 18, 675-689), the gos2 promoter (de Pater et al., The Plant J (1992) 2, 834-844), the emu promoter (Last et al., Theor Appl Genet, (1990) 81, 581-588), actin promoters such as the promoter described by An et al. (The Plant J, (1996) 10, 107), the rice actin promoter described by Zhang et al. (The Plant Cell, (1991) 3, 1155-1165); promoters of the Cassava vein mosaic virus (WO 97/48819, Verdaguer et al. (Plant Mol Biol, (1998) 37, 1055-1067), the pPLEX series of promoters from Subterranean Clover Stunt Virus (WO 96/06932, particularly the S4 or S7 promoter), an alcohol dehydrogenase promoter, e.g., pAdh1S (GenBank accession numbers X04049, X00581), and the TR1' promoter and the TR2' promoter (the "TR1' promoter" and "TR2' promoter", respectively) which drive the expression of the 1' and 2' genes, respectively, of the T DNA (Velten et al., EMBO J, (1984) 3, 2723 2730).

Alternatively, a plant-expressible promoter can be a tissue-specific promoter, i.e., a promoter directing a higher level of expression in some cells or tissues of the plant, e.g., in root epidermal cells or root cortex cells. In preferred embodiments, LysM receptor promoters will be used. Non-limiting examples include NFR1 promoters, NFR5/NFP promoters, LYK3 promoters, CERK6 promoters, NFR5/NFP promoters, the *Lotus japonicus* NFR5 promoter (SEQ ID NO: 261), the *Lotus japonicus* NFR1 promoter (SEQ ID NO: 261), the *Lotus japonicus* CERK6 promoter (SEQ ID NO: 264), the *Medicago truncatula* NFP promoter (SEQ ID NO: 263), and the *Medicago truncatula* LYK3 promoter (SEQ ID NO: 262). In additional preferred embodiments, root specific promoters will be used. Non-limiting examples include the promoter of the maize allothioneine (DE FRA-MOND et al, FEBS 290, 103.-106, 1991 Application EP 452269), the chitinase promoter (SAMAC et al. Plant Physiol 93, 907-914, 1990), the glutamine synthetase soybean root promoter (HIREL et al. Plant Mol. Biol. 20, 207-218, 1992), the RCC3 promoter (PCT Application WO 2009/016104), the rice antiquitine promoter (PCT Application WO 2007/076115), the LRR receptor kinase promoter (PCT application WO 02/46439), the maize ZRP2 promoter (U.S. Pat. No. 5,633,363), the tomato LeExtl promoter (Bucher et al. Plant Physiol. 128, 911-923, 2002), and the *Arabidopsis* pCO2 promoter (HEIDSTRA et al, Genes Dev. 18, 1964-1969, 2004). These plant promoters can be combined with enhancer elements, they can be combined with minimal promoter elements, or can comprise repeated elements to ensure the expression profile desired.

Examples of constitutive promoters that are often used in plant cells are the cauliflower mosaic (CaMV) 35S promoter (KAY et al. Science, 236, 4805, 1987), and various derivatives of the promoter, virus promoter vein mosaic cassava (International Application WO 97/48819), the maize ubiquitin promoter (CHRISTENSEN & QUAIL, Transgenic Res, 5, 213-8, 1996), trefoil (Ljubql, MAEKAWA et al. Mol Plant Microbe Interact. 21, 375-82, 2008) and *Arabidopsis* UBQ10 (Norris et al. Plant Mol. Biol. 21, 895-906, 1993).

In some embodiments, genetic elements to increase expression in plant cells can be utilized. For example, an intron at the 5' end or 3' end of an introduced gene, or in the coding sequence of the introduced gene, e.g., the hsp70 intron. Other such genetic elements can include, but are not limited to, promoter enhancer elements, duplicated or triplicated promoter regions, 5' leader sequences different from another transgene or different from an endogenous (plant host) gene leader sequence, 3' trailer sequences different from another transgene used in the same plant or different from an endogenous (plant host) trailer sequence.

An introduced gene of the present invention can be inserted in host cell DNA so that the inserted gene part is upstream (i.e., 5') of suitable 3' end transcription regulation signals (e.g., transcript formation and polyadenylation signals). This is preferably accomplished by inserting the gene in the plant cell genome (nuclear or chloroplast). Preferred polyadenylation and transcript formation signals include those of the nopaline synthase gene (Depicker et al., J. Molec Appl Gen, (1982) 1, 561-573), the octopine synthase gene (Gielen et al., EMBO J, (1984) 3:835 845), the SCSV or the Malic enzyme terminators (Schunmann et al., Plant Funct Biol, (2003) 30:453-460), and the T DNA gene 7 (Velten and Schell, Nucleic Acids Res, (1985) 13, 6981 6998), which act as 3' untranslated DNA sequences in transformed plant cells. In some embodiments, one or more of the introduced genes are stably integrated into the nuclear genome. Stable integration is present when the nucleic acid sequence remains integrated into the nuclear genome and continues to be expressed (e.g., detectable mRNA transcript or protein is produced) throughout subsequent plant generations. Stable integration into and/or editing of the nuclear genome can be accomplished by any known method in the art (e.g., microparticle bombardment, *Agrobacterium*-mediated transformation, CRISPR/Cas9, electroporation of protoplasts, microinjection, etc.).

The term recombinant or modified nucleic acids refers to polynucleotides which are made by the combination of two otherwise separated segments of sequence accomplished by the artificial manipulation of isolated segments of polynucleotides by genetic engineering techniques or by chemical synthesis. In so doing one may join together polynucleotide segments of desired functions to generate a desired combination of functions.

As used herein, the terms "overexpression" and "upregulation" refer to increased expression (e.g., of mRNA, polypeptides, etc.) relative to expression in a wild type organism (e.g., plant) as a result of genetic modification. In some embodiments, the increase in expression is a slight increase of about 10% more than expression in wild type. In some embodiments, the increase in expression is an increase of 50% or more (e.g., 60%, 70%, 80%, 100%, etc.) relative to expression in wild type. In some embodiments, an endogenous gene is overexpressed. In some embodiments, an exogenous gene is overexpressed by virtue of being expressed. Overexpression of a gene in plants can be achieved through any known method in the art, including but not limited to, the use of constitutive promoters, inducible promoters, high expression promoters (e.g., PsaD promoter), enhancers, transcriptional and/or translational regulatory sequences, codon optimization, modified transcription factors, and/or mutant or modified genes that control expression of the gene to be overexpressed.

Where a recombinant nucleic acid is intended for expression, cloning, or replication of a particular sequence, DNA constructs prepared for introduction into a host cell will typically comprise a replication system (e.g. vector) recognized by the host, including the intended DNA fragment encoding a desired polypeptide, and can also include transcription and translational initiation regulatory sequences operably linked to the polypeptide-encoding segment. Additionally, such constructs can include cellular localization signals (e.g., plasma membrane localization signals). In preferred embodiments, such DNA constructs are introduced into a host cell's genomic DNA, chloroplast DNA or mitochondrial DNA.

In some embodiments, a non-integrated expression system can be used to induce expression of one or more introduced genes. Expression systems (expression vectors) can include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Signal peptides can also be included where appropriate from secreted polypeptides of the same or related species, which allow the protein to cross and/or lodge in cell membranes, cell wall, or be secreted from the cell.

Selectable markers useful in practicing the methodologies of the invention disclosed herein can be positive selectable markers. Typically, positive selection refers to the case in which a genetically altered cell can survive in the presence of a toxic substance only if the recombinant polynucleotide of interest is present within the cell. Negative selectable markers and screenable markers are also well known in the art and are contemplated by the present invention. One of skill in the art will recognize that any relevant markers available can be utilized in practicing the inventions disclosed herein.

Screening and molecular analysis of recombinant strains of the present invention can be performed utilizing nucleic acid hybridization techniques. Hybridization procedures are useful for identifying polynucleotides, such as those modified using the techniques described herein, with sufficient homology to the subject regulatory sequences to be useful as taught herein. The particular hybridization techniques are not essential to the subject invention. As improvements are made in hybridization techniques, they can be readily applied by one of skill in the art. Hybridization probes can be labeled with any appropriate label known to those of skill in the art. Hybridization conditions and washing conditions, for example temperature and salt concentration, can be altered to change the stringency of the detection threshold. See, e.g., Sambrook et al. (1989) vide infra or Ausubel et al. (1995) Current Protocols in Molecular Biology, John Wiley & Sons, NY, N.Y., for further guidance on hybridization conditions.

Additionally, screening and molecular analysis of genetically altered strains, as well as creation of desired isolated nucleic acids can be performed using Polymerase Chain Reaction (PCR). PCR is a repetitive, enzymatic, primed synthesis of a nucleic acid sequence. This procedure is well known and commonly used by those skilled in this art (see Mullis, U.S. Pat. Nos. 4,683,195, 4,683,202, and 4,800,159; Saiki et al. (1985) Science 230:1350-1354). PCR is based on the enzymatic amplification of a DNA fragment of interest that is flanked by two oligonucleotide primers that hybridize to opposite strands of the target sequence. The primers are oriented with the 3' ends pointing towards each other. Repeated cycles of heat denaturation of the template, annealing of the primers to their complementary sequences, and extension of the annealed primers with a DNA polymerase result in the amplification of the segment defined by the 5' ends of the PCR primers. Because the extension product of each primer can serve as a template for the other primer, each cycle essentially doubles the amount of DNA template produced in the previous cycle. This results in the exponential accumulation of the specific target fragment, up to several million-fold in a few hours. By using a thermostable DNA polymerase such as the Taq polymerase, which is isolated from the thermophilic bacterium *Thermus aquaticus*, the amplification process can be completely automated. Other enzymes which can be used are known to those skilled in the art.

Nucleic acids and proteins of the present invention can also encompass homologues of the specifically disclosed sequences. Homology (e.g., sequence identity) can be 50%-100%. In some instances, such homology is greater than 80%, greater than 85%, greater than 90%, or greater than 95%. The degree of homology or identity needed for any intended use of the sequence(s) is readily identified by one of skill in the art. As used herein percent sequence identity of two nucleic acids is determined using an algorithm known in the art, such as that disclosed by Karlin and Altschul (1990) Proc. Natl. Acad. Sci. USA 87:2264-2268, modified as in Karlin and Altschul (1993) Proc. Natl. Acad. Sci. USA 90:5873-5877. Such an algorithm is incorporated into the NBLAST and)(BLAST programs of Altschul et al. (1990) J. Mol. Biol. 215:402-410. BLAST nucleotide searches are performed with the NBLAST program, score=100, word-length=12, to obtain nucleotide sequences with the desired percent sequence identity. To obtain gapped alignments for comparison purposes, Gapped BLAST is used as described in Altschul et al. (1997) Nucl. Acids. Res. 25:3389-3402. When utilizing BLAST and Gapped BLAST programs, the default parameters of the respective programs (NBLAST and)(BLAST) are used. See www.ncbi.nih.gov.

Preferred host cells are plant cells. Recombinant host cells, in the present context, are those which have been genetically modified to contain an isolated nucleic molecule, contain one or more deleted or otherwise non-functional genes normally present and functional in the host cell, or contain one or more genes to produce at least one recombinant protein. The nucleic acid(s) encoding the protein(s) of the present invention can be introduced by any means known to the art which is appropriate for the particular type of cell, including without limitation, transformation, lipofection, electroporation or any other methodology known by those skilled in the art.

"Isolated", "isolated DNA molecule" or an equivalent term or phrase is intended to mean that the DNA molecule or other moiety is one that is present alone or in combination with other compositions, but altered from or not within its natural environment. For example, nucleic acid elements such as a coding sequence, intron sequence, untranslated leader sequence, promoter sequence, transcriptional termination sequence, and the like, that are naturally found within the DNA of the genome of an organism are not considered to be "isolated" so long as the element is within the genome of the organism and at the location within the genome in which it is naturally found. However, each of these elements, and subparts of these elements, would be "isolated" from its natural setting within the scope of this disclosure so long as the element is not within the genome of the organism in which it is naturally found, the element is altered from its natural form, or the element is not at the location within the genome in which it is naturally found. Similarly, a nucleotide sequence encoding a protein or any naturally occurring variant of that protein would be an isolated nucleotide sequence so long as the nucleotide sequence was not within the DNA of the organism from which the sequence encoding the protein is naturally found in its natural location or if that nucleotide sequence was altered from its natural form. A synthetic nucleotide sequence encoding the amino acid sequence of the naturally occurring protein would be considered to be isolated for the purposes of this disclosure. For the purposes of this disclosure, any transgenic nucleotide sequence, i.e., the nucleotide sequence of the DNA inserted into the genome of the cells of a plant, alga, fungus, or bacterium, or present in an extrachromosomal vector, would be considered to be an isolated nucleotide sequence whether it is present within the plasmid or similar structure used to transform the cells, within the genome of the plant or bacterium, or present in detectable amounts in tissues, progeny, biological samples or commodity products derived from the plant or bacterium.

Having generally described this invention, the same will be better understood by reference to certain specific examples, which are included herein to further illustrate the invention and are not intended to limit the scope of the invention as defined by the claims.

EXAMPLES

The present disclosure is described in further detail in the following examples which are not in any way intended to limit the scope of the disclosure as claimed. The attached figures are meant to be considered as integral parts of the specification and description of the disclosure. The following examples are offered to illustrate, but not to limit the claimed disclosure.

Example 1: Identification of LysM Receptor Kinase Domains Necessary for Nodulation and CO8-Induced Immune Responses The following example describes the identification of domains of the *Lotus japonicus* LysM receptor kinases NFR1 and CERK6 required for nodulation and CO8-induced immune responses. Further, experiments to determine which of the three LysM domains in the ectodomain of NFR1 and CERK6 determine ligand specificity are described.

Materials and Methods

Plant Lines and Growth Conditions

The *Lotus japonicus* Gifu ecotype background was used. The LORE1 insertion DK09-030067625 (cerk6-1) mutant line and the Lj2g3v2904690.1 (nfr1-1) mutant line containing the proNin-GUS construct (nfr1-1_pNin-gus; Radutoiu S. et al. *Nature* 2003 425(6958): 585-92) were used for ROS and nodulation assays, respectively (Bozsoki, Z. et al. *Proc. Natl. Acad. Sci.* 2017 114: E8118-E8127).

Figure 3A:
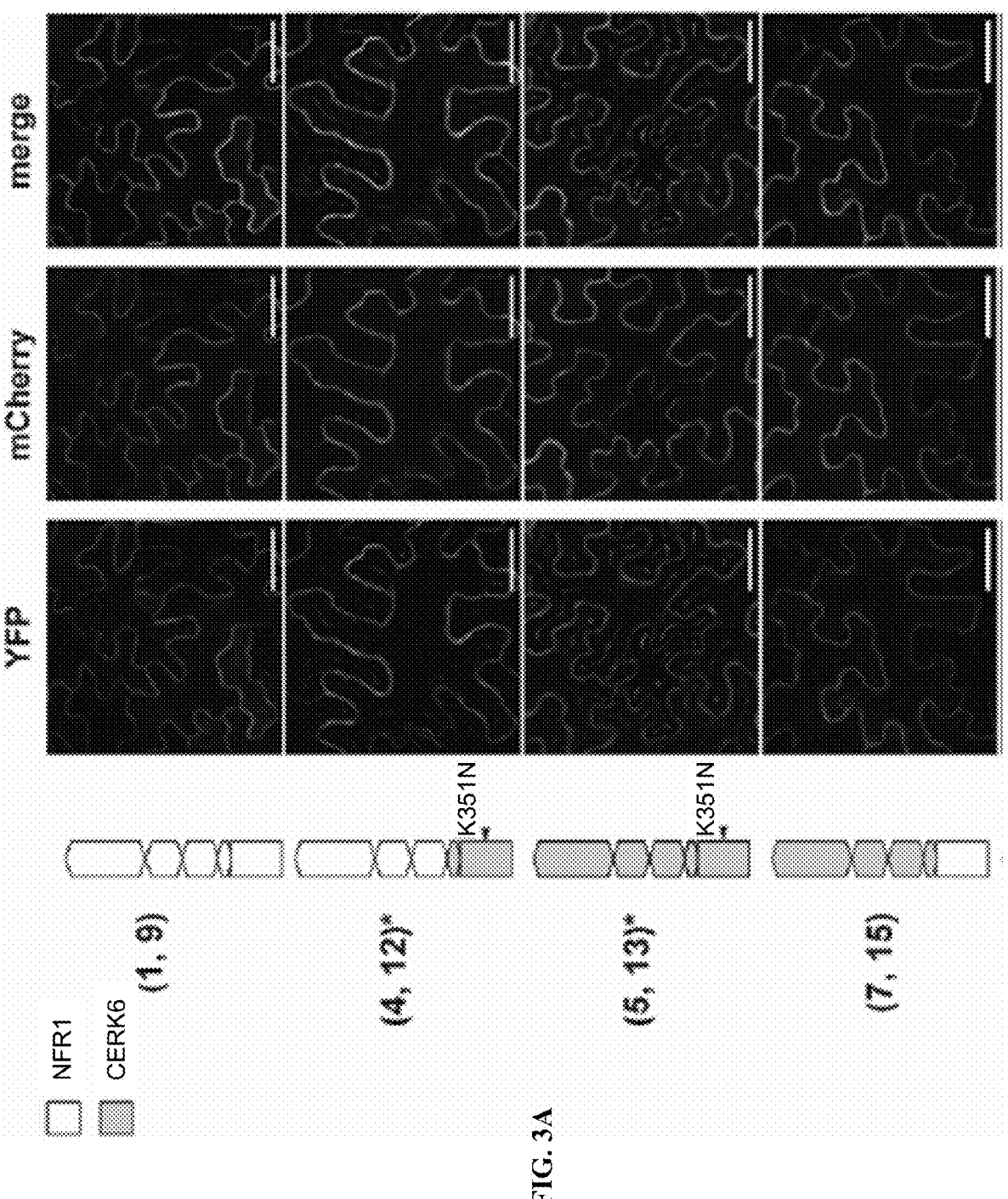
FIGS. 3A-3B show images of YFP-tagged LysM receptor kinase proteins transiently expressed in *N. benthamiana* (tobacco) leaves under control of the 35S promoter and 35S terminator. The plasma membrane marker AtPIP2A-mCherry was co-expressed. Schematic diagrams, at left, show the composition of the LysM receptor kinase constructs, with NFR1 domains in white and CERK6 domains in green. From left to right columns, the images show YFP, mCherry, and a merge of the two. The scale bars indicate 50 μm.
Figure 3B:
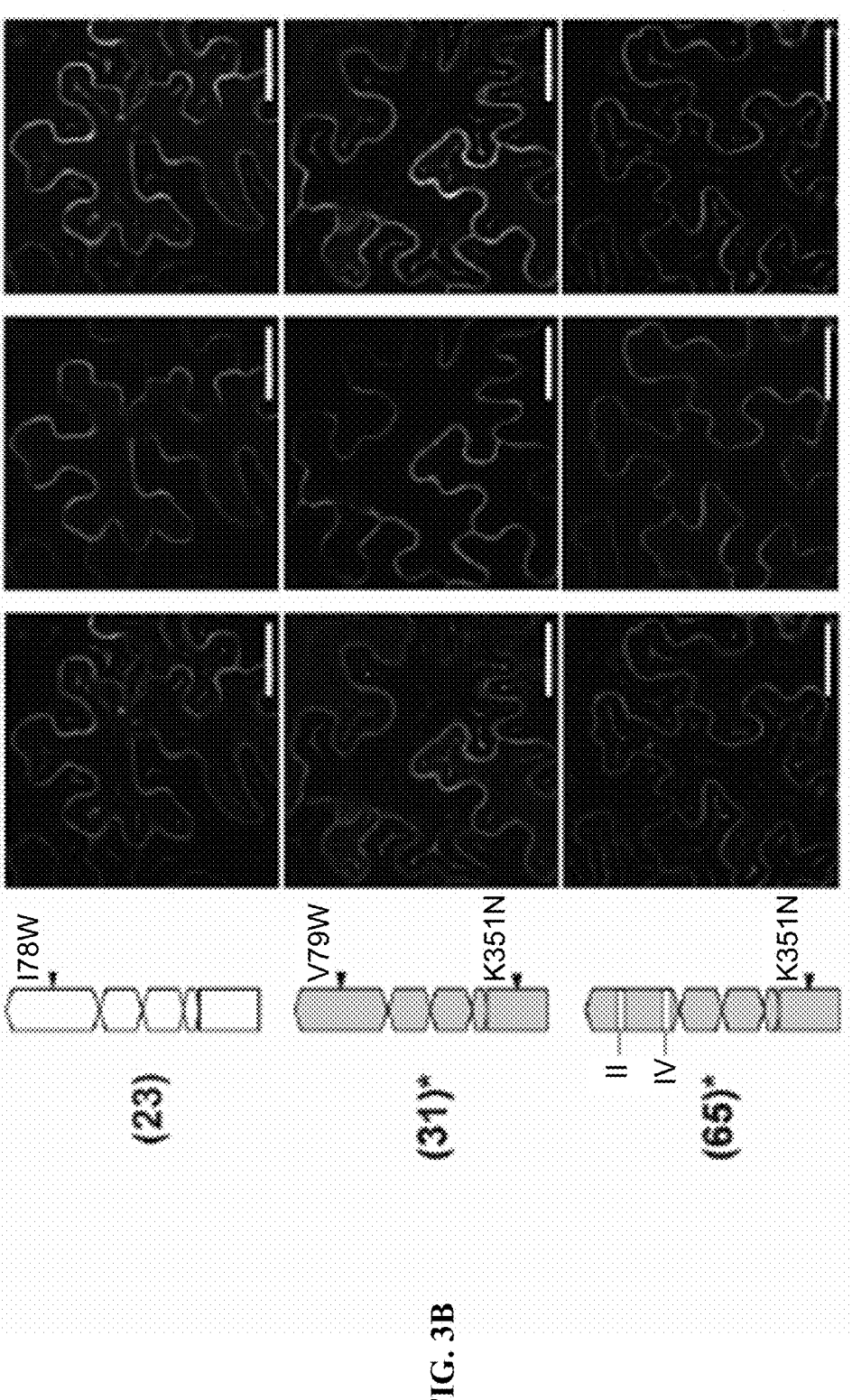

*Nicotiana benthamiana* was used for transient expression and localization studies (FIGS. 3A-3B).

All plants were grown at 21° C. under 16 hour light/8 hour dark conditions. For germination, *L. japonicus* seeds were scarified with sandpaper and surface sterilized for 10 minutes with 1% sodium hypochlorite. Seedlings were germinated on wet filter paper (AGF 651; Frisenette ApS) in an upright position in sterile square Petri dishes at 21° C. for two days. Then, seedlings were transferred to slanted agar plates solidified with 0.8% Gelrite (Duchefa Biochemie) supplemented with ½ Gamborg's B5 nutrient solution (Duchefa Biochemie).

Bacterial Strains and Culture Conditions

Chemically competent *E. coli* TOP10 (ThermoFisherScientific) were used for molecular cloning and were grown in LB medium at 37° C.

*Mesorhizobium loti* strain R7A constitutively expressing the fluorescent protein DsRed (Kelly, S. J. et al. *Mol Plant Microbe Interact* 2013 26: 319-329) was grown in TY/YMB medium at 28° C.

*Agrobacterium rhizogenes* strain AR1193 (Stougaard, *J. Methods Mol Biol* 1995 49:49-61) was used for all hairy root transformation experiments and *Agrobacterium tumefaciens* strain AGL1 was used for transient transformation of *N. benthamiana*. Both *Agrobacterium* strains were cultured in LB medium at 28° C.

Generation of Plant Expression Vectors

For hairy root transformation of *L. japonicus*, the pIV10 expression vector (Hansen, J. et al. *Plant Cell Rep* 1989 8: 12-15) was used. This expression vector contains a sequence encoding triple YFP fused to a nuclear localization signal (pIV10_tYFP-NLS) that serves as a transformation control.

Figures 1D, 1E:
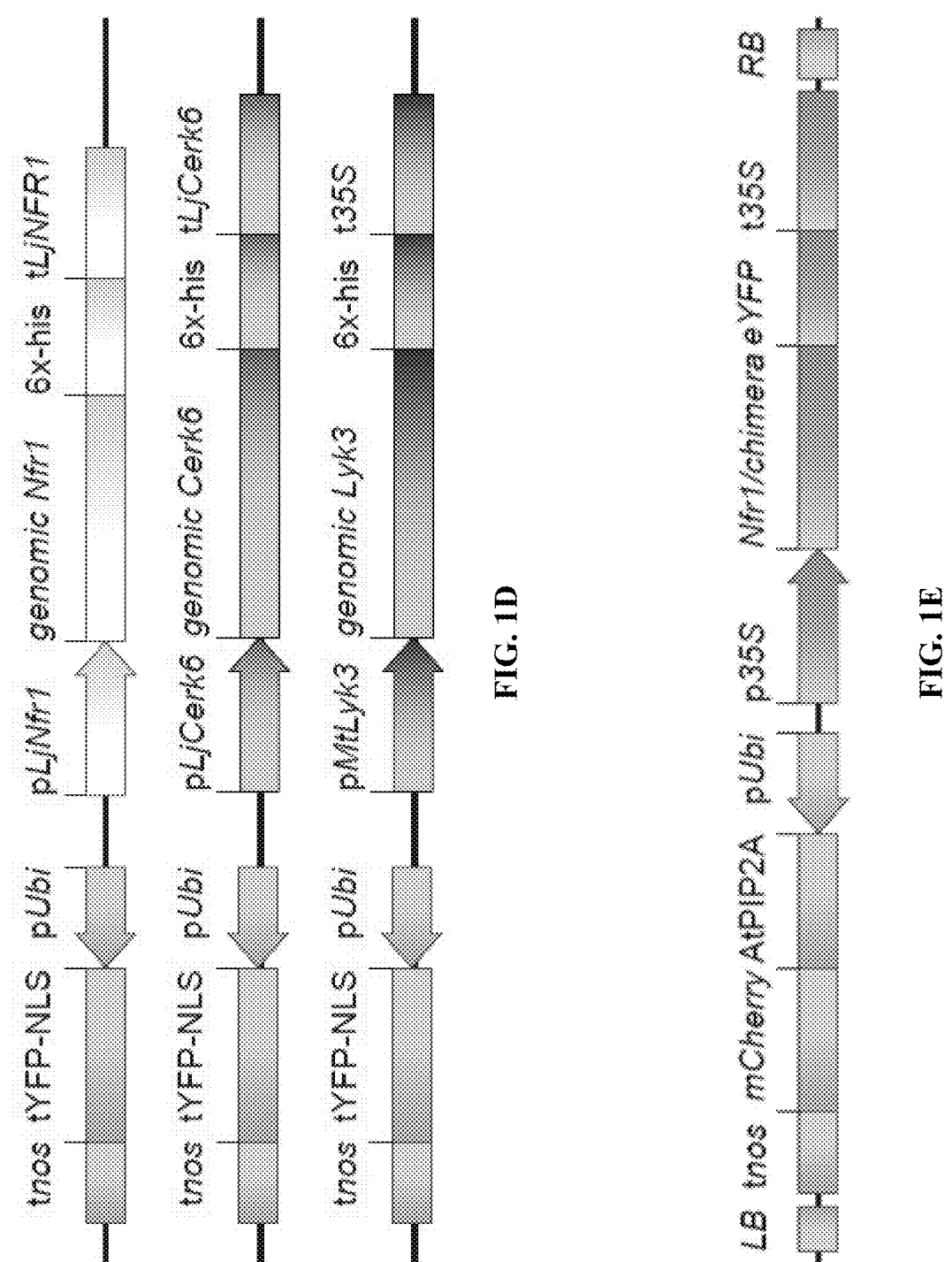

Expression constructs were generated to express LysM receptor kinases in *L. japonicus* (FIG. 1D). LysM receptor kinase coding sequences were placed under control of the *L. japonicus* Nfr1 (SEQ ID NO: 261) or Cerk6 promoters (SEQ ID NO: 264). Plasmids containing gene fragments encoding the respective domains or regions of *L. japonicus* NFR1 and *L. japonicus* CERK6 were assembled with the appropriate promoter and cloned into the pIV10_tYFP-NLS expression vector via Golden Gate cloning (FIG. 1D; Engler, C. et al. *PLoS One* 2008 3: e3647). Expression constructs were generated to express NFR1, CERK6, chimeric alleles of NFR1 and CERK6, or alleles of NFR1 and CERK6 with point mutations (see FIGS. 1A-1E, FIG. 4A). Chimeric alleles of LysM receptor kinases were designed based on their modular structure, which has, from N to C terminus, an extracellular region also known as the ectodomain ("EC") made up of three LysM domains (LysM1, LysM2, and LysM3), a transmembrane segment and an intracellular region with a juxtamembrane segment ("TJ"), and a kinase domain ("KD"), as shown in FIG. 1A and FIG. 4A.

Figure 4A:
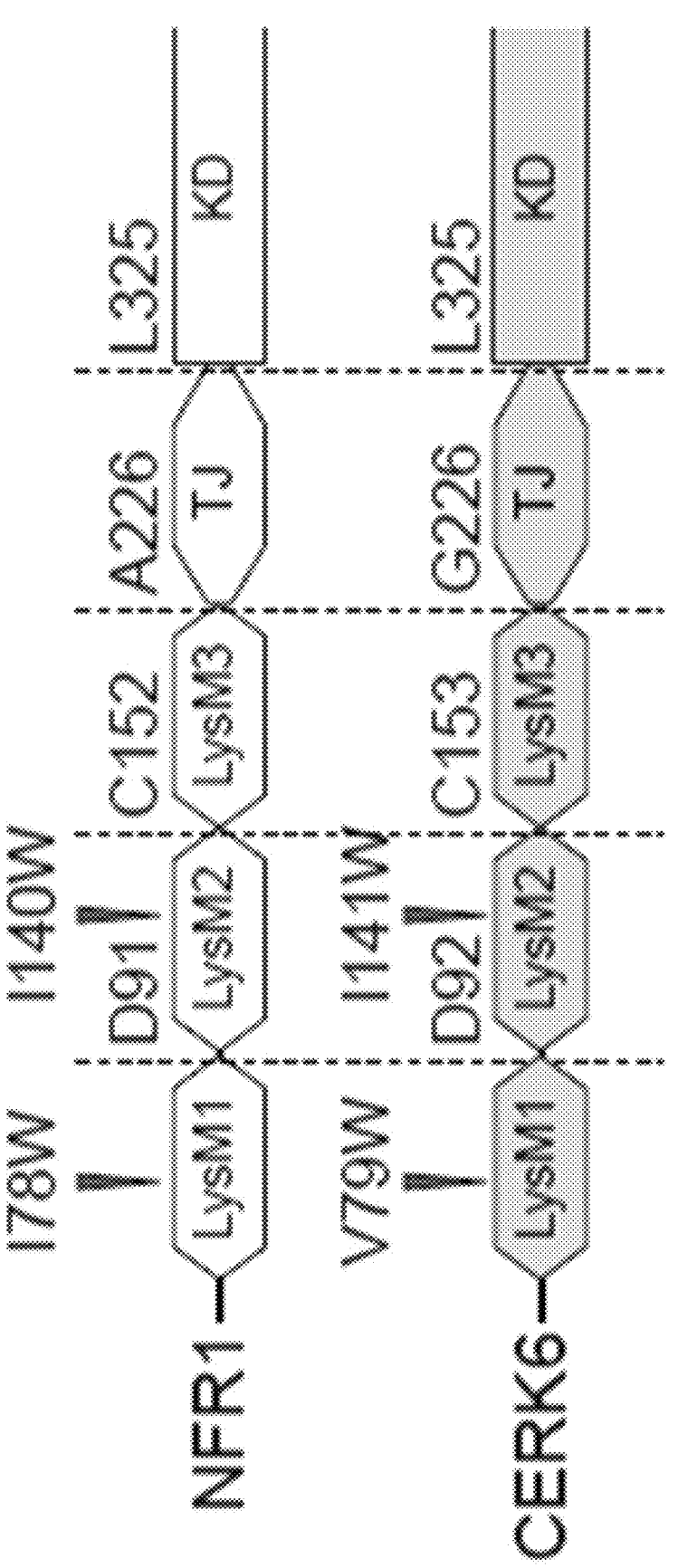
FIGS. 4A-4B show results of functional studies measuring nodulation using chimeras of the *L. japonicus* LysM receptor kinase proteins NFR1 and CERK6 in which the LysM1, LysM2, and LysM3 domains are swapped.

Schematic diagrams showing the domain structure of NFR1 and CERK6, including the amino acid boundaries used for the purpose of swapping domains to generate chimeric proteins, are provided in FIG. 1A and FIG. 4A. As shown in FIG. 1A and FIG. 4A, the NFR1 TJ began at residue A226, and the KD began at residue L325. The CERK6 TJ began at residue G226, and the KD began at L325. As shown in FIG. 4A, the NFR1 LysM2 domain began at residue D91, and the LysM3 domain began at residue C152. The CERK6 LysM2 domain began at residue D92, and the LysM3 domain began at residue C153.

LysM receptor kinase expression constructs were assigned numerical labels that correspond to the schematic diagrams of the constructs presented in the FIGS. Table 1 provides a description of the LysM receptor kinase expression constructs used in this example.

TABLE 1

Figure 2A:
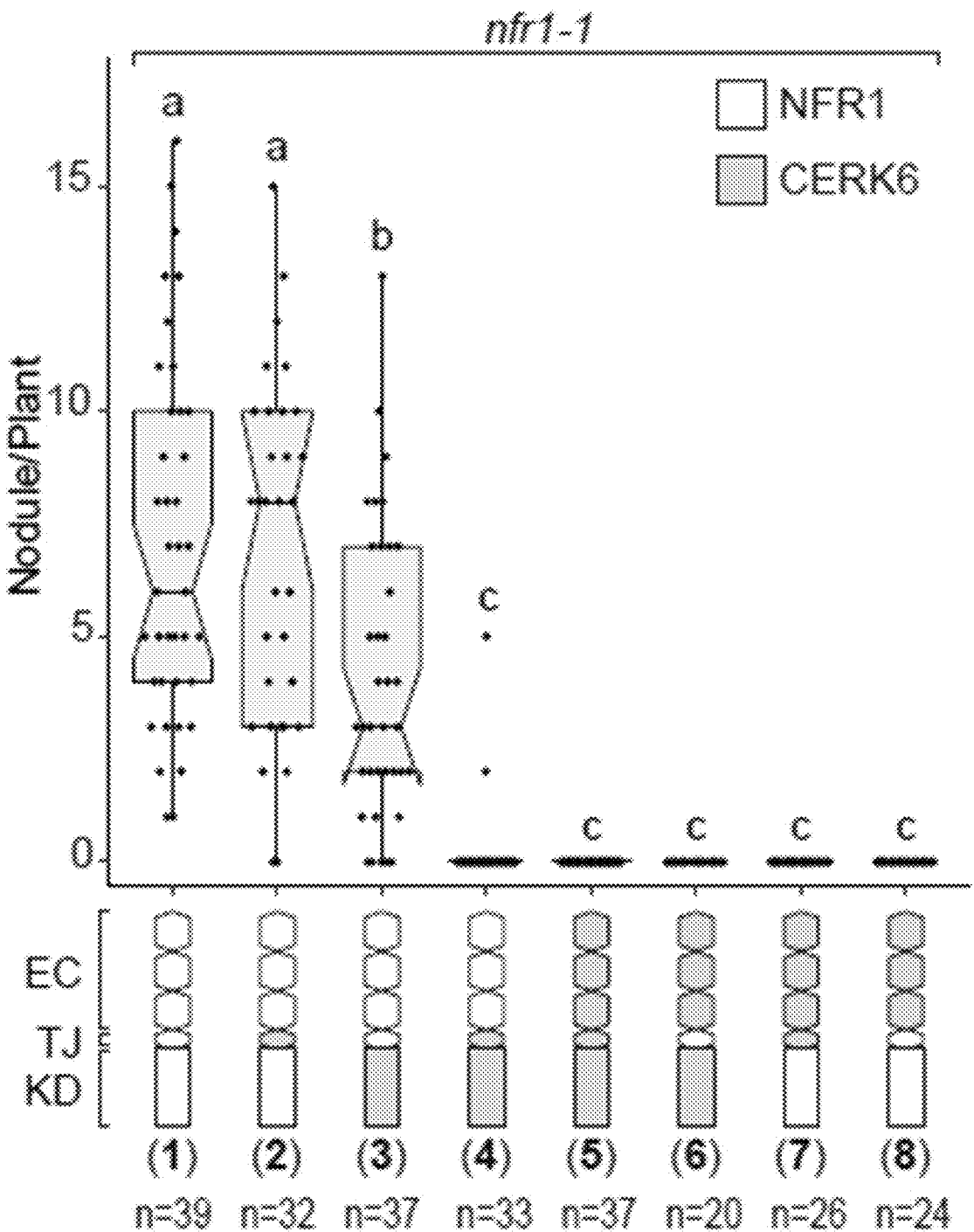
FIGS. 2A-2C show results of functional studies measuring nodulation and reactive oxygen species (ROS) formation using chimeras of the *L. japonicus* LysM receptor kinase proteins NFR1 and CERK6.
Figure 2B:
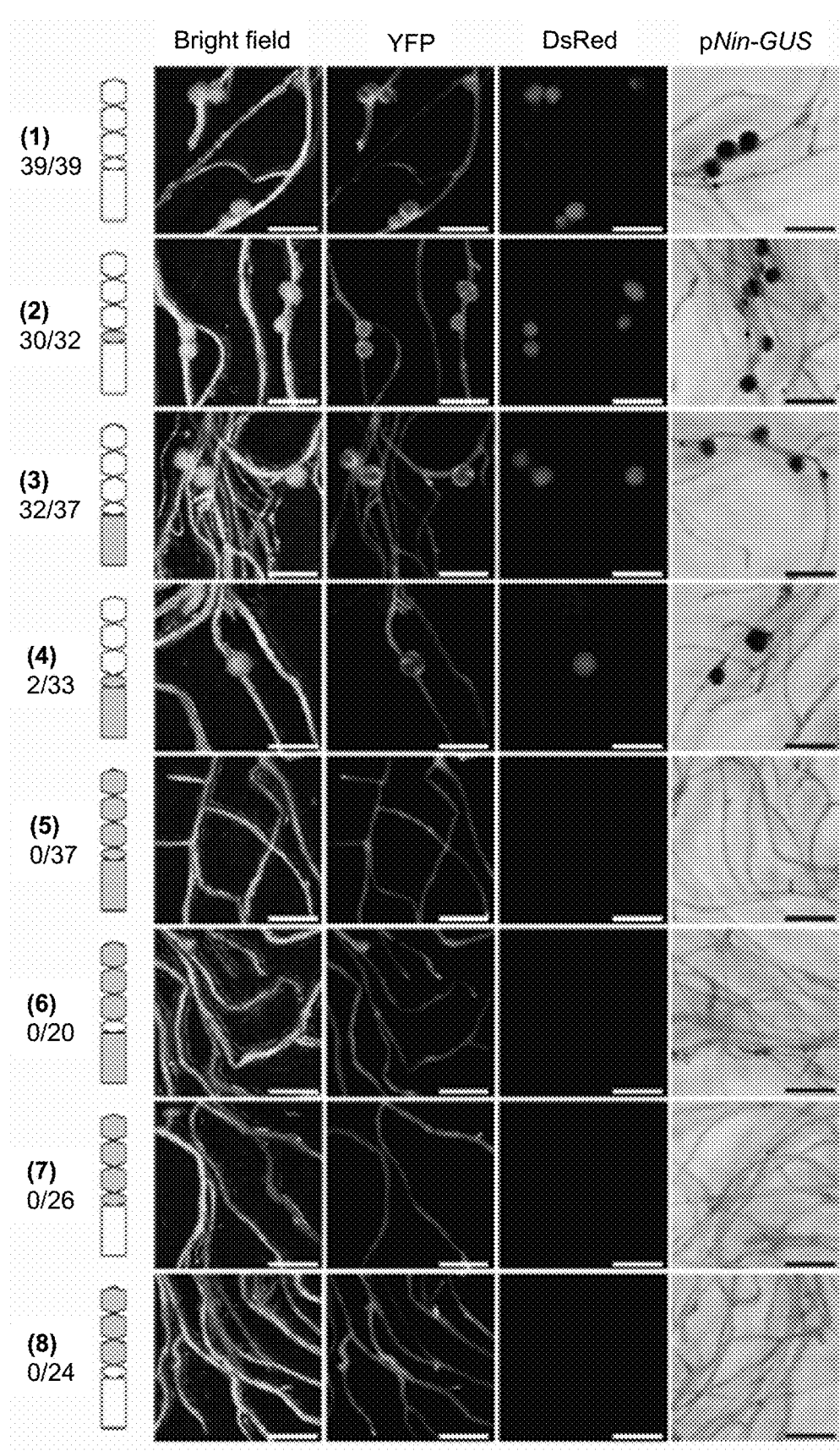
Figure 2C:
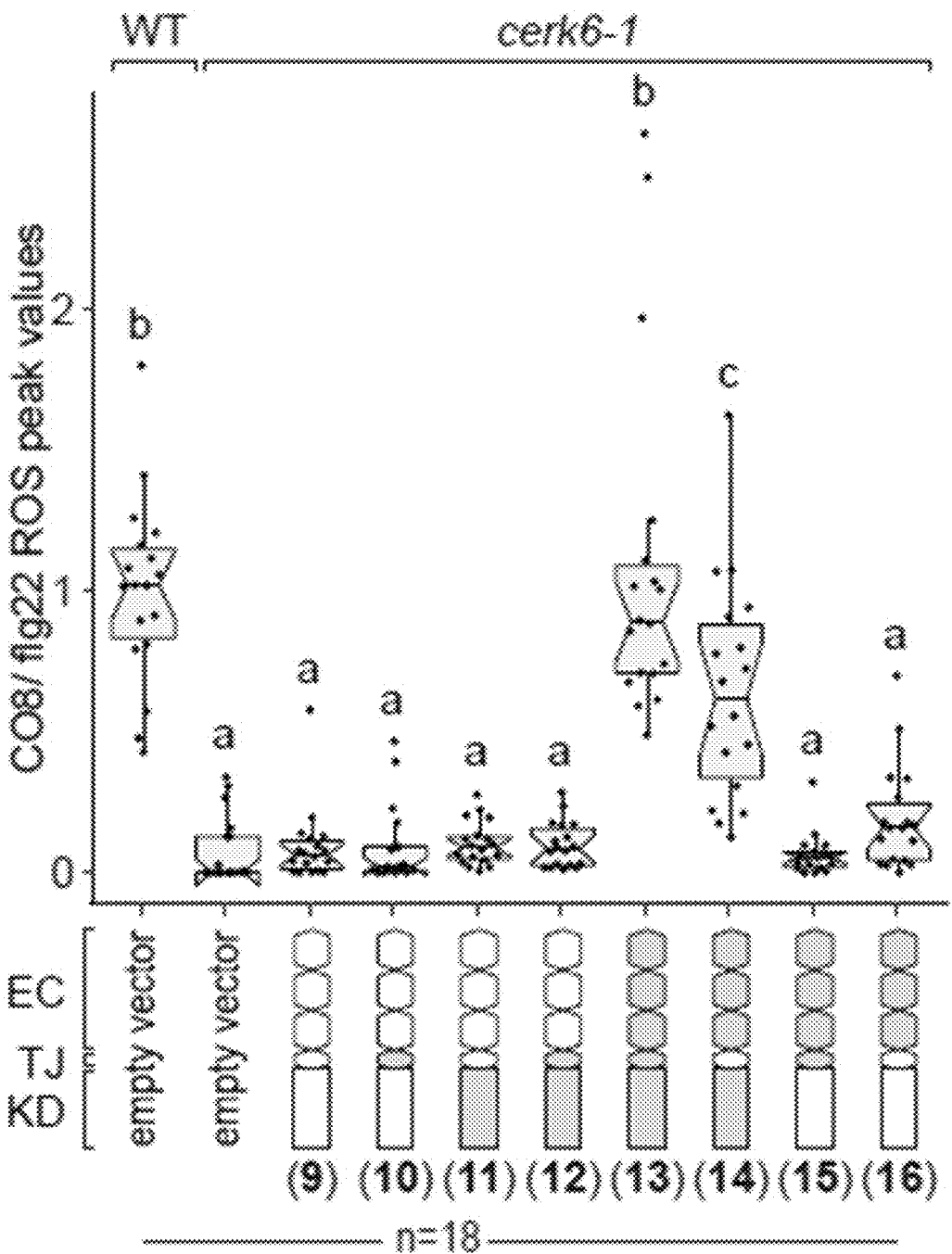
Figure 4B:
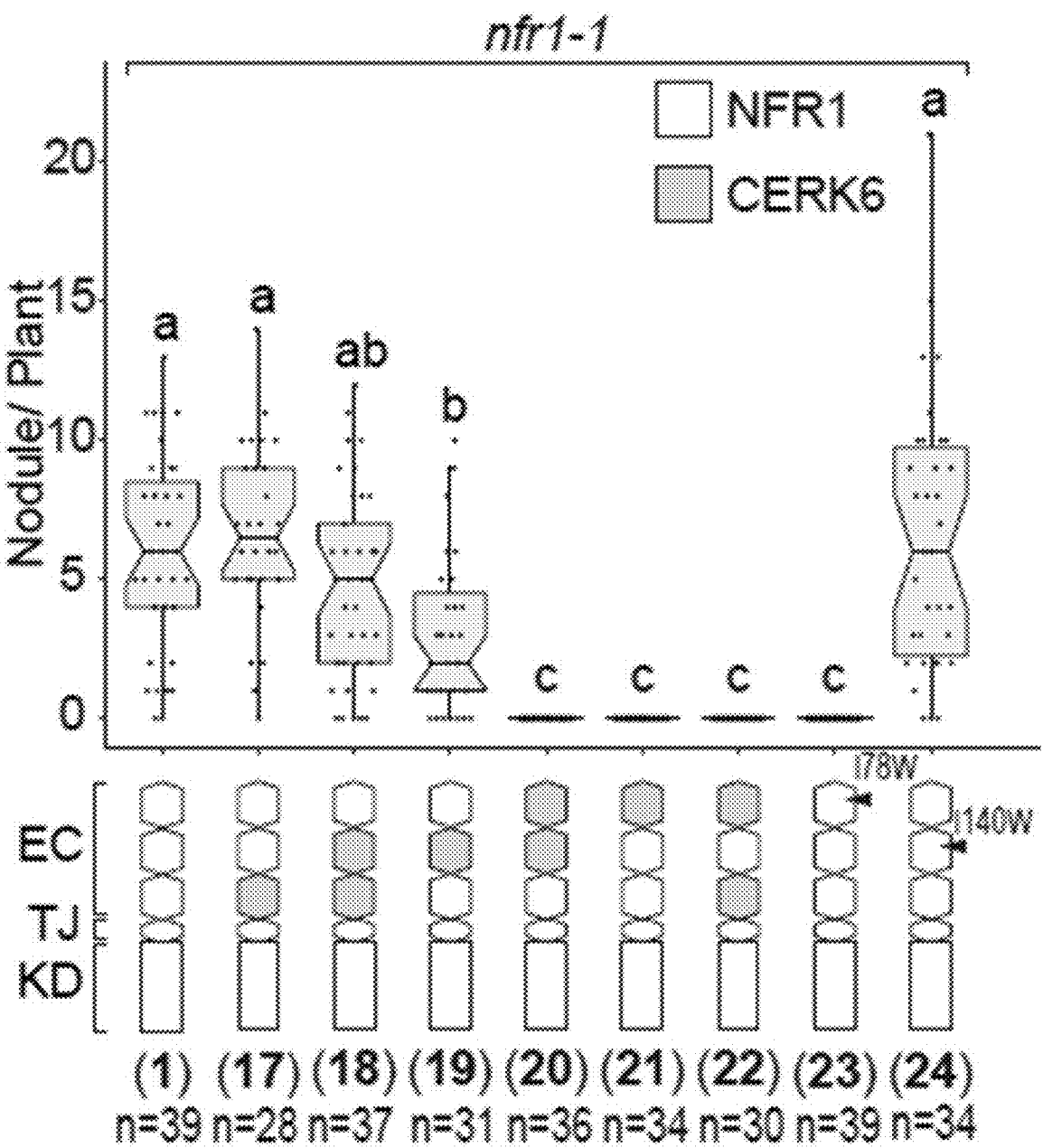
Figure 6A:
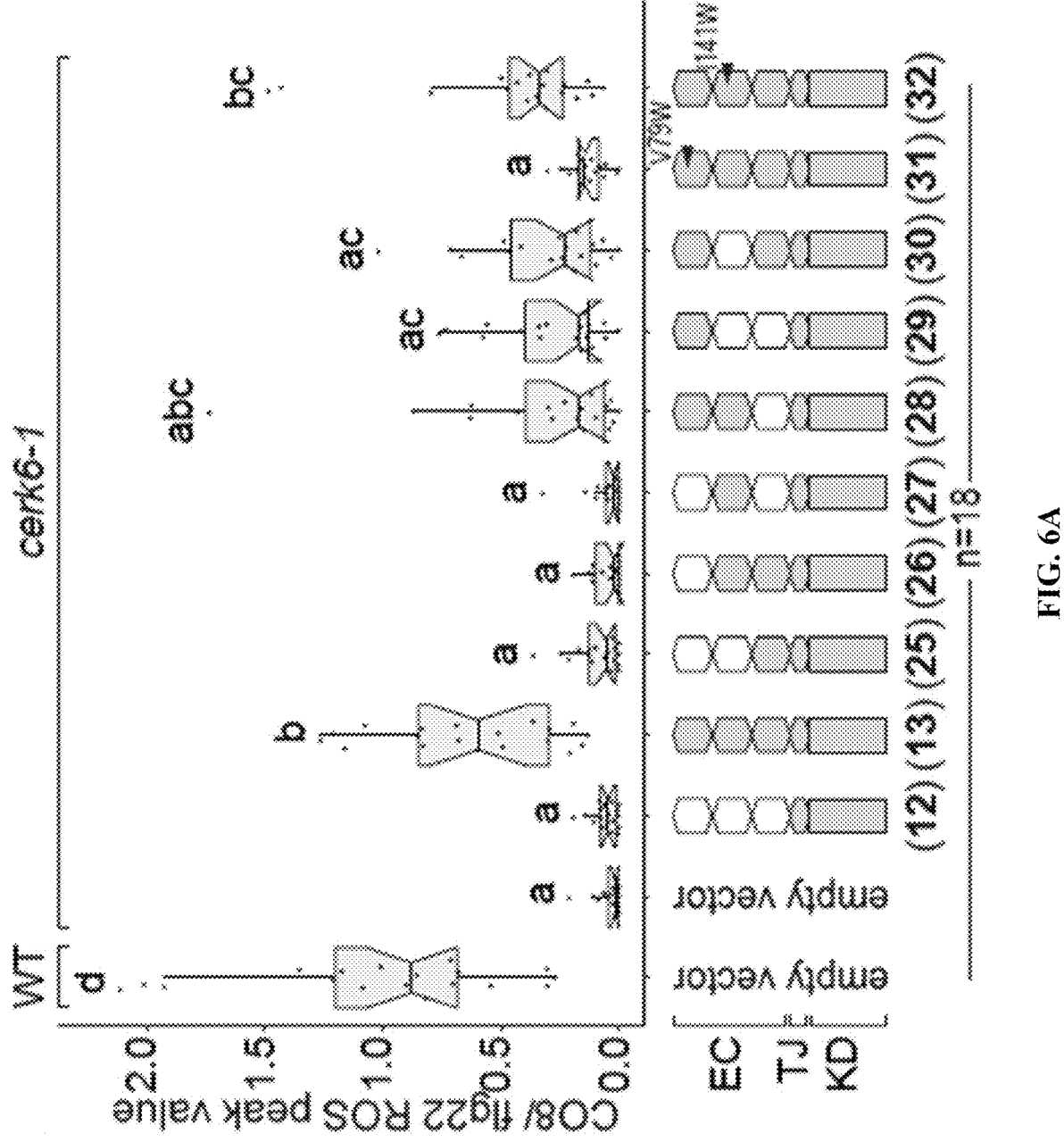
FIGS. 6A-6B show results of functional studies measuring nodulation and ROS formation using chimeras of the *L. japonicus* LysM receptor kinase proteins NFR1 and CERK6 in which the LysM1, LysM2, and LysM3 domains are swapped and structural models of CERK6.

| LysM receptor kinase expression constructs | | | |
|---|---|---|---|
| Construct Number | Promoter | Description of LysM Receptor Kinase | FIGS. |
| 1 | Nfr1 | NFR1 | FIGS. 2A-2B, 4B |
| 2 | Nfr1 | NFR1 with CERK6 TJ | FIGS. 2A-2B |
| 3 | Nfr1 | NFR1 with CERK6 KD | FIGS. 2A-2B |
| 4 | Nfr1 | NFR1 with CERK6 TJ and KD | FIGS. 2A-2B |
| 5 | Nfr1 | CERK6 | FIGS. 2A-2B |
| 6 | Nfr1 | CERK6 with NFR1 TJ | FIGS. 2A-2B |
| 7 | Nfr1 | CERK6 with NFR1 KD | FIGS. 2A-2B |
| 8 | Nfr1 | CERK6 with NFR1 TJ and KD | FIGS. 2A-2B |
| 9 | Cerk6 | NFR1 | FIG. 2C |
| 10 | Cerk6 | NFR1 with CERK6 TJ | FIG. 2C |
| 11 | Cerk6 | NFR1 with CERK6 KD | FIG. 2C |
| 12 | Cerk6 | NFR1 with CERK6 TJ and KD | FIGS. 2C, 6A |
| 13 | Cerk6 | CERK6 | FIGS. 2C, 6A |
| 14 | Cerk6 | CERK6 with NFR1 TJ | FIG. 2C |
| 15 | Cerk6 | CERK6 with NFR1 KD | FIG. 2C |

TABLE 1-continued

LysM receptor kinase expression constructs

Figure 5A:
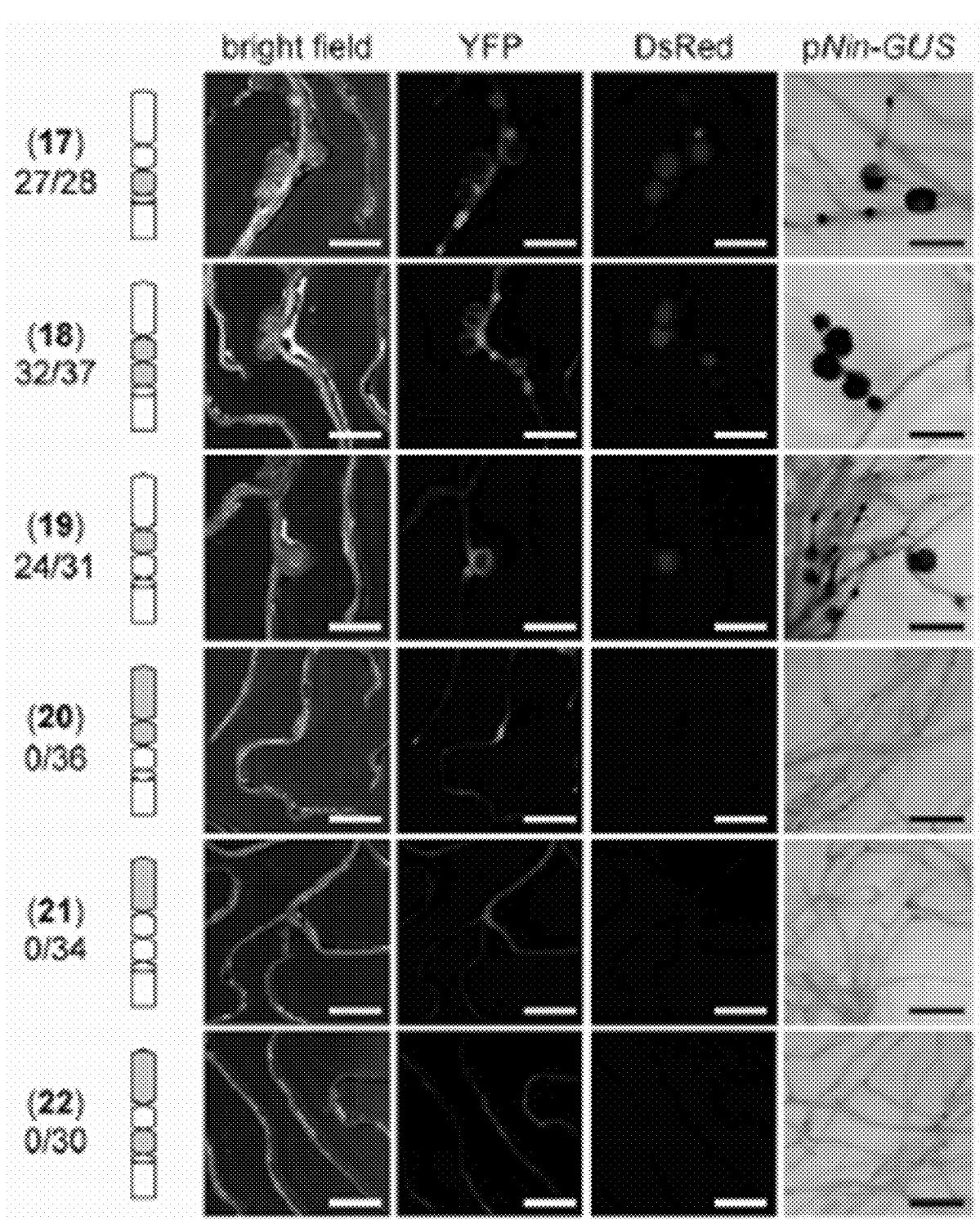
FIGS. 5A-5B show representative images of nodulation phenotypes of *L. japonicus* nfr1-1 roots expressing LysM receptor kinase constructs, including NFR1/CERK6 chimeras (constructs 17-22, and 33-26), or NFR1 with point mutations (constructs 23-24), under control of the Nfr1 promoter. As indicated in the schematic diagrams.

| Construct Number | Promoter | Description of LysM Receptor Kinase | FIGS. |
|---|---|---|---|
| 16 | Cerk6 | CERK6 with NFR1 TJ and KD | FIG. 2C |
| 17 | Nfr1 | NFR1 with CERK6 LysM3 | FIGS. 4B, 5A |
| 18 | Nfr1 | NFR1 with CERK6 LysM2 and LysM3 | FIGS. 4B, 5A |
| 19 | Nfr1 | NFR1 with CERK6 LysM2 | FIGS. 4B, 5A |
| 20 | Nfr1 | NFR1 with CERK6 LysM1 and LysM2 | FIGS. 4B, 5A |
| 21 | Nfr1 | NFR1 with CERK6 LysM1 | FIGS. 4B, 5A |
| 22 | Nfr1 | NFR1 with CERK6 LysM1 and LysM3 | FIGS. 4B, 5A |
| 23 | Nfr1 | NFR1 with I78W point mutation | FIGS. 4B, 5A |
| 24 | Nfr1 | NFR1 with I140W point mutation | FIGS. 4B, 5A |
| 25 | Cerk6 | CERK6 with NFR1 LysM1 and LysM2 | FIG. 6A |
| 26 | Cerk6 | CERK6 with NFR1 LysM1 | FIG. 6A |
| 27 | Cerk6 | CERK6 with NFR1 LysM1 and LysM3 | FIG. 6A |
| 28 | Cerk6 | CERK6 with NFR1 LysM3 | FIG. 6A |
| 29 | Cerk6 | CERK6 with NFR1 LysM2 and LysM3 | FIG. 6A |
| 30 | Cerk6 | CERK6 with NFR1 LysM2 | FIG. 6A |
| 31 | Cerk6 | CERK6 with V79W point mutation | FIG. 6A |
| 32 | Cerk6 | CERK6 with I141W point mutation | FIG. 6A |

To study the localization of LysM receptor kinases in *N. benthamiana* (tobacco) leaves (see FIGS. 3A-3B), Nfr1, Cerk6, or chimeric sequences were cloned downstream of the 35S promoter and upstream of the sequence encoding eYFP into a pICH binary vector (Weber, E. et al. *PLoS One* 2011 6) backbone containing a membrane-localized mCherry under control of the ubiquitin promoter (see FIG. 1E). The composition of the LysM receptor kinase coding sequences in FIGS. 3A-3B correspond to the numerical construct labels in Table 1. A summary of *N. benthamiana* LysM receptor kinase expression constructs is provided below in Table 2.

TABLE 2

*N. benthamiana* LysM receptor kinase expression constructs

| Corresponding Construct Numbers | Promoter | Description of LysM Receptor Kinase | FIGS. |
|---|---|---|---|
| 1 and 9 | 35S | NFR1 | FIG. 3A |
| 4 and 12 | 35S | NFR1 with CERK6 TJ and KD and K351N point mutation | FIG. 3A |
| 5 and 13 | 35S | CERK6 with K351N point mutation | FIG. 3A |
| 7 and 15 | 35S | CERK6 with NFR1 KD | FIG. 3A |
| 23 | 35S | NFR1 with I78W point mutation | FIG. 3B |
| 31 | 35S | CERK6 with V79W and K351N point mutations | FIG. 3B |
| 65 | 35S | CERK6 with NFR1 LysM1 regions II and IV and K351N point mutation; see Example 5, below | FIG. 3B |

Expression in *N. benthamiana* leaf cells of the YFP-tagged LysM receptor kinases with domain structures corresponding to constructs 4 and 12, 5 and 13, or 7 and 15 showed they were localized at the plasma membrane. This mirrored the protein synthesis and expression observed for full-length NFR1 (corresponding to constructs 1 and 9) or CERK6 (corresponding to constructs 5 and 13) YFP-tagged LysM receptor kinases (FIGS. 3A-3B). The constructs with CERK6 KDs contained K351N mutations in the KD that rendered the kinase inactive, thereby circumventing activation of cell death and enabling receptor localization.

Hairy Root Transformation

*A. rhizogenes* carrying the expression constructs of interest were grown for two days on solid medium. The cells of one plate were resuspended in 2 ml YMB media, and this process was repeated for each construct. A 1 ml syringe with a needle (Sterican Ø0.40×20 mm) was then used to transform the plants, whereby the needle was used to puncture the hypocotyl and a droplet with the bacterial suspension was placed on the wound. Petri dishes containing the transformed roots were sealed and left in the dark for two days and then moved to 21° C. under 16 hour light/8 hour dark conditions. After three weeks, plants with transformed roots were moved to Magenta boxes (Sigma-Aldrich) filled with a 4:1 mixture of lightweight expanded clay aggregate (LECA, 2-4 mm; Saint-Gobain Weber A/S) and vermiculite (size M; Damolin A/S) supplemented with 80 ml nitrogen-free ¼× B&D nutrient solution. All plants were grown at 21° C. under 16 hour light/8 hour dark conditions.

Nodulation Assays

Chimeric receptors under the control of the Nfr1 promoter were tested for their ability to complement a *L. japonicus* nfr1-1 loss-of-function mutant that is unable to develop root nodules (Radutoiu, S. et al. Nature 2003 425). Transformed *L. japonicus* plants were inoculated with 400 μl per plant of *M. loti* R7A DsRed strain at a final concentration of ° Da)=0.04. At five weeks post inoculation, nodules were counted and images were acquired with a Leica FluoStereo M165FC microscope equipped with the Leica DFC310 FX camera.

Oxidative Burst Assays

Chimeric receptors under the control of the Cerk6 promoter were tested for their ability to complement the *L. japonicus* cerk6-1 loss-of-function mutant that is unable to produce chitin-induced reactive oxygen species (ROS; Bozsoki, Z. et al. *Proc. Natl. Acad. Sci.* 2017 114: E8118-E8127). Three-week-old transformed *L. japonicus* roots were cut into 1 mm pieces, collected into white 96-well flat-bottomed polystyrene plates (Greiner Bio-One), and kept overnight in sterile water. The water on the root pieces was then replaced with a reaction mixture consisting of 0.5 mM L-012 (Wako Chemicals), 5 μg $ml^{-1}$ horseradish peroxidase (Sigma), and either 1 μM octa-N-acetyl-chitooctaose (CO8, obtained from Isosep) or 0.5 μM flg22 (EZBiolab). Luminescence was recorded with a Varioskan LUX multimode microplate reader (ThermoFisherScientific) in a time course manner. The ratio between CO8-induced ROS peak and flg22 peptide-induced ROS peak in each sample was obtained. Flg22 treatment was used as internal control for root responsiveness to elicitors. This ratio was normalized to that obtained for wild-type included in the assay as a control. (FIG. 2C, FIG. 6A).

GUS Staining 5-week-old transformed *L. japonicus* roots were stained with 0.5 mg $ml^{-1}$ 5-bromo-4-chloro-3-indolyl-β-D-glucuronic acid (X-Gluc), 100 mM potassium phosphate buffer (pH 7.0), 10 mM EDTA (pH 8.0), 1 mM potassium ferricyanide, 1 mM potassium ferrocyanide, and 0.1% Triton X-100. The stained roots were incubated at 37° C. overnight. Roots were washed with EtOH 70% twice before image acquisition (FIG. 2B).

*Agrobacterium* Mediated Transient Transformation of *N. benthamiana*

*A. tumefaciens* carrying LysM receptor kinase expression constructs were grown overnight in liquid medium (28° C. at 180 rpm). The cells were pelleted and resuspended in water to a final density of $OD_{600}$=0.6-0.8, and incubated at room temperature for 2 hours. The bacterial suspension was then infiltrated into leaves of 4-week-old *N. benthamiana* plants with a needleless syringe (FIGS. 3A-3B).

Confocal Microscopy and Image Processing

Confocal imaging was performed using Zeiss LSM780 with the following excitation/emission parameters for generating composite images: i) YFP-514/520-560 nm, ii) mCherry-561/570-600 nm. Fluorescence of YFP and mCherry was acquired separately. Channels were arranged using Fiji (Schindelin, J. et al. *Nat Methods* 2012 9:676-682).

Quantification and Statistical Analysis

Data analyses were conducted with R using ggplot2 (The R core team, R Foundation for Statistical Computing, Vienna, Austria, 2019; Villanueva, R. A. *M. and Chen, Z. J. Meas-Interdiscip Res* 2019 17: 160-167). For statistical analysis, one-way analysis of variance (ANOVA) with Tukey's multiple comparisons test were used.

Results

The Ectodomains of NFR1 and CERK6 are Necessary for Nodulation and CO8-Induced Immune Responses The contribution of LysM receptor kinase ectodomains (EC), transmembrane and juxtamembrane domains (TJ), and the kinase domains (KD) to nodulation after *M. loti* inoculation, or reactive oxygen species (ROS) formation in response to CO8 treatment was investigated. In *L. japonicus*, the LysM receptor kinase NFR1 is required for nodule formation upon inoculation with *M. loti*, and the LysM receptor kinase CERK6 is required for CO8-induced ROS formation. Introduction of NFR1 (construct 1 in FIGS. 2A-2B) and all chimeras with the ectodomain of NFR1 (constructs 2, 3, and 4 in FIGS. 2A-2B) restored nodule formation to *L. japonicus* nfr1-1 (nfr1 henceforth) loss-of-function mutant roots, but were not able to restore ROS production in a cerk6-1 (cerk6 henceforth) loss-of-function mutant after CO8 treatment (constructs 9, 10, 11, and 12 in FIG. 2C).

Chimeras complemented the absence of nodule formation phenotype of the nfr1 mutant roots to different extents. Expression of construct 3 containing the KD of CERK6 resulted in to a significantly lower level of nodulation compared to constructs 1 or 2, while exchanging both the TJ and KD with CERK6 in construct 4 had a dramatic consequence on the nodulation phenotype. Indeed, only 2 out of the 33 plants expressing construct 4 formed nodules (FIG. 2A), indicating that combining molecular elements present in the KD and TJ regions of CERK6 had a negative impact on nodulation signaling. All nodules formed on roots expressing constructs 1, 2, 3, and 4 were infected by *M. loti* bacteria (FIG. 2B), showing that both nodulation and infection processes were activated. Furthermore, induction of the symbiotic marker pNin-GUS was detected only in the nodulated roots (constructs 1, 2, 3, and 4, FIG. 2B), showing that in *L. japonicus M. loti*-induced signaling activated by the functional chimeras progressed all the way to nodulation. In contrast, none of the chimeras containing the ectodomain of CERK6 were able to trigger nodulation in the nfr1 mutant (constructs 5, 6, 7, and 8 in FIG. 2A).

Similarly, chimeras complemented the deficiency of ROS production in the cerk6 mutant to different extents. Both CERK6 (construct 13 in FIG. 2C) and one of the chimeras containing the CERK6 ectodomain (construct 14) complemented CO8-dependent ROS production in cerk6 (FIG. 2C). Interestingly, chimeric constructs 15 and 16, containing the NFR1 KD, were unable to complement cerk6. These results showed that NFR1 KD, even when coupled to the CERK6 ectodomain, could not activate the immune signaling pathway leading to ROS production after CO8 treatment.

Previous studies based on overexpression of chimeric receptors between *L. japonicus* and *A. thaliana* LysM proteins pinpointed the role of NFR1 ectodomains in Nod factor recognition (Nakagawa, T. et al. *Plant J* 2011 65:169-180; Wang, W. et al. *Plant J* 2014 78:56-69). The results presented herein based on native expression levels (rather than overexpression) of chimeric receptors from paralogous *L. japonicus* proteins showed that the ectodomains of NFR1 and CERK6 contained major determinants for ligand perception and signaling specificity, and demonstrated that this can be further modulated by their intracellular domains.

Figure 5B:
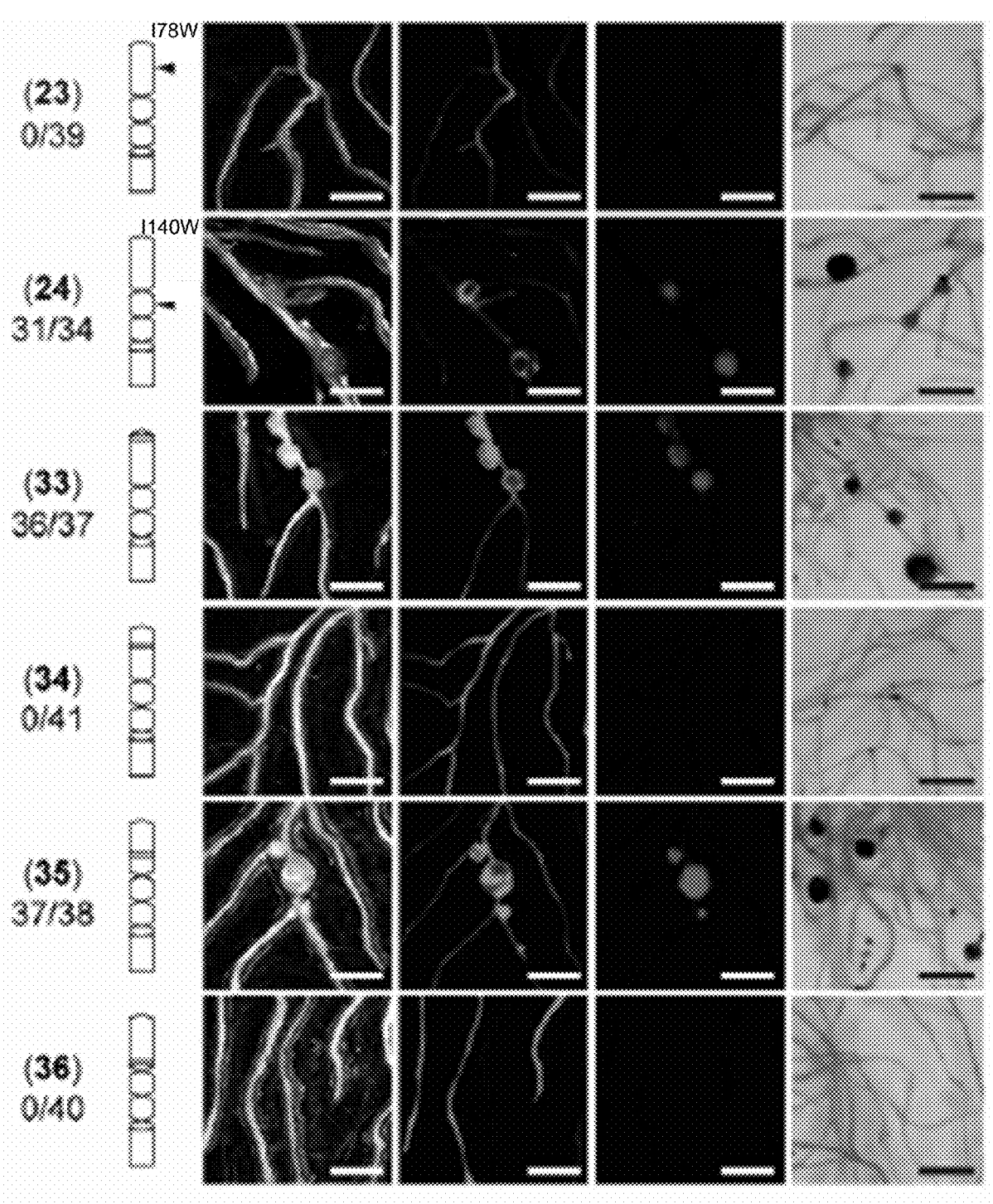

Specificity for Nod Factor and Chitin Recognition is Determined by the LysM1 Domains To determine which of the three LysM domains in the ectodomains of NFR1 and CERK6 harbored ligand specificity determinants, a series of chimeric receptors was tested. The chimeric receptors had combinations of the three LysM domains originating from NFR1 or CERK6 receptors, which were coupled either to NFR1 or CERK6 TJs and KDs (FIG. 4A). Surprisingly, nodulation and ROS production was dependent on the origin of the LysM1 domain. The three chimeric proteins (constructs 17, 18, and 19) containing the NFR1 LysM1 domain were able to restore *M. loti*-dependent nodulation (FIG. 4B) and infection in nfr1 *L. japonicus* (FIGS. 5A-5B). The corresponding three chimeras (constructs 20, 21, and 22) with the CERK6 LysM1 domain did not restore nodulation of nfr1 mutants (FIGS. 4B, 5A-5B).

Reciprocal results were obtained in assays of cerk6 complementation for CO8-dependent ROS production. *L. japonicus* cerk6 roots expressing constructs 28, 29, and 30, which contained the LysM1 domain of CERK6, produced ROS after CO8 treatment. In contrast, roots expressing constructs 25, 26, and 27, which contained the LysM1 domain from NFR1, failed to complement the cerk6 mutant phenotype (FIG. 6A).

Results from expression of constructs 18 and 19 revealed a lower complementation efficiency of nfr1 when compared to NFR1 (construct 1) or construct 17 receptors, indicating that CERK6 LysM2 was detrimental to nodulation (FIG. 4B). Besides this modest impact of the CERK6 LysM2 domain on nfr1 complementation, the origin of the LysM2 and LysM3 domains (i.e., CERK6 or NFR1) had no major impact on nodulation or ROS production. Without wishing to be bound by theory, this indicated that LysM2 and LysM3 did not play a critical role in determining the specificity for Nod factor and chitin perception in NFR1 and CERK6, respectively.

Analysis of Point Mutations in Putative LysM1 and LysM2 Ligand-Binding Sites

Figure 6B:
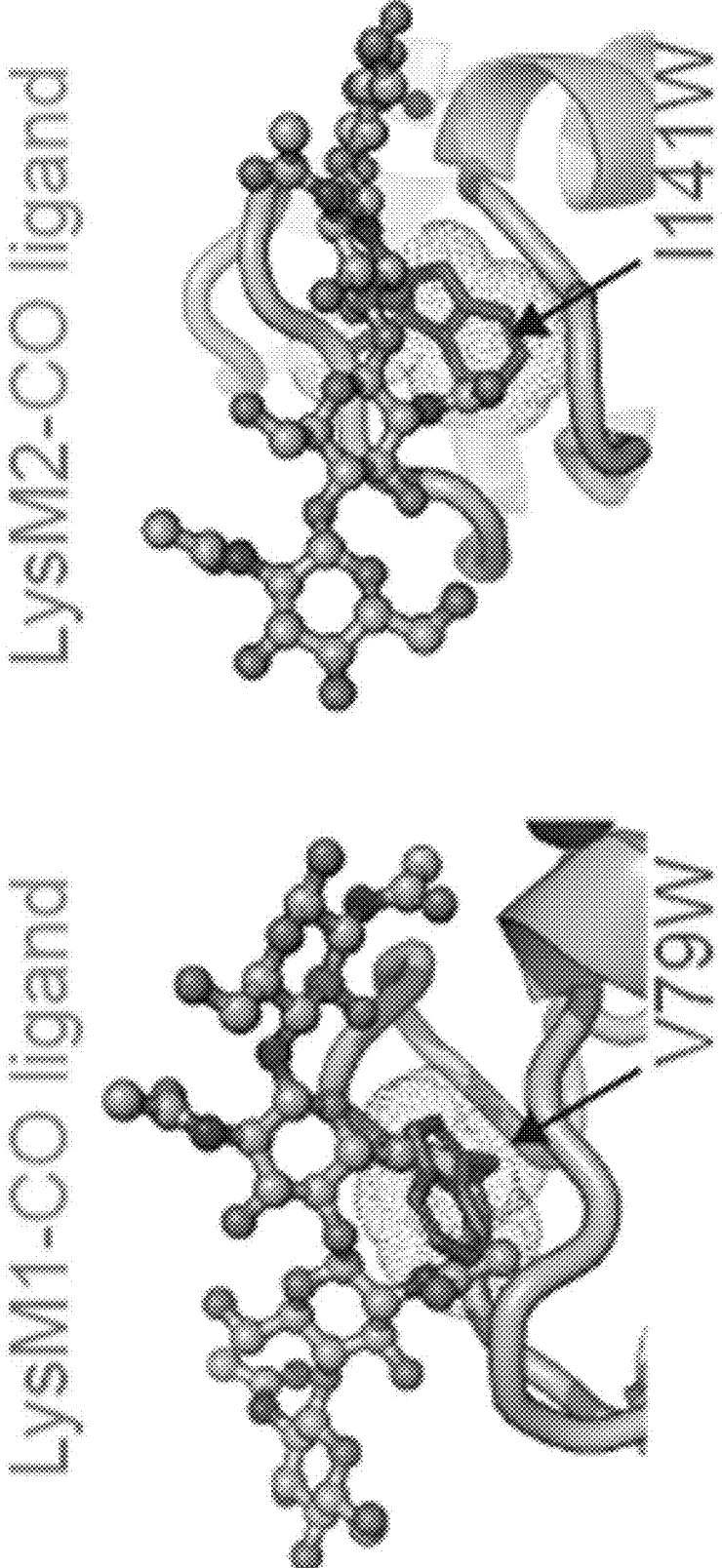

Previous structural studies of the *A. thaliana* CERK1 (AtCERK1) ectodomain identified a chitin binding site in LysM2 (Liu, T. et al. *Science* 2012 336: 1160-1164). The results presented herein from *L. japonicus* identified LysM1 domains as critical for functional specificity. Therefore, whether the putative binding sites within LysM1 or LysM2 were necessary for LysM receptor kinase function was assessed. The structure of *L. japonicus* CERK6 and the chitin-bound structure of AtCERK1 were used to investigate potential ligand binding sites in LysM1 and LysM2 of CERK6, and to identify conserved amino acids that, when mutated to a bulky residue (i.e., tryptophan), could disrupt the possible binding pockets (FIG. 6B) (Liu, T. et al. *Science* 2012 336: 1160-1164). As shown in FIG. 6B, the CERK6 LysM1 and LysM2 domains both had predicted CO ligand-binding pockets. To disrupt these putative ligand binding pockets, amino acid substitutions were introduced in LysM1 and LysM2 of CERK6 and NFR1 at corresponding positions. In particular, the CERK6 LysM1 domain residue V79 was mutated to tryptophan (V79W, construct 31), and the LysM2 domain residue I141 was mutated to tryptophan (I141W, construct 32), as shown in FIG. 6B. Corresponding mutations were also introduced into NFR1 LysM1 and LysM2, with residue 178 mutated to tryptophan in LysM1 (I78W, construct 23), and residue 1140 mutated to tryptophan in LysM2 (I140W, construct 24). The positions of these point mutations are shown in the schematic diagram provided in FIG. 4A.

Functional analyses of the receptor mutants with these tryptophan substitutions in LysM1 (constructs 23 and 31) or LysM2 (constructs 24 and 32) revealed that only mutations in the LysM1 domain impaired the ability of NFR1 and CERK6 receptors to complement mutants for their defective phenotypes in root nodule symbiosis and immunity, respectively (FIGS. 3B, 4B, 5B, and 6A). These results provided a molecular basis and explanation of previous observations from analyses of mutations in Nod factor receptors from P. sativum (Sym37) and M. truncatula (Lyk3). In SYM37, an L77 to P substitution in the RisNod4 mutants results in impaired symbiosis (Zhukov, V. et al. Mol Plant Microbe Interact 2008 21: 1600-1608), and in M. truncatula the lyk3-3 allele contains a P87S mutation with similar defective symbiotic phenotype (Smit, P. et al. Plant Physiol 2007 145: 183-191). FIG. 13E indicates the location of the P87S mutation in M. truncatula lyk3-3 on a structural model of LysM1 from LYK3, and also indicates the position of the L77P mutation in P. sativum SYM37 mutants. Both of these mutations are located at the predicted ligand binding site in the LysM1 domain.

Together, these observations provided strong evidence for the role of the LysM1 domain in determining the specificity of Nod factor and chitin perception. Furthermore, results from analyses of point mutations in L. japonicus (FIGS. 4B, 6A) and A. thaliana receptors (Liu, T. et al. Science 2012 336: 1160-1164) illustrated the plasticity of glycan (e.g., chitin or Nod factor) recognition and functionality of LysM receptors in plants.

Example 2: Identification of Regions in the LysM1 Domain that are Required for Nodulation, CO8-Induced Immune Response, and Nod Factor Recognition The following example describes experiments assessing the contribution of regions within the LysM1 domain to nodulation, CO8-dependent ROS production, and specific Nod factor recognition.

Materials and Methods

L. japonicus materials and growth conditions, bacterial strains and culture conditions, hairy root transformation, nodulation assays, and ROS formation assays were all as described in Example 1, above.

M. truncatula Lines, Growth Conditions, and Nodulation Assays

Medicago truncatula cv. Jemalong A17 was the wild-type M. truncatula variety. The lyk3-1 (hcl-1) EMS mutant line was used as the background for nodulation assays (see FIG. 9B).

M. truncatula germination and nodulation assays were performed as described for L. japonicus in Example 1, above, except that M. truncatula was inoculated with S. meliloti 1021 DsRed for nodulation assays.

S. meliloti Strain and Culture Conditions

Sinorhizobium meliloti strain 1021 expressing the fluorescent protein DsRed was used, and was grown in TY/YMB medium at 28° C.

Generation of Plant Expression Vectors

For hairy root transformation of L. japonicus and M. truncatula, the pIV10 expression vector (Hansen, J. et al. Plant Cell Rep 1989 8: 12-15) was used. This expression vector contains a sequence encoding triple YFP fused to a nuclear localization signal (pIV10_tYFP-NLS) that serves as a transformation control.

Expression constructs were generated to express LysM receptor kinases in L. japonicus or M. truncatula. LysM receptor kinase coding sequences were placed under control of the L. japonicus Nfr1 (SEQ ID NO: 261) or L. japonicus Cerk6 promoters (SEQ ID NO: 264), or the M. truncatula Lyk3 promoter (SEQ ID NO: 262). Plasmids containing gene fragments encoding the respective domains or regions of L. japonicus NFR1, L. japonicus CERK6 and or M. truncatula LYK3 were assembled with the appropriate promoter and cloned into the pIV10_tYFP-NLS expression vector via Golden Gate cloning (FIG. 1D; Engler, C. et al. PLoS One 2008 3: e3647). Expression constructs were generated to express NFR1, CERK6, LYK3, chimeric alleles of NFR1 and CERK6, and chimeric alleles of NFR1 and LYK3 (see FIGS. 7A-7C, 8A-8B, and 9A-9B). As described in Example 1, chimeric alleles of LysM receptor kinases were designed based on their modular structure, which has, from N to C terminus, an extracellular region also known as the ectodomain ("EC") made up of three LysM domains (LysM1, LysM2, and LysM3), a transmembrane segment and an intracellular region with a juxtamembrane segment ("TJ"), and a kinase domain ("KD").

Figures 8A, 8B:
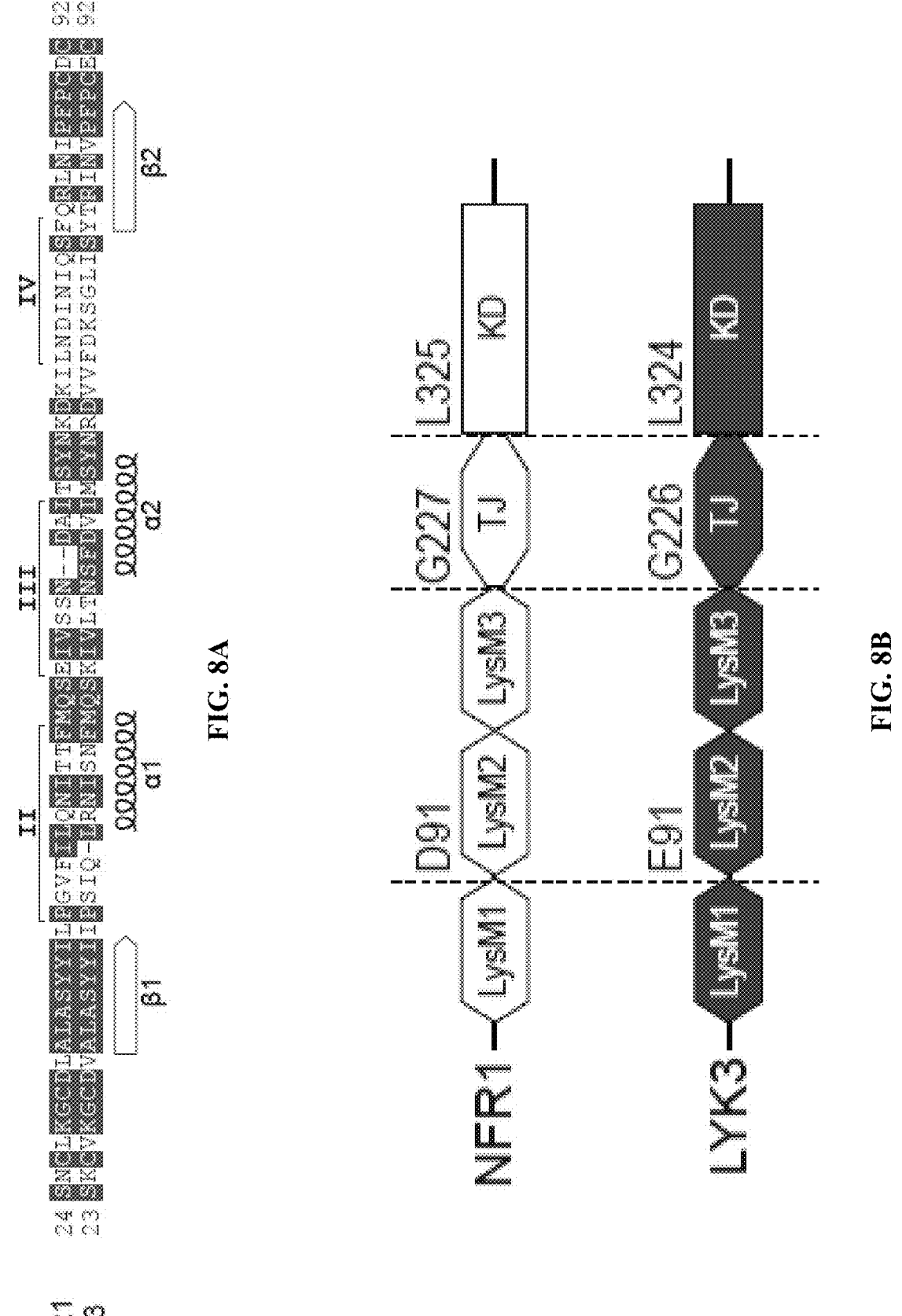

Amino acid boundaries for the purpose of exchanging domains between NFR1 and CERK6 were defined as described in Example 1, above. To exchange domains between NFR1 and LYK3, amino acid boundaries were defined as diagrammed in FIG. 8B. As shown in FIG. 8B, the NFR1 LysM2 domain began at residue D91, the TJ began at residue G227, and the KD began at residue L325. The LYK3 LysM2 domain began at residue E91, the TJ began at residue G226, and the KD began at residue L324.

Further, regions within the LysM1 domain were identified and exchanged between LysM receptor kinases. Junction points between the regions were chosen based on the LysM1 domain structure, to preserve the overall topology of the LysM1 domain. This structure-guided design of the junction point was used to create functional and well-folded receptor chimeras.

Figure 7A:
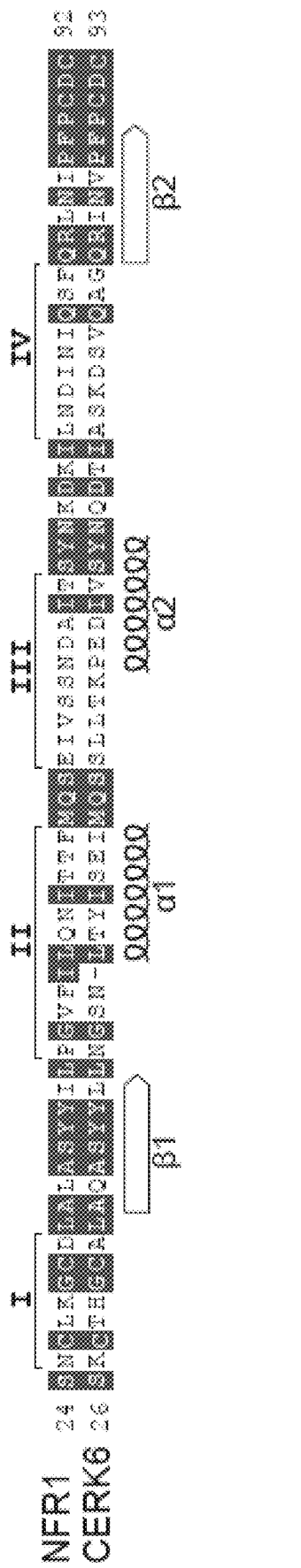
FIGS. 7A-7C shows the LysM1 domain and results of functional studies measuring nodulation and ROS formation using chimeras of the *L. japonicus* LysM receptor kinase proteins NFR1 and CERK6 in which regions within the LysM1 domain are swapped.

As shown in FIG. 7A and FIG. 8A, the NFR1 LysM1 region I contained amino acid residues NCLKGCDL (SEQ ID NO: 144), region II contained residues PGVFILQNITTF (SEQ ID NO: 145), region III contained residues EIVSSNDAIT (SEQ ID NO: 108), and region IV contained residues LNDINIQSF (SEQ ID NO: 147). As shown in FIG. 7A, the CERK6 LysM1 region I contained amino acid residues KCTHGCA (SEQ ID NO: 148), region II contained residues NGSNLTYISEI (SEQ ID NO: 149), region III contained residues SLLTKPEDIV (SEQ ID NO: 150), and region IV contained residues ASKDSVQAG (SEQ ID NO: 151). As shown in FIG. 8A, the LYK3 LysM1 region II contained amino acid residues PSIQLRNISNF (SEQ ID NO: 152), region III contained residues KIVLTNSFDVI (SEQ ID NO: 153), and region IV contained residues FDKSGLISY (SEQ ID NO: 154).

LysM receptor kinase expression constructs were assigned numerical labels that correspond to the schematic diagrams of the constructs presented in the FIGS. Table 3 provides a description of the LysM receptor kinase expression constructs used in this example.

TABLE 3

LysM receptor kinase expression constructs

Figure 7B:
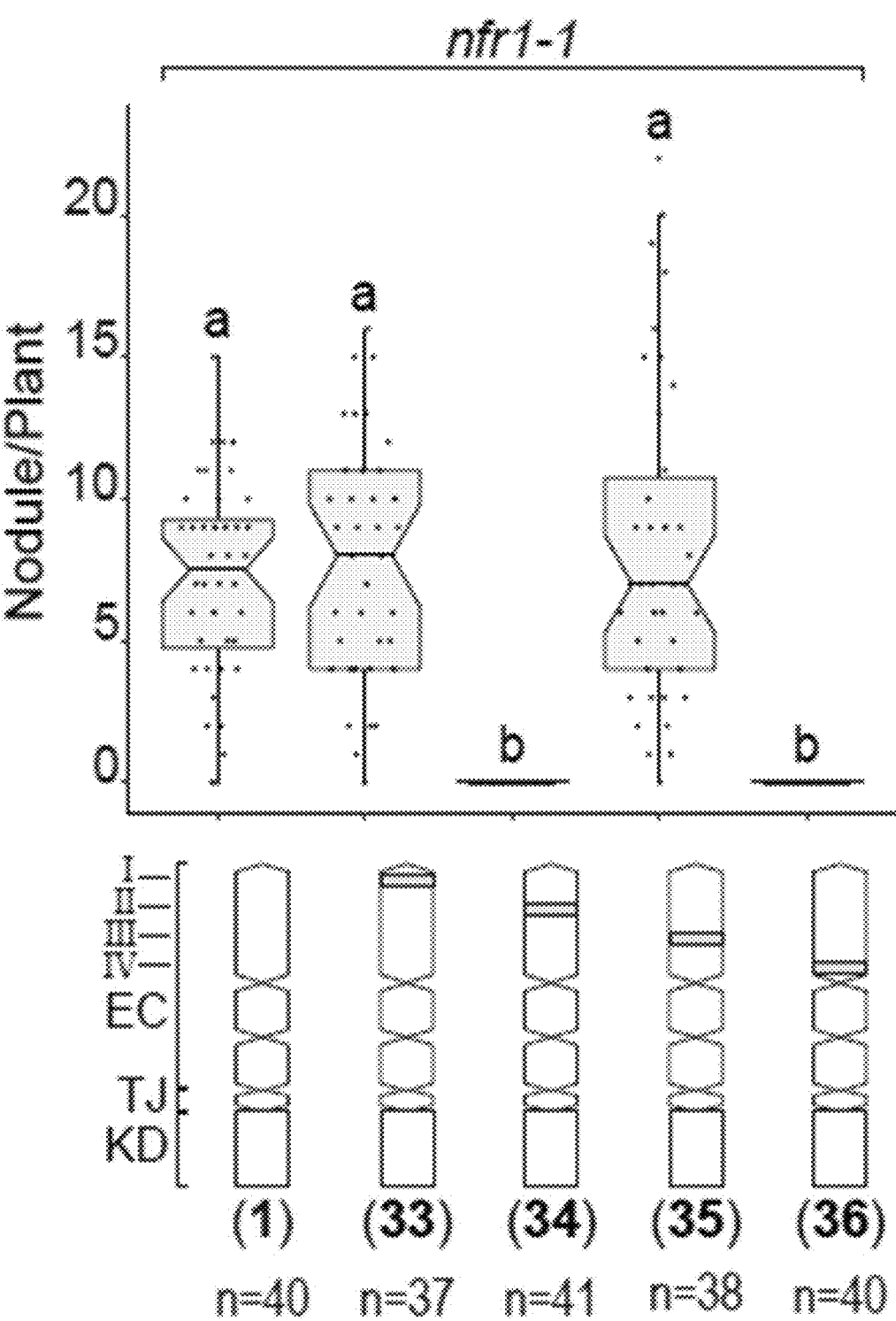
Figure 7C:
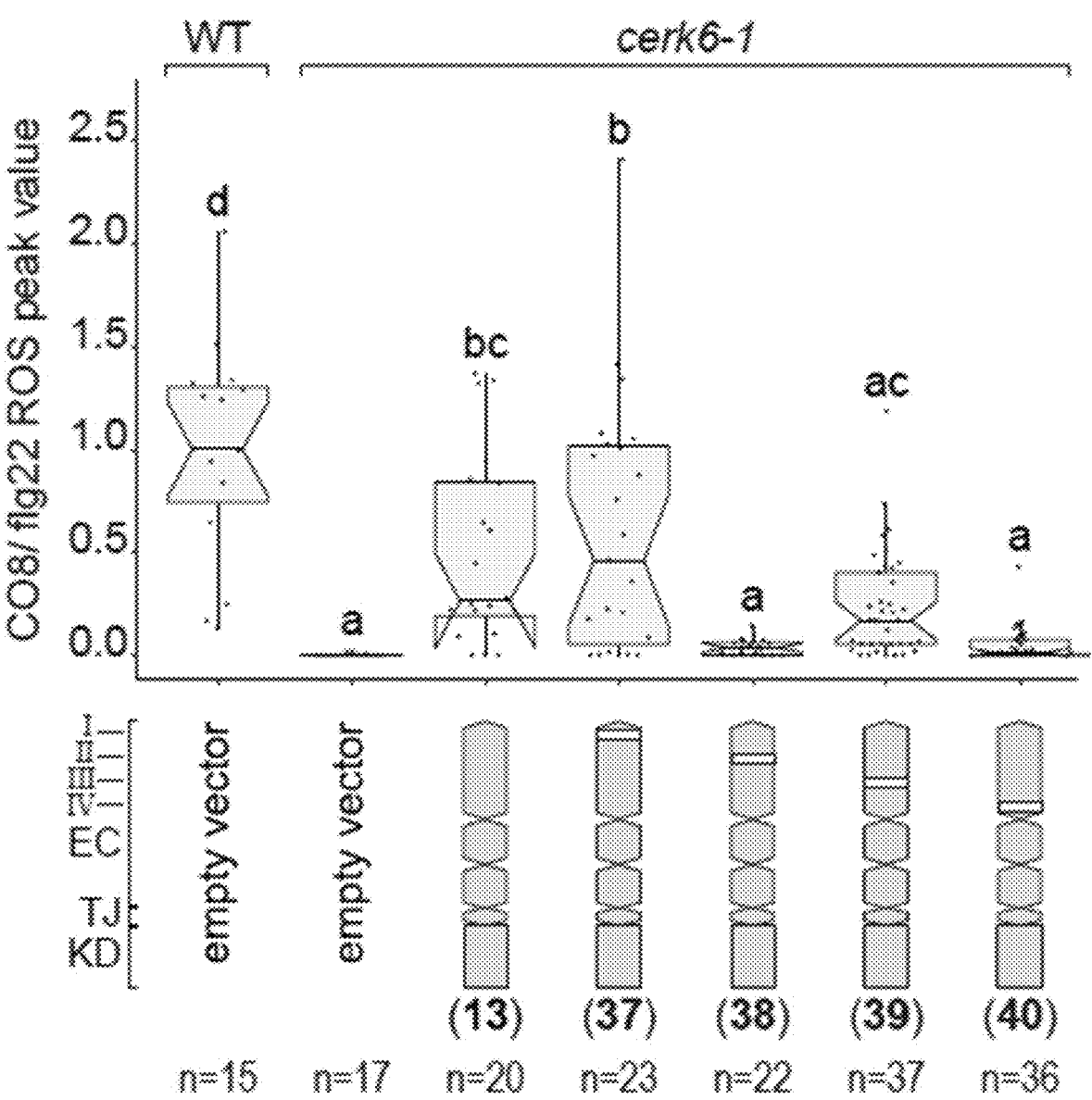
Figure 9B:
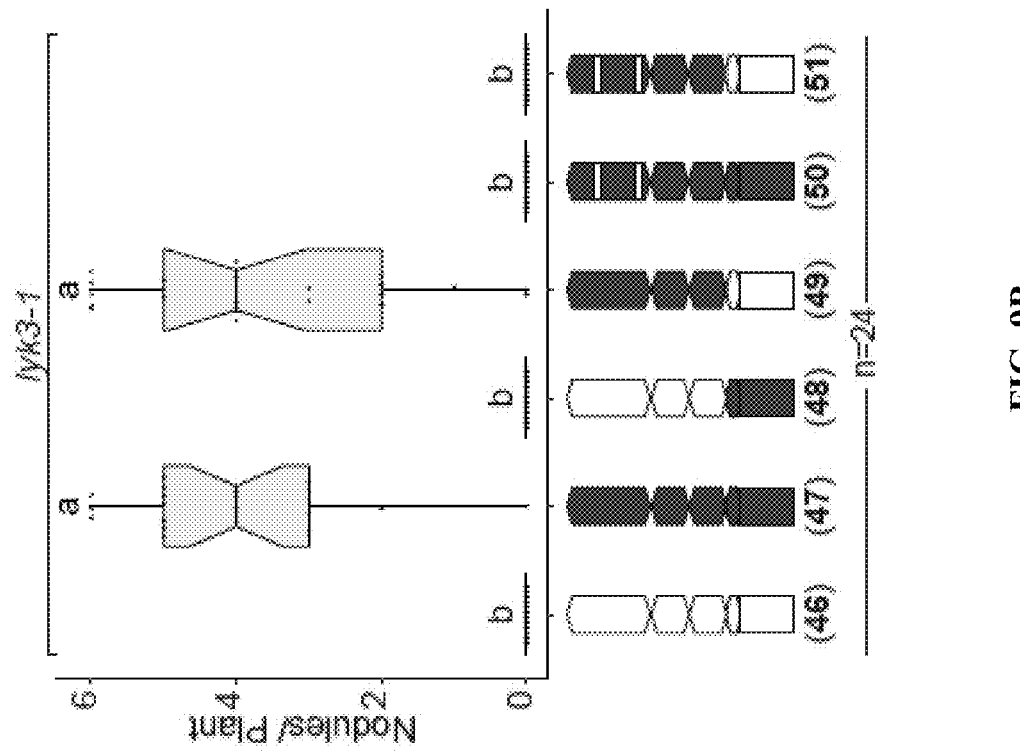
FIGS. 9A-9B show results of functional studies measuring nodulation using chimeras of the *L. japonicus* LysM receptor kinase protein NFR1 and the *M. truncatula* LysM receptor kinase protein LYK3.
Figure 9A:
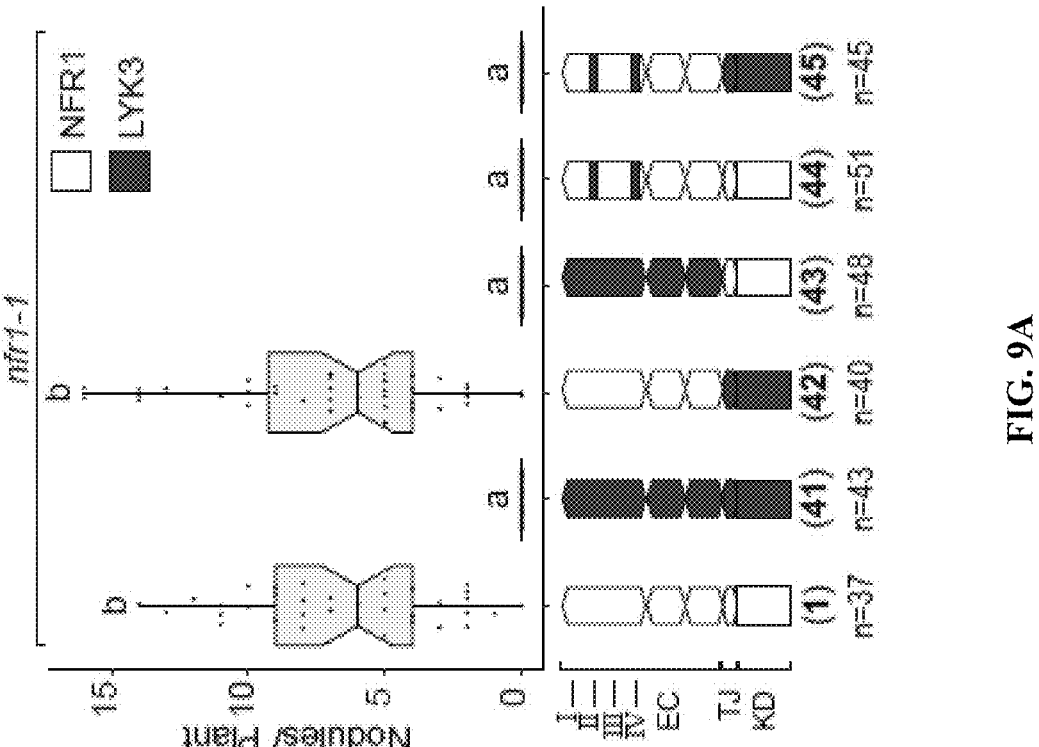
Figure 10B:
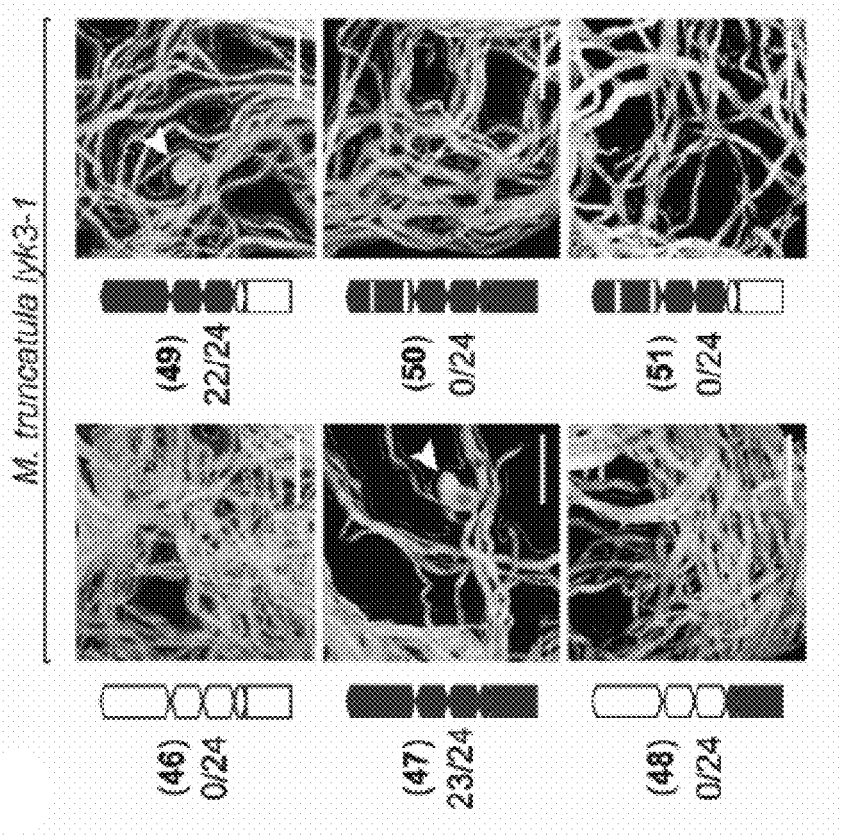
FIGS. 10A-10D show results of functional studies measuring nodulation using chimeras of the *L. japonicus* LysM receptor kinase proteins NFR1 and CERK6, or *L. japonicus* NFR1 and the *M. truncatula* LysM receptor kinase protein LYK3.
Figure 10A:
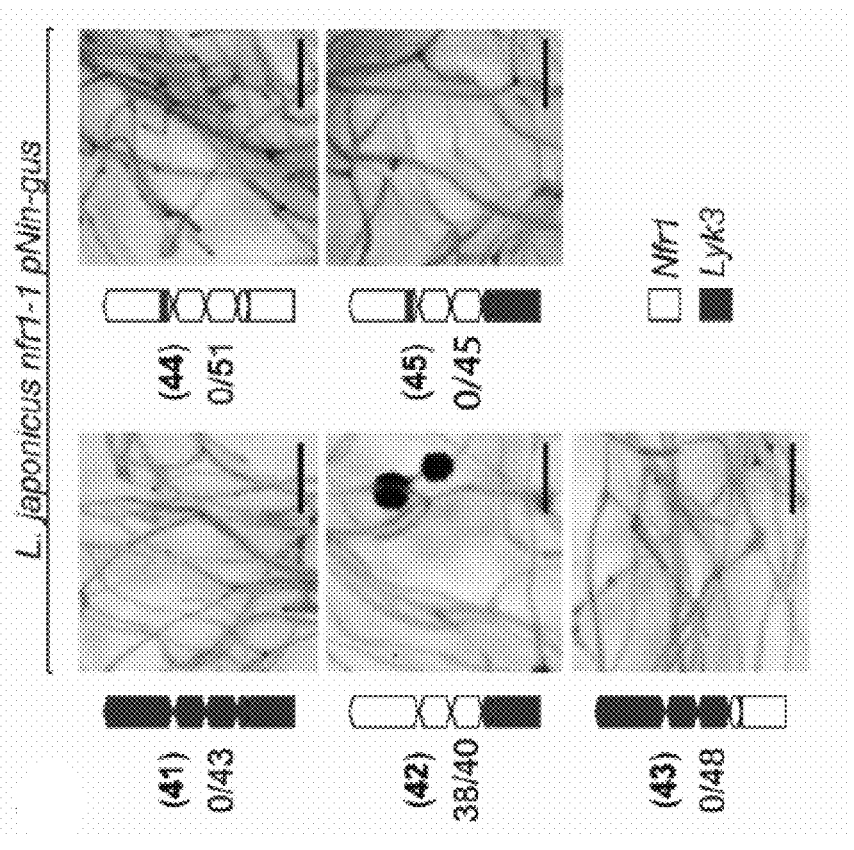

| Construct Number | Promoter | Description of LysM Receptor Kinase | FIGS. |
|---|---|---|---|
| 1 | Nfr1 | NFR1 | FIGS. 7B, 9A |
| 13 | Cerk6 | CERK6 | FIG. 7C |
| 33 | Nfr1 | NFR1 with CERK LysM1 region I | FIG. 7B |
| 34 | Nfr1 | NFR1 with CERK LysM1 region II | FIG. 7B |
| 35 | Nfr1 | NFR1 with CERK LysM1 region III | FIG. 7B |
| 36 | Nfr1 | NFR1 with CERK LysM1 region IV | FIG. 7B |
| 37 | Cerk6 | CERK6 with NFR1 LysM1 region I | FIG. 7C |
| 38 | Cerk6 | CERK6 with NFR1 LysM1 region II | FIG. 7C |
| 39 | Cerk6 | CERK6 with NFR1 LysM1 region III | FIG. 7C |
| 40 | Cerk6 | CERK6 with NFR1 LysM1 region IV | FIG. 7C |
| 41 | Nfr1 | LYK3 | FIGS. 9A, 10A |
| 42 | Nfr1 | LYK3 with NFR1 EC | FIGS. 9A, 10A |
| 43 | Nfr1 | NFR1 with LYK3 EC | FIGS. 9A, 10A |
| 44 | Nfr1 | NFR1 with LYK3 LysM1 regions II and IV | FIGS. 9A, 10A |
| 45 | Nfr1 | NFR1 with LYK3 LysM1 regions II and IV, TJ, and KD | FIGS. 9A, 10A |
| 46 | Lyk3 | NFR1 | FIGS. 9B, 10B |
| 47 | Lyk3 | LYK3 | FIGS. 9B, 10B |
| 48 | Lyk3 | LYK3 with NFR1 EC | FIGS. 9B, 10B |
| 49 | Lyk3 | NFR1 with LYK3 EC | FIGS. 9B, 10B |
| 50 | Lyk3 | LYK3 with NFR1 LysM1 regions II and IV | FIGS. 9B, 10B |
| 51 | Lyk3 | LYK3 with NFR1 LysM1 regions II and IV, TJ, and KD | FIGS. 9B, 10B |

Expression and Purification of LysM Receptor Ectodomains

The *M. truncatula* LYK3 ectodomain (residues 23-229) was codon-optimized for expression in insect cells (Genscript, Piscataway, USA). The native signal peptide was predicted using SignalP 4.1 (residues 1-23) and replaced with the signal peptide of the AcMNPV major glycoprotein 67 (MLLVNQSHQGFNKEHTSKMVSAIVLYVL-LAAAAHSAFA (SEQ ID NO: 155)). The C-terminal boundary was predicted with TMHMM version 2.0 (residue 229) and a hexahistidine tag was added. The insert containing MtLYK3 (23-229), the N-terminal gp67 secretion signal, and the C-terminal hexahistidine tag was cloned into the transfer vector pOET4 (Oxford expression technologies) using the XhoI/HindIII restriction sites. Expression and purification of *L. japonicus* CERK6 and NFR1 was performed as previously described by Bozsoki, Z. et al. *Proc. Natl. Acad. Sci.* 2017 114: E8118-E8127 and Murakami, E. et al. Elife 2018 7. Chimeric ectodomains of CERK6 and NFR1 with exchanged regions II (CERK6 N43-I53 (SEQ ID NO: 149), NFR1 P41-F52 (SEQ ID NO: 145)) and IV (CERK6 Å74-G82 (SEQ ID NO: 156), NFR1 L73-F81 (SEQ ID NO: 147)) were based on the expression constructs for CERK6 (residue 27-223 (SEQ ID NO: 157)) and NFR1 (residue 25-222 (SEQ ID NO: 158)) ectodomains and purchased as codon-optimized pOET4 transfer vector constructs for insect cell expression (GenScript, Piscataway, USA). The native signal peptides (CERK6 residues 1-26 (SEQ ID NO: 159), NFR1 residue 1-24 (SEQ ID NO: 160)), were replaced with a shortened signal peptide from the AcMNPV major glycoprotein 67 (MVSAIVLYVL-LAAAAHSAFA (SEQ ID NO: 161)). NFR1, CERK6 and chimeric ectodomains were all cloned with a C-terminal hexadistidine tag. All recombinant viruses were produced in Sf9 cells using the flashBAC GOLD kit (Oxford expression technologies) according to the manufacturer's instructions. Lipofectin (ThermoFisher Scientific) was used as a transfection reagent.

Protein expression and purification was performed as follows. *Spodoptera frugiperda* SD cells were grown in suspension at 26° C. in serum-free MAX-XP (BD Biosciences, discontinued) or HyClone SFX (GE Healthcare) insect cell medium supplemented with 1% (v/v) Pen/Strep (10000 U/ml, Life technologies) and 1% (v/v) chemically defined lipid concentrate (Gibco). Protein expression was induced by addition of passage 3 virus (MOI=1-3) to a cell density of $10^6$ cells/ml. After 4-7 days of expression, medium containing proteins of interest was harvested by centrifugation and dialyzed overnight against 50 mM Tris-HCl pH 8, 200 mM NaCl at 4° C. Ectodomains were captured from the medium and purified by two subsequent steps of Ni-IMAC purification (HisTrap excel and His Trap HP, GE Healthcare). As a final purification step, all ectodomains were subjected to SEC (see FIGS. 11A-11E) on a Superdex 75 10/300 GL, Superdex 200 10/300 GL, Superdex Increase 75 10/300 GL, Superdex Increase 200 10/300 GL, HiLoad Superdex 75 16/600 pg, or HiLoad Superdex 200 16/600 pg (all GE Healthcare) on an AKTA purifier or AKTA pure system (GE Healthcare) in phosphate buffered saline, pH 7.2 supplemented to a total of 500 mM NaCl (for binding assays) or 50 mM Tris-HCl pH 8, 200 mM NaCl (for crystallography).

Biolayer Interferometry (BLI)

Direct binding of receptor ectodomains to Nod factor conjugates was measured using an Octed RED 96 biolayer interferometry system (ForteBio, Molecular Devices) (see FIGS. 12A-12D). Binding experiments were performed in phosphate buffered saline pH 7.2, 500 mM NaCl, 0.01% Tween-20 at 30° C. under 1000 rpm agitation using black polystyrene 96-well plates (Sarstedt). Biotinylated Nod factor conjugates were immobilized on streptavidin biosensors (kinetic quality, ForteBio, Molecular Devices) at a concentration of 100-250 nM for 5 minutes. After a 60 seconds wash step, association was measured for 10 minutes and dissociation for 5 minutes. In parallel, unspecific binding to biosensors was accounted for by measuring binding of receptor to biosensors, where biotin was immobilized on the active surface. Binding data were analyzed using ForteBio Data analysis 7.0 (ForteBio, Molecular Devices) and Graphpad Prism version 8.3.0 (Graphpad Software LLC). Fits were performed by non-linear regression (Association then dissociation model with interstep correction) on data where the biotin reference sensors were subtracted. The goodness of fit is described by the global $R^2$ on the mean value of each point.

Biotinylated *S. meliloti* Nod factor IV (Ac, C16:2, S) conjugate was obtained on a Dionex UltiMate 3000 HPLC system using a Reprosil-Pur C4 (300 Å, 5 μm, 150×4.6 mm) column. A gradient of CH3CN—H2O, 1:19®1:0, containing 0.1% HCOOH with a flow rate of 1 mL/minute for 10 minutes was applied.

Results

Specific Regions in LysM1 are Required for Nod Factor and Chitin Signaling

To dissect which elements within LysM1 were important for the specific functions of NFR1 and CERK6, four regions in LysM1 with substantial sequence differences were identified (regions I to IV, see FIG. 7A). The requirement of these specific regions for Nod factor and CO8 recognition was tested using chimeric receptors (FIG. 7B, FIG. 6A).

Regions I and III could be swapped between NFR1 and CERK6 receptors with no significant impact on the ability of the chimeric receptors to function in *M. loti*-induced nodulation (constructs 33 and 35 in FIG. 7B) or CO8-dependent ROS production (constructs 37 and 39 in FIG. 7C). In contrast, regions II and IV were both necessary for the ability of the respective receptors to function in planta (FIGS. 6A and 7B). Chimeric receptors in which region II (construct 34) or IV (construct 36) from CERK6 were inserted into NFR1 were not able to restore nodulation to the nfr1 mutant (FIG. 7B and FIGS. 5A-5B). Similarly, chimeric receptors in which region II (construct 38) or IV (construct 40) from NFR1 was inserted into CERK6 failed to induce ROS after CO8 treatment when expressed in cerk6 roots (FIG. 7C).

Expression in *N. benthamiana* (tobacco) leaves revealed that the CERK6 chimeric receptor in which regions II and IV were replaced by corresponding regions of NFR1 was produced and localized at the plasma membrane, like full-length NFR1 and CERK6 (see domain construct corresponding to construct 65 in FIG. 3B). This indicated that the structure-aided strategy for exchanging regions between paralogous receptors was appropriate and preserved protein stability. Therefore, the absence of nodulation or ROS production in the region II and IV swaps, as described above, was not merely due to the generation of an unstable protein product.

The results presented herein identify regions II and IV in NFR1 and CERK6 as necessary for Nod factor and chitin receptor functions.

Figure 8C:
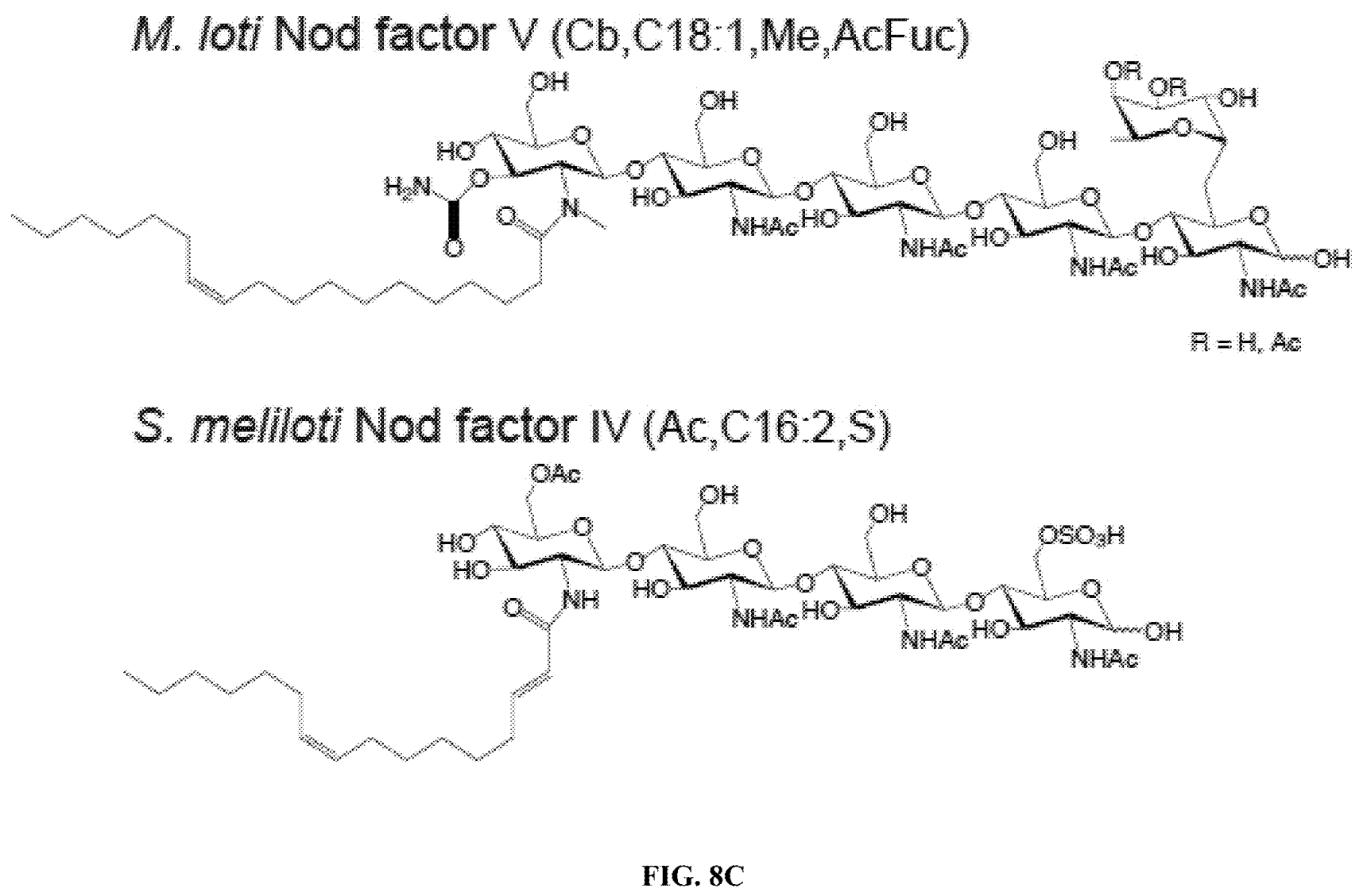
Figure 8D:
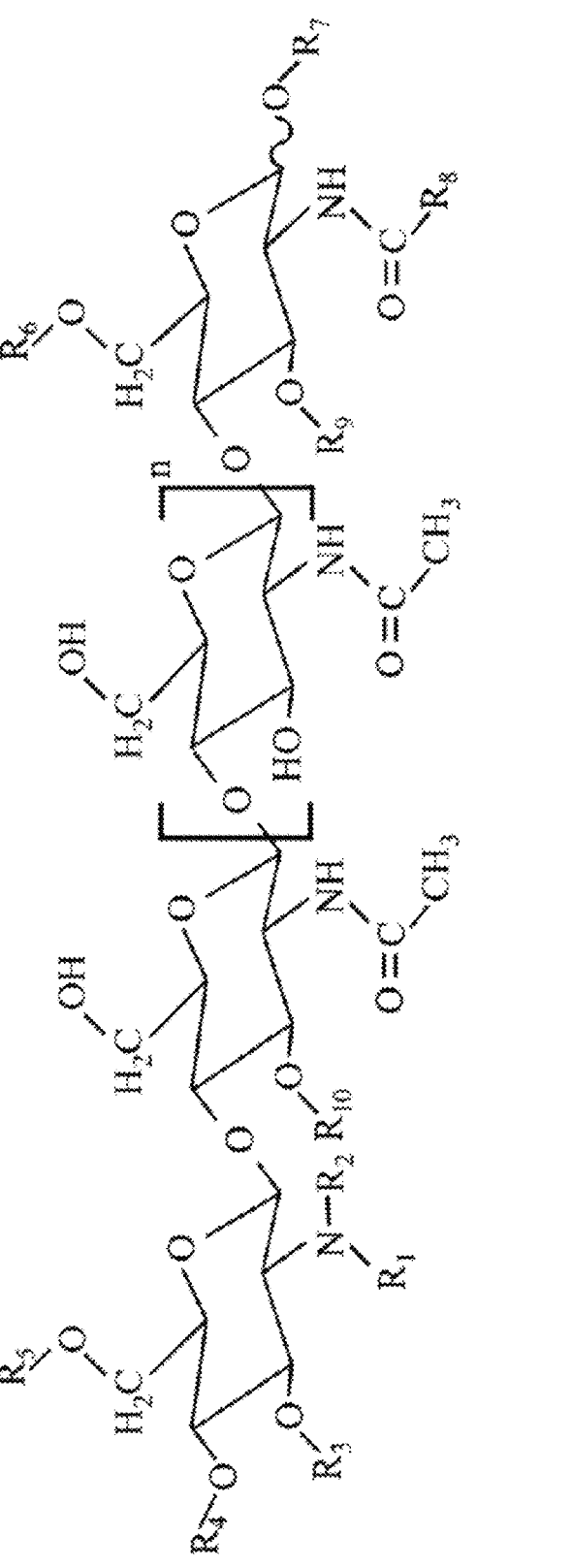

Regions II and IV of LysM1 from NFR1 and LYK3 are Necessary for Perception of Specific Nod Factors Legume-*rhizobia* symbiosis is characterized by Nod-factor dependent host-symbiont specificity, and mutant studies have demonstrated that NFR1 and LYK3 are critical for recognition of Nod factors in *L. japonicus* and *M. truncatula*, respectively (Radutoiu, S. et al. *EMBO J* 2007 26: 3923-3935; Radutoiu, S. et al. *Nature* 2003 425: 585-592; Smit, P. et al. *Plant Physiol* 2007 145: 183-191). The present disclosure based on NFR1 and CERK6 receptors has identified two regions in the LysM1 domain as necessary for signaling from CO8 (chitin) and Nod factors. Without wishing to be bound by theory, it was hypothesized that the corresponding regions in *L. japonicus* NFR1 and *M. truncatula* LYK3 (FIGS. 8A-8B) were required for specific recognition of Nod factors produced by the two symbionts, varying in their moieties at the reducing and non-reducing ends (FIG. 8C, Tables 4 and 5), and known to be important for host specificity (Lerouge, P. et al. *Nature* 1990 344: 781-784; Rodpothong, P. et al. *Mol Plant Microbe Interact* 2009 22: 1546-1554). Tables 4 and 5, below, provides a summary of the structures of Nod factors of various species and strains, with the specific moieties at the ten R groups as indicated in FIG. 8D. Tables 4 and 5 also lists the number of N-Acetylglucosamine monomers indicated by the bracketed monomer in FIG. 8D in column "n".

TABLE 4

| Summary of Nod factor structure features R1-R6 | | | | | | | |
|---|---|---|---|---|---|---|---|
| Host | Rhizobial species and strain | R1 | R2 | R3 | R4 | R5 | R6 |
| *Glycine soja* (Soybean) | *B. elkanii* USDA61 | C18:1, C16:0 | Me, H | Cb, Ac | Cb, Ac | Cb, Ac, H | 2-O—Me |
| | *B. japonicum* USDA110 | C18:1 | H | H | H | H | 2-O—Me |
| | *B. japonicum* USDA135 | C18:1, C16:0, C16:1 | H | H | H | Ac, H | 2-O—Me |
| | *S. fredii* HH103 | C16:0, C16:1 C18:0, C18:1 | H | H | H | H | 2-O—Me |
| | *S. fredii* USDA191w | C16:0, C16:1 C18:0, C18:1 | H | H | H | H | 2-O—Me |
| | *S. fredii* USDA257 | C18:1 | H | H | H | H | 2-O—Me |
| *Phaseolus vulgaris* | *R. etli* CE3 | C18:0, C18:1 | Me | H | Cb | H | 4-O—AcFuc |
| | *R. etli* CFN42 | C18:1 | Me | Cb, H | Cb, H | Cb, H | 4-O—AcFuc |
| | *Rhizobium* sp. GRH2 | C16:0, C18:0, C18:1 C20:1 | Me, H | H | H | H | S, H |
| | *R. tropici* CFN299 | C18:1 | Me | H | H | H | S, H |
| | *R. tropici* CIAT899 | C16:0, C16:1, C18:0 C18:1, C20:0, C20:1 | Me, H | H | H | H | S, H |
| *L. japonicus* | *M. loti* E1Ri | C18:1, C18:0 | Me | H | Cb | H | 4-O—AcFuc |
| | *M. loti* JRL501 | C18:1 | Me | Cb, H | Cb, H | Cb, H | Fuc, 4-O—AcFuc |
| | *M. loti* NZP2037 | C18:1, C18:0 | Me | Cb, H | Cb | Cb, H | 4-O—AcFuc |

TABLE 4-continued

| Summary of Nod factor structure features R1-R6 | | | | | | | |
|---|---|---|---|---|---|---|---|
| Host | Rhizobial species and strain | R1 | R2 | R3 | R4 | R5 | R6 |
| | *M. loti* NZP2213 | C16:0, C16:1, C18:0 C18:1, C20:0, C20:1 C18:1, C18:0 | Me, H | Cb, H | H | Ac, H | 4-O—AcFuc Fuc, H |
| | NZP2309 | C18:1, C18:0 | Me | Cb | H | Cb | Fuc, 4-O—AcFuc |
| *M. truncatula* | *S. meliloti* RCR2011 | C16:1, C16:2, C16:3 C18-C26(ω-1)-OH | H | H | H | Ac, H | S |

TABLE 5

| Summary of Nod factor structure features R7-R10 | | | | | | | |
|---|---|---|---|---|---|---|---|
| Host | Rhizobial species and strain | R7 | R8 | R9 | R10 | n | Reference(s) |
| *Glycine soja* (Soybean) | *B. elkanii* USDA61 | Gro, H | Me | H | H | 1, 2 | Carlson et al. (1993) Stokkermans et al. (1996) |
| | *B. japonicum* USDA110 | H | Me | H | H | 2 | Sanjuan et al. (1992) |
| | *B. japonicum* USDA135 | H | Me | H | H | 2 | Carlson et al. (1993) |
| | *S. fredii* HH103 | H | Me | H | H | 0, 1, 2 | Gil-Serrano et al. (1997) |
| | *S. fredii* USDA191w | H | Me | H | H | 0, 1, 2 | Bec-Ferté et al. (1996) |
| | *S. fredii* USDA257 | H | Me | H | H | 0, 1, 2 | Bec-Ferté et al. (1994) |
| *Phaseolus vulgaris* | *R. etli* CE3 | H | Me | H | H | 2 | Cárdenas et al. (1995) |
| | *R. etli* CFN42 | H | Me | H | H | 2 | Poupot et al. (1995) |
| | *Rhizobium* sp. GRH2 | H | Me | H | H | 1, 2, 3 | López-Lara et al. (1995b) |
| | *R. tropici* CFN299 | H | Me | H | H | 2 | Poupot et al. (1993) |
| | *R. tropici* CIAT899 | Man H | Me | H | H | 1, 2 | Folch-Mallol et al. (1996) |
| *L. japonicus* | *M. loti* E1Ri | H | Me | H | H | 2 | López-Lara et al. (1995a) |
| | *M. loti* JRL501 | H | Me | H | H | 2 | Niwa et al. (2001) |
| | *M. loti* NZP2037 | H | Me | H | H | 2 | López-Lara et al. (1995a) |
| | *M. loti* NZP2213 | H | Me | H | Fuc, H | 1, 0 1, 2 | Olsthoorn et al. (1998) |
| | NZP2309 | H | Me | H | H | 2 | Bek et al., 2009 |
| *M. truncatula* | *S. meliloti* RCR2011 | H | Me | H | H | 0, 1, 2 | Lerouge et al. (1990) Demont et al. (1993) |

To test whether regions in *L. japonicus* NFR1 and *M. truncatula* LYK3 were required for recognizing specific Nod factors, the capacity of LYK3 to complement nfr1 and of NFR1 to complement Lyk3 (i.e., *M. truncatula* lyk3-1) when expressed under the control of the Nfr1 or Lyk3 promoters was investigated (FIGS. 9A-9B and FIGS. 10A-10D). In particular, construct 41 expressed LYK3 under control of the *L. japonicus* Nfr1 promoter in the *L. japonicus* nfr1 mutant background, and construct 46 expressed NFR1 under control of the *M. truncatula* Lyk3 promoter in the *M. truncatula* Lyk3 mutant background. The absence of nodulation in the plants expressing construct 41 in FIG. 9A and construct 46 in FIG. 9B supported the role of these two receptors in the recognition of specific symbionts.

Next, whether the ectodomains of the two receptors were required for specific Nod factor recognition was tested. Chimeric constructs were designed (FIG. 8B) to test the requirement of the extracellular and intracellular regions of NFR1 and LYK3 for nodule formation (see constructs 42 and 43 in FIG. 9A, and 48 and 49 in FIG. 9B). This complementation study revealed that in both *L. japonicus* and *M. truncatula*, the ectodomains of NFR1 and LYK3 receptors were required for nodule formation, and therefore for signaling after rhizobial inoculation (FIGS. 9A-9B and FIGS. 10A-10D).

The role of regions II and IV of the LysM1 domains of NFR1 and LYK3 (FIG. 8A) in determining signaling specificity was then investigated. Complementation studies in *L. japonicus* revealed that embedding II and IV of LYK3 into NFR1 or a chimera with the ectodomain of NFR1 (construct 42) abolished the native capacity of these receptors to recognize *M. loti* and induce nodulation in the nfr1 mutant (constructs 44 and 45 in FIG. 9A). The reciprocal experiments in *M. truncatula* in which regions II and IV of NFR1 were embedded into LYK3 or a chimera with the ectodomain of LYK3 revealed a similar nodulation deficient phenotype (constructs 50 and 51 in FIG. 9B and FIGS. 10A-10D). Together, these results from in planta experiments provided support for the hypothesis that molecular determinants for Nod factor signaling specificity are located in the LysM1 domain of NFR1 and LYK3.

Nod Factor Binding by Purified LysM Receptor Kinase Ectodomains

In parallel with the in planta studies, the ectodomains of NFR1, LYK3 and CERK6 were expressed in insect cells and purified (FIGS. 11A-11E). As seen in FIGS. 11A-11E, the purified proteins yielded slightly broadened SEC peaks also visible in coomassie-stained SDS-PAGE gels, due to heterologous glycosylation.

Figure 12A:
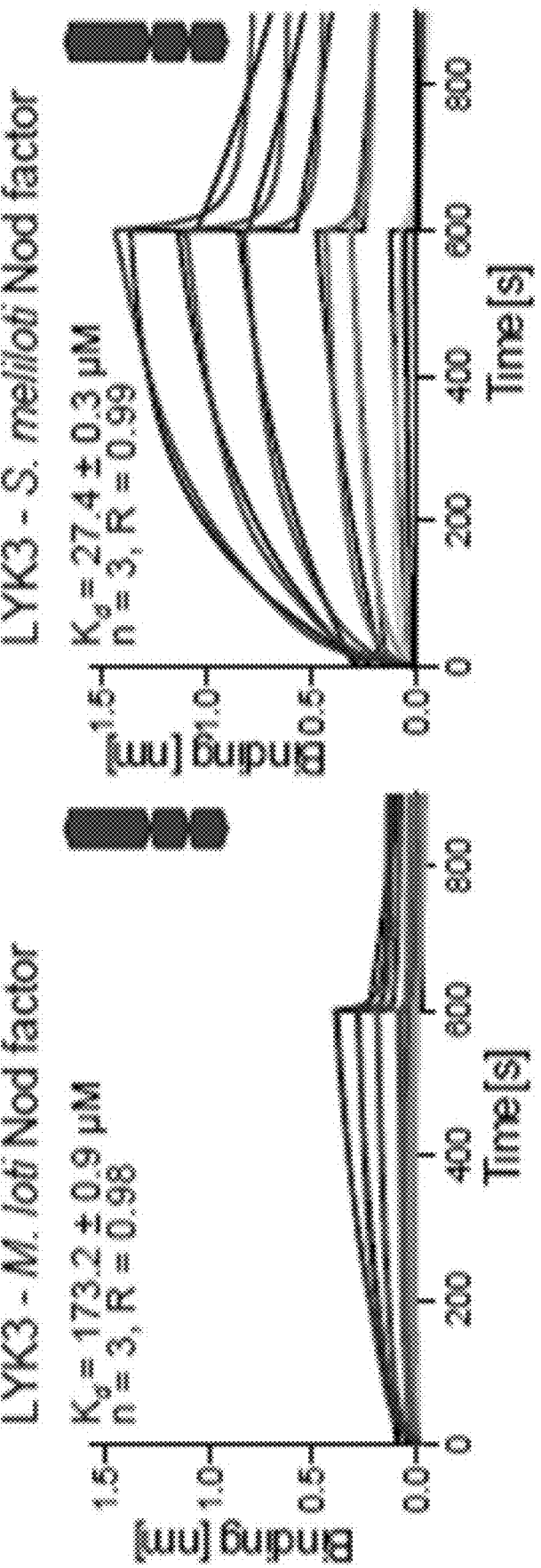
FIGS. 12A-12D show biolayer interferometry (BLI) measurements of *M. loti* and *S. meliloti* Nod factors binding to LysM receptor kinase ectodomains.
Figure 12B:
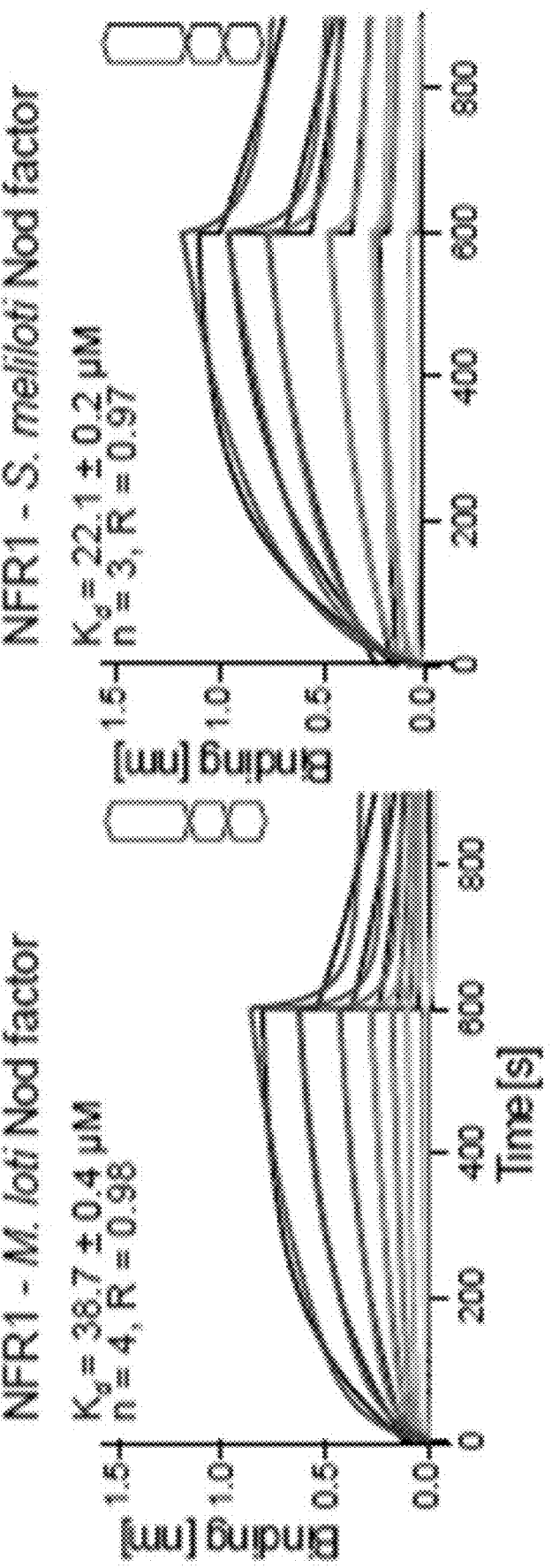
Figures 12C, 12D:
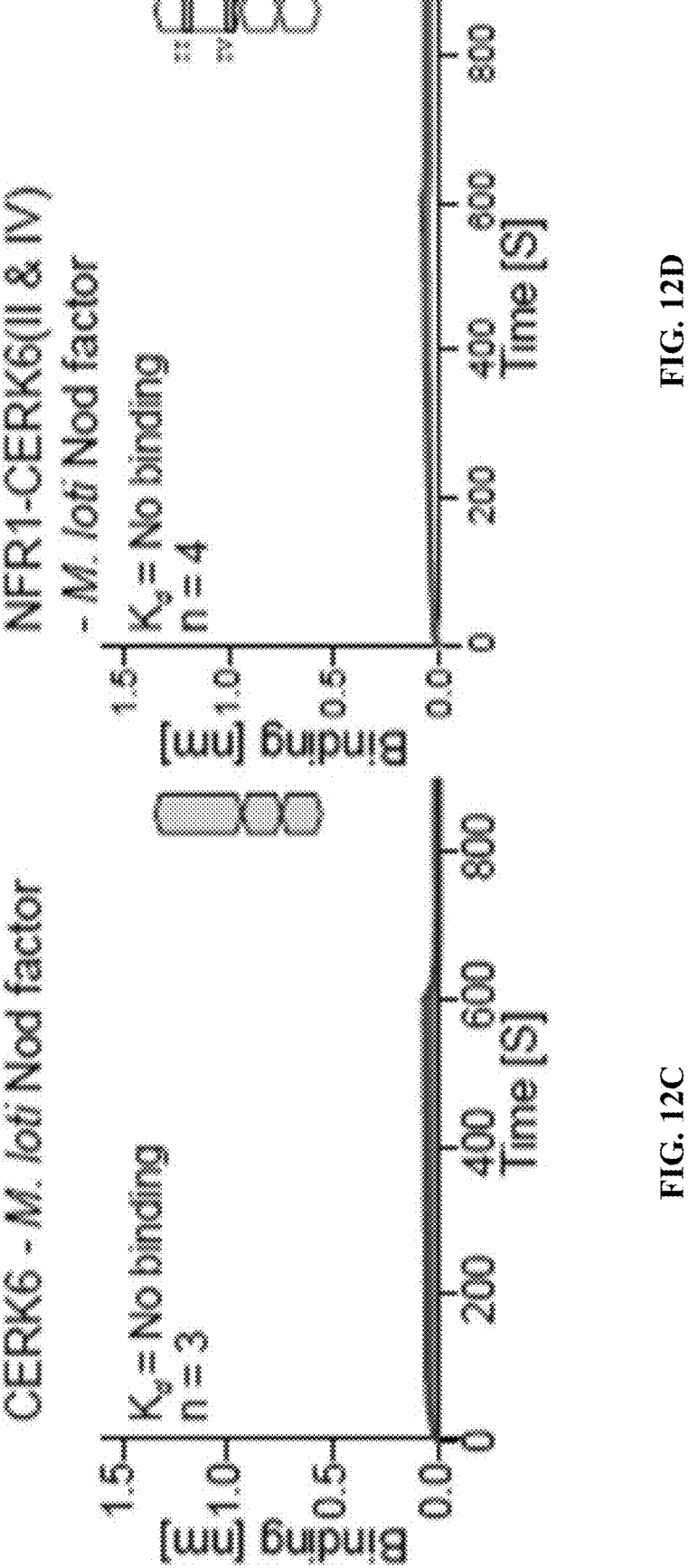

The capacity of the ectodomains of NFR1, LYK3 and CERK6 to bind *M. loti* or *S. meliloti* Nod factors was tested using biolayer interferometry (BLI; FIGS. 12A-12D). This revealed that the NFR1 and LYK3 receptors differed in their binding specificity in vitro. LYK3 bound its cognate *S. meliloti* Nod factor with a Kd of $27.4\pm0.4$ µM and showed an approximate 6-fold reduction in binding to the non-cognate Nod factor from *M. loti* (Kd=$173.2\pm0.9$ µM; FIG. 12A). By contrast and less expected, the NFR1 ectodomain bound both cognate *M. loti* Nod factor and non-cognate *S. meliloti* Nod factor with similar affinities of Kd=$38.7\pm0.4$ and Kd=$22.1\pm0.2$ respectively (FIG. 12B). CERK6 showed no binding to *M. loti* Nod factor (FIG. 12C).

Next, whether regions II and IV were required for Nod factor binding was tested. A chimeric NFR1 ectodomain in which regions II and IV were derived from CERK6 was recombinantly expressed in insect cells. A stable protein was produced, purified (FIG. 11C), and tested for its ability to bind *M. loti* Nod factor. This chimera was not able to bind *M. loti* Nod factor (FIG. 12D), demonstrating that the regions II and IV in LysM1 of NFR1 are required for Nod factor recognition.

Together, the results herein from in planta and in vitro binding assays demonstrated the requirement of LysM1 regions II and IV for perception of specific Nod factors produced by symbiotic *rhizobia*.

Example 3: Crystal Structure of the LYK3 Ectodomain

The following example describes the determination of the structure of the *M. truncatula* LYK3 ectodomain by X-ray crystallography. The LYK3 ectodomain structure revealed structural differences in the LysM1 ligand-binding sites of NFR1/LYK3-type Nod factor receptors and CERK6-type chitin receptors.

Materials and Methods

Expression and Purification of LysM Receptor Ectodomains

The *M. truncatula* LYK3 ectodomain was expressed and purified as described in Example 2, above.

Crystallization and Structure Determination

The *M. truncatula* LYK3 ectodomain was crystallized in a sitting drop vapor diffusion setup at 5 mg/ml in 0.2 M ammonium sulphate, 0.1 M Bis-Tris pH 6.5, 31% PEG-3350, 450 µM *Sinorhizobium meliloti* Nod factor LCO-IV (Ac, $C_{16:2}$, S), and 2.25% (v/v) acetonitrile (from the lipochitooligosaccharide solvent) at 4° C. Crystals were cryoprotected by supplementation of 10% (w/v) PEG-400 to the crystallization condition. A complete dataset to 1.49 Å resolution was collected at the 1911-3 beamline (MaxLab II, Lund, SE). Data was processed and reduced using XDS (Kabsch, W. Crystallogr *D Biol Crystallogr* 2010 66: 133-144). The phase problem was solved by molecular replacement with a polyalanine model of the AtCERK1 ectodomain crystal structure (PDB: 4EBZ) as a search model using Phaser (McCoy, A. J. et al. *J. Appl Crystallogr* 2007 40: 658-674). The model was built in Coot (Emsley, P. et al. *Acta Crystallogr D Biol Crystallogr* 2010 66: 486-501), and refinement was performed with phenix.refine from the PHENIX program suite (Adams, P. D. et al. *Acta Crystallogr D Biol Crystallogr* 2010 66: 213-221). No density for the lipochitooligosaccharide present in the crystallization condition was found in the electron density. Data collection and refinement statistics are reported in Table 6, below. The atomic coordinates and structure factors have been deposited in the Protein Data Bank, www.wwpdb.org, PDB ID: 6XWE. Figures of the crystal structure were prepared using PyMol 2.3.2 (Schrodinger LLC) (see FIGS. 13A-13E).

Results

The detailed analyses of ectodomain domains and regions described in Examples 1 and 2, above, were aided by the available crystal structure of the chitin receptor CERK6 (Bozsoki, Z. et al. *Proc. Natl. Acad. Sci.* 2017 114: E8118-E8127). For the NFR1/LYK3-type Nod factor receptors, no structural information was available, limiting the understanding of how these proteins distinguish different Nod factors and chitin ligands at the molecular level. To gain insight into this class of receptors the ectodomain of *M. truncatula* LYK3 was crystallized, and the structure was determined at an atomic resolution of 1.5 Å (Table 6, FIGS. 13A-13E). Table 6 provides statistics for X-ray data collection and model refinement for the LYK3 ectodomain structure. In Table 6, values in parentheses correspond to the highest resolution shell.

TABLE 6

| X-ray crystallography data collection and refinement statistics | |
| --- | --- |
| Data Collection | |
| Dataset | LYK3 |
| Beamline | MaxLab I911-3 |
| Wavelength (Å) | 1.00 |
| Temperature (K) | 100 |
| Resolution range (Å) | 19.97-1.49 (1.543-1.49) |
| Space group | P $2_1$ 2 $2_1$ |

TABLE 6-continued

| X-ray crystallography data collection and refinement statistics | |
|---|---|
| Unit cell dimensions (Å) | a = 44.21 b = 53.53 c = 95.00 |
| | α = β = γ = 90 |
| Total reflections | 271545 (26783) |
| Unique reflections | 37598 (3712) |
| Multiplicity | 7.2 (7.2) |
| Completeness (%) | 99.81 (99.81) |
| Mean I/σ (I) | 18.46 (2.32) |
| Wilson B-factor (Å$^2$) | 12.77 |
| $R_{merge}$ (%) | 0.08527 (0.9369) |
| $R_{meas}$ (%) | 0.09193 (1.011) |
| $R_{pim}$ (%) | 0.03404 (0.375) |
| CC1/2 | 0.999 (0.77) |
| CC* | 1 (0.933) |
| Refinement | |
| Reflections used in refinement | 37572 (3712) |
| Reflections used for R-free | 2000 (198) |
| $R_{work}$ | 0.1394 (0.1998) |
| $R_{free}$ | 0.1798 (0.2408) |
| CC(work) | 0.974 (0.902) |
| CC(free) | 0.960 (0.863) |
| Number of non-hydrogen atoms | 2191 |
| Number of macromolecules | 1678 |
| Number of ligands | 91 |
| Number of solvent | 422 |
| Protein residues | 211 |
| RMSD (bonds) (Å) | 0.008 |
| RMSD (angles) (°) | 1.50 |
| Ramachandran Plot favored (%) | 97.52 |
| Ramachandran Plot allowed (%) | 2.48 |
| Ramachandran Plot outliers (%) | 0.00 |
| Rotamer outliers (%) | 0.00 |
| Clashscore | 2.83 |
| Average B-factor (Å$^2$) | 21.65 |
| Average macromolecules (Å$^2$) | 16.66 |
| Average ligands (Å$^2$) | 72.96 |
| Average solvent (Å$^2$) | 30.43 |

Figure 13A:
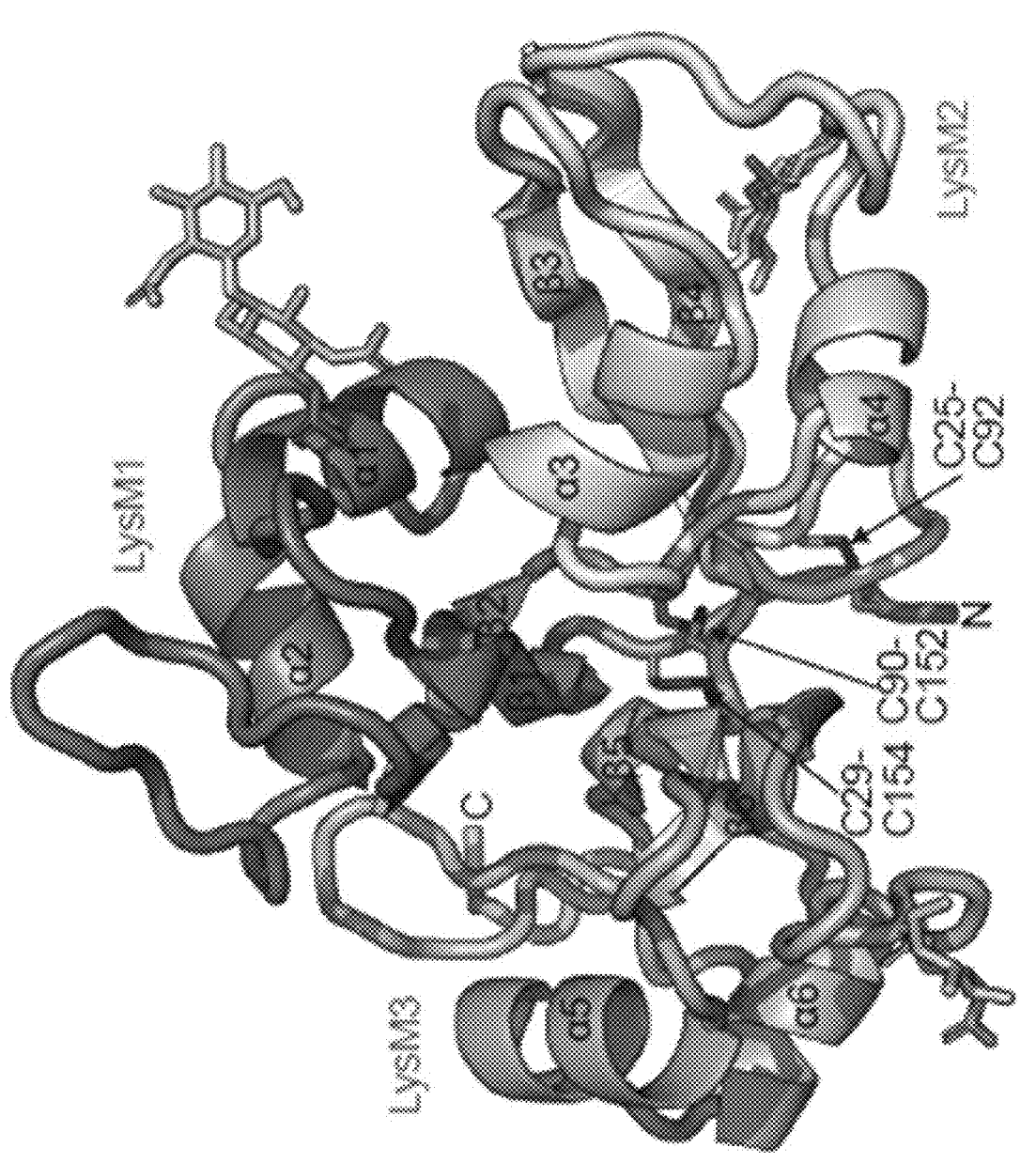
FIGS. 13A-13E show ribbon diagrams of LysM receptor kinase structures.
Figure 13B:
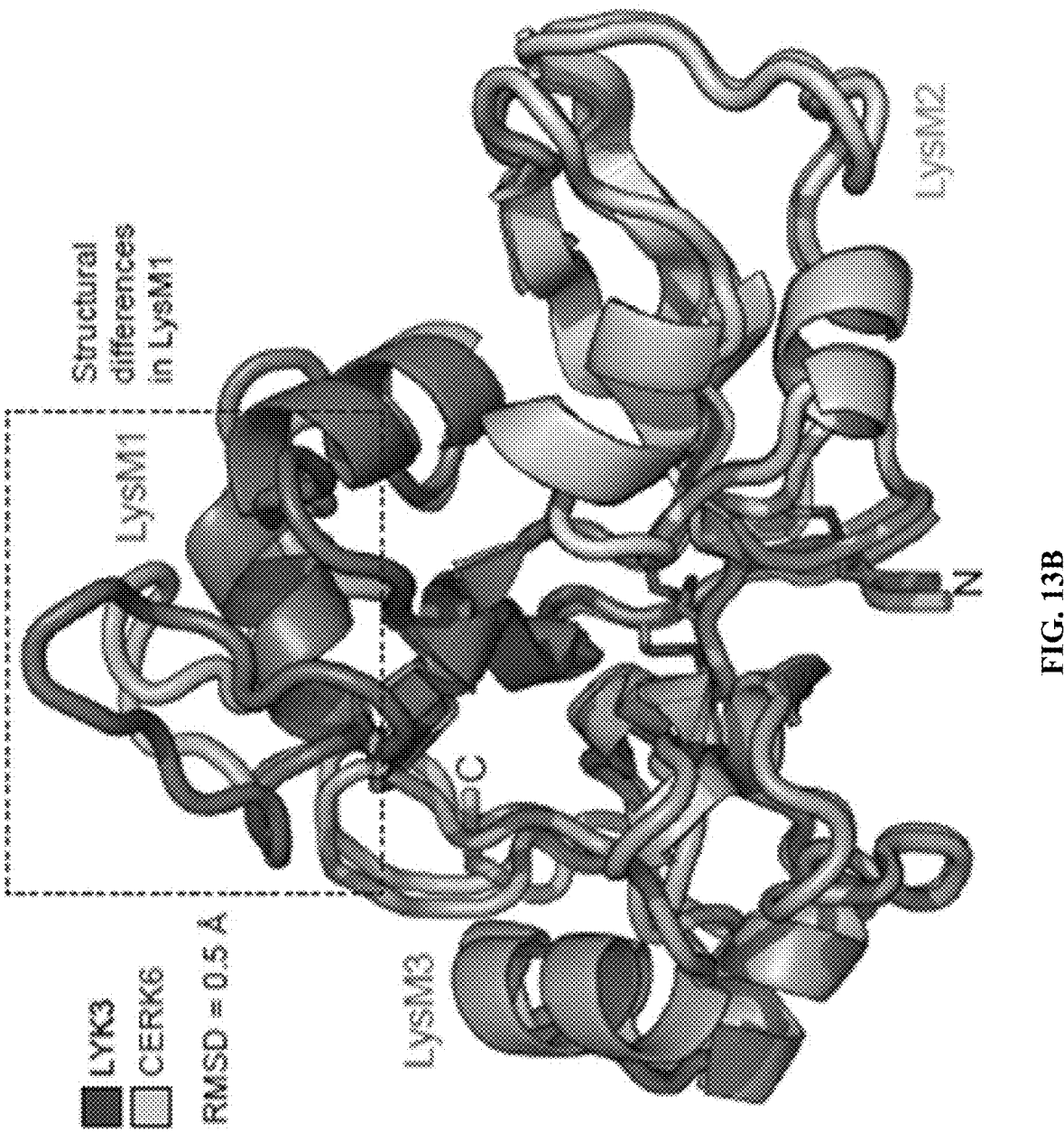

The structure revealed a classical fold of three LysM domains in a clover-leaf arrangement stabilized by three disulfide bridges (FIG. 13A). Comparison of LYK3 and CERK6 ectodomain structures showed that the overall fold was conserved and the two structures aligned surprisingly well with a root mean square difference (RMSD) of 0.5 Å$^2$ (181 backbone atoms aligned) (FIG. 13B).

Figure 13C:
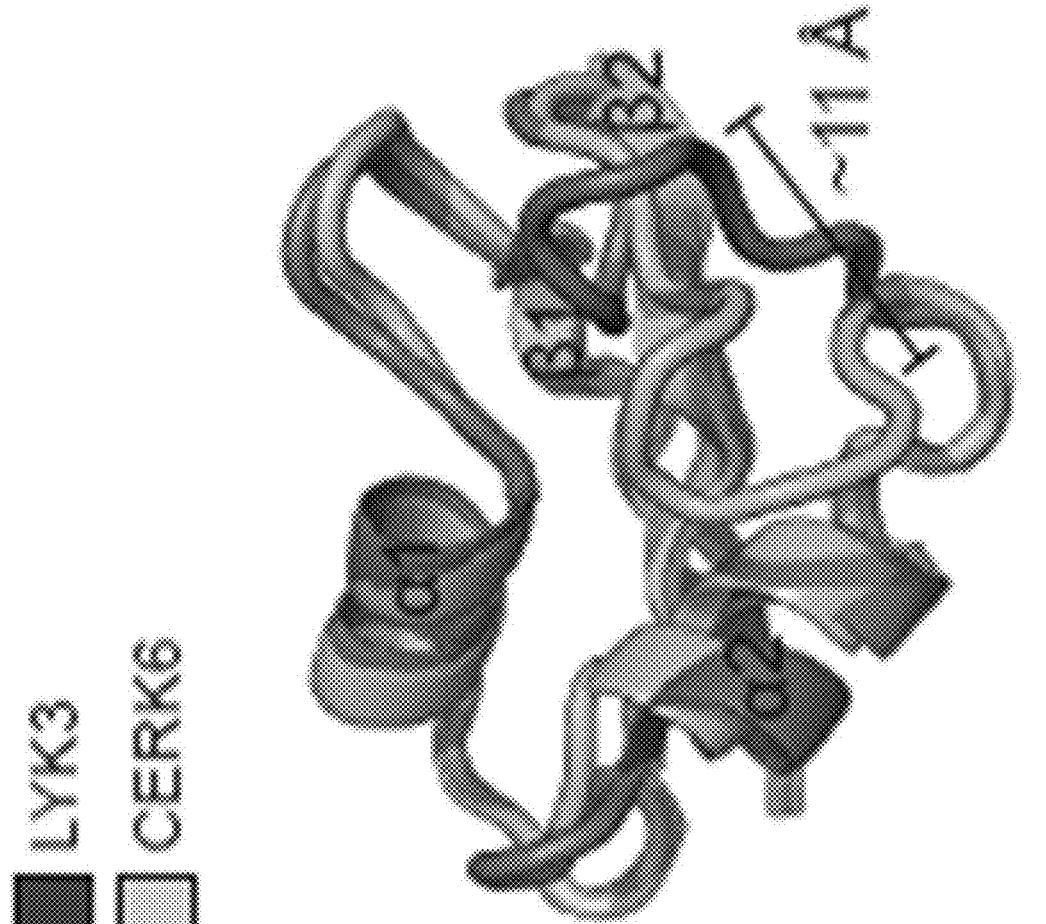
Figure 13D:
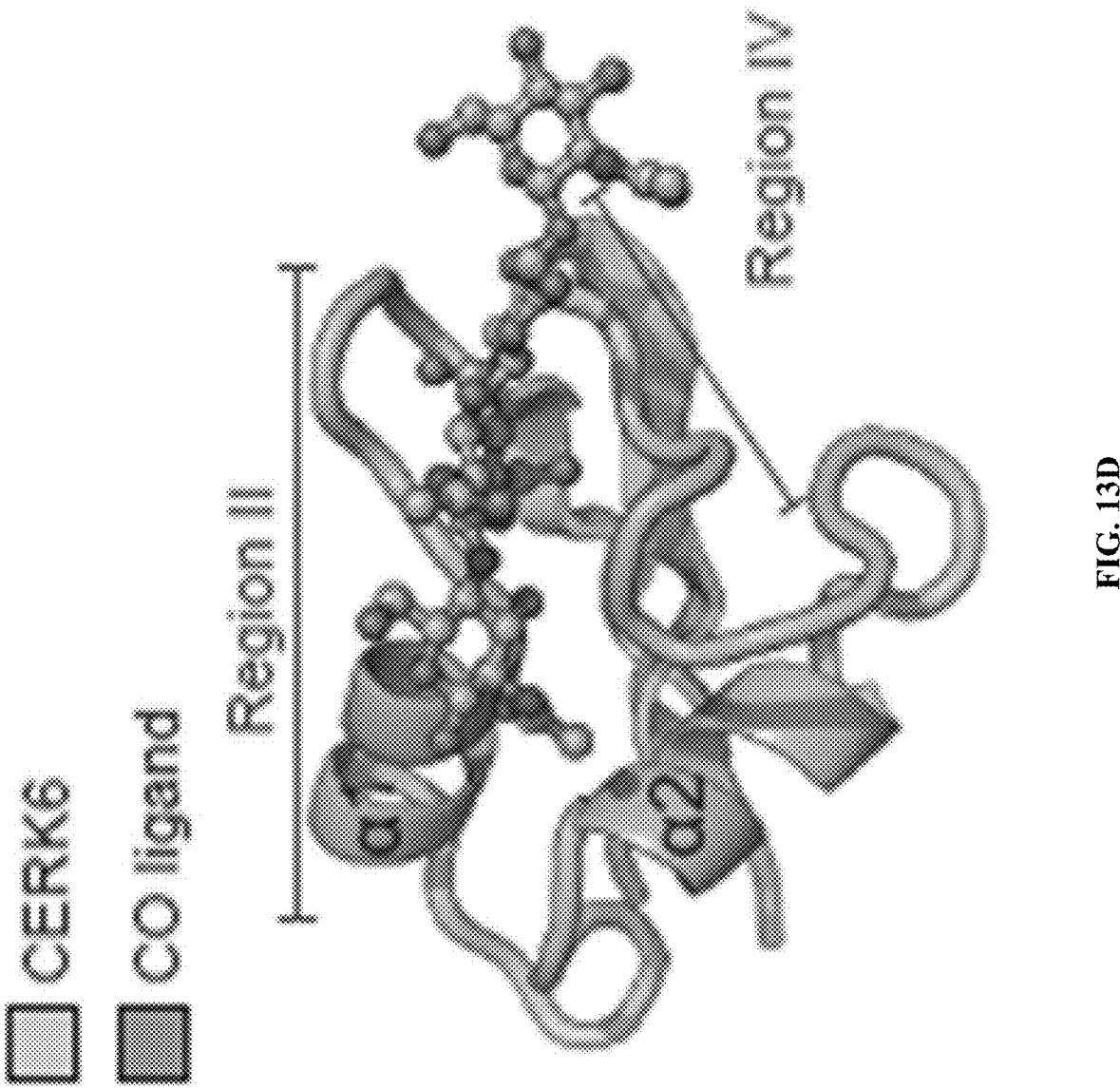
Figure 13E:
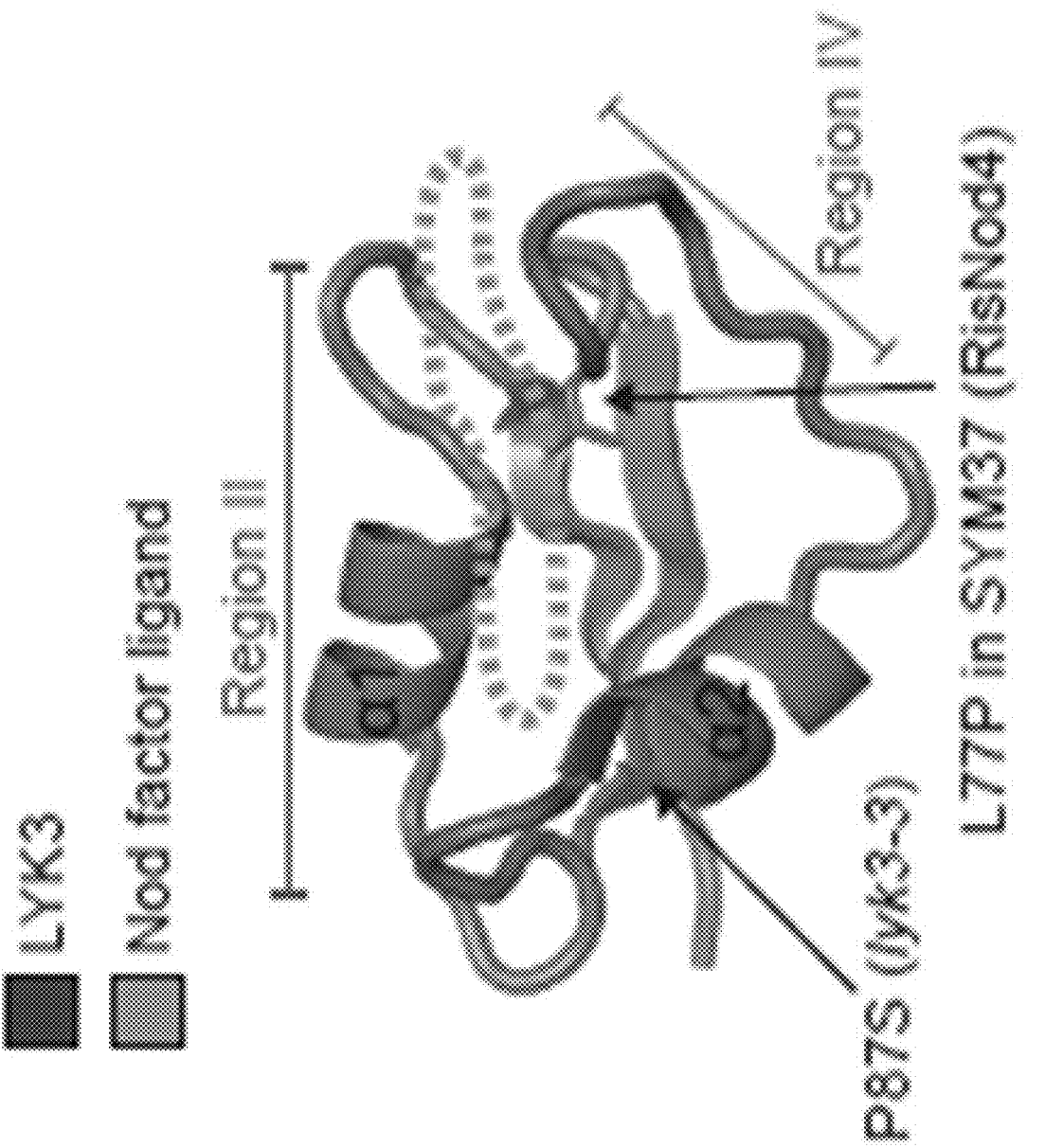

Interestingly, the main structural differences observed were in the LysM1 domain. In particular, region IV identified herein revealed a completely different conformation in LYK3 as compared to CERK6 (FIG. 13C). Mapping both regions II and IV onto the LYK3 structure showed that these constituted the major part of a putative ligand binding site containing the functionally important residues L77 from SYM37 (Zhukov et al. Mol Plant Microbe Interact 2008 21: 1600-1608), and the NFR1-178 mutant analyzed in construct 23 (FIG. 4B, FIG. 13E). A superposition of chitotetraose (chitin, C04) from the Arabidopsis thaliana CERK1 crystal structure onto LysM1 from CERK6 revealed no steric clashes between CERK6 and the superpositioned chitooligosaccharide ligand (FIG. 13D).

Together, these observations further supported the conclusion that regions II and IV of the LysM1 domain defined a ligand-binding site within NFR1-type receptor ectodomains.

Example 4: Comparisons of LysM1 Domains of Nod Factor and Chitin-Binding LysM Receptor Kinases The following example describes comparisons of the amino acid sequences, predicted structures, and conservation of the LysM1 domains of LysM receptor kinases. In particular, contrasting motifs in the LysM1 domain of NFR1/LYK3-type Nod factor receptors and CERK6-type chitin receptors are described.

Materials and Methods

Motifs of LysM1 regions II and IV sequences were generated based on the amino acid sequences shown in FIGS. 14A-14C and FIGS. 15A-15C. In particular, the NFR-type receptor motifs were generated using the ectodomain sequences of Phaseolus vulgaris (XP_007141617.1), Arachis hypogaea (XP_029150476.1 and XP_029144024.1), Cajanus cajan (XP_020213700.2), Cicer arietinum (XP_004491136.1), Abrus precatorius (XP_027332267.1), M. truncatula (Q6UD73.1|LYK3), Glycine max (XP_006575588.1, XP_006595821.2), Lupinus angustifolius (XP_019434083.1, XP_019461629.1), L. japonicus (CAE02590.1/NFR1), Pisum sativum (ARX80051.1|Sym37), Vigna angularis (KOM467 48.1), Vigna radiata var. radiata (XP_014504127.1), Vigna unguiculata (XP_027939826.1), Arachis duranensis (XP_020982945.1), Arachis ipaensis (XP_020962820.1), Chamaecrista fasciculata (2879S20281), Mimosa pudica (Scaffold15743), Lupinus albus (Chr04g0249871), Spatholobus suberectus (TKY57029.1), and Prosopis alba (XP_028753017.1) NFR1-type receptors (FIGS. 14A-14C).

CERK-type receptor motifs were generated using the ectodomain sequences of Phaseolus vulgaris (XP_007146026.1), Arachis ipaensis (XP_016196976.1), Arachis duranensis (XP_015958400.1), Cajanus cajan (XP_020220445.1), Cicer arietinum (XP_004502028.1), Abrus precatorius (XP_027343427.1), M. truncatula (XP_003601376.2|LYK9), Glycine max (XP_003555584.1 and XP_003518454.1), Lupinus angustifolius (XP_019425563.1 and XP_019455825.1), L. japonicus (BAI79273.1|CERK6), Vigna angularis (XP_017436810.1), Vigna radiata (XP_014509761.1), Vigna unguiculata (XP_027932400.1), Arachis hypogaea (XP_025693415.1), Mimosa pudica (Scaffold8584), Chamaecrista fasciculata (QANZ01053660), Lupinus albus (Chr04g0263521), Pisum sativum (LYK9), Arachis hypogaea (XP_025645378.1), Spatholobus suberectus (TKY72192.1), and Prosopis alba (XP_028758101.1) CERK6-type receptors (FIGS. 15A-15C).

Skylign was used to generate the motifs and the logos of the motifs as shown in FIGS. 14E and 15E (Wheeler T. J., et al. BMC Bioinformatics 2014 15:7).

Results

The identification of specific regions in the LysM1 domain of NFR1, LYK3, and CERK6 which were necessary and structurally positioned for the recognition of ligands prompted the investigation of whether these regions represent general features in Nod factor and chitin receptors from legume species. It was hypothesized that amino acid residues responsible for Nod factor recognition would be diverse between species, to recognize variable and species-specific versions of Nod factors. By contrast, the chitin receptors were hypothesized to be conserved in the corresponding regions, given the invariable structure of this ligand.

Alignments and modelling of the entire ectodomain revealed a high level of surface conservation across the core LysM2 and LysM3 domains of both NFR1-type and CERK6-type receptors (FIGS. 14A-14E, 15A-15E). Most of the differences between species were found to be present in the LysM1 domain of NFR1-type receptors (FIGS. 14A-

14C). Further dissection of this domain revealed that residues within regions II and IV were the most variable portions of LysM1 domains of NFR1-type receptors (FIGS. 14A-14E). By contrast, the corresponding regions in CERK6-type receptors were found to be highly conserved (FIGS. 15A-15E).

Superposition of a chitin oligomer onto the structure of the CERK6 LysM1 domain and prediction of the ligand interaction properties based on binding of *A. thaliana* CERK1 to chitin (Liu, T. et al. *Science* 2012 336: 1160-1164), identified six residues in each of region II (GSNLTY (SEQ ID NO: 14)) and region IV (KDSVQA (SEQ ID NO: 40)) that were structurally positioned to enable contact with the chitin molecule (FIG. 15E). These residues were highly conserved among legume CERK6-type receptors and, without wishing to be bound by theory, could represent a CO-binding motif (FIG. 15E).

Additional comparisons of LysM1 domain structures are provided in FIGS. 17A-17G.

Together, these observations strongly supported the notion that motifs in regions II and IV of LysM1 define a ligand-binding site within the NFR1/CERK6-type receptor ectodomains.

Example 5: Reprogramming the Nod Factor Specificity of LysM Receptor Kinases The following example describes engineering LysM receptor kinases for the recognition of specific Nod factors.

Materials and Methods

Plant materials and growth conditions, bacterial strains and culture conditions, generation of plant expression vectors, hairy root transformation, nodulation assays, ROS formation assays, and BLI assays were all performed as described in Examples 1 and 2, above.
Generation of Plant Expression Vectors Expression constructs were generated to express LysM receptor kinases in *L. japonicus* or *M. truncatula*, as described in Examples 1 and 2, above. As above, chimeric alleles of LysM receptor kinases were designed based on their modular structure, which has, from N to C terminus, an extracellular region also known as the ectodomain ("EC") made up of three LysM domains (LysM1, LysM2, and LysM3), a transmembrane segment and an intracellular region with a juxtamembrane segment ("TJ"), and a kinase domain ("KD"). Further, the boundaries between domains and regions of the LysM receptor kinases were defined as described in Examples 1 and 2, above. LysM receptor kinase expression constructs were assigned numerical labels that correspond to the schematic diagrams of the constructs presented in the FIGS. Table 7 provides a description of the LysM receptor kinase expression constructs used in this example. Schematic diagrams of the LysM receptor kinase constructs are shown in FIGS. 16A-16B.

TABLE 7

LysM receptor kinase expression constructs

Figure 10C:
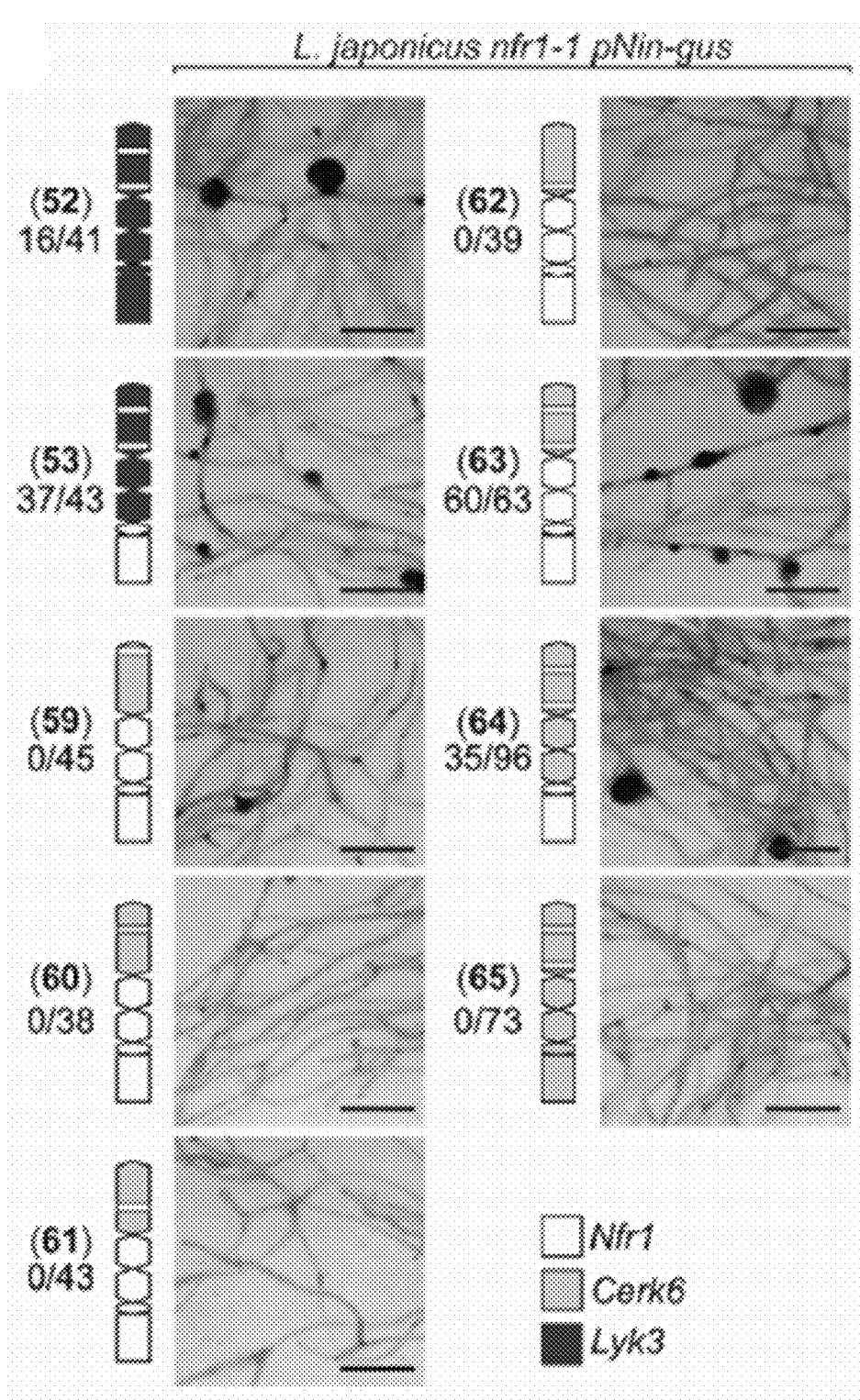
Figure 16A:
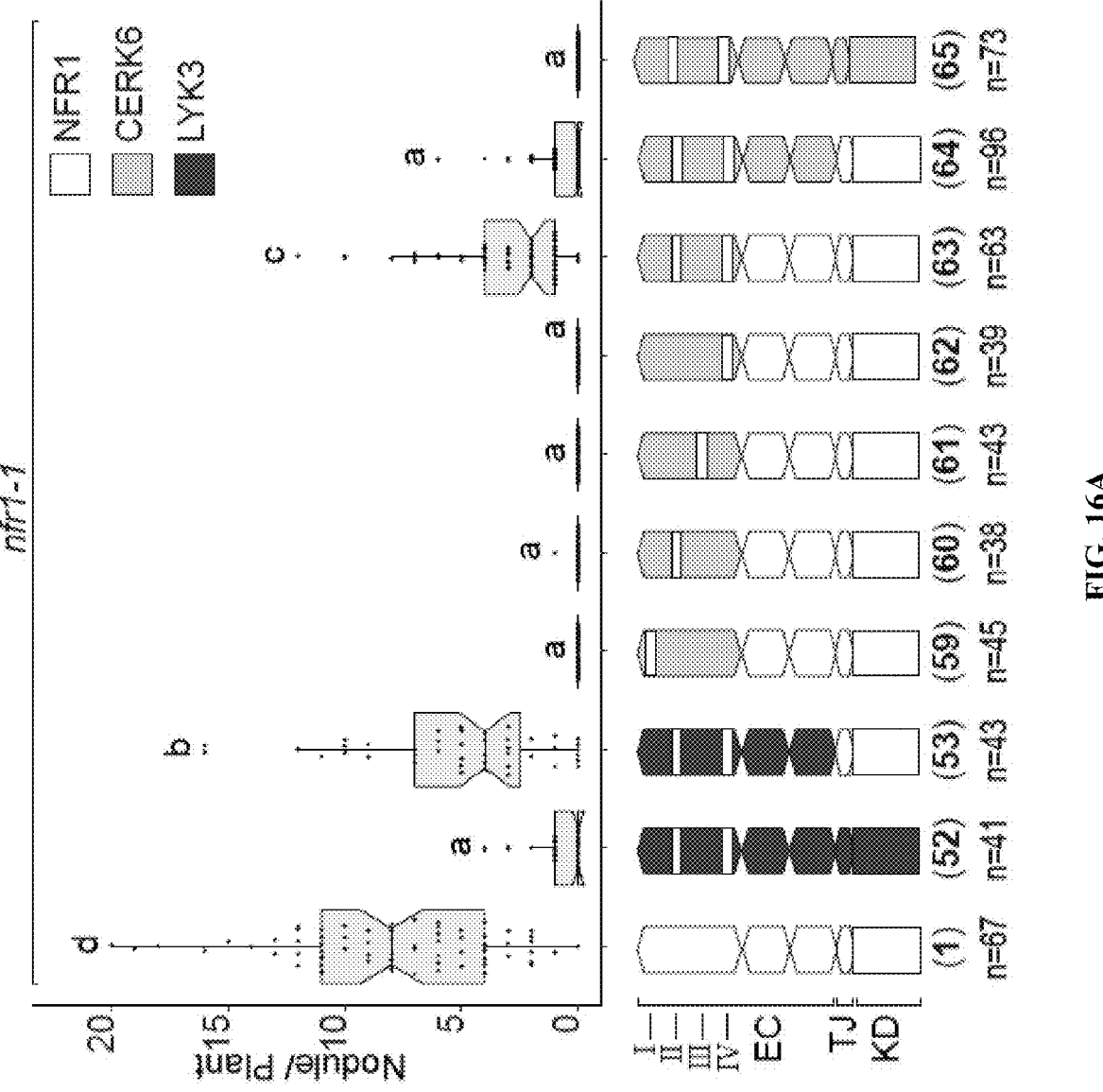
FIGS. 16A-16C show results of functional studies measuring nodulation using chimeras of the *L. japonicus* LysM receptor kinase proteins NFR1 and CERK6, or *L. japonicus* NFR1 and the *M. truncatula* LysM receptor kinase protein LYK3.
Figure 16C:
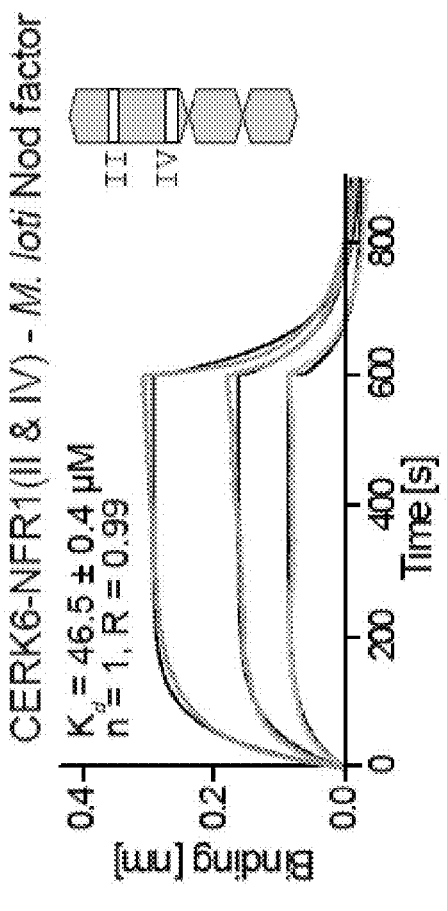
Figure 16B:
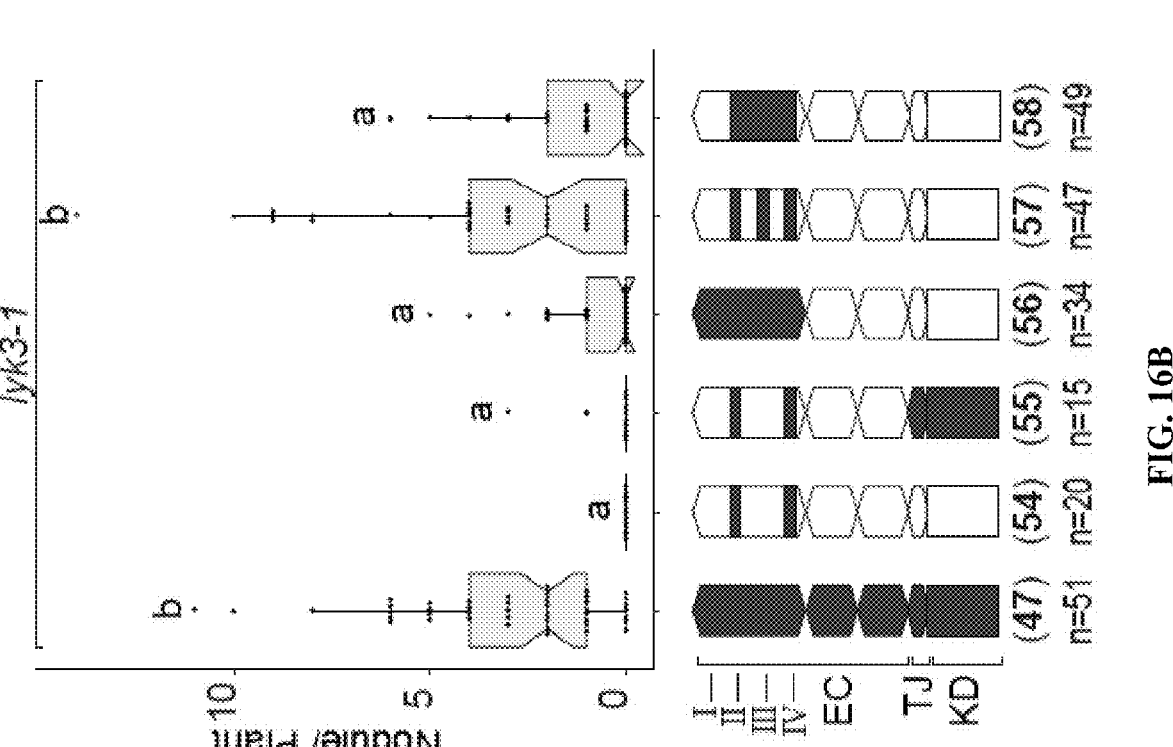
Figure 17A:
FIGS. 17A-17G show comparisons of LysM receptor kinase LysM1 domain structures as ribbon diagrams. FIG.
Figure 17B:
Figure 17C:
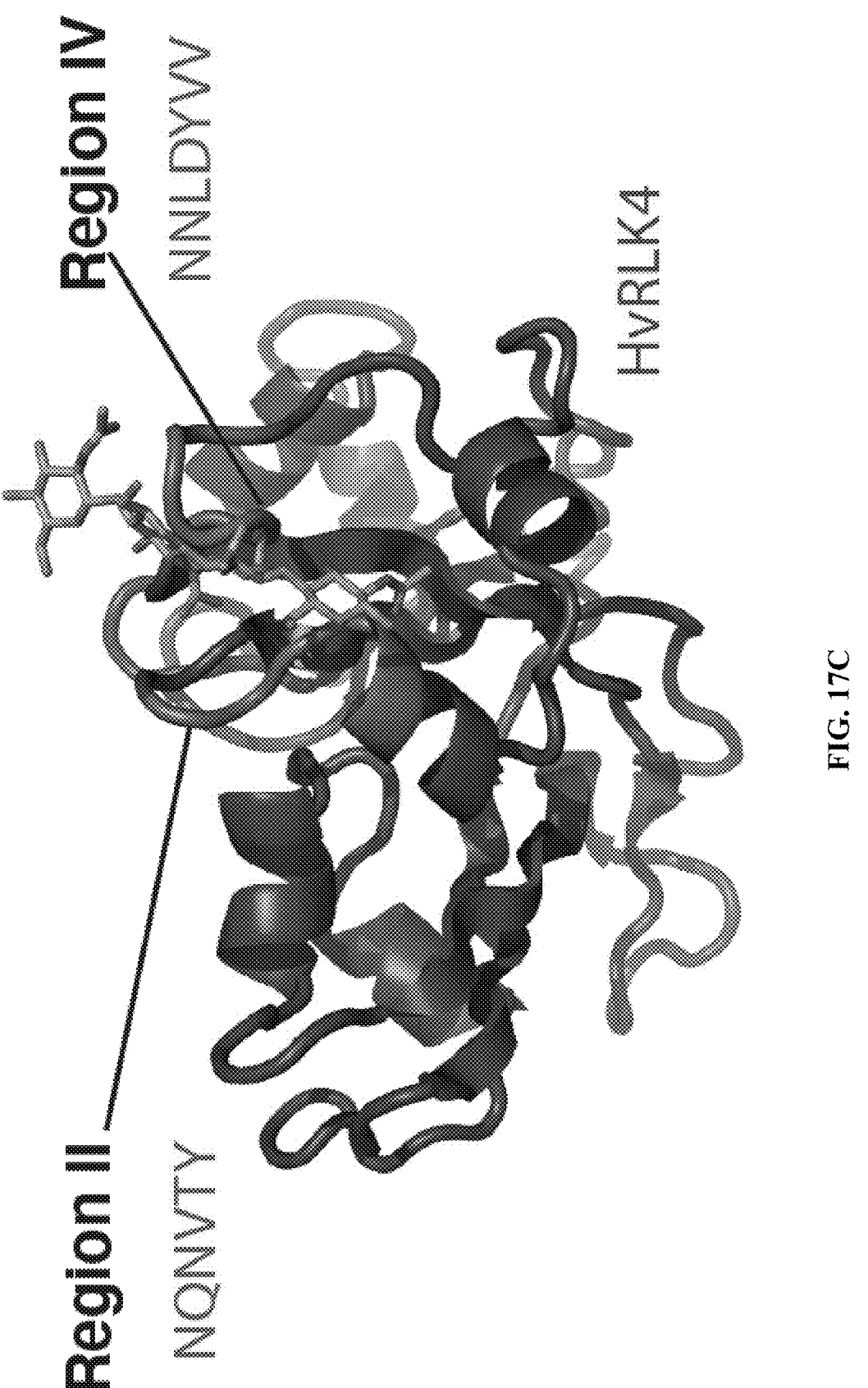
Figure 17D:
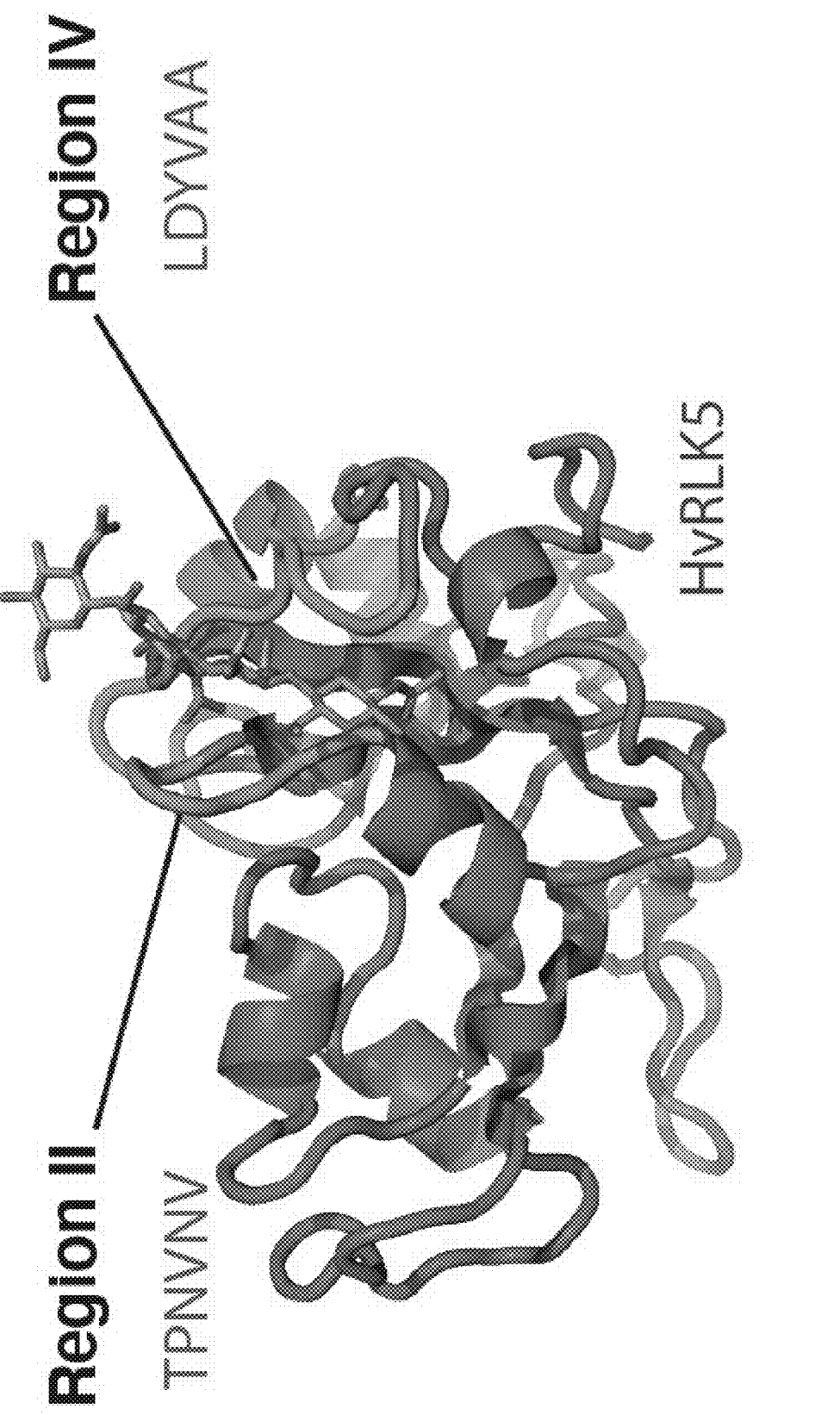
Figure 17E:
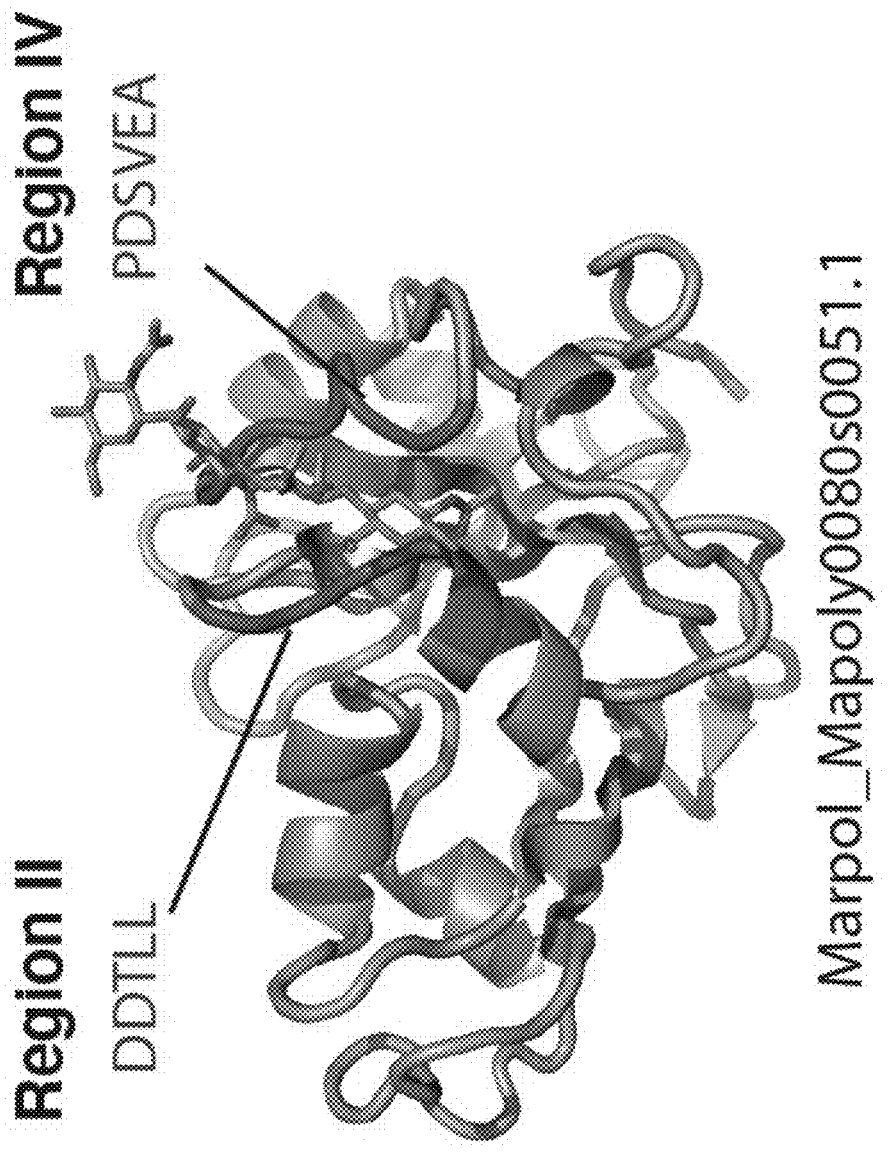
Figure 17F:
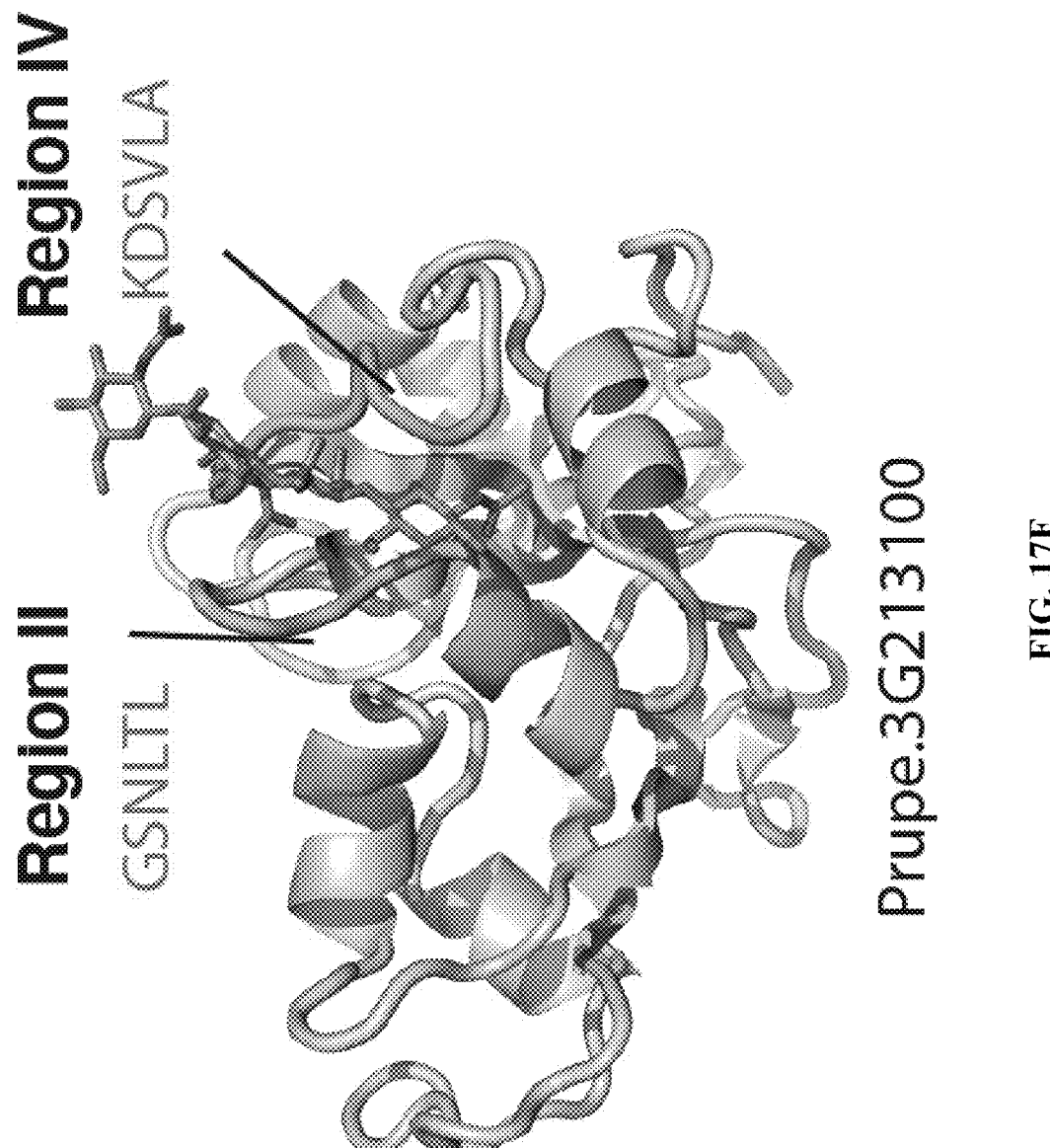
Figure 17G:
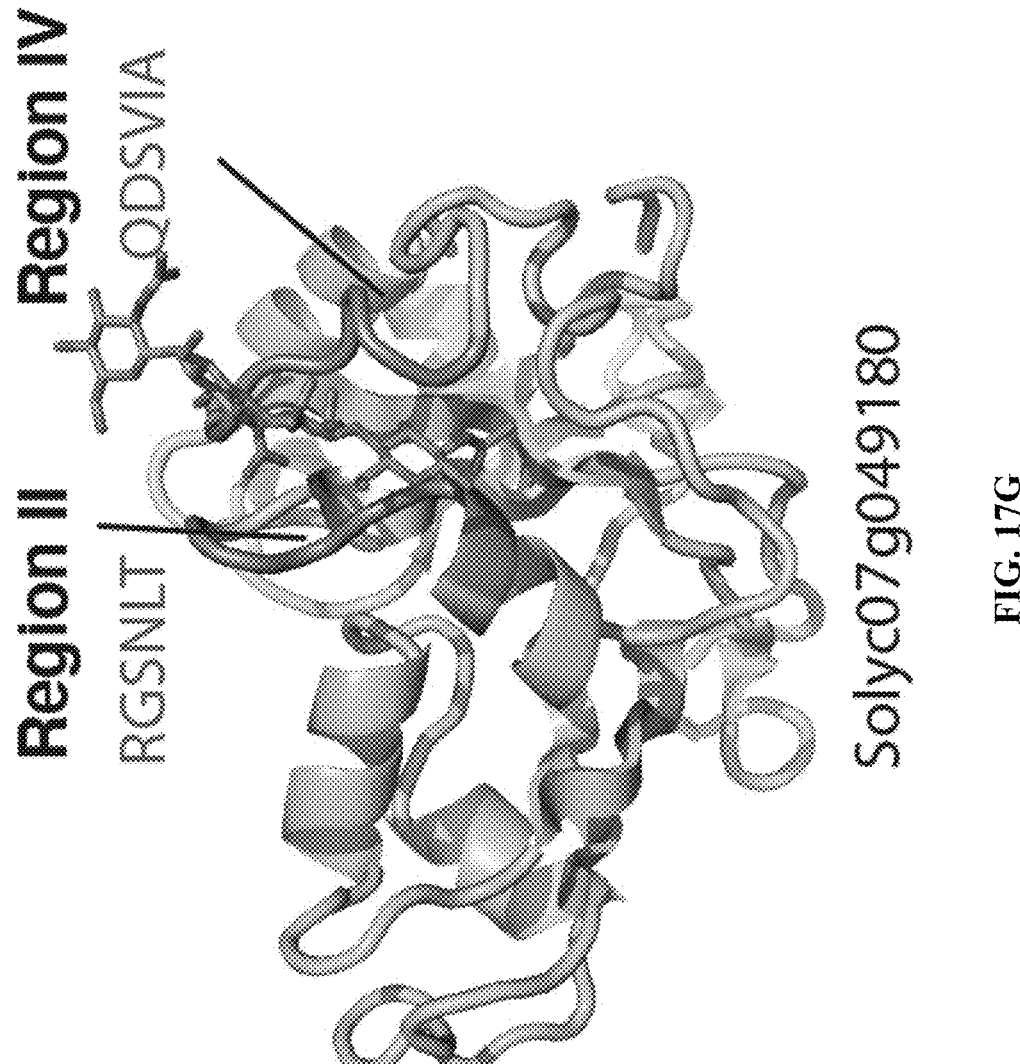

| Construct Number | Promoter | Description of LysM Receptor Kinase | FIGS. |
|---|---|---|---|
| 1 | Nfr1 | NFR1 | FIG. 16A |
| 47 | Lyk3 | LYK3 | FIG. 16B |
| 52 | Nfr1 | LYK3 with NFR1 LysM1 regions II and IV | FIGS. 10C, 16A |

TABLE 7-continued

LysM receptor kinase expression constructs

Figure 10D:
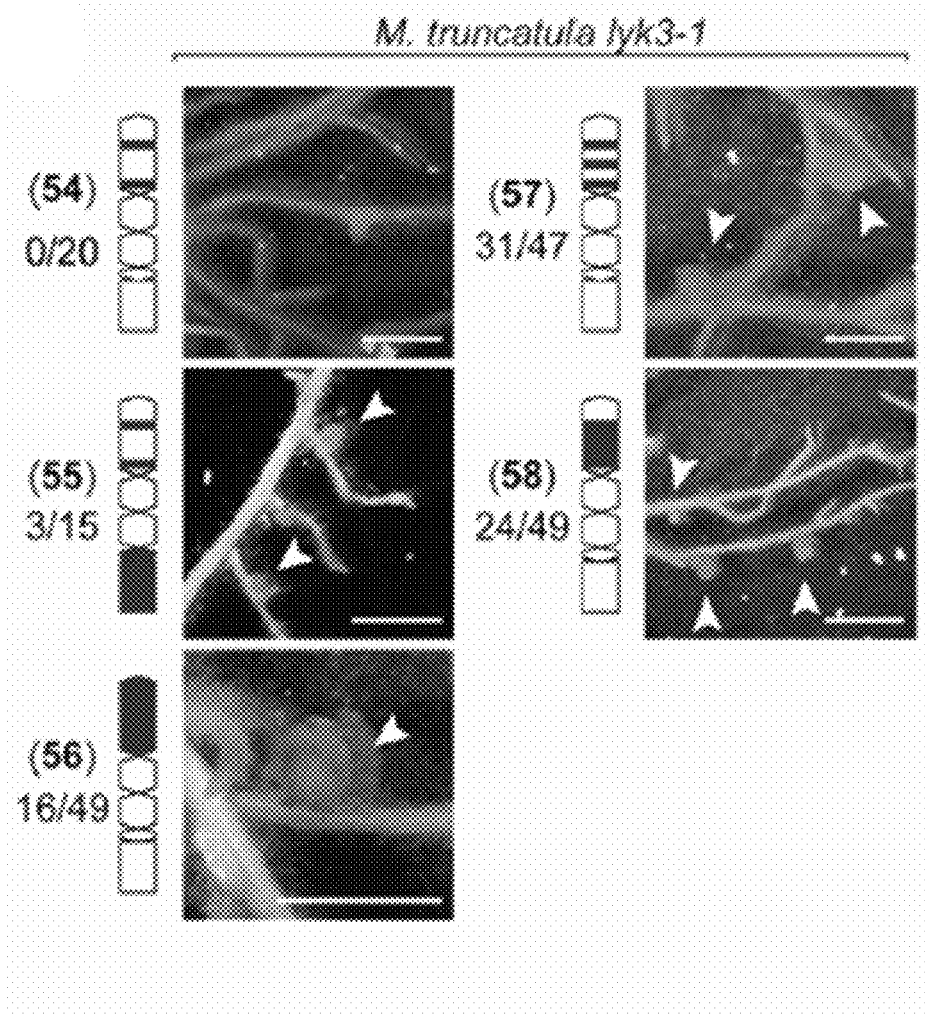
Figure 11A:
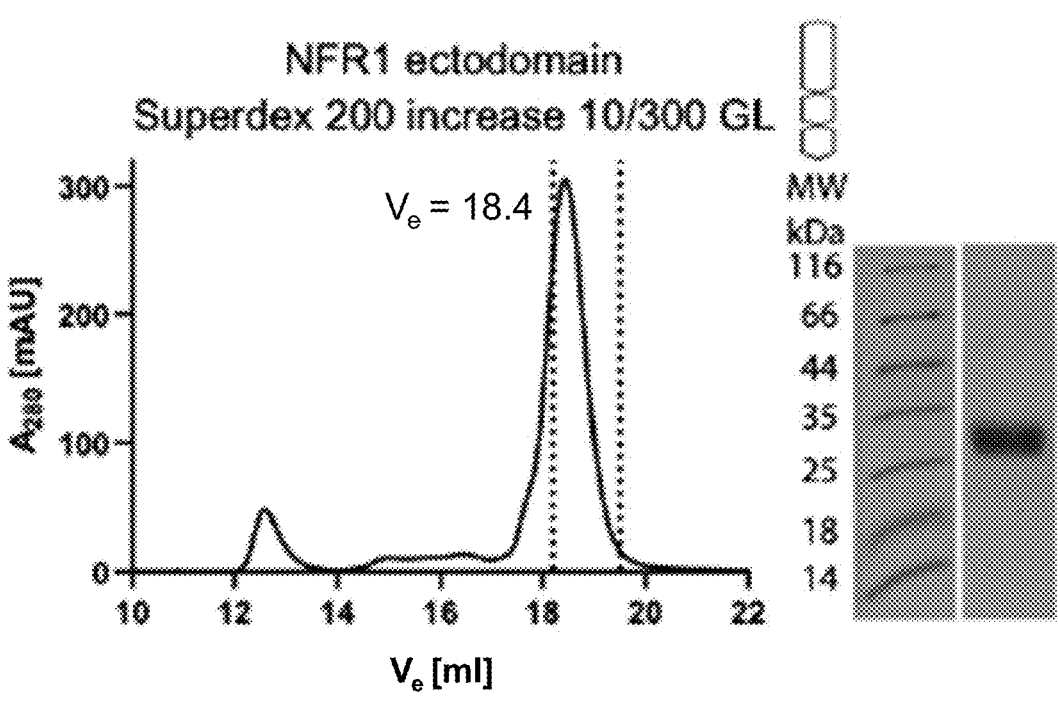
FIGS. 11A-11H show the purification of LysM receptor kinase ectodomain and *S. meliloti* Nod factor conjugates.
Figure 11B:
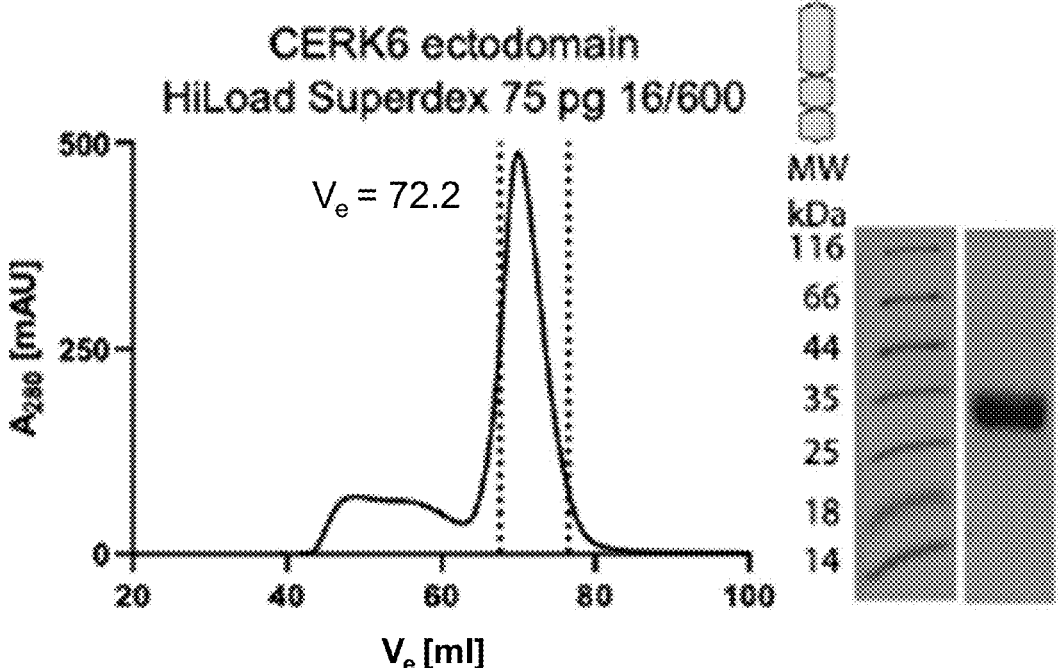
Figure 11C:
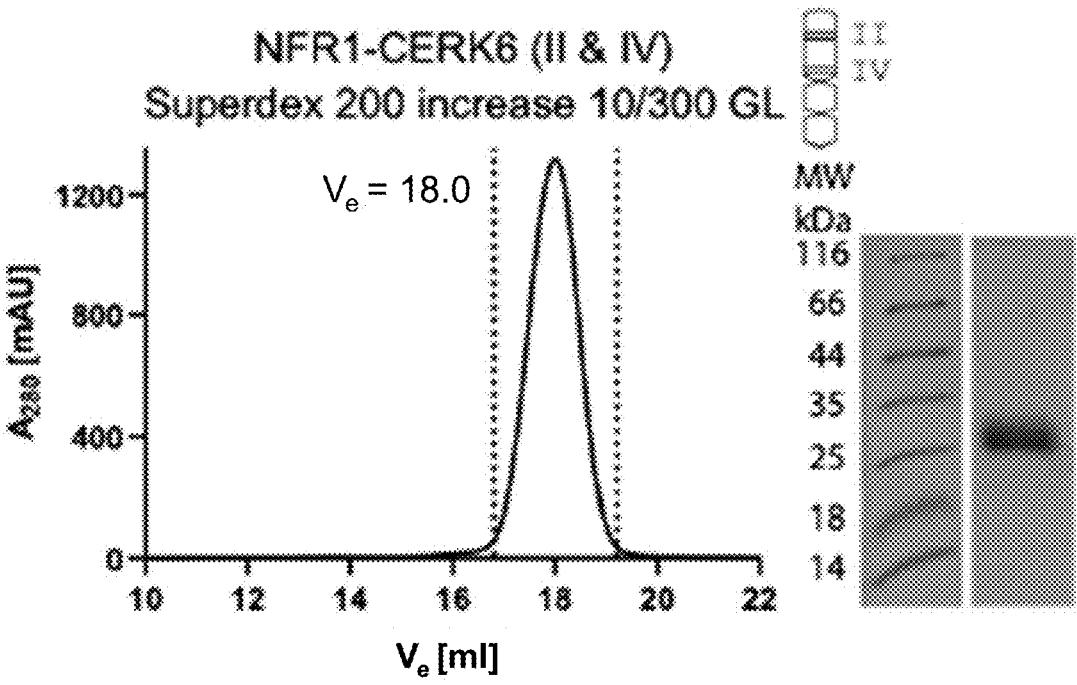
Figure 11D:
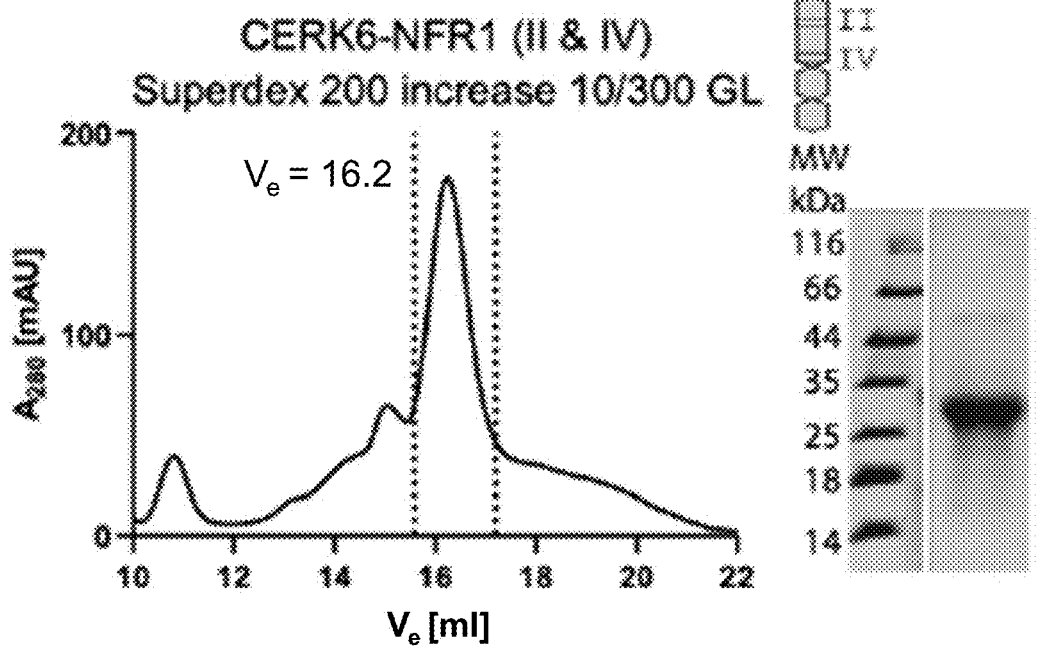
Figure 11E:
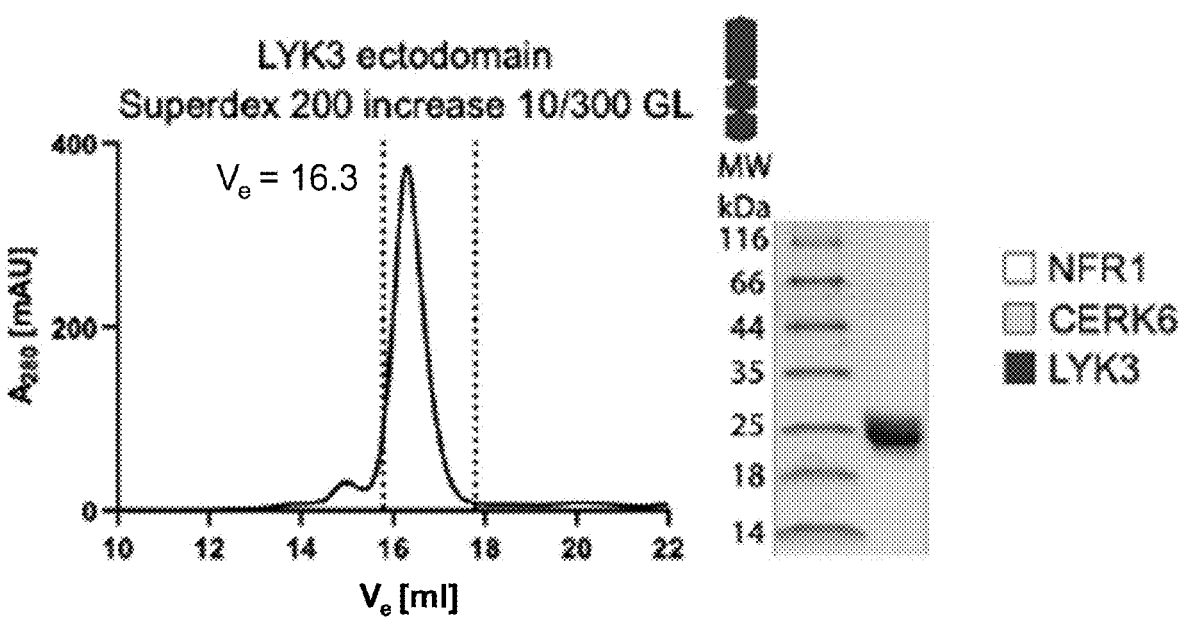
Figure 11F:
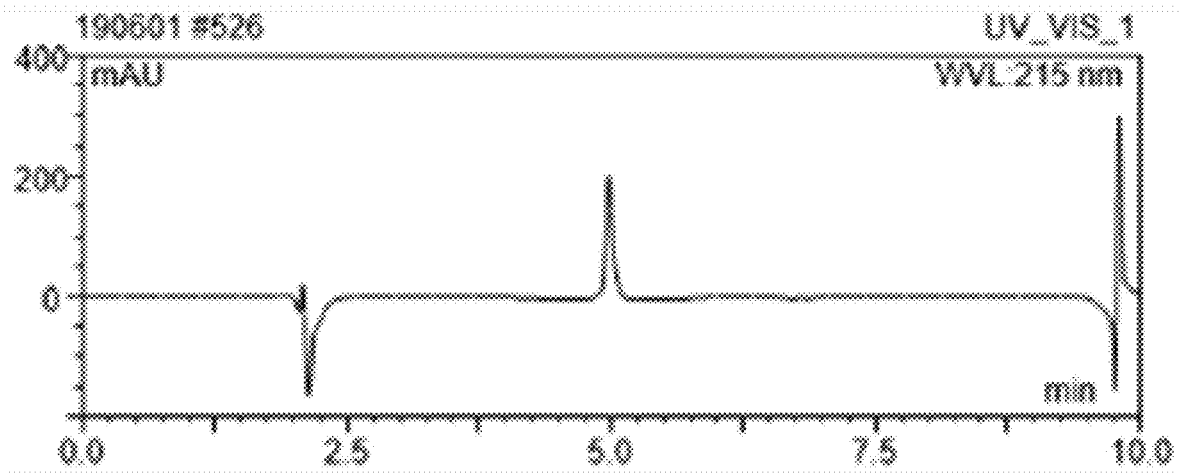
Figures 11G, 11H:
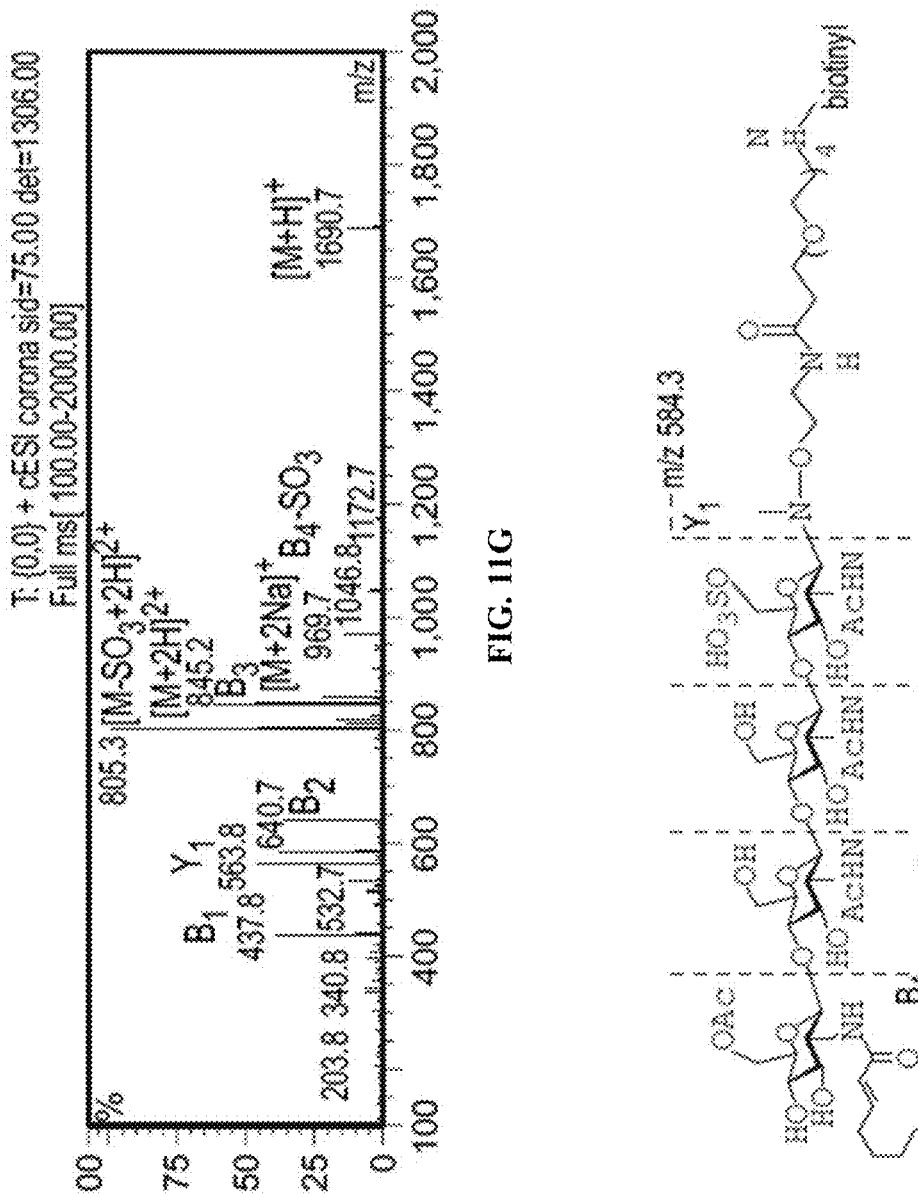

| Construct Number | Promoter | Description of LysM Receptor Kinase | FIGS. |
|---|---|---|---|
| 53 | Nfr1 | LYK3 with NFR1 LysM1 regions II and IV, TJ, and KD | FIGS. 10C, 16A |
| 54 | Lyk3 | NFR1 with LYK3 LysM1 regions II and IV | FIGS. 10D, 16B |
| 55 | Lyk3 | NFR1 with LYK3 LysM1 regions II and IV, TJ, and KD | FIGS. 10D, 16B |
| 56 | Lyk3 | NFR1 with LYK3 EC | FIGS. 10D, 16B |
| 57 | Lyk3 | NFR1 with LYK3 LysM1 regions II, III, and IV | FIGS. 10D, 16B |
| 58 | Lyk3 | NFR1 with LYK3 LysM1 regions II through IV, inclusive | FIGS. 10D, 16B |
| 59 | Nfr1 | NFR1 with CERK6 EC with NFR1 LysM1 region I | FIGS. 10C, 16A |
| 60 | Nfr1 | NFR1 with CERK6 EC with NFR1 LysM1 region II | FIGS. 10C, 16A |
| 61 | Nfr1 | NFR1 with CERK6 EC with NFR1 LysM1 region III | FIGS. 10C, 16A |
| 62 | Nfr1 | NFR1 with CERK6 EC with NFR1 LysM1 region IV | FIGS. 10C, 16A |
| 63 | Nfr1 | NFR1 with CERK6 EC with NFR1 LysM1 regions II and IV | FIGS. 10C, 16A |
| 64 | Nfr1 | CERK6 with NFR1 LysM1 regions II and IV, TJ, and KD | FIGS. 10C, 16A |
| 65 | Nfr1 | CERK6 with NFR1 LysM1 regions II and IV | FIGS. 10C, 16A |

Results
Swapping Specific Regions in the LysM1 Domain was Sufficient to Engineer Specific Nod Factor Recognition Two regions in LysM1 domains distinguishing chitin and Nod factor receptors were identified (FIG. 14E, FIG. 15E), and for NFR1 and LYK3 receptors these regions were necessary for the specific recognition of *M. loti* and *S. meliloti* Nod factors (FIGS. 9A-9B). This raised the question of whether Nod factor specificity in *L. japonicus* and *M. truncatula* LysM receptor kinases could be reprogrammed by using these molecular fingerprints. To answer this, signaling incompetent receptors (see constructs 41 and 43, FIG. 9A) containing the ectodomains of LYK3 were modified by exchanging regions II and IV with the corresponding regions of NFR1. It was then tested whether *M. loti* nodulation occurred in the nfr1 mutant expressing these new receptors (see constructs 52 and 53, FIG. 16A). Reciprocal experiments were performed in *M. truncatula* lyk3 in which signaling incompetent receptors containing the ectodomains of NFR1 were modified by exchanging regions II and IV with the corresponding regions of LYK3 (see constructs 54 and 55, FIG. 16B). These new chimeras enabled complementation of nfr1 (constructs 52 and 53 in FIG. 16A and FIG. 10C), but not of lyk3 (constructs 54 and 55 in FIG. 16B and FIG. 10D). This indicated that symbiosis with *M. loti* in *L. japonicus* can be gained by exchanging regions II and IV of the LysM1 domain of LYK3. In contrast, a similar engineering strategy for NFR1 was not sufficient to restore symbiosis with *S. meliloti* in *M. truncatula*.

To locate additional elements that contributed to *S. meliloti* Nod factor recognition, the previously analyzed 23 sequences from NFR- or CERK-type receptors from legume species were inspected (FIGS. 14A-14C and FIGS. 15A-15C). In addition to the motifs in region II and IV, region III in NFR-type receptors (residues 54-65 in LYK3) contained considerable variation among legume species (FIGS. 14A-14D). This region was spatially close to the proposed ligand binding site (FIG. 14E). Therefore, it was hypothesized that amino acids present in region III could be important for recognition of *S. meliloti* Nod factor. This was examined by testing additional NFR1-LYK3 chimeras (constructs 56, 57, 58, see FIG. 16B). NFR1 receptors containing region III in addition to regions II and IV from LYK3 were functional in complementing the *M. truncatula* lyk3 mutant for symbiosis with *S. meliloti* (FIG. 16B and FIG. 10D). These phenotypes from chimeric receptors showed that regions around the Nod factor-binding site were important for engineering specificity into these receptors, and further that region III was important for ensuring host-symbiont compatibility in the nodulation of *M. truncatula* by *S. meliloti*.

Reprogramming CERK6 Receptor to Recognize Nod Factors and Mediate Nodulation Signaling Initiation of nodulation by Nod factor-producing *rhizobia* is restricted to leguminous plants and *Parasponia* species (Trinick, M. *J. Nature* 1975 244: 459-460), while chitin recognition is ubiquitous among plants. Based on the above results from engineering LYK3 and NFR1 receptors for specific Nod factor signaling (FIGS. 16A-16B), it was examined whether the chitin receptor CERK6 could be engineered to recognize *M. loti* Nod factor. In particular, whether systematic replacement of regions I, II, III and IV was sufficient to induce a change in ligand specificity in the signaling-incompetent chimeric receptor (construct 21) (FIG. 4A) in which CERK6 LysM1 replaced the corresponding domain of NFR1 was tested. Swapping individual regions with corresponding ones from NFR1 was insufficient to introduce perception of *M. loti* Nod factor, and no nodulation of nfr 1 was observed (constructs 59, 60, 61, and 62 in FIG. 16A and FIG. 10C). This indicated that a more complex chimera was required for reprogramming CERK6.

As described above, structural and phylogenetic analyses indicated that regions II and IV featured a ligand binding site (FIG. 14E and FIG. 15E). The cooperative involvement of the two regions was tested by engineering a chimeric receptor in which both regions were concomitantly exchanged from CERK6 into NFR1 in the signaling incompetent receptor (construct 21). This new receptor (construct 63) was functional and enabled recognition of *M. loti* when expressed in nfr1 (FIG. 16A and FIG. 10C). The overall level of nodulation induced by construct 63 was lower than nodulation induced by NFR1, but the frequency of complementation was high (60 out of 63 transformed plants formed nodules), indicating that the engineered CERK6 protein (construct 63) functioned as Nod factor receptor and complemented nfr1 with a high level of penetrance.

Next, it was assessed whether regions II and IV of NFR1 were sufficient for *M. loti* Nod factor recognition when embedded in the CERK6 ectodomain (construct 8 in FIG. 2A) or the CERK6 full-length receptor (construct 5 in FIG. 2A). Construct 64, containing NFR1 regions II and IV as well as the NFR1 TJ and KD, was able to complement nfr1, but construct 65, containing NFR1 regions II and IV, was not (FIG. 16A, FIG. 10C). Expression of construct 64 resulted in fewer nodules formed on the transformed roots of nfr1, and a low penetrance (35 out of 95 transformed plants, FIG. 10C), when compared to construct 63 or full-length NFR1 (FIG. 16A). This reduction in the penetrance of restoring the nodulation phenotype may have occurred as a result of the observed negative impact of CERK6 LysM2 (constructs 18 and 19 in FIG. 4B), and CERK6 TJ and KD (construct 4 in FIG. 2A) on nfr1 complementation for nodulation.

To resolve whether these findings from in planta studies were a result of changes in the Nod factor binding properties of CERK6 (FIG. 12C), the chimeric ectodomain of construct 64 (containing CERK6 ectodomain with regions II and IV from NFR1) was expressed in insect cells, purified, and tested for in vitro binding of *M. loti* Nod factor. The purified chimeric ectodomain gained the capacity to bind *M. loti* Nod Factor (FIG. 16C) with a Kd=46.5 μM. This binding affinity was similar to that of the NFR1 ectodomain (FIG. 12B), demonstrating that regions II and IV played a major role in Nod factor recognition.

The examples herein describe the molecular mechanism behind the recognition of immunogenic and symbiotic chitin-based glycans (e.g., chitin or Nod factor) by LysM receptor kinases. Comparative structural and functional studies revealed a critical role of two distinct regions (regions II and IV) in LysM1 domains. These regions created a structurally defined binding pocket that discriminated between chitin (CO8) and Nod factor ligands. Two motifs with a high degree of conservation were identified in regions II and IV of legume chitin receptors (FIG. 16B), which likely reflected their ability to recognize and bind the structurally invariable chitin (FIG. 16B and FIGS. 15A-15D). In contrast, Nod factor receptors showed a high degree of sequence degeneration in corresponding motifs (FIG. 16A), reflecting the diversity in legume-*rhizobia* compatibility (FIG. 16A and FIGS. 14A-14D). The LYK3 and NFR1 receptors were found to vary in their signaling flexibility. Regions II and IV from NFR1 were sufficient to enable recognition of *M. loti* by LYK3 in *L. japonicus* (FIG. 14E), while regions II, III and IV from LYK3 were required for *S. meliloti* recognition by NFR1 in *M. truncatula* (FIG. 15E). Region III of LysM1 was also found to be highly variable between legume species (FIG. 16A and FIGS. 14A-14D), and, without wishing to be bound by theory, it is envisioned this could be required for establishing species-specific interactions with the ligand-bound or unbound co-receptor of the NFR5/NFP class.

In summary, the examples herein demonstrated that LysM receptor kinases have a programmable capacity for ligand perception, thus enabling rational engineering of specific signaling. The findings therefore provide a basis for engineering highly sensitive receptor complexes, which will allow symbiotic signaling with Nod factor-producing *rhizobia* for plant hosts outside of the nodulation Glade.

Example 6: Generation and Testing of LysM Receptor Kinases with Exchanged Nod Factor and Chitin-Binding Motifs The following example describes the generation of chimeric LysM receptor kinases. In particular, LysM receptor kinases with swaps of amino acid motifs associated with LysM1 domain ligand-binding sites of NFR1/LYK3-type Nod factor receptors, and LysM1 domain ligand-binding sites of CERK6-type chitin receptors are described. Further, the motif-swapped chimeras are assessed using in vivo and in vitro functional assays.

Materials and Methods

Plant materials and growth conditions, bacterial strains and culture conditions, hairy root transformation, nodulation assays, and ROS formation assays are all performed as described in Examples 1 and 2, above.

Generation of Plant Expression Vectors

Expression constructs are generated to express LysM receptor kinases in *Hordeum vulgare* (barley), *Marchantia polymorpha*, or *L. japonicus*. Expression constructs are summarized in Table 7, below.

Four constructs are generated to test for LCO perception (constructs 7.1-7.4). In constructs 7.1 and 7.2, LysM1 regions II and IV or the entire LysM1 domain of *L. japonicus* NFR1 are introduced into *H. vulgare* RLK4 (HvRLK4), and expression is driven by the *Brachipodium distachion* ubiquitin promoter (BdUbi10). Constructs 7.1 and 7.2 are transformed into *H. vulgare*.

In constructs 7.3 and 7.4, LysM1 regions II and IV or the entire LysM1 domain of *L. japonicus* NFR1 are introduced into the *Marchantia polymorpha* 51.1 receptor (Marpol_51.1) and expression is driven by the 35S promoter. Constructs 7.3 and 7.4 are transformed into *M. polymorpha*.

In addition, an expression construct is generated to test the role of the LysM1 domain in CO perception (construct 7.5). In construct 7.5, the LysM1 domain of *L. japonicus* CERK6 is introduced into *M. truncatula* LYK9 (MtLYK9), and expression is driven by the Cerk6 promoter. Construct 7.5 is transformed into *L. japonicus*.

TABLE 7

LysM receptor kinase expression constructs

| Construct Number | Promoter | Description of LysM Receptor Kinase | SEQ ID NO of full-length LysM Receptor Kinase |
|---|---|---|---|
| 7.1 | BdUbi10 | HvRLK4 with NFR1 LysM1 regions II and IV | SEQ ID NO: 265 |
| 7.2 | BdUbi10 | HvRLK4 with NFR1 LysM1 | SEQ ID NO: 266 |
| 7.3 | 35S | Marpol_51.1 with NFR1 LysM1 regions II and IV | SEQ ID NO: 268 |
| 7.4 | 35S | Marpol_51.1 with NFR1 LysM | SEQ ID NO: 269 |
| 7.5 | Cerk6 | MtLYK9 with CERK6 LysM1 | SEQ ID NO: 270 |

Results

The ability of *H. vulgare* plants expressing constructs 7.1 or 7.2 to recognize *M. loti* Nod factor will be tested. Constructs 7.1 and/or 7.2 will enable *H. vulgare* plants to recognize *M. loti* Nod factor with higher specificity.

The ability of M *polymorpha* plants expressing constructs 7.3 or 7.4 to respond to *M. loti* Nod factor will be tested. Constructs 7.3 and/or 7.4 will enable M *polymorpha* to respond to *M. loti* Nod factor.

The ability of cerk6 mutant *L. japonicus* plants expressing construct 7.5 to generate ROS will be tested. Construct 7.5 will induce a ROS response in cerk6 mutant plants.

Example 7: Identification of Important Residues in the LysM2 Domain for Nod Factor Perception The following example describes the structural characterization of the ectodomain of the *M. truncatula* LysM receptor NFP, and the use of a structurally-guided approach to identify important residues for Nod factor perception in the LysM2 domain. After identifying important residues, point mutations in *M. truncatula* NFP were created and tested using ligand-binding assays. To confirm the biochemical observations, a complementation test was performed in *M. truncatula* nfp mutants using hairy root transformation.

Materials and Methods

Expression and Purification of the Ectodomain of the *M. truncatula* LysM Receptor NFP The *M. truncatula* NFP ectodomain (residues 28-246) was codon-optimized for insect cell expression (Genscript, Piscataway, USA) and cloned into the pOET4 baculovirus transfer vector (Oxford Expression Technologies). The native NFP signal peptide (residues 1-27, predicted by SignalP 4.1) was replaced with the AcMNPV gp67 signal peptide to facilitate secretion and a hexa-histidine tag was added to the C-terminus. Recombinant baculoviruses were produced in SD cells (*Spodoptera frugiperda*) using the FlashBac Gold kit (Oxford Expression technologies) according to the manufacturer's instructions with Lipofectin (ThermoFisher Scientific) as a transfection reagent. Protein expression was performed as follows. Suspension-cultured Sf9 cells were maintained with shaking at 299 K in serum-free MAX-XP (BD-Biosciences, discontinued) or HyClone SFX (GE Healthcare) medium supplemented with 1% Pen-Strep (10000 U/ml, Life technologies) and 1% CD lipid concentrate (Gibco). Protein expression was induced by adding recombinant passage 3 virus once the Sf9 cells reached a cell density of $1.0*10^6$ cells/ml. After 5-7 days of expression, medium supernatant containing NFP ectodomains was harvested by centrifugation. This was followed by an overnight dialysis step against 50 mM Tris-HCl pH 8, 200 mM NaCl at 277 K. The NFP ectodomain was enriched by two subsequent steps of Ni-IMAC purification (HisTrap excel/HisTrap HP, both GE Healthcare). For crystallography, N-glycans were removed using the endoglycosidase PNGase F (1:15 (w/w), room temperature, overnight). As a final purification step, NFP ectodomains was purified by SEC on a Superdex 200 10/300 or HiLoad Superdex 200 16/600 (both GE Healthcare) in phosphate buffered saline at pH 7.2 supplemented to a total of 500 mM NaCl (for binding assays) or 50 mM Tris-HCl, 200 mM NaCl (for crystallography). NFP ectodomain eluted as a single, homogeneous peak corresponding to a monomer.

Crystals of deglycosylated NFP ectodomain were obtained using a vapor diffusion setup at 3-5 mg/ml in 0.2 M Na-acetate, 0.1 M Na-cacodylate pH 6.5, and 30% (w/v) PEG-8000. Crystals were cryoprotected in their crystallization condition by supplementing with 5% (w/v) PEG-400 before being snap-frozen in liquid nitrogen. Complete diffraction data to 2.85 Å resolution was obtained at the MaxLab 1911-3 beamline. The phase problem was solved by molecular replacement using Phaser from the PHENIX suite with a homology model based on the *A. thaliana* CERK1 ectodomain structure (PDB coordinates 4EBZ) as a search model. Model building and refinement was done using COOT and the PHENIX suite, respectively. The output pdb filled structural model was generated and its electrostatic surface potential was calculated using the PDB2PQR and APBS webservers (PMID: 21425296). The results were visualized in PyMol using APBS tools 2.1 (DeLano, W. L. (2002). PyMOL. DeLano Scientific, San Carlos, CA, 700.).

Structurally-Guided Residue Identification

The *M. truncatula* NFP ectodomain (LysM Nod factor receptor) was structurally aligned to the ligand-bound ectodomain of *A. thaliana* CERK1 (LysM chitin receptor). Then, the electrostatic surface potential was mapped to the previously-developed structure of the *M. truncatula* NFP ectodomain. The predicted ligand-binding location and electrostatic surface potential are depicted in FIG. 18B.

Creation of Point Mutations in the Ectodomain of *M. truncatula* NFP

The *M. truncatula* NFP leucine residues L147 and L154 were replaced with aspartate residues. Aspartate is similar in size to leucine, but negatively charged where leucine is hydrophobic. Point mutants of NFP were engineered using site-directed mutagenesis. In particular, a double-mutated NFP was engineered where the leucine residues L147 and L154 were replaced with aspartate residues to create the mutant NFP L147D L154D. Point mutated versions of the NFP ectodomain were expressed and purified as described above.

Binding Assays

The binding assay using NFP wild type (WT) was replicated seven times, while the binding assay using the NFP mutant NFP L147D L154D was replicated four times. A summary of results is shown in Table 8.

TABLE 8

Summary of binding assay results

| Protein | A (M−1 min−1) | D (min−1) | Kd (µM) | n |
|---|---|---|---|---|
| NFP WT | 57.5 ± 0.28 | 0.00149 ± 0.0000062 | 25.98 ± 0.21 | 7 |
| NFP L147D L154D | 468.4 ± 8.85 | 0.022 ± 0.00012 | 47.99 ± 1.01 | 4 |

Biolayer Interferometry (BLI)

Figure 18C:
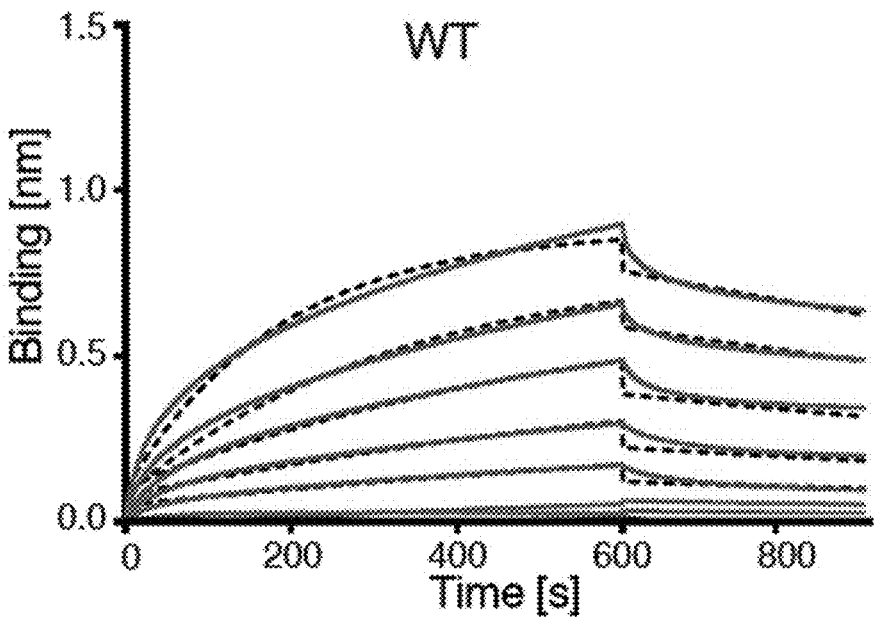
Figure 18D:
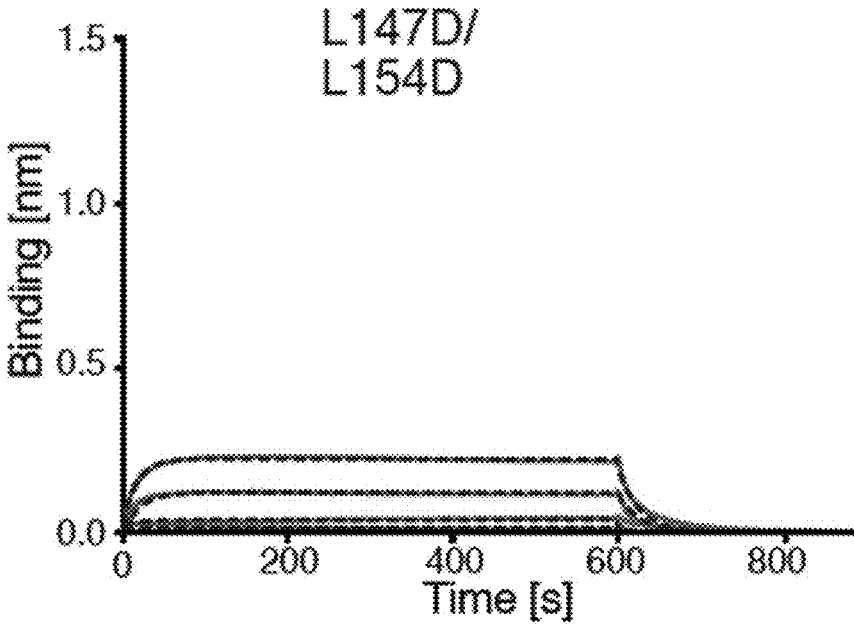

Binding of NFP WT and NFP L147D/L154D mutant to *S. meliloti* Nod factor LCO-IV was measured on an Octet RED 96 system (Pall ForteBio). *S. meliloti* Nod factor LCO-IV consists of a tetrameric/pentameric N-acetylglucosamine backbone that is O-sulfated on the reducing terminal residue, O-acetylated on the non-reducing terminal residue, and mono-N-acylated by unsaturated C16 acyl groups. Biotinylated ligand conjugates were immobilized on streptavidin biosensors (kinetic quality, Pall ForteBio) at a concentration of 125-250 nM for 5 minutes. The binding assays were replicated 7 times for the NFP WT, and 4 times for the NFP L147D/L154D mutant. Data analysis was performed in GraphPad Prism 6 software (GraphPad Software, Inc.). Equilibrium dissociation constants derived from the steady-state were determined by applying a non-linear regression (one site, specific binding) to the response at equilibrium plotted against the protein concentration. Kinetic parameters were determined by non-linear regression (association followed by dissociation) on the subtracted data. Results are shown in FIGS. 18C-18D. Table 9 summarizes the kinetic parameters of FIGS. 18C-18D, with goodness of fit described by the global fit $R^2$ on the mean value of each point, and number of replicates performed using independent protein preparations (n) indicated.

TABLE 9

Summary of BLI kinetic parameters

| | NFP WT | NFP L147D L154D |
|---|---|---|
| $K_d$ (µM) | 12.7 ± 0.1 | 166.7 ± 4.2 |
| $k_{on}$ (M−1s−1) | 50.3 | 227.7 |
| $k_{off}$ (s−1) | 6.4 × 10−4 | 379.9 × 10−4 |
| $R^2$ | 0.99 | 0.99 |
| n | 7 | 4 |

Figure 18F:
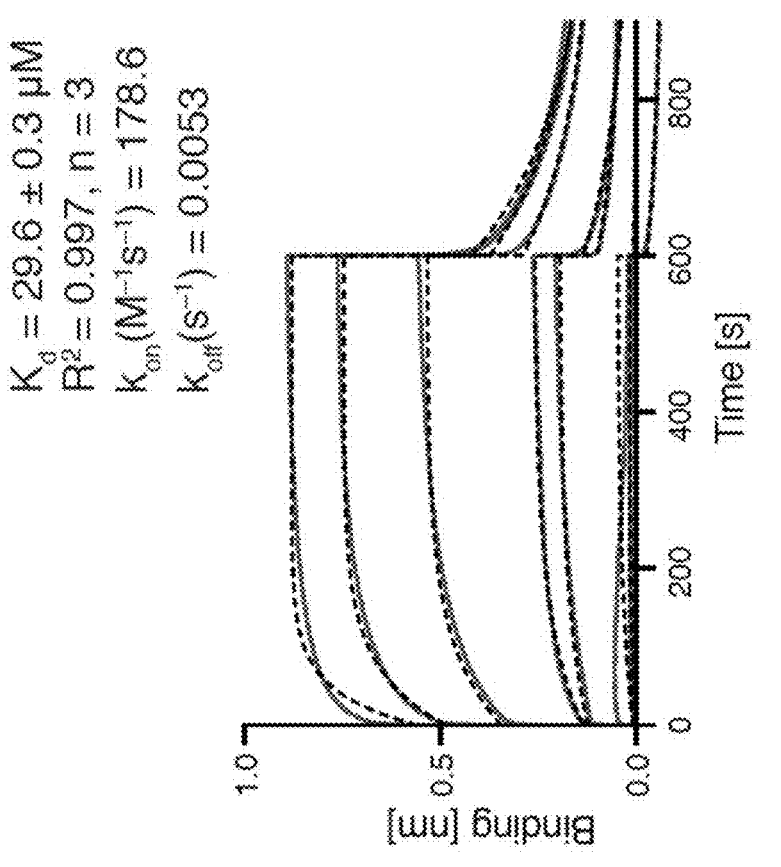
Figure 18E:
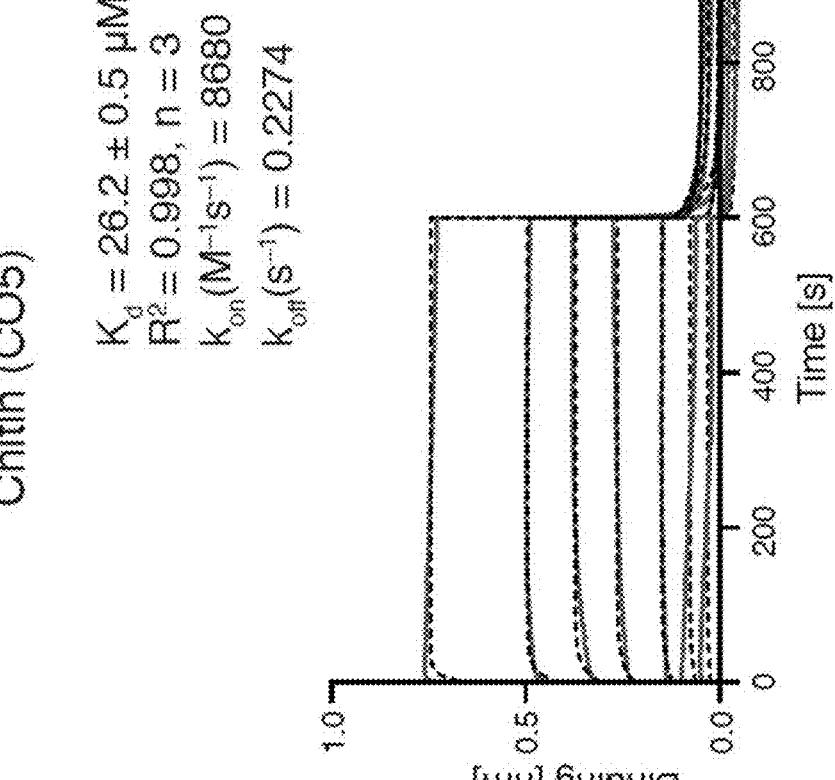

Binding of *A. thaliana* CERK1 (AtCERK1) to chitopentaose (CO5) and chitooctaose (CO8) was measured in the same way. Results are shown in FIGS. 18E-18F.

Complementation Assay

Figure 18G:
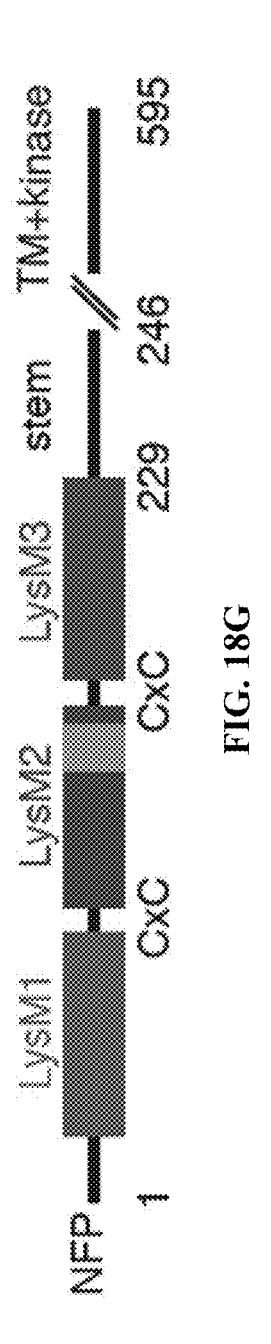
Figure 18H:
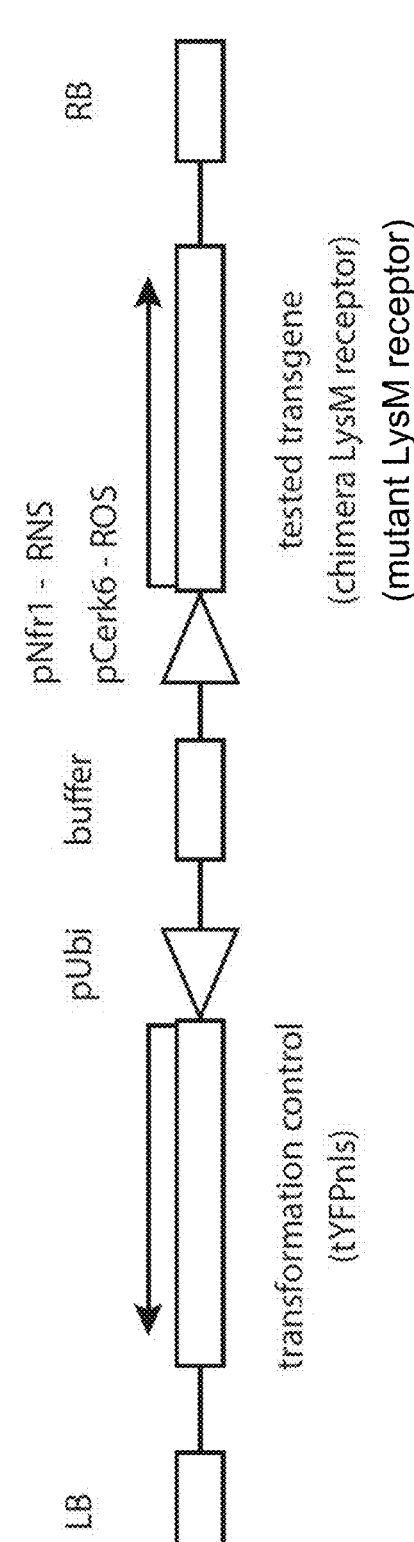

Construct assembly, plant growth conditions, hairy root transformations, nodulation and ROS assays were generally conducted as described in Bozsoki, et al. 2017 (Bozsoki, Z. et al. *Proc. Natl. Acad. Sci.* 2017 114: E8118-E8127). A general schematic of the construct is provided in FIG. 18H. The tested transgenes were the mutated LysM receptors described above.

Results

Structural Characterization of the *M. truncatula* NFP Ectodomain

The structure of *M. truncatula* NFP was determined by molecular replacement using a homology model based on the inner low B-factor scaffold of *A. thaliana* CERK1. The complete structure of NFP (residues 33-233) was built this way, including four N-glycosylations that were clearly resolved in the 2.8 Å electron density map. NFP forms a compact structure where three classical βααβ LysM domains are tightly interconnected and stabilized by 3 conserved disulfide bridges (C3-C104, C47-C166 and C102-C164) (FIG. 18A). The disulfide connectivity pattern and the overall scaffold arrangement is shared with other LysM receptors involved in chitin defense signaling, supporting a common evolutionary origin of this class of receptors.

Identification of Important Residues in the LysM2 Domain for Nod Factor Perception FIG. 18B shows modelling of the *M. truncatula* NFP ectodomain bound to a Nod factor ligand with predicted chitin and fatty acid chain locations. Structural alignment of the *M. truncatula* NFP ectodomain with the ligand-bound ectodomain of *A. thaliana* CERK1 positions chitin in the LysM2 binding groove of *M. truncatula* NFP without any obvious clashes. Strikingly, the electrostatic surface potential revealed a hydrophobic patch on the NFP ectodomain that is located near the non-reducing moiety of the docked chitin molecule, which potentially could accommodate the fatty acid chain of the Nod factor ligand. Two leucine residues (L147 and L154) were identified as the residues that give this patch its hydrophobic character.

To test the contribution of these two residues to Nod factor binding, both residues were replaced with similarly sized but negatively charged aspartate residues to produce the NFP ectodomain double mutant L147D L154D. Interestingly, the double mutated NFP L147D L154D ectodomain bound *S. meliloti* Nod factor LCO-IV with approximately two times lower affinity; Kd of 48.0±1.0 µM (Table 8). Closer inspection of the binding kinetics revealed that the association ($K_{on}$) was almost unaffected whereas the dissociation ($K_{off}$) was approximately 15 times faster in the double mutant. These results show that the hydrophobic patch of the NFP ectodomain is stabilizing the Nod factor bound state, and that this stabilization is most likely occurring via the fatty acid chain. Docking the Nod factor fatty acid in this hydrophobic patch and the chitin backbone in the LysM2 binding site would place the sulphate and acetyl side groups facing K141.

Biochemical analysis of Nod factor binding to the hydrophobic patch mutant reveals that the double mutated NFP L147D L154D ectodomain bound *S. meliloti* Nod factor LCO-IV with 13-fold lower affinity (Kd of 166.7±4.2 µM) compared to the WT NFP ectodomain (FIGS. 18C-18D, Table 9). The association rate ($k_{on}$) was 4.5-fold faster and the dissociation rate ($k_{off}$) was dramatically increased with 59-fold in the double mutant compared to the WT NFP ectodomain, suggesting that the hydrophobic patch had a strong stabilizing effect on Nod factor binding mediated by the acyl chain.

The binding kinetics of *A. thaliana* CERK1 binding to chitin fragments were measured as a comparison. As shown in FIGS. 18E-18F, fast association and dissociation rates were seen. These kinetics were reminiscent of the kinetics observed for the NFP ectodomain double mutant L147D L154D (FIG. 18D). The binding kinetics of the chitin receptor *A. thaliana* CERK1 to chitin fragments were clearly different than the binding kinetics of the Nod factor receptor NFP to Nod factors (FIG. 18C).

Complementation Test in *M. truncatula* nfp Mutants

Figures 18I, 18J:
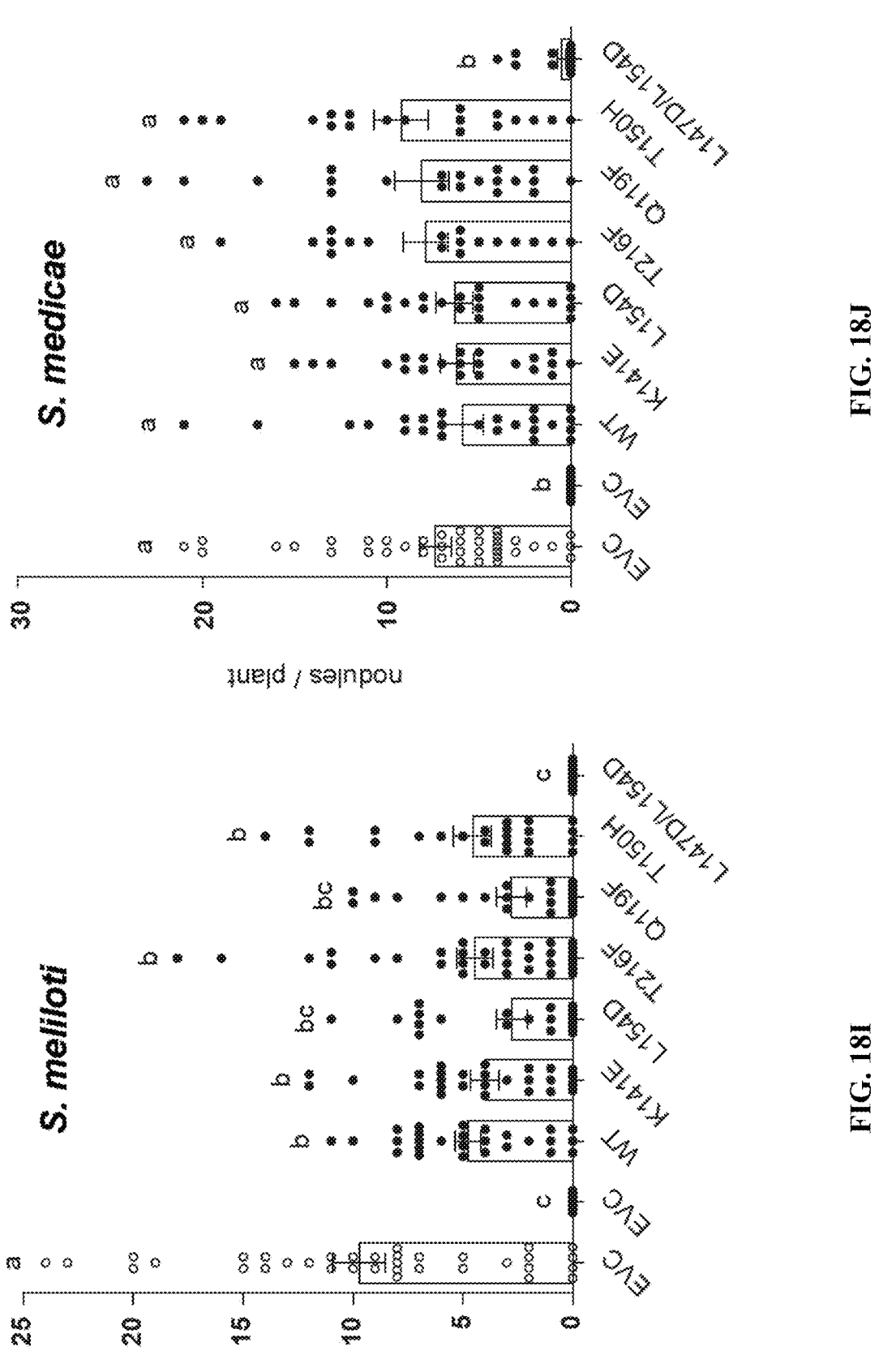

FIG. 18I shows the results of complementation tests where the plants were inoculated with *S. meliloti* strain 2011. When *M. truncatula* nfp mutants were transformed with the wild type *M. truncatula* NFP gene, complementation was seen, which was defined as an average of 10 nodules per plant 6-7 weeks after inoculation with *S. meliloti* strain 2011. In contrast, roots transformed with the double mutant construct (L147D L154D) did not develop any nodules per plant 6-7 weeks after inoculation with *S. meliloti* strain 2011.

FIG. 18J shows the results of complementation tests where the plants were inoculated with *S. medicae*, which has been reported to nodulate *Medicago* with higher efficiency. The *S. medicae* results confirmed that the double mutant construct (L147D L154D) complemented poorly.

Together, the data provided evidence that the hydrophobic patch in the LysM2 domain of *M. truncatula* NFP (shown in FIG. 18G) was a conserved structural imprint critical for Nod factor perception and symbiotic signaling.

Example 8: Engineering Specific LCO Perception

The following example describes engineering of the *L. japonicus* LysM receptor LYS11 to specifically perceive Nod factors. This was done using domain swaps, by measuring ligand binding, and by measuring nodulation to assess complementation.

Materials and Methods

Expression and Purification of the Ectodomain of the *L. japonicus* LysM Receptor LYS11

The *L. japonicus* LYS11 ectodomain (residues 26-234 of SEQ ID NO: 255) was codon-optimized for insect cell expression (Genscript, Piscataway, USA) and cloned into the pOET4 baculovirus transfer vector (Oxford Expression Technologies). The native *L. japonicus* LYS11 signal peptide was replaced with the gp64 signal peptide to facilitate secretion and a hexa-histidine (6×His) tag was added to the C-terminus (*L. japonicus* LYS11-ecto (26-234), N-term gp64, C-term 6His). Recombinant baculoviruses were produced in Sf9 cells (*Spodoptera frugiperda*) using the Flash-Bac Gold kit (Oxford Expression technologies) according to the manufacturer's instructions with Lipofectin (ThermoFisher Scientific) as a transfection reagent. Protein expression was performed as follows. Suspension-cultured Sf9 cells were maintained with shaking at 299 K in serum-free MAX-XP (BD-Biosciences, discontinued) or HyClone SFX (GE Healthcare) medium supplemented with 1% Pen-Strep (10000 U/ml, Life technologies) and 1% CD lipid concentrate (Gibco). Protein expression was induced by adding recombinant passage 3 virus once the Sf9 cells reached a cell density of $1.0*10^6$ cells/ml. After 5-7 days of expression, medium supernatant containing *L. japonicus* LYS11 ectodomains was harvested by centrifugation. This was followed by an overnight dialysis step against 50 mM Tris-HCl pH 8, 200 mM NaCl at 277 K. The *L. japonicus* LYS11 ectodomain was enriched by two subsequent steps of Ni-IMAC purification (HisTrap excel/HisTrap HP, both GE Healthcare). For crystallography experiments, N-glycans were removed using the endoglycosidase PNGase F (1:15 (w/w), room temperature, overnight). As a final purification step, *L. japonicus* LYS11 ectodomain was purified by SEC on a Superdex 200 10/300 or HiLoad Superdex 200 16/600 (both GE Healthcare) in phosphate buffered saline at pH 7.2 supplemented to a total of 500 mM NaCl (for binding assays) or 50 mM Tris-HCl, 200 mM NaCl (for crystallography).

Biolayer Interferometry (BLI)

Binding of *L. japonicus* LYS11 ectodomain and domain-swapped versions of *L. japonicus* LYS11 ectodomain to ligands was measured on an Octet RED 96 system (Pall ForteBio). The ligands used were CO5 chitin oligomer (corresponding to the backbone of *S. meliloti* Nod factor LCO-V), *M. loti* Nod factor LCO, and *S. meliloti* Nod factor LCO. *S. meliloti* LCO consists of a tetrameric/pentameric N-acetylglucosamine backbone that is O-sulfated on the reducing terminal residue, O-acetylated on the non-reducing terminal residue, and mono-N-acylated by unsaturated C16 acyl groups. *M. loti* LCO is a pentameric N-acetylglucosamine with a cis-vaccenic acid and a carbamoyl group at the non-reducing terminal residue together with a 2,4-O-acetylfucose at the reducing terminal residue. Biotinylated ligand conjugates were immobilized on streptavidin biosensors (kinetic quality, Pall ForteBio) at a concentration of 125-250 nM for 5 minutes. Data analysis was performed in GraphPad Prism 6 software (GraphPad Software, Inc.). Equilibrium dissociation constants derived from the steady-state were determined by applying a non-linear regression (one site, specific binding) to the response at equilibrium plotted against the protein concentration. Kinetic parameters were determined by non-linear regression (association followed by dissociation) on the subtracted data. The tested chimeric receptors are depicted as block diagrams in FIG. 19B, with *L. japonicus* LYS11 domains shown in black and *L. japonicus* NFR5 domains shown in grey, and the block diagrams are shown again above the binding assay results in FIGS. 19C-19E.

Complementation Assay

The complementation assay was done as in Example 7. The tested chimeric receptors are depicted as block diagrams in FIG. 19F, where *L. japonicus* NFR5 domains are shown in light grey, *L. japonicus* LYS11 domains are shown in grey, and transverse lines across the block depicting the LysM2 domain indicate regions QLGDSYD (SEQ ID NO: 214) and GV (SEQ ID NO: 215) from *L. japonicus* NFR5. Empty vector and full-length *L. japonicus* LYS11 were used as negative controls (zero nodulation). Nodules were counted on hairy root transformed *L. japonicus* 0'5-2 mutant roots 35 days post inoculation with *M. loti* R7Å. *M. loti* R7A is the cognate N-fixing bacterial strain for *L. japonicus*.

Results

Figures 19C, 19D:
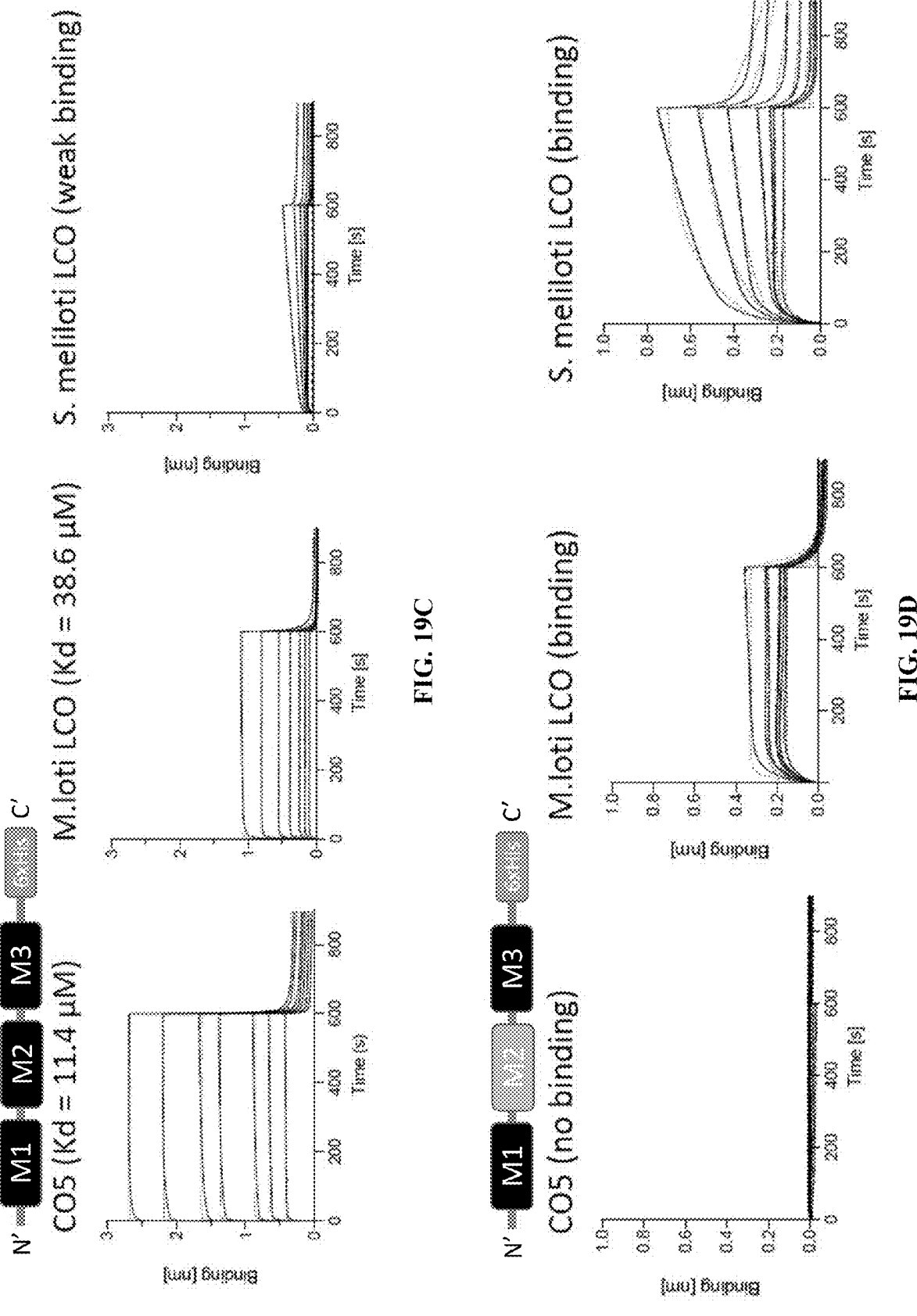

Based on modelling and crystal structure determination of *L. japonicus* LYS11 ectodomain (FIG. 19A), it was predicted that the receptor would likely be a Nod factor receptor. To experimentally validate this prediction, binding experiments were performed. As shown in FIG. 19C, *L. japonicus* LYS11 ectodomain was able to bind CO5 (left graph), *M. loti* Nod factor LCO (middle graph; *M. loti* is the cognate N-fixing bacterial strain for *L. japonicus*), and *S. meliloti* Nod factor LCO (right graph; weak binding). This result indicated that the identified hydrophobic patch in the *L. japonicus* LYS11 ectodomain allowed it to bind Nod factor. Therefore, the hydrophobic patch was predictive of Nod factor-binding ability.

Figure 19E:
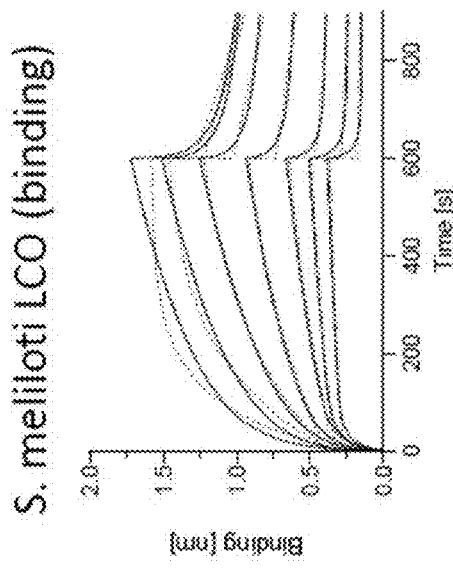
Figure 19E:
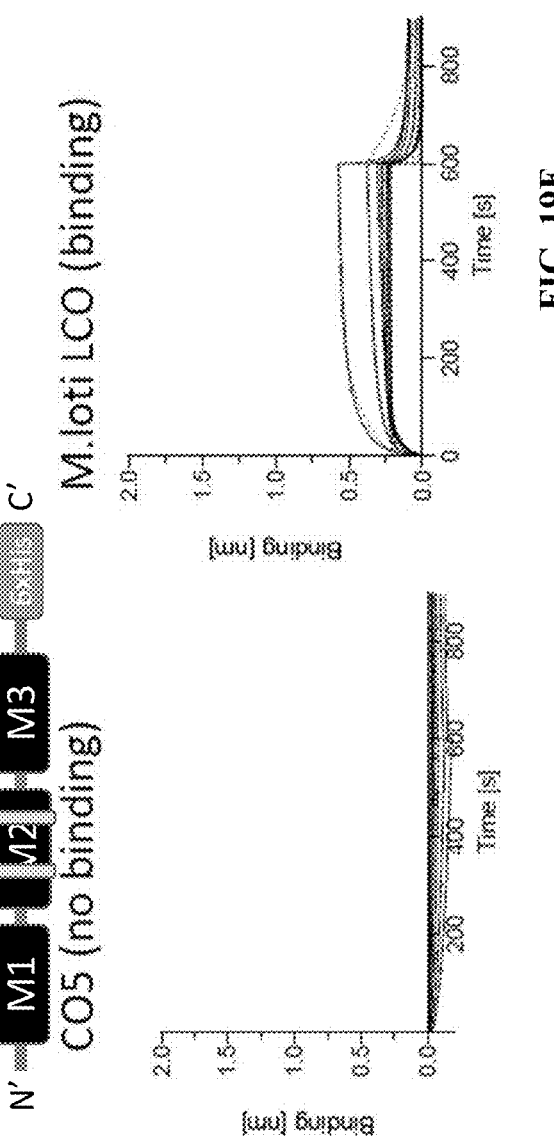

Next, it was tested whether stringent and specific Nod factor recognition could be engineered. For these tests, *L. japonicus* LYS11 ectodomains were engineered to contain parts of *L. japonicus* NFR5 receptors. Either the entire LysM2 domain or key residues from the LysM2 domain hydrophobic patch from *L. japonicus* LYS11 were replaced with the corresponding regions QLGDSYD (SEQ ID NO:

214) and GV (SEQ ID NO: 215) from *L. japonicus* NFR5, and ligand binding of these chimeric ectodomains was measured. As shown in FIG. 19D, replacing the entire LysM2 domain resulted in improved affinity to Nod factors (both *M. loti* and *S. meliloti* Nod factors), and resulted in a loss of ability to bind chitin. A similar result was seen when only key residues of the LysM2 domain were replaced (FIG. 19E).

Figure 19F:
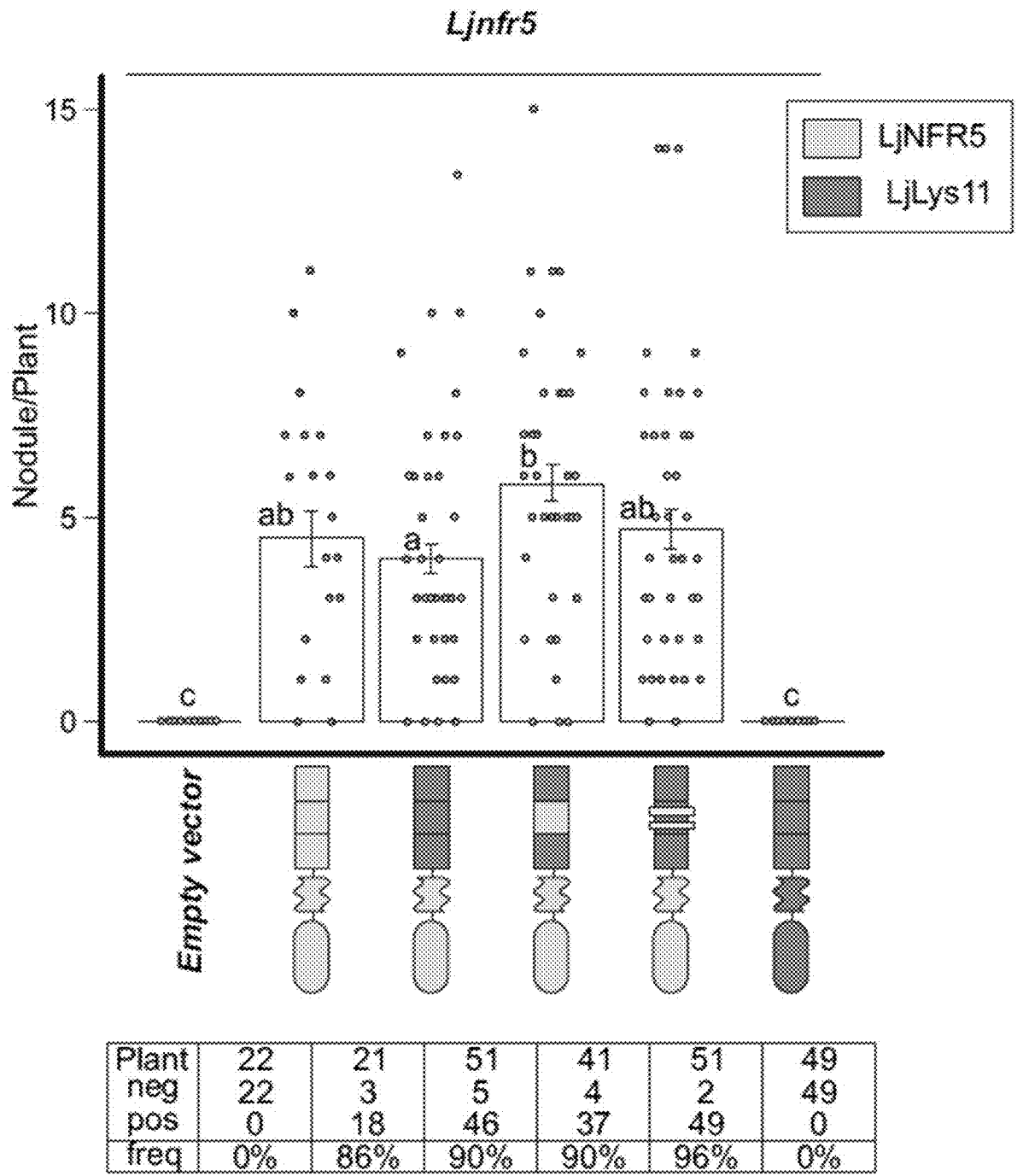

Then, chimeric receptors were tested in planta. For these tests, the same chimeric *L. japonicus* LYS11 ectodomains were used (the entire LysM2 domain, or key residues from the LysM2 domain from *L. japonicus* LYS11 were replaced with the corresponding regions from *L. japonicus* NFR5) or the entire *L. japonicus* LYS11 ectodomain (LysM1, LysM2, and LysM3 domains) was used, and these were attached to the transmembrane domain (wavy shape in schematic of FIG. 19F) and kinase domain (oval shape in schematic of FIG. 19F) of *L. japonicus* NFR5. In addition, full-length *L. japonicus* NFR5 and full-length *L. japonicus* LYS11 were tested. As shown in FIG. 19F, chimeric receptors with any one of these modifications (the receptors fourth from right, third from right, and second from right) retained their capacity to perceive the *M. loti* Nod factor and to initiate a symbiotic signaling event with similar efficiency as *L. japonicus* NFR5.

Interestingly, the chimeric *L. japonicus* LYS11/NFR5 ectodomains had different Nod factor binding kinetics with slow on/off rates that resembled the binding kinetics of *M. truncatula* NFP. As shown in FIG. 20B, slow on/off rate binding kinetics are thought to be important for functional symbiotic signaling. The fast on/off rate binding kinetics seen with hydrophobic patch mutants does not result in symbiotic signaling (FIG. 20C). Further, fast on/off kinetics also appear to be a hallmark of chitin perception (FIG. 20A). As shown in FIG. 20D, *M. truncatula* NFP shared the cysteine bridge connectivity pattern and the overall arrangement of the scaffold with other LysM receptors involved in chitin defense signaling. This result supported the hypothesis that despite their different function, these LysM receptors shared a common evolutionary origin (Zhang, X.-C. et al. *Plant Physiol.* 2007 144, 623-636). The shared structural features of the LysM receptors provided further support for the ability to engineer these receptors to have different binding kinetics. For example, the altered binding kinetics observed with the chimeric *L. japonicus* LYS11/NFR5 ectodomains indicated that LysM receptors can be engineered to have Nod factor binding kinetics characteristics of functional symbiotic signaling.

Taken together, the results seen with chimeric *L. japonicus* LYS11/NFR5 ectodomains show that engineering the LysM2 domain hydrophobic patch can create receptors with higher stringency toward Nod factors as well as higher specificity toward Nod factors.

Example 9: Exemplary Structural Alignment to Identify of Target Residues to Modify for Insertion of a Hydrophobic Patch One of skill in the art would have no difficulty applying the teachings of this disclosure to genetically alter LysM receptors to include a hydrophobic patch or alter an existing hydrophobic patch. Exemplary steps would be:
1. Align the target LysM receptor amino acid sequence with one or more known Nod factor LysM receptor sequences to identify the sequence of the LysM1-3 domains in the target amino acid sequence. Known Nod factor LysM receptor sequences include: SEQ ID NO:

223, SEQ ID NO: 249, SEQ ID NO: 250, SEQ ID NO: 251, SEQ ID NO: 254, SEQ ID NO: 257, or SEQ ID NO: 258.

Applying this step to the *H. vulgare* LysM-RLK2/37-247 (SEQ ID NO: 248) sequence produced the following amino acid sequence:

```
>HvLysM-RLK2/37-247
SVEGFNCSANGTYPCQAYALYRAGLAGVPPDLSAAGDLFGVSRFMLAHAN

NLSTSAAPAAGQPLLVPLQCGCPSGSPNAYAPTQYQISSGDTFWIVSVTK

LQNLTQYQAVERVNPTVVPTKLEVGDMVTFPIFCQCPTAAQNATALVTYV

MQQGDTYASIAAAFAVDAQSLVSLNGPEQGTQLFSEILVPLRRQVPKWLP

PIVTRNDASAT
```

2. Use the LysM1-3 domain amino acid sequence as the input sequence to be modeled in an appropriate molecular modeling program such as SWISS-MODEL (Biasini 2014). SWISS-MODEL can be readily accessed at swissmodel.expasy.org under interactive # structure.
3. Input the structural template to the molecular modelling program, for example from a structural coordinate file (e.g., a pdb format file).

The *H. vulgare* LysM-RLK2/37-247 LysM1-3 domain amino acid sequence was entered into SWISS-MODEL as was the *M. truncatula* NFP receptor ectodomain crystal structure .pdb file (the atomic coordinates are reproduced at the end of the specification). The SWISS-MODEL program was run by the command 'Build Model'. The *M. truncatula* NFP receptor ectodomain crystal structure was chosen as it has a known hydrophobic patch. One of skill in the art can readily select others based upon the teachings in this specification.

4. Optionally create an electrostatic surface potential of the target model and structurally align with a structure with chitin (or glycan) bound to the LysM2 domain to align the ligand binding grooves.

Figure 21A:
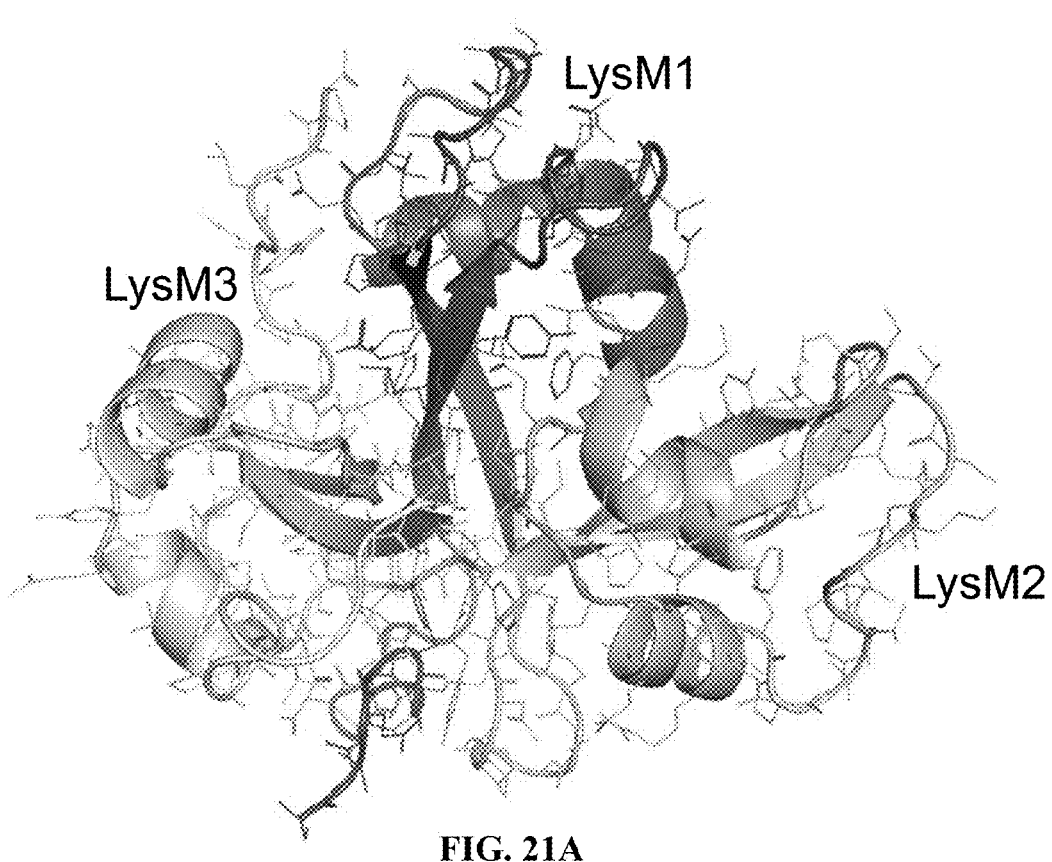
FIGS. 21A-21B show structural modelling of the *H. vulgare* LysM receptor RLK2 ectodomain (residues 37-247) containing LysM1, LysM2, and LysM3 domains.
Figure 21B:
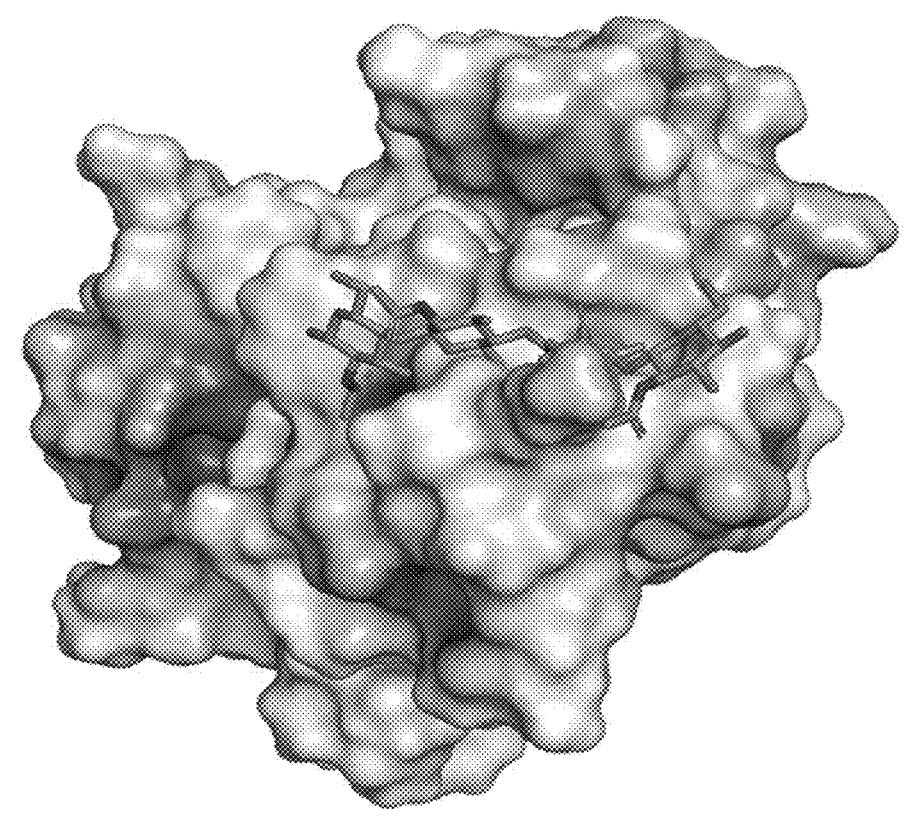

An electrostatic surface potential of the output target (.pdb) model generated with SWISS-MODEL was calculated using PDB2PQR & APBS webservers (PMID: 21425296) and visualized in PyMol using APBS tools 2.1 (DeLano, W. L. 2002). The *A. thaliana* CERK1 ectodomain structure (PDB coordinates 4EBZ) which has the chitin bound in the structure was aligned to the target model in PyMol. One of skill in the art would readily understand the position of the chitin binding domain as the LysM chitin binding motif is defined structurally in Liu et al. Science 2012 for *A. thaliana* CERK1. This aligned the chitin (C04) ligand in the LysM2 ligand binding groove of the target model. FIGS. 21A-21B show the PyMol visualization of the LysM1-3 domains of the *H. vulgare* LysM-RLK2/37-247 model with the LysM1, LysM2, and LysM3 domains labeled (FIG. 21A), and the electrostatic surface potential of the model with chitin modeled in the binding groove (FIG. 21B).

5. Select the residues from the alignment in the target model that align with the known hydrophobic patch.

From the sequence alignment (1), structural alignment of the target model with the crystal structure of *M. truncatula* NFP and the electrostatic surface potential information (5) the hydrophobic patch was identified (with the placed chitin from *A. thaliana* CERK1 as reference for locating the chitin (CO) binding groove as shown in (FIG. 21B). Hot-spot residues corresponding to the *M. truncatula* NFP ectodomain hydrophobic patch (L147, L151, L152, L154, T156, K157 and V158) were identified based on the amino acid being within 3 Å of an alpha carbon of a known hydrophobic patch amino acid residue (*M. truncatula* NFP L147, L151, L152, L154, T156, K157 and V158) in the structural alignment. As one of skill in the art would appreciate, residues like lysine (K) and arginine (R) that are not classically characterized as hydrophobic, do contain hydrophobic properties related to the Calpha, Cbeta, Cgamma, Cdelta and Cepsilon atoms that might be important for Nod factor (LCO) binding, selectivity, promiscuity, stringency, and affinity and therefore are still potentially important (e.g., K157 of the *M. truncatula* NFP hydrophobic patch). The identified residues in the *H. vulgare* LysM-RLK2/37-247 model (SEQ ID NO: 248) can be mutated, preferably with additional modeling, to obtain engineered Nod factor (LCO) binding, chitin/Nod factor (LCO/CO) selectivity, Nod factor (LCO) promiscuity, Nod factor (LCO) stringency, Nod factor (LCO) affinity. The *M. truncatula* NFP ectodomain crystal structure is disclosed in U.S. Prov. App. No. 62/718,282 and PCT App. No. PCT/EP2019/071705, published as WO 2020/035488, both of which are hereby incorporated by reference.

One of skill in the art would appreciate that similar structural modeling can be used to structurally align LysM1 domains to identify motifs in regions II, III, and IV in order to substitute and alter specificity, affinity and selectivity of a target LysM receptor for an agonist.

---

The invention claimed is:

1. A method of making a modified plant LYK3 or CERK6 LysM receptor polypeptide comprising modifying a nucleic acid encoding a wild-type plant LYK3 or CERK6 LysM receptor polypeptide to produce a modified nucleic acid that encodes the modified plant LYK3 or CERK6 LysM receptor polypeptide, wherein the wild-type plant LYK3 or CERK6 LysM receptor polypeptide comprises a region II characterized by the amino acids that align to residues 44-49 of SEQ ID NO: 164 and comprises a region IV characterized by the amino acids that align to residues 76-81 of SEQ ID NO: 164, wherein the modified plant LYK3 or CERK6 LysM receptor polypeptide comprises SEQ ID NO: 87 at region II and SEQ ID NO: 129 at region IV, and wherein the modified plant LYK3 or CERK6 LysM receptor polypeptide has altered binding kinetics for one or more Nod factors as compared to its respective wild-type plant LYK3 or CERK6 LysM receptor polypeptide.

2. The method of claim 1, wherein the Nod factor is a Nod factor produced by nitrogen-fixing bacteria and the nitrogen fixing bacteria is *Mesorhizobium* or *Sinorhizobium*.

3. The method of claim 1, wherein the modified plant LYK3 or CERK6 LysM receptor polypeptide binds one or more Nod factors with;

(a) higher selectivity and higher affinity as compared to the respective wild-type plant LYK3 or CERK6 LysM receptor polypeptide; or (b) altered specificity as compared to the respective wild-type plant LYK3 or CERK6 LysM receptor polypeptide.

4. The method of claim 1, wherein the nucleic acid is modified by site-directed mutagenesis, by chemical synthesis, by genetic editing, or by genetic engineering.

5. The method of claim 1, wherein the nucleic acid encoding the wild-type plant LYK3 or CERK6 LysM receptor polypeptide is an endogenous plant gene in a plant cell.

6. A genetically altered nodulating plant comprising the modified plant LYK3 or CERK6 LysM receptor polypeptide encoded by the modified nucleic acid produced by the method of claim 1.

7. The plant of claim 6, wherein the nodulating plant is a leguminous plant.

8. The genetically altered plant of claim 6, wherein the modified nucleic acid is a transgene.

9. The genetically altered plant of claim 6, wherein the nucleic acid encoding the wild-type plant LYK3 or CERK6 LysM receptor polypeptide is an endogenous plant LYK3 or CERK6 LysM receptor gene.

10. The plant of claim 7, wherein the leguminous plant is bean, soybean, pea, chickpea, cowpea, pigeon pea, lentil, Bambara groundnut, lupin, pulses, *Medicago* spp., Lotus spp., forage legumes, indigo, or legume trees.

* * * * *

SEQUENCE LISTING

```
<160> NUMBER OF SEQ ID NOS: 341

<210> SEQ ID NO 1
<211> LENGTH: 6
<212> TYPE: PRT
<213> ORGANISM: Vigna angularis

<400> SEQUENCE: 1

Gly Ser Asn Leu Thr Tyr
1               5

<210> SEQ ID NO 2
<211> LENGTH: 6
<212> TYPE: PRT
<213> ORGANISM: Vigna radiata

<400> SEQUENCE: 2

Gly Ser Asn Leu Thr Tyr
1               5

<210> SEQ ID NO 3
<211> LENGTH: 6
<212> TYPE: PRT
<213> ORGANISM: Vigna unguiculata

<400> SEQUENCE: 3

Gly Ser Asn Leu Thr Tyr
1               5

<210> SEQ ID NO 4
<211> LENGTH: 6
<212> TYPE: PRT
<213> ORGANISM: Phaseolus vulgaris

<400> SEQUENCE: 4

Asn Ser Asn Leu Thr Tyr
1               5

<210> SEQ ID NO 5
<211> LENGTH: 6
<212> TYPE: PRT
<213> ORGANISM: Cajanus cajan

<400> SEQUENCE: 5

Gly Ser Lys Leu Thr Tyr
1               5

<210> SEQ ID NO 6
<211> LENGTH: 6
<212> TYPE: PRT
```

```
<213> ORGANISM: Lupinus angustiiolius

<400> SEQUENCE: 6

Gly Ser Thr Leu Thr Ser
1               5

<210> SEQ ID NO 7
<211> LENGTH: 6
<212> TYPE: PRT
<213> ORGANISM: Lupinus albus

<400> SEQUENCE: 7

Gly Ser Thr Leu Thr Ser
1               5

<210> SEQ ID NO 8
<211> LENGTH: 6
<212> TYPE: PRT
<213> ORGANISM: Arachis ipaensis

<400> SEQUENCE: 8

Gly Ser Asn Leu Thr Tyr
1               5

<210> SEQ ID NO 9
<211> LENGTH: 6
<212> TYPE: PRT
<213> ORGANISM: Arachis hypogaea

<400> SEQUENCE: 9

Gly Ser Asn Leu Thr Tyr
1               5

<210> SEQ ID NO 10
<211> LENGTH: 6
<212> TYPE: PRT
<213> ORGANISM: Arachis duranensis

<400> SEQUENCE: 10

Gly Ser Asn Leu Thr Tyr
1               5

<210> SEQ ID NO 11
<211> LENGTH: 6
<212> TYPE: PRT
<213> ORGANISM: Arachis hypogaea

<400> SEQUENCE: 11

Gly Ser Asn Leu Thr Tyr
1               5

<210> SEQ ID NO 12
<211> LENGTH: 6
<212> TYPE: PRT
<213> ORGANISM: Abrus precatorius

<400> SEQUENCE: 12

Gly Ser Asn Leu Thr Tyr
1               5

<210> SEQ ID NO 13
<211> LENGTH: 6
<212> TYPE: PRT
<213> ORGANISM: Glycine max
```

```
<400> SEQUENCE: 13

Gly Ser Asn Leu Thr Tyr
1               5

<210> SEQ ID NO 14
<211> LENGTH: 6
<212> TYPE: PRT
<213> ORGANISM: Lotus japonicus

<400> SEQUENCE: 14

Gly Ser Asn Leu Thr Tyr
1               5

<210> SEQ ID NO 15
<211> LENGTH: 6
<212> TYPE: PRT
<213> ORGANISM: Chamaecrista fascimIlata

<400> SEQUENCE: 15

Gly Ser Asn Leu Thr Tyr
1               5

<210> SEQ ID NO 16
<211> LENGTH: 6
<212> TYPE: PRT
<213> ORGANISM: Mimosa pudica

<400> SEQUENCE: 16

Gly Thr Asn Leu Thr Phe
1               5

<210> SEQ ID NO 17
<211> LENGTH: 6
<212> TYPE: PRT
<213> ORGANISM: Prosopis alba

<400> SEQUENCE: 17

Gly Ser Asn Leu Thr Tyr
1               5

<210> SEQ ID NO 18
<211> LENGTH: 6
<212> TYPE: PRT
<213> ORGANISM: Cicer arietinum

<400> SEQUENCE: 18

Gly Ala Asn Leu Thr His
1               5

<210> SEQ ID NO 19
<211> LENGTH: 6
<212> TYPE: PRT
<213> ORGANISM: Pisum sativum

<400> SEQUENCE: 19

Gly Thr Asn Leu Thr Tyr
1               5

<210> SEQ ID NO 20
<211> LENGTH: 6
<212> TYPE: PRT
<213> ORGANISM: Medicago truncatula

<400> SEQUENCE: 20
```

```
Gly Ser Asn Leu Thr Tyr
1               5

<210> SEQ ID NO 21
<211> LENGTH: 6
<212> TYPE: PRT
<213> ORGANISM: Lupinus angustifolius

<400> SEQUENCE: 21

Gly Ser Asn Leu Thr Tyr
1               5

<210> SEQ ID NO 22
<211> LENGTH: 5
<212> TYPE: PRT
<213> ORGANISM: Glycine max

<400> SEQUENCE: 22

Gly Asp Leu Thr Tyr
1               5

<210> SEQ ID NO 23
<211> LENGTH: 6
<212> TYPE: PRT
<213> ORGANISM: Mimosa pudica

<400> SEQUENCE: 23

Asn Ile Thr Leu Ser Asn
1               5

<210> SEQ ID NO 24
<211> LENGTH: 5
<212> TYPE: PRT
<213> ORGANISM: Prosopis alba

<400> SEQUENCE: 24

Asn Asn Leu Gly Asn
1               5

<210> SEQ ID NO 25
<211> LENGTH: 6
<212> TYPE: PRT
<213> ORGANISM: Spatholobus suberectus

<400> SEQUENCE: 25

Gly Thr Asn Leu Thr Tyr
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Asn
<220> FEATURE:
<221> NAME/KEY: VARIANT
<222> LOCATION: 2
<223> OTHER INFORMATION: Xaa = Ser, Thr, Ala, or Ile
<220> FEATURE:
<221> NAME/KEY: VARIANT
<222> LOCATION: 3
<223> OTHER INFORMATION: Xaa = Asn, Lys, Thr, or Asp
<220> FEATURE:
<221> NAME/KEY: VARIANT
```

```
<222> LOCATION: 5
<223> OTHER INFORMATION: Xaa = Thr, Ser, or Gly
<220> FEATURE:
<221> NAME/KEY: VARIANT
<222> LOCATION: 6
<223> OTHER INFORMATION: Xaa = Tyr, Ser, Phe, His, or Asn

<400> SEQUENCE: 26

Xaa Xaa Xaa Leu Xaa Xaa
1               5

<210> SEQ ID NO 27
<211> LENGTH: 6
<212> TYPE: PRT
<213> ORGANISM: Vigna angularis

<400> SEQUENCE: 27

Lys Asp Ser Val Gln Ala
1               5

<210> SEQ ID NO 28
<211> LENGTH: 6
<212> TYPE: PRT
<213> ORGANISM: Vigna radiata

<400> SEQUENCE: 28

Lys Asp Ser Val Gln Ala
1               5

<210> SEQ ID NO 29
<211> LENGTH: 6
<212> TYPE: PRT
<213> ORGANISM: Vigna unguiculata

<400> SEQUENCE: 29

Lys Asp Ser Val Gln Ala
1               5

<210> SEQ ID NO 30
<211> LENGTH: 6
<212> TYPE: PRT
<213> ORGANISM: Phaseolus vulgaris

<400> SEQUENCE: 30

Lys Asp Ser Val Gln Ala
1               5

<210> SEQ ID NO 31
<211> LENGTH: 6
<212> TYPE: PRT
<213> ORGANISM: Cajanus cajan

<400> SEQUENCE: 31

Lys Asp Ser Val Gln Ala
1               5

<210> SEQ ID NO 32
<211> LENGTH: 6
<212> TYPE: PRT
<213> ORGANISM: Lupinus angustiiolius

<400> SEQUENCE: 32

Lys Asp Ser Val Gln Ala
1               5
```

```
<210> SEQ ID NO 33
<211> LENGTH: 6
<212> TYPE: PRT
<213> ORGANISM: Lupinus albus

<400> SEQUENCE: 33

Lys Asp Ser Val Gln Ala
1               5

<210> SEQ ID NO 34
<211> LENGTH: 6
<212> TYPE: PRT
<213> ORGANISM: Arachis ipaensis

<400> SEQUENCE: 34

Lys Asp Ser Val Gln Ala
1               5

<210> SEQ ID NO 35
<211> LENGTH: 6
<212> TYPE: PRT
<213> ORGANISM: Arachis hypogaea

<400> SEQUENCE: 35

Lys Asp Ser Val Gln Ala
1               5

<210> SEQ ID NO 36
<211> LENGTH: 6
<212> TYPE: PRT
<213> ORGANISM: Arachis duranensis

<400> SEQUENCE: 36

Lys Asp Ser Val Gln Ala
1               5

<210> SEQ ID NO 37
<211> LENGTH: 6
<212> TYPE: PRT
<213> ORGANISM: Arachis hypogaea

<400> SEQUENCE: 37

Lys Asp Ser Val Gln Ala
1               5

<210> SEQ ID NO 38
<211> LENGTH: 6
<212> TYPE: PRT
<213> ORGANISM: Abrus precatorius

<400> SEQUENCE: 38

Lys Asp Ser Ile Gln Ala
1               5

<210> SEQ ID NO 39
<211> LENGTH: 6
<212> TYPE: PRT
<213> ORGANISM: Glycine max

<400> SEQUENCE: 39

Lys Asp Ile Ile Ile Ala
1               5

<210> SEQ ID NO 40
<211> LENGTH: 6
```

-continued

```
<212> TYPE: PRT
<213> ORGANISM: Lotus japonicus

<400> SEQUENCE: 40

Lys Asp Ser Val Gln Ala
1               5

<210> SEQ ID NO 41
<211> LENGTH: 6
<212> TYPE: PRT
<213> ORGANISM: Chamaecrista fascimIlata

<400> SEQUENCE: 41

Lys Asp Ser Val Pro Ser
1               5

<210> SEQ ID NO 42
<211> LENGTH: 6
<212> TYPE: PRT
<213> ORGANISM: Mimosa pudica

<400> SEQUENCE: 42

Lys Asp Ser Leu Ser Ala
1               5

<210> SEQ ID NO 43
<211> LENGTH: 6
<212> TYPE: PRT
<213> ORGANISM: Prosopis alba

<400> SEQUENCE: 43

Lys Asp Ser Val Pro Ala
1               5

<210> SEQ ID NO 44
<211> LENGTH: 6
<212> TYPE: PRT
<213> ORGANISM: Cicer arietinum

<400> SEQUENCE: 44

Lys Asp Thr Ile Ile Ala
1               5

<210> SEQ ID NO 45
<211> LENGTH: 6
<212> TYPE: PRT
<213> ORGANISM: Pisum sativum

<400> SEQUENCE: 45

Lys Asp Ile Ile Leu Gly
1               5

<210> SEQ ID NO 46
<211> LENGTH: 6
<212> TYPE: PRT
<213> ORGANISM: Medicago truncatula

<400> SEQUENCE: 46

Lys Asp Ser Val Gln Ala
1               5

<210> SEQ ID NO 47
<211> LENGTH: 6
<212> TYPE: PRT
<213> ORGANISM: Lupinus angustifolius
```

```
<400> SEQUENCE: 47

Lys Asp Lys Val Gln Pro
1               5

<210> SEQ ID NO 48
<211> LENGTH: 6
<212> TYPE: PRT
<213> ORGANISM: Glycine max

<400> SEQUENCE: 48

Lys Asp Leu Leu Pro Ala
1               5

<210> SEQ ID NO 49
<211> LENGTH: 4
<212> TYPE: PRT
<213> ORGANISM: Mimosa pudica

<400> SEQUENCE: 49

Asn Ile Gln Phe
1

<210> SEQ ID NO 50
<211> LENGTH: 7
<212> TYPE: PRT
<213> ORGANISM: Prosopis alba

<400> SEQUENCE: 50

Asn Gly Met Tyr Val Gln Ser
1               5

<210> SEQ ID NO 51
<211> LENGTH: 6
<212> TYPE: PRT
<213> ORGANISM: Spatholobus suberectus

<400> SEQUENCE: 51

Pro Asp Val Ile Gln Ser
1               5

<210> SEQ ID NO 52
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Lys, Asn, or Pro
<220> FEATURE:
<221> NAME/KEY: VARIANT
<222> LOCATION: 2
<223> OTHER INFORMATION: Xaa = Asp, Gly, or none
<220> FEATURE:
<221> NAME/KEY: VARIANT
<222> LOCATION: 3
<223> OTHER INFORMATION: Xaa = Met or none
<220> FEATURE:
<221> NAME/KEY: VARIANT
<222> LOCATION: 4
<223> OTHER INFORMATION: Xaa = Ser, Ile, Thr, Lys, Leu, Asn, Tyr, or Val
<220> FEATURE:
<221> NAME/KEY: VARIANT
<222> LOCATION: 5
<223> OTHER INFORMATION: Xaa = Val, Ile, or Leu
<220> FEATURE:
<221> NAME/KEY: VARIANT
```

```
<222> LOCATION: 6
<223> OTHER INFORMATION: Xaa = Gln, Ile, Pro, Ser, or Leu
<220> FEATURE:
<221> NAME/KEY: VARIANT
<222> LOCATION: 7
<223> OTHER INFORMATION: Xaa = Ala, Ser, Gly, Pro, or Phe

<400> SEQUENCE: 52

Xaa Xaa Xaa Xaa Xaa Xaa Xaa
1               5

<210> SEQ ID NO 53
<211> LENGTH: 6
<212> TYPE: PRT
<213> ORGANISM: Solanum lycopersicum

<400> SEQUENCE: 53

Gly Ser Asn Leu Thr Leu
1               5

<210> SEQ ID NO 54
<211> LENGTH: 6
<212> TYPE: PRT
<213> ORGANISM: Prunus persica

<400> SEQUENCE: 54

Gly Ser Asn Leu Thr Leu
1               5

<210> SEQ ID NO 55
<211> LENGTH: 6
<212> TYPE: PRT
<213> ORGANISM: Artificial Sequence
<220> FEATURE:
<223> OTHER INFORMATION: Synthetic Construct

<400> SEQUENCE: 55

Gly Ser Asn Leu Thr Leu
1               5

<210> SEQ ID NO 56
<211> LENGTH: 6
<212> TYPE: PRT
<213> ORGANISM: Solanum lycopersicum

<400> SEQUENCE: 56

Gln Asp Ser Val Ile Ala
1               5

<210> SEQ ID NO 57
<211> LENGTH: 6
<212> TYPE: PRT
<213> ORGANISM: Prunus persica

<400> SEQUENCE: 57

Lys Asp Ser Val Leu Ala
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
```

-continued

```
<223> OTHER INFORMATION: Xaa = Gln or Lys
<220> FEATURE:
<221> NAME/KEY: VARIANT
<222> LOCATION: 5
<223> OTHER INFORMATION: Xaa = Ile or Leu

<400> SEQUENCE: 58

Xaa Asp Ser Val Xaa Ala
1               5

<210> SEQ ID NO 59
<211> LENGTH: 6
<212> TYPE: PRT
<213> ORGANISM: Arabidopsis thaliana

<400> SEQUENCE: 59

Gly Thr Thr Leu Ser Val
1               5

<210> SEQ ID NO 60
<211> LENGTH: 6
<212> TYPE: PRT
<213> ORGANISM: Hordeum vulgare

<400> SEQUENCE: 60

Asn Val Asn Val Ser Tyr
1               5

<210> SEQ ID NO 61
<211> LENGTH: 6
<212> TYPE: PRT
<213> ORGANISM: Hordeum vulgare

<400> SEQUENCE: 61

Asp Thr Asn Leu Thr Phe
1               5

<210> SEQ ID NO 62
<211> LENGTH: 6
<212> TYPE: PRT
<213> ORGANISM: Hordeum vulgare

<400> SEQUENCE: 62

Asn Gln Asn Val Thr Tyr
1               5

<210> SEQ ID NO 63
<211> LENGTH: 6
<212> TYPE: PRT
<213> ORGANISM: Zea mays

<400> SEQUENCE: 63

Asn Gln Asn Leu Thr Tyr
1               5

<210> SEQ ID NO 64
<211> LENGTH: 6
<212> TYPE: PRT
<213> ORGANISM: Zea mays

<400> SEQUENCE: 64

Glu Ser Asn Leu Ser Phe
1               5

<210> SEQ ID NO 65
```

```
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asn, Asp, or Glu
<220> FEATURE:
<221> NAME/KEY: VARIANT
<222> LOCATION: 2
<223> OTHER INFORMATION: Xaa = Val, Thr, Gln, or Ser
<220> FEATURE:
<221> NAME/KEY: VARIANT
<222> LOCATION: 4
<223> OTHER INFORMATION: Xaa = Val or Leu
<220> FEATURE:
<221> NAME/KEY: VARIANT
<222> LOCATION: 5
<223> OTHER INFORMATION: Xaa = Ser or Thr
<220> FEATURE:
<221> NAME/KEY: VARIANT
<222> LOCATION: 6
<223> OTHER INFORMATION: Xaa = Tyr or Phe

<400> SEQUENCE: 65

Xaa Xaa Asn Xaa Xaa Xaa
1               5

<210> SEQ ID NO 66
<211> LENGTH: 5
<212> TYPE: PRT
<213> ORGANISM: Marchantia paleacea

<400> SEQUENCE: 66

Asp Asp Thr Leu Leu
1               5

<210> SEQ ID NO 67
<211> LENGTH: 5
<212> TYPE: PRT
<213> ORGANISM: Marchantia polymorpha

<400> SEQUENCE: 67

Asp Asp Thr Leu Leu
1               5

<210> SEQ ID NO 68
<211> LENGTH: 5
<212> TYPE: PRT
<213> ORGANISM: Artificial Sequence
<220> FEATURE:
<223> OTHER INFORMATION: Synthetic Construct

<400> SEQUENCE: 68

Asp Asp Thr Leu Leu
1               5

<210> SEQ ID NO 69
<211> LENGTH: 6
<212> TYPE: PRT
<213> ORGANISM: Arabidopsis thaliana

<400> SEQUENCE: 69

Lys Asp Arg Ile Gln Met
1               5

<210> SEQ ID NO 70
```

```
<211> LENGTH: 6
<212> TYPE: PRT
<213> ORGANISM: Hordeum vulgare

<400> SEQUENCE: 70

Leu Asp Tyr Val Ala Ala
1               5

<210> SEQ ID NO 71
<211> LENGTH: 6
<212> TYPE: PRT
<213> ORGANISM: Hordeum vulgare

<400> SEQUENCE: 71

Leu Asp Asn Ala Ala Ala
1               5

<210> SEQ ID NO 72
<211> LENGTH: 6
<212> TYPE: PRT
<213> ORGANISM: Hordeum vulgare

<400> SEQUENCE: 72

Leu Asp Tyr Val Val Ala
1               5

<210> SEQ ID NO 73
<211> LENGTH: 6
<212> TYPE: PRT
<213> ORGANISM: Zea mays

<400> SEQUENCE: 73

Leu Asp Tyr Ile Gln Ala
1               5

<210> SEQ ID NO 74
<211> LENGTH: 6
<212> TYPE: PRT
<213> ORGANISM: Zea mays

<400> SEQUENCE: 74

Pro Asn Tyr Ile Val Thr
1               5

<210> SEQ ID NO 75
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu or Pro
<220> FEATURE:
<221> NAME/KEY: VARIANT
<222> LOCATION: 2
<223> OTHER INFORMATION: Xaa = Asp or Asn
<220> FEATURE:
<221> NAME/KEY: VARIANT
<222> LOCATION: 3
<223> OTHER INFORMATION: Xaa = Tyr or Asn
<220> FEATURE:
<221> NAME/KEY: VARIANT
<222> LOCATION: 4
<223> OTHER INFORMATION: Xaa = Val, Ala, or Ile
<220> FEATURE:
<221> NAME/KEY: VARIANT
<222> LOCATION: 5
```

-continued

```
<223> OTHER INFORMATION: Xaa = Ala, Val, or Gln
<220> FEATURE:
<221> NAME/KEY: VARIANT
<222> LOCATION: 6
<223> OTHER INFORMATION: Xaa = Ala or Thr

<400> SEQUENCE: 75

Xaa Xaa Xaa Xaa Xaa Xaa
1               5

<210> SEQ ID NO 76
<211> LENGTH: 6
<212> TYPE: PRT
<213> ORGANISM: Marchantia paleacea

<400> SEQUENCE: 76

Pro Asp Ser Val Glu Ala
1               5

<210> SEQ ID NO 77
<211> LENGTH: 6
<212> TYPE: PRT
<213> ORGANISM: Marchantia polymorpha

<400> SEQUENCE: 77

Pro Asp Ser Val Glu Ala
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Construct

<400> SEQUENCE: 78

Pro Asp Ser Val Glu Ala
1               5

<210> SEQ ID NO 79
<211> LENGTH: 6
<212> TYPE: PRT
<213> ORGANISM: Vigna angularis

<400> SEQUENCE: 79

Gly Leu Thr Leu Asp Asp
1               5

<210> SEQ ID NO 80
<211> LENGTH: 6
<212> TYPE: PRT
<213> ORGANISM: Vigna radiata

<400> SEQUENCE: 80

Gly Leu Ser Leu Asp Asn
1               5

<210> SEQ ID NO 81
<211> LENGTH: 6
<212> TYPE: PRT
<213> ORGANISM: Vigna unguiculata

<400> SEQUENCE: 81

Gly Met Ser Leu Asp Val
1               5
```

-continued

<210> SEQ ID NO 82
<211> LENGTH: 7
<212> TYPE: PRT
<213> ORGANISM: Phaseolus vulgaris

<400> SEQUENCE: 82

Gly Ile Ser Thr Leu Asp Asp
1               5

<210> SEQ ID NO 83
<211> LENGTH: 7
<212> TYPE: PRT
<213> ORGANISM: Glycine max

<400> SEQUENCE: 83

Gly Tyr Leu Leu Leu Glu Asn
1               5

<210> SEQ ID NO 84
<211> LENGTH: 7
<212> TYPE: PRT
<213> ORGANISM: Spatholobus suberectus

<400> SEQUENCE: 84

Gly Tyr Phe Pro Leu Glu Asn
1               5

<210> SEQ ID NO 85
<211> LENGTH: 7
<212> TYPE: PRT
<213> ORGANISM: Abrus precatorius

<400> SEQUENCE: 85

Lys Phe Leu Ser Leu Asp Asn
1               5

<210> SEQ ID NO 86
<211> LENGTH: 7
<212> TYPE: PRT
<213> ORGANISM: Cajanus cajan

<400> SEQUENCE: 86

Gly Tyr Leu Thr Val Glu Asn
1               5

<210> SEQ ID NO 87
<211> LENGTH: 7
<212> TYPE: PRT
<213> ORGANISM: Lotus japonicus

<400> SEQUENCE: 87

Gly Val Phe Ile Leu Gln Asn
1               5

<210> SEQ ID NO 88
<211> LENGTH: 6
<212> TYPE: PRT
<213> ORGANISM: Glycine max

<400> SEQUENCE: 88

Asp Leu Ser Leu Glu Asn
1               5

<210> SEQ ID NO 89

```
<211> LENGTH: 6
<212> TYPE: PRT
<213> ORGANISM: Arachis hypogaea

<400> SEQUENCE: 89

Lys Val Met Leu Gly Ser
1               5

<210> SEQ ID NO 90
<211> LENGTH: 6
<212> TYPE: PRT
<213> ORGANISM: Arachis ipaensis

<400> SEQUENCE: 90

Lys Val Met Leu Gly Ser
1               5

<210> SEQ ID NO 91
<211> LENGTH: 6
<212> TYPE: PRT
<213> ORGANISM: Arachis duranensis

<400> SEQUENCE: 91

Gly Val Met Leu Gly Ser
1               5

<210> SEQ ID NO 92
<211> LENGTH: 6
<212> TYPE: PRT
<213> ORGANISM: Arachis hypogaea

<400> SEQUENCE: 92

Arg Val Lys Leu Gly Ser
1               5

<210> SEQ ID NO 93
<211> LENGTH: 6
<212> TYPE: PRT
<213> ORGANISM: Lupinus angustifolius

<400> SEQUENCE: 93

Ile Val Ser Leu Gly Asn
1               5

<210> SEQ ID NO 94
<211> LENGTH: 6
<212> TYPE: PRT
<213> ORGANISM: Lupinus albus

<400> SEQUENCE: 94

Thr Val Ser Leu Gly Asn
1               5

<210> SEQ ID NO 95
<211> LENGTH: 6
<212> TYPE: PRT
<213> ORGANISM: Lupinus angustifolius

<400> SEQUENCE: 95

Ser Ile Ser Leu Gly Asn
1               5

<210> SEQ ID NO 96
<211> LENGTH: 6
<212> TYPE: PRT
```

```
<213> ORGANISM: Medicago truncatula

<400> SEQUENCE: 96

Ser Ile Gln Leu Arg Asn
1               5

<210> SEQ ID NO 97
<211> LENGTH: 6
<212> TYPE: PRT
<213> ORGANISM: Pisum sativum

<400> SEQUENCE: 97

Leu Val Glu Leu Leu Asn
1               5

<210> SEQ ID NO 98
<211> LENGTH: 6
<212> TYPE: PRT
<213> ORGANISM: Cicer arietinum

<400> SEQUENCE: 98

Pro Phe Glu Phe Thr Asn
1               5

<210> SEQ ID NO 99
<211> LENGTH: 6
<212> TYPE: PRT
<213> ORGANISM: Chamaecrista fasciculata

<400> SEQUENCE: 99

Phe Phe Thr Leu Gln Asn
1               5

<210> SEQ ID NO 100
<211> LENGTH: 10
<212> TYPE: PRT
<213> ORGANISM: Vigna angularis

<400> SEQUENCE: 100

Ser Val Val Ser Asn Ser Asp Asp Ile Ile
1               5                   10

<210> SEQ ID NO 101
<211> LENGTH: 10
<212> TYPE: PRT
<213> ORGANISM: Vigna radiata

<400> SEQUENCE: 101

Ser Val Val Ser Asn Ser Asp Asp Ile Ile
1               5                   10

<210> SEQ ID NO 102
<211> LENGTH: 10
<212> TYPE: PRT
<213> ORGANISM: Vigna unguiculata

<400> SEQUENCE: 102

Ser Val Val Ser Asn Ser Asp Asp Ile Ile
1               5                   10

<210> SEQ ID NO 103
<211> LENGTH: 10
<212> TYPE: PRT
<213> ORGANISM: Phaseolus vulgaris
```

```
<400> SEQUENCE: 103

Ser Val Val Ser Asn Ser Asp Asp Ile Val
1               5                   10

<210> SEQ ID NO 104
<211> LENGTH: 10
<212> TYPE: PRT
<213> ORGANISM: Glycine max

<400> SEQUENCE: 104

Ile Val Leu Ser Asn Ser Asp Val Ile Ile
1               5                   10

<210> SEQ ID NO 105
<211> LENGTH: 10
<212> TYPE: PRT
<213> ORGANISM: Spatholobus suberectus

<400> SEQUENCE: 105

Ser Val Leu Ser Asn Ser Asp Val Val Thr
1               5                   10

<210> SEQ ID NO 106
<211> LENGTH: 10
<212> TYPE: PRT
<213> ORGANISM: Abrus precatorius

<400> SEQUENCE: 106

Lys Ile Leu Ser Thr Ser Asp Val Ile Arg
1               5                   10

<210> SEQ ID NO 107
<211> LENGTH: 10
<212> TYPE: PRT
<213> ORGANISM: Cajanus cajan

<400> SEQUENCE: 107

Ser Val Leu Ser Asn Ser Asp Val Ile Lys
1               5                   10

<210> SEQ ID NO 108
<211> LENGTH: 10
<212> TYPE: PRT
<213> ORGANISM: Lotus japonicus

<400> SEQUENCE: 108

Glu Ile Val Ser Ser Asn Asp Ala Ile Thr
1               5                   10

<210> SEQ ID NO 109
<211> LENGTH: 6
<212> TYPE: PRT
<213> ORGANISM: Glycine max

<400> SEQUENCE: 109

Ser Ile Glu Val Ile Ile
1               5

<210> SEQ ID NO 110
<211> LENGTH: 10
<212> TYPE: PRT
<213> ORGANISM: Arachis hypogaea

<400> SEQUENCE: 110
```

```
Asn Val Val Pro Asn Ser Asn Val Ile Ile
1               5                   10

<210> SEQ ID NO 111
<211> LENGTH: 10
<212> TYPE: PRT
<213> ORGANISM: Arachis ipaensis

<400> SEQUENCE: 111

Asn Val Val Pro Asn Ser Asn Val Ile Ile
1               5                   10

<210> SEQ ID NO 112
<211> LENGTH: 10
<212> TYPE: PRT
<213> ORGANISM: Arachis duranensis

<400> SEQUENCE: 112

Asn Val Val Pro Asn Ser Asn Val Ile Ile
1               5                   10

<210> SEQ ID NO 113
<211> LENGTH: 10
<212> TYPE: PRT
<213> ORGANISM: Arachis hypogaea

<400> SEQUENCE: 113

Asn Val Val Pro Asn Ser Asn Val Ile Ile
1               5                   10

<210> SEQ ID NO 114
<211> LENGTH: 10
<212> TYPE: PRT
<213> ORGANISM: Lupinus angustifolius

<400> SEQUENCE: 114

Asn Val Leu Thr Asn Pro Asn Val Val Thr
1               5                   10

<210> SEQ ID NO 115
<211> LENGTH: 10
<212> TYPE: PRT
<213> ORGANISM: Lupinus albus

<400> SEQUENCE: 115

Asn Val Leu Thr Lys Ser Asn Val Ile Ile
1               5                   10

<210> SEQ ID NO 116
<211> LENGTH: 10
<212> TYPE: PRT
<213> ORGANISM: Lupinus angustifolius

<400> SEQUENCE: 116

Asn Val Leu Thr Asn Ser Asp Val Ile Ile
1               5                   10

<210> SEQ ID NO 117
<211> LENGTH: 12
<212> TYPE: PRT
<213> ORGANISM: Medicago truncatula

<400> SEQUENCE: 117

Lys Ile Val Leu Thr Asn Ser Phe Asp Val Ile Met
1               5                   10
```

-continued

```
<210> SEQ ID NO 118
<211> LENGTH: 11
<212> TYPE: PRT
<213> ORGANISM: Pisum sativum

<400> SEQUENCE: 118

Lys Leu Val Thr Asn Ser Ser Glu Val Ile Val
1               5                   10

<210> SEQ ID NO 119
<211> LENGTH: 6
<212> TYPE: PRT
<213> ORGANISM: Cicer arietinum

<400> SEQUENCE: 119

Asn Ser Asp Ile Ile Ile
1               5

<210> SEQ ID NO 120
<211> LENGTH: 10
<212> TYPE: PRT
<213> ORGANISM: Chamaecrista fasciculata

<400> SEQUENCE: 120

Lys Val Leu Ser Asp Tyr Gln Val Ile Ala
1               5                   10

<210> SEQ ID NO 121
<211> LENGTH: 5
<212> TYPE: PRT
<213> ORGANISM: Vigna angularis

<400> SEQUENCE: 121

Lys Asn Ile Phe Leu
1               5

<210> SEQ ID NO 122
<211> LENGTH: 5
<212> TYPE: PRT
<213> ORGANISM: Vigna radiata

<400> SEQUENCE: 122

Lys Asn Val Phe Met
1               5

<210> SEQ ID NO 123
<211> LENGTH: 5
<212> TYPE: PRT
<213> ORGANISM: Vigna unguiculata

<400> SEQUENCE: 123

Lys Asn Val Phe Tyr
1               5

<210> SEQ ID NO 124
<211> LENGTH: 5
<212> TYPE: PRT
<213> ORGANISM: Phaseolus vulgaris

<400> SEQUENCE: 124

Lys Asn Val Leu Phe
1               5
```

-continued

```
<210> SEQ ID NO 125
<211> LENGTH: 5
<212> TYPE: PRT
<213> ORGANISM: Glycine max

<400> SEQUENCE: 125

Glu Asn Val Leu Ala
1               5

<210> SEQ ID NO 126
<211> LENGTH: 5
<212> TYPE: PRT
<213> ORGANISM: Spatholobus suberectus

<400> SEQUENCE: 126

Asp Met Val Gln Ser
1               5

<210> SEQ ID NO 127
<211> LENGTH: 5
<212> TYPE: PRT
<213> ORGANISM: Abrus precatorius

<400> SEQUENCE: 127

Asp Asn Val Pro Ser
1               5

<210> SEQ ID NO 128
<211> LENGTH: 5
<212> TYPE: PRT
<213> ORGANISM: Cajanus cajan

<400> SEQUENCE: 128

Asp Asn Leu Pro Ser
1               5

<210> SEQ ID NO 129
<211> LENGTH: 6
<212> TYPE: PRT
<213> ORGANISM: Lotus japonicus

<400> SEQUENCE: 129

Asp Ile Asn Ile Gln Ser
1               5

<210> SEQ ID NO 130
<211> LENGTH: 5
<212> TYPE: PRT
<213> ORGANISM: Glycine max

<400> SEQUENCE: 130

Gly Tyr Pro Leu Ser
1               5

<210> SEQ ID NO 131
<211> LENGTH: 5
<212> TYPE: PRT
<213> ORGANISM: Arachis hypogaea

<400> SEQUENCE: 131

Asn Leu Pro Val Ser
1               5

<210> SEQ ID NO 132
<211> LENGTH: 5
```

```
<212> TYPE: PRT
<213> ORGANISM: Arachis ipaensis

<400> SEQUENCE: 132

Asn Leu Pro Val Ser
1               5

<210> SEQ ID NO 133
<211> LENGTH: 5
<212> TYPE: PRT
<213> ORGANISM: Arachis duranensis

<400> SEQUENCE: 133

Asn Leu Pro Val Ser
1               5

<210> SEQ ID NO 134
<211> LENGTH: 5
<212> TYPE: PRT
<213> ORGANISM: Arachis hypogaea

<400> SEQUENCE: 134

Asn Leu Pro Val Ser
1               5

<210> SEQ ID NO 135
<211> LENGTH: 6
<212> TYPE: PRT
<213> ORGANISM: Lupinus angustifolius

<400> SEQUENCE: 135

Gly Asp Val Met Leu Ala
1               5

<210> SEQ ID NO 136
<211> LENGTH: 6
<212> TYPE: PRT
<213> ORGANISM: Lupinus albus

<400> SEQUENCE: 136

Gly Asp Val Met Leu Ala
1               5

<210> SEQ ID NO 137
<211> LENGTH: 6
<212> TYPE: PRT
<213> ORGANISM: Lupinus angustifolius

<400> SEQUENCE: 137

Gly Asp Val Leu Leu Ser
1               5

<210> SEQ ID NO 138
<211> LENGTH: 6
<212> TYPE: PRT
<213> ORGANISM: Medicago truncatula

<400> SEQUENCE: 138

Lys Ser Gly Leu Ile Ser
1               5

<210> SEQ ID NO 139
<211> LENGTH: 6
<212> TYPE: PRT
<213> ORGANISM: Pisum sativum
```

```
<400> SEQUENCE: 139

Asn Asp Asn Leu Phe Ser
1               5

<210> SEQ ID NO 140
<211> LENGTH: 6
<212> TYPE: PRT
<213> ORGANISM: Cicer arietinum

<400> SEQUENCE: 140

Asn Gly Lys Leu Phe Ser
1               5

<210> SEQ ID NO 141
<211> LENGTH: 6
<212> TYPE: PRT
<213> ORGANISM: Chamaecrista fasciculata

<400> SEQUENCE: 141

Gly Val Asn Ile Lys Ser
1               5

<210> SEQ ID NO 142
<211> LENGTH: 7
<212> TYPE: PRT
<213> ORGANISM: Hordeum vulgare

<400> SEQUENCE: 142

Asn Asn Leu Asp Tyr Val Val
1               5

<210> SEQ ID NO 143
<211> LENGTH: 6
<212> TYPE: PRT
<213> ORGANISM: Hordeum vulgare

<400> SEQUENCE: 143

Thr Pro Asn Val Asn Val
1               5

<210> SEQ ID NO 144
<211> LENGTH: 8
<212> TYPE: PRT
<213> ORGANISM: Lotus japonicus

<400> SEQUENCE: 144

Asn Cys Leu Lys Gly Cys Asp Leu
1               5

<210> SEQ ID NO 145
<211> LENGTH: 12
<212> TYPE: PRT
<213> ORGANISM: Lotus japonicus

<400> SEQUENCE: 145

Pro Gly Val Phe Ile Leu Gln Asn Ile Thr Thr Phe
1               5                   10

<210> SEQ ID NO 146

<400> SEQUENCE: 146

000
```

-continued

```
<210> SEQ ID NO 147
<211> LENGTH: 9
<212> TYPE: PRT
<213> ORGANISM: Lotus japonicus

<400> SEQUENCE: 147

Leu Asn Asp Ile Asn Ile Gln Ser Phe
1               5

<210> SEQ ID NO 148
<211> LENGTH: 7
<212> TYPE: PRT
<213> ORGANISM: Lotus japonicus

<400> SEQUENCE: 148

Lys Cys Thr His Gly Cys Ala
1               5

<210> SEQ ID NO 149
<211> LENGTH: 11
<212> TYPE: PRT
<213> ORGANISM: Lotus japonicus

<400> SEQUENCE: 149

Asn Gly Ser Asn Leu Thr Tyr Ile Ser Glu Ile
1               5                   10

<210> SEQ ID NO 150
<211> LENGTH: 10
<212> TYPE: PRT
<213> ORGANISM: Lotus japonicus

<400> SEQUENCE: 150

Ser Leu Leu Thr Lys Pro Glu Asp Ile Val
1               5                   10

<210> SEQ ID NO 151
<211> LENGTH: 9
<212> TYPE: PRT
<213> ORGANISM: Lotus japonicus

<400> SEQUENCE: 151

Ala Ser Lys Asp Ser Val Gln Ala Gly
1               5

<210> SEQ ID NO 152
<211> LENGTH: 11
<212> TYPE: PRT
<213> ORGANISM: Medicago truncatula

<400> SEQUENCE: 152

Pro Ser Ile Gln Leu Arg Asn Ile Ser Asn Phe
1               5                   10

<210> SEQ ID NO 153
<211> LENGTH: 11
<212> TYPE: PRT
<213> ORGANISM: Medicago truncatula

<400> SEQUENCE: 153

Lys Ile Val Leu Thr Asn Ser Phe Asp Val Ile
1               5                   10

<210> SEQ ID NO 154
```

<211> LENGTH: 9
<212> TYPE: PRT
<213> ORGANISM: Medicago truncatula

<400> SEQUENCE: 154

Phe Asp Lys Ser Gly Leu Ile Ser Tyr
1               5

<210> SEQ ID NO 155
<211> LENGTH: 38
<212> TYPE: PRT
<213> ORGANISM: Artificial Sequence
<220> FEATURE:
<223> OTHER INFORMATION: Synthetic Construct

<400> SEQUENCE: 155

Met Leu Leu Val Asn Gln Ser His Gln Gly Phe Asn Lys Glu His Thr
1               5                   10                  15

Ser Lys Met Val Ser Ala Ile Val Leu Tyr Val Leu Leu Ala Ala Ala
                20                  25                  30

Ala His Ser Ala Phe Ala
            35

<210> SEQ ID NO 156
<211> LENGTH: 10
<212> TYPE: PRT
<213> ORGANISM: Lotus japonicus

<400> SEQUENCE: 156

Ile Ala Ser Lys Asp Ser Val Gln Ala Gly
1               5                   10

<210> SEQ ID NO 157
<211> LENGTH: 197
<212> TYPE: PRT
<213> ORGANISM: Lotus japonicus

<400> SEQUENCE: 157

Lys Cys Thr His Gly Cys Ala Leu Ala Gln Ala Ser Tyr Tyr Leu Leu
1               5                   10                  15

Asn Gly Ser Asn Leu Thr Tyr Ile Ser Glu Ile Met Gln Ser Ser Leu
                20                  25                  30

Leu Thr Lys Pro Glu Asp Ile Val Ser Tyr Asn Gln Asp Thr Ile Ala
            35                  40                  45

Ser Lys Asp Ser Val Gln Ala Gly Gln Arg Ile Asn Val Pro Phe Pro
    50                  55                  60

Cys Asp Cys Ile Glu Gly Glu Phe Leu Gly His Thr Phe Gln Tyr Asp
65                  70                  75                  80

Val Gln Lys Gly Asp Arg Tyr Asp Thr Ile Ala Gly Thr Asn Tyr Ala
                85                  90                  95

Asn Leu Thr Thr Val Glu Trp Leu Arg Arg Phe Asn Ser Tyr Pro Pro
                100                 105                 110

Asp Asn Ile Pro Asp Thr Gly Thr Leu Asn Val Thr Val Asn Cys Ser
            115                 120                 125

Cys Gly Asp Ser Gly Val Gly Asp Tyr Gly Leu Phe Val Thr Tyr Pro
        130                 135                 140

Leu Arg Pro Gly Glu Thr Leu Gly Ser Val Ala Ser Asn Val Lys Leu
145                 150                 155                 160

Asp Ser Ala Leu Leu Gln Lys Tyr Asn Pro Asn Val Asn Phe Asn Gln
                165                 170                 175

Gly Ser Gly Ile Val Tyr Ile Pro Ala Lys Asp Gln Asn Gly Ser Tyr
              180                     185                 190

Val Leu Leu Gly Ser
        195

<210> SEQ ID NO 158
<211> LENGTH: 198
<212> TYPE: PRT
<213> ORGANISM: Lotus japonicus

<400> SEQUENCE: 158

Asn Cys Leu Lys Gly Cys Asp Leu Ala Leu Ala Ser Tyr Tyr Ile Leu
1               5                   10                  15

Pro Gly Val Phe Ile Leu Gln Asn Ile Thr Thr Phe Met Gln Ser Glu
              20                  25                  30

Ile Val Ser Ser Asn Asp Ala Ile Thr Ser Tyr Asn Lys Asp Lys Ile
        35                  40                  45

Leu Asn Asp Ile Asn Ile Gln Ser Phe Gln Arg Leu Asn Ile Pro Phe
    50                  55                  60

Pro Cys Asp Cys Ile Gly Gly Glu Phe Leu Gly His Val Phe Glu Tyr
65                  70                  75                  80

Ser Ala Ser Lys Gly Asp Thr Tyr Glu Thr Ile Ala Asn Leu Tyr Tyr
              85                  90                  95

Ala Asn Leu Thr Thr Val Asp Leu Leu Lys Arg Phe Asn Ser Tyr Asp
              100                 105                 110

Pro Lys Asn Ile Pro Val Asn Ala Lys Val Asn Val Thr Val Asn Cys
              115                 120                 125

Ser Cys Gly Asn Ser Gln Val Ser Lys Asp Tyr Gly Leu Phe Ile Thr
    130                 135                 140

Tyr Pro Ile Arg Pro Gly Asp Thr Leu Gln Asp Ile Ala Asn Gln Ser
145                 150                 155                 160

Ser Leu Asp Ala Gly Leu Ile Gln Ser Phe Asn Pro Ser Val Asn Phe
              165                 170                 175

Ser Lys Asp Ser Gly Ile Ala Phe Ile Pro Gly Arg Tyr Lys Asn Gly
              180                 185                 190

Val Tyr Val Pro Leu Tyr
        195

<210> SEQ ID NO 159
<211> LENGTH: 26
<212> TYPE: PRT
<213> ORGANISM: Lotus japonicus

<400> SEQUENCE: 159

Met Glu His Pro Arg Leu Gly Phe Pro Ile Thr Leu Leu Leu Phe Ser
1               5                   10                  15

Phe Ile Leu Leu Pro Ser Thr Ser Gln Ser
              20                  25

<210> SEQ ID NO 160
<211> LENGTH: 24
<212> TYPE: PRT
<213> ORGANISM: Lotus japonicus

<400> SEQUENCE: 160

Met Lys Leu Lys Thr Gly Leu Leu Leu Phe Phe Ile Leu Leu Leu Gly
1               5                   10                  15

His Val Cys Phe His Val Glu Ser
            20

<210> SEQ ID NO 161
<211> LENGTH: 20
<212> TYPE: PRT
<213> ORGANISM: Artificial Sequence
<220> FEATURE:
<223> OTHER INFORMATION: Synthetic Construct

<400> SEQUENCE: 161

Met Val Ser Ala Ile Val Leu Tyr Val Leu Leu Ala Ala Ala Ala His
1               5                   10                  15

Ser Ala Phe Ala
            20

<210> SEQ ID NO 162
<211> LENGTH: 623
<212> TYPE: PRT
<213> ORGANISM: Lotus japonicus

<400> SEQUENCE: 162

Met Lys Leu Lys Thr Gly Leu Leu Leu Phe Phe Ile Leu Leu Leu Gly
1               5                   10                  15

His Val Cys Phe His Val Glu Ser Asn Cys Leu Lys Gly Cys Asp Leu
            20                  25                  30

Ala Leu Ala Ser Tyr Tyr Ile Leu Pro Gly Val Phe Ile Leu Gln Asn
        35                  40                  45

Ile Thr Thr Phe Met Gln Ser Glu Ile Val Ser Ser Asn Asp Ala Ile
    50                  55                  60

Thr Ser Tyr Asn Lys Asp Lys Ile Leu Asn Asp Ile Asn Ile Gln Ser
65                  70                  75                  80

Phe Gln Arg Leu Asn Ile Pro Phe Pro Cys Asp Cys Ile Gly Gly Glu
                85                  90                  95

Phe Leu Gly His Val Phe Glu Tyr Ser Ala Ser Lys Gly Asp Thr Tyr
            100                 105                 110

Glu Thr Ile Ala Asn Leu Tyr Tyr Ala Asn Leu Thr Thr Val Asp Leu
        115                 120                 125

Leu Lys Arg Phe Asn Ser Tyr Asp Pro Lys Asn Ile Pro Val Asn Ala
    130                 135                 140

Lys Val Asn Val Thr Val Asn Cys Ser Cys Gly Asn Ser Gln Val Ser
145                 150                 155                 160

Lys Asp Tyr Gly Leu Phe Ile Thr Tyr Pro Ile Arg Pro Gly Asp Thr
                165                 170                 175

Leu Gln Asp Ile Ala Asn Gln Ser Ser Leu Asp Ala Gly Leu Ile Gln
            180                 185                 190

Ser Phe Asn Pro Ser Val Asn Phe Ser Lys Asp Ser Gly Ile Ala Phe
        195                 200                 205

Ile Pro Gly Arg Tyr Lys Asn Gly Val Tyr Val Pro Leu Tyr His Arg
    210                 215                 220

Thr Ala Gly Leu Ala Ser Gly Ala Ala Val Gly Ile Ser Ile Ala Gly
225                 230                 235                 240

Thr Phe Val Leu Leu Leu Leu Ala Phe Cys Met Tyr Val Arg Tyr Gln
                245                 250                 255

Lys Lys Glu Glu Glu Lys Ala Lys Leu Pro Thr Asp Ile Ser Met Ala
            260                 265                 270

Leu Ser Thr Gln Asp Gly Asn Ala Ser Ser Ser Ala Glu Tyr Glu Thr

-continued

```
                275                 280                 285
Ser Gly Ser Ser Gly Pro Gly Thr Ala Ser Ala Thr Gly Leu Thr Ser
    290                 295                 300
Ile Met Val Ala Lys Ser Met Glu Phe Ser Tyr Gln Glu Leu Ala Lys
305                 310                 315                 320
Ala Thr Asn Asn Phe Ser Leu Asp Asn Lys Ile Gly Gln Gly Gly Phe
                325                 330                 335
Gly Ala Val Tyr Tyr Ala Glu Leu Arg Gly Lys Lys Thr Ala Ile Lys
                340                 345                 350
Lys Met Asp Val Gln Ala Ser Thr Glu Phe Leu Cys Glu Leu Lys Val
                355                 360                 365
Leu Thr His Val His His Leu Asn Leu Val Arg Leu Ile Gly Tyr Cys
    370                 375                 380
Val Glu Gly Ser Leu Phe Leu Val Tyr Glu His Ile Asp Asn Gly Asn
385                 390                 395                 400
Leu Gly Gln Tyr Leu His Gly Ser Gly Lys Glu Pro Leu Pro Trp Ser
                405                 410                 415
Ser Arg Val Gln Ile Ala Leu Asp Ala Ala Arg Gly Leu Glu Tyr Ile
                420                 425                 430
His Glu His Thr Val Pro Val Tyr Ile His Arg Asp Val Lys Ser Ala
                435                 440                 445
Asn Ile Leu Ile Asp Lys Asn Leu Arg Gly Lys Val Ala Asp Phe Gly
    450                 455                 460
Leu Thr Lys Leu Ile Glu Val Gly Asn Ser Thr Leu Gln Thr Arg Leu
465                 470                 475                 480
Val Gly Thr Phe Gly Tyr Met Pro Pro Glu Tyr Ala Gln Tyr Gly Asp
                485                 490                 495
Ile Ser Pro Lys Ile Asp Val Tyr Ala Phe Gly Val Val Leu Phe Glu
                500                 505                 510
Leu Ile Ser Ala Lys Asn Ala Val Leu Lys Thr Gly Glu Leu Val Ala
                515                 520                 525
Glu Ser Lys Gly Leu Val Ala Leu Phe Glu Glu Ala Leu Asn Lys Ser
    530                 535                 540
Asp Pro Cys Asp Ala Leu Arg Lys Leu Val Asp Pro Arg Leu Gly Glu
545                 550                 555                 560
Asn Tyr Pro Ile Asp Ser Val Leu Lys Ile Ala Gln Leu Gly Arg Ala
                565                 570                 575
Cys Thr Arg Asp Asn Pro Leu Leu Arg Pro Ser Met Arg Ser Leu Val
                580                 585                 590
Val Ala Leu Met Thr Leu Ser Ser Leu Thr Glu Asp Cys Asp Asp Glu
                595                 600                 605
Ser Ser Tyr Glu Ser Gln Thr Leu Ile Asn Leu Leu Ser Val Arg
    610                 615                 620
```

<210> SEQ ID NO 163
<211> LENGTH: 620
<212> TYPE: PRT
<213> ORGANISM: Medicago truncatula

<400> SEQUENCE: 163

```
Met Asn Leu Lys Asn Gly Leu Leu Leu Phe Ile Leu Phe Leu Asp Cys
1               5                   10                  15
Val Phe Phe Lys Val Glu Ser Lys Cys Val Lys Gly Cys Asp Val Ala
                20                  25                  30
```

-continued

```
Leu Ala Ser Tyr Tyr Ile Ile Pro Ser Ile Gln Leu Arg Asn Ile Ser
        35                  40                  45

Asn Phe Met Gln Ser Lys Ile Val Leu Thr Asn Ser Phe Asp Val Ile
        50                  55                  60

Met Ser Tyr Asn Arg Asp Val Val Phe Asp Lys Ser Gly Leu Ile Ser
65                  70                  75                  80

Tyr Thr Arg Ile Asn Val Pro Phe Pro Cys Glu Cys Ile Gly Gly Glu
                    85                  90                  95

Phe Leu Gly His Val Phe Glu Tyr Thr Thr Lys Glu Gly Asp Asp Tyr
                    100                 105                 110

Asp Leu Ile Ala Asn Thr Tyr Tyr Ala Ser Leu Thr Thr Val Glu Leu
                    115                 120                 125

Leu Lys Lys Phe Asn Ser Tyr Asp Pro Asn His Ile Pro Val Lys Ala
        130                 135                 140

Lys Ile Asn Val Thr Val Ile Cys Ser Cys Gly Asn Ser Gln Ile Ser
145                 150                 155                 160

Lys Asp Tyr Gly Leu Phe Val Thr Tyr Pro Leu Arg Ser Asp Asp Thr
                    165                 170                 175

Leu Ala Lys Ile Ala Thr Lys Ala Gly Leu Asp Glu Gly Leu Ile Gln
                    180                 185                 190

Asn Phe Asn Gln Asp Ala Asn Phe Ser Ile Gly Ser Gly Ile Val Phe
                    195                 200                 205

Ile Pro Gly Arg Asp Gln Asn Gly His Phe Phe Pro Leu Tyr Ser Arg
        210                 215                 220

Thr Gly Ile Ala Lys Gly Ser Ala Val Gly Ile Ala Met Ala Gly Ile
225                 230                 235                 240

Phe Gly Leu Leu Leu Phe Val Ile Tyr Ile Tyr Ala Lys Tyr Phe Gln
                    245                 250                 255

Lys Lys Glu Glu Glu Lys Thr Lys Leu Pro Gln Thr Ser Arg Ala Phe
                    260                 265                 270

Ser Thr Gln Asp Ala Ser Gly Ser Ala Glu Tyr Glu Thr Ser Gly Ser
        275                 280                 285

Ser Gly His Ala Thr Gly Ser Ala Ala Gly Leu Thr Gly Ile Met Val
        290                 295                 300

Ala Lys Ser Thr Glu Phe Thr Tyr Gln Glu Leu Ala Lys Ala Thr Asn
305                 310                 315                 320

Asn Phe Ser Leu Asp Asn Lys Ile Gly Gln Gly Gly Phe Gly Ala Val
                    325                 330                 335

Tyr Tyr Ala Glu Leu Arg Gly Glu Lys Thr Ala Ile Lys Lys Met Asp
                    340                 345                 350

Val Gln Ala Ser Ser Glu Phe Leu Cys Glu Leu Lys Val Leu Thr His
        355                 360                 365

Val His His Leu Asn Leu Val Arg Leu Ile Gly Tyr Cys Val Glu Gly
        370                 375                 380

Ser Leu Phe Leu Val Tyr Glu His Ile Asp Asn Gly Asn Leu Gly Gln
385                 390                 395                 400

Tyr Leu His Gly Ile Gly Thr Glu Pro Leu Pro Trp Ser Ser Arg Val
                    405                 410                 415

Gln Ile Ala Leu Asp Ser Ala Arg Gly Leu Glu Tyr Ile His Glu His
                    420                 425                 430

Thr Val Pro Val Tyr Ile His Arg Asp Val Lys Ser Ala Asn Ile Leu
        435                 440                 445

Ile Asp Lys Asn Leu Arg Gly Lys Val Ala Asp Phe Gly Leu Thr Lys
```

-continued

```
        450                 455                 460

Leu Ile Glu Val Gly Asn Ser Thr Leu His Thr Arg Leu Val Gly Thr
465                 470                 475                 480

Phe Gly Tyr Met Pro Pro Glu Tyr Ala Gln Tyr Gly Asp Val Ser Pro
                485                 490                 495

Lys Ile Asp Val Tyr Ala Phe Gly Val Val Leu Tyr Glu Leu Ile Thr
                500                 505                 510

Ala Lys Asn Ala Val Leu Lys Thr Gly Glu Ser Val Ala Glu Ser Lys
            515                 520                 525

Gly Leu Val Gln Leu Phe Glu Glu Ala Leu His Arg Met Asp Pro Leu
            530                 535                 540

Glu Gly Leu Arg Lys Leu Val Asp Pro Arg Leu Lys Glu Asn Tyr Pro
545                 550                 555                 560

Ile Asp Ser Val Leu Lys Met Ala Gln Leu Gly Arg Ala Cys Thr Arg
                565                 570                 575

Asp Asn Pro Leu Leu Arg Pro Ser Met Arg Ser Ile Val Val Ala Leu
                580                 585                 590

Met Thr Leu Ser Ser Pro Thr Glu Asp Cys Asp Asp Asp Ser Ser Tyr
            595                 600                 605

Glu Asn Gln Ser Leu Ile Asn Leu Leu Ser Thr Arg
        610                 615                 620

<210> SEQ ID NO 164
<211> LENGTH: 622
<212> TYPE: PRT
<213> ORGANISM: Lotus japonicus

<400> SEQUENCE: 164

Met Glu His Pro Arg Leu Gly Phe Pro Ile Thr Leu Leu Leu Phe Ser
1                   5                   10                  15

Phe Ile Leu Leu Pro Ser Thr Ser Gln Ser Lys Cys Thr His Gly Cys
                20                  25                  30

Ala Leu Ala Gln Ala Ser Tyr Tyr Leu Leu Asn Gly Ser Asn Leu Thr
            35                  40                  45

Tyr Ile Ser Glu Ile Met Gln Ser Ser Leu Leu Thr Lys Pro Glu Asp
        50                  55                  60

Ile Val Ser Tyr Asn Gln Asp Thr Ile Ala Ser Lys Asp Ser Val Gln
65                  70                  75                  80

Ala Gly Gln Arg Ile Asn Val Pro Phe Pro Cys Asp Cys Ile Glu Gly
                85                  90                  95

Glu Phe Leu Gly His Thr Phe Gln Tyr Asp Val Gln Lys Gly Asp Arg
                100                 105                 110

Tyr Asp Thr Ile Ala Gly Thr Asn Tyr Ala Asn Leu Thr Thr Val Glu
            115                 120                 125

Trp Leu Arg Arg Phe Asn Ser Tyr Pro Pro Asp Asn Ile Pro Asp Thr
        130                 135                 140

Gly Thr Leu Asn Val Thr Val Asn Cys Ser Cys Gly Asp Ser Gly Val
145                 150                 155                 160

Gly Asp Tyr Gly Leu Phe Val Thr Tyr Pro Leu Arg Pro Gly Glu Thr
                165                 170                 175

Leu Gly Ser Val Ala Ser Asn Val Lys Leu Asp Ser Ala Leu Leu Gln
            180                 185                 190

Lys Tyr Asn Pro Asn Val Asn Phe Asn Gln Gly Ser Gly Ile Val Tyr
            195                 200                 205
```

-continued

```
Ile Pro Ala Lys Asp Gln Asn Gly Ser Tyr Val Leu Leu Gly Ser Ser
    210             215                 220

Ser Gly Gly Leu Ala Gly Gly Ala Ile Ala Gly Ile Ala Ala Gly Val
225             230                 235                 240

Ala Val Cys Leu Leu Leu Leu Ala Gly Phe Ile Tyr Val Gly Tyr Phe
            245                 250                 255

Arg Lys Lys Arg Ile Gln Lys Glu Glu Leu Leu Ser Gln Glu Thr Arg
            260                 265                 270

Ala Ile Phe Pro Gln Asp Gly Lys Asp Glu Asn Pro Arg Ser Thr Val
            275                 280                 285

Asn Glu Thr Pro Gly Pro Gly Gly Pro Ala Ala Met Ala Gly Ile Thr
    290                 295                 300

Val Asp Lys Ser Val Glu Phe Ser Tyr Asp Glu Leu Ala Thr Ala Thr
305                 310                 315                 320

Asp Asn Phe Ser Leu Ala Asn Lys Ile Gly Gln Gly Gly Phe Gly Ser
            325                 330                 335

Val Tyr Tyr Ala Glu Leu Arg Gly Glu Arg Ala Ala Ile Lys Lys Met
            340                 345                 350

Asp Met Gln Ala Ser Lys Glu Phe Leu Ala Glu Leu Lys Val Leu Thr
            355                 360                 365

Arg Val His His Leu Asn Leu Val Arg Leu Ile Gly Tyr Ser Ile Glu
    370                 375                 380

Gly Ser Leu Phe Leu Val Tyr Glu Phe Ile Glu Asn Gly Asn Leu Ser
385                 390                 395                 400

Gln His Leu Arg Gly Ser Gly Arg Asp Pro Leu Pro Trp Ala Thr Arg
            405                 410                 415

Val Gln Ile Ala Leu Asp Ser Ala Arg Gly Leu Glu Tyr Ile His Glu
            420                 425                 430

His Thr Val Pro Val Tyr Ile His Arg Asp Ile Lys Ser Ala Asn Ile
            435                 440                 445

Leu Ile Asp Lys Asn Tyr Arg Gly Lys Val Ala Asp Phe Gly Leu Thr
    450                 455                 460

Lys Leu Thr Glu Val Gly Ser Ser Ser Leu Pro Thr Gly Arg Leu Val
465                 470                 475                 480

Gly Thr Phe Gly Tyr Met Pro Pro Glu Tyr Ala Gln Tyr Gly Asp Val
            485                 490                 495

Ser Pro Lys Val Asp Val Tyr Ala Phe Gly Val Val Leu Tyr Glu Leu
            500                 505                 510

Ile Ser Ala Lys Asp Ala Ile Val Lys Thr Ser Glu Ser Ile Thr Asp
            515                 520                 525

Ser Lys Gly Leu Val Ala Leu Phe Glu Gly Val Leu Ser Gln Pro Asp
    530                 535                 540

Pro Thr Glu Asp Leu Arg Lys Leu Val Asp Gln Arg Leu Gly Asp Asn
545                 550                 555                 560

Tyr Pro Val Asp Ser Val Arg Lys Met Ala Gln Leu Ala Lys Ala Cys
            565                 570                 575

Thr Gln Asp Asn Pro Gln Leu Arg Pro Ser Met Arg Ser Ile Val Val
            580                 585                 590

Ala Leu Met Thr Leu Ser Ser Thr Thr Asp Asp Trp Asp Val Gly Ser
            595                 600                 605

Phe Tyr Glu Asn Gln Asn Leu Val Asn Leu Met Ser Gly Arg
    610                 615                 620
```

<210> SEQ ID NO 165
<211> LENGTH: 69
<212> TYPE: PRT
<213> ORGANISM: Lotus japonicus

<400> SEQUENCE: 165

Ser Asn Cys Leu Lys Gly Cys Asp Leu Ala Leu Ala Ser Tyr Tyr Ile
1               5                   10                  15

Leu Pro Gly Val Phe Ile Leu Gln Asn Ile Thr Thr Phe Met Gln Ser
                20                  25                  30

Glu Ile Val Ser Ser Asn Asp Ala Ile Thr Ser Tyr Asn Lys Asp Lys
            35                  40                  45

Ile Leu Asn Asp Ile Asn Ile Gln Ser Phe Gln Arg Leu Asn Ile Pro
        50                  55                  60

Phe Pro Cys Asp Cys
65

<210> SEQ ID NO 166
<211> LENGTH: 68
<212> TYPE: PRT
<213> ORGANISM: Lotus japonicus

<400> SEQUENCE: 166

Ser Lys Cys Thr His Gly Cys Ala Leu Ala Gln Ala Ser Tyr Tyr Leu
1               5                   10                  15

Leu Asn Gly Ser Asn Leu Thr Tyr Ile Ser Glu Ile Met Gln Ser Ser
                20                  25                  30

Leu Leu Thr Lys Pro Glu Asp Ile Val Ser Tyr Asn Gln Asp Thr Ile
            35                  40                  45

Ala Ser Lys Asp Ser Val Gln Ala Gly Gln Arg Ile Asn Val Pro Phe
        50                  55                  60

Pro Cys Asp Cys
65

<210> SEQ ID NO 167
<211> LENGTH: 70
<212> TYPE: PRT
<213> ORGANISM: Medicago truncatula

<400> SEQUENCE: 167

Ser Lys Cys Val Lys Gly Cys Asp Val Ala Leu Ala Ser Tyr Tyr Ile
1               5                   10                  15

Ile Pro Ser Ile Gln Leu Arg Asn Ile Ser Asn Phe Met Gln Ser Lys
                20                  25                  30

Ile Val Leu Thr Asn Ser Phe Asp Val Ile Met Ser Tyr Asn Arg Asp
            35                  40                  45

Val Val Phe Asp Lys Ser Gly Leu Ile Ser Tyr Thr Arg Ile Asn Val
        50                  55                  60

Pro Phe Pro Cys Glu Cys
65                  70

<210> SEQ ID NO 168
<211> LENGTH: 189
<212> TYPE: PRT
<213> ORGANISM: Medicago truncatula

<400> SEQUENCE: 168

Lys Cys Val Lys Gly Cys Asp Val Ala Leu Ala Ser Tyr Tyr Ile Ile
1               5                   10                  15

-continued

```
Pro Ser Ile Gln Leu Arg Asn Ile Ser Asn Phe Met Gln Ser Lys Ile
        20                  25                  30

Val Leu Thr Asn Ser Phe Asp Val Ile Met Ser Tyr Asn Arg Asp Val
        35                  40                  45

Val Phe Asp Lys Ser Gly Leu Ile Ser Tyr Thr Arg Ile Asn Val Pro
        50                  55                  60

Phe Pro Cys Glu Cys Ile Gly Gly Glu Phe Leu Gly His Val Phe Glu
65                  70                  75                  80

Tyr Thr Thr Lys Glu Gly Asp Asp Tyr Asp Leu Ile Ala Asn Thr Tyr
                85                  90                  95

Tyr Ala Ser Leu Thr Thr Val Glu Leu Leu Lys Lys Phe Asn Ser Tyr
        100                 105                 110

Asp Pro Asn His Ile Pro Val Lys Ala Lys Ile Asn Val Thr Val Ile
        115                 120                 125

Cys Ser Cys Gly Asn Ser Gln Ile Ser Lys Asp Tyr Gly Leu Phe Val
        130                 135                 140

Thr Tyr Pro Leu Arg Ser Asp Asp Thr Leu Ala Lys Ile Ala Thr Lys
145                 150                 155                 160

Ala Gly Leu Asp Glu Gly Leu Ile Gln Asn Phe Asn Gln Asp Ala Asn
                165                 170                 175

Phe Ser Ile Gly Ser Gly Ile Val Phe Ile Pro Gly Arg
                180                 185
```

<210> SEQ ID NO 169
<211> LENGTH: 187
<212> TYPE: PRT
<213> ORGANISM: Phaseolus vulgaris

<400> SEQUENCE: 169

```
Lys Cys Leu Lys Gly Cys Gly Ala Ala Leu Ala Ser Tyr Tyr Val Ser
1                   5                   10                  15

Pro Gly Ile Ser Thr Leu Asp Asp Ile Thr His Leu Met Lys Ser Ser
        20                  25                  30

Val Val Ser Asn Ser Asp Asp Ile Val Ser Tyr Asn Lys Asp Arg Ile
        35                  40                  45

Phe Asn Lys Asn Val Leu Phe Phe Tyr Arg Ile Asn Ile Pro Phe Pro
        50                  55                  60

Cys Glu Cys Ile Arg Asp Glu Phe Leu Gly His Val Phe Glu Tyr Ser
65                  70                  75                  80

Ala Ala Ala Gly Asp Thr Tyr Asp Ser Ile Ala Lys Val Thr Tyr Ala
                85                  90                  95

Asn Leu Thr Thr Val Glu Leu Leu Arg Arg Phe Asn Ser Tyr Gly Gln
        100                 105                 110

Asn Asp Ile Pro Thr Asn Ala Lys Val Asn Val Thr Val Asn Cys Ser
        115                 120                 125

Cys Gly Asn Ser Gln Val Ser Gln Asp Tyr Gly Leu Phe Ile Thr Tyr
        130                 135                 140

Pro Leu Arg Pro Gly Asn Asn Leu His Asp Ile Ala Asn Glu Thr Gln
145                 150                 155                 160

Leu Asp Ala Gln Leu Leu Gln Asn Tyr Asn Pro Gly Val Asn Phe Ser
                165                 170                 175

Gln Glu Ser Gly Ile Val Phe Ile Pro Gly Arg
                180                 185
```

<210> SEQ ID NO 170

-continued

```
<211> LENGTH: 186
<212> TYPE: PRT
<213> ORGANISM: Arachis hypogaea

<400> SEQUENCE: 170

Lys Cys Leu Lys Gly Cys Asp Leu Ala Ile Ala Ser Tyr Phe Val Tyr
1               5                   10                  15

Pro Lys Val Met Leu Gly Ser Ile Ala Ser Phe Met His Ser Asn Val
                20                  25                  30

Val Pro Asn Ser Asn Val Ile Ile Ser Tyr Asn Lys Asp Lys Met Pro
            35                  40                  45

Asn Asn Leu Pro Val Ser Phe Thr Arg Ile Asn Ile Pro Phe Pro Cys
        50                  55                  60

Asp Cys Ile Asn Gly Glu Phe Leu Gly His Val Phe Glu Tyr Ser Ala
65                  70                  75                  80

Ile Glu Gly Asp Thr Tyr Asp Leu Ile Ala Asn Met Arg Tyr Ser Asp
                85                  90                  95

Leu Thr Thr Val Glu Ile Leu Gln Arg Phe Asn Asn Tyr Asp Pro Asn
                100                 105                 110

His Val Pro Val Asn Ala Lys Val Asn Val Thr Val Asn Cys Ser Cys
            115                 120                 125

Gly Asn Ser Asn Val Ser Lys Asp Tyr Gly Leu Phe Val Thr Phe Pro
        130                 135                 140

Leu Ser Glu Gly Asn Thr Leu Leu Gln Ile Ala Asn Gln Thr Lys Leu
145                 150                 155                 160

Asp Pro Lys Leu Leu Gln Gly Tyr Asn Pro Gly Val Asn Phe Asn Gln
                165                 170                 175

Thr Arg Gly Ile Val Phe Ile Pro Gly Arg
                180                 185

<210> SEQ ID NO 171
<211> LENGTH: 186
<212> TYPE: PRT
<213> ORGANISM: Arachis hypogaea

<400> SEQUENCE: 171

Lys Cys Leu Lys Gly Cys Asp Leu Ala Ile Ala Ser Tyr Phe Val Tyr
1               5                   10                  15

Pro Arg Val Lys Leu Gly Ser Ile Ala Ser Phe Met His Ser Asn Val
                20                  25                  30

Val Pro Asn Ser Asn Val Ile Ile Ser Tyr Asn Lys Asp Lys Met Pro
            35                  40                  45

Asn Asn Leu Pro Val Ser Phe Thr Thr Ile Asn Ile Pro Phe Pro Cys
        50                  55                  60

Asp Cys Ile Asn Gly Glu Phe Leu Gly His Val Phe Glu Tyr Ser Ala
65                  70                  75                  80

Ile Glu Gly Asp Thr Tyr Tyr Leu Ile Ala Asn Met Arg Tyr Ser Asp
                85                  90                  95

Leu Thr Thr Val Glu Ile Leu Gln Arg Phe Asn Asn Tyr Asp Pro Asn
                100                 105                 110

His Val Pro Val Asn Ala Lys Val Asn Val Thr Val Asn Cys Ser Cys
            115                 120                 125

Gly Asn Ser His Val Ser Lys Asp Tyr Gly Leu Phe Val Thr Phe Pro
        130                 135                 140

Leu Ser Glu Gly Asn Thr Leu Leu Gln Ile Ala Asn Gln Thr Lys Leu
145                 150                 155                 160
```

-continued

```
Asp Pro Lys Leu Leu Gln Ser Tyr Asn Pro Gly Val Asn Phe Asn Gln
            165                 170                 175

Thr Arg Gly Ile Val Phe Ile Pro Gly Arg
            180                 185

<210> SEQ ID NO 172
<211> LENGTH: 186
<212> TYPE: PRT
<213> ORGANISM: Cajanus cajan

<400> SEQUENCE: 172

Met Cys Val Lys Glu Cys Asp Val Ala Leu Ala Ser Tyr Tyr Ile Leu
1               5                   10                  15

Pro Gly Tyr Leu Thr Val Glu Asn Val Thr Gly Trp Leu Glu Ser Ser
            20                  25                  30

Val Leu Ser Asn Ser Asp Val Ile Lys Ser Tyr Asn Lys Asp Lys Ile
            35                  40                  45

Ile Lys Asp Asn Leu Pro Ser Phe Asp Arg Ile Asn Val Pro Phe Pro
        50                  55                  60

Cys Asp Cys Ile His Glu Glu Phe Leu Gly His Val Phe Glu Tyr Ser
65                  70                  75                  80

Ala Ala Ala Gly Asp Thr Tyr Asp Ser Ile Ala Lys Val Thr Tyr Ala
                85                  90                  95

Asn Leu Thr Thr Val Glu Leu Leu Thr Arg Phe Asn Ser Tyr Gly His
            100                 105                 110

Asp Ile Pro Gln Asn Ala Lys Ile Asn Val Thr Val Lys Cys Ser Cys
            115                 120                 125

Gly Asn Ser Gln Val Ser Lys Asp Tyr Gly Leu Phe Ile Thr Tyr Pro
        130                 135                 140

Leu Arg Pro Gly Asn Asn Leu His Asp Ile Ala Asn Glu Val His Leu
145                 150                 155                 160

Asp Ala Gln Leu Leu Glu Lys Tyr Asn Pro Gly Val Asn Phe Ser Lys
                165                 170                 175

Asp Ser Gly Ile Val Phe Ile Pro Gly Arg
            180                 185

<210> SEQ ID NO 173
<211> LENGTH: 184
<212> TYPE: PRT
<213> ORGANISM: Cicer arietinum

<400> SEQUENCE: 173

Lys Cys Val Lys Gly Cys Asp Leu Ala Leu Ala Ser Tyr Tyr Ile Lys
1               5                   10                  15

Pro Pro Phe Glu Phe Thr Asn Ile Thr Asn Phe Met Gln Ser Asn Ser
            20                  25                  30

Asp Ile Ile Ile Ser Tyr Asn Lys Gln Leu Val Ser Asn Asn Gly Lys
        35                  40                  45

Leu Phe Ser Phe Ser Arg Ile Asn Ile Pro Phe Gln Cys Glu Cys Ile
        50                  55                  60

Gln Gly Glu Phe Leu Gly His Met Phe Glu Tyr Thr Thr Asn Glu Gly
65                  70                  75                  80

Asp Thr Tyr Asp Leu Ile Ala Asn Ser Tyr Tyr Ala Ser Leu Thr Thr
                85                  90                  95

Ile Asp Leu Leu Gln Lys Phe Asn Lys Tyr Asp His Asn Gln Thr Leu
            100                 105                 110
```

```
Pro Ser Lys Val Lys Val Asn Val Thr Val Asn Cys Ser Cys Gly Asn
        115             120             125

Ser Gln Ile Ser Lys Glu Tyr Gly Leu Phe Leu Thr Tyr Pro Leu Arg
        130             135             140

Ser Ser Asp Thr Leu Gln Ile Ile Ala Ile Glu Ser Lys Val Asp Glu
145             150             155             160

Val Leu Ile Gln Asn Tyr Asn Pro Asn Val Asn Phe Ser Arg Gly Ser
                165             170             175

Gly Ile Val Phe Ile Pro Gly Arg
            180

<210> SEQ ID NO 174
<211> LENGTH: 187
<212> TYPE: PRT
<213> ORGANISM: Abrus precatorius

<400> SEQUENCE: 174

Lys Cys Met Lys Gly Cys His Val Ala Leu Ala Ser Tyr Tyr Val Arg
1               5               10              15

Pro Lys Phe Leu Ser Leu Asp Asn Ile Met Arg Leu Met Gln Ser Lys
            20              25              30

Ile Leu Ser Thr Ser Asp Val Ile Arg Ser Tyr Asn Lys Asp Lys Ile
        35              40              45

Leu Asn Asp Asn Val Pro Ser Phe Ser Arg Val Asn Ile Pro Phe Pro
    50              55              60

Cys Asp Cys Ile Gly Asp Glu Phe Leu Gly His Val Phe Glu Tyr Ser
65              70              75              80

Thr Ala Ala Gly Asp Thr Tyr Asp Leu Ile Ala Lys Val Lys Tyr Ala
            85              90              95

Asn Leu Thr Thr Val Glu Leu Leu Gln Arg Phe Asn Ser Tyr Asp Gln
            100             105             110

Asp Asp Ile Pro Ala Asn Ser Lys Leu Asn Val Thr Val Asn Cys Tyr
            115             120             125

Cys Gly Asn Ser Gln Ile Ser Lys Asp Tyr Gly Met Phe Ile Thr Tyr
        130             135             140

Pro Leu Arg Pro Gly Asn Thr Leu Gln Asp Ile Ser Asn Glu Thr Asn
145             150             155             160

Leu Asp Ala His Leu Leu Gln Ser Tyr Asn Pro Gly Val Asn Phe Ser
                165             170             175

Ser Glu Ser Gly Ile Val Phe Ile Pro Gly Arg
            180             185

<210> SEQ ID NO 175
<211> LENGTH: 182
<212> TYPE: PRT
<213> ORGANISM: Glycine max

<400> SEQUENCE: 175

Lys Cys Val Lys Gly Cys Asp Val Ala Phe Ala Ser Tyr Tyr Val Ser
1               5               10              15

Pro Asp Leu Ser Leu Glu Asn Ile Ala Arg Leu Met Glu Ser Ser Ile
            20              25              30

Glu Val Ile Ile Ser Phe Asn Glu Asp Asn Ile Ser Asn Gly Tyr Pro
        35              40              45

Leu Ser Phe Tyr Arg Leu Asn Ile Pro Phe Pro Cys Asp Cys Ile Gly
    50              55              60
```

```
Gly Glu Phe Leu Gly His Val Phe Glu Tyr Ser Ala Ser Ala Gly Asp
65              70                  75                  80

Thr Tyr Asp Ser Ile Ala Lys Val Thr Tyr Ala Asn Leu Thr Thr Val
                85                  90                  95

Glu Leu Leu Arg Arg Phe Asn Gly Tyr Asp Gln Asn Gly Ile Pro Ala
            100                 105                 110

Asn Ala Arg Val Asn Val Thr Val Asn Cys Ser Cys Gly Asn Ser Gln
            115                 120                 125

Val Ser Lys Asp Tyr Gly Met Phe Ile Thr Tyr Pro Leu Arg Pro Gly
        130                 135                 140

Asn Asn Leu His Asp Ile Ala Asn Glu Ala Arg Leu Asp Ala Gln Leu
145                 150                 155                 160

Leu Gln Arg Tyr Asn Pro Gly Val Asn Phe Ser Lys Glu Ser Gly Thr
                165                 170                 175

Val Phe Ile Pro Gly Arg
            180

<210> SEQ ID NO 176
<211> LENGTH: 187
<212> TYPE: PRT
<213> ORGANISM: Glycine max

<400> SEQUENCE: 176

Lys Cys Val Lys Gly Cys Asp Val Ala Leu Ala Ser Tyr Tyr Val Ser
1               5                   10                  15

Pro Gly Tyr Leu Leu Leu Glu Asn Ile Thr Arg Leu Met Glu Ser Ile
            20                  25                  30

Val Leu Ser Asn Ser Asp Val Ile Ile Tyr Asn Lys Asp Lys Ile Phe
        35                  40                  45

Asn Glu Asn Val Leu Ala Phe Ser Arg Leu Asn Ile Pro Phe Pro Cys
    50                  55                  60

Gly Cys Ile Asp Gly Glu Phe Leu Gly His Val Phe Glu Tyr Ser Ala
65              70                  75                  80

Ser Ala Gly Asp Thr Tyr Asp Ser Ile Ala Lys Val Thr Tyr Ala Asn
                85                  90                  95

Leu Thr Thr Val Glu Leu Leu Arg Arg Phe Asn Ser Tyr Asp Gln Asn
            100                 105                 110

Gly Ile Pro Ala Asn Ala Thr Val Asn Val Thr Val Asn Cys Ser Cys
        115                 120                 125

Gly Asn Ser Gln Val Ser Lys Asp Tyr Gly Leu Phe Ile Thr Tyr Leu
        130                 135                 140

Leu Arg Pro Gly Asn Asn Leu His Asp Ile Ala Asn Glu Ala Arg Leu
145                 150                 155                 160

Asp Ala Gln Leu Leu Gln Ser Tyr Asn Pro Gly Val Asn Phe Ser Lys
                165                 170                 175

Glu Ser Gly Asp Ile Val Phe Ile Pro Gly Lys
            180                 185

<210> SEQ ID NO 177
<211> LENGTH: 189
<212> TYPE: PRT
<213> ORGANISM: Lupinus angustifolius

<400> SEQUENCE: 177

Lys Cys Ile Lys Gly Cys Asp Leu Ala Leu Ala Ser Tyr Tyr Val Pro
1               5                   10                  15
```

```
Val Trp Pro Ile Val Ser Leu Gly Asn Ile Thr Ser Phe Met His Ser
        20                  25                  30

Asn Val Leu Thr Asn Pro Asn Val Val Thr Ser Tyr Asn Lys Asp Lys
        35                  40                  45

Val Phe Asn Gly Asp Val Met Leu Ala Leu Tyr Arg Thr Asn Val Pro
    50                  55                  60

Phe Pro Cys Asp Cys Ile Gly Gly Glu Phe Leu Gly His Val Phe Glu
65                  70                  75                  80

Tyr Ser Ala Val Glu Gly Asp Thr Tyr Gly Leu Ile Ala Met Lys Arg
                85                  90                  95

Tyr Ser Asn Leu Thr Thr Val Glu Ile Leu Lys Arg Phe Asn Ser Tyr
            100                 105                 110

Asp Pro Asn His Ile Pro Val Asn Ala Lys Val Asn Val Thr Val Lys
            115                 120                 125

Cys Ser Cys Gly Asn Ser Gln Ile Ser Lys Asp Tyr Gly Leu Phe Ile
        130                 135                 140

Thr Tyr Pro Leu Arg Pro Gly Asn Asn Leu Gln Glu Leu Ser Lys Glu
145                 150                 155                 160

Thr Lys Ile Asp Ala Lys Leu Leu Gln Ser Tyr Asn Pro Gly Val Asn
                165                 170                 175

Phe Ser Gln Glu Asn Gly Ile Val Phe Ile Pro Gly Lys
            180                 185
```

<210> SEQ ID NO 178
<211> LENGTH: 189
<212> TYPE: PRT
<213> ORGANISM: Lupinus angustifolius

<400> SEQUENCE: 178

```
Lys Cys Ile Lys Gly Cys Asp Leu Ala Leu Ala Ser Tyr Tyr Val Ser
1               5                   10                  15

Val Trp Pro Ser Ile Ser Leu Gly Asn Ile Thr Asn Phe Met His Ser
        20                  25                  30

Asn Val Leu Thr Asn Ser Asp Val Ile Ile Ser Tyr Asn Lys Gly Lys
        35                  40                  45

Ile Phe Asn Gly Asp Val Leu Leu Ser Leu Thr Arg Thr Asn Val Pro
    50                  55                  60

Phe Pro Cys Asp Cys Ile Gly Gly Glu Phe Leu Gly His Val Phe Gln
65                  70                  75                  80

Tyr Ser Ser Val Ala Gly Asp Thr Tyr Asp Thr Ile Ala Met Lys Ser
                85                  90                  95

Tyr Ser Asn Leu Thr Thr Val Glu Phe Leu Lys Arg Phe Asn Ser Tyr
            100                 105                 110

Asp Pro Asn His Ile Pro Val Asn Ser Lys Val Asn Val Thr Ile Asn
            115                 120                 125

Cys Ser Cys Gly Asn Ser Leu Ile Ser Lys Asp Tyr Gly Leu Phe Thr
        130                 135                 140

Thr Tyr Pro Leu Arg Pro Gly Asn Asn Leu Gln Glu Leu Ser Lys Glu
145                 150                 155                 160

Thr Asn Ile Asp Ala Lys Leu Leu Gln Ser Tyr Asn Pro Gly Ala Asn
                165                 170                 175

Phe Ser Gln Glu Ser Arg Ile Val Phe Ile Pro Gly Arg
            180                 185
```

```
<210> SEQ ID NO 179
<211> LENGTH: 188
<212> TYPE: PRT
<213> ORGANISM: Lotus japonicus

<400> SEQUENCE: 179

Asn Cys Leu Lys Gly Cys Asp Leu Ala Leu Ala Ser Tyr Tyr Ile Leu
1               5                   10                  15

Pro Gly Val Phe Ile Leu Gln Asn Ile Thr Thr Phe Met Gln Ser Glu
            20                  25                  30

Ile Val Ser Ser Asn Asp Ala Ile Thr Ser Tyr Asn Lys Asp Lys Ile
        35                  40                  45

Leu Asn Asp Ile Asn Ile Gln Ser Phe Gln Arg Leu Asn Ile Pro Phe
    50                  55                  60

Pro Cys Asp Cys Ile Gly Gly Glu Phe Leu Gly His Val Phe Glu Tyr
65                  70                  75                  80

Ser Ala Ser Lys Gly Asp Thr Tyr Glu Thr Ile Ala Asn Leu Tyr Tyr
                85                  90                  95

Ala Asn Leu Thr Thr Val Asp Leu Leu Lys Arg Phe Asn Ser Tyr Asp
            100                 105                 110

Pro Lys Asn Ile Pro Val Asn Ala Lys Val Asn Val Thr Val Asn Cys
            115                 120                 125

Ser Cys Gly Asn Ser Gln Val Ser Lys Asp Tyr Gly Leu Phe Ile Thr
    130                 135                 140

Tyr Pro Ile Arg Pro Gly Asp Thr Leu Gln Asp Ile Ala Asn Gln Ser
145                 150                 155                 160

Ser Leu Asp Ala Gly Leu Ile Gln Ser Phe Asn Pro Ser Val Asn Phe
                165                 170                 175

Ser Lys Asp Ser Gly Ile Ala Phe Ile Pro Gly Arg
            180                 185

<210> SEQ ID NO 180
<211> LENGTH: 188
<212> TYPE: PRT
<213> ORGANISM: Pisum sativum

<400> SEQUENCE: 180

Lys Cys Val Ile Gly Cys Asp Ile Ala Leu Ala Ser Tyr Tyr Val Met
1               5                   10                  15

Pro Leu Val Glu Leu Leu Asn Ile Thr Thr Phe Met Gln Ser Lys Leu
            20                  25                  30

Val Thr Asn Ser Ser Glu Val Ile Val Arg Tyr Asn Arg Asp Ile Val
        35                  40                  45

Phe Ser Asn Asp Asn Leu Phe Ser Tyr Phe Arg Ile Asn Ile Pro Phe
    50                  55                  60

Pro Cys Glu Cys Ile Gly Gly Glu Phe Leu Gly His Val Phe Glu Tyr
65                  70                  75                  80

Thr Ala Asn Glu Gly Asp Thr Tyr Asp Leu Ile Ala Asn Thr Tyr Tyr
                85                  90                  95

Ala Ser Leu Thr Thr Val Glu Val Leu Lys Lys Phe Asn Ser Tyr Asp
            100                 105                 110

Pro Asn His Ile Pro Ala Lys Ala Lys Val Asn Val Thr Val Asn Cys
            115                 120                 125

Ser Cys Gly Asn Ser Gln Ile Ser Lys Asp Tyr Gly Leu Phe Ile Thr
    130                 135                 140

Tyr Pro Leu Arg Pro Arg Asp Thr Leu Glu Lys Ile Ala Ser His Ser
```

```
145                150                155                160
Lys Leu Asp Glu Gly Val Ile Gln Ser Tyr Asn Leu Gly Val Asn Phe
               165                170                175

Ser Lys Gly Ser Gly Ile Val Phe Phe Pro Gly Arg
           180                185

<210> SEQ ID NO 181
<211> LENGTH: 186
<212> TYPE: PRT
<213> ORGANISM: Vigna angularis

<400> SEQUENCE: 181

Lys Cys Leu Lys Gly Cys Asp Leu Ala Leu Ala Ser Tyr Tyr Val Ser
1               5                   10                  15

Ser Gly Leu Thr Leu Asp Asp Ile Thr His Leu Met Lys Ser Ser Val
               20                  25                  30

Val Ser Asn Ser Asp Asp Ile Ile Ser Tyr Asn Lys Asp Lys Thr Phe
           35                  40                  45

Asn Lys Asn Ile Phe Leu Phe Asp Arg Ile Asn Val Pro Phe Pro Cys
       50                  55                  60

Asp Cys Ile His Asp Glu Phe Leu Gly His Val Phe Glu Tyr Ser Ala
65                  70                  75                  80

Ala Glu Gly Asp Thr Tyr Asp Ser Ile Ala Lys Val Glu Tyr Ala Asp
               85                  90                  95

Leu Thr Thr Val Glu Leu Leu Arg Arg Phe Asn Ser Tyr Gly Gln Asn
           100                 105                 110

Gly Ile Pro Lys Asn Ala Lys Val Asn Val Thr Val Asn Cys Ser Cys
           115                 120                 125

Gly Asn Ser Gln Val Ser Gln Glu Tyr Gly Leu Phe Ile Thr Tyr Pro
       130                 135                 140

Leu Arg Pro Asp Asn Asn Leu His Asp Ile Ala Asn Glu Ala His Leu
145                 150                 155                 160

Asp Ala Gln Leu Leu Gln Asn Tyr Asn Pro Gly Val Asn Phe Ser Lys
               165                 170                 175

Glu Ser Gly Ile Val Phe Ile Pro Gly Arg
           180                 185

<210> SEQ ID NO 182
<211> LENGTH: 186
<212> TYPE: PRT
<213> ORGANISM: Vigna radiata var. radiata

<400> SEQUENCE: 182

Lys Cys Leu Lys Gly Cys Asp Leu Ala Leu Ala Ser Tyr Tyr Val Asn
1               5                   10                  15

Arg Gly Leu Ser Leu Asp Asn Ile Thr His Leu Met Lys Ser Ser Val
               20                  25                  30

Val Ser Asn Ser Asp Asp Ile Ile Ser Tyr Asn Lys Asn Lys Ile Phe
           35                  40                  45

Asn Lys Asn Val Phe Met Phe Asn Arg Tyr Asn Val Pro Phe Pro Cys
       50                  55                  60

Asp Cys Ile Arg Asp Glu Phe Leu Gly His Val Phe Glu Tyr Ser Ala
65                  70                  75                  80

Ala Glu Gly Asp Thr Tyr Asp Ser Ile Ala Lys Val Glu Tyr Ala Asp
               85                  90                  95

Leu Thr Thr Val Glu Leu Leu Arg Arg Phe Asn Ser Tyr Gly Gln Asn
```

-continued

```
              100               105               110

Gly Ile Pro Lys Asn Ala Lys Val Asn Val Thr Val Asn Cys Ser Cys
              115               120               125

Gly Asn Ser Gln Val Ser Gln Glu Tyr Gly Leu Phe Ile Thr Tyr Pro
              130               135               140

Leu Arg Pro Asp Asn Asn Leu His Asp Ile Ala Asn Glu Ala His Leu
145               150               155               160

Asp Ala Gln Leu Leu Gln Asn Tyr Asn Pro Gly Val Asn Phe Ser Lys
              165               170               175

Glu Ser Gly Ile Val Phe Ile Pro Gly Arg
              180               185
```

<210> SEQ ID NO 183
<211> LENGTH: 186
<212> TYPE: PRT
<213> ORGANISM: Vigna unguiculata

<400> SEQUENCE: 183

```
Lys Cys Leu Lys Gly Cys Asn Val Ala Leu Gly Ser Tyr Tyr Val Asn
1               5                 10                15

Thr Gly Met Ser Leu Asp Val Ile Thr Pro Leu Met Lys Ser Ser Val
              20                25                30

Val Ser Asn Ser Asp Asp Ile Ile Ser Tyr Asn Lys Asp Lys Ile Phe
              35                40                45

Asn Lys Asn Val Phe Tyr Phe Asp Arg Ile Asn Val Pro Phe Pro Cys
              50                55                60

Asp Cys Ile Ser Asp Glu Phe Leu Gly His Val Phe Glu Tyr Ser Ala
65                70                75                80

Ala Glu Gly Asp Thr Tyr Asp Ser Ile Ala Lys Val Glu Tyr Ala Asp
              85                90                95

Leu Thr Thr Val Glu Leu Leu Arg Arg Phe Asn Ser Tyr Gly Gln Asn
              100               105               110

Gly Ile Pro Lys Asn Ala Lys Val Asn Val Thr Val Asn Cys Ser Cys
              115               120               125

Gly Asn Ser Gln Val Ser Gln Asp Tyr Gly Leu Phe Ile Thr Tyr Pro
              130               135               140

Leu Arg Pro Gly Asn Asn Leu His Asp Ile Ala Asn Glu Ala His Leu
145               150               155               160

Asp Ala Gln Leu Leu Gln Asn Tyr Asn Pro Gly Val Asn Phe Ser Lys
              165               170               175

Glu Ser Gly Ile Val Phe Ile Pro Gly Arg
              180               185
```

<210> SEQ ID NO 184
<211> LENGTH: 186
<212> TYPE: PRT
<213> ORGANISM: Arachis duranensis

<400> SEQUENCE: 184

```
Lys Cys Leu Lys Gly Cys Asp Leu Ala Ile Ala Ser Tyr Phe Val Tyr
1               5                 10                15

Pro Gly Val Met Leu Gly Ser Ile Ala Ser Phe Met His Ser Asn Val
              20                25                30

Val Pro Asn Ser Asn Val Ile Ile Ser Tyr Asn Lys Asp Lys Met Pro
              35                40                45

Asn Asn Leu Pro Val Ser Phe Ser Arg Ile Asn Ile Pro Phe Pro Cys
```

-continued

```
             50                    55                    60

Asp Cys Ile Asn Gly Glu Phe Leu Gly His Val Phe Glu Tyr Ser Ala
65                  70                  75                  80

Ile Glu Gly Asp Thr Tyr Asp Leu Ile Ala Asn Leu Arg Tyr Ser Asp
                85                  90                  95

Leu Thr Thr Val Glu Ile Leu Gln Arg Phe Asn Asn Tyr Asp Pro Asn
            100                 105                 110

His Val Pro Val Asn Ala Lys Val Asn Val Thr Val Asn Cys Ser Cys
        115                 120                 125

Gly Asn Ser Asn Val Ser Lys Asp Tyr Gly Leu Phe Val Thr Phe Pro
        130                 135                 140

Leu Ser Glu Gly Asn Thr Leu Leu Gln Ile Ala Asn Gln Thr Lys Leu
145                 150                 155                 160

Asp Pro Lys Leu Leu Gln Ser Tyr Asn Pro Gly Val Asn Phe Asn Gln
            165                 170                 175

Thr Arg Gly Ile Val Phe Ile Pro Ala Arg
            180                 185

<210> SEQ ID NO 185
<211> LENGTH: 186
<212> TYPE: PRT
<213> ORGANISM: Arachis ipaensis

<400> SEQUENCE: 185

Lys Cys Leu Lys Gly Cys Asp Leu Ala Ile Ala Ser Tyr Phe Val Tyr
1               5                   10                  15

Pro Lys Val Met Leu Gly Ser Ile Ala Ser Phe Met His Ser Asn Val
            20                  25                  30

Val Pro Asn Ser Asn Val Ile Ile Ser Tyr Asn Lys Asp Lys Met Pro
        35                  40                  45

Asn Asn Leu Pro Val Ser Phe Thr Arg Ile Asn Ile Pro Phe Pro Cys
        50                  55                  60

Asp Cys Ile Asn Gly Glu Phe Leu Gly His Val Phe Glu Tyr Ser Ala
65                  70                  75                  80

Ile Glu Gly Asp Thr Tyr Asp Leu Ile Ala Asn Met Arg Tyr Ser Asp
                85                  90                  95

Leu Thr Thr Val Glu Ile Leu Gln Arg Phe Asn Asn Tyr Asp Pro Asn
            100                 105                 110

His Val Pro Val Asn Ala Lys Val Asn Val Thr Val Asn Cys Ser Cys
        115                 120                 125

Gly Asn Ser Asn Val Ser Lys Asp Tyr Gly Leu Phe Val Thr Phe Pro
        130                 135                 140

Leu Ser Glu Gly Asn Thr Leu Leu Gln Ile Ala Asn Gln Thr Lys Leu
145                 150                 155                 160

Asp Pro Lys Leu Leu Gln Gly Tyr Asn Pro Gly Val Asn Phe Asn Gln
            165                 170                 175

Thr Arg Gly Ile Val Phe Ile Pro Gly Arg
            180                 185

<210> SEQ ID NO 186
<211> LENGTH: 188
<212> TYPE: PRT
<213> ORGANISM: Chamaecrista fasciculata

<400> SEQUENCE: 186

Met Cys Ile Lys Gly Cys Asp Leu Ala Leu Ala Ser Tyr Tyr Ile Pro
```

-continued

```
1               5                   10                  15
Leu Phe Phe Thr Leu Gln Asn Leu Thr Ile Leu Leu Gln Ser Lys Val
            20                  25                  30

Leu Ser Asp Tyr Gln Val Ile Ala Ser Phe Asn Lys Asp Ser Ile Phe
            35                  40                  45

Asn Gly Val Asn Ile Lys Ser Tyr Gln Ser Ile Asn Val Pro Phe Pro
    50                  55                  60

Cys Asp Cys Ile Asp Gly Asp Phe Leu Gly His Val Phe Glu Tyr Thr
65                  70                  75                  80

Ile Ala Asn Gly Asp Thr Tyr Glu Arg Ile Ala Ser Arg Lys Tyr Ala
                85                  90                  95

Met Leu Thr Ser Val Glu Leu Leu Lys Lys Tyr Asn Asn Tyr Ser Asp
            100                 105                 110

Pro Asn His Leu Pro Ile Asn Gly Lys Leu Asn Val Thr Val Asn Cys
            115                 120                 125

Tyr Cys Gly Asp Arg Gln Ile Ser Lys Asp Tyr Gly Leu Phe Val Thr
    130                 135                 140

Tyr Pro Leu Arg Asp Gly Asp Ser Leu Gln Thr Ile Ala Glu Lys Thr
145                 150                 155                 160

Asn Leu Asp Leu Gly Leu Leu Glu Arg Tyr Asn Gln Gly Met Asn Phe
            165                 170                 175

Ser Gln Gly Ser Gly Leu Val Phe Tyr Pro Gly Lys
            180                 185
```

```
<210> SEQ ID NO 187
<211> LENGTH: 189
<212> TYPE: PRT
<213> ORGANISM: Mimosa pudica

<400> SEQUENCE: 187
```

```
Lys Cys His Lys Gly Cys Pro Leu Ala Leu Ala Ser Tyr Leu Cys His
1               5                   10                  15

Gln Asn Ile Thr Leu Ser Asn Ile Thr His Leu Leu Lys Ser Asn Leu
            20                  25                  30

Val Ser Leu Asp Phe Gln Ile Ile Ser Ser Tyr Asn Lys Glu Gly Ile
            35                  40                  45

Val Pro Asn Asn Ile Gln Phe Phe Thr Arg Ile Asn Ile Pro Phe Pro
    50                  55                  60

Cys Glu Cys Ile Asn Asn Asp Asp Phe Leu Gly His Val Phe Glu Tyr
65                  70                  75                  80

Thr Ile Ser Lys Gly Asp Thr Tyr His Ser Ile Ala Thr Gln Thr Tyr
                85                  90                  95

Ser Ser Leu Thr Ser Val Asp Leu Leu Arg Arg Phe Asn Asn Tyr Ser
            100                 105                 110

Asp Pro Asn Gln Leu Pro Pro Asn Gly Lys Leu Asn Val Thr Val Lys
            115                 120                 125

Cys Ser Cys Gly Asn Arg Gln Ile Ser Lys Asp Tyr Gly Leu Phe Ile
    130                 135                 140

Thr Tyr Pro Leu Gly Phe Glu Asp Ser Leu Glu Ser Ile Val Asn Gln
145                 150                 155                 160

Thr Gly Ile Asp Ala Leu Leu Leu Gln Ser Tyr Asn Pro Gly Ala Asn
            165                 170                 175

Phe Ser Gln Gln Ser Gly Val Val Phe Ile Pro Gly Arg
            180                 185
```

-continued

<210> SEQ ID NO 188
<211> LENGTH: 189
<212> TYPE: PRT
<213> ORGANISM: Lupinus albus

<400> SEQUENCE: 188

```
Lys Cys Ile Lys Gly Cys Asp Ile Ala Leu Ala Ser Tyr Tyr Val Pro
1               5                   10                  15

Val Trp Pro Thr Val Ser Leu Gly Asn Ile Thr Asn Tyr Met Tyr Ser
            20                  25                  30

Asn Val Leu Thr Lys Ser Asn Val Ile Ile Ser Tyr Asn Lys Asp Lys
        35                  40                  45

Val Phe Asn Gly Asp Val Met Leu Ala Leu Tyr Arg Thr Asn Ile Pro
    50                  55                  60

Ile Pro Cys Asp Cys Ile Gly Gly Glu Phe Leu Gly His Val Phe Glu
65                  70                  75                  80

Tyr Thr Ala Val Ala Gly Asp Thr Tyr Asp Leu Ile Ala Met Lys Arg
                85                  90                  95

Tyr Ser Asn Leu Thr Thr Val Glu Phe Leu Lys Arg Phe Asn Ser Tyr
            100                 105                 110

Asp Pro Asn His Ile Pro Val Asn Ala Lys Val Asn Val Thr Val Asn
        115                 120                 125

Cys Ser Cys Gly Asn Ser Leu Ile Ser Lys Asp Tyr Gly Leu Phe Ile
    130                 135                 140

Thr Tyr Pro Leu Arg Pro Gly Asn Asn Leu Gln Glu Leu Ser Lys Glu
145                 150                 155                 160

Thr Asn Ile Asp Ala Lys Leu Leu Gln Ser Tyr Asn Pro Ser Val Asn
                165                 170                 175

Phe Ser Gln Glu Asn Gly Ile Val Phe Ile Pro Gly Arg
            180                 185
```

<210> SEQ ID NO 189
<211> LENGTH: 187
<212> TYPE: PRT
<213> ORGANISM: Spatholobus suberectus

<400> SEQUENCE: 189

```
Lys Cys Val Lys Gly Cys Asp Val Ala Leu Ala Ser Tyr Tyr Val Ser
1               5                   10                  15

Pro Gly Tyr Phe Pro Leu Glu Asn Ile Thr Arg Leu Met Glu Ser Ser
            20                  25                  30

Val Leu Ser Asn Ser Asp Val Val Thr Ser Tyr Asn Lys Asp Lys Ile
        35                  40                  45

Phe Asn Asp Met Val Gln Ser Phe Val Arg Leu Asn Ile Pro Phe Ser
    50                  55                  60

Cys Gly Cys Ile Gly Gly Glu Phe Leu Gly His Val Phe Glu Tyr Ser
65                  70                  75                  80

Ala Ala Ala Gly Asp Thr Tyr Asp Ser Ile Ala Lys Val Thr Tyr Ala
                85                  90                  95

Asn Leu Thr Thr Val Glu Leu Leu Arg Arg Phe Asn Ser Tyr Asp Gln
            100                 105                 110

Asn Asp Ile Pro Ala Asn Ala Lys Leu Asn Val Thr Val Asn Cys Ser
        115                 120                 125

Cys Gly Asn Ser Gln Val Ser Lys Asp Tyr Gly Leu Phe Ile Thr Tyr
    130                 135                 140
```

-continued

```
Pro Leu Arg Pro Gly Asn Asn Leu His Asp Ile Ala Asn Glu Thr Gln
145             150             155             160

Leu Asp Ala Gln Leu Leu Gln Ser Tyr Asn Pro Gly Val Asn Phe Ser
                165             170             175

Gln Glu Ser Gly Ile Val Phe Ile Pro Gly Arg
            180             185
```

```
<210> SEQ ID NO 190
<211> LENGTH: 189
<212> TYPE: PRT
<213> ORGANISM: Prosopis alba

<400> SEQUENCE: 190

Lys Cys Leu Gln Gly Cys Pro Leu Ala Leu Ala Ser Tyr Tyr Ala Tyr
1               5               10              15

Lys Asn Asn Leu Gly Asn Ile Thr Lys Phe Leu Arg Ser Asp Leu Val
                20              25              30

Ser Asp Phe Gly Val Val Ser Ser Tyr Asn Glu Gly Lys Val Ser Asn
        35              40              45

Asn Gly Met Tyr Val Gln Ser Leu Thr Arg Ile Asn Ile Pro Phe Pro
    50              55              60

Cys Asp Cys Ile Asn Asn Gly Asp Phe Leu Gly His Val Phe Glu Tyr
65              70              75              80

Thr Ile Ala Glu Gly Asp Thr Tyr Asp Ser Ile Ala Thr Gln Thr Tyr
                85              90              95

Ser Ser Leu Thr Thr Val Asp Leu Leu Arg Arg Phe Asn Ser Tyr Lys
            100             105             110

Asp Pro Asn Gln Leu Pro Leu Asn Gly Lys Leu Asn Val Thr Val Asn
        115             120             125

Cys Ser Cys Gly Asp Arg Gln Ile Ser Lys Asp Tyr Gly Leu Phe Leu
    130             135             140

Thr Tyr Pro Leu Arg Phe Gly Asp Ser Leu Glu Ser Ile Val Asp Gln
145             150             155             160

Thr Gly Ile Asp Ala Thr Leu Leu Gln Lys Tyr Asn Leu Arg Val Asn
                165             170             175

Phe Ser Gln Glu Ser Gly Val Val Phe Ile Pro Gly Arg
            180             185
```

```
<210> SEQ ID NO 191
<211> LENGTH: 186
<212> TYPE: PRT
<213> ORGANISM: Lotus japonicus

<400> SEQUENCE: 191

Lys Cys Thr His Gly Cys Ala Leu Ala Gln Ala Ser Tyr Tyr Leu Leu
1               5               10              15

Asn Gly Ser Asn Leu Thr Tyr Ile Ser Glu Ile Met Gln Ser Ser Leu
                20              25              30

Leu Thr Lys Pro Glu Asp Ile Val Ser Tyr Asn Gln Asp Thr Ile Ala
            35              40              45

Ser Lys Asp Ser Val Gln Ala Gly Gln Arg Ile Asn Val Pro Phe Pro
    50              55              60

Cys Asp Cys Ile Glu Gly Glu Phe Leu Gly His Thr Phe Gln Tyr Asp
65              70              75              80

Val Gln Lys Gly Asp Arg Tyr Asp Thr Ile Ala Gly Thr Asn Tyr Ala
                85              90              95
```

-continued

```
Asn Leu Thr Thr Val Glu Trp Leu Arg Arg Phe Asn Ser Tyr Pro Pro
            100                 105                 110

Asp Asn Ile Pro Asp Thr Gly Thr Leu Asn Val Thr Val Asn Cys Ser
            115                 120                 125

Cys Gly Asp Ser Gly Val Gly Asp Tyr Gly Leu Phe Val Thr Tyr Pro
            130                 135                 140

Leu Arg Pro Gly Glu Thr Leu Gly Ser Val Ala Ser Asn Val Lys Leu
145                 150                 155                 160

Asp Ser Ala Leu Leu Gln Lys Tyr Asn Pro Asn Val Asn Phe Asn Gln
                165                 170                 175

Gly Ser Gly Ile Val Tyr Ile Pro Ala Lys
            180                 185
```

```
<210> SEQ ID NO 192
<211> LENGTH: 186
<212> TYPE: PRT
<213> ORGANISM: Phaseolus vulgaris

<400> SEQUENCE: 192
```

```
Ala Cys Lys Glu Gly Cys Pro Leu Ala Leu Gly Ser Tyr Tyr Met Trp
1               5                   10                  15

Gln Asn Ser Asn Leu Thr Tyr Ile Ser Gln Ile Met Ala Ser Ser Leu
                20                  25                  30

Leu Thr Thr Ala Asp Asp Ile Val Leu Tyr Asn Lys Asp Thr Ile Pro
            35                  40                  45

Asn Lys Asp Ser Val Gln Ala Phe Ile Arg Val Asn Val Pro Phe Pro
        50                  55                  60

Cys Asp Cys Ile Asp Gly Gln Phe Leu Ala His Thr Phe Lys Tyr Asp
65                  70                  75                  80

Val Gln Ser Gln Asp Ser Tyr Glu Tyr Val Ala Arg Thr Val Tyr Ser
                85                  90                  95

Asn Leu Thr Asp Val Ala Trp Leu Arg Asn Phe Asn Ser Tyr Glu Pro
            100                 105                 110

Asp Asn Ile Pro Asp Thr Ala Thr Leu Asn Val Thr Val Asn Cys Ser
            115                 120                 125

Cys Gly Asn Ser Asp Val Ala Asp Tyr Gly Leu Phe Ile Thr Tyr Pro
            130                 135                 140

Leu Arg Thr Gly Glu Thr Leu Gly Ser Val Ala Ala Ala Val Ser Leu
145                 150                 155                 160

Asp Ser Gly Leu Leu Gln Arg Tyr Asn Pro Gly Val Asn Phe Asn Gln
                165                 170                 175

Gly Ser Gly Leu Val Tyr Ile Pro Gly Lys
            180                 185
```

```
<210> SEQ ID NO 193
<211> LENGTH: 186
<212> TYPE: PRT
<213> ORGANISM: Arachis ipaensis

<400> SEQUENCE: 193
```

```
Gln Cys Ser Lys Gly Cys Pro Leu Ala Leu Ala Ser Tyr Tyr Met Trp
1               5                   10                  15

Thr Gly Ser Asn Leu Thr Tyr Val Ser Gln Ile Met Lys Ser Asn Val
                20                  25                  30

Leu Ser Asp Pro Asn Gly Ile Val Asn Tyr Asn Lys Asp Thr Ile Pro
            35                  40                  45
```

-continued

```
Asn Lys Asp Ser Val Gln Ala Phe Ile Arg Val Asn Val Pro Phe Pro
    50                  55                  60

Cys Asp Cys Ile Asn Gly Glu Phe Leu Gly His Thr Phe Lys Tyr Asp
65                  70                  75                  80

Ile Gln Ser Gly Asp Thr Tyr Glu His Val Ala Thr Asn Asn Tyr Ala
                85                  90                  95

Asn Leu Thr Asn Val Asn Trp Leu Arg Lys Phe Asn Thr Tyr Pro Pro
                100                 105                 110

Asn Asn Ile Pro Asn Thr Gly Thr Leu Asn Val Thr Val Asn Cys Ser
                115                 120                 125

Cys Gly Asn Arg Gln Val Ala Asn Tyr Gly Leu Phe Ile Thr Tyr Pro
    130                 135                 140

Leu Arg Pro Gly Asp Thr Leu Gln Ala Val Ala Lys Asn Gln Ser Val
145                 150                 155                 160

Asp Ala Phe Leu Leu Gln Lys Tyr Asn Pro Ser Val Asn Phe Asn Gln
                165                 170                 175

Gly Ser Gly Leu Val Tyr Ile Pro Gly Lys
                180                 185

<210> SEQ ID NO 194
<211> LENGTH: 186
<212> TYPE: PRT
<213> ORGANISM: Arachis duranensis

<400> SEQUENCE: 194

Gln Cys Ser Lys Gly Cys Pro Leu Ala Leu Ala Ser Tyr Tyr Met Trp
1               5                   10                  15

Thr Gly Ser Asn Leu Thr Tyr Val Ser Glu Ile Met Lys Ser Asn Val
                20                  25                  30

Leu Ser Asp Pro Asn Asp Ile Val Asn Tyr Asn Lys Asp Thr Ile Pro
                35                  40                  45

Asn Lys Asp Ser Val Gln Ala Ser Ile Arg Val Asn Val Pro Phe Pro
    50                  55                  60

Cys Asp Cys Ile Asn Gly Glu Phe Leu Gly His Thr Phe Gln Tyr Asp
65                  70                  75                  80

Ile Gln Ser Gly Asp Thr Tyr Glu His Val Ala Thr Asn Asn Tyr Ala
                85                  90                  95

Asn Leu Thr Asn Val Asn Trp Leu Arg Lys Phe Asn Ser Tyr Pro Pro
                100                 105                 110

Asn Asn Ile Pro Asp Thr Gly Thr Leu Asn Val Thr Val Asn Cys Ser
                115                 120                 125

Cys Gly Asn Arg Gln Val Ala Asn Tyr Gly Leu Phe Ile Thr Tyr Pro
    130                 135                 140

Leu Arg Pro Gly Asp Thr Leu Gln Ala Val Ala Lys Asn Gln Ser Val
145                 150                 155                 160

Asp Ala Phe Leu Leu Gln Lys Tyr Asn Pro Ser Val Asn Phe Asn Gln
                165                 170                 175

Gly Ser Gly Leu Val Tyr Ile Pro Gly Lys
                180                 185

<210> SEQ ID NO 195
<211> LENGTH: 186
<212> TYPE: PRT
<213> ORGANISM: Cajanus cajan

<400> SEQUENCE: 195
```

```
Ala Cys Lys Gln Gly Cys Pro Val Ala Leu Gly Ser Tyr Tyr Met Trp
1               5                   10                  15

Ser Gly Ser Lys Leu Thr Tyr Ile Ser Gln Ile Met Pro Ser Ala Leu
            20                  25                  30

Leu Thr Lys Pro Glu Asp Ile Val Ala Tyr Asn Lys Asp Thr Val Pro
            35                  40                  45

Asn Lys Asp Ser Val Gln Ala Phe Ile Arg Val Asn Val Pro Phe Pro
        50                  55                  60

Cys Asp Cys Val Asp Gln Gln Phe Leu Ala His Thr Phe Gln Tyr Asp
65                  70                  75                  80

Val Gln Ser Gln Asp Thr Tyr Asp Tyr Val Ala Arg Thr Val Phe Ala
                85                  90                  95

Asn Leu Thr Asp Val Ala Trp Leu Arg Arg Phe Asn Ser Tyr Ala Pro
            100                 105                 110

Asp Asn Ile Pro Asp Thr Gly Thr Leu Asn Val Thr Val Asn Cys Ser
        115                 120                 125

Cys Gly Asn Ser Asp Val Gly Gly Tyr Gly Leu Phe Val Thr Tyr Pro
        130                 135                 140

Leu Arg Pro Gly Asp Thr Leu Gly Ser Val Ala Ser Ser Val Gly Leu
145                 150                 155                 160

Asp Ser Gly Leu Leu Gln Arg Tyr Asn Pro Gly Val Asn Phe Asn Gln
                165                 170                 175

Gly Thr Gly Leu Val Tyr Ile Pro Gly Lys
            180                 185

<210> SEQ ID NO 196
<211> LENGTH: 186
<212> TYPE: PRT
<213> ORGANISM: Cicer arietinum

<400> SEQUENCE: 196

Lys Cys Thr Lys Gly Cys Ser Pro Ala Leu Ala Ser Tyr Tyr Leu Asn
1               5                   10                  15

Ser Gly Ala Asn Leu Thr His Ile Ser Gly Ile Phe Ser Ser Ser Ile
            20                  25                  30

Leu Thr Lys Pro Glu Asp Ile Val Asp Tyr Asn Gln Asp Thr Ile Ala
            35                  40                  45

Asn Lys Asp Thr Ile Ile Ala Gly Lys Arg Ile Asn Ile Pro Phe Pro
        50                  55                  60

Cys Asp Cys Ile Ala Gly Glu Phe Leu Ala His Thr Phe Ser Tyr Asp
65                  70                  75                  80

Val Gln Thr Gly Asp Thr Tyr Glu Thr Val Ala Thr Asn Asn Tyr Ala
                85                  90                  95

Asn Leu Thr Asn Val Gln Trp Leu Gln Arg Phe Asn Ser Tyr Pro Ala
            100                 105                 110

Asn Asn Ile Pro Asp Thr Gly Thr Leu Asn Val Thr Val Asn Cys Ser
        115                 120                 125

Cys Gly Asn Ser Asp Val Ala Asn Tyr Gly Leu Phe Leu Thr Tyr Pro
        130                 135                 140

Leu Arg Pro Gly Glu Thr Leu Gly Ser Val Ala Asn Ser Ser Asn Ile
145                 150                 155                 160

Asp Ser Ser Leu Leu Arg Ser Tyr Asn Pro Gly Val Asn Phe Asn Gln
                165                 170                 175

Gly Ser Gly Leu Val Phe Ile Pro Gly Lys
            180                 185
```

-continued

<210> SEQ ID NO 197
<211> LENGTH: 186
<212> TYPE: PRT
<213> ORGANISM: Abrus precatorius

<400> SEQUENCE: 197

```
Lys Cys Thr Glu Gly Cys Pro Leu Ala Leu Ala Ser Tyr Phe Leu Trp
1               5                   10                  15

Arg Gly Ser Asn Leu Thr Tyr Val Ser Gln Ile Met Ala Ser Asn Val
            20                  25                  30

Leu Thr Arg Pro Glu Asp Ile Val Ser Tyr Asn Lys Asp Thr Val Pro
        35                  40                  45

Asn Lys Asp Ser Ile Gln Ala Leu Ser Arg Val Asn Val Pro Phe Pro
    50                  55                  60

Cys Asp Cys Ile Asn Gly Glu Phe Leu Gly Tyr Thr Phe Lys Tyr Asp
65                  70                  75                  80

Val Gln Thr Gly Asp Thr Tyr Glu Thr Val Ala Gly Thr Asn Tyr Ala
                85                  90                  95

Asn Leu Thr Asn Val Ala Trp Leu Arg Arg Phe Asn Ser Tyr Pro Pro
            100                 105                 110

Asn Asn Ile Pro Asp Thr Gly Thr Leu Asn Val Thr Val Asn Cys Ser
        115                 120                 125

Cys Gly Met Ser Glu Val Ser Asn Tyr Gly Leu Phe Ile Thr Tyr Pro
    130                 135                 140

Leu Arg Pro Gly Glu Thr Leu Gly Thr Val Ala Ser Ser Val Gly Leu
145                 150                 155                 160

Asp Ser Ala Leu Leu Gln Ser Tyr Asn Pro Ser Val Asn Phe Asn Gln
                165                 170                 175

Gly Ser Gly Leu Val Phe Ile Pro Gly Lys
            180                 185
```

<210> SEQ ID NO 198
<211> LENGTH: 186
<212> TYPE: PRT
<213> ORGANISM: Medicago truncatula

<400> SEQUENCE: 198

```
Lys Cys Thr Lys Gly Cys Ser Leu Ala Leu Ala Asn Phe Tyr Val Ser
1               5                   10                  15

Gln Gly Ser Asn Leu Thr Tyr Ile Ser Ser Ile Met Arg Ser Asn Ile
            20                  25                  30

Gln Thr Arg Pro Glu Asp Ile Val Glu Tyr Ser Arg Glu Ile Ile Pro
        35                  40                  45

Ser Lys Asp Ser Val Gln Ala Gly Gln Arg Leu Asn Val Pro Phe Pro
    50                  55                  60

Cys Asp Cys Ile Asp Gly Gln Phe Leu Gly His Lys Phe Ser Tyr Asp
65                  70                  75                  80

Val Glu Thr Gly Asp Thr Tyr Glu Thr Val Ala Thr Asn Asn Tyr Ala
                85                  90                  95

Asn Leu Thr Asn Val Glu Trp Leu Arg Arg Phe Asn Thr Tyr Pro Pro
            100                 105                 110

Asn Asp Ile Pro Asp Thr Gly Thr Leu Asn Val Thr Val Asn Cys Ser
        115                 120                 125

Cys Gly Asp Ala Asp Val Gly Asn Tyr Ala Leu Phe Val Thr Tyr Pro
    130                 135                 140
```

Leu Arg Pro Gly Glu Thr Leu Val Ser Val Ala Asn Ser Ser Lys Val
145                 150                 155                 160

Asp Ser Ser Leu Leu Gln Arg Tyr Asn Pro Gly Val Asn Phe Asn Gln
                165                 170                 175

Gly Ser Gly Ile Val Phe Val Pro Gly Lys
            180                 185

<210> SEQ ID NO 199
<211> LENGTH: 186
<212> TYPE: PRT
<213> ORGANISM: Glycine max

<400> SEQUENCE: 199

Ala Cys Lys Glu Gly Cys Gly Val Ala Leu Gly Ser Tyr Tyr Leu Trp
1               5                   10                  15

Arg Gly Ser Asn Leu Thr Tyr Ile Ser Ser Ile Met Ala Ser Ser Leu
                20                  25                  30

Leu Thr Thr Pro Asp Asp Ile Val Asn Tyr Asn Lys Asp Thr Val Pro
            35                  40                  45

Ser Lys Asp Ile Ile Ile Ala Asp Gln Arg Val Asn Val Pro Phe Pro
        50                  55                  60

Cys Asp Cys Ile Asp Gly Gln Phe Leu Gly His Thr Phe Arg Tyr Asp
65                  70                  75                  80

Val Gln Ser Gln Asp Thr Tyr Glu Thr Val Ala Arg Ser Trp Phe Ala
                85                  90                  95

Asn Leu Thr Asp Val Ala Trp Leu Arg Arg Phe Asn Thr Tyr Pro Pro
                100                 105                 110

Asp Asn Ile Pro Asp Thr Gly Thr Leu Asn Val Thr Val Asn Cys Ser
            115                 120                 125

Cys Gly Asn Thr Asp Val Ala Asn Tyr Gly Leu Phe Val Thr Tyr Pro
        130                 135                 140

Leu Arg Ile Gly Asp Thr Leu Gly Ser Val Ala Ala Asn Leu Ser Leu
145                 150                 155                 160

Asp Ser Ala Leu Leu Gln Arg Tyr Asn Pro Asp Val Asn Phe Asn Gln
                165                 170                 175

Gly Thr Gly Leu Val Tyr Val Pro Gly Lys
            180                 185

<210> SEQ ID NO 200
<211> LENGTH: 186
<212> TYPE: PRT
<213> ORGANISM: Glycine max

<400> SEQUENCE: 200

Lys Cys Ser Arg Gly Cys Asp Leu Ala Leu Ala Ser Tyr Tyr Leu Ser
1               5                   10                  15

Gln Gly Asp Leu Thr Tyr Val Ser Lys Leu Met Glu Ser Glu Val Val
                20                  25                  30

Ser Lys Pro Glu Asp Ile Leu Ser Tyr Asn Thr Asp Thr Ile Thr Asn
            35                  40                  45

Lys Asp Leu Leu Pro Ala Ser Ile Arg Val Asn Val Pro Phe Pro Cys
        50                  55                  60

Asp Cys Ile Asp Glu Glu Phe Leu Gly His Thr Phe Gln Tyr Asn Leu
65                  70                  75                  80

Thr Thr Gly Asp Thr Tyr Leu Ser Ile Ala Thr Gln Asn Tyr Ser Asn
                85                  90                  95

-continued

```
Leu Thr Thr Ala Glu Trp Leu Arg Ser Phe Asn Arg Tyr Leu Pro Ala
            100                 105                 110

Asn Ile Pro Asp Ser Gly Thr Leu Asn Val Thr Ile Asn Cys Ser Cys
            115                 120                 125

Gly Asn Ser Glu Val Ser Lys Asp Tyr Gly Leu Phe Ile Thr Tyr Pro
            130                 135                 140

Leu Arg Pro Glu Asp Ser Leu Gln Ser Ile Ala Asn Glu Thr Gly Val
145                 150                 155                 160

Asp Arg Asp Leu Leu Val Lys Tyr Asn Pro Gly Val Asn Phe Ser Gln
                165                 170                 175

Gly Ser Gly Leu Val Tyr Ile Pro Gly Lys
            180                 185
```

```
<210> SEQ ID NO 201
<211> LENGTH: 186
<212> TYPE: PRT
<213> ORGANISM: Lupinus angustifolius

<400> SEQUENCE: 201
```

```
Lys Cys Thr Gln Gly Cys Ser Leu Ala Leu Ala Ser Tyr Tyr Met Tyr
1               5                   10                  15

Ser Gly Ser Thr Leu Thr Ser Ile Ser Gln Val Met Ser Ser Gln Leu
            20                  25                  30

Leu Gln Ile Pro Glu Asp Ile Val Thr Tyr Asn Lys Asp Thr Ile Pro
            35                  40                  45

Asn Lys Asp Ser Val Gln Ala Phe Ile Arg Val Asn Val Pro Phe Pro
        50                  55                  60

Cys Asp Cys Ile Asp Gly Glu Phe Leu Gly His Met Phe Gln Tyr Asp
65                  70                  75                  80

Val Lys Thr Gly Asp Thr Tyr Gln Leu Val Ala Glu Thr Glu Tyr Ala
                85                  90                  95

Asn Leu Thr Asn Ile Asp Trp Leu Met Lys Phe Asn Ser Tyr Pro Ala
            100                 105                 110

Asn Asn Ile Pro Asp Thr Gly Thr Leu Asn Val Thr Val Asn Cys Ser
            115                 120                 125

Cys Gly Glu Lys Asn Val Ser Asn Tyr Gly Leu Phe Ile Thr Tyr Pro
        130                 135                 140

Leu Arg Pro Gly Asp Thr Leu Asp Ser Val Ser Lys Ser Val Asp Leu
145                 150                 155                 160

Asp Ser Gly Leu Leu Gln Arg Tyr Asn Pro Gly Val Asn Phe Asn Gln
                165                 170                 175

Gly Ser Gly Leu Val Tyr Ile Pro Gly Lys
            180                 185
```

```
<210> SEQ ID NO 202
<211> LENGTH: 180
<212> TYPE: PRT
<213> ORGANISM: Lupinus angustifolius

<400> SEQUENCE: 202
```

```
Lys Cys Thr Gln Gly Cys Pro Ile Ala Leu Ala Ser Tyr Tyr Met Leu
1               5                   10                  15

Ser Gly Ser Asn Leu Thr Tyr Ile Ser Gln Ile Met Ser Ser His Val
            20                  25                  30

Leu His Ser Pro Glu Asp Ile Val Ser Tyr Asn Lys Asp Lys Val Gln
            35                  40                  45
```

Pro Phe Thr Arg Val Asn Val Pro Phe Pro Cys Asp Cys Ile Lys Gly
    50              55              60

Glu Phe Leu Gly His Met Phe Gln Tyr Val Val Gln Thr Gly Asp Thr
65              70              75              80

Tyr Glu Thr Val Ala Gly Thr Asn Tyr Ala Asn Leu Thr Asn Val Glu
                85              90              95

Trp Leu Arg Arg Phe Asn Thr Tyr Leu Pro Asp Asn Ile Ser Ser Thr
            100             105             110

Gly Met Leu Asn Val Thr Val Asn Cys Ser Cys Gly Asn Ser Asp Val
        115             120             125

Ser Asp Tyr Glu Leu Phe Ile Thr Tyr Pro Leu Arg Pro Gly Glu Thr
    130             135             140

Leu Gly Ser Val Ala Lys Ser Val Lys Leu Asp Ser Gly Leu Leu Gln
145             150             155             160

Arg Tyr Asn Pro Ser Val Asn Phe Asn Gln Gly Ser Gly Leu Val Tyr
            165             170             175

Ile Pro Gly Lys
            180

<210> SEQ ID NO 203
<211> LENGTH: 186
<212> TYPE: PRT
<213> ORGANISM: Vigna angularis

<400> SEQUENCE: 203

Ala Cys Lys Lys Gly Cys Ser Leu Ala Leu Gly Ser Tyr Tyr Met Trp
1               5               10              15

Ser Gly Ser Asn Leu Thr Tyr Ile Ser Glu Val Met Ser Ser Ser Leu
            20              25              30

Leu Thr Thr Pro Asp Asp Ile Val Leu Tyr Asn Lys Asp Thr Ile Pro
        35              40              45

Asn Lys Asp Ser Val Gln Ala Phe Ile Arg Val Asn Val Pro Phe Pro
    50              55              60

Cys Asp Cys Ile Asp Gly Gln Phe Leu Gly His Thr Phe His Tyr Asp
65              70              75              80

Val Gln Thr Gln Asp Thr Tyr Glu Gln Val Ala Arg Thr Val Phe Ser
                85              90              95

Asn Leu Thr Asp Val Thr Trp Leu Arg Arg Phe Asn Ser Tyr Glu Pro
            100             105             110

Asp Asn Ile Pro Asp Thr Gly Thr Leu Asn Val Thr Val Asn Cys Ser
        115             120             125

Cys Gly Asn Thr Asp Val Ala Asp Tyr Gly Leu Phe Val Thr Tyr Pro
    130             135             140

Leu Arg Thr Gly Glu Thr Leu Gly Ser Val Ala Ser Asp Val Ser Leu
145             150             155             160

Asp Ser Gly Leu Leu Gln Arg Tyr Asn Pro Asp Val Asn Phe Asn Gln
            165             170             175

Gly Ser Gly Leu Val Tyr Ile Pro Gly Lys
            180             185

<210> SEQ ID NO 204
<211> LENGTH: 186
<212> TYPE: PRT
<213> ORGANISM: Vigna radiata

<400> SEQUENCE: 204

-continued

```
Ala Cys Lys Gln Gly Cys Pro Leu Ala Leu Gly Ser Tyr Tyr Met Trp
1               5                   10                  15

Ser Gly Ser Asn Leu Thr Tyr Ile Ser Glu Val Met Ser Ser Ser Leu
            20                  25                  30

Leu Thr Thr Pro Asp Asp Ile Val Leu Tyr Asn Lys Asp Thr Ile Pro
        35                  40                  45

Asn Lys Asp Ser Val Gln Ala Phe Ile Arg Val Asn Val Pro Phe Pro
    50                  55                  60

Cys Asp Cys Ile Asp Gly Gln Phe Leu Ala His Thr Phe Gln Tyr Asp
65                  70                  75                  80

Val Gln Thr Gln Asp Thr Tyr Glu Gln Val Ala Arg Val Val Phe Ser
                85                  90                  95

Asn Leu Thr Asp Val Thr Trp Leu Arg Arg Phe Asn Thr Tyr Glu Pro
            100                 105                 110

Asp Asn Ile Pro Asp Thr Gly Thr Leu Asn Val Thr Val Asn Cys Ser
        115                 120                 125

Cys Gly Asn Thr Asp Val Ala Asp Tyr Gly Leu Phe Ile Thr Tyr Pro
    130                 135                 140

Leu Arg Thr Gly Glu Thr Leu Gly Ser Val Ala Ser Asp Val Ser Leu
145                 150                 155                 160

Asp Ser Gly Leu Leu Gln Arg Tyr Asn Pro Asp Val Asn Phe Asn Gln
            165                 170                 175

Gly Ser Gly Leu Val Tyr Ile Pro Gly Lys
            180                 185
```

```
<210> SEQ ID NO 205
<211> LENGTH: 186
<212> TYPE: PRT
<213> ORGANISM: Vigna unguiculata

<400> SEQUENCE: 205

Ala Cys Arg Gln Gly Cys Ser Leu Ala Leu Gly Ser Tyr Tyr Met Trp
1               5                   10                  15

Ser Gly Ser Asn Leu Thr Tyr Ile Ser Glu Val Met Ser Ser Pro Leu
            20                  25                  30

Leu Thr Thr Pro Asp Asp Ile Val Leu Tyr Asn Lys Asp Thr Ile Pro
        35                  40                  45

Asn Lys Asp Ser Val Gln Ala Phe Ile Arg Val Asn Val Pro Phe Pro
    50                  55                  60

Cys Asp Cys Ile Asp Gly Gln Phe Leu Ala His Thr Phe Gln Tyr Asp
65                  70                  75                  80

Val Gln Thr Gln Asp Thr Tyr Glu Tyr Val Ala Arg Thr Val Phe Ser
                85                  90                  95

Asn Leu Thr Asp Val Thr Trp Leu Arg Arg Phe Asn Ser Tyr Glu Pro
            100                 105                 110

Asn Asn Ile Pro Asp Thr Gly Thr Leu Asn Val Thr Val Asn Cys Ser
        115                 120                 125

Cys Gly Asn Thr Asp Val Ala Asp Tyr Gly Leu Phe Ile Thr Tyr Pro
    130                 135                 140

Leu Arg Thr Gly Glu Thr Leu Gly Ser Val Ala Ala Asp Val Ser Leu
145                 150                 155                 160

Asp Ser Gly Leu Leu Gln Arg Tyr Asn Pro Asp Val Asn Phe Asn Gln
            165                 170                 175

Gly Ser Gly Leu Val Tyr Ile Pro Gly Lys
```

-continued

```
        180                 185
```

```
<210> SEQ ID NO 206
<211> LENGTH: 186
<212> TYPE: PRT
<213> ORGANISM: Arachis hypogaea

<400> SEQUENCE: 206

Gln Cys Ser Lys Gly Cys Pro Leu Ala Leu Ala Ser Tyr Tyr Met Trp
1               5                   10                  15

Thr Gly Ser Asn Leu Thr Tyr Val Ser Glu Ile Met Lys Ser Asn Val
            20                  25                  30

Leu Ser Asp Pro Asn Asp Ile Val Asn Tyr Asn Lys Asp Thr Ile Pro
        35                  40                  45

Asn Lys Asp Ser Val Gln Ala Ser Ile Arg Val Asn Val Pro Phe Pro
    50                  55                  60

Cys Asp Cys Ile Asn Gly Glu Phe Leu Gly His Thr Phe Gln Tyr Asp
65                  70                  75                  80

Ile Gln Ser Gly Asp Thr Tyr Glu His Val Ala Thr Asn Asn Tyr Ala
                85                  90                  95

Asn Leu Thr Asn Val Asn Trp Leu Arg Lys Phe Asn Ser Tyr Pro Pro
            100                 105                 110

Asn Asn Ile Pro Asp Thr Gly Thr Leu Asn Val Thr Val Asn Cys Ser
            115                 120                 125

Cys Gly Asn Arg Gln Val Ala Asn Tyr Gly Leu Phe Ile Thr Tyr Pro
        130                 135                 140

Leu Arg Pro Gly Asp Thr Leu Gln Ala Val Ala Lys Asn Gln Ser Val
145                 150                 155                 160

Asp Ala Phe Leu Leu Gln Lys Tyr Asn Pro Ser Val Asn Phe Asn Gln
                165                 170                 175

Gly Ser Gly Leu Val Tyr Ile Pro Gly Lys
            180                 185
```

```
<210> SEQ ID NO 207
<211> LENGTH: 188
<212> TYPE: PRT
<213> ORGANISM: Mimosa pudica

<400> SEQUENCE: 207

Gln Cys Ser Glu Ser Cys Asp Thr Ala Leu Ala Ser Tyr Tyr Val Lys
1               5                   10                  15

Asn Gly Thr Asn Leu Thr Phe Ile Ser Lys Leu Met Thr Ser Lys Leu
            20                  25                  30

Val Ser Thr Pro Asp Asp Ile Val Ser Tyr Asn Lys Asp Lys Ile Pro
        35                  40                  45

Asn Lys Asp Ser Leu Ser Ala Ser Ile Arg Ile Asn Ile Pro Phe Pro
    50                  55                  60

Cys Asp Cys Ile Asn Gly Gln Phe Leu Gly His Met Phe Gln Tyr Asp
65                  70                  75                  80

Val Ala Thr Gly Asp Thr Tyr Asp Lys Ile Ala Ser Thr Asp Phe Ala
                85                  90                  95

Asn Leu Thr Thr Val Glu Trp Leu Gln Lys Phe Asn Ser Tyr Ala Ala
            100                 105                 110

Asp Asn Ile Pro Asp Thr Ala Thr Leu Asn Val Thr Val Asn Cys Ser
            115                 120                 125

Cys Gly Asn Arg Asp Val Ser Asp Asp Tyr Gly Leu Phe Ile Thr Tyr
```

-continued

```
              130                 135                 140

Pro Leu Leu Pro Gly Glu Thr Leu Gln Ser Val Ala Ser Glu Val Gly
145                 150                 155                 160

Phe Asn Asp Thr Gly Leu Leu Gln Arg Tyr Asn Pro Ser Val Asn Phe
                165                 170                 175

Asn Gln Gly Ser Gly Leu Val Phe Leu Pro Gly Lys
            180                 185

<210> SEQ ID NO 208
<211> LENGTH: 187
<212> TYPE: PRT
<213> ORGANISM: Chamaecrista fasciculata

<400> SEQUENCE: 208

Lys Cys Ser Glu Thr Cys Asn Leu Ala Leu Ala Ser Tyr Tyr Ile Gln
1               5                   10                  15

Asp Gly Ser Asn Leu Thr Tyr Ile Ser Thr Ile Leu Lys Ser Gln Leu
                20                  25                  30

Val Ser Ser Pro Asp Asp Ile Val Ser Tyr Asn Lys Asp Lys Ile Pro
            35                  40                  45

Asn Lys Asp Ser Val Pro Ser Asp Ile Arg Leu Asn Val Pro Phe Pro
        50                  55                  60

Cys Asp Cys Ile Glu Asp Glu Phe Leu Gly Tyr Asn Phe Leu Tyr Asp
65                  70                  75                  80

Val Gln Thr Gly Asp Thr Tyr Glu Arg Ile Ala Arg Thr Asn Phe Ala
                85                  90                  95

Asn Leu Thr Thr Val Asp Trp Leu Gln Lys Phe Asn Ser Tyr Pro Pro
                100                 105                 110

Asn Asn Ile Pro Asp Thr Gly Thr Leu Asn Val Thr Ile Asn Cys Ser
            115                 120                 125

Cys Gly Asn Arg Asp Val Ser Lys Asp Tyr Gly Leu Phe Ile Thr Tyr
        130                 135                 140

Pro Leu Met Pro Gly Gln Thr Leu Gln Ser Val Ala Gln Glu Val Asn
145                 150                 155                 160

Leu Asp Thr Gly Leu Leu Gln Arg Tyr Asn Pro Ser Val Asn Phe Asn
                165                 170                 175

Gln Gly Ser Gly Leu Val Tyr Ile Pro Gly Lys
            180                 185

<210> SEQ ID NO 209
<211> LENGTH: 186
<212> TYPE: PRT
<213> ORGANISM: Lupinus albus

<400> SEQUENCE: 209

Lys Cys Lys Gln Gly Cys Ser Leu Ala Leu Ala Ser Tyr Tyr Met Tyr
1               5                   10                  15

Ser Gly Ser Thr Leu Thr Ser Ile Ser Gln Val Met Ser Ser Gln Leu
                20                  25                  30

Leu Thr Val Pro Glu Asp Ile Val Thr Tyr Asn Lys Asp Thr Ile Pro
            35                  40                  45

Asn Lys Asp Ser Val Gln Ala Phe Ile Arg Val Asn Val Pro Phe Pro
        50                  55                  60

Cys Asp Cys Ile Asn Gly Glu Phe Leu Gly His Met Phe Arg Tyr Asp
65                  70                  75                  80

Val Lys Thr Asn Asp Thr Tyr Thr Ser Val Ala Glu Thr Glu Tyr Ala
```

-continued

```
                        85              90              95
Asn Leu Thr Asn Val Asn Trp Leu Met Lys Phe Asn Asn Tyr Pro Ala
                100             105             110

Ser Asn Ile Pro Asp Thr Gly Thr Leu Asn Val Thr Val Asn Cys Ser
            115             120             125

Cys Gly Glu Ser Ser Val Ser Asn Tyr Gly Leu Phe Ile Thr Tyr Pro
        130             135             140

Leu Arg Pro Gly Asp Thr Leu Asp Ser Val Ser Lys Ser Val Asn Leu
145             150             155             160

Asp Ser Gly Leu Leu Gln Ser Tyr Asn Pro Gly Val Asn Phe Asn Gln
                165             170             175

Gly Ser Gly Leu Val Tyr Ile Pro Gly Lys
            180             185

<210> SEQ ID NO 210
<211> LENGTH: 186
<212> TYPE: PRT
<213> ORGANISM: Pisum sativum

<400> SEQUENCE: 210

Lys Cys Thr Lys Gly Cys Ser Leu Ala Leu Ala Asn Phe Tyr Leu Ala
1               5               10              15

Ser Gly Thr Asn Leu Thr Tyr Val Ala Gly Ile Leu Lys Ser Pro Ile
                20              25              30

Leu Thr Lys Pro Glu Asp Ile Val Asp Tyr Asn Arg Asp Thr Val Pro
            35              40              45

Asn Lys Asp Ile Ile Leu Gly Gly Glu Arg Val Asn Ile Pro Phe Pro
        50              55              60

Cys Asp Cys Ile Asn Gly Asp Phe Leu Ala His Asn Phe Ser Tyr Asp
65              70              75              80

Val Gln Thr Gly Asp Thr Tyr Ala Ser Val Ala Gly Ser Asn Tyr Ala
                85              90              95

Asn Leu Thr Asn Val Gln Trp Leu Arg Asn Phe Asn Thr Tyr Pro Pro
                100             105             110

Asn Ser Ile Pro Asp Thr Gly Thr Leu Asn Val Met Ile Asn Cys Ser
            115             120             125

Cys Gly Asp Arg Glu Ile Ala Asp Tyr Gly Leu Phe Val Thr Tyr Pro
        130             135             140

Leu Arg Pro Gly Glu Thr Leu Gly Ser Val Ala Asn Ser Thr Lys Leu
145             150             155             160

Asp Ser Ala Leu Leu Gln Arg Tyr Asn Pro Gly Val Asn Phe Asn Gln
                165             170             175

Gly Ser Gly Leu Val Phe Ile Pro Gly Lys
            180             185

<210> SEQ ID NO 211
<211> LENGTH: 186
<212> TYPE: PRT
<213> ORGANISM: Arachis hypogaea

<400> SEQUENCE: 211

Gln Cys Ser Lys Gly Cys Pro Leu Ala Leu Ala Ser Tyr Tyr Met Trp
1               5               10              15

Thr Gly Ser Asn Leu Thr Tyr Val Ser Gln Ile Met Lys Ser Asn Val
                20              25              30

Leu Ser Asp Pro Asn Gly Ile Val Asn Tyr Asn Lys Asp Thr Ile Pro
```

-continued

```
            35                    40                    45

Asn Lys Asp Ser Val Gln Ala Phe Ile Arg Val Asn Val Pro Phe Pro
        50                    55                    60

Cys Asp Cys Ile Asn Gly Glu Phe Leu Gly His Thr Phe Lys Tyr Asp
65                    70                    75                    80

Ile Gln Ser Gly Asp Thr Tyr Glu His Val Ala Thr Asn Asn Tyr Ala
                    85                    90                    95

Asn Leu Thr Asn Val Asn Trp Leu Arg Lys Phe Asn Thr Tyr Pro Pro
                100                   105                   110

Asn Asn Ile Pro Asn Thr Gly Thr Leu Asn Val Thr Val Asn Cys Ser
                115                   120                   125

Cys Gly Asn Arg Gln Val Ala Asn Tyr Gly Leu Phe Ile Thr Tyr Pro
            130                   135                   140

Leu Arg Pro Gly Asp Thr Leu Gln Ala Val Ala Lys Asn Gln Ser Val
145                   150                   155                   160

Asp Ala Phe Leu Leu Gln Lys Tyr Asn Pro Ser Val Asn Phe Asn Gln
                165                   170                   175

Gly Ser Gly Leu Val Tyr Ile Pro Gly Lys
                180                   185
```

<210> SEQ ID NO 212
<211> LENGTH: 182
<212> TYPE: PRT
<213> ORGANISM: Spatholobus suberectus

<400> SEQUENCE: 212

```
Ser Cys Phe Thr Gly Cys Asn Leu Ala Leu Ala Ser Tyr Tyr Ile Trp
1                    5                    10                    15

Asn Gly Thr Asn Leu Thr Tyr Ile Ser Asn Leu Phe Gly Arg Pro Thr
                20                    25                    30

Ser Glu Ile Leu Lys Tyr Asn Pro Ser Val Glu Asn Pro Asp Val Ile
            35                    40                    45

Gln Ser Gln Thr Arg Ile Asn Val Pro Phe Thr Cys Asp Cys Leu Asn
        50                    55                    60

Gly Val Phe Leu Gly His Thr Phe Ser Phe Ala Thr Gln His Gly Asp
65                    70                    75                    80

Thr Tyr Lys Val Ile Ala Glu Val Gly Phe Ser Asn Leu Thr Thr Glu
                    85                    90                    95

Asp Trp Val Ser Arg Val Asn Arg Tyr Pro Pro Asn Gln Ile Pro Asp
                100                   105                   110

Asn Val Asn Ile Asn Val Thr Val Asn Cys Ser Cys Gly Asp Arg His
                115                   120                   125

Val Ser Lys Asp Tyr Gly Leu Phe Ala Thr Tyr Pro Leu Arg Val Gly
            130                   135                   140

Asp Asn Leu His Arg Ile Ala Ala Glu Ser Gly Val Pro Ala Glu Leu
145                   150                   155                   160

Leu Leu Arg Tyr Asn Pro Thr Ser Asp Phe Ser Ala Gly Asn Gly Leu
                165                   170                   175

Val Phe Val Pro Ala Lys
                180
```

<210> SEQ ID NO 213
<211> LENGTH: 187
<212> TYPE: PRT
<213> ORGANISM: Prosopis alba

<400> SEQUENCE: 213

```
Gln Cys Ser Glu Thr Cys Asp Phe Ala Leu Gly Ser Tyr Tyr Val Arg
1               5                   10                  15

Asn Gly Ser Asn Leu Thr Tyr Val Ser Lys Val Met Lys Ser Gln Leu
            20                  25                  30

Leu Ser Thr Pro Asp Asp Ile Val Asn Tyr Asn Lys Asp Lys Ile Pro
        35                  40                  45

Asn Lys Asp Ser Val Pro Ala Leu Thr Arg Val Asn Val Pro Phe Pro
    50                  55                  60

Cys Lys Cys Ile Asn Gly Glu Phe Leu Gly His Thr Phe Gln Tyr Val
65                  70                  75                  80

Val Glu Thr Gly Asp Thr Tyr Glu Lys Val Ala Val Thr Asn Tyr Ala
                85                  90                  95

Asn Leu Thr Thr Val Asp Trp Leu Arg Lys Phe Asn Ser Tyr Pro Pro
            100                 105                 110

Asp Asn Ile Pro Asp Thr Gly Thr Leu Asn Val Thr Val Asn Cys Ser
            115                 120                 125

Cys Gly Asn Ser Asp Val Ser Lys Asp Tyr Gly Leu Phe Ile Thr Tyr
    130                 135                 140

Pro Leu Arg Pro Gly Gln Thr Leu Gln Ser Val Ala Gly Glu Ala Gly
145                 150                 155                 160

Leu Asp Thr Gly Leu Leu Gln Arg Tyr Asn Pro Ser Val Asn Phe Asn
                165                 170                 175

Gln Gly Ser Gly Leu Val Tyr Ile Pro Gly Lys
            180                 185
```

<210> SEQ ID NO 214
<211> LENGTH: 7
<212> TYPE: PRT
<213> ORGANISM: Lotus japonicus

<400> SEQUENCE: 214

```
Gln Leu Gly Asp Ser Tyr Asp
1               5
```

<210> SEQ ID NO 215
<211> LENGTH: 2
<212> TYPE: PRT
<213> ORGANISM: Lotus japonicus

<400> SEQUENCE: 215

```
Gly Val
1
```

<210> SEQ ID NO 216
<211> LENGTH: 621
<212> TYPE: PRT
<213> ORGANISM: Medicago truncatula

<400> SEQUENCE: 216

```
Met Glu His Gln Pro Arg Phe Thr Ser Phe Ile Ser Leu Pro Leu Phe
1               5                   10                  15

Ser Ile Phe Leu Ala Ser Ile Pro Phe Ile Thr Glu Ser Lys Cys Thr
            20                  25                  30

Lys Gly Cys Ser Leu Ala Leu Ala Asn Phe Tyr Val Ser Gln Gly Ser
        35                  40                  45

Asn Leu Thr Tyr Ile Ser Ser Ile Met Arg Ser Asn Ile Gln Thr Arg
    50                  55                  60
```

-continued

```
Pro Glu Asp Ile Val Glu Tyr Ser Arg Glu Ile Ile Pro Ser Lys Asp
65                  70                  75                  80

Ser Val Gln Ala Gly Gln Arg Leu Asn Val Pro Phe Pro Cys Asp Cys
                85                  90                  95

Ile Asp Gly Gln Phe Leu Gly His Lys Phe Ser Tyr Asp Val Glu Thr
                100                 105                 110

Gly Asp Thr Tyr Glu Thr Val Ala Thr Asn Asn Tyr Ala Asn Leu Thr
                115                 120                 125

Asn Val Glu Trp Leu Arg Arg Phe Asn Thr Tyr Pro Pro Asn Asp Ile
    130                 135                 140

Pro Asp Thr Gly Thr Leu Asn Val Thr Val Asn Cys Ser Cys Gly Asp
145                 150                 155                 160

Ala Asp Val Gly Asn Tyr Ala Leu Phe Val Thr Tyr Pro Leu Arg Pro
                165                 170                 175

Gly Glu Thr Leu Val Ser Val Ala Asn Ser Ser Lys Val Asp Ser Ser
                180                 185                 190

Leu Leu Gln Arg Tyr Asn Pro Gly Val Asn Phe Asn Gln Gly Ser Gly
        195                 200                 205

Ile Val Phe Val Pro Gly Lys Asp Gln Asn Gly Ser Phe Val Phe Leu
    210                 215                 220

Gly Ser Ser Ser Gly Leu Gly Gly Gly Ala Ile Gly Gly Ile Ala Val
225                 230                 235                 240

Gly Ile Val Val Val Leu Leu Leu Val Ala Ala Ala Ile Tyr Phe Gly
                245                 250                 255

Tyr Phe Arg Lys Lys Lys Ile Gln Lys Glu Glu Leu Phe Ser Arg Asp
        260                 265                 270

Ser Thr Ala Leu Phe Ser Gln Asp Gly Lys Asp Glu Asn Ser His Gly
        275                 280                 285

Ala Ala Asn Val Thr Gln Arg Pro Gly Val Met Thr Gly Ile Thr Val
    290                 295                 300

Asp Lys Ser Val Glu Phe Ser Tyr Asp Glu Leu Ala Ala Ala Ser Asp
305                 310                 315                 320

Asn Phe Ser Met Ala Asn Lys Ile Gly Gln Gly Gly Phe Gly Ser Val
                325                 330                 335

Tyr Tyr Ala Glu Leu Arg Gly Glu Lys Ala Ala Ile Lys Lys Met Asp
                340                 345                 350

Met Gln Ala Thr Lys Glu Phe Leu Ala Glu Leu Lys Val Leu Thr Arg
        355                 360                 365

Val His His Leu Asn Leu Val Arg Leu Ile Gly Tyr Ser Ile Glu Gly
    370                 375                 380

Ser Leu Phe Leu Val Tyr Glu Tyr Ile Glu Asn Gly Asn Leu Ser Gln
385                 390                 395                 400

His Leu Arg Gly Ser Gly Arg Asp Pro Leu Pro Trp Ala Thr Arg Val
                405                 410                 415

Gln Ile Ala Leu Asp Ser Ala Arg Gly Leu Glu Tyr Ile His Glu His
                420                 425                 430

Thr Val Pro Val Tyr Ile His Arg Asp Ile Lys Pro Ala Asn Ile Leu
                435                 440                 445

Ile Asp Lys Asn Phe Arg Gly Lys Val Ala Asp Phe Gly Leu Thr Lys
    450                 455                 460

Leu Thr Glu Val Gly Ser Ser Ser Leu Pro Thr Gly Arg Leu Val Gly
465                 470                 475                 480
```

```
Thr Phe Gly Tyr Met Pro Pro Glu Tyr Ala Gln Tyr Gly Asp Val Ser
                485             490             495

Pro Lys Val Asp Val Tyr Ala Phe Gly Val Val Leu Tyr Glu Leu Ile
                500             505             510

Ser Ala Lys Glu Ala Ile Val Lys Ser Ser Glu Ser Val Ala Asp Ser
                515             520             525

Lys Gly Leu Val Gly Leu Phe Glu Gly Val Leu Ser Gln Pro Asp Pro
        530             535             540

Thr Glu Asp Leu Arg Lys Ile Val Asp Pro Arg Leu Gly Asp Asn Tyr
545             550             555             560

Pro Ala Asp Ser Val Arg Lys Met Ala Gln Leu Ala Lys Ala Cys Thr
                565             570             575

Gln Glu Asn Pro Gln Leu Arg Pro Ser Met Arg Ser Ile Val Val Ala
                580             585             590

Leu Met Thr Leu Ser Ser Thr Thr Asp Asp Trp Asp Val Gly Ser Phe
                595             600             605

Tyr Glu Asn Gln Asn Leu Val Asn Leu Met Ser Gly Arg
        610             615             620

<210> SEQ ID NO 217
<211> LENGTH: 617
<212> TYPE: PRT
<213> ORGANISM: Zea mays

<400> SEQUENCE: 217

Met Ala Arg Ile Leu Met Arg Leu Leu Leu Leu Ala Ala Ala Ala Ala
1               5               10              15

Val Ala Ala Gly Asp Gly Cys Leu Asn Ser Gly Cys Val Ala Leu Gly
                20              25              30

Ser Tyr Leu Val Ala Arg Asn Gln Asn Leu Thr Tyr Ile Ala Ser Leu
        35              40              45

Phe Gly Ile Gly Asp Tyr His Ala Leu Ala Arg Tyr Asn Pro Gly Thr
        50              55              60

Thr Asn Leu Asp Tyr Ile Gln Ala Gly Gln Ser Val Asn Ile Ser Phe
65              70              75              80

Thr Cys Gly Cys His Thr Phe Pro Asn Ser Asp Ala Thr Tyr Leu Gly
                85              90              95

Gly Ser Phe Pro His Lys Val Val Thr Gly Asp Thr Tyr Gly Gly Ile
                100             105             110

Ala Gln Asn Tyr Asn Asn Leu Thr Ser Ala Ala Trp Leu Ala Val Thr
                115             120             125

Asn Pro Tyr Pro Thr Asn Asn Ile Pro Asp Thr Asn Thr Val Val Asn
        130             135             140

Val Thr Val Asn Cys Thr Cys Gly Asp Pro Lys Ile Ser Ser Asp Tyr
145             150             155             160

Gly Phe Phe Leu Thr Tyr Pro Leu Met Gly Gln Thr Leu Ala Ala Val
                165             170             175

Ala Ala Asn Tyr Ser Phe Asn Ser Ser Ser Gln Leu Asp Leu Leu Arg
                180             185             190

Lys Tyr Asn Pro Gly Met Asp Thr Ala Thr Ser Gly Leu Val Phe Ile
                195             200             205

Pro Val Lys Asp Gly Asn Gly Ser Tyr His Pro Leu Lys Pro Pro Gly
        210             215             220

Asn Gly Gly Ser Ile Gly Ala Ile Val Gly Gly Val Val Gly Gly Val
225             230             235             240
```

-continued

```
Ala Ile Leu Val Leu Gly Val Leu Leu Tyr Ile Met Phe Tyr Arg Arg
            245                 250                 255

Lys Lys Ala Asn Lys Ala Ala Leu Leu Pro Ser Ser Glu Asp Ser Thr
            260                 265                 270

Gln Leu Ala Thr Thr Ser Met Asp Lys Ser Ala Leu Ser Thr Ser Gln
            275                 280                 285

Ala Asp Ser Ser Ser Gly Val Pro Gly Ile Thr Val Asp Lys Ser Val
        290                 295                 300

Glu Phe Ser Tyr Glu Glu Leu Phe Asn Ala Thr Glu Gly Phe Ser Met
305                 310                 315                 320

Ser Asn Lys Ile Gly Gln Gly Gly Phe Gly Ala Val Tyr Tyr Ala Glu
                325                 330                 335

Leu Arg Gly Glu Lys Ala Ala Ile Lys Lys Met Asp Met Gln Ala Ser
            340                 345                 350

His Glu Phe Leu Ala Glu Leu Lys Val Leu Thr His Val His His Leu
            355                 360                 365

Asn Leu Val Arg Leu Ile Gly Phe Cys Thr Glu Ser Ser Leu Phe Leu
        370                 375                 380

Val Tyr Glu Phe Ile Glu Asn Gly Asn Leu Ser Gln His Leu Arg Gly
385                 390                 395                 400

Thr Gly Tyr Glu Pro Leu Ser Trp Ala Ala Arg Val Gln Ile Ala Leu
                405                 410                 415

Asp Ser Ala Arg Gly Leu Glu Tyr Ile His Glu His Thr Val Pro Val
            420                 425                 430

Tyr Ile His Arg Asp Ile Lys Ser Ala Asn Ile Leu Ile Asp Lys Asn
            435                 440                 445

Tyr Arg Ala Lys Val Ala Asp Phe Gly Leu Thr Lys Leu Thr Glu Val
        450                 455                 460

Gly Asn Thr Ser Leu Pro Thr Arg Gly Ile Val Gly Thr Phe Gly Tyr
465                 470                 475                 480

Met Pro Pro Glu Tyr Ala Arg Tyr Gly Asp Val Ser Pro Lys Val Asp
                485                 490                 495

Val Tyr Ala Phe Gly Val Val Leu Tyr Glu Leu Ile Ser Ala Lys Asp
            500                 505                 510

Ala Ile Val Arg Ser Thr Glu Ser Ser Ser Asp Ser Lys Gly Leu Val
            515                 520                 525

Tyr Leu Phe Glu Glu Ala Leu Asn Thr Pro Asp Pro Lys Glu Gly Leu
        530                 535                 540

Gln Arg Leu Ile Asp Pro Ala Leu Gly Glu Asp Tyr Pro Ile Asp Ser
545                 550                 555                 560

Ile Leu Lys Met Thr Val Leu Ala Arg Ala Cys Thr Gln Glu Asp Pro
                565                 570                 575

Lys Ala Arg Pro Thr Met Arg Ser Ile Val Val Ala Leu Met Thr Leu
            580                 585                 590

Ser Ser Thr Ser Glu Phe Trp Asp Met Asn Ala Ile Gln Glu Asn Gln
            595                 600                 605

Gly Val Val Asn Leu Met Ser Gly Arg
        610                 615
```

<210> SEQ ID NO 218
<211> LENGTH: 626
<212> TYPE: PRT
<213> ORGANISM: Hordeum vulgare

<400> SEQUENCE: 218

```
Met Glu Ala Pro Leu His Ser Leu Leu Leu Leu Leu Leu Ala Ala
1               5                   10                  15

Ala Ala Gly Pro Lys Thr Ala Ala Val Gly Asp Gly Cys Ser Arg
                20                  25                  30

Gly Cys Asp Leu Ala Leu Ala Ser Tyr Tyr Ile Ala Pro Asn Gln Asn
            35                  40                  45

Val Thr Tyr Ile Ala Ser Leu Phe Gly Phe Ser Glu Tyr Arg Val Leu
    50                  55                  60

Gly Gln Tyr Asn Pro Gly Val Asn Asn Leu Asp Tyr Val Val Ala Gly
65                  70                  75                  80

Asp Arg Leu Asn Val Ser Leu Thr Cys Lys Cys Leu Ala Ser Leu Ser
            85                  90                  95

Ala Pro Ala Ser Thr Phe Leu Ala Ala Ser Ile Pro Tyr Lys Val Ala
            100                 105                 110

Thr Gly Glu Thr Tyr Leu Arg Ile Ala Asp Asn Tyr Asn Asn Leu Thr
            115                 120                 125

Thr Ala Asp Trp Leu Val Ala Thr Asn Thr Tyr Pro Ala Asn Asn Ile
    130                 135                 140

Pro Asp Val Ala Thr Val Asn Ala Thr Val Asn Cys Ser Cys Gly Asp
145                 150                 155                 160

Ala Gly Ile Ser Thr Asp Tyr Gly Leu Phe Leu Thr Tyr Pro Leu Arg
            165                 170                 175

Asp Arg Glu Thr Leu Ala Ser Val Ala Ala Asn His Gly Phe Ser Ser
            180                 185                 190

Pro Glu Lys Met Asp Leu Leu Lys Lys Tyr Asn Pro Gly Met Asp Gly
            195                 200                 205

Val Thr Gly Ser Gly Ile Val Tyr Ile Pro Ala Lys Asp Pro Asn Gly
    210                 215                 220

Ser Tyr Arg Pro Leu Glu Ser Pro Gly Lys Lys Ser Ser Ala Gly Ala
225                 230                 235                 240

Ile Ala Gly Gly Val Val Ala Gly Val Val Ala Leu Val Leu Gly Val
            245                 250                 255

Val Leu Phe Leu Phe Tyr Arg Arg Arg Lys Ala Lys Lys Asp Ala Leu
            260                 265                 270

Leu Pro Ser Ser Glu Glu Ser Thr Arg Leu Ala Ser Ala Ile Ser Met
            275                 280                 285

Gln Lys Val Thr Pro Ser Thr Ser Gln Ala Asp Gly Ala Ser Pro Ala
    290                 295                 300

Ala Gly Ile Thr Val Asp Lys Ser Val Glu Phe Ser Tyr Glu Glu Leu
305                 310                 315                 320

Phe Asn Ala Thr Glu Gly Phe Asn Ile Ile His Lys Ile Gly Gln Gly
            325                 330                 335

Gly Phe Gly Ala Val Tyr Tyr Ala Glu Leu Arg Gly Glu Lys Ala Ala
            340                 345                 350

Ile Lys Lys Met Asp Met Gln Ala Thr Gln Glu Phe Leu Ala Glu Leu
            355                 360                 365

Lys Val Leu Thr His Val His His Leu Asn Leu Val Arg Leu Ile Gly
    370                 375                 380

Tyr Cys Thr Glu Ser Ser Leu Phe Leu Val Tyr Glu Phe Ile Glu Asn
385                 390                 395                 400

Gly Asn Leu Ser Gln His Leu Arg Gly Thr Gly Tyr Glu Pro Leu Ser
            405                 410                 415
```

```
Trp Val Glu Arg Val Gln Ile Ala Leu Asp Ser Ala Arg Gly Leu Glu
            420             425             430

Tyr Ile His Glu His Thr Val Pro Val Tyr Ile His Arg Asp Ile Lys
            435             440             445

Ser Ala Asn Ile Leu Ile Asp Lys Asn Thr Arg Ala Lys Val Ala Asp
            450             455             460

Phe Gly Leu Thr Lys Leu Thr Glu Val Gly Gly Gly Thr Ser Leu Gln
465             470             475             480

Thr Arg Val Val Gly Thr Phe Gly Tyr Met Pro Pro Glu Tyr Ala Arg
            485             490             495

Tyr Gly Asp Val Ser Pro Lys Val Asp Val Tyr Ala Phe Gly Val Val
            500             505             510

Leu Tyr Glu Leu Ile Ser Ala Lys Asp Ala Ile Val Arg Ser Ala Glu
            515             520             525

Ser Thr Ser Asp Ser Lys Gly Leu Val Tyr Leu Phe Glu Glu Ala Leu
            530             535             540

Ser Ala Pro Asp Pro Lys Glu Gly Ile Arg Arg Leu Met Asp Pro Lys
545             550             555             560

Leu Gly Asp Asp Tyr Pro Ile Asp Ala Ile Leu Lys Met Thr His Leu
            565             570             575

Ala Asn Ala Cys Thr Gln Glu Asp Pro Lys Leu Arg Pro Thr Met Arg
            580             585             590

Ser Val Val Val Ala Leu Met Thr Leu Ser Ser Thr Ser Glu Phe Trp
            595             600             605

Asp Met Asn Ala Leu Tyr Glu Asn Pro Gly Leu Val Asn Leu Met Ser
            610             615             620

Gly Arg
625
```

<210> SEQ ID NO 219
<211> LENGTH: 613
<212> TYPE: PRT
<213> ORGANISM: Oryza sativa Japonica Group

<400> SEQUENCE: 219

```
Met Phe Ser Leu Pro Ala Leu Leu Ile Gly Ala Cys Ala Phe Ala Ala
1               5               10              15

Ala Ala Val Ala Ala Ser Gly Asp Gly Cys Arg Ala Gly Cys Ser Leu
            20              25              30

Ala Ile Ala Ala Tyr Tyr Phe Ser Glu Gly Ser Asn Leu Thr Phe Ile
            35              40              45

Ala Thr Ile Phe Ala Ile Gly Gly Gly Tyr Gln Ala Leu Leu Pro
            50              55              60

Tyr Asn Pro Ala Ile Thr Asn Pro Asp Tyr Val Val Thr Gly Asp Arg
65              70              75              80

Val Leu Val Pro Phe Pro Cys Ser Cys Leu Gly Leu Pro Ala Ala Pro
            85              90              95

Ala Ser Thr Phe Leu Ala Gly Ala Ile Pro Tyr Pro Leu Pro Leu Pro
            100             105             110

Arg Gly Gly Gly Asp Thr Tyr Asp Ala Val Ala Ala Asn Tyr Ala Asp
            115             120             125

Leu Thr Thr Ala Ala Trp Leu Glu Ala Thr Asn Ala Tyr Pro Pro Gly
            130             135             140

Arg Ile Pro Gly Gly Asp Gly Arg Val Asn Val Thr Ile Asn Cys Ser
```

-continued

```
145               150               155               160

Cys Gly Asp Glu Arg Val Ser Pro Arg Tyr Gly Leu Phe Leu Thr Tyr
                165               170               175

Pro Leu Trp Asp Gly Glu Thr Leu Glu Ser Val Ala Ala Gln Tyr Gly
                180               185               190

Phe Ser Ser Pro Ala Glu Met Glu Leu Ile Arg Arg Tyr Asn Pro Gly
            195               200               205

Met Gly Gly Val Ser Gly Lys Gly Ile Val Phe Ile Pro Val Lys Asp
            210               215               220

Pro Asn Gly Ser Tyr His Pro Leu Lys Ser Gly Val Gly Ile Val Leu
225               230               235               240

Leu Phe Cys Gly Met Gly Asn Ser Leu Ser Gly Gly Ala Ile Ala Gly
                245               250               255

Ile Val Ile Ala Cys Ile Ala Ile Phe Ile Val Ala Ile Trp Leu Ile
                260               265               270

Ile Met Phe Tyr Arg Trp Gln Lys Phe Arg Lys Ala Thr Ser Arg Pro
            275               280               285

Ser Pro Glu Glu Thr Ser His Leu Asp Asp Ala Ser Gln Ala Glu Gly
            290               295               300

Ile Lys Val Glu Arg Ser Ile Glu Phe Ser Tyr Glu Glu Ile Phe Asn
305               310               315               320

Ala Thr Gln Gly Phe Ser Met Glu His Lys Ile Gly Gln Gly Gly Phe
                325               330               335

Gly Ser Val Tyr Tyr Ala Glu Leu Arg Gly Glu Lys Thr Ala Ile Lys
            340               345               350

Lys Met Gly Met Gln Ala Thr Gln Glu Phe Leu Ala Glu Leu Lys Val
            355               360               365

Leu Thr His Val His His Leu Asn Leu Val Arg Leu Ile Gly Tyr Cys
        370               375               380

Val Glu Asn Cys Leu Phe Leu Val Tyr Glu Phe Ile Asp Asn Gly Asn
385               390               395               400

Leu Ser Gln His Leu Gln Arg Thr Gly Tyr Ala Pro Leu Ser Trp Ala
                405               410               415

Thr Arg Val Gln Ile Ala Leu Asp Ser Ala Arg Gly Leu Glu Tyr Leu
            420               425               430

His Glu His Val Val Pro Val Tyr Val His Arg Asp Ile Lys Ser Ala
            435               440               445

Asn Ile Leu Leu Asp Lys Asp Phe Arg Ala Lys Ile Ala Asp Phe Gly
        450               455               460

Leu Ala Lys Leu Thr Glu Val Gly Ser Met Ser Gln Ser Leu Ser Thr
465               470               475               480

Arg Val Ala Gly Thr Phe Gly Tyr Met Pro Pro Glu Ala Arg Tyr Gly
                485               490               495

Glu Val Ser Pro Lys Val Asp Val Tyr Ala Phe Gly Val Val Leu Tyr
            500               505               510

Glu Leu Leu Ser Ala Lys Gln Ala Ile Val Arg Ser Ser Glu Ser Val
            515               520               525

Ser Glu Ser Lys Gly Leu Val Phe Leu Phe Glu Glu Ala Leu Ser Ala
        530               535               540

Pro Asn Pro Thr Glu Ala Leu Asp Glu Leu Ile Asp Pro Ser Leu Gln
545               550               555               560

Gly Asp Tyr Pro Val Asp Ser Ala Leu Lys Ile Ala Ser Leu Ala Lys
                565               570               575
```

-continued

```
Ser Cys Thr His Glu Glu Pro Gly Met Arg Pro Thr Met Arg Ser Val
            580             585             590

Val Val Ala Leu Met Ala Leu Thr Ala Asn Thr Asp Leu Arg Asp Met
            595             600             605

Asp Tyr His Pro Phe
    610

<210> SEQ ID NO 220
<211> LENGTH: 617
<212> TYPE: PRT
<213> ORGANISM: Arabidopsis thaliana

<400> SEQUENCE: 220

Met Lys Leu Lys Ile Ser Leu Ile Ala Pro Ile Leu Leu Leu Phe Ser
1               5                   10                  15

Phe Phe Phe Ala Val Glu Ser Lys Cys Arg Thr Ser Cys Pro Leu Ala
            20                  25                  30

Leu Ala Ser Tyr Tyr Leu Glu Asn Gly Thr Thr Leu Ser Val Ile Asn
            35                  40                  45

Gln Asn Leu Asn Ser Ser Ile Ala Pro Tyr Asp Gln Ile Asn Phe Asp
    50                  55                  60

Pro Ile Leu Arg Tyr Asn Ser Asn Ile Lys Asp Lys Asp Arg Ile Gln
65                  70                  75                  80

Met Gly Ser Arg Val Leu Val Pro Phe Pro Cys Glu Cys Gln Pro Gly
            85                  90                  95

Asp Phe Leu Gly His Asn Phe Ser Tyr Ser Val Arg Gln Glu Asp Thr
            100                 105                 110

Tyr Glu Arg Val Ala Ile Ser Asn Tyr Ala Asn Leu Thr Thr Met Glu
            115                 120                 125

Ser Leu Gln Ala Arg Asn Pro Phe Pro Ala Thr Asn Ile Pro Leu Ser
    130                 135                 140

Ala Thr Leu Asn Val Leu Val Asn Cys Ser Cys Gly Asp Glu Ser Val
145                 150                 155                 160

Ser Lys Asp Phe Gly Leu Phe Val Thr Tyr Pro Leu Arg Pro Glu Asp
            165                 170                 175

Ser Leu Ser Ser Ile Ala Arg Ser Ser Gly Val Ser Ala Asp Ile Leu
            180                 185                 190

Gln Arg Tyr Asn Pro Gly Val Asn Phe Asn Ser Gly Asn Gly Ile Val
            195                 200                 205

Tyr Val Pro Gly Arg Asp Pro Asn Gly Ala Phe Pro Pro Phe Lys Ser
    210                 215                 220

Ser Lys Gln Asp Gly Val Gly Ala Gly Val Ile Ala Gly Ile Val Ile
225                 230                 235                 240

Gly Val Ile Val Ala Leu Leu Leu Ile Leu Phe Ile Val Tyr Tyr Ala
            245                 250                 255

Tyr Arg Lys Asn Lys Ser Lys Gly Asp Ser Phe Ser Ser Ser Ile Pro
            260                 265                 270

Leu Ser Thr Lys Ala Asp His Ala Ser Ser Thr Ser Leu Gln Ser Gly
            275                 280                 285

Gly Leu Gly Gly Ala Gly Val Ser Pro Gly Ile Ala Ala Ile Ser Val
    290                 295                 300

Asp Lys Ser Val Glu Phe Ser Leu Glu Glu Leu Ala Lys Ala Thr Asp
305                 310                 315                 320

Asn Phe Asn Leu Ser Phe Lys Ile Gly Gln Gly Gly Phe Gly Ala Val
```

-continued

```
                325                 330                 335

Tyr Tyr Ala Glu Leu Arg Gly Glu Lys Ala Ala Ile Lys Lys Met Asp
            340                 345                 350

Met Glu Ala Ser Lys Gln Phe Leu Ala Glu Leu Lys Val Leu Thr Arg
                355                 360                 365

Val His His Val Asn Leu Val Arg Leu Ile Gly Tyr Cys Val Glu Gly
        370                 375                 380

Ser Leu Phe Leu Val Tyr Glu Tyr Val Glu Asn Gly Asn Leu Gly Gln
385                 390                 395                 400

His Leu His Gly Ser Gly Arg Glu Pro Leu Pro Trp Thr Lys Arg Val
                405                 410                 415

Gln Ile Ala Leu Asp Ser Ala Arg Gly Leu Glu Tyr Ile His Glu His
            420                 425                 430

Thr Val Pro Val Tyr Val His Arg Asp Ile Lys Ser Ala Asn Ile Leu
            435                 440                 445

Ile Asp Gln Lys Phe Arg Ala Lys Val Ala Asp Phe Gly Leu Thr Lys
        450                 455                 460

Leu Thr Glu Val Gly Gly Ser Ala Thr Arg Gly Ala Met Gly Thr Phe
465                 470                 475                 480

Gly Tyr Met Ala Pro Glu Thr Val Tyr Gly Glu Val Ser Ala Lys Val
                485                 490                 495

Asp Val Tyr Ala Phe Gly Val Val Leu Tyr Glu Leu Ile Ser Ala Lys
            500                 505                 510

Gly Ala Val Val Lys Met Thr Glu Ala Val Gly Glu Phe Arg Gly Leu
            515                 520                 525

Val Gly Val Phe Glu Glu Ser Phe Lys Glu Thr Asp Lys Glu Glu Ala
        530                 535                 540

Leu Arg Lys Ile Ile Asp Pro Arg Leu Gly Asp Ser Tyr Pro Phe Asp
545                 550                 555                 560

Ser Val Tyr Lys Met Ala Glu Leu Gly Lys Ala Cys Thr Gln Glu Asn
                565                 570                 575

Ala Gln Leu Arg Pro Ser Met Arg Tyr Ile Val Val Ala Leu Ser Thr
            580                 585                 590

Leu Phe Ser Ser Thr Gly Asn Trp Asp Val Gly Asn Phe Gln Asn Glu
            595                 600                 605

Asp Leu Val Ser Leu Met Ser Gly Arg
    610                 615
```

<210> SEQ ID NO 221
<211> LENGTH: 620
<212> TYPE: PRT
<213> ORGANISM: Lotus japonicus

<400> SEQUENCE: 221

```
Met Phe Tyr Asp Phe Thr Thr Met Ala Ser Leu Thr His Pro Leu Cys
1               5                   10                  15

Val Leu Leu Thr Leu Met Ala Ala Ala Ser Phe Ala Ser Val Phe Ser
                20                  25                  30

Leu Glu Val Ser Ser Lys Thr Thr Tyr Met Glu Pro Phe Asn Cys Ser
            35                  40                  45

Thr Lys Ile Arg Thr Cys Asn Ser Leu Leu Tyr His Ile Ser Ile Gly
        50                  55                  60

Leu Lys Val Glu Glu Ile Ala Arg Phe Tyr Ser Val Asn Leu Ser Arg
65                  70                  75                  80
```

```
Ile Lys Pro Ile Thr Arg Gly Thr Lys Gln Asp Tyr Leu Val Ser Val
                85              90              95

Pro Cys Thr Cys Arg Asn Thr Asn Gly Leu Asn Gly Tyr Phe Tyr His
            100             105             110

Thr Ser Tyr Lys Val Lys Val Asn Asp Ser Phe Val Asp Ile Gln Asn
        115             120             125

Leu Phe Tyr Ser Gly Gln Ala Trp Pro Val Asn Glu Asp Leu Val Val
    130             135             140

Pro Asn Glu Thr Met Thr Ile His Ile Pro Cys Gly Cys Ser Glu Ser
145             150             155             160

Gly Ser Gln Ile Val Val Thr Tyr Thr Val Gln Arg Asn Asp Thr Pro
                165             170             175

Leu Ser Ile Ala Leu Leu Leu Asn Ala Thr Val Glu Gly Met Val Ser
            180             185             190

Val Asn Ser Val Met Ala Pro Asn Pro Thr Phe Ile Asp Val Gly Trp
        195             200             205

Val Leu Tyr Val Pro Lys Glu Leu Asn Pro Ile Ser His Gly Lys Glu
    210             215             220

Asn Lys His Lys Leu Glu Lys Ile Ile Gly Ile Leu Ala Gly Val Ile
225             230             235             240

Leu Leu Ser Ile Ile Thr Leu Ile Ile Leu Ile Val Arg Arg Asn Arg
                245             250             255

Ser Tyr Glu Thr Cys Lys Asp Asp Pro Arg Ala Ile Ser Lys Arg Ser
            260             265             270

Ile Gly Lys Arg Thr Ser Ser Leu Met Asn Arg Asp Phe His Lys Glu
        275             280             285

Tyr Met Glu Asp Ala Thr Ser Phe Asp Ser Glu Arg Pro Val Ile Tyr
    290             295             300

Thr Leu Glu Glu Ile Glu Gln Ala Thr Asn Asp Phe Asp Glu Thr Arg
305             310             315             320

Arg Ile Gly Val Gly Gly Tyr Gly Thr Val Tyr Phe Gly Val Leu Gly
                325             330             335

Glu Lys Glu Val Ala Ile Lys Lys Met Lys Ser Asn Lys Ser Lys Glu
            340             345             350

Phe Tyr Ala Glu Leu Lys Ala Leu Cys Lys Ile His His Ile Asn Ile
        355             360             365

Val Glu Leu Leu Gly Tyr Ala Ser Gly Asp Asp His Leu Tyr Leu Val
    370             375             380

Tyr Glu Tyr Val Pro Asn Gly Ser Leu Ser Glu His Leu His Asp Pro
385             390             395             400

Leu Leu Lys Gly His Gln Pro Leu Ser Trp Cys Ala Arg Ile Gln Ile
            405             410             415

Ala Leu Asp Ser Ala Lys Gly Ile Glu Tyr Ile His Asp Tyr Thr Lys
        420             425             430

Ala Gln Tyr Val His Arg Asp Ile Lys Thr Ser Asn Ile Leu Leu Asp
        435             440             445

Glu Lys Leu Arg Ala Lys Val Ala Asp Phe Gly Leu Ala Lys Leu Val
    450             455             460

Glu Arg Thr Asn Asp Glu Glu Phe Ile Ala Thr Arg Leu Val Gly Thr
465             470             475             480

Pro Gly Tyr Leu Pro Pro Glu Ser Leu Lys Glu Leu Gln Val Thr Val
            485             490             495

Lys Thr Asp Val Phe Ala Phe Gly Val Val Met Leu Glu Leu Ile Thr
```

-continued

```
              500                 505                 510

Gly Lys Arg Ala Leu Phe Arg Asp Asn Gln Glu Ala Asn Asn Met Arg
          515                 520                 525

Ser Leu Val Ala Val Val Asn Gln Ile Phe Gln Glu Asp Asn Pro Glu
          530                 535                 540

Thr Ala Leu Glu Val Thr Val Asp Gly Asn Leu Gln Arg Ser Tyr Pro
545                 550                 555                 560

Met Glu Asp Val Tyr Asn Met Ala Glu Leu Ser His Trp Cys Leu Arg
                  565                 570                 575

Glu Asn Pro Val Asp Arg Pro Glu Met Ser Glu Ile Val Val Lys Leu
              580                 585                 590

Ser Lys Ile Ile Met Ser Ser Ile Glu Trp Glu Ala Ser Leu Gly Gly
          595                 600                 605

Asp Ser Gln Val Phe Ser Gly Val Phe Asp Gly Arg
          610                 615                 620
```

<210> SEQ ID NO 222
<211> LENGTH: 613
<212> TYPE: PRT
<213> ORGANISM: Medicago truncatula

<400> SEQUENCE: 222

```
Met Ala Ser Leu Ile Gln Leu Leu Ser Ile Phe Leu Pro Leu Leu Ala
1                 5                 10                  15

Ser Ser Leu Pro Thr Ile Phe Ser Ile Glu Val Ser Met Lys Lys Ala
              20                 25                 30

Tyr Met Glu Pro Tyr Lys Cys Ser Thr Lys Met Arg Thr Cys Asn Ala
          35                 40                 45

Ser Leu Tyr His Ile Asn Tyr Asn His Asn Ile Glu Gln Ile Ala Asn
          50                 55                 60

Phe Tyr Ser Ile Asp Pro Ser Gln Ile Lys Pro Ile Ile Arg Ser Thr
65                 70                 75                 80

Lys Gln Asp Tyr Leu Val Lys Val Pro Cys Ser Cys Lys Asn Ile Lys
                  85                 90                 95

Asp Leu Ser Gly Tyr Phe Tyr Glu Thr Thr Tyr Lys Val Ser Pro Asn
              100                105                110

Glu Thr Ser Val Asp Ile Met Asn Leu Ile Tyr Ser Gly Gln Ala Trp
          115                120                125

Gln Val Asn Glu Asp Leu Val Ala Asn Glu Asn Val Thr Ile His Ile
          130                135                140

Pro Cys Gly Cys Ser Glu Phe Glu Ser Gln Ile Val Val Thr Tyr Thr
145                150                155                160

Val Gln Gln Ser Asp Thr Pro Thr Ser Ile Ser Leu Leu Leu Asn Ala
                  165                170                175

Thr Ile Asp Gly Met Val Arg Ile Asn Gln Ile Leu Gly Pro Asn Pro
              180                185                190

Thr Phe Ile Asp Ile Gly Trp Val Leu Tyr Val Pro Lys Glu Leu Lys
          195                200                205

Gly Ser Pro Leu Tyr His Gly Lys Glu Lys Lys His Lys Trp Val Ile
          210                215                220

Ile Ile Gly Ile Leu Val Ser Val Thr Leu Leu Ser Val Ile Thr Leu
225                230                235                240

Ile Ile Phe Ile Leu Arg Arg Asn Lys Ala Tyr Glu Thr Ser Lys Tyr
                  245                250                255
```

-continued

Asp Pro Lys Thr Val Ser Lys Arg Ser Phe Gly Asn Arg Thr Ile Ser
                260                 265                 270

Leu Arg Asn His Glu Phe His Lys Glu Tyr Met Glu Asp Ala Thr Gln
            275                 280                 285

Phe Asp Ser Glu Arg Pro Val Ile Tyr Asp Phe Glu Glu Ile Glu His
        290                 295                 300

Ala Thr Asn Asn Phe Asp Glu Thr Arg Arg Ile Gly Val Gly Gly Tyr
305                 310                 315                 320

Gly Thr Val Tyr Phe Gly Met Leu Glu Glu Lys Glu Val Ala Val Lys
                325                 330                 335

Lys Met Lys Ser Asn Lys Ser Lys Glu Phe Tyr Ala Glu Leu Lys Ala
            340                 345                 350

Leu Cys Lys Ile His His Ile Asn Ile Val Glu Leu Leu Gly Tyr Ala
            355                 360                 365

Ser Gly Asp Asp His Leu Tyr Leu Val Tyr Glu Tyr Val Pro Asn Gly
    370                 375                 380

Ser Leu Ser Glu His Leu His Asp Pro Leu Leu Lys Gly His Gln Pro
385                 390                 395                 400

Leu Ser Trp Cys Ala Arg Thr Gln Ile Ala Leu Asp Ser Ala Lys Gly
            405                 410                 415

Ile Glu Tyr Ile His Asp Tyr Thr Lys Ala Arg Tyr Val His Arg Asp
            420                 425                 430

Ile Lys Thr Ser Asn Ile Leu Leu Asp Glu Lys Leu Arg Ala Lys Val
            435                 440                 445

Ala Asp Phe Gly Leu Ala Lys Leu Val Glu Arg Thr Asn Asp Glu Glu
    450                 455                 460

Phe Leu Ala Thr Arg Leu Val Gly Thr Pro Gly Tyr Leu Pro Pro Glu
465                 470                 475                 480

Ser Val Lys Glu Leu Gln Val Thr Ile Lys Thr Asp Val Phe Ala Phe
            485                 490                 495

Gly Val Val Ile Ser Glu Leu Ile Thr Gly Lys Arg Ala Leu Phe Arg
            500                 505                 510

Asp Asn Lys Glu Ala Asn Asn Met Lys Ser Leu Ile Ala Val Val Asn
            515                 520                 525

Lys Ile Phe Gln Asp Glu Asp Pro Val Ala Ala Leu Glu Ala Val Val
    530                 535                 540

Asp Gly Asn Leu Leu Arg Asn Tyr Pro Ile Glu Gly Val Tyr Lys Met
545                 550                 555                 560

Ala Glu Leu Ser His Trp Cys Leu Ser Glu Glu Pro Val Asp Arg Pro
            565                 570                 575

Glu Met Lys Glu Ile Val Val Ala Val Ser Lys Ile Val Met Ser Ser
            580                 585                 590

Ile Glu Trp Glu Ala Ser Leu Gly Gly Asp Ser Gln Val Phe Ser Gly
        595                 600                 605

Val Phe Asp Gly Arg
    610

<210> SEQ ID NO 223
<211> LENGTH: 595
<212> TYPE: PRT
<213> ORGANISM: Lotus japonicus
<220> FEATURE:
<221> NAME/KEY: VARIANT
<222> LOCATION: 146, 150, 151, 153-158
<223> OTHER INFORMATION: Xaa = hydrophobic patch residues
<220> FEATURE:

<221> NAME/KEY: VARIANT
<222> LOCATION: 145, 147, 149, 152, 159
<223> OTHER INFORMATION: Xaa = residues immediately adjacent to
      hydrophobic patch residues

<400> SEQUENCE: 223

Met Ala Val Phe Phe Leu Thr Ser Gly Ser Leu Ser Leu Phe Leu Ala
1               5                   10                  15

Leu Thr Leu Leu Phe Thr Asn Ile Ala Ala Arg Ser Glu Lys Ile Ser
                20                  25                  30

Gly Pro Asp Phe Ser Cys Pro Val Asp Ser Pro Pro Ser Cys Glu Thr
            35                  40                  45

Tyr Val Thr Tyr Thr Ala Gln Ser Pro Asn Leu Leu Ser Leu Thr Asn
    50                  55                  60

Ile Ser Asp Ile Phe Asp Ile Ser Pro Leu Ser Ile Ala Arg Ala Ser
65                  70                  75                  80

Asn Ile Asp Ala Gly Lys Asp Lys Leu Val Pro Gly Gln Val Leu Leu
                85                  90                  95

Val Pro Val Thr Cys Gly Cys Ala Gly Asn His Ser Ser Ala Asn Thr
                100                 105                 110

Ser Tyr Gln Ile Gln Leu Gly Asp Ser Tyr Asp Phe Val Ala Thr Thr
                115                 120                 125

Leu Tyr Glu Asn Leu Thr Asn Trp Asn Ile Val Gln Ala Ser Asn Pro
    130                 135                 140

Gly Val Asn Pro Tyr Leu Leu Pro Glu Arg Val Lys Val Val Phe Pro
145                 150                 155                 160

Leu Phe Cys Arg Cys Pro Ser Lys Asn Gln Leu Asn Lys Gly Ile Gln
                165                 170                 175

Tyr Leu Ile Thr Tyr Val Trp Lys Pro Asn Asp Asn Val Ser Leu Val
                180                 185                 190

Ser Ala Lys Phe Gly Ala Ser Pro Ala Asp Ile Leu Thr Glu Asn Arg
                195                 200                 205

Tyr Gly Gln Asp Phe Thr Ala Ala Thr Asn Leu Pro Ile Leu Ile Pro
    210                 215                 220

Val Thr Gln Leu Pro Glu Leu Thr Gln Pro Ser Ser Asn Gly Arg Lys
225                 230                 235                 240

Ser Ser Ile His Leu Leu Val Ile Leu Gly Ile Thr Leu Gly Cys Thr
                245                 250                 255

Leu Leu Thr Ala Val Leu Thr Gly Thr Leu Val Tyr Val Tyr Cys Arg
                260                 265                 270

Arg Lys Lys Ala Leu Asn Arg Thr Ala Ser Ser Ala Glu Thr Ala Asp
    275                 280                 285

Lys Leu Leu Ser Gly Val Ser Gly Tyr Val Ser Lys Pro Asn Val Tyr
    290                 295                 300

Glu Ile Asp Glu Ile Met Glu Ala Thr Lys Asp Phe Ser Asp Glu Cys
305                 310                 315                 320

Lys Val Gly Glu Ser Val Tyr Lys Ala Asn Ile Glu Gly Arg Val Val
                325                 330                 335

Ala Val Lys Lys Ile Lys Glu Gly Gly Ala Asn Glu Glu Leu Lys Ile
                340                 345                 350

Leu Gln Lys Val Asn His Gly Asn Leu Val Lys Leu Met Gly Val Ser
    355                 360                 365

Ser Gly Tyr Asp Gly Asn Cys Phe Leu Val Tyr Glu Tyr Ala Glu Asn
    370                 375                 380

-continued

```
Gly Ser Leu Ala Glu Trp Leu Phe Ser Lys Ser Ser Gly Thr Pro Asn
385                 390                 395                 400

Ser Leu Thr Trp Ser Gln Arg Ile Ser Ile Ala Val Asp Val Ala Val
                405                 410                 415

Gly Leu Gln Tyr Met His Glu His Thr Tyr Pro Arg Ile Ile His Arg
                420                 425                 430

Asp Ile Thr Thr Ser Asn Ile Leu Leu Asp Ser Asn Phe Lys Ala Lys
                435                 440                 445

Ile Ala Asn Phe Ala Met Ala Arg Thr Ser Thr Asn Pro Met Met Pro
                450                 455                 460

Lys Ile Asp Val Phe Ala Phe Gly Val Leu Leu Ile Glu Leu Leu Thr
465                 470                 475                 480

Gly Arg Lys Ala Met Thr Thr Lys Glu Asn Gly Glu Val Val Met Leu
                485                 490                 495

Trp Lys Asp Met Trp Glu Ile Phe Asp Ile Glu Glu Asn Arg Glu Glu
                500                 505                 510

Arg Ile Arg Lys Trp Met Asp Pro Asn Leu Glu Ser Phe Tyr His Ile
                515                 520                 525

Asp Asn Ala Leu Ser Leu Ala Ser Leu Ala Val Asn Cys Thr Ala Asp
                530                 535                 540

Lys Ser Leu Ser Arg Pro Ser Met Ala Glu Ile Val Leu Ser Leu Ser
545                 550                 555                 560

Phe Leu Thr Gln Gln Ser Ser Asn Pro Thr Leu Glu Arg Ser Leu Thr
                565                 570                 575

Ser Ser Gly Leu Asp Val Glu Asp Asp Ala His Ile Val Thr Ser Ile
                580                 585                 590

Thr Ala Arg
        595

<210> SEQ ID NO 224
<211> LENGTH: 632
<212> TYPE: PRT
<213> ORGANISM: Medicago truncatula

<400> SEQUENCE: 224

Met Lys Thr Leu Lys Pro His His His Gln Leu Ser Thr Phe Ile Phe
1               5                   10                  15

Ile Leu Leu Phe Pro Phe Leu Lys Ser Gln Thr Ala Arg Gln Gln Asn
                20                  25                  30

Asn Thr Gly Tyr Thr Cys Pro Asn Asn Asn Asn Asn Asn Asn Asn Thr
            35                  40                  45

Tyr Pro Cys Gln Thr Tyr Val Tyr Tyr Lys Ala Thr Pro Pro Asn Tyr
        50                  55                  60

Leu Asp Leu Ala Thr Ile Ser Asp Leu Phe Gln Leu Ser Arg Leu Met
65                  70                  75                  80

Ile Ser Lys Pro Ser Asn Ile Ser Ser Pro Ser Ser Pro Leu Leu Pro
                85                  90                  95

Asn Gln Pro Leu Leu Ile Pro Leu Thr Cys Ser Cys Asn Phe Ile Asn
                100                 105                 110

Thr Thr Phe Gly Ser Ile Ser Tyr Ser Asn Ile Thr Tyr Thr Ile Lys
            115                 120                 125

Pro Asn Asp Thr Phe Phe Leu Val Ser Thr Ile Asn Phe Gln Asn Leu
        130                 135                 140

Thr Thr Tyr Pro Ser Val Gln Val Val Asn Pro Asn Leu Val Ala Thr
145                 150                 155                 160
```

```
Asn Leu Ser Ile Gly Asp Asn Ala Val Phe Pro Ile Phe Cys Lys Cys
            165                 170                 175

Pro Asp Lys Thr Lys Thr Asn Ser Ser Phe Met Ile Ser Tyr Val Val
            180                 185                 190

Gln Pro His Asp Asn Val Ser Ser Ile Ala Ser Met Phe Gly Thr Ser
            195                 200                 205

Glu Lys Ser Ile Val Asp Val Asn Gly Glu Arg Leu Tyr Asp Tyr Asp
        210                 215                 220

Thr Ile Phe Val Pro Val Thr Glu Leu Pro Val Leu Lys Gln Pro Ser
225                 230                 235                 240

Thr Ile Val Pro Ser Pro Ala Pro Arg Gly Asn Ser Asp Asp Gly Asp
                245                 250                 255

Asp Asp Asp Asp Lys Ser Gly Ile Val Lys Gly Leu Ala Ile Gly Leu
                260                 265                 270

Gly Ile Leu Gly Phe Leu Leu Ile Leu Val Ile Val Phe Trp Phe Tyr
            275                 280                 285

Arg Glu Val Leu Phe Lys Lys Glu Lys Lys Gly Lys Gly Leu Tyr Phe
        290                 295                 300

Gly Asp Lys Gly Tyr Lys Gly Asn Asp Glu Lys Lys Lys Met Asp
305                 310                 315                 320

Val Asn Phe Met Ala Asn Val Ser Asp Cys Leu Asp Lys Tyr Arg Val
                325                 330                 335

Phe Gly Phe Asp Glu Leu Val Glu Ala Thr Asp Gly Phe Asp Glu Arg
                340                 345                 350

Phe Leu Ile Gln Gly Ser Val Tyr Lys Gly Glu Ile Asp Gly Gln Val
            355                 360                 365

Tyr Ala Ile Lys Lys Met Lys Trp Asn Ala Tyr Glu Glu Leu Lys Ile
        370                 375                 380

Leu Gln Lys Val Asn His Gly Asn Leu Val Lys Leu Glu Gly Phe Cys
385                 390                 395                 400

Ile Glu Pro Glu Glu Ser Asn Cys Tyr Leu Val Tyr Glu Tyr Val Glu
                405                 410                 415

Asn Gly Ser Leu Tyr Ser Trp Leu His Glu Asp Lys Asn Glu Lys Leu
            420                 425                 430

Asn Trp Val Thr Arg Leu Arg Ile Ala Val Asp Ile Ala Asn Gly Leu
            435                 440                 445

Leu Tyr Ile His Glu His Thr Arg Pro Lys Val Val His Lys Asp Ile
        450                 455                 460

Lys Ser Ser Asn Ile Leu Leu Asp Ser Asn Met Arg Ala Lys Ile Ala
465                 470                 475                 480

Asn Phe Gly Leu Ala Lys Ser Gly Ile Asn Ala Ile Thr Met His Ile
                485                 490                 495

Val Gly Thr Gln Gly Tyr Ile Ser Pro Glu Tyr Leu Ala Asp Gly Ile
            500                 505                 510

Val Ser Thr Lys Met Asp Val Phe Ser Phe Gly Ile Val Leu Leu Glu
            515                 520                 525

Leu Ile Ser Gly Lys Glu Val Ile Asp Glu Glu Gly Asn Val Leu Trp
        530                 535                 540

Ala Ser Ala Ile Lys Thr Phe Glu Val Lys Asn Glu Gln Glu Lys Ala
545                 550                 555                 560

Arg Arg Leu Lys Glu Trp Leu Asp Arg Thr Met Leu Lys Glu Thr Cys
                565                 570                 575
```

```
Ser Met Glu Ser Leu Met Gly Val Leu His Val Ala Ile Ala Cys Leu
        580             585             590

Asn Arg Asp Pro Ser Lys Arg Pro Ser Ile Ile Asp Ile Val Tyr Ser
        595             600             605

Leu Ser Lys Cys Glu Glu Ala Gly Phe Glu Leu Ser Asp Asp Gly Phe
        610             615             620

Gly Ser Glu Arg Leu Val Ala Arg
625             630

<210> SEQ ID NO 225
<211> LENGTH: 423
<212> TYPE: PRT
<213> ORGANISM: Arabidopsis thaliana

<400> SEQUENCE: 225

Met Lys Asn Pro Glu Lys Pro Leu Leu Leu Phe Leu Ile Leu Ala Ser
1               5               10              15

Ser Leu Ala Ser Met Ala Thr Ala Lys Ser Thr Ile Glu Pro Cys Ser
        20              25              30

Ser Lys Asp Thr Cys Asn Ser Leu Leu Gly Tyr Thr Leu Tyr Thr Asp
        35              40              45

Leu Lys Val Thr Glu Val Ala Ser Leu Phe Gln Val Asp Pro Val Ser
        50              55              60

Met Leu Leu Ser Asn Ser Ile Asp Ile Ser Tyr Pro Asp Val Glu Asn
65              70              75              80

His Val Leu Pro Ala Lys Leu Phe Leu Lys Ile Pro Ile Thr Cys Ser
                85              90              95

Cys Val Asp Gly Ile Arg Lys Ser Leu Ser Thr His Tyr Lys Thr Arg
        100             105             110

Thr Ser Asp Thr Leu Gly Ser Ile Ala Asp Ser Val Tyr Gly Gly Leu
        115             120             125

Val Ser Pro Glu Gln Ile Gln Val Ala Asn Ser Glu Thr Asp Leu Ser
        130             135             140

Val Leu Asp Val Gly Thr Lys Leu Val Ile Pro Leu Pro Cys Ala Cys
145             150             155             160

Phe Asn Gly Thr Asp Glu Ser Leu Pro Ala Leu Tyr Leu Ser Tyr Val
                165             170             175

Val Arg Gly Ile Asp Thr Met Ala Gly Ile Ala Lys Arg Phe Ser Thr
        180             185             190

Ser Val Thr Asp Leu Thr Asn Val Asn Ala Met Gly Ala Pro Asp Ile
        195             200             205

Asn Pro Gly Asp Ile Leu Ala Val Pro Leu Leu Ala Cys Ser Ser Asn
        210             215             220

Phe Pro Lys Tyr Ala Thr Asp Tyr Gly Leu Ile Ile Pro Asn Gly Ser
225             230             235             240

Tyr Ala Leu Thr Ala Gly His Cys Val Gln Cys Ser Cys Val Leu Gly
                245             250             255

Ser Arg Ser Met Tyr Cys Glu Pro Ala Ser Ile Ser Val Ser Cys Ser
        260             265             270

Ser Met Arg Cys Arg Asn Ser Asn Phe Met Leu Gly Asn Ile Thr Ser
        275             280             285

Gln Gln Ser Ser Ser Gly Cys Lys Leu Thr Thr Cys Ser Tyr Asn Gly
        290             295             300

Phe Ala Ser Gly Thr Ile Leu Thr Thr Leu Ser Met Ser Leu Gln Pro
305             310             315             320
```

Arg Cys Pro Gly Pro Gln Gln Leu Ala Pro Leu Ile Ala Pro Pro Asp
            325                 330                 335

Asn Val Pro Lys Glu Leu Met Tyr Leu Pro Ser Pro Ser Pro Ser Pro
            340                 345                 350

Ser Pro Glu Phe Asp Asp Ile Ala Gly Gly Gly Ser Ser Ile Ala Ala
            355                 360                 365

Val Pro Ala Ala Ser Pro Gly Gly Ala Thr Val Ser Ser Ser Asn Ser
            370                 375                 380

Ile Pro Gly Asn Pro Ala Asn Gly Pro Gly Gly Ser Ile Ser Ile Ala
385                 390                 395                 400

Ser Cys Pro Leu Ser Tyr Tyr Ser Phe Ile Ala Leu Leu Ile Pro Ile
            405                 410                 415

Gly Ser Cys Phe Phe Val Phe
            420

<210> SEQ ID NO 226
<211> LENGTH: 382
<212> TYPE: PRT
<213> ORGANISM: Oryza sativa Japonica Group

<400> SEQUENCE: 226

Pro Ala Pro Val Ser Thr Arg Gln Ser Asn Lys His Gln Ala Ser His
1               5                   10                  15

Ser His Leu Ser Arg Arg Ala Phe Pro Thr Met Ala Ser Leu Thr Ala
            20                  25                  30

Ala Leu Ala Thr Pro Ala Ala Ala Ala Leu Leu Leu Leu Val Leu Leu
            35                  40                  45

Ala Ala Pro Ala Ser Ala Ala Asn Phe Thr Cys Ala Val Ala Ser Gly
            50                  55                  60

Thr Thr Cys Lys Ser Ala Ile Leu Tyr Thr Ser Pro Asn Ala Thr Thr
65                  70                  75                  80

Tyr Gly Asn Leu Val Ala Arg Phe Asn Thr Thr Thr Leu Pro Asp Leu
            85                  90                  95

Leu Gly Ala Asn Gly Leu Pro Asp Gly Thr Leu Ser Ser Ala Pro Val
            100                 105                 110

Ala Ala Asn Ser Thr Val Lys Ile Pro Phe Arg Cys Arg Cys Asn Gly
            115                 120                 125

Asp Val Gly Gln Ser Asp Arg Leu Pro Ile Tyr Val Val Gln Pro Gln
            130                 135                 140

Asp Gly Leu Asp Ala Ile Ala Arg Asn Val Phe Asn Ala Phe Val Thr
145                 150                 155                 160

Tyr Gln Glu Ile Ala Ala Ala Asn Asn Ile Pro Asp Pro Asn Lys Ile
            165                 170                 175

Asn Val Ser Gln Thr Leu Trp Ile Pro Leu Pro Cys Ser Cys Asp Lys
            180                 185                 190

Glu Glu Gly Ser Asn Val Met His Leu Ala Tyr Ser Val Gly Lys Gly
            195                 200                 205

Glu Asn Thr Ser Ala Ile Ala Ala Lys Tyr Gly Val Thr Glu Ser Thr
            210                 215                 220

Leu Leu Thr Arg Asn Lys Ile Asp Asp Pro Thr Lys Leu Gln Met Gly
225                 230                 235                 240

Gln Ile Leu Asp Val Pro Leu Pro Val Cys Arg Ser Ser Ile Ser Asp
            245                 250                 255

Thr Ser Ala Asp His Asn Leu Met Leu Leu Pro Asp Gly Thr Tyr Gly

-continued

```
              260              265               270
Phe Thr Ala Gly Asn Cys Ile Arg Cys Ser Cys Ser Ser Thr Thr Tyr
        275             280             285

Gln Leu Asn Cys Thr Ala Val Gln Asn Lys Gly Cys Pro Ser Val Pro
    290             295             300

Leu Cys Asn Gly Thr Leu Lys Leu Gly Glu Thr Asn Gly Thr Gly Cys
305             310             315             320

Gly Ser Thr Thr Cys Ala Tyr Ser Gly Tyr Ser Asn Ser Ser Ser Leu
            325             330             335

Ile Ile Gln Thr Ser Leu Ala Thr Asn Gln Thr Thr Ala Cys Gln Arg
            340             345             350

Gly Gly Ser Gly Arg Ser Gln Phe Ala Arg Ser Met Trp Ser Met Ser
            355             360             365

Val Ile Ser Phe His Met Val Leu Ile Ile Ile Cys Phe Leu
    370             375             380

<210> SEQ ID NO 227
<211> LENGTH: 350
<212> TYPE: PRT
<213> ORGANISM: Arabidopsis thaliana

<400> SEQUENCE: 227

Met Glu Thr Ser Cys Phe Thr Leu Leu Gly Leu Leu Val Ser Leu Ser
1               5               10              15

Phe Phe Leu Thr Leu Ser Ala Gln Met Thr Gly Asn Phe Asn Cys Ser
            20              25              30

Gly Ser Thr Ser Thr Cys Gln Ser Leu Val Gly Tyr Ser Ser Lys Asn
        35              40              45

Ala Thr Thr Leu Arg Asn Ile Gln Thr Leu Phe Ala Val Lys Asn Leu
    50              55              60

Arg Ser Ile Leu Gly Ala Asn Asn Leu Pro Leu Asn Thr Ser Arg Asp
65              70              75              80

Gln Arg Val Asn Pro Asn Gln Val Val Arg Val Pro Ile His Cys Ser
                85              90              95

Cys Ser Asn Gly Thr Gly Val Ser Asn Arg Asp Ile Glu Tyr Thr Ile
            100             105             110

Lys Lys Asp Asp Ile Leu Ser Phe Val Ala Thr Glu Ile Phe Gly Gly
        115             120             125

Leu Val Thr Tyr Glu Lys Ile Ser Glu Val Asn Lys Ile Pro Asp Pro
    130             135             140

Asn Lys Ile Glu Ile Gly Gln Lys Phe Trp Ile Pro Leu Pro Cys Ser
145             150             155             160

Cys Asp Lys Leu Asn Gly Glu Asp Val Val His Tyr Ala His Val Val
            165             170             175

Lys Leu Gly Ser Ser Leu Gly Glu Ile Ala Ala Gln Phe Gly Thr Asp
            180             185             190

Asn Thr Thr Leu Ala Gln Leu Asn Gly Ile Ile Gly Asp Ser Gln Leu
        195             200             205

Leu Ala Asp Lys Pro Leu Asp Val Pro Leu Lys Ala Cys Ser Ser Ser
    210             215             220

Val Arg Lys Asp Ser Leu Asp Ala Pro Leu Leu Leu Ser Asn Asn Ser
225             230             235             240

Tyr Val Phe Thr Ala Asn Asn Cys Val Lys Cys Thr Cys Asp Ala Leu
            245             250             255
```

```
Lys Asn Trp Thr Leu Ser Cys Gln Ser Ser Ser Glu Ile Lys Pro Ser
        260             265             270

Asn Trp Gln Thr Cys Pro Pro Phe Ser Gln Cys Asp Gly Ala Leu Leu
        275             280             285

Asn Ala Ser Cys Arg Gln Pro Arg Asp Cys Val Tyr Ala Gly Tyr Ser
    290             295             300

Asn Gln Thr Ile Phe Thr Thr Ala Ser Pro Ala Cys Pro Asp Ser Ala
305             310             315             320

Gly Pro Asp Asn Tyr Ala Ser Thr Leu Ser Ser Ser Phe Asn Phe Val
            325             330             335

Ile Val Leu Ile Gln Cys Ala Leu Leu Cys Leu Cys Leu Leu
        340             345             350

<210> SEQ ID NO 228
<211> LENGTH: 638
<212> TYPE: PRT
<213> ORGANISM: Zea mays
<220> FEATURE:
<221> NAME/KEY: VARIANT
<222> LOCATION: 145-158
<223> OTHER INFORMATION: Xaa = hydrophobic patch residues
<220> FEATURE:
<221> NAME/KEY: VARIANT
<222> LOCATION: 144, 159
<223> OTHER INFORMATION: Xaa = residues immediately adjacent to
      hydrophobic patch residues

<400> SEQUENCE: 228

Met Glu Pro Arg His Phe Cys Arg Ala Leu Leu Leu Leu Val Val
1               5               10              15

Leu Leu Leu Gly Phe Arg Arg Ala Gly Ala Gln Asp Ser Thr Asn Tyr
        20              25              30

Thr Val Pro Ala Arg Phe Ala Cys Asn Val Ser Ser Pro Cys Asp Thr
        35              40              45

Tyr Val Val Tyr Arg Thr Gln Ser Pro Gly Tyr Leu Asp Leu Gly Ser
    50              55              60

Ile Ser Asp Leu Phe Gly Thr Ser Gln Ala Arg Ile Ala Ser Ala Asn
65              70              75              80

Gly Leu Ser Ser Glu Asp Gly Val Leu Gln Pro Gly Gln Pro Leu Leu
            85              90              95

Val Pro Val Arg Cys Gly Cys Thr Gly Ala Trp Ser Phe Ala Asn Ala
        100             105             110

Thr Tyr Pro Ile Arg Gln Gly Asp Thr Phe Tyr Asn Leu Ala Arg Leu
        115             120             125

Ser Tyr Glu Asn Leu Thr Glu Tyr His Leu Ile His Asp Leu Asn Pro
    130             135             140

Arg Ser Glu Pro Thr Ser Leu Gln Ile Gly Gln Glu Val Thr Val Pro
145             150             155             160

Leu Leu Cys Arg Cys Pro Pro Ala Arg Ala Val Gln Ser Phe Ile Thr
            165             170             175

Tyr Val Trp Gln Pro Gly Asp Thr Leu Ser Gln Val Ser Lys Leu Met
            180             185             190

Asn Ala Thr Ala Asp Glu Ile Ala Glu Ala Asn Asn Val Thr Ser Ser
        195             200             205

Ser Val Ser Ser Ala Ser Ala Ala Gly Leu Pro Met Leu Ile Pro Val
    210             215             220

Gln Gln Arg Pro Arg Leu Pro Pro Leu Leu Tyr Ala Ala Ser Ala Gly
225             230             235             240
```

```
Glu Gly Arg Ser Ser Arg Ser Arg Arg Arg Ala Leu Ile Ile Ile Gly
            245                 250                 255

Ala Ser Val Ser Gly Ser Leu Val Ala Leu Ala Ala Leu Leu Val Ala
            260                 265                 270

Ile Met Ala Gln Arg Arg Tyr Arg Arg Lys Lys Pro Ser Met Arg Leu
            275                 280                 285

Gly Ser Pro Phe Ala Val Asn Thr Lys Leu Ser Trp Ser Val Asn Gln
        290                 295                 300

Tyr Gly His Gly Ser Ser Asn Ser Phe Ala His Val Met Lys Gly Gly
305                 310                 315                 320

Lys Leu Leu Thr Gly Val Ser Gln Phe Ile Asp Lys Pro Ile Ile Phe
                325                 330                 335

Val Glu Glu Glu Ile Val Glu Ala Thr Met Asn Leu Asp Glu Arg Cys
            340                 345                 350

Lys Ile Gly Ser Thr Tyr Tyr Arg Ala Lys Leu Asp Gly Glu Val Phe
            355                 360                 365

Ala Val Lys Pro Ala Lys Gly Asp Val Ser Ala Glu Leu Arg Met Met
        370                 375                 380

Gln Met Val Asn His Ala Asn Leu Ile Lys Leu Ala Gly Ile Ser Ile
385                 390                 395                 400

Gly Ala Asp Gly Asp Tyr Ala Phe Leu Val Tyr Glu Phe Ala Glu Lys
                405                 410                 415

Ala Ser Leu Asp Lys Trp Leu Tyr His Asn His Gln Lys Pro Pro Ser
            420                 425                 430

Ala Leu Leu Pro Ser Ser Ser Cys Thr Val Pro Thr Thr Leu Ser Trp
            435                 440                 445

Gly Gln Arg Leu Ser Ile Ala Leu Asp Val Ala Asn Gly Leu Leu Tyr
        450                 455                 460

Met His Glu His Thr Gln Pro Ser Met Val His Gly Asp Ile Arg Ala
465                 470                 475                 480

Arg Asn Ile Leu Leu Thr Ala Asp Phe Arg Ala Lys Ile Ser Ser Phe
                485                 490                 495

Ser Leu Ala Lys Pro Ala Thr Ala Asp Ala Ala Ala Thr Ser Ser Asp
            500                 505                 510

Val Phe Ala Phe Gly Leu Leu Leu Leu Glu Leu Met Ser Gly Arg Arg
            515                 520                 525

Ala Met Glu Ala Arg Ile Gly Ser Glu Ile Gly Met Leu Trp Arg Glu
        530                 535                 540

Ile Arg Ala Val Leu Glu Ala Gly Asp Lys Arg Glu Ala Lys Leu Arg
545                 550                 555                 560

Lys Trp Met Asp Pro Ala Leu Gly Ser Glu Tyr Gln Met Asp Ala Ala
                565                 570                 575

Leu Ser Leu Ala Gly Met Ala Arg Ala Cys Thr Asp Glu Asp Ala Ala
            580                 585                 590

Arg Arg Pro Asn Met Thr Glu Val Val Phe Ser Leu Ser Met Leu Ala
        595                 600                 605

Gln Pro Leu Ser Val Ala Asp Gly Phe Glu Lys Leu Trp Gln Pro Ser
        610                 615                 620

Ser Glu Asp Asn Ile Arg Ile Ala Gly Ser Val Ala Ala Arg
625                 630                 635
```

<210> SEQ ID NO 229
<211> LENGTH: 636

```
<212> TYPE: PRT
<213> ORGANISM: Zea mays
<220> FEATURE:
<221> NAME/KEY: VARIANT
<222> LOCATION: 147-161
<223> OTHER INFORMATION: Xaa = hydrophobic patch residues
<220> FEATURE:
<221> NAME/KEY: VARIANT
<222> LOCATION: 146, 162
<223> OTHER INFORMATION: Xaa = residues immediately adjacent to
      hydrophobic patch residues

<400> SEQUENCE: 229

Met Glu Leu Arg His Phe Arg Cys Cys Ala Ser Arg Leu Leu Leu Leu
1               5                   10                  15

Val Thr Leu Leu Leu Gly Phe Arg Arg Ala Gly Ala Gln Asp Ser Thr
            20                  25                  30

Ser Tyr Thr Val Pro Ala Gln Phe Ala Cys Asp Val Ser Ser Pro Cys
        35                  40                  45

Asp Thr Tyr Val Val Tyr Arg Thr Gln Ser Pro Gly Tyr Leu Asp Leu
    50                  55                  60

Gly Ser Ile Ser Asp Leu Phe Gly Thr Ser Gln Ala Arg Ile Ala Ser
65                  70                  75                  80

Ala Asn Gly Leu Ser Ser Glu Asp Gly Val Leu Gln Pro Gly Gln Pro
                85                  90                  95

Leu Leu Val Pro Val Arg Cys Gly Cys Ala Gly Ala Trp Ser Phe Ala
            100                 105                 110

Asn Val Thr Tyr Pro Ile Arg Gln Gly Asp Thr Phe Tyr Asn Leu Ala
            115                 120                 125

Lys Ala Ser Tyr Glu Asn Leu Thr Glu Tyr His Leu Ile Gln Asn Leu
    130                 135                 140

Asn Pro Gly Ser Glu Pro Thr Ser Leu Gln Ile Gly Gln Glu Val Thr
145                 150                 155                 160

Val Pro Leu Leu Cys Arg Cys Pro Ala Arg Ala Glu Arg Ser Arg Gly
            165                 170                 175

Val Gln Ser Leu Ile Thr Tyr Met Trp Gln Ala Gly Asp Thr Met Ser
            180                 185                 190

Gln Val Ser Lys Leu Met Asn Ala Thr Val Asp Glu Ile Ala Glu Ala
        195                 200                 205

Asn Asn Val Thr Ala Asn Thr Ser Ala Ser Ala Ser Phe Val Gly Gln
    210                 215                 220

Pro Met Leu Ile Pro Val Arg Gln Arg Pro Arg Leu Pro Ala Pro Leu
225                 230                 235                 240

Tyr Ala Ala Ala Ala Ala Asp Gly Lys Ser Arg Ser Arg Arg Arg Ala
            245                 250                 255

Ala Val Ile Gly Ala Ser Val Ser Gly Ser Leu Val Ala Leu Ala Ala
            260                 265                 270

Leu Phe Val Ala Ile Leu Ala Arg Arg Arg Tyr Arg Lys Lys Pro Ser
            275                 280                 285

Met Arg Leu Gly Ser Arg Phe Ala Val Asn Thr Lys Leu Ser Trp Ser
        290                 295                 300

Arg Asn Gln Phe Gly His Asp Gly Ser Asn Ser Phe Ala His Val Met
305                 310                 315                 320

Lys Gly Gly Lys Leu Leu Thr Gly Val Ser Gln Phe Ile Asp Lys Pro
            325                 330                 335

Ile Ile Phe Val Glu Glu Glu Ile Met Glu Ala Thr Met Asn Leu Asp
            340                 345                 350
```

```
Glu Arg Cys Lys Ile Gly Ser Thr Tyr Tyr Arg Ala Lys Leu Asp Gly
        355             360             365

Glu Val Phe Ala Val Lys Pro Ala Lys Gly Asp Val Ser Ala Glu Leu
    370             375             380

Lys Met Met Gln Met Val Asn His Ala Asn Leu Ile Lys Leu Ala Gly
385             390             395             400

Ile Ser Ile Gly Ala Asp Gly Asp Tyr Ala Phe Leu Val Tyr Glu Phe
                405             410             415

Ala Glu Lys Gly Ser Leu Asp Lys Trp Leu Tyr Glu Lys Pro Pro Ser
            420             425             430

Ala Leu Pro Ser Ser Ser Cys Thr Val Ala Thr Leu Ser Trp Gly Gln
        435             440             445

Arg Leu Ser Ile Ala Leu Asp Val Ala Asn Gly Leu Leu Tyr Met His
    450             455             460

Glu His Thr Gln Pro Ser Met Val His Asp Asp Ile Arg Ala Arg Asn
465             470             475             480

Ile Leu Leu Thr Ala Asp Phe Arg Ala Lys Ile Ser Gly Phe Ser Leu
                485             490             495

Ala Lys Pro Ala Met Val Asp Ala Ala Ala Thr Ser Ser Asp Val Phe
            500             505             510

Ala Phe Gly Leu Leu Leu Leu Glu Leu Leu Ser Gly Arg Arg Ala Met
        515             520             525

Glu Ala Arg Ile Gly Ser Glu Ile Gly Met Leu Trp Arg Glu Ile Arg
    530             535             540

Gly Val Leu Glu Thr Gly Asp Lys Arg Glu Ala Lys Leu Arg Lys Trp
545             550             555             560

Met Asp Pro Ala Leu Gly Ser Glu Tyr His Met Asp Val Ala Leu Ser
                565             570             575

Leu Ala Ser Met Ala Arg Ala Cys Thr Glu Glu Asp Ala Ala Arg Arg
            580             585             590

Pro Asn Met Thr Glu Val Val Phe Ser Leu Ser Val Leu Ala Gln Pro
        595             600             605

Leu Ser Val Ala Asp Gly Phe Glu Lys Leu Trp Gln Pro Ser Ser Glu
    610             615             620

Asp Asn Ile Arg Ile Ala Gly Ser Val Ala Ala Arg
625             630             635
```

```
<210> SEQ ID NO 230
<211> LENGTH: 633
<212> TYPE: PRT
<213> ORGANISM: Hordeum vulgare
<220> FEATURE:
<221> NAME/KEY: VARIANT
<222> LOCATION: 144-157
<223> OTHER INFORMATION: Xaa = hydrophobic patch residues
<220> FEATURE:
<221> NAME/KEY: VARIANT
<222> LOCATION: 143, 158
<223> OTHER INFORMATION: Xaa = residues immediately adjacent to
      hydrophobic patch residues

<400> SEQUENCE: 230
```

```
Met Glu Pro Arg Arg Phe Leu Cys Cys Cys Leu Val Ala Val Leu Ala
1               5               10              15

Val Ala Ser Arg Arg Cys Asp Ala Gln Gly Gly Ala Gly Asn Gly Thr
            20              25              30

Gly Arg Phe Ala Cys Val Val Pro Ala Pro Cys Asp Thr Phe Val Leu
```

-continued

```
                35                    40                    45

Tyr Arg Thr Gln Ser Pro Gly Ser Leu Asp Leu Gly Ala Ile Ser Asp
    50                    55                    60

Leu Phe Gly Val Ser Arg Ala Met Ile Ala Ala Ala Asn Asn Leu Ser
65                    70                    75                    80

Leu Ile Asp Glu Asp Ala Ala Leu Leu Pro Asp Gln Pro Leu Leu Val
                85                    90                    95

Pro Val Arg Cys Gly Cys Thr Gly Asn Arg Ser Phe Val Asn Val Thr
                100                   105                   110

Tyr Pro Ile His Ser Gly Asp Thr Phe Tyr Ala Leu Ala Leu Thr Gly
                115                   120                   125

Tyr Glu Asn Leu Thr Thr Pro Asp Val Ile Gln Glu Leu Asn Pro Gln
    130                   135                   140

Ala Val Phe Asn Lys Leu Asn Val Ser Gln Leu Val Thr Val Pro Leu
145                   150                   155                   160

Phe Cys Arg Cys Pro Thr Pro Ala Glu Arg Ser Ala Gly Val Leu Gln
                165                   170                   175

Gln Ile Thr Tyr Met Trp Arg Pro Val Asp Thr Met Ser Arg Val Ser
                180                   185                   190

Lys Leu Met Gly Ser Asp Ala Ser Ala Ile Ala Ala Ala Asn Asn Val
                195                   200                   205

Ser Ala Asp Phe Thr Ser Thr Thr Met Leu Pro Met Leu Ile Pro Val
    210                   215                   220

Ala Arg Pro Pro Val Leu Pro Pro Leu Arg Tyr Gly Pro Ser Ala Thr
225                   230                   235                   240

Thr Gly Asp Pro Gly Ala Thr Lys Arg Phe Ser Gly Ala Thr Val Ala
                245                   250                   255

Ala Ser Ile Ala Gly Ser Leu Val Ala Val Ala Ala Leu Cys Val Ala
                260                   265                   270

Ile Phe Gly Tyr Arg Arg Tyr Arg Arg Lys Lys Ala Thr Val His Ser
                275                   280                   285

Ala Ser Arg Phe Ala Ser Pro Arg Phe Cys Phe Asn Gln Asn Ala Tyr
    290                   295                   300

Gly Ile Gln Ser Ser Ser Ser Ile Ala Arg Met Ile Asn Gly Gly Asp
305                   310                   315                   320

Lys Leu Leu Thr Ser Val Ser Gln Phe Ile Asp Lys Pro Val Ile Phe
                325                   330                   335

Gly Thr Ala Glu Ile Met Glu Ala Thr Met Asn Leu Asp Glu Arg Cys
                340                   345                   350

Arg Ile Gly Ser Ser Tyr Tyr Arg Ala Lys Leu Glu Gly Glu Val Phe
                355                   360                   365

Ala Val Lys Pro Ala Lys Gly Asp Val Ser Ala Glu Leu Arg Met Met
    370                   375                   380

Gln Met Val Asn His Ala Asn Leu Ile Arg Leu Ala Gly Ile Ser Ile
385                   390                   395                   400

Gly Ala Asp Gly Asp Tyr Thr Phe Leu Val Tyr Glu Phe Ala Glu Lys
                405                   410                   415

Gly Ser Leu Asp Lys Trp Leu Tyr Gln Lys Pro Pro Ser Ser Leu Pro
                420                   425                   430

Ser Ser Ser Ser Ser Val Asp Thr Leu Ser Trp Asn Gln Arg Leu Gly
                435                   440                   445

Ile Ala Leu Asp Val Ala Asn Gly Leu Leu Tyr Met His Glu His Thr
    450                   455                   460
```

-continued

```
Gln Pro Ser Met Val His Gly Asp Val Arg Ala Arg Asn Ile Leu Leu
465                 470                 475                 480

Thr Ala Asp Phe Arg Ala Arg Ile Ser Asn Phe Ser Val Ala Thr Pro
                485                 490                 495

Ala Met Ala Asp Ala Ala Ala Thr Ser Ser Asp Val Phe Ala Phe Gly
                500                 505                 510

Leu Leu Val Leu Glu Leu Leu Ser Gly Arg Thr Ala Met Glu Ala Arg
                515                 520                 525

Val Gly Ala Glu Ile Gly Met Leu Trp Arg Asp Ile Arg Ala Val Leu
                530                 535                 540

Glu Ala Gly Asp Lys Arg Asp Ala Lys Leu Arg Lys Trp Met Asp Pro
545                 550                 555                 560

Ala Leu Gly Asp Glu Tyr Tyr Leu Asp Ala Ala Leu Ser Leu Ala Gly
                565                 570                 575

Met Ala Arg Ala Cys Thr Glu Glu Asp Ala Ala Arg Arg Pro Lys Met
                580                 585                 590

Ala Asp Val Val Phe Ser Leu Ser Met Leu Val Gln Pro Leu Pro Val
                595                 600                 605

Gly Asp Ala Phe Glu Lys Leu Trp Gln Pro Ser Ser Glu Glu Asn Ile
                610                 615                 620

Arg Ile Val Asn Glu Val Ala Ala Arg
625                 630
```

```
<210> SEQ ID NO 231
<211> LENGTH: 650
<212> TYPE: PRT
<213> ORGANISM: Hordeum vulgare
<220> FEATURE:
<221> NAME/KEY: VARIANT
<222> LOCATION: 152-165
<223> OTHER INFORMATION: Xaa = hydrophobic patch residues
<220> FEATURE:
<221> NAME/KEY: VARIANT
<222> LOCATION: 151, 166
<223> OTHER INFORMATION: Xaa = residues immediately adjacent to
     hydrophobic patch residues

<400> SEQUENCE: 231
```

```
Met Ala Pro Leu Thr Arg Arg Arg Leu Leu Ala Thr Leu Leu Cys
1               5                   10                  15

Leu Cys Ala Leu Pro Ala Pro Ala Arg Ser Gln Asn Ala Ser Ala Thr
                20                  25                  30

Pro Ala Pro Ala Ser Val Glu Gly Phe Asn Cys Ser Ala Asn Gly Thr
                35                  40                  45

Tyr Pro Cys Gln Ala Tyr Ala Leu Tyr Arg Ala Gly Leu Ala Gly Val
                50                  55                  60

Pro Pro Asp Leu Ser Ala Ala Gly Asp Leu Phe Gly Val Ser Arg Phe
65                  70                  75                  80

Met Leu Ala His Ala Asn Asn Leu Ser Thr Ser Ala Ala Pro Ala Ala
                85                  90                  95

Gly Gln Pro Leu Leu Val Pro Leu Gln Cys Gly Cys Pro Ser Gly Ser
                100                 105                 110

Pro Asn Ala Tyr Ala Pro Thr Gln Tyr Gln Ile Ser Ser Gly Asp Thr
                115                 120                 125

Phe Trp Ile Val Ser Val Thr Lys Leu Gln Asn Leu Thr Gln Tyr Gln
                130                 135                 140

Ala Val Glu Arg Val Asn Pro Thr Val Val Pro Thr Lys Leu Glu Val
```

```
145              150              155              160

Gly Asp Met Val Thr Phe Pro Ile Phe Cys Gln Cys Pro Thr Ala Ala
                 165              170              175

Gln Asn Ala Thr Ala Leu Val Thr Tyr Val Met Gln Gln Gly Asp Thr
                 180              185              190

Tyr Ala Ser Ile Ala Ala Ala Phe Ala Val Asp Ala Gln Ser Leu Val
                 195              200              205

Ser Leu Asn Gly Pro Glu Gln Gly Thr Gln Leu Phe Ser Glu Ile Leu
                 210              215              220

Val Pro Leu Arg Arg Gln Val Pro Lys Trp Leu Pro Pro Ile Val Thr
225              230              235              240

Arg Asn Asp Ala Ser Ala Thr Pro Pro Ser Pro Ser Pro Pro Thr
                 245              250              255

Thr Thr Pro Gly Pro Ser Asp Val Ala Asp Asn Arg Asp Gly Val Val
                 260              265              270

Thr Gly Leu Ala Val Gly Leu Gly Val Val Gly Gly Leu Trp Leu Leu
                 275              280              285

Gln Leu Leu Leu Leu Gly Cys Leu Trp Arg Arg Leu Lys Ala Lys Gly
                 290              295              300

Arg Arg Gly Asp Ala Val Ala Ser Gly Glu Gly Gly Glu Gly Gly Arg
305              310              315              320

Ser Ala Lys Thr Ala Ser Ala Ser Gly Gly Val Gly Gly Glu Arg Phe
                 325              330              335

Leu Val Thr Asp Ile Ser Glu Trp Leu Asp Lys Tyr Arg Val Phe Lys
                 340              345              350

Val Glu Glu Leu Glu Arg Gly Thr Asp Gly Phe Asp Asp Ala His Leu
                 355              360              365

Ile Gln Gly Ser Val Tyr Lys Ala Asn Ile Gly Gly Glu Val Phe Ala
370              375              380

Val Lys Lys Met Lys Trp Asp Ala Cys Glu Glu Leu Lys Ile Leu Gln
385              390              395              400

Lys Val Asn His Ser Asn Leu Val Lys Leu Glu Gly Phe Cys Ile Asn
                 405              410              415

Thr Ala Thr Gly Asp Cys Phe Leu Val Tyr Glu Tyr Val Glu Asn Gly
                 420              425              430

Ser Leu Asp Leu Cys Leu Leu Asp Arg Gly Arg Ala Arg Arg Leu Asp
                 435              440              445

Trp Arg Thr Arg Leu His Ile Ala Leu Asp Leu Ala His Gly Leu Gln
                 450              455              460

Tyr Ile His Glu His Thr Trp Pro Arg Val Val His Lys Asp Val Lys
465              470              475              480

Ser Ser Asn Val Leu Leu Asp Ala Arg Met Arg Ala Lys Ile Ala Asn
                 485              490              495

Phe Gly Leu Ala Lys Thr Gly His Asn Ala Val Thr Thr His Ile Val
                 500              505              510

Gly Thr Gln Gly Tyr Ile Ala Pro Glu Tyr Leu Val Asp Gly Leu Val
                 515              520              525

Thr Thr Lys Met Asp Val Phe Ala Tyr Gly Val Val Leu Leu Glu Leu
                 530              535              540

Val Ser Gly Arg Glu Ala Ala Gly Asp Gly Gly Asp Leu Leu Leu Ala
545              550              555              560

Asp Ala Glu Glu Arg Val Phe Arg Gly Arg Glu Asp Arg Leu Glu Ala
                 565              570              575
```

-continued

```
Arg Ala Ala Ala Trp Met Asp Pro Val Leu Ala Glu Gln Thr Cys Pro
            580             585             590

Pro Gly Ser Val Ala Thr Val Met Gly Val Ala Arg Ala Cys Leu Gln
            595             600             605

Arg Asp Pro Ser Lys Arg Pro Ser Met Val Asp Val Ala Tyr Thr Leu
            610             615             620

Ser Arg Ala Asp Glu Tyr Phe Ala Asp Tyr Ser Gly Glu Ser Val Ser
625             630             635             640

Val Asp Gly Ser Gly Glu Ile Ala Ala Arg
            645             650

<210> SEQ ID NO 232
<211> LENGTH: 647
<212> TYPE: PRT
<213> ORGANISM: Zea mays

<400> SEQUENCE: 232

Met Arg Pro Pro Ala Leu Arg Leu Ser Ala Leu Leu Leu Phe Leu Cys
1               5               10              15

Leu Tyr Ala Ala Pro Ala Arg Ser Gln Asn Ala Thr Thr Val Thr Ala
            20              25              30

Ala Pro Ala Ser Val Glu Gly Phe Asn Cys Ser Val Asn Arg Thr Tyr
            35              40              45

Pro Cys Gln Ala Tyr Ala Leu Tyr Arg Ala Gly Phe Ala Gly Val Pro
            50              55              60

Leu Asn Leu Ala Ala Ile Gly Asp Leu Phe Ala Ala Ser Arg Phe Met
65              70              75              80

Val Ala His Ala Asn Asn Leu Ser Thr Ala Ala Ala Pro Ala Thr Gly
            85              90              95

Gln Pro Leu Leu Val Pro Leu Gln Cys Gly Cys Pro Ser Gly Ser Pro
            100             105             110

Asn Ser Tyr Ala Pro Met Gln Tyr Gln Ile Ala Ser Gly Asp Thr Tyr
            115             120             125

Trp Ile Ile Ser Thr Thr Lys Leu Gln Asn Leu Thr Gln Tyr Gln Ala
            130             135             140

Val Glu Arg Val Asn Pro Thr Leu Val Pro Thr Asn Leu Asp Val Gly
145             150             155             160

Thr Met Val Thr Phe Pro Ile Phe Cys Gln Cys Pro Ala Ala Ala Asp
            165             170             175

Asn Ala Thr Ala Leu Val Thr Tyr Val Met Gln Pro Gly Asp Thr Tyr
            180             185             190

Ser Thr Ile Ala Ala Ala Phe Ser Val Asp Ala Gln Ser Leu Val Ser
            195             200             205

Leu Asn Gly Pro Glu Pro Arg Thr Gln Gln Phe Ala Glu Ile Leu Val
            210             215             220

Pro Leu Arg Arg Gln Val Pro Gly Trp Leu Pro Pro Ile Val Leu Arg
225             230             235             240

Asn Asn Ala Ser Ala Thr Pro Ala Ala Pro Pro Ser Ala Ser Pro
            245             250             255

Asn Ala Thr Val Val Arg Asn Asp Arg Asn Gly Val Val Thr Gly Leu
            260             265             270

Ala Val Gly Leu Gly Val Val Gly Ala Leu Trp Leu Leu Gln Met Leu
            275             280             285

Leu Leu Ala Cys Leu Cys Arg Arg Leu Arg Ala Asn Gly Arg Arg Gly
```

```
        290              295              300
Asp Ala Val Leu Ser Gly Asp Gly Val Glu Gly Gly Val Phe Ala Lys
305              310              315              320

Gly Ser Ser Ala Ala Ala Ala Gly Gly Gly Glu Arg Phe Leu Val Ser
                 325              330              335

Asp Met Ser Glu Trp Leu Asp Lys Tyr Arg Val Phe Thr Val Glu Glu
                 340              345              350

Leu Glu Arg Gly Thr Gly Gly Phe Asp Asp Ala His Leu Val Asn Gly
                 355              360              365

Ser Val Tyr Lys Ala Asn Ile Asp Gly Leu Val Phe Ala Val Lys Lys
                 370              375              380

Met Lys Trp Asp Ala Cys Glu Glu Leu Lys Ile Leu Gln Lys Val Asn
385              390              395              400

His Ser Asn Leu Val Lys Leu Glu Gly Phe Cys Ile Asp Ser Ala Thr
                 405              410              415

Gly Asp Cys Tyr Leu Val Tyr Glu Tyr Val Glu Asn Gly Ser Leu Asp
                 420              425              430

Leu Trp Leu Leu Asp Arg Asp His Ala Arg Arg Leu Asn Trp Arg Ala
                 435              440              445

Arg Leu His Ile Ala Leu Asp Leu Ala His Gly Leu Gln Tyr Ile His
     450              455              460

Glu His Thr Trp Pro Arg Val Val His Lys Asp Met Lys Ser Ser Asn
465              470              475              480

Val Leu Leu Asp Ala Arg Met Arg Ala Lys Ile Ala Asn Phe Gly Leu
                 485              490              495

Ala Lys Thr Gly His Asn Ala Ile Thr Thr His Ile Val Gly Thr Gln
                 500              505              510

Gly Tyr Ile Ala Pro Glu Tyr Leu Ala Asp Gly Leu Val Thr Thr Lys
                 515              520              525

Ile Asp Val Phe Ala Tyr Gly Val Val Leu Leu Glu Leu Val Ser Gly
     530              535              540

Arg Glu Ala Ala Asp Glu Ser Gly Glu Pro Leu Trp Ala Asp Ala Glu
545              550              555              560

Asp Arg Val Phe Arg Gly Arg Asp Glu Arg Leu Glu Ala Arg Val Ala
                 565              570              575

Ala Trp Met Asp Pro Ala Leu Ala Glu Gln Thr Cys Pro Leu Gly Ser
                 580              585              590

Val Ala Thr Val Val Ser Val Ala Arg Ala Cys Leu His Lys Asp Pro
                 595              600              605

Ser Lys Arg Pro Ser Met Val Asp Val Ala Tyr Thr Leu Ser Lys Ala
     610              615              620

Asp Glu His Phe Ala Asp Tyr Ser Gly Glu Ser Val Ser Val Asp Gly
625              630              635              640

Ser Gly Glu Ile Ala Ala Arg
                 645
```

```
<210> SEQ ID NO 233
<211> LENGTH: 670
<212> TYPE: PRT
<213> ORGANISM: Hordeum vulgare
<220> FEATURE:
<221> NAME/KEY: VARIANT
<222> LOCATION: 162-174
<223> OTHER INFORMATION: Xaa = hydrophobic patch residues
<220> FEATURE:
<221> NAME/KEY: VARIANT
```

<222> LOCATION: 161, 175
<223> OTHER INFORMATION: Xaa = residues immediately adjacent to
      hydrophobic patch residues

<400> SEQUENCE: 233

```
Met Ala Ala Pro Pro Gly Arg Arg Gly Leu Ala Phe Gly Thr Ala Ala
1               5                   10                  15

Leu Ala Leu Leu Ala Ile Leu Ala Val Ala Arg Gly Gln Gln Gln Tyr
                20                  25                  30

Glu Ala Asn Ala Gln Thr Asn Cys Tyr Gly Arg Asn Gly Ser Ser Val
            35                  40                  45

Leu Gly Tyr Val Cys Asn Ala Thr Ala Ala Ala Pro Cys Ala Thr
    50                  55                  60

Tyr Val Val Phe Arg Ser Ser Pro Pro Tyr Tyr Gly Thr Ala Val Ser
65                  70                  75                  80

Ile Ser Tyr Leu Leu Gly Ser Asp Pro Glu Ala Val Ala Asp Ala Asn
                85                  90                  95

Gly Val Pro Thr Val Ser Pro Leu Ala Asp Ser Arg Leu Val Leu Ala
            100                 105                 110

Pro Val Pro Cys Gly Cys Ser Pro Arg Gly Tyr Tyr Gln His Asn Ser
            115                 120                 125

Ser His Thr Ile Glu Leu Arg Gly Glu Thr Tyr Phe Ile Ile Ala Asn
    130                 135                 140

Asn Thr Tyr Gln Gly Leu Thr Thr Cys Gln Ala Leu Leu Ala Gln Asn
145                 150                 155                 160

Pro Arg His Gly Ser Arg Asp Leu Val Ala Gly Asn Asn Leu Thr Val
            165                 170                 175

Pro Ile Arg Cys Ala Cys Pro Thr Pro Ala Gln Ala Ala Ala Gly Val
            180                 185                 190

Arg His Leu Leu Thr Tyr Leu Val Thr Trp Gly Asp Ser Val Ser Ala
    195                 200                 205

Ile Ala Asp Arg Phe Arg Val Asp Ala Gln Ala Val Phe Gln Ala Asn
    210                 215                 220

Asn Leu Thr Ala Arg Glu Ile Ile Phe Pro Phe Thr Thr Leu Leu Ile
225                 230                 235                 240

Pro Leu Lys Ser Ala Pro Thr Pro Asp Met Leu Val Ser Pro Ala Pro
            245                 250                 255

Pro Pro Ala Pro Ala Pro Gln Ala Gln Gln Pro Pro Ala Ser Gly
            260                 265                 270

Ser Gly Lys Trp Ile Ala Val Gly Val Gly Val Gly Val Gly Val Leu
    275                 280                 285

Ala Leu Ala Ser Leu Ile Gly Leu Met Leu Leu Cys Val Arg Arg Arg
    290                 295                 300

Arg Thr Arg Gln Gly Val Arg Glu Arg Gly Arg Leu Ser Lys Val Val
305                 310                 315                 320

Leu Asp Val Pro Ser Ser Ala Asp Tyr Asn Ala Leu Ala Ser Gly Lys
            325                 330                 335

His Ala Ser Ser Ala Thr Thr Thr Ser Ala Ser Ser Ser Ala Leu Val
            340                 345                 350

Ser Ser Asp Ala Arg Ala Ala Val Glu Ser Leu Thr Val Tyr Lys Tyr
            355                 360                 365

Ser Glu Leu Glu Lys Ala Thr Ala Gly Phe Ser Glu Asp Arg Arg Val
    370                 375                 380

Lys Asn Ala Ser Val Tyr Arg Ala Glu Ile Asn Gly Asp Ala Ala Ala
```

-continued

```
385                 390                 395                 400

Val Lys Arg Val Ala Gly Asp Val Ser Gly Glu Val Gly Ile Leu Lys
            405                 410                 415

Arg Val Asn His Ser Ser Leu Val Arg Leu Ser Gly Leu Cys Val His
            420                 425                 430

His Gly Glu Thr Tyr Leu Val Phe Glu Phe Ala Glu Asn Gly Ala Leu
            435                 440                 445

Ser Asp Trp Leu His Gly Gly Gly Ala Thr Leu Val Trp Lys Gln Arg
    450                 455                 460

Val Gln Ala Ala Phe Asp Val Ala Asp Gly Leu Asn Tyr Leu His His
465                 470                 475                 480

Tyr Thr Asn Pro Pro Cys Val His Lys Asn Leu Lys Ser Ser Asn Val
                485                 490                 495

Leu Leu Asp Ala Asn Leu Arg Ala Lys Val Ser Ser Phe Ala Leu Ala
            500                 505                 510

Arg Ser Val Pro Thr Gly Ala Asp Gly Gly Asp Ala Gln Leu Thr Arg
            515                 520                 525

His Val Val Gly Thr Gln Gly Tyr Leu Ala Pro Glu Tyr Leu Glu His
    530                 535                 540

Gly Leu Ile Thr Pro Lys Leu Asp Val Phe Ala Phe Gly Val Ile Leu
545                 550                 555                 560

Leu Glu Leu Leu Ser Gly Lys Glu Ala Met Phe Asn Gly Gly Asp Lys
            565                 570                 575

Arg Gly Glu Thr Leu Leu Trp Glu Ser Ala Glu Gly Leu Val Val Asp
            580                 585                 590

Asn Glu Asp Ala Arg Gly Lys Val Arg Pro Phe Met Asp Pro Arg Leu
            595                 600                 605

His Gly Asp Tyr Pro Leu Asp Leu Ala Val Ala Val Ala Ser Leu Ala
    610                 615                 620

Val Arg Cys Val Ala Arg Glu Pro Arg Arg Pro Ser Ile Asp Val
625                 630                 635                 640

Val Phe Ala Thr Leu Ser Ala Val Tyr Asn Ser Thr Leu Asp Trp Asp
            645                 650                 655

Pro Ser Asp Asp Gly Asn Ser Arg Ser Ser Ile Val Gly Arg
            660                 665                 670

<210> SEQ ID NO 234
<211> LENGTH: 681
<212> TYPE: PRT
<213> ORGANISM: Hordeum vulgare
<220> FEATURE:
<221> NAME/KEY: VARIANT
<222> LOCATION: 169-182
<223> OTHER INFORMATION: Xaa = hydrophobic patch residues
<220> FEATURE:
<221> NAME/KEY: VARIANT
<222> LOCATION: 168, 183
<223> OTHER INFORMATION: Xaa = residues immediately adjacent to
      hydrophobic patch residues

<400> SEQUENCE: 234

Met Ala Thr Pro Thr Arg Trp Arg Gly Leu Ala Ala Val Gly Arg Ala
1               5                   10                  15

Ala Leu Ala Phe Leu Val Leu Leu Ala Val Ala Ala Pro Trp Cys Pro
            20                  25                  30

Val Ala Arg Gly Gln Gln Glu Tyr Glu Ala Asn Ala Gln Asn Asn Cys
        35                  40                  45
```

-continued

```
Tyr Gly Asn Asn Gly Ser Ser Val Leu Gly Tyr Thr Cys Asn Ala Thr
    50              55                  60

Ala Ala Val Arg Pro Cys Ala Ser Tyr Val Val Phe Arg Ser Ser Pro
65              70                  75                  80

Pro Tyr Glu Ser Pro Ile Thr Ile Ser Tyr Leu Leu Asn Thr Thr Pro
            85                  90                  95

Ala Ala Leu Ala Asp Ala Asn Ala Val Pro Thr Val Ser Ser Val Ala
            100             105             110

Ala Ser Arg Leu Val Leu Ala Pro Leu Asn Cys Gly Cys Ala Pro Gly
            115             120             125

Gly Tyr Tyr Gln His Asn Ala Ser Tyr Thr Leu Gln Phe Ser Asn Glu
    130             135             140

Thr Tyr Phe Ile Thr Ala Asn Ile Thr Tyr Gln Gly Leu Thr Thr Cys
145             150             155             160

Gln Ala Leu Met Ala Gln Asn Pro Asn His Asp Ser Arg Asn Leu Val
            165             170             175

Val Gly Asn Asn Leu Thr Val Pro Ile Arg Cys Ala Cys Pro Ser Pro
            180             185             190

Ala Gln Ala Ala Ser Gly Val Arg His Leu Leu Thr Tyr Leu Val Ala
            195             200             205

Ser Gly Asp Thr Ile Ala Asp Ile Ala Thr Arg Phe Arg Val Asp Ala
    210             215             220

Gln Ala Val Leu Arg Ala Asn Arg Leu Thr Asp Ser Glu Asn Ile Tyr
225             230             235             240

Pro Phe Thr Thr Leu Leu Ile Pro Leu Lys Ser Ala Pro Thr Pro Asp
            245             250             255

Met Leu Val Ser Pro Ala Pro Pro Ala Pro Val Pro Pro Gln Ala
            260             265             270

Gln Gln Pro Leu Pro Thr Gly Gly Ser Gly Ser Gly Lys Gly Val Ala
    275             280             285

Ile Gly Val Gly Val Gly Val Gly Val Leu Ala Leu Ala Gly Leu Leu
    290             295             300

Gly Leu Met Phe Leu Cys Val Arg Arg Arg Arg Leu Arg Pro Gly
305             310             315             320

Val Gly Glu Asn Gly His Pro Gly Lys Val Val Ile Asp Val Pro Ser
            325             330             335

Ser Ala Asp Tyr Asp Pro Leu Ala Ser Gly Lys His Thr Ser Ser Ala
            340             345             350

Thr Thr Thr Ser Ser Ser Ser Ser Ala Phe Val Ser Ser Asp Ala Arg
            355             360             365

Ala Ala Val Glu Ser Leu Thr Val Tyr Lys Tyr Ser Glu Leu Glu Lys
    370             375             380

Ala Thr Ala Gly Phe Ser Glu Asp Arg Arg Val Lys Asp Ala Ser Val
385             390             395             400

Tyr Arg Ala Val Ile Asn Gly Asp Thr Ala Ala Val Lys Arg Val Ala
            405             410             415

Gly Asp Val Ser Gly Glu Val Gly Ile Leu Lys Arg Val Asn His Ser
            420             425             430

Ser Leu Val Arg Leu Ser Gly Leu Cys Val His His Gly Asp Thr Tyr
            435             440             445

Leu Val Phe Glu Phe Ala Glu Asn Gly Ala Leu Ser Asp Trp Leu His
    450             455             460

Gly Gly Gly Ala Thr Leu Val Trp Lys Gln Arg Val Gln Ala Ala Phe
```

-continued

```
465                470                475                480

Asp Val Ala Asp Gly Leu Asn Tyr Leu His His Tyr Ser Thr Pro Pro
                485                490                495

Cys Val His Lys Asn Leu Lys Ser Ser Asn Val Leu Leu Asp Ala Asp
                500            505                510

Leu Arg Ala Lys Val Ser Ser Phe Ala Leu Ala Arg Ser Val Pro Thr
            515                520                525

Gly Ala Glu Gly Gly Asp Ala Gln Leu Thr Arg His Val Val Gly Thr
        530                535                540

Gln Gly Tyr Leu Ala Pro Glu Tyr Leu Glu His Gly Leu Ile Thr Pro
545                550                555                560

Lys Leu Asp Val Phe Ala Phe Gly Val Ile Leu Leu Glu Leu Leu Ser
                565                570                575

Gly Lys Glu Ala Thr Phe Asn Gly Gly Asp Lys Arg Gly Glu Lys Leu
                580                585                590

Leu Trp Glu Ser Ala Glu Gly Leu Val Val Asp Gly Glu Asp Ala Arg
            595                600                605

Ser Lys Val Arg Ala Phe Met Asp Pro Gln Leu Ser Gly Asp Tyr Pro
        610                615                620

Leu Asp Leu Ala Val Ala Val Ala Ser Leu Ala Leu Arg Cys Val Ala
625                630                635                640

Arg Glu Pro Arg Gly Arg Pro Ser Met Tyr Glu Val Phe Val Thr Leu
                645                650                655

Ser Ala Val Tyr Asn Ser Thr Leu Asp Trp Asp Pro Ser Asp Tyr Ser
                660                665                670

Asn Ser Arg Ser Ser Ile Val Gly Arg
        675                680
```

<210> SEQ ID NO 235
<211> LENGTH: 680
<212> TYPE: PRT
<213> ORGANISM: Zea mays

<400> SEQUENCE: 235

```
Met Ala Pro Pro Pro Gln Pro Glu Leu Pro Ala Ala Ala Leu Ala Leu
1                5                10                15

Leu Val Leu Leu Leu Ala Ala Ala Val Pro Ala Arg Ala Gln Gln Glu
                20                25                30

Tyr Glu Ala Asn Lys Gln Asn Ala Cys Tyr Ala Thr Asn Ala Ser Ser
            35                40                45

Val Leu Gly Tyr Thr Cys Asn Ala Thr Ala Ala Ser Thr Pro Ala Cys
        50                55                60

Glu Ser Tyr Leu Ile Phe Arg Ser Ser Pro Ser Tyr Tyr Asn Thr Pro
65                70                75                80

Val Ser Ile Ser Tyr Leu Leu Asn Ser Ser Pro Ala Thr Val Ala Ala
                85                90                95

Ala Asn Ala Val Pro Thr Val Ser Pro Leu Ala Ala Ser Ser Leu Val
                100                105                110

Leu Val Pro Val Pro Cys Ala Cys Thr Pro Gly Gly Tyr Tyr Gln His
            115                120                125

Asn Ser Ser Tyr Thr Ile Glu Phe Gln Ser Glu Thr Tyr Phe Ile Ile
        130                135                140

Ala Asn Ile Thr Tyr Gln Gly Leu Thr Thr Cys Gln Ala Leu Ile Ala
145                150                155                160
```

-continued

```
Gln Asn Pro Leu His Asp Ser Arg Gly Leu Val Ala Gly Asn Asn Leu
                165                 170                 175

Thr Val Pro Leu Arg Cys Ala Cys Pro Ser Pro Ala Gln Ala Ala Lys
            180                 185                 190

Gly Phe Arg Tyr Leu Leu Ser Tyr Leu Val Met Trp Gly Asp Gly Val
            195                 200                 205

Pro Ser Ile Ala Ala Arg Phe Arg Val Asp Pro Gln Ala Val Leu Asp
        210                 215                 220

Ala Asn Ser Leu Thr Ala Asp Asp Ile Ile Phe Pro Phe Thr Thr Leu
225                 230                 235                 240

Leu Ile Pro Leu Lys Ala Ala Pro Thr Pro Asp Met Leu Ala Ser Pro
                245                 250                 255

Ala Pro Pro Pro Ser Pro Thr Pro Pro Gln Pro Thr Pro Ala Pro Ser
            260                 265                 270

Gly Gly Ser Gly Ser Gly Lys Trp Val Gly Val Gly Val Gly Leu Gly
            275                 280                 285

Cys Gly Ala Leu Ala Leu Ala Ala Ile Leu Gly Leu Leu Phe Leu Arg
        290                 295                 300

Thr Arg Arg Arg Arg Gly Gln Arg Phe Ala Asp Gly Glu Ser Val Arg
305                 310                 315                 320

Gln Gly Ser Lys Val Val Ile Asp Val Ser Ser Ser Ala Glu Tyr Gly
            325                 330                 335

Ala Leu Ala Ser Gly Lys Gln Thr Ser Asn Thr Thr Thr Ser Thr Thr
            340                 345                 350

Ser Ser Ala Thr Arg Ser Leu Val Ala Ser Asp Val Arg Gly Ala Val
            355                 360                 365

Glu Ser Leu Thr Val Tyr Lys Tyr Ser Glu Leu Glu Lys Ala Thr Ala
        370                 375                 380

Gly Phe Ala Glu Glu Arg Gln Val Pro Gly Thr Ser Val Phe Arg Ala
385                 390                 395                 400

Val Ile Asn Gly Asp Ala Ala Ala Val Lys Leu Val Ala Gly Asp Val
                405                 410                 415

Arg Asp Glu Val Ser Ile Leu Met Arg Val Asn His Ser Cys Leu Val
            420                 425                 430

Arg Leu Ser Gly Leu Cys Val His Arg Gly Asp Thr Tyr Leu Val Phe
            435                 440                 445

Glu Phe Ala Glu Asn Gly Ala Leu Ser Asp Trp Ile His Gly Gly Gly
        450                 455                 460

Gly Ser Thr Leu Arg Trp Arg Gln Arg Val Gln Val Ala Phe Asp Val
465                 470                 475                 480

Ala Asp Gly Leu Asn Tyr Leu His His Tyr Thr Asn Pro Pro Cys Val
                485                 490                 495

His Lys Asn Leu Lys Ser Ser Asn Val Leu Leu Asp Ala Asp Leu Arg
            500                 505                 510

Ala Lys Val Ser Ser Phe Gly Leu Ala Arg Thr Val Ala Ala Ser Asp
            515                 520                 525

Gly Gly Ala Gln Leu Thr Arg His Val Ala Gly Thr Gln Gly Tyr Leu
        530                 535                 540

Ala Pro Glu Tyr Leu Glu Asp Gly Leu Ile Thr Pro Lys Leu Asp Val
545                 550                 555                 560

Phe Ala Phe Gly Val Val Leu Leu Glu Leu Leu Ser Gly Lys Glu Ala
                565                 570                 575

Ala Phe Ala Asp Ala Gly Thr Gly Glu Glu Thr Leu Leu Trp Glu Ala
```

-continued

```
                580                    585                    590

Ala Glu Glu Ala Leu Val Ala Asp Gly Gly Glu Asp Val Asp Arg Ala
            595                    600                    605

Lys Val Arg Ala Phe Met Asp Pro Arg Leu His Gly Asp Phe Pro Ile
        610                    615                    620

Asp Leu Ala Leu Ala Met Ala Ala Leu Ala Leu Arg Cys Val Ala Thr
625                    630                    635                    640

Glu Pro Arg Ala Arg Pro Ala Met Asp Glu Val Phe Val Ser Leu Thr
                645                    650                    655

Ala Val His Asn Ser Thr Leu Asp Trp Asp Pro Ser Asp Tyr Gly Thr
                660                    665                    670

Ser Gly Ser Ser Met Val Gly Arg
                675                    680

<210> SEQ ID NO 236
<211> LENGTH: 684
<212> TYPE: PRT
<213> ORGANISM: Zea mays

<400> SEQUENCE: 236

Met Met Ala Ser Pro Pro Gln Thr Glu Leu Gln Ala Val Ala Leu Ala
1                    5                    10                    15

Leu Leu Val Leu Leu Leu Ala Gly Ala Ala Pro Ala Arg Ala Gln Gln
                20                    25                    30

Glu Tyr Glu Ala Asn Lys Gln Asn Ala Cys Tyr Ala Thr Asn Ala Ser
            35                    40                    45

Ser Val Leu Gly Tyr Thr Cys Asn Ala Thr Thr Ala Ser Thr Pro Ala
        50                    55                    60

Cys Asp Ser Tyr Leu Ile Phe Arg Ser Ser Pro Thr Tyr Tyr Asn Thr
65                    70                    75                    80

Pro Val Ser Ile Ser Tyr Leu Leu Asn Ser Ser Val Ser Ala Thr Ala
                85                    90                    95

Ala Ala Asn Ala Val Pro Ser Val Ser Pro Leu Ala Pro Ser Ser Leu
            100                   105                   110

Val Leu Val Pro Val Pro Cys Ala Cys Thr Pro Gly Gly Tyr Tyr Gln
        115                   120                   125

His Asn Ser Ser Tyr Thr Ile Gln Phe Arg Gly Glu Thr Tyr Phe Ile
        130                   135                   140

Ile Ala Asn Ile Thr Tyr Gln Gly Leu Thr Thr Cys Gln Ala Leu Ile
145                   150                   155                   160

Ala His Asn Pro Leu His Asp Ser Arg Gly Leu Val Ala Gly Asn Asn
                165                   170                   175

Leu Thr Val Pro Leu Arg Cys Ala Cys Pro Ser Pro Ala Gln Ala Ala
                180                   185                   190

Lys Gly Phe Lys Tyr Leu Leu Ser Tyr Leu Ile Met Trp Gly Asp Asp
            195                   200                   205

Val Thr Ser Ile Ala Ala Arg Phe Arg Ala Asp Pro Gln Ala Val Leu
        210                   215                   220

Asp Ala Asn Ser Leu Thr Ala Asp Asp Ile Ile Phe Pro Phe Thr Thr
225                   230                   235                   240

Leu Leu Ile Pro Leu Lys Thr Ala Pro Thr Leu Asp Met Leu Ala Ser
                245                   250                   255

Thr Ala Pro Pro Pro Ala Pro Thr Pro Pro Gln Pro Ala Pro Ala Pro
            260                   265                   270
```

```
Ser Gly Arg Ser Gly Ser Gly Lys Leu Val Gly Phe Gly Val Gly Leu
        275             280             285

Gly Cys Gly Ala Leu Ala Leu Ala Gly Ile Leu Gly Leu Leu Phe Leu
        290             295             300

Arg Ala Arg Arg Arg Gln Arg Leu Pro Val Gly Glu Ser Val Arg Gln
305             310             315             320

Gly Ser Lys Val Val Ile Asp Val Ser Ser Ser Ala Asp Tyr Gly Ala
            325             330             335

Leu Ala Ser Gly Lys Lys Ile Thr Asn Thr Thr Thr Ser Ser Met Ser
            340             345             350

Ser Ala Ala Trp Ser Leu Val Ala Ser Asp Val Arg Gly Ala Val Glu
        355             360             365

Ser Leu Thr Val Tyr Lys Tyr Ser Glu Leu Glu Lys Ala Thr Ala Gly
    370             375             380

Phe Ala Glu Glu His Gln Val Pro Gly Thr Ser Val Tyr Arg Ala Val
385             390             395             400

Ile Asn Gly Asp Ala Ala Ala Val Lys Arg Leu Ala Gly Asp Val Ser
            405             410             415

Gly Glu Val Gly Ile Leu Met Arg Val Asn His Ser Cys Leu Val Arg
            420             425             430

Leu Ser Gly Leu Cys Val His Arg Gly Asp Thr Tyr Leu Val Phe Glu
        435             440             445

Phe Ala Glu Asn Gly Ala Leu Ser Asp Trp Ile His Gly Gly Ser Gly
        450             455             460

Ser Cys Ser Gly Ser Asn Thr Leu Arg Trp Arg Gln Arg Val Gln Val
465             470             475             480

Ala Phe Asp Ile Ala Asp Gly Leu Asn Tyr Leu His His Tyr Thr Asn
            485             490             495

Pro Pro Cys Val His Lys Asn Leu Lys Ser Ser Asn Val Leu Leu Asp
        500             505             510

Ala Asp Leu Arg Ala Lys Val Ser Gly Phe Gly Leu Ala Arg Ala Val
        515             520             525

Thr Ala Ala His Gly Gly Ala Gln Leu Thr Gly His Val Val Gly Thr
        530             535             540

Gln Gly Tyr Leu Ala Pro Glu Tyr Leu Glu Asp Gly Leu Ile Thr Pro
545             550             555             560

Lys Leu Asp Val Phe Ala Phe Gly Val Val Leu Leu Glu Leu Leu Ser
            565             570             575

Gly Lys Glu Ala Gly Phe Ala Asp Ala Gly Thr Gly Glu Glu Ile Leu
            580             585             590

Leu Cys Glu Ser Ala Glu Glu Ala Leu Val Ala Asp Gly Gly Glu Asp
        595             600             605

Met Asp Arg Ala Lys Val Arg Ala Phe Met Asp Pro Arg Leu His Gly
        610             615             620

Asp Phe Pro Met Asp Leu Ala Leu Ser Met Ala Ala Leu Ala Leu Arg
625             630             635             640

Cys Val Ala Met Glu Pro Arg Ala Arg Pro Ala Met Asp Glu Val Phe
            645             650             655

Ile Ser Leu Ser Ala Val Tyr Asn Ser Thr Met Asp Cys Asp Pro Ser
            660             665             670

Asp Tyr Gly Thr Ser Gly Ser Ser Met Ile Gly Arg
        675             680
```

```
<210> SEQ ID NO 237
<211> LENGTH: 723
<212> TYPE: PRT
<213> ORGANISM: Zea mays

<400> SEQUENCE: 237

Met Asn Phe Ser Thr Trp Lys Thr Lys Glu Val Gln Val Arg Ser Phe
1               5                   10                  15

Thr Thr Arg Lys Pro Thr Pro Gln Ala Ala Cys Ala Met Ala Ser Phe
            20                  25                  30

His Asp Leu Thr Ala Thr Ala Val Leu Leu Leu Phe Ser Ile Leu
        35                  40                  45

Ser Gly Gly Leu Ala Pro Leu Gln Val Gln Ala Gln Gln Pro Tyr Gly
        50                  55                  60

Ser Gln Ile Ala Asp Cys Thr Asn Gln His Asn Ser Ser Ser Leu Leu
65                  70                  75                  80

Gly Tyr Phe Cys Gly Ala Ala Gly Ser Ala Pro Ser Cys Pro Thr Phe
                85                  90                  95

Leu Thr Phe Thr Ala Arg Ala Gln Tyr Ser Ser Leu Ala Thr Ile Gly
            100                 105                 110

Ala Leu Leu Gly Ala Asp Pro Ala Ser Val Leu Ala Pro Asn Glu Ala
            115                 120                 125

Thr Gly Ala Asp Ala Pro Leu Pro Ala Gly Thr Arg Val Leu Val Pro
    130                 135                 140

Ala Thr Cys Ala Cys Thr Ala Thr Pro Gly Gly Arg Phe Tyr Gln Arg
145                 150                 155                 160

Asn Ala Thr Tyr Val Ala Val Ala Gly Asp Thr Leu Leu Ile Ile Ala
                165                 170                 175

Asn Asn Thr Phe Gln Gly Leu Thr Ser Cys Gln Ala Leu Glu Ala Gln
            180                 185                 190

Ala Leu Arg Gly Ala Pro Pro Gln Ser Leu Asp Val Gly Gln Ser Leu
            195                 200                 205

Pro Val Pro Leu Arg Cys Ala Cys Pro Ser Ala Ala Gln Ala Ala Ala
    210                 215                 220

Gly Ala Arg Tyr Leu Val Ser Tyr Leu Val Asp Val Phe Asp Asp Leu
225                 230                 235                 240

Thr Thr Val Ala Ala Arg Phe Gly Val Asp Met Gly Thr Val Ala Ala
                245                 250                 255

Ser Asn Gln Leu Gln Pro Pro Phe Thr Ile Asp Pro Tyr Thr Thr Leu
            260                 265                 270

Leu Ile Pro Val Ser Ala Gln Pro Asn Val Ser Arg Ile Gln Thr Pro
        275                 280                 285

Pro Ser Pro Pro Pro Pro Pro Val Val Ala Arg Ala Pro Ala Pro
    290                 295                 300

Gly Lys Lys Ser Ser Asn His Val Gly Val Tyr Ile Gly Val Ala Val
305                 310                 315                 320

Ala Val Val Val Ala Ala Ile Val Ser Ala Gly Ala Phe Leu Ala
                325                 330                 335

Val Arg Ala Arg Arg Arg Arg Ala Gly Ala Val Leu Ala Thr Gly Glu
            340                 345                 350

Val Ala Lys Lys Glu Ser Lys Ala Gly Asn Asp Arg Ala Ala Thr Ser
        355                 360                 365

Ser Gly Phe Thr Gly Gly Glu Phe Ser Leu Ser Thr Ser Glu Ala Phe
    370                 375                 380
```

Ser Ser Ile Ser Val Thr Asp Ile Lys Ser Ser Leu Lys Val Tyr Thr
385                 390                 395                 400

Tyr Ala Glu Leu Lys Ala Ala Thr Asp Asp Phe Ser Pro Glu His Arg
                405                 410                 415

Ile Gly Gly Ser Val Tyr Arg Ala Ala Phe Asn Gly Asp Ala Ala Ala
                420                 425                 430

Val Glu Val Val Asp Arg Asn Val Ser Thr Glu Val Glu Ile Met Arg
                435                 440                 445

Lys Ile Asn His Leu Asn Leu Ile Arg Leu Ile Gly Leu Cys His His
                450                 455                 460

Arg Gly Arg Trp Tyr Leu Val Thr Glu Tyr Ala Glu His Gly Ala Leu
465                 470                 475                 480

Arg Asp Arg Leu Leu Ala Ser Ala Thr Gly Thr Ala Ala Pro Leu Thr
                485                 490                 495

Trp Ala Gln Arg Val His Ile Ala Leu Asp Val Ala Glu Gly Leu Arg
                500                 505                 510

Tyr Leu His Glu Tyr Ala Arg Pro Ala Trp Val His Met Asp Val Ser
                515                 520                 525

Ser Gly Ser Val Leu Leu Ala Gly Asp Gly Pro Arg Ala Lys Leu Arg
                530                 535                 540

Gly Phe Gly Ala Ala Arg Ala Ile Thr Gly Ala Thr Ala Gly Val Asp
545                 550                 555                 560

Gly Glu Glu Gly Ala Glu Glu Ala Leu Phe Thr Met Thr Ser Arg Ile
                565                 570                 575

Ala Gly Thr Arg Gly Tyr Ile Ala Pro Glu Tyr Leu Glu His Gly Val
                580                 585                 590

Val Ser Pro Lys Ala Asp Val Tyr Ser Leu Gly Val Val Leu Leu Glu
                595                 600                 605

Leu Val Thr Gly Arg Asp Ala Glu Glu Leu Val Gly Asp Gly Val Gly
                610                 615                 620

Asp Pro Phe Val Ala Leu Arg Glu Leu Ala Glu Glu Leu Asp Gly Gly
625                 630                 635                 640

Gly Asp Ala Val Leu Gln Arg Leu Glu Glu Leu Val Asp Pro Ala Leu
                645                 650                 655

Pro Ala Gly Ser Cys Pro Gln Asp Ala Val Val Met Val Val Arg Leu
                660                 665                 670

Ile Glu Arg Cys Val Arg Gln Asp Pro Ala Arg Arg Pro Thr Thr Gly
                675                 680                 685

Glu Val Ala Gln Arg Leu Leu Lys Leu Ser Gly Val Ser Val Val Ser
                690                 695                 700

Trp Arg Asn Ser Pro Glu Ser Pro Arg Ser Ser Gly Ser Gly Lys Gly
705                 710                 715                 720

Leu Met Tyr

<210> SEQ ID NO 238
<211> LENGTH: 587
<212> TYPE: PRT
<213> ORGANISM: Zea mays

<400> SEQUENCE: 238

Met Thr Lys His Gly Leu Leu Phe Phe Leu Ala Ile Ala Leu Leu Leu
1               5                   10                  15

His Arg His Tyr Thr Ser Ala Ser Ser Thr Gly Gln Pro Thr Arg Ser
                20                  25                  30

-continued

```
Ser Ser Thr Ala Ser Arg Ser Thr Ala Glu Trp Gln Pro Leu His Cys
    35              40              45

Ser Pro Val Ser Ser Cys Gly Ser Phe Leu Tyr Val Thr Pro Gly Gly
    50              55              60

Arg Asn Leu Ser Glu Ile Ala Ser Val Phe Asn Gly Asn Ala Ser Leu
65              70              75              80

Ile Gln Pro Val Lys Arg Leu Ser Gly Ser Glu Asp Leu Leu Met Ala
                85              90              95

Val Ala Cys Glu Cys Gln Ala Ile Ser Asn Thr Thr Thr Ala Ala Ala
            100             105             110

Phe Leu His Asp Thr Gln Tyr Lys Val Glu Pro Asp Ala Ile Pro Asp
        115             120             125

Asp Val Lys Ser Asn Thr Phe Ser Gly Leu Ala Met Asp Val Gly Asp
    130             135             140

Gly Phe Pro Leu Thr Pro Gly Ala Thr Val Thr Val Arg Leu Pro Cys
145             150             155             160

Gly Cys Ser Ser Ser Thr Ala Ser Lys Gly Val Leu Ser Tyr Ser Val
            165             170             175

Gln Glu Glu Asp Thr Leu Ser Thr Ile Ala Ser Leu Phe Ser Ser Ser
            180             185             190

Pro Glu Ala Ile Leu Asn Leu Asn Pro Ser Val Lys Asn Pro Asp Phe
        195             200             205

Ile Lys Pro Gly Trp Ile Leu Phe Val Pro Met Gly Val Ala Gly Ser
    210             215             220

Ser Lys Lys Lys Arg Val Gly Ser Thr Thr Ile Thr Ile Ala Ala Ser
225             230             235             240

Val Ser Ala Ile Ile Leu Ser Val Cys Val Leu Thr Val Ile Leu Arg
            245             250             255

Leu Arg Arg Arg Pro Ser Gln Gln Asn Ala Glu Ala Pro Glu Ile Lys
            260             265             270

Met Glu Arg Ala Pro Asn Ile Asp Pro Phe Gln Thr Glu Arg Pro Val
        275             280             285

Ile Phe Ser Leu Lys Val Val Gly Asp Ala Thr Ala Asn Phe Asp Glu
    290             295             300

Lys Arg Lys Ile Gly Glu Gly Gly Tyr Gly Ser Val Tyr Leu Gly Phe
305             310             315             320

Ile Gly Thr His Glu Ile Ala Val Lys Lys Met Arg Ala Ser Lys Ser
            325             330             335

Lys Glu Phe Phe Ala Glu Leu Lys Ala Leu Cys Lys Val His His Ile
        340             345             350

Asn Val Val Glu Leu Ile Gly Tyr Ala Ala Gly Asp Asp His Leu Tyr
        355             360             365

Leu Val Tyr Glu Tyr Val Gln Asn Gly Ser Leu Ser Glu His Leu His
    370             375             380

Asp Pro Leu Leu Lys Gly His Gln Pro Leu Ser Trp Thr Ala Arg Thr
385             390             395             400

Gln Ile Ala Leu Asp Ala Ala Arg Gly Ile Glu Tyr Ile His Asp His
            405             410             415

Thr Lys Ala Cys Tyr Val Ala Asp Phe Gly Leu Val Lys Leu Val Glu
            420             425             430

Arg Ser Asp Glu Glu Glu Trp Val Ala Thr Arg Leu Val Gly Thr Pro
    435             440             445

Gly Tyr Leu Pro Pro Glu Ser Val Leu Glu Leu His Met Thr Thr Lys
```

-continued

```
      450                455                460

Ser Asp Val Tyr Ala Phe Gly Val Val Leu Ala Glu Leu Ile Thr Gly
465                470                475                480

Leu Arg Ala Leu Ile Arg Asp Asn Lys Glu Val Asn Lys Thr Lys Ser
                485                490                495

Ile Ile Ser Ile Met Arg Lys Ala Phe Asp Ser Glu Asp Leu Glu Arg
                500                505                510

Ser Leu Glu Thr Ile Ile Asp Pro Asn Leu Lys Asp Ser Tyr Pro Ile
                515                520                525

Glu Glu Val Cys Lys Met Ala Asn Val Ser Met Trp Cys Leu Ser Glu
                530                535                540

Asp Pro Leu Asn Arg Pro Glu Met Arg Asp Thr Met Pro Ala Leu Cys
545                550                555                560

Gln Ile His Leu Ala Ser Ile Glu Trp Glu Ala Ser Leu Gly Gly Asp
                565                570                575

Gly Glu Val Phe Ser Gly Val Ser Tyr Gly Arg
                580                585

<210> SEQ ID NO 239
<211> LENGTH: 629
<212> TYPE: PRT
<213> ORGANISM: Zea mays

<400> SEQUENCE: 239

Met Leu Tyr Pro His Ser Ala Gln Gln Thr Arg Thr Ala Trp Thr Thr
1                5                10                15

Arg Ser Arg Ser Arg Met Asp Thr Ala Cys His His Tyr Thr Ser Ala
                20                25                30

Ser Phe Thr Asp Gln Pro Ser Ser Ile Ala Ser Ala Ala Glu Trp Gln
                35                40                45

Pro Leu Thr Cys Asn Ala Ala Val Ser Asn Asn Pro Ser Cys Gly Ser
                50                55                60

Phe Leu Tyr Val Thr Pro Arg Gly Arg Thr Leu Ser Glu Val Val Ser
65                70                75                80

Val Phe Asn Gly Asn Ala Ser Leu Ile Gln Pro Ile Lys Arg Leu Ser
                85                90                95

Gly Ser Glu Asp Leu Leu Val Gly Val Ala Cys Lys Cys Glu Ala Ile
                100                105                110

Asn Asp Thr Met Thr Ala Phe Phe His Asp Thr Gln Tyr Glu Val Glu
                115                120                125

Pro Gly Asp Thr Pro Asp Asn Val Lys Ser Asn Asn Phe Ser Gly Leu
                130                135                140

Ala Met Asn Val Gly Asp Gly Arg Thr Leu Ile Ala Gly Thr Thr Ile
145                150                155                160

Ala Val His Leu Pro Cys Gly Cys Ser Ser Thr Ala Pro Glu Gly Val
                165                170                175

Leu Ser Tyr Ser Val Gln Glu Glu Asp Thr Leu Ser Thr Ile Ala Ser
                180                185                190

Leu Phe Ser Ser Arg Gln Gln Asp Ile Leu Asn Leu Asn Pro Ile Leu
                195                200                205

Arg Asn Ala Asp Phe Ile Arg Thr Gly Trp Ile Leu Phe Ile Pro Met
                210                215                220

Gly Val Ala Gly Ser Ser Lys Lys Gly Ile Gly Ser Met Arg Ile Ile
225                230                235                240
```

```
Ile Ala Ala Ser Val Ser Ala Ala Val Leu Leu Phe Cys Val Leu Ala
             245                 250                 255

Val Ile Leu Arg Arg Arg Arg Ser Ser Gln His Asn Val Glu Ala
             260             265                 270

Pro Glu Ile Lys Met Glu Arg Ala Pro Ser Asn Thr Ser Ile Ala Ala
             275             280                 285

Leu Glu Ser Arg Phe Phe Pro Thr Met Arg Thr Asn Asp Thr Asp Pro
        290             295             300

Phe Gln Thr Glu Arg Pro Val Ile Phe Ser Leu Lys Gln Val Gly Asp
305             310             315                 320

Ala Thr Ala Asp Phe Ser Glu Lys Arg Lys Ile Gly Glu Gly Gly Tyr
             325             330                 335

Gly Ser Val Tyr Leu Gly Phe Ile Gly Ala His Glu Ile Ala Ile Lys
             340             345             350

Lys Met Lys Ala Ser Lys Ser Lys Glu Phe Phe Ala Glu Leu Lys Ala
             355             360             365

Leu Cys Lys Val His His Ile Asn Val Val Glu Leu Ile Gly Tyr Ala
        370             375             380

Ala Gly Asp Asp His Leu Tyr Leu Val Tyr Glu Tyr Val Gln Asn Gly
385             390             395                 400

Ser Leu Thr Asp His Leu His Asp Pro Leu Leu Lys Gly His Gln Pro
             405             410             415

Leu Ser Trp Thr Ala Arg Thr Gln Ile Ala Leu Asp Ala Ala Arg Gly
             420             425             430

Ile Glu Tyr Ile His Asp His Thr Lys Ala Cys Tyr Val His Arg Asp
             435             440             445

Ile Lys Thr Ser Asn Ile Leu Leu Asp Asn Gly Leu Arg Ala Lys Val
        450             455             460

Ala Asp Phe Gly Leu Val Lys Leu Val Glu Arg Ser Asp Glu Glu Glu
465             470             475                 480

Phe Val Ala Thr Arg Leu Val Gly Thr Pro Gly Tyr Leu Pro Pro Glu
             485             490             495

Ser Val Leu Glu Leu His Met Thr Thr Lys Ser Asp Val Tyr Ala Phe
             500             505             510

Gly Val Val Leu Ala Glu Leu Ile Thr Gly Leu Arg Ala Leu Ile Arg
             515             520             525

Asp Asn Lys Glu Val Asn Lys Thr Lys Ser Ile Thr Ser Ile Met Arg
        530             535             540

Glu Val Phe Lys Ser Glu Asp Leu Glu Arg Ser Leu Glu Thr Ile Ile
545             550             555                 560

Asp Pro Asn Leu Lys Asp Ser Tyr Pro Ile Glu Glu Val Cys Lys Met
             565             570             575

Ala Asn Val Ser Met Trp Cys Leu Ser Glu Asp Pro Leu Asn Arg Pro
             580             585             590

Glu Thr Arg Asp Ile Met Ser Thr Leu Gly Gln Ile His Leu Ala Ser
             595             600             605

Ile Glu Trp Glu Ala Ser Leu Cys Gly Asp Gly Glu Val Phe Ser Gly
        610             615             620

Val Ser Tyr Gly Arg
625
```

<210> SEQ ID NO 240
<211> LENGTH: 612
<212> TYPE: PRT

<213> ORGANISM: Hordeum vulgare

<400> SEQUENCE: 240

Met Ala Arg His Ser Leu Phe Phe Phe Phe Leu Ala Leu Ser Leu Gln
1               5                   10                  15

His Leu His Ile Ser Val Gly Leu Pro Gly Arg Ser Leu Ala Thr Ala
            20                  25                  30

Thr Glu Gln Trp Gln Pro Met Gln Cys Asp Ala Ala Ser Leu Asn Ala
        35                  40                  45

Ser Cys Ser Ser Tyr Leu Tyr Val Thr Pro Gln Gly Arg Ser Leu Ser
    50                  55                  60

Glu Ile Ala Ser Leu Phe Asn Gly Ser Ala Ser Arg Thr Gln Pro Ile
65                  70                  75                  80

Lys Arg Leu Ser Gly Ser Glu Asp Leu Leu Val Pro Val Pro Cys Met
            85                  90                  95

Cys Asp Ala Ile Asn Asp Asn Met Ser Gly Leu Phe His Asp Thr Ala
            100                 105                 110

Tyr Lys Val Asn Leu Asn Asp Thr Ala Asp Asn Ile Asn Ser Ile Phe
        115                 120                 125

Ser Gly Leu Ala Trp Asn Ile Thr Ala Thr Ala Asn Thr Thr Ile Thr
    130                 135                 140

Val His Leu Leu Cys Gly Cys Ser Ser Thr Ala Pro Glu Gly Val Ile
145                 150                 155                 160

Ser Tyr Met Val Gln Ala Arg Asp Thr Leu Ser Asn Ile Ala Thr Leu
            165                 170                 175

Phe Arg Ser Gly Ser Ser Glu Ile Leu Ser Leu Asn Ala Gly Val Thr
            180                 185                 190

Asp Pro Asp Phe Leu Gln Pro Gly Trp Ile Leu Phe Ile Pro Met Gly
        195                 200                 205

Val Ala Ser Ser Ser Lys Arg Lys Phe Gly Gly Leu Pro Ile Ile Ile
    210                 215                 220

Ala Val Ser Ile Ser Ala Ala Ile Met Leu Leu Cys Thr Leu Thr Ile
225                 230                 235                 240

Val Leu Arg Leu Arg Arg Arg Ser Leu Val Pro Asn Ala Glu Val Pro
            245                 250                 255

Lys Lys Glu Met Glu Arg Val Pro Ser Asn Thr Ser Ile Ala Ile Leu
            260                 265                 270

Glu Ser Arg Tyr Phe Pro Ser Lys Arg Ile Asp Asp Ile Asp Pro Phe
        275                 280                 285

Gln Thr Glu Arg Pro Val Ile Phe Ser Leu Lys Ala Val Gly Glu Ala
    290                 295                 300

Thr Ala Asn Phe Asp Glu Lys Arg Lys Ile Gly Glu Gly Gly Tyr Gly
305                 310                 315                 320

Met Val Tyr Leu Gly Phe Ile Gly Thr His Glu Ile Ala Val Lys Met
            325                 330                 335

Met Lys Asp Ser Lys Ser Lys Glu Phe Phe Ala Glu Leu Lys Val Leu
            340                 345                 350

Cys Lys Val His His Ile Asn Val Val Glu Leu Ile Gly Tyr Ala Ser
        355                 360                 365

Gly Glu Asp His Leu Tyr Leu Val Tyr Glu Tyr Val Gln Asn Gly Ser
    370                 375                 380

Leu Ser Glu His Leu His Asp Pro Leu Leu Lys Gly His Gln Pro Leu
385                 390                 395                 400

```
Ser Trp Thr Ala Arg Thr Gln Ile Ala Thr Asp Ala Ala Arg Gly Ile
                405                 410                 415

Glu Tyr Ile His Asp His Thr Lys Ala Cys Tyr Val His Arg Asp Ile
            420                 425                 430

Lys Thr Ser Asn Ile Leu Leu Asp Asp Gly Leu Arg Ala Lys Val Ala
            435                 440                 445

Asp Phe Gly Leu Val Lys Leu Val Glu Arg Ser Asp Glu Glu Asp Cys
        450                 455                 460

Leu Ala Thr Arg Leu Val Gly Thr Pro Gly Tyr Leu Pro Pro Glu Ser
465                 470                 475                 480

Val Arg Glu Leu His Met Thr Thr Lys Ser Asp Val Tyr Ala Phe Gly
                485                 490                 495

Val Val Leu Ala Glu Leu Ile Thr Gly Leu Arg Ala Leu Val Arg Asp
            500                 505                 510

Asn Lys Glu Ala Asn Lys Thr Lys Ser Leu Ile Ser Thr Met Arg Lys
            515                 520                 525

Ala Phe Lys Ser Glu Asp Val Glu Ser Ser Leu Glu Asn Ile Ile Asp
        530                 535                 540

Pro Ser Leu Lys Asp Asn Tyr Pro Ile Glu Glu Val Cys Lys Leu Ala
545                 550                 555                 560

Asn Ile Ser Met Trp Cys Leu Ser Glu Asp Pro Leu Asp Arg Pro Glu
                565                 570                 575

Met Arg Glu Ile Met Pro Met Leu Ser Arg Ile His Leu Thr Ser Ile
            580                 585                 590

Glu Trp Glu Ala Ser Leu Gly Gly Asp His Glu Val Phe Ser Gly Val
            595                 600                 605

Phe Asn Gly Arg
    610

<210> SEQ ID NO 241
<211> LENGTH: 673
<212> TYPE: PRT
<213> ORGANISM: Zea mays

<400> SEQUENCE: 241

Met Pro Pro His Arg Leu Leu Pro Leu Leu Leu Leu Leu Pro Leu
1               5               10                  15

Gly Val Ser Gly Ala Ala Ala Ala Gly Gly Asn Ala Thr Ser Ala Pro
            20                  25                  30

Leu Pro Cys Ser Glu Leu Ser Arg Val Cys Thr Ala Phe Ile Ala Phe
            35                  40                  45

Pro Thr Ala Gly Ala Gly Pro Ala Asn Ala Thr Val Leu Glu Ser Met
        50                  55                  60

Phe Asp Ala Ala Pro Gly Asp Leu Thr Ala Asp Ala Ala Ala Ser Pro
65                  70                  75                  80

Arg Tyr Ala Phe Val Arg Lys Asn Cys Ser Cys Leu Pro Ser Arg Thr
                85                  90                  95

Tyr Leu Ala Asn Thr Thr Tyr Thr Ile Pro Ser Ser Ala Thr Thr Ser
            100                 105                 110

Phe Pro Asn Thr Thr Ala Ala Asp Val Ala Ala Ala Ala Tyr Ser Gly
        115                 120                 125

Leu Ala Val Pro Pro Pro Gly Gly Ala Ala Gln Arg Pro Pro Arg Pro
        130                 135                 140

Gly Ala Val Val Ala Leu His Leu Leu Cys Gly Cys Ser Ser Gly Pro
145                 150                 155                 160
```

-continued

```
Trp Asn Tyr Leu Leu Thr Tyr Val Gly Val Glu Gly Asp Thr Val Glu
            165             170             175

Ser Leu Ser Ser Arg Phe Gly Ala Ser Met Asp Ala Ile Glu Thr Ala
            180             185             190

Asn Ala Met Ala Gly Pro Asp Pro Ile Thr Ala Gly Lys Val Tyr Tyr
            195             200             205

Ile Pro Leu Asn Ser Val Pro Gly Gln Ala Tyr Val Thr Leu Pro Ala
    210             215             220

Pro Pro Ala Pro Ala Pro Ala Pro Thr Asp Tyr Thr Leu Ser Gly Thr
225             230             235             240

Pro Asp Tyr His Ser Ser Lys Phe Pro Tyr Gly Trp Val Ile Gly Ser
            245             250             255

Met Gly Val Ala Leu Ala Leu Ile Val Ile Ala Val Leu Ala Leu Val
            260             265             270

Leu Trp Lys Phe Phe Gly Tyr Lys Pro Gln Asp Arg Asn Gly Gln Arg
            275             280             285

Lys Ser Pro Asp Arg His Lys Phe Gln Leu Leu Lys Ser Gly Ser Phe
    290             295             300

Cys Tyr Gly Ser Gly Arg Tyr Leu Cys Cys Gln Phe Gly Asn Ala Lys
305             310             315             320

Pro Thr Arg Ala Asp Gly Gly Glu His His Ile Asn Val Pro Lys Gly
            325             330             335

Val Ala Ala Asp Val Phe Asp Arg Glu Lys Pro Ile Val Phe Thr His
            340             345             350

Glu Glu Ile Leu Ile Ser Thr Asp Ser Phe Ser Asp Ala Asn Leu Leu
            355             360             365

Gly His Gly Thr Tyr Gly Ser Val Tyr Tyr Gly Val Leu Arg Glu Gln
    370             375             380

Glu Val Ala Ile Lys Arg Met Met Ala Thr Lys Thr Lys Glu Phe Ile
385             390             395             400

Val Glu Met Lys Val Leu Cys Lys Val His His Ala Ser Leu Val Glu
            405             410             415

Leu Ile Gly Tyr Ala Ala Gly Lys Asp Glu Leu Phe Leu Val Tyr Glu
            420             425             430

Tyr Ser Gln Asn Gly Ser Leu Lys Asn His Leu His Asp Pro Glu Arg
            435             440             445

Lys Gly Cys Ser Ser Leu Ser Trp Ile Phe Arg Val Gln Ile Ala Leu
    450             455             460

Asp Ala Ala Arg Gly Leu Glu Tyr Ile His Glu His Thr Lys Asp His
465             470             475             480

Tyr Val His Arg Asp Ile Lys Ser Ser Asn Ile Leu Leu Asp Gly Ser
            485             490             495

Phe Arg Ala Lys Ile Ser Asp Phe Gly Leu Ala Lys Leu Val Val Lys
            500             505             510

Ser Asn Asp Ala Glu Ala Ser Val Thr Lys Val Val Gly Thr Phe Gly
            515             520             525

Tyr Leu Ala Pro Glu Tyr Leu Arg Asp Gly Leu Ala Thr Thr Lys Ser
            530             535             540

Asp Val Tyr Ala Phe Gly Val Val Leu Phe Glu Leu Ile Ser Gly Lys
545             550             555             560

Glu Ala Ile Thr Arg Ala Glu Gly Met Gly Ala Ser Ser Asn Ser Glu
            565             570             575
```

```
Arg Cys Ser Leu Ala Ser Val Met Leu Ala Ala Val Arg Lys Cys Pro
            580                 585                 590

Asn Ser Thr Tyr Met Gly Asn Leu Lys Asp Cys Ile Asp His Asn Leu
            595                 600                 605

Arg Asp Leu Tyr Pro Tyr Asp Cys Ala Tyr Lys Met Ala Met Leu Ala
            610                 615                 620

Lys Gln Cys Val Asp Glu Asp Pro Val Leu Arg Pro Asp Met Lys Gln
625                 630                 635                 640

Val Val Ile Thr Leu Ser Gln Ile Leu Leu Ser Ser Ile Glu Trp Glu
                    645                 650                 655

Ala Thr Gln Ala Gly Asn Ser Gln Val Phe Ser Gly Leu Val Ala Gly
                    660                 665                 670

Arg
```

```
<210> SEQ ID NO 242
<211> LENGTH: 722
<212> TYPE: PRT
<213> ORGANISM: Hordeum vulgare

<400> SEQUENCE: 242
```

```
Met Pro Pro Arg Arg Arg Leu Leu Leu Leu Leu Leu Ala Leu Ala Cys
1                 5                   10                  15

Ser Gly Gly Gly Ala Ala Val Asp Thr Ala Pro Gly Asn Gly Thr Ser
                    20                  25                  30

Ser Pro Leu Ala Cys Ser Glu Leu Ser Arg Val Cys Thr Ala Phe Leu
            35                  40                  45

Ala Phe Pro Ala Ala Gly Asn Ala Ser Val Leu Gln Ser Met Phe Asp
            50                  55                  60

Ala Ser Pro Gly Asp Leu Thr Ser Asp Pro Ala Ala Ser Pro Gly Tyr
65                  70                  75                  80

Ala Phe Val Arg Lys Asn Cys Ser Cys Leu Ala Ser Arg Thr Tyr Leu
                    85                  90                  95

Ala Asn Thr Thr Tyr Thr Ile Pro Ser Thr Val Pro Leu Asn Ala Thr
                    100                 105                 110

Ala Ala Gln Val Ala Ala Ala Ala Tyr Gly Gly Leu Ala Val Pro Pro
            115                 120                 125

Pro Gly Gly Ala Leu Gln Arg Pro Pro Arg Pro Gly Ala Val Val Ala
            130                 135                 140

Leu His Leu Ile Cys Gly Cys Ser Ser Gly Pro Trp Asn Tyr Leu Leu
145                 150                 155                 160

Ser Tyr Val Gly Ser Asp Gly Asp Thr Val Glu Ser Leu Ser Ser Arg
                    165                 170                 175

Phe Gly Ala Ser Met Asp Ala Ile Glu Ala Ala Asn Gly Met Pro Gly
                    180                 185                 190

Pro Asp Pro Ile Thr Thr Gly Lys Val Tyr Tyr Ile Pro Leu Asn Ser
            195                 200                 205

Val Pro Gly Gln Pro Tyr Val Ala Met Ser Ser Ala Pro Val Pro Ala
            210                 215                 220

Pro Ala Pro Thr Gln Asn Thr Leu Ser Glu Ile Ser Asp His His Ser
225                 230                 235                 240

Ala Lys Phe Pro Tyr Gly Trp Val Ile Gly Gly Met Gly Val Ala Leu
                    245                 250                 255

Ala Leu Ile Ala Ile Ala Leu Leu Ala Leu Leu Met Cys Lys Ser Phe
                    260                 265                 270
```

-continued

```
Gln Tyr Asn His Gln Gly Ser Asn Asn Gln Gly Lys Ser Pro Asp Gln
        275                 280                 285

Pro Met Pro His Asn Phe Gln Leu Leu Lys Ser Gly Ser Phe Cys Tyr
        290                 295                 300

Gly Ser Gly Arg Tyr Phe Cys Cys Gln Phe Gly Asn Ala Lys Gln Ser
305                 310                 315                 320

Arg Lys Gly Gly Glu Asp His His Ile Asn Val Pro Lys Gly Met Val
                325                 330                 335

Val Asp Val Phe Asp Arg Glu Lys Pro Ile Val Phe Thr Tyr Glu Glu
                340                 345                 350

Ile Leu Ala Ser Thr Asp Leu Phe Ser Asp Ala Asn Leu Leu Gly His
        355                 360                 365

Gly Thr Tyr Gly Ser Val Tyr Tyr Gly Val Leu Arg Asp Gln Glu Val
        370                 375                 380

Ala Ile Lys Arg Met Thr Ser Thr Asn Thr Lys Glu Phe Ile Val Glu
385                 390                 395                 400

Met Lys Val Leu Cys Lys Val His His Ala Ser Leu Val Glu Leu Ile
                405                 410                 415

Gly Tyr Ala Ala Ser Lys Asp Glu Leu Phe Leu Val Tyr Glu Tyr Ser
                420                 425                 430

Gln Lys Gly Ser Leu Arg Asn His Leu His Asp Pro Gln Ser Lys Gly
        435                 440                 445

Tyr Thr Ser Leu Ser Trp Ile Tyr Arg Val Gln Ile Ala Leu Asp Ala
        450                 455                 460

Ala Arg Gly Leu Glu Tyr Ile His Glu His Thr Lys Asp His Tyr Val
465                 470                 475                 480

His Arg Asp Ile Lys Ser Ser Asn Ile Leu Leu Asp Gly Ser Phe Arg
                485                 490                 495

Ala Lys Ile Ser Asp Phe Gly Leu Ala Lys Leu Gly Leu Arg Ser Asn
                500                 505                 510

Asp Ala Glu Ala Ser Val Thr Lys Val Val Gly Thr Phe Gly Tyr Leu
        515                 520                 525

Ala Pro Glu Tyr Leu Arg Asp Gly Leu Ala Thr Ala Lys Cys Asp Val
        530                 535                 540

Tyr Ala Phe Gly Val Val Leu Phe Glu Leu Ile Ser Gly Lys Glu Ala
545                 550                 555                 560

Ile Thr Lys Ala Asp Ala Val Gly Ala Ser Ser Asn Ser Glu Arg Arg
                565                 570                 575

Ser Leu Ala Ser Val Val Ser Phe Leu Thr Cys Thr Gln Ala Val Ile
                580                 585                 590

Gln Ser Thr Ala Cys Val Phe Ala Val Ile Ser Leu Pro Lys Val Tyr
        595                 600                 605

Ile Gly Ile Ser Ser Thr Ser Phe Tyr Thr Ser Asn Leu Lys Asp Leu
        610                 615                 620

Ser Arg Phe Gly Leu Thr Gly Gln Met Leu Thr Ala Leu Arg Asn Cys
625                 630                 635                 640

His Asp Pro Thr Cys Val Gly Ser Leu Lys Asp Cys Ile Asp Pro Asn
                645                 650                 655

Leu Met Asp Leu Tyr Pro His Asp Cys Ile Tyr Gln Met Ala Met Leu
                660                 665                 670

Ala Lys Gln Cys Ala Asp Glu Asp Pro Val Leu Arg Pro Asp Met Lys
        675                 680                 685

Gln Ala Val Ile Thr Leu Ser Gln Ile Leu Leu Ser Ser Ile Glu Trp
```

-continued

```
              690                    695                    700

Glu Ala Thr Leu Gly Gly Asn Ser Gln Val Phe Ser Gly Leu Val Ala
705                    710                    715                    720

Gly Arg

<210> SEQ ID NO 243
<211> LENGTH: 613
<212> TYPE: PRT
<213> ORGANISM: Hordeum vulgare

<400> SEQUENCE: 243

Met Pro Pro Pro Pro Ala Tyr His His Leu Leu Leu Leu Leu Leu Leu
1               5                    10                   15

Leu Leu Arg Leu His Gly Ala Ile Ala Ser Ala Thr Gly Phe Thr Cys
                20                  25                   30

Thr Lys Pro Ser Thr Cys Gln Ser Ala Val Ile Gly Tyr Val Val Pro
                35                  40                   45

Asn Thr Ile Thr Tyr Lys Glu Leu Ile Ser Gln Phe Ser Pro Thr Thr
    50                  55                   60

Leu His Asp Val Val Ala Ala Asn Gln Leu Pro Phe Asn Thr Ala Thr
65                  70                   75                   80

Lys Gln Val Ile Pro Pro Lys Thr Thr Leu Thr Ile Pro Phe Arg Cys
                85                  90                   95

Arg Cys Thr Gly Asn Gly Ile Gly Gln Ser Gly Leu Tyr Ile Ala Gln
                100                 105                  110

Asn Lys Leu Asp Asp Gly Leu Ala Thr Tyr Gln Pro Glu Ile Val Ser
                115                 120                  125

Ser Lys Ser Ile Ala Asp Asn Ala Ala Asn Trp Lys Gly Trp Ile Pro
    130                 135                  140

Leu Pro Cys Ser Cys Asp Gly Ala Asp Val Thr His Phe Pro Tyr Ile
145                 150                  155                  160

Val Arg Ser Gly Asp Ser Ala Leu Ala Ile Ala Ala Lys Tyr Gly Val
                165                 170                  175

Leu Leu Ser Val Leu Leu Glu Ile Asn Asn Ile Thr Asn His Ala Ser
                180                 185                  190

Leu Tyr Gln Gly Gln Val Leu Asp Ile Pro Leu Gln Gly Lys Val Gly
                195                 200                  205

Glu Glu Leu Ser Ser Met Gly Arg Trp Ser Arg Val Tyr Tyr Ile Ser
    210                 215                  220

Gly Tyr Arg Lys Arg Arg Leu Gly Trp Phe Asn Ser Ala Ala Ala Glu
225                 230                  235                  240

Gln Ser Ala His Ala Ala Ala Glu Ala Val Ala Ala Thr Lys Glu Ala
                245                 250                  255

Ala Glu Asn Ser His Tyr Ser Pro Glu Ala Ala Asp Thr Val Val Lys
                260                 265                  270

Arg Val Leu Val Leu Leu Leu Ile Ile Ile Ile Leu Ser Leu Leu Tyr
                275                 280                  285

Phe Thr Phe Tyr Tyr Trp Lys Ser Ala Cys Glu Ser Leu Ser Ser Arg
    290                 295                  300

Thr Asn Gly Val Ile Gln Phe Tyr Tyr Ser Asp Leu Ala Arg Ala Thr
305                 310                  315                  320

His Arg Phe Ser Lys Glu Ser Lys Ile Gly Glu Gly Gln Tyr Gly Thr
                325                 330                  335

Val Tyr Lys Ala Thr Ile Lys Gly His Glu Met Ala Val Lys Lys Leu
```

-continued

```
                340                 345                 350

Lys Ala Glu Gly Glu Thr Lys Glu Leu His Arg Glu Leu Gln Thr Ile
        355                 360                 365

Ser Asn Thr Lys His Thr Asn Leu Val Ser Leu Lys Gly Trp Cys Gly
        370                 375                 380

Arg Leu Arg Leu Ile Asp Gly Lys Ser Cys Trp Lys Arg Gln Ile Lys
385                 390                 395                 400

Val Glu Leu Leu Leu Val Phe Glu Trp Ile Pro Asn Gly Asn Leu Ala
                405                 410                 415

Asp His Leu His Asn Arg Glu Gln Val Leu Ser Trp Glu Lys Arg Tyr
                420                 425                 430

Lys Ile Val Lys Gly Ile Gly Ser Ala Leu Arg Tyr Leu His His Glu
                435                 440                 445

Cys Lys Pro Ser Ile Leu His Arg Asp Ile Lys Pro Asp Asn Ile Leu
                450                 455                 460

Leu Asp Tyr His Phe Asn Ala Lys Leu Ala Asp Phe Gly Leu Ser Met
465                 470                 475                 480

Ile Thr Asp Gln Asn Gly Ala Thr Val Phe Thr Ile Ala Ile Gly Pro
                485                 490                 495

Arg Arg Tyr Met Asp Pro Gln Leu Met Lys Glu Gly Glu Phe Arg Phe
                500                 505                 510

Asn His Lys Ser Asp Ile Tyr Ser Phe Gly Ile Val Leu Leu Glu Ile
                515                 520                 525

Ala Cys Thr Gly Lys Ser Arg Glu Asn Ile Leu His Ile Leu Gly Gly
                530                 535                 540

Gly Ser Gly Gln His Val Gln Val Asp Gly Leu Ala Asp His Arg Leu
545                 550                 555                 560

Ser Ile Phe Asp Arg Thr Glu Met Ala Arg Val Val Val Leu Gly Leu
                565                 570                 575

Gln Cys Ser His Pro Asp Glu Arg Gln Arg Pro Ser Met Tyr Met Ala
                580                 585                 590

Met Arg Phe Leu Glu Glu Gly Ile Glu Leu Pro Ile Ala Ser His Asn
                595                 600                 605

Arg Arg Glu Arg Leu
        610
```

```
<210> SEQ ID NO 244
<211> LENGTH: 416
<212> TYPE: PRT
<213> ORGANISM: Arabidopsis thaliana

<400> SEQUENCE: 244

Met Lys Ile Pro Glu Lys Pro Ile Phe Leu Ile Phe Val Ser Leu Ile
1               5                   10                  15

Leu Ala Ser Ser Leu Thr Phe Thr Ala Thr Ala Lys Ser Thr Ile Glu
                20                  25                  30

Pro Cys Ser Ser Asn Asp Thr Cys Asn Ala Leu Leu Gly Tyr Thr Leu
        35                  40                  45

Tyr Thr Asp Leu Lys Val Ser Glu Val Ala Ser Leu Phe Gln Val Asp
        50                  55                  60

Pro Ile Ser Ile Leu Leu Ala Asn Ala Ile Asp Ile Ser Tyr Pro Asp
65                  70                  75                  80

Val Glu Asn His Ile Leu Pro Ser Lys Leu Phe Leu Lys Ile Pro Ile
                85                  90                  95
```

```
Thr Cys Ser Cys Val Asp Gly Ile Arg Lys Ser Val Ser Thr His Tyr
            100                 105                 110

Lys Thr Arg Pro Ser Asp Asn Leu Gly Ser Ile Ala Asp Ser Val Tyr
            115                 120                 125

Gly Gly Leu Val Ser Ala Glu Gln Ile Gln Glu Ala Asn Ser Val Asn
    130                 135                 140

Asp Pro Ser Leu Leu Asp Val Gly Thr Ser Leu Val Ile Pro Leu Pro
145                 150                 155                 160

Cys Ala Cys Phe Asn Gly Thr Asp Asn Ser Leu Pro Ala Val Tyr Leu
            165                 170                 175

Ser Tyr Val Val Lys Glu Ile Asp Thr Leu Val Gly Ile Ala Arg Arg
            180                 185                 190

Tyr Ser Thr Thr Ile Thr Asp Leu Met Asn Val Asn Ala Met Gly Ala
            195                 200                 205

Pro Asp Val Ser Ser Gly Asp Ile Leu Ala Val Pro Leu Ser Ala Cys
    210                 215                 220

Ala Ser Lys Phe Pro Arg Tyr Ala Ser Asp Phe Gly Leu Ile Val Pro
225                 230                 235                 240

Asn Gly Ser Tyr Ala Leu Ala Ala Gly His Cys Val Gln Cys Ser Cys
            245                 250                 255

Ala Leu Gly Ser Arg Asn Leu Tyr Cys Glu Pro Ala Ser Leu Ala Val
            260                 265                 270

Ser Cys Ser Ser Met Gln Cys Arg Asn Ser Asn Leu Met Leu Gly Asn
            275                 280                 285

Ile Thr Val Gln Gln Thr Ser Ala Gly Cys Asn Val Thr Thr Cys Asp
    290                 295                 300

Tyr Asn Gly Ile Ala Asn Gly Thr Ile Leu Thr Met Leu Thr Arg Ser
305                 310                 315                 320

Leu Gln Pro Arg Cys Pro Gly Pro Gln Gln Phe Ala Pro Leu Leu Ala
            325                 330                 335

Pro Pro Asp Thr Val Pro Arg Asp Val Met Tyr Ala Pro Ala Pro Ser
            340                 345                 350

Pro Asp Phe Asp Gly Pro Gly Ser Ile Ala Ser Ser Pro Arg Ser Ser
            355                 360                 365

Met Leu Pro Gly Gly Gly Ile Leu Pro Gly Asn Pro Ala Asn Gly Pro
    370                 375                 380

Ala Gly Ser Ile Ser Thr Ala Ser Ala Ser Ser Val Ser Tyr Phe Phe
385                 390                 395                 400

Ile Thr Phe Leu Ile Ser Ile Ala Ser Phe Ser Leu Ala Leu Ser Ser
            405                 410                 415
```

<210> SEQ ID NO 245
<211> LENGTH: 415
<212> TYPE: PRT
<213> ORGANISM: Lotus japonicus

<400> SEQUENCE: 245

```
Met Arg Met Gln Gln Gln Gln Ser Thr Leu Leu Phe Leu Val Val Leu
1               5                   10                  15

Leu Phe His Ser Leu Thr Thr Thr Thr Cys Lys Ser Thr Ile Glu Pro
            20                  25                  30

Cys Thr Asn Ser Asp Ser Cys Asn Ala Leu Leu Gly Tyr Thr Leu Tyr
            35                  40                  45

Thr Asp Leu Lys Val Ser Glu Val Ala Ser Leu Phe Gly Ile Asp Pro
    50                  55                  60
```

```
Ile Ser Leu Leu Thr Ala Asn Ala Ile Asp Ile Ser Tyr Pro Asp Ala
65                  70                  75                  80

Glu His His Ile Leu Pro Pro Lys Leu Phe Leu Lys Ile Pro Ile Ser
                85                  90                  95

Cys Ser Cys Val Asp Gly Ile Arg Lys Ser Val Ser Thr Ser Tyr Lys
            100                 105                 110

Thr Arg Pro Ser Asp Thr Leu Ser Ser Ile Ala Asp Ser Val Tyr Gly
        115                 120                 125

Gly Leu Val Ser Ala Asp Gln Leu Thr Asp Pro Ser Val Leu Asp Val
        130                 135                 140

Gly Gln Ser Leu Val Val Pro Leu Pro Cys Thr Cys Phe Asn Gly Ser
145                 150                 155                 160

Asp Asn Ser Leu Pro Ala Ile Tyr Leu Ser Tyr Val Val Gln Pro Val
                165                 170                 175

Asp Ser Leu Ala Ala Ile Ala Ala Arg Tyr Leu Thr Thr Leu Thr Asp
            180                 185                 190

Leu Met Asn Val Asn Ala Met Gly Ser Thr Ala Ile Ser Asp Gly Asp
        195                 200                 205

Ile Leu Ala Val Pro Ile Pro Ala Cys Ala Ser Asn Phe Pro Lys Ser
        210                 215                 220

Ala Ser Asp Phe Gly Leu Leu Val Pro Asn Gly Ser Tyr Ala Ile Thr
225                 230                 235                 240

Ala Gly His Cys Val Gln Cys Ser Cys Gly Pro Arg Asn Leu Asn Leu
                245                 250                 255

Tyr Cys Met Pro Thr Ser Leu Ser Ala Ser Cys Ser Ser Met Gln Cys
            260                 265                 270

Lys Asn Ser Asn Leu Met Leu Gly Asn Val Thr Ala Gln Gln Ser Ser
        275                 280                 285

Ala Gly Cys Asn Val Ser Ser Cys Ser Tyr Asp Gly Leu Val Asn Gly
        290                 295                 300

Thr Ile Ala Thr Thr Leu Ser Ala Ser Leu Gln Pro Arg Cys Pro Gly
305                 310                 315                 320

Leu Gln Glu Phe Pro Pro Leu Val Ala Pro Pro Thr Ser Val Glu Lys
                325                 330                 335

Asp Pro Thr Phe Ala Ser Gly Pro Ala Pro Ser Pro Ser Pro Gln Ser
            340                 345                 350

His Gly Ser Gly Leu Pro Ser Pro Lys Ser Ser Gly Met Pro Gly Leu
        355                 360                 365

Pro Gly Phe Ser Pro Ala Asn Gly Pro Val Ser Gly Ile Ser Ser Gly
        370                 375                 380

Ala Ser Ala Ala Cys Ser Leu Val Lys Pro Ser Pro Thr Leu Thr Ser
385                 390                 395                 400

Ala Leu Val Leu Leu Leu Ala Met Leu Val Ile Pro Val Ala Leu
                405                 410                 415

<210> SEQ ID NO 246
<211> LENGTH: 394
<212> TYPE: PRT
<213> ORGANISM: Lotus japonicus

<400> SEQUENCE: 246

Met Arg Asn His Leu Gln Phe Leu Trp Arg His Ile Leu Val Phe Leu
1               5                   10                  15

Leu Leu Ser Val Ser Tyr Gln Val Glu Ala Lys Ser Thr Ile Glu Pro
```

-continued

```
             20                  25                  30

Cys Ser Ser Gly Phe Pro Cys Pro Ser Leu Leu Ser Tyr Ile Leu Pro
             35                  40                  45

Trp Asp Ser Lys Leu Ser Glu Ile Ala Thr Arg Phe Ser Val Asn Val
    50                  55                  60

Ser Asn Ile Leu Ala Ala Asn Ser Val Phe Pro Ile Thr Pro Ser Ser
65                  70                  75                  80

Gly His Gln Ile Leu Ser Ala Lys Ser Ile Val Lys Ile Pro Phe Ser
                85                  90                  95

Cys Pro Cys Val Asp Gly Ile Arg Arg Ser Ile Ser Thr Ile Tyr Asn
                100                 105                 110

Val Glu Ala Ser Asp Thr Leu Ala Ser Ile Ser Glu Gly Tyr Gly Gly
        115                 120                 125

Leu Val Ser Ala Glu Gln Ile Lys Thr Met Asn Ser Ile Asn Glu Thr
        130                 135                 140

Asn Pro Leu Thr Tyr Gly Ser Ser Ile Val Ile Pro Leu Pro Cys Lys
145                 150                 155                 160

Cys Leu Asn Asn Val Asn Asn Gly Asp Thr Thr Val Tyr Met Ser Tyr
                165                 170                 175

Val Val Gln Lys Gly Gln Ser Leu Gly Ser Ile Ala Thr Met Tyr Gly
                180                 185                 190

Thr Thr Val Ser Asp Leu Glu Ser Val Asn Gly Leu Gly Gln Asn Ala
        195                 200                 205

Val Asp Pro Gly Asp Ile Leu Ser Val Pro Val Ala Ala Cys Ser Ser
    210                 215                 220

Ala Thr Leu Asn Trp Tyr Ser Glu Asn Leu Ile Val Pro Asn Gly Ser
225                 230                 235                 240

Tyr Ile Leu Thr Ala Ser Asn Cys Ile Gln Cys Thr Cys Thr Pro Arg
                245                 250                 255

Asp Leu Lys Met Glu Cys Leu Pro Ser Gly Met Asp Val Pro Cys Tyr
                260                 265                 270

Asn Leu His Cys Lys Gly Ser Asn Leu Ile Ile Gly Asn Glu Tyr Val
        275                 280                 285

Glu His Ser Gln Thr Ser Cys Asn Val Ser Gln Cys Val Tyr Arg Gly
        290                 295                 300

His Arg Gly Gly Lys Ile Leu Ser Ser Ile Ile Asn Ser Ser Tyr Leu
305                 310                 315                 320

Gln Cys Pro Asp Asn Gln Ser Tyr Ser Gly Pro Ser Arg Trp Pro Ser
                325                 330                 335

Leu Thr Pro Tyr Ala Ala Glu Tyr Pro Phe Asp Ile Ser Pro Ser Pro
                340                 345                 350

Ser Ser Pro Pro Leu Pro Val Ser Glu Ala Ala Leu Arg Thr Arg Ala
        355                 360                 365

Ser Gly Gly Trp Gln Gly Gln Ser Leu Ile Asn Val Met Gln Leu Phe
    370                 375                 380

Leu Ile Lys Leu Ile Leu Tyr Phe Ile Met
385                 390
```

<210> SEQ ID NO 247
<211> LENGTH: 370
<212> TYPE: PRT
<213> ORGANISM: Lotus japonicus

<400> SEQUENCE: 247

-continued

```
Met Gly Thr Val Trp Leu Ser Lys Leu Val Ala Thr Thr Met Leu Val
1               5                   10                  15

Ala Val Leu Gly Leu Leu Ala Glu Ala Gln Ile Glu Ala Lys Phe Lys
            20                  25                  30

Cys Ile Ser Glu Asn Ala Pro Cys His Ala Leu Ala Asp Tyr Ser His
            35                  40                  45

Pro Asn Gly Thr Thr Leu Arg Arg Ile Gln Thr Leu Phe Thr Val Lys
    50                  55                  60

Tyr Leu Pro Asp Ile Leu Gly Ala Asn Asn Leu Pro Ala Asn Thr Thr
65                  70                  75                  80

Arg Val Ala Pro Asp Gln Val Ile Lys Val Pro Phe Pro Cys Arg Cys
            85                  90                  95

Ser Asn Gly Thr Gly Leu Ser Asn Lys Val Pro Arg Tyr Lys Ile Lys
            100                 105                 110

Lys Gly Asp Thr Leu Tyr Asp Ile Ala Thr Thr Val Phe Ala Gly Leu
            115                 120                 125

Val Lys Tyr Pro Gln Ile Gln Val Ala Asn Glu Ile Pro Asp Ala Asn
    130                 135                 140

Asn Ile Thr Ala Gly Asp Thr Ile Trp Ile Pro Leu Pro Cys Ser Cys
145                 150                 155                 160

Asp Ala Val Ala Gly Ser Ser Val Val His Tyr Ala His Leu Val Gln
            165                 170                 175

Asp Gly Ser Ser Val Glu Ser Ile Ala Gln Glu Tyr Gly Ser Thr Gln
            180                 185                 190

Gln Ile Leu Leu Ser Leu Asn Gly Ile Ser Asp Pro Lys Leu Leu Gln
            195                 200                 205

Ala Arg Gln Leu Leu Asp Val Pro Leu Gln Ala Cys Ser Ser Ser Val
    210                 215                 220

Lys Asn Asp Ser Pro Asp Tyr Pro Leu Leu Val Pro Asn Ala Thr Tyr
225                 230                 235                 240

Val Tyr Thr Ala Lys Glu Cys Val Lys Cys Lys Cys Asp Ser Ser Asn
            245                 250                 255

Asn Phe Arg Leu Gln Cys Glu Pro Ser Gln His Lys Pro Ile Asn Asp
            260                 265                 270

Trp Ser Val Cys Pro Ser Met Glu Cys Ser Lys Asn Val Leu Ile Gly
            275                 280                 285

Asn Thr Thr Ser Thr Asp Ser Cys Asn Arg Thr Ile Cys Asp Tyr Ala
    290                 295                 300

Gly Tyr Ser Asn Ser Lys Ile Ser Thr Ile Leu Ala Thr Gln Asn Thr
305                 310                 315                 320

Cys Ala Val Pro Pro Ser Gly Ser Gly Thr Ser Ser Gly Ser Gly Ser
            325                 330                 335

Gly Asp Ser Gly Ser Gly Ala Ser Arg Ser Asn Leu His Gly Trp Val
            340                 345                 350

Trp Ser Ser Pro Leu Ile Val Ile His Phe Leu Leu Phe Val Val Phe
            355                 360                 365

Leu Leu
    370
```

<210> SEQ ID NO 248
<211> LENGTH: 211
<212> TYPE: PRT
<213> ORGANISM: Hordeum vulgare
<220> FEATURE:
<221> NAME/KEY: VARIANT

```
<222> LOCATION: 116-129
<223> OTHER INFORMATION: Xaa = hydrophobic patch residues
<220> FEATURE:
<221> NAME/KEY: VARIANT
<222> LOCATION: 115, 130
<223> OTHER INFORMATION: Xaa = residues immediately adjacent to
      hydrophobic patch residues

<400> SEQUENCE: 248

Ser Val Glu Gly Phe Asn Cys Ser Ala Asn Gly Thr Tyr Pro Cys Gln
1               5                   10                  15

Ala Tyr Ala Leu Tyr Arg Ala Gly Leu Ala Gly Val Pro Pro Asp Leu
            20                  25                  30

Ser Ala Ala Gly Asp Leu Phe Gly Val Ser Arg Phe Met Leu Ala His
        35                  40                  45

Ala Asn Asn Leu Ser Thr Ser Ala Ala Pro Ala Ala Gly Gln Pro Leu
    50                  55                  60

Leu Val Pro Leu Gln Cys Gly Cys Pro Ser Gly Ser Pro Asn Ala Tyr
65                  70                  75                  80

Ala Pro Thr Gln Tyr Gln Ile Ser Ser Gly Asp Thr Phe Trp Ile Val
                85                  90                  95

Ser Val Thr Lys Leu Gln Asn Leu Thr Gln Tyr Gln Ala Val Glu Arg
            100                 105                 110

Val Asn Pro Thr Val Val Pro Thr Lys Leu Glu Val Gly Asp Met Val
            115                 120                 125

Thr Phe Pro Ile Phe Cys Gln Cys Pro Thr Ala Ala Gln Asn Ala Thr
    130                 135                 140

Ala Leu Val Thr Tyr Val Met Gln Gln Gly Asp Thr Tyr Ala Ser Ile
145                 150                 155                 160

Ala Ala Ala Phe Ala Val Asp Ala Gln Ser Leu Val Ser Leu Asn Gly
            165                 170                 175

Pro Glu Gln Gly Thr Gln Leu Phe Ser Glu Ile Leu Val Pro Leu Arg
            180                 185                 190

Arg Gln Val Pro Lys Trp Leu Pro Pro Ile Val Thr Arg Asn Asp Ala
        195                 200                 205

Ser Ala Thr
    210

<210> SEQ ID NO 249
<211> LENGTH: 595
<212> TYPE: PRT
<213> ORGANISM: Medicago truncatula
<220> FEATURE:
<221> NAME/KEY: VARIANT
<222> LOCATION: 147, 151, 152, 154, 156-158
<223> OTHER INFORMATION: Xaa = hydrophobic patch residues
<220> FEATURE:
<221> NAME/KEY: VARIANT
<222> LOCATION: 146, 148, 150, 153, 155, 159
<223> OTHER INFORMATION: Xaa = residues immediately adjacent to
      hydrophobic patch residues

<400> SEQUENCE: 249

Met Ser Ala Phe Phe Leu Pro Ser Ser His Ala Leu Phe Leu Val
1               5                   10                  15

Leu Met Leu Phe Phe Leu Thr Asn Ile Ser Ala Gln Pro Leu Tyr Ile
            20                  25                  30

Ser Glu Thr Asn Phe Thr Cys Pro Val Asp Ser Pro Pro Ser Cys Glu
        35                  40                  45

Thr Tyr Val Ala Tyr Arg Ala Gln Ser Pro Asn Phe Leu Ser Leu Ser
```

-continued

```
        50              55              60

Asn Ile Ser Asp Ile Phe Asn Leu Ser Pro Leu Arg Ile Ala Lys Ala
65              70              75              80

Ser Asn Ile Glu Ala Glu Asp Lys Lys Leu Ile Pro Asp Gln Leu Leu
                85              90              95

Leu Val Pro Val Thr Cys Gly Cys Thr Lys Asn His Ser Phe Ala Asn
                100             105             110

Ile Thr Tyr Ser Ile Lys Gln Gly Asp Asn Phe Phe Ile Leu Ser Ile
            115             120             125

Thr Ser Tyr Gln Asn Leu Thr Asn Tyr Leu Glu Phe Lys Asn Phe Asn
        130             135             140

Pro Asn Leu Ser Pro Thr Leu Leu Pro Leu Asp Thr Lys Val Ser Val
145             150             155             160

Pro Leu Phe Cys Lys Cys Pro Ser Lys Asn Gln Leu Asn Lys Gly Ile
                165             170             175

Lys Tyr Leu Ile Thr Tyr Val Trp Gln Asp Asn Asp Asn Val Thr Leu
            180             185             190

Val Ser Ser Lys Phe Gly Ala Ser Gln Val Glu Met Leu Ala Glu Asn
            195             200             205

Asn His Asn Phe Thr Ala Ser Thr Asn Arg Ser Val Leu Ile Pro Val
    210             215             220

Thr Ser Leu Pro Lys Leu Asp Gln Pro Ser Ser Asn Gly Arg Lys Ser
225             230             235             240

Ser Ser Gln Asn Leu Ala Leu Ile Ile Gly Ile Ser Leu Gly Ser Ala
            245             250             255

Phe Phe Ile Leu Val Leu Thr Leu Ser Leu Val Tyr Val Tyr Cys Leu
            260             265             270

Lys Met Lys Arg Leu Asn Arg Ser Thr Ser Ser Ser Glu Thr Ala Asp
        275             280             285

Lys Leu Leu Ser Gly Val Ser Gly Tyr Val Ser Lys Pro Thr Met Tyr
    290             295             300

Glu Ile Asp Ala Ile Met Glu Gly Thr Thr Asn Leu Ser Asp Asn Cys
305             310             315             320

Lys Ile Gly Glu Ser Val Tyr Lys Ala Asn Ile Asp Gly Arg Val Leu
            325             330             335

Ala Val Lys Lys Ile Lys Lys Asp Ala Ser Glu Glu Leu Lys Ile Leu
            340             345             350

Gln Lys Val Asn His Gly Asn Leu Val Lys Leu Met Gly Val Ser Ser
        355             360             365

Asp Asn Asp Gly Asn Cys Phe Leu Val Tyr Glu Tyr Ala Glu Asn Gly
    370             375             380

Ser Leu Glu Glu Trp Leu Phe Ser Glu Ser Ser Lys Thr Ser Asn Ser
385             390             395             400

Val Val Ser Leu Thr Trp Ser Gln Arg Ile Thr Ile Ala Met Asp Val
            405             410             415

Ala Ile Gly Leu Gln Tyr Met His Glu His Thr Tyr Pro Arg Ile Ile
            420             425             430

His Arg Asp Ile Thr Thr Ser Asn Ile Leu Leu Gly Ser Asn Phe Lys
        435             440             445

Ala Lys Ile Ala Asn Phe Gly Met Ala Arg Thr Ser Thr Asn Ser Met
    450             455             460

Met Pro Lys Ile Asp Val Phe Ala Phe Gly Val Val Leu Ile Glu Leu
465             470             475             480
```

-continued

```
Leu Thr Gly Lys Lys Ala Met Thr Thr Lys Glu Asn Gly Glu Val Val
            485                 490                 495

Ile Leu Trp Lys Asp Phe Trp Lys Ile Phe Asp Leu Glu Gly Asn Arg
            500                 505                 510

Glu Glu Arg Leu Arg Lys Trp Met Asp Pro Lys Leu Glu Ser Phe Tyr
            515                 520                 525

Pro Ile Asp Asn Ala Leu Ser Leu Ala Ser Leu Ala Val Asn Cys Thr
            530                 535                 540

Ala Asp Lys Ser Leu Ser Arg Pro Thr Ile Ala Glu Ile Val Leu Cys
545                 550                 555                 560

Leu Ser Leu Leu Asn Gln Pro Ser Ser Glu Pro Met Leu Glu Arg Ser
            565                 570                 575

Leu Thr Ser Gly Leu Asp Ala Glu Ala Thr His Val Val Thr Ser Val
            580                 585                 590

Ile Ala Arg
        595
```

```
<210> SEQ ID NO 250
<211> LENGTH: 594
<212> TYPE: PRT
<213> ORGANISM: Pisum sativum
<220> FEATURE:
<221> NAME/KEY: VARIANT
<222> LOCATION: 146, 150, 151, 154-159
<223> OTHER INFORMATION: Xaa = hydrophobic patch residues
<220> FEATURE:
<221> NAME/KEY: VARIANT
<222> LOCATION: 145, 147, 149, 152, 153, 160
<223> OTHER INFORMATION: Xaa = residues immediately adjacent to
      hydrophobic patch residues
```

```
<400> SEQUENCE: 250
```

```
Met Ala Ile Phe Phe Leu Pro Ser Ser Ser His Ala Leu Phe Leu Ala
1                 5                   10                  15

Leu Met Phe Phe Val Thr Asn Ile Ser Ala Gln Pro Leu Gln Leu Ser
            20                  25                  30

Gly Thr Asn Phe Ser Cys Pro Val Asp Ser Pro Pro Ser Cys Glu Thr
            35                  40                  45

Tyr Val Thr Tyr Phe Ala Arg Ser Pro Asn Phe Leu Ser Leu Thr Asn
        50                  55                  60

Ile Ser Asp Ile Phe Asp Met Ser Pro Leu Ser Ile Ala Lys Ala Ser
65                  70                  75                  80

Asn Ile Glu Asp Glu Asp Lys Lys Leu Val Glu Gly Gln Val Leu Leu
            85                  90                  95

Ile Pro Val Thr Cys Gly Cys Thr Arg Asn Arg Tyr Phe Ala Asn Phe
            100                 105                 110

Thr Tyr Thr Ile Lys Leu Gly Asp Asn Tyr Phe Ile Val Ser Thr Thr
            115                 120                 125

Ser Tyr Gln Asn Leu Thr Asn Tyr Val Glu Met Glu Asn Phe Asn Pro
            130                 135                 140

Asn Leu Ser Pro Asn Leu Leu Pro Pro Glu Ile Lys Val Val Val Pro
145                 150                 155                 160

Leu Phe Cys Lys Cys Pro Ser Lys Asn Gln Leu Ser Lys Gly Ile Lys
            165                 170                 175

His Leu Ile Thr Tyr Val Trp Gln Ala Asn Asp Asn Val Thr Arg Val
            180                 185                 190

Ser Ser Lys Phe Gly Ala Ser Gln Val Asp Met Phe Thr Glu Asn Asn
```

-continued

```
              195                 200                 205

Gln Asn Phe Thr Ala Ser Thr Asn Val Pro Ile Leu Ile Pro Val Thr
    210                 215                 220

Lys Leu Pro Val Ile Asp Gln Pro Ser Ser Asn Gly Arg Lys Asn Ser
225                 230                 235                 240

Thr Gln Lys Pro Ala Phe Ile Ile Gly Ile Ser Leu Gly Cys Ala Phe
                245                 250                 255

Phe Val Val Val Leu Thr Leu Ser Leu Val Tyr Val Tyr Cys Leu Lys
                260                 265                 270

Met Lys Arg Leu Asn Arg Ser Thr Ser Leu Ala Glu Thr Ala Asp Lys
                275                 280                 285

Leu Leu Ser Gly Val Ser Gly Tyr Val Ser Lys Pro Thr Met Tyr Glu
    290                 295                 300

Met Asp Ala Ile Met Glu Ala Thr Met Asn Leu Ser Glu Asn Cys Lys
305                 310                 315                 320

Ile Gly Glu Ser Val Tyr Lys Ala Asn Ile Asp Gly Arg Val Leu Ala
                325                 330                 335

Val Lys Lys Ile Lys Lys Asp Ala Ser Glu Glu Leu Lys Ile Leu Gln
                340                 345                 350

Lys Val Asn His Gly Asn Leu Val Lys Leu Met Gly Val Ser Ser Asp
                355                 360                 365

Asn Asp Gly Asn Cys Phe Leu Val Tyr Glu Tyr Ala Glu Asn Gly Ser
    370                 375                 380

Leu Asp Glu Trp Leu Phe Ser Glu Ser Ser Lys Thr Ser Asn Ser Val
385                 390                 395                 400

Val Ser Leu Thr Trp Ser Gln Arg Ile Thr Val Ala Val Asp Val Ala
                405                 410                 415

Val Gly Leu Gln Tyr Met His Glu His Thr Tyr Pro Arg Ile Ile His
                420                 425                 430

Arg Asp Ile Thr Thr Ser Asn Ile Leu Leu Asp Ser Asn Phe Lys Ala
                435                 440                 445

Lys Ile Ala Asn Phe Ser Met Ala Arg Thr Ser Thr Asn Ser Met Met
    450                 455                 460

Pro Lys Ile Asp Val Phe Ala Phe Gly Val Val Leu Ile Glu Leu Leu
465                 470                 475                 480

Thr Gly Lys Lys Ala Ile Thr Thr Met Glu Asn Gly Glu Val Val Ile
                485                 490                 495

Leu Trp Lys Asp Phe Trp Lys Ile Phe Asp Leu Glu Gly Asn Arg Glu
                500                 505                 510

Glu Ser Leu Arg Lys Trp Met Asp Pro Lys Leu Glu Asn Phe Tyr Pro
                515                 520                 525

Ile Asp Asn Ala Leu Ser Leu Ala Ser Leu Ala Val Asn Cys Thr Ala
    530                 535                 540

Asp Lys Ser Leu Ser Arg Pro Ser Ile Ala Glu Ile Val Leu Cys Leu
545                 550                 555                 560

Ser Leu Leu Asn Gln Ser Ser Ser Glu Pro Met Leu Glu Arg Ser Leu
                565                 570                 575

Thr Ser Gly Leu Asp Val Glu Ala Thr His Val Val Thr Ser Ile Val
                580                 585                 590

Ala Arg

<210> SEQ ID NO 251
<211> LENGTH: 598
```

-continued

```
<212> TYPE: PRT
<213> ORGANISM: Glycine max
<220> FEATURE:
<221> NAME/KEY: VARIANT
<222> LOCATION: 144, 147, 148, 151-153, 155-161
<223> OTHER INFORMATION: Xaa = hydrophobic patch residues
<220> FEATURE:
<221> NAME/KEY: VARIANT
<222> LOCATION: 143, 145, 146, 149, 150, 154, 162
<223> OTHER INFORMATION: Xaa = residues immediately adjacent to
      hydrophobic patch residues

<400> SEQUENCE: 251

Met Ala Val Phe Phe Pro Phe Leu Pro Leu His Ser Gln Ile Leu Cys
1               5                   10                  15

Leu Val Ile Met Leu Phe Ser Thr Asn Ile Val Ala Gln Ser Gln Gln
            20                  25                  30

Asp Asn Arg Thr Asn Phe Ser Cys Pro Ser Asp Ser Pro Pro Ser Cys
            35                  40                  45

Glu Thr Tyr Val Thr Tyr Ile Ala Gln Ser Pro Asn Phe Leu Ser Leu
        50                  55                  60

Thr Asn Ile Ser Asn Ile Phe Asp Thr Ser Pro Leu Ser Ile Ala Arg
65                  70                  75                  80

Ala Ser Asn Leu Glu Pro Met Asp Asp Lys Leu Val Lys Asp Gln Val
                85                  90                  95

Leu Leu Val Pro Val Thr Cys Gly Cys Thr Gly Asn Arg Ser Phe Ala
            100                 105                 110

Asn Ile Ser Tyr Glu Ile Asn Gln Gly Asp Ser Phe Tyr Phe Val Ala
            115                 120                 125

Thr Thr Ser Tyr Glu Asn Leu Thr Asn Trp Arg Ala Val Met Asp Leu
        130                 135                 140

Asn Pro Val Leu Ser Pro Asn Lys Leu Pro Ile Gly Ile Gln Val Val
145                 150                 155                 160

Phe Pro Leu Phe Cys Lys Cys Pro Ser Lys Asn Gln Leu Asp Lys Glu
            165                 170                 175

Ile Lys Tyr Leu Ile Thr Tyr Val Trp Lys Pro Gly Asp Asn Val Ser
            180                 185                 190

Leu Val Ser Asp Lys Phe Gly Ala Ser Pro Glu Asp Ile Met Ser Glu
        195                 200                 205

Asn Asn Tyr Gly Gln Asn Phe Thr Ala Ala Asn Asn Leu Pro Val Leu
        210                 215                 220

Ile Pro Val Thr Arg Leu Pro Val Leu Ala Arg Ser Pro Ser Asp Gly
225                 230                 235                 240

Arg Lys Gly Gly Ile Arg Leu Pro Val Ile Ile Gly Ile Ser Leu Gly
            245                 250                 255

Cys Thr Leu Leu Val Leu Val Leu Ala Val Leu Leu Val Tyr Val Tyr
            260                 265                 270

Cys Leu Lys Met Lys Thr Leu Asn Arg Ser Ala Ser Ser Ala Glu Thr
            275                 280                 285

Ala Asp Lys Leu Leu Ser Gly Val Ser Gly Tyr Val Ser Lys Pro Thr
        290                 295                 300

Met Tyr Glu Thr Asp Ala Ile Met Glu Ala Thr Met Asn Leu Ser Glu
305                 310                 315                 320

Gln Cys Lys Ile Gly Glu Ser Val Tyr Lys Ala Asn Ile Glu Gly Lys
            325                 330                 335

Val Leu Ala Val Lys Arg Phe Lys Glu Asp Val Thr Glu Glu Leu Lys
            340                 345                 350
```

-continued

```
Ile Leu Gln Lys Val Asn His Gly Asn Leu Val Lys Leu Met Gly Val
        355                 360                 365

Ser Ser Asp Asn Asp Gly Asn Cys Phe Val Val Tyr Glu Tyr Ala Glu
        370                 375                 380

Asn Gly Ser Leu Asp Glu Trp Leu Phe Ser Lys Ser Cys Ser Asp Thr
385                 390                 395                 400

Ser Asn Ser Arg Ala Ser Leu Thr Trp Cys Gln Arg Ile Ser Met Ala
                405                 410                 415

Val Asp Val Ala Met Gly Leu Gln Tyr Met His Glu His Ala Tyr Pro
                420                 425                 430

Arg Ile Val His Arg Asp Ile Thr Ser Ser Asn Ile Leu Leu Asp Ser
        435                 440                 445

Asn Phe Lys Ala Lys Ile Ala Asn Phe Ser Met Ala Arg Thr Phe Thr
        450                 455                 460

Asn Pro Met Met Pro Lys Ile Asp Val Phe Ala Phe Gly Val Val Leu
465                 470                 475                 480

Ile Glu Leu Leu Thr Gly Arg Lys Ala Met Thr Thr Lys Glu Asn Gly
                485                 490                 495

Glu Val Val Met Leu Trp Lys Asp Ile Trp Lys Ile Phe Asp Gln Glu
                500                 505                 510

Glu Asn Arg Glu Glu Arg Leu Lys Lys Trp Met Asp Pro Lys Leu Glu
        515                 520                 525

Ser Tyr Tyr Pro Ile Asp Tyr Ala Leu Ser Leu Ala Ser Leu Ala Val
        530                 535                 540

Asn Cys Thr Ala Asp Lys Ser Leu Ser Arg Pro Thr Ile Ala Glu Ile
545                 550                 555                 560

Val Leu Ser Leu Ser Leu Leu Thr Gln Pro Ser Pro Ala Thr Leu Glu
                565                 570                 575

Arg Ser Leu Thr Ser Ser Gly Leu Asp Val Glu Ala Thr Gln Ile Val
        580                 585                 590

Thr Ser Ile Ala Ala Arg
        595
```

```
<210> SEQ ID NO 252
<211> LENGTH: 557
<212> TYPE: PRT
<213> ORGANISM: Cicer arietinum
<220> FEATURE:
<221> NAME/KEY: VARIANT
<222> LOCATION: 146, 150, 151, 155-159
<223> OTHER INFORMATION: Xaa = hydrophobic patch residues
<220> FEATURE:
<221> NAME/KEY: VARIANT
<222> LOCATION: 145, 147, 149, 152, 154, 160
<223> OTHER INFORMATION: Xaa = residues immediately adjacent to
      hydrophobic patch residues

<400> SEQUENCE: 252

Met Ser Val Phe Phe Leu Pro Ser Arg Ser His Val Leu Phe Leu Ala
1               5                   10                  15

Leu Met Leu Phe Leu Thr Asn Ile Ser Ala Gln Ser Gln His Leu Ser
                20                  25                  30

Gly Thr Asn Phe Ser Cys Pro Val Asp Ser Pro Pro Ser Cys Glu Thr
                35                  40                  45

Tyr Val Thr Tyr Ile Ala Gln Ser Pro Asn Phe Leu Ser Leu Thr Asn
        50                  55                  60

Ile Ser Asp Leu Phe Asp Ile Ser Pro Leu Ser Ile Ala Arg Ala Ser
```

-continued

```
65                    70                    75                    80

Asn Ile Asp Asp Glu Asp Lys Glu Leu Ile Pro Gly Gln Val Leu Leu
                85                    90                    95

Val Pro Val Thr Cys Gly Cys Thr Lys His Arg Ser Phe Ala Asn Asn
                100                   105                   110

Thr Tyr Thr Ile Lys Leu Gly Asp Ser Tyr Ile Leu Val Ser Thr Thr
                115                   120                   125

Ser Tyr Gln Asn Leu Thr Asn Tyr Leu Glu Met Glu Asp Ser Asn Pro
                130                   135                   140

Gly Leu Asn Pro Asn Leu Ile Pro Pro Phe Ile Lys Val Val Val Pro
145                   150                   155                   160

Ile Phe Cys Arg Cys Pro Ser Lys Thr Gln Leu Asn Lys Gly Ile Lys
                165                   170                   175

Tyr Leu Ile Thr Tyr Val Trp His Ala Asn Asp Asn Val Ser Thr Val
                180                   185                   190

Ser Ser Lys Phe Gly Ala Ser Gln Val Asp Ile Leu Thr Glu Asn Asn
                195                   200                   205

Tyr Asn Gln Asn Phe Ala Ser Ala Ala Asn Leu Pro Val Leu Ile Pro
                210                   215                   220

Val Thr Arg Leu Pro Ile Leu Ala Gln Pro Ser Ser Asn Gly Arg Lys
225                   230                   235                   240

Arg Ser Ile Gln Leu Pro Val Ile Ile Asp Lys Leu Leu Ser Gly Val
                245                   250                   255

Ser Gly Tyr Val Ser Lys Pro Thr Met Tyr Glu Met Asp Val Ile Met
                260                   265                   270

Glu Ala Thr Met Asn Leu Ser Asp Gln Cys Lys Ile Gly Glu Ser Val
                275                   280                   285

Tyr Lys Ala Asn Ile Asp Gly Lys Val Leu Ala Val Lys Lys Thr Lys
                290                   295                   300

Lys Asp Ala Ser Glu Glu Leu Lys Ile Leu Gln Lys Val Asn His Gly
305                   310                   315                   320

Asn Leu Val Lys Leu Met Gly Val Ser Ser Asp Asn Glu Gly Asn Cys
                325                   330                   335

Phe Leu Val Tyr Glu Tyr Ala Glu Asn Gly Ser Leu Asp Glu Trp Leu
                340                   345                   350

Phe Leu Glu Ser Ser Lys Thr Ser Asp Ser Thr Val Ser Leu Thr Trp
                355                   360                   365

Ser Gln Arg Ile Gly Ile Ala Val Asp Val Ala Val Gly Leu Gln Tyr
                370                   375                   380

Met His Glu His Thr Tyr Pro Arg Ile Ile His Arg Asp Ile Thr Thr
385                   390                   395                   400

Ser Asn Ile Leu Leu Asp Ala Asn Phe Lys Ala Lys Ile Ala Asn Phe
                405                   410                   415

Ser Met Ala Arg Thr Ser Thr Asn Pro Met Met Pro Lys Ile Asp Val
                420                   425                   430

Phe Ala Phe Gly Val Val Leu Ile Glu Leu Leu Thr Gly Lys Lys Gly
                435                   440                   445

Val Thr Thr Lys Glu Asn Gly Glu Val Val Ile Met Trp Lys Asp Phe
                450                   455                   460

Trp Met Ile Phe Asp Leu Glu Gly Asn Lys Glu Glu Arg Leu Arg Lys
465                   470                   475                   480

Trp Met Asp Pro Lys Leu Glu Asn Phe Tyr Pro Ile Asp Asn Ala Leu
                485                   490                   495
```

-continued

```
Ser Leu Ala Ser Leu Ala Val Asn Cys Thr Ala Asp Lys Ser Leu Ser
            500                 505                 510

Arg Pro Thr Ile Glu Glu Ile Val Leu Cys Leu Asn Leu Leu Asn Gln
        515                 520                 525

Pro Ser Ser Glu Pro Thr Leu Glu Arg Ser Leu Thr Phe Gly Leu Asp
        530                 535                 540

Val Glu Asp Thr Gln Ile Val Thr Ser Ile Ala Ala Arg
545                 550                 555

<210> SEQ ID NO 253
<211> LENGTH: 597
<212> TYPE: PRT
<213> ORGANISM: Phaseolus vulgaris
<220> FEATURE:
<221> NAME/KEY: VARIANT
<222> LOCATION: 143, 146-148, 150-152, 154-160
<223> OTHER INFORMATION: Xaa = hydrophobic patch residues
<220> FEATURE:
<221> NAME/KEY: VARIANT
<222> LOCATION: 142, 144, 145, 149, 153, 161
<223> OTHER INFORMATION: Xaa = residues immediately adjacent to
      hydrophobic patch residues

<400> SEQUENCE: 253

Met Ala Val Phe Phe Val Ser Leu Thr Leu Gly Ala Gln Ile Leu Tyr
1               5                   10                  15

Val Val Leu Met Phe Phe Thr Cys Ile Glu Ala Gln Ser Gln Gln Thr
            20                  25                  30

Asn Gly Thr Asn Phe Ser Cys Pro Ser Asn Ser Pro Pro Ser Cys Glu
        35                  40                  45

Thr Tyr Val Thr Tyr Ile Ser Gln Ser Pro Asn Phe Leu Ser Leu Thr
        50                  55                  60

Ser Val Ser Asn Ile Phe Asp Thr Ser Pro Leu Ser Ile Ala Arg Ala
65                  70                  75                  80

Ser Asn Leu Gln His Glu Glu Asp Lys Leu Ile Pro Gly Gln Val Leu
                85                  90                  95

Leu Ile Pro Val Thr Cys Gly Cys Thr Gly Asn Arg Ser Phe Ala Asn
            100                 105                 110

Ile Ser Tyr Glu Ile Asn Gln Gly Asp Ser Phe Tyr Phe Val Ala Thr
        115                 120                 125

Thr Leu Tyr Gln Asn Leu Thr Asn Trp His Ala Val Met Asp Leu Asn
        130                 135                 140

Pro Gly Leu Ser Pro Phe Thr Leu Pro Ile Gly Ile Gln Val Val Ile
145                 150                 155                 160

Pro Leu Phe Cys Lys Cys Pro Ser Lys Asn Gln Leu Asp Arg Gly Ile
            165                 170                 175

Lys Tyr Leu Ile Thr His Val Trp Gln Pro Asn Asp Asn Val Ser Phe
            180                 185                 190

Val Ser Asn Lys Leu Gly Ala Ser Pro Gln Asp Ile Leu Ser Glu Asn
            195                 200                 205

Asn Tyr Gly Gln Asn Phe Thr Ala Ala Ser Asn Leu Pro Val Leu Ile
        210                 215                 220

Pro Val Thr Leu Leu Pro Asp Leu Ile Gln Ser Pro Ser Asp Gly Arg
225                 230                 235                 240

Lys His Arg Ile Gly Leu Pro Val Ile Gly Ile Ser Leu Gly Cys
            245                 250                 255

Thr Leu Leu Val Val Val Ser Ala Ile Leu Leu Val Cys Val Cys Cys
```

-continued

```
                 260                 265                 270
Leu Lys Met Lys Ser Leu Asn Arg Ser Ala Ser Ser Ala Glu Thr Ala
        275                 280                 285

Asp Lys Leu Leu Ser Gly Val Ser Gly Tyr Val Ser Lys Pro Thr Met
    290                 295                 300

Tyr Glu Thr Gly Ala Ile Leu Glu Ala Thr Met Asn Leu Ser Glu Gln
305                 310                 315                 320

Cys Lys Ile Gly Glu Ser Val Tyr Lys Ala Asn Ile Glu Gly Lys Val
                325                 330                 335

Leu Ala Val Lys Arg Phe Lys Glu Asp Val Thr Glu Glu Leu Lys Ile
            340                 345                 350

Leu Gln Lys Val Asn His Gly Asn Leu Val Lys Leu Met Gly Val Ser
        355                 360                 365

Ser Asp Asn Asp Gly Asn Cys Phe Val Val Tyr Glu Tyr Ala Glu Asn
        370                 375                 380

Gly Ser Leu Gln Glu Trp Leu Phe Ala Lys Ser Cys Ser Glu Thr Leu
385                 390                 395                 400

Asn Ser Arg Thr Ser Leu Thr Trp Cys Gln Arg Ile Ser Ile Ala Val
                405                 410                 415

Asp Val Ser Met Gly Leu Gln Tyr Met His Glu His Ala Tyr Pro Arg
                420                 425                 430

Ile Val His Arg Asp Ile Thr Ser Ser Asn Ile Leu Leu Asp Ser Asn
            435                 440                 445

Phe Lys Ala Lys Ile Ala Asn Phe Ser Met Ala Arg Thr Phe Thr Asn
        450                 455                 460

Pro Met Met Ser Lys Ile Asp Val Phe Ala Phe Gly Val Val Leu Ile
465                 470                 475                 480

Glu Leu Leu Thr Gly Arg Lys Ala Met Thr Thr Lys Glu Asn Gly Glu
                485                 490                 495

Val Val Met Leu Trp Thr Asp Ile Trp Lys Ile Phe Asp Gln Glu Glu
                500                 505                 510

Asn Arg Glu Glu Arg Leu Arg Lys Trp Met Asp Pro Lys Leu Asp Asn
            515                 520                 525

Tyr Tyr Pro Ile Asp Tyr Ala Leu Ser Leu Ala Ser Leu Ala Met Asn
        530                 535                 540

Cys Thr Ala Asp Lys Ser Leu Ser Arg Pro Thr Ile Ala Glu Ile Val
545                 550                 555                 560

Leu Ser Leu Ser Leu Leu Thr Gln Pro Ser Pro Ala Thr Leu Glu Arg
                565                 570                 575

Ser Leu Thr Ser Ser Gly Leu Asp Val Glu Ala Thr Gln Ile Val Thr
            580                 585                 590

Ser Ile Ser Ala Arg
        595
```

```
<210> SEQ ID NO 254
<211> LENGTH: 595
<212> TYPE: PRT
<213> ORGANISM: Arachis hypogaea subsp. hypogaea
<220> FEATURE:
<221> NAME/KEY: VARIANT
<222> LOCATION: 146, 149-151, 153-159, 161, 162
<223> OTHER INFORMATION: Xaa = hydrophobic patch residues
<220> FEATURE:
<221> NAME/KEY: VARIANT
<222> LOCATION: 145, 147, 148, 152, 160, 163
<223> OTHER INFORMATION: Xaa = residues immediately adjacent to
     hydrophobic patch residues
```

<400> SEQUENCE: 254

Met Ala Phe Phe Leu Pro Ser Leu Ser Ser Ser Ile Phe Leu Ala Phe
1               5                   10                  15

Met Leu Phe Ser Val Thr Ser Ile Pro Thr Gln Ser Gln Gln Val Asn
            20                  25                  30

Gly Thr Asp Phe Ser Cys Pro Val Asp Ser Pro Ser Ser Cys Gly Thr
        35                  40                  45

Tyr Val Thr Tyr Ile Ala Lys Ser Pro Asn Phe Leu Ser Leu Ser Asn
    50                  55                  60

Ile Ser Asp Ile Phe Asp Thr Ser Pro Leu Ser Ile Ala Arg Ala Ser
65                  70                  75                  80

Asn Ile Lys Asn Glu Gly Asp Lys Leu Val Pro Gly Gln Val Leu Leu
                85                  90                  95

Ile Pro Val Thr Cys Gly Cys Thr Gln Asn Gln Ser Phe Ala Asn Ile
            100                 105                 110

Thr Tyr Glu Leu Arg Gln Gly Asp Val Tyr Asp Ile Val Ser Lys Thr
            115                 120                 125

Thr Tyr Glu Asn Leu Thr Asn Trp Arg Ala Val Asn Asn Ser Asn Pro
    130                 135                 140

Asp Leu Asn Pro Val Leu Leu Pro Ile Gly Val Lys Val Leu Phe Pro
145                 150                 155                 160

Leu Phe Cys Arg Cys Pro Ser Lys Lys Gln Leu Gln Lys Gly Ile Glu
                165                 170                 175

Tyr Met Ile Thr Tyr Val Trp Gln Asn Asn Asp Asn Val Ser Ser Val
            180                 185                 190

Ala Ala Lys Phe Gly Ala Ser Pro Val Asp Ile Leu Ser Glu Asn Asn
            195                 200                 205

Tyr Gly Gly Asn Phe Thr Ala Ala Thr Tyr Leu Pro Val Leu Ile Pro
    210                 215                 220

Val Thr Lys Leu Pro Val Leu Thr Gln Pro Glu Ala Ser His Gly Arg
225                 230                 235                 240

Lys Arg Ser Ile Gln Ile Pro Val Ile Ile Ser Ile Ser Leu Gly Phe
            245                 250                 255

Thr Leu Val Val Ala Val Ile Val Ile Ser Met Val Tyr Ala Tyr Leu
            260                 265                 270

Tyr Gln Arg Lys Arg Thr Leu Asn Arg Gly Asp Leu Ser Ala Gly Thr
    275                 280                 285

Ala Asp Lys Leu Leu Ser Gly Val Ser Gly Tyr Val Ser Lys Pro Thr
    290                 295                 300

Val Tyr Glu Ala Asn Glu Val Ile Lys Ala Thr Met Asn Leu Ser Gly
305                 310                 315                 320

Gln Cys Lys Leu Gly Gly Thr Val Tyr Lys Ala Lys Ile Glu Gly Gln
            325                 330                 335

Val Leu Ala Val Lys Lys Val Asn Gln Val Val Ser Glu Glu Leu Asn
            340                 345                 350

Ile Leu Gln Lys Val Asn His Gly Asn Leu Val Lys Leu Met Gly Val
            355                 360                 365

Ser Ser Asp Ser Asp Gly Asn His Phe Leu Val Tyr Glu Tyr Ala Asp
    370                 375                 380

Asn Gly Ser Leu Asp Gly Trp Leu Phe Ser Lys Leu Ser Leu Lys Ala
385                 390                 395                 400

Ser Leu Thr Trp Tyr Gln Arg Ile Asn Ile Ala Leu Asp Val Ala Met

-continued

```
              405             410             415
Gly Leu Gln Tyr Leu His Glu His Thr Tyr Pro Arg Ile Val His Arg
            420             425             430

Asp Ile Thr Thr Ser Asn Ile Leu Leu Asp Ser Asn Phe Lys Ala Lys
        435             440             445

Ile Gly Asn Phe Ser Met Val Arg Thr Thr Thr Asn Pro Met Ile Ser
    450             455             460

Lys Ile Asp Val Phe Ala Phe Gly Ala Val Leu Ile Glu Leu Leu Thr
465             470             475             480

Gly Met Lys Ala Met Thr Thr Lys Ala Asp Gly Glu Val Val Met Leu
            485             490             495

Trp Lys Asp Ile Arg Lys Met Phe Glu Val Glu Asp Glu Lys Glu Lys
            500             505             510

Glu Glu Cys Leu Arg Arg Trp Met Asp Pro Lys Leu Glu Cys Leu Tyr
            515             520             525

Pro Val Asp Tyr Ala Leu Ser Leu Ala Thr Leu Ala Ala Asn Cys Thr
        530             535             540

Ala Asp Val Ser Leu Ser Arg Pro Thr Met Ala Glu Val Val Leu Gly
545             550             555             560

Leu Ser Leu Leu Thr Gln Pro Ser Gln Ala Ala Leu Glu Arg Ser Leu
            565             570             575

Thr Ser Ser Ala Leu Glu Ala Glu Val Thr His Val Ala Thr Ser Ile
        580             585             590

Thr Ala Arg
        595
```

```
<210> SEQ ID NO 255
<211> LENGTH: 591
<212> TYPE: PRT
<213> ORGANISM: Lotus japonicus
<220> FEATURE:
<221> NAME/KEY: VARIANT
<222> LOCATION: 146-160
<223> OTHER INFORMATION: Xaa = hydrophobic patch residues
<220> FEATURE:
<221> NAME/KEY: VARIANT
<222> LOCATION: 145, 161
<223> OTHER INFORMATION: Xaa = residues immediately adjacent to
      hydrophobic patch residues

<400> SEQUENCE: 255

Met Thr Ser Phe Phe Leu Phe Thr Asn Thr Leu Phe Leu Ala Leu Met
1               5               10              15

Met Phe Phe Ser Thr Thr His His Ile Leu Ala Gln Leu Ser His Thr
            20              25              30

Asn Gly Thr Asn Phe Ser Cys Pro Val Asp Ser Pro Pro Ser Cys Asp
        35              40              45

Thr Tyr Val Thr Tyr Phe Ala Gln Ser Pro Asn Phe Leu Thr Leu Thr
    50              55              60

Ser Ile Ser Asp Leu Phe Asp Thr Ser Pro Leu Ser Ile Ala Arg Ala
65              70              75              80

Ser Asn Ile Lys Asp Glu Asn Gln Asn Leu Val Pro Gly Gln Leu Leu
            85              90              95

Leu Val Pro Val Thr Cys Ala Cys Ser Gly Ser Asn Ser Phe Ser Asn
            100             105             110

Ile Ser His Met Ile Lys Glu Gly Glu Ser Tyr Tyr Tyr Leu Ser Thr
        115             120             125
```

Thr Ser Tyr Glu Asn Leu Thr Asn Trp Glu Thr Val Gln Asp Ser Asn
    130                 135                 140

Pro Asn Tyr Asn Pro Tyr Leu Leu Pro Val Gly Ile Lys Val Val Ile
145                 150                 155                 160

Pro Leu Phe Cys Lys Cys Pro Ser Asn Tyr His Leu Asn Lys Gly Ile
                165                 170                 175

Glu Tyr Leu Ile Thr Tyr Val Trp His Asn Asn Asp Asn Val Ser Leu
                180                 185                 190

Val Ala Ser Lys Phe Gly Val Ser Thr Gln Asp Ile Ile Ser Glu Asn
                195                 200                 205

Asn Phe Ser His Gln Asn Phe Thr Ala Ala Thr Asn Phe Pro Ile Leu
    210                 215                 220

Ile Pro Val Thr Gln Leu Pro Ser Leu Ser Gln Ser Tyr Ser Ser Ser
225                 230                 235                 240

Glu Arg Lys Arg Ser Asn His Ile His Ile Ile Ser Ile Gly Ile
                245                 250                 255

Ser Leu Gly Ser Thr Leu Leu Ile Ala Leu Leu Val Leu Val Ser Val
                260                 265                 270

Thr Cys Leu Arg Lys Arg Lys Ser Ser Glu Asn Lys Ser Leu Leu Ser
    275                 280                 285

Val Glu Ile Ala Gly Lys Lys Leu Ile Ser Gly Val Ser Asn Tyr Val
    290                 295                 300

Ser Lys Ser Ile Leu Tyr Glu Phe Arg Leu Ile Met Glu Ala Thr Leu
305                 310                 315                 320

Asn Leu Asn Glu Gln Cys Lys Ile Gly Glu Ser Val Tyr Lys Ala Lys
                325                 330                 335

Leu Asp Gly Gln Val Leu Ala Val Lys Lys Val Lys Glu Asp Val Thr
                340                 345                 350

Glu Glu Val Met Ile Leu Gln Lys Val Asn His Leu Asn Leu Val Lys
    355                 360                 365

Leu Met Gly Val Ser Ser Gly His Asp Gly Asn His Phe Leu Val Tyr
    370                 375                 380

Glu Phe Ala Glu Asn Gly Ser Leu His Asn Trp Leu Phe Ser Asn Ser
385                 390                 395                 400

Ser Thr Gly Ser Arg Phe Leu Thr Trp Ser Gln Arg Ile Ser Ile Ala
                405                 410                 415

Val Asp Val Ala Met Gly Leu Gln Tyr Met His Glu His Thr Gln Pro
                420                 425                 430

Ser Ile Val His Arg Asp Ile Thr Ser Ser Asn Ile Leu Leu Asp Ser
                435                 440                 445

Asn Phe Lys Ala Lys Ile Ala Asn Phe Ser Val Ala Arg Thr Ser Ile
    450                 455                 460

Asn Pro Met Ile Leu Lys Val Asp Val Phe Gly Tyr Gly Val Val Leu
465                 470                 475                 480

Leu Glu Leu Leu Ser Gly Lys Lys Ser Leu Thr Asn Asn Glu Ile Asn
                485                 490                 495

His Ile Arg Glu Ile Phe Asp Leu Lys Glu Lys Arg Glu Glu Arg Ile
                500                 505                 510

Arg Arg Trp Met Asp Pro Lys Ile Glu Ser Leu Tyr Pro Ile Asp Asp
                515                 520                 525

Ala Leu Ser Leu Ala Phe Leu Ala Met Asn Cys Thr Ser Glu Lys Pro
    530                 535                 540

Leu Ser Arg Pro Thr Met Gly Glu Val Val Leu Ser Leu Ser Leu Leu

-continued

```
545              550              555              560

Met Thr Gln His Ser Pro Thr Thr Leu Glu Arg Ser Trp Thr Cys Gly
                565              570              575

Leu Asp Val Asp Val Thr Glu Met Gln Thr Leu Ile Ala Ala Arg
                580              585              590

<210> SEQ ID NO 256
<211> LENGTH: 590
<212> TYPE: PRT
<213> ORGANISM: Medicago truncatula
<220> FEATURE:
<221> NAME/KEY: VARIANT
<222> LOCATION: 144-156
<223> OTHER INFORMATION: Xaa = hydrophobic patch residues
<220> FEATURE:
<221> NAME/KEY: VARIANT
<222> LOCATION: 143, 157
<223> OTHER INFORMATION: Xaa = residues immediately adjacent to
      hydrophobic patch residues

<400> SEQUENCE: 256

Met Val Ser Ser Phe Phe His Thr Leu Ile Phe Phe Ser Ala Thr His
1               5               10              15

Ile Leu Leu Gln Leu Pro Gln Ala Asn Gly Lys Asn Phe Ser Cys Thr
                20              25              30

Leu Asn Ser Ser Pro Ser Cys Asp Thr Tyr Val Ala Tyr Phe Ala Asn
                35              40              45

Ser Pro Asn Phe Leu Thr Leu Thr Ala Ile Ser Asp Ile Phe Asp Thr
     50              55              60

Ser Pro Gln Ser Ile Ala Arg Ala Ser Asn Ile Lys Asp Glu Asn Met
65              70              75              80

Asn Leu Ile His Gly Gln Leu Leu Leu Ile Pro Ile Thr Cys Gly Cys
                85              90              95

Asn Gly Asn Gly Asn Tyr Ser Phe Ala Asn Ile Ser His Leu Ile Lys
                100             105             110

Glu Ser Glu Ser Tyr Tyr Tyr Leu Ser Thr Ile Ser Tyr Gln Asn Leu
                115             120             125

Thr Asn Trp Gln Thr Val Glu Asp Ser Asn Pro Asn Leu Asn Pro Tyr
     130             135             140

Leu Leu Lys Ile Gly Thr Lys Ile Asn Ile Pro Leu Phe Cys Arg Cys
145             150             155             160

Pro Ser Asn Tyr Phe Ala Lys Gly Ile Glu Tyr Leu Ile Thr Tyr Val
                165             170             175

Trp Gln Pro Asn Asp Asn Leu Thr Leu Val Ala Ser Lys Leu Gly Ala
                180             185             190

Ser Pro Lys Asp Ile Ile Thr Ala Asn Thr Asn Asn Phe Gly Gln Asn
                195             200             205

Phe Thr Val Ala Ile Asn Leu Pro Val Phe Ile Pro Val Lys Asn Leu
     210             215             220

Pro Ala Leu Ser Gln Ser Tyr Tyr Ser Ser Ser Glu Arg Lys Arg Ile
225             230             235             240

Asn His Phe Ser Ile Ile Ile Ser Ile Gly Ile Cys Leu Gly Cys Thr
                245             250             255

Ile Leu Ile Ser Leu Leu Leu Leu Phe Tyr Val Tyr Cys Leu Arg
                260             265             270

Lys Arg Lys Ala Cys Glu Asn Lys Cys Val Pro Ser Val Glu Ile Thr
                275             280             285
```

-continued

```
Asp Lys Leu Ile Ser Glu Val Ser Asn Tyr Val Ser Lys Pro Thr Val
    290             295             300

Tyr Glu Val Gly Met Ile Met Lys Ala Thr Met Asn Leu Asn Glu Met
305             310             315             320

Cys Lys Ile Gly Lys Ser Val Tyr Lys Ala Lys Ile Asp Gly Leu Val
            325             330             335

Leu Ala Val Lys Asn Val Lys Gly His Ile Thr Val Thr Glu Glu Leu
        340             345             350

Met Ile Leu Gln Lys Val Asn His Ala Asn Leu Val Lys Leu Val Gly
        355             360             365

Val Ser Ser Gly Tyr Asp Gly Asn His Phe Leu Val Tyr Glu Tyr Ala
    370             375             380

Glu Asn Gly Ser Leu Tyr Asn Trp Leu Leu Ser Glu Phe Cys Thr Leu
385             390             395             400

Ser Trp Ser Gln Arg Leu Ser Ile Ala Val Asp Ile Ala Ile Gly Leu
                405             410             415

Gln Tyr Leu His Glu His Thr Gln Pro Cys Ile Val His Arg Asn Ile
            420             425             430

Lys Ser Ser Asn Ile Leu Leu Asp Ser Lys Phe Lys Ala Lys Ile Ala
        435             440             445

Asn Phe Ser Val Ala Arg Thr Thr Lys Asn Pro Met Ile Thr Lys Val
    450             455             460

Asp Val Leu Gly Tyr Gly Met Val Leu Met Glu Leu Ile Thr Gly Lys
465             470             475             480

Lys Phe Leu Ser Tyr Ser Glu His Ser Glu Val Asn Met Leu Trp Lys
                485             490             495

Asp Phe Lys Cys Val Phe Asp Thr Glu Gln Lys Arg Glu Glu Ile Val
            500             505             510

Arg Arg Trp Met Asp Pro Lys Leu Gly Arg Phe Tyr Asn Val Val Glu
            515             520             525

Ala Leu Ser Leu Phe Thr Leu Ala Val Asn Cys Ile Glu Glu Gln Pro
    530             535             540

Leu Leu Arg Pro Thr Met Gly Glu Val Val Leu Ser Leu Ser Leu Leu
545             550             555             560

Thr Gln Pro Ser Pro Thr Leu Leu Glu Val Ser Trp Thr Tyr Gly Leu
            565             570             575

Asp Val Glu Val Ala Glu Met Val Thr Pro Ile Ile Ala Arg
            580             585             590
```

<210> SEQ ID NO 257
<211> LENGTH: 613
<212> TYPE: PRT
<213> ORGANISM: Parasponia andersonii
<220> FEATURE:
<221> NAME/KEY: VARIANT
<222> LOCATION: 136-138, 142, 143, 145-151
<223> OTHER INFORMATION: Xaa = hydrophobic patch residues
<220> FEATURE:
<221> NAME/KEY: VARIANT
<222> LOCATION: 135, 139, 141, 144, 152
<223> OTHER INFORMATION: Xaa = residues immediately adjacent to
      hydrophobic patch residues

<400> SEQUENCE: 257

```
Met Ala Ile Ser Leu Tyr Leu Leu Phe Phe Ile Thr His Ile Ser
1               5               10              15

Ala Gln Ser Pro Pro Thr Leu Ala Thr Asn Phe Ser Cys Ser Thr Asn
        20              25              30
```

-continued

```
Ser Ser Gln Pro Ser Cys Lys Thr Tyr Val Ala Tyr Phe Ala Gln Pro
        35              40              45

Pro Leu Phe Met Asp Leu Lys Ser Ile Ser Asn Leu Phe Gly Val Ser
    50              55              60

Pro Ser Ser Ile Ser Glu Ala Ser Asn Leu Val Ser Glu Ser Thr Lys
65              70              75              80

Leu Thr Arg Gly Gln Leu Leu Leu Ile Pro Leu Ser Cys Ser Cys Asn
                85              90              95

Gly Ser His Tyr Phe Ser Asn Val Thr Tyr Asn Ile Thr Met Gly Asp
                100             105             110

Ser Tyr Tyr Leu Val Ser Ile His Ser Phe Glu Asn Leu Thr Asn Trp
        115             120             125

Pro Leu Val Arg Asp Thr Asn Pro Thr Leu Asn Pro Asn Leu Leu Gln
    130             135             140

Ile Gly Thr Lys Val Ile Phe Pro Leu Tyr Cys Gly Cys Pro Ser Lys
145             150             155             160

Ser His Ser Lys Asn Gly Ile Lys Tyr Leu Ile Thr Tyr Val Trp Gln
                165             170             175

Pro Ser Asp Asp Ile Tyr Arg Val Ser Ala Met Phe Asn Ala Ser Glu
                180             185             190

Val Asp Ile Ile Ile Glu Asn Asn Tyr Gln Asp Phe Lys Ala Ala Val
        195             200             205

Gly Tyr Pro Val Leu Ile Pro Val Ser Arg Met Pro Ala Leu Ser Gln
    210             215             220

Pro Pro Tyr Pro Ser His Ser His His Arg Ser Gln Leu Lys His Arg
225             230             235             240

Trp Phe Leu Ile Ala Val Ile Ser Ser Ala Gly Ala Leu Leu Ile Leu
                245             250             255

Phe Leu Ala Thr Phe Leu Val His Ser Ile Gly Leu Tyr Glu Lys Lys
                260             265             270

Lys Asn Leu Ser His Glu Glu Ser Ser Leu Glu Thr Thr Asp Leu Ile
        275             280             285

Gln Val Lys Asn Phe Ser Lys Ser Asp Thr Leu Glu Leu Gln Ala Lys
    290             295             300

His Asp Lys Leu Leu Pro Gly Val Ser Val Tyr Leu Gly Lys Pro Ile
305             310             315             320

Met Tyr Glu Ile Lys Met Ile Met Glu Ala Thr Met Asn Phe Asn Asp
                325             330             335

Gln Tyr Lys Ile Gly Gly Ser Val Tyr Arg Ala Met Ile Asn Gly Ser
                340             345             350

Phe Leu Ala Val Lys Lys Ala Lys Glu Asn Val Thr Glu Glu Leu His
        355             360             365

Ile Leu Gln Lys Val Asn His Gly Asn Leu Val Lys Leu Met Gly Ile
    370             375             380

Ser Leu Asp Arg Asp Gly Asn Cys Phe Phe Val Tyr Glu Tyr Ala Glu
385             390             395             400

Asn Gly Ser Leu Asp Lys Trp Leu Asn Pro Gln Ser Ser Thr Ser Thr
                405             410             415

Ser Ser Ser Val Gly Ile Leu Ser Trp Ser Gln Arg Leu Asn Ile Ala
                420             425             430

Leu Asp Val Ala Asn Gly Leu Gln Tyr Met His Glu His Thr Gln Pro
        435             440             445
```

```
Ser Ile Val His Lys Glu Ile Arg Thr Ser Asn Ile Leu Leu Asp Ser
    450             455             460

Arg Phe Lys Ala Lys Ile Ala Asn Phe Ser Met Ala Arg Ser Ala Ala
465             470             475             480

Ser Ala Gly Met Thr Lys Val Asp Val Phe Ala Phe Gly Val Val Leu
                485             490             495

Leu Lys Leu Leu Ser Gly Arg Lys Ala Met Ala Thr Arg Glu Asn Gly
            500             505             510

Glu Ile Val Met Leu Trp Lys Glu Ala Lys Ala Val Leu Glu Glu Glu
            515             520             525

Glu Lys Arg Ala Glu Lys Val Arg Glu Trp Ile Asp Pro Lys Leu Glu
    530             535             540

Ser Phe Tyr Pro Ile Asp Gly Ala Leu Ser Leu Met Thr Leu Ala Lys
545             550             555             560

Ala Cys Thr Gln Glu Lys Ala Ser Ala Arg Pro Ser Ile Gly Glu Val
                565             570             575

Val Phe Ser Leu Cys Val Leu Thr Gln Ser Phe Ser Glu Thr Leu Glu
            580             585             590

Pro Ser Trp Thr Cys Thr Leu Glu Gly Glu Asp Val Val Gln Ile Thr
            595             600             605

Ser Pro Ile Val Ala
    610
```

<210> SEQ ID NO 258
<211> LENGTH: 582
<212> TYPE: PRT
<213> ORGANISM: Parasponia andersonii
<220> FEATURE:
<221> NAME/KEY: VARIANT
<222> LOCATION: 144-159
<223> OTHER INFORMATION: Xaa = hydrophobic patch residues
<220> FEATURE:
<221> NAME/KEY: VARIANT
<222> LOCATION: 143, 160
<223> OTHER INFORMATION: Xaa = residues immediately adjacent to
     hydrophobic patch residues

<400> SEQUENCE: 258

```
Met Ala Asp Ser Tyr Phe Pro Phe Gln Ala Ile Phe Leu Leu Leu Leu
1               5               10              15

Leu Phe Ser Thr Leu Asn Met Ala Ala Ser Gln Leu Asn Asn Ser Ala
            20              25              30

Thr Asp Phe Ser Cys Ser Asp Ser Pro Pro Ser Cys Glu Ala Tyr Val
            35              40              45

Ala Tyr Phe Ser Gln Pro Pro Asn Tyr Met Asn Val Gly Asn Ile Ser
    50              55              60

Asp Leu Phe Gly Ile Ser Gln Ala Leu Ile Ala Lys Ser Ser Asn Leu
65              70              75              80

Val Ser Lys Asp Ser Pro Leu Ile Pro Gln Gln Leu Leu Leu Ile Pro
                85              90              95

Leu Thr Cys Thr Cys Thr Gly Asn His Tyr Phe Ala Asn Ile Thr Tyr
            100             105             110

Gln Val Glu Pro Gly Asp Thr Tyr His Tyr Leu Ser Thr Leu Leu Phe
            115             120             125

Glu Asn Leu Thr Asn Ser Gln Val Met Lys Lys Met Asn Pro Glu Ile
    130             135             140

Ser Pro Glu Tyr Val Leu Pro Tyr Ile Asp Ile Ile Ile Pro Val Phe
145             150             155             160
```

-continued

```
Cys Arg Cys Pro Ser Lys Ser His Leu Lys Ser Glu Ile Gln Gln Phe
            165             170             175

Ile Thr Tyr Val Trp Gln Pro Asn Asp Gln Val Ser Asn Val Ser Ala
            180             185             190

Lys Phe Asn Thr Ser Ala Ser Glu Ile Val Asn Glu Asn Lys Tyr Asn
            195             200             205

Asn Phe Ser Ser Ala Val Gly Leu Pro Val Leu Ile Pro Val Ser Lys
        210             215             220

Leu Pro Val Leu Ala Arg Val Lys Pro Pro Lys Ser Val Arg Ser Lys
225             230             235             240

Lys Gln Trp Ile Leu Ile Gly Val Glu Ser Leu Gly Gly Ile Val Leu
            245             250             255

Ile Thr Leu Phe Ala Thr Leu Leu Val Tyr Ser Asn Arg Leu Leu Lys
            260             265             270

Lys Arg Arg Lys Ile Leu Glu Ala Arg Arg Leu Glu Pro Arg Ile Ile
            275             280             285

Ile Gln Asp Lys Leu Leu Ser Gly Val Ser Glu Tyr Leu Gly Arg Pro
        290             295             300

Ile Met Tyr Asp Asn Lys Met Val Val Glu Gly Thr Met Asp Phe Ser
305             310             315             320

Glu Gln Cys Arg Ile Gly Gly Ser Val Tyr Arg Gly Glu Ile Tyr Gly
            325             330             335

Glu Val Phe Ala Val Lys Lys Thr Lys Gln Asp Ile Thr Asp Glu Leu
            340             345             350

Asn Leu Leu Gln Lys Val Asn His Val Asn Leu Val Asn Leu Met Gly
            355             360             365

Ala Ser Tyr Asp Thr Asp Gly Asn Arg Phe Leu Val Tyr Glu Tyr Val
        370             375             380

Glu Asn Gly Ser Leu Glu Arg Trp Leu Asp Leu Lys Pro Ser Ser Leu
385             390             395             400

Ala Ala Ala Ser Ser Ser Ser Val Gln Phe Leu Ser Trp Ser Gln
            405             410             415

Arg Ile Gln Ile Ala Leu Asp Val Ala Asn Gly Leu Gln Tyr Leu His
            420             425             430

Glu His Thr Gln Pro Asn Ile Ala His Trp Asn Ile Arg Thr Ser Thr
            435             440             445

Ile Leu Leu Asp Ser Lys Phe Arg Ala Lys Ile Ala Asn Phe Glu Val
        450             455             460

Ala Arg Pro Val Gly Asn Pro Ala Met Leu Lys Val Asp Ile Phe Ala
465             470             475             480

Phe Gly Ile Val Leu Leu Ala Leu Val Ser Gly Lys Lys Ala Leu Gln
            485             490             495

Thr Ile Glu Asn Gly Glu Val Ile Met Leu Trp Lys Asp Leu Ala Lys
            500             505             510

Glu Val Phe Glu Val Glu Glu Lys Lys Glu Asp Arg Leu Arg Lys Trp
            515             520             525

Met Asp Pro Asn Leu Gln Ser Phe Tyr Pro Ile Asp Gly Ala Leu Ser
        530             535             540

Leu Ser Ser Leu Ala Arg Ala Cys Ile Arg Glu Lys Ser Ser Ala Arg
545             550             555             560

Pro Lys Met Ala Glu Ile Val Phe Ser Leu Ser Val Leu Ala Gln Ser
            565             570             575
```

```
Ser Ser Pro Gly Thr Pro
            580

<210> SEQ ID NO 259
<211> LENGTH: 620
<212> TYPE: PRT
<213> ORGANISM: Malus domestica
<220> FEATURE:
<221> NAME/KEY: VARIANT
<222> LOCATION: 145-158
<223> OTHER INFORMATION: Xaa = hydrophobic patch residues
<220> FEATURE:
<221> NAME/KEY: VARIANT
<222> LOCATION: 144-159
<223> OTHER INFORMATION: Xaa = residues immediately adjacent to
      hydrophobic patch residues

<400> SEQUENCE: 259

Met Ala Ile Ser Phe Leu Cys Ser Lys Pro Leu Cys Ile Leu Leu Leu
1               5                   10                  15

Leu Leu Phe Phe Thr Ala Arg Ile Leu Ala Gln Ser Thr Pro Ser Asn
            20                  25                  30

Ser Ser Thr Ser Phe Ser Cys Ser Val Asp Ala Pro Pro Ser Cys Asp
            35                  40                  45

Thr Tyr Val Ser Tyr Phe Ala Arg Pro Gln Phe Met Ser Leu Glu Asn
    50                  55                  60

Ile Ser His Leu Phe Gly Val Ser Pro Leu Ser Ile Ala Lys Ala Ser
65                  70                  75                  80

Asn Leu Val Ser Glu His Ile Arg Leu Ile Ala Gly Gln Leu Leu Leu
                85                  90                  95

Val Pro Ile Ser Cys Gly Cys Ser Gly Asn Ser Tyr Phe Ser Asn Ile
            100                 105                 110

Thr Tyr Glu Ile Lys Ser Gly Asp Ser Phe Tyr Leu Val Ser Ile Asn
            115                 120                 125

Ser Phe Glu Asn Leu Thr Asp Trp His Glu Val Leu Asn Met Asn Pro
    130                 135                 140

Thr Leu Asp Pro Ser Leu Leu Gln Ile Gly Gln Lys Val Ile Phe Pro
145                 150                 155                 160

Leu Phe Cys Lys Cys Pro Ser Lys Met Tyr Thr Glu Asn Gly Ile Lys
                165                 170                 175

Tyr His Ile Thr Tyr Ile Trp Gln Pro Asn Asp Asp Ile Ser Arg Val
            180                 185                 190

Ser Ser Arg Phe Asn Val Ser Thr Leu Asp Ile Ser Ser Ala Asn Asn
            195                 200                 205

Leu His Asn Asp Ser Ala Ala Val Glu Leu Pro Val Val Ile Pro Val
    210                 215                 220

Ser Arg Leu Pro Ala Leu Val Gln Pro Lys Pro Pro Gln Gly Arg Asn
225                 230                 235                 240

Ile Phe Lys Gln Arg Trp Trp Leu Ile Leu Ile Ile Leu Gly Gly
                245                 250                 255

Val Leu Leu Val Ser Ser Leu Leu Ala Ile Phe Ala Val Tyr Thr Arg
            260                 265                 270

His Gln His Lys Val Lys Lys Ala Leu Asp Gly Pro Gly Ser Ser Leu
            275                 280                 285

Glu Ser Ala Glu Trp Phe Lys Met Lys Glu Gly Lys Ile Asp Glu Asn
    290                 295                 300

Phe Asp Leu Lys Phe Ile Gln Asp Lys Leu Leu Pro Gly Val Ser Ser
305                 310                 315                 320
```

-continued

```
Tyr Leu Gly Lys Pro Ile Met Tyr Glu Val Lys Thr Ile Met Glu Ala
                325                 330                 335

Thr Met Asn Leu Asn Glu His Cys Arg Ile Gly Gly Ser Val Tyr Arg
                340                 345                 350

Ala Ile Val Asp Gly Gln Val Leu Ala Val Lys Asn Thr Lys Glu Asp
                355                 360                 365

Val Thr Glu Glu Leu Asn Ile Leu Gln Lys Val Asn His Ala Asn Leu
        370                 375                 380

Val Lys Leu Met Gly Val Ser Ser Glu Thr Asp Gly Ser Arg Phe Leu
385                 390                 395                 400

Val Tyr Glu Tyr Ala Ala Asn Gly Ser Leu Asp Lys Trp Leu Tyr Ser
                405                 410                 415

Lys Ser Ser Ala Thr Ser Ser Ser Ala Glu Leu Leu Thr Trp Asn Gln
                420                 425                 430

Arg Leu Ser Ile Ala Leu Asp Ile Ala Asn Gly Leu Gln Tyr Met His
                435                 440                 445

Glu His Thr Gln Arg Ser Ile Val His Met Asp Ile Arg Thr Ser Asn
        450                 455                 460

Ile Leu Leu Asp Ser Lys Phe Lys Ala Lys Ile Ala Asn Phe Ser Met
465                 470                 475                 480

Ala Arg Ala Ala Ala Asn Asp Val Thr Pro Lys Val Asp Val Phe Ala
                485                 490                 495

Phe Gly Val Val Leu Leu Ala Leu Leu Ser Gly Lys Lys Gly Met Glu
                500                 505                 510

Ala Lys Glu Asn Gly Glu Ala Ile Met Leu Trp Lys Asp Val Arg Trp
                515                 520                 525

Val Leu Glu Ala Glu Glu Glu Lys Val Glu Arg Leu Arg Lys Trp Met
        530                 535                 540

Asp Pro Asn Leu Glu Asn Phe Tyr Pro Ile Asp Gly Ala Leu Ser Leu
545                 550                 555                 560

Thr Ala Leu Ala Arg Ala Cys Thr Gln Glu Lys Pro Ser Thr Arg Pro
                565                 570                 575

Ser Met Gly Glu Val Val Phe Asn Leu Ser Val Leu Thr His Ser Ser
                580                 585                 590

Ser Gln Ser Thr Leu Glu Arg Ser Trp Thr Ser Ala Leu Glu Ala Glu
                595                 600                 605

Glu Val Leu Glu Thr Ile Ser Pro Ile Ala Ala Arg
        610                 615                 620
```

<210> SEQ ID NO 260
<211> LENGTH: 624
<212> TYPE: PRT
<213> ORGANISM: Fragaria vesca subsp. Vesca
<220> FEATURE:
<221> NAME/KEY: VARIANT
<222> LOCATION: 149-162
<223> OTHER INFORMATION: Xaa = hydrophobic patch residues
<220> FEATURE:
<221> NAME/KEY: VARIANT
<222> LOCATION: 148, 163
<223> OTHER INFORMATION: Xaa = residues immediately adjacent to
     hydrophobic patch residues

<400> SEQUENCE: 260

```
Met Ala Val Ser Phe Leu Cys Ser Ser Met Val Cys Ile Leu Leu Leu
1               5                   10                  15

Phe Phe Phe Thr Ser Gln Ile Leu Ala Gln Pro Ala Pro Gln Ser Asn
```

-continued

```
                20                    25                    30

Ser Thr Thr Ser Phe Ser Cys Ala Val Asp Ala Pro Ser Ser Cys Glu
            35                    40                    45

Thr Tyr Val Ala Tyr Phe Val Glu Ser Pro Gly Tyr Met Asn Leu Glu
        50                    55                    60

Asn Ile Ser Asp Leu Phe Gly Val Ser Val Ser Ser Ile Ser Gln Ala
65                    70                    75                    80

Ser Asn Leu Ala Ser Ser Tyr Thr Gly Gln Thr Arg Leu Val Ala Gly
                85                    90                    95

Gln Leu Leu Leu Val Pro Ile Thr Cys Gly Cys Thr Gly Asn Arg Ser
            100                   105                   110

Phe Ala Asn Ile Thr Tyr Ser Ile Lys Arg Gly Asp Ser Tyr Tyr Val
            115                   120                   125

Val Ser Met Tyr Thr Phe Glu Asn Leu Thr Arg Trp Pro Leu Val Val
        130                   135                   140

Glu Met Asn Pro Ala Leu Val Pro Ser Leu Leu Gln Ile Gly Val Lys
145                   150                   155                   160

Val Ile Phe Pro Leu Phe Cys Lys Cys Pro Ser Lys Met Tyr Ser Asp
            165                   170                   175

Leu Gly Ile Lys Tyr Leu Leu Thr Tyr Val Trp Gln Thr Asn Asp Asp
            180                   185                   190

Ile Phe Arg Val Ser Ala Lys Phe Asn Ile Ser Ala Leu Asn Ile Ser
            195                   200                   205

Gly Ala Asn Asn Phe Asp Asn Gly Ser Pro Val Val Gly Gln Pro Val
        210                   215                   220

Leu Ile Pro Leu Thr Lys Leu Pro Ala Leu Ser Gln Pro Leu Pro Pro
225                   230                   235                   240

His Gly Lys His Ile Phe Lys His Arg Leu Met Leu Ile Val Ile Ile
            245                   250                   255

Cys Leu Gly Val Ala Leu Ser Val Ala Ser Leu Leu Ala Ile Phe Leu
            260                   265                   270

Val His Thr His Arg Leu Arg Lys Arg Gln Lys Leu Leu Asn Asp Lys
        275                   280                   285

Ser Leu Ser Leu Glu Ser Ala Glu Trp Phe Arg Met Lys Glu Gly Lys
    290                   295                   300

Ser Glu Glu Lys Ile Glu Met Lys Phe Ile Gln Asp Lys Leu Leu Pro
305                   310                   315                   320

Gly Val Ser Ser Tyr Leu Gly Lys Ala Ile Leu Tyr Asp Val Lys Thr
            325                   330                   335

Ile Met Glu Ala Thr Met Asn Leu Asn Asp His Cys Gly Ile Gly Gly
            340                   345                   350

Ser Val Tyr Arg Ala Val Ile Asp Gly Lys Val Leu Ala Val Lys Lys
            355                   360                   365

Thr Lys Glu Asp Val Thr Glu Glu Leu Asn Ile Leu Gln Lys Val Asn
        370                   375                   380

His Ala Asn Leu Val Lys Leu Met Gly Ile Ser Ser Glu Ile Asp Gly
385                   390                   395                   400

Val Arg Phe Leu Val Tyr Glu Tyr Ala Glu Asn Gly Ser Leu Asp Lys
            405                   410                   415

Trp Leu Tyr His Lys Thr Ser Thr Asn Ser Ser Ser Gly Ala Phe Leu
            420                   425                   430

Thr Trp Ser Gln Arg Leu Ser Ile Ala Leu Asp Val Ala Asn Gly Leu
            435                   440                   445
```

-continued

```
Gln Tyr Leu His Glu His Thr Gln Pro Ser Ile Val His Met Asp Ile
    450                 455                 460

Arg Thr Ser Asn Ile Leu Leu Asp Ser Lys Tyr Lys Ala Lys Ile Ala
465                 470                 475                 480

Asn Phe Ser Met Ala Arg Thr Ala Ala Asn Ser Val Thr Pro Lys Val
                485                 490                 495

Asp Val Phe Ser Phe Gly Val Ile Leu Leu Ser Leu Leu Ser Gly Lys
                500                 505                 510

Lys Gly Met Glu Thr Thr Asp Asn Gly Glu Val Ile Met Leu Trp Lys
                515                 520                 525

Asp Val Arg Gly Val Leu Glu Ala Glu Glu Lys Lys Gln Glu Lys Leu
    530                 535                 540

Arg Ala Trp Met Asp Pro Thr Leu Glu Ser Phe Tyr Pro Ile Asp Gly
545                 550                 555                 560

Ala Leu Ser Leu Thr Ala Leu Ala Ser Ala Cys Thr Gln Glu Lys Ser
                565                 570                 575

Ser Ala Arg Pro Ser Met Ala Glu Val Val Phe Asn Leu Ser Val Leu
                580                 585                 590

Thr His Ser Ser Ser Glu Ser Thr Leu Glu Arg Ser Trp Asn Ser Ala
                595                 600                 605

Leu Glu Val Glu Glu Val Leu Gln Thr Ile Ser Pro Ile Lys Ala Arg
    610                 615                 620

<210> SEQ ID NO 261
<211> LENGTH: 1317
<212> TYPE: DNA
<213> ORGANISM: Lotus japonicus

<400> SEQUENCE: 261
ggacatgaga ttgaagctcc aaaattagct cttttttctg atgaatactt aatgctttgt      60
tgtattcact tgattaagtg ctagaaatca tctttgcatg atcatagatt aaatgaattt     120
ccagttggtg tgtggagagc tattttgtta tgctgacatc tgcaatttgc agggcatcta     180
atgattgtca tttcttaaat tattattggt tgtttccgtt tctttaatta tctgttttaa     240
tcttgcaggt catacaaatt aaaatactag ccaccaccca agacatacta aatggggtag     300
tagagggaag ggtaaggtcg ataaggatga cttttttattc tataaaattt aggagaattt     360
gagcttaagt ggcaaggcaa acgacattac tatacgaatt ggctttgtac cagaaacagg     420
gaacaaataa tattttacaa ataagctatt atcatgtcag ctcatttgtt caactttgat     480
ttgattaaaa attaaatgaa gttgaatttg ttgagctgct ttattatata tgccactgga     540
tgtttccgca ttctaagtgc atgtttgaaa acatttctac aattgattac gaaggaaaaa     600
ttaatcatgg agagaagctt atgtgcgtag cttctgtatt tctgaattga ttctatctgt     660
acagtagcat ttagataatg aatgatcttg gttctcgcta agcatcaaac caatctctac     720
ccttttaaaa ttgcaagaat tataagtcat gcattgaccc aaatccttct gtggttatgc     780
cccttaaaaa tccggcaaga catcaagtta gttggtcatt agggttccac cagctagctg     840
acaccttgta caacaactgg ccgtcctaaa gttgggtaag cattacaata ctaaatgcca     900
ttttattata ttttgcgcat ggttatatac ctaagtagga tttgtccaca gtttctttga     960
ttcggaaagg aaaaaatatt tagttgacac tgacagaagc agattttata tacatatatt    1020
atgaaatgac tcctacatga gatacacgaa tctcatcccc atgagttgca gtttgacaga    1080
gtacacactt atcaacttgc tggaatatag gaaagtctaa ccaatgatgt cgatccgtat    1140
```

-continued

```
tgccttaatt ttggtaaatt tagtattaca tgatcattat tgatatacta aaccacagga    1200
tattttattg acaatgtgaa tgttccatat tttcaacaat gctgattccc tctgataaag    1260
aacaagttcc ttttctcttt ccctgttaac tatcatttgt tccccacttc acaaaca       1317

<210> SEQ ID NO 262
<211> LENGTH: 2000
<212> TYPE: DNA
<213> ORGANISM: Artificial Sequence
<220> FEATURE:
<223> OTHER INFORMATION: Synthetic Construct

<400> SEQUENCE: 262
aaataatgtg tctaaaatta acaaagatat tttatggtta atttattgag cttagttaaa      60
gtcattttct aaaacgagac attgtagttg ttagataaat aatttccttt aattttcatc     120
aaagtttgta ataattata gggcaggaca catatgtcca tcaattgata tatatatatc      180
ttttgtaata acgatcttat agaagaatca atatctacaa agaaagttat cacttgtctc     240
aaattatgct ttatgcaact ggtattgtca tgtagattcc attttggttt atatgatatt     300
gaagtcaacg aatcacagct gcttaggcgt ggttcataat ttaaaattga aactatggtg     360
tttgttggaa ttatgagagg acagactgtg aagtggttgc acagctaccg acagggttgc     420
cattactgat gcaaaggatt aaacaataga acattttcaa tcaacttaat ctatgtttga     480
catcacgctc gatgtgtcag aatcacgacg acccactgta attttttaaaa aaattacatt    540 ttataatttt tgtagaatca cggtgtatca cagtgatttt gacatacccca ctgtaatacc    600 aaacatgcac ttgcattctt tcttccgttt gatgccaaaa atggtattgt ttataataca     660
cttaaaataa ttcatatcca agttgttgta taaaaaaata aacaatgtga tttcccaaaa     720
aaaaaaaata ataagtgatt ggcatgcaac atcagatttt gttgtccaag tggtcacatt     780
tgaaatattt gagtttacat ttttctcact aatatctttta tattgaactt caatctgtct     840
agctataatc aaatggttga ctaaaatggt taataagctt caattaaatt caaattattt     900
gaaagaactt gaatttaaat cttaacttga acataaccccc gaagtggatg atttacccaa     960
aaaaattacc taactactct aataatcatt ttaacaataa gagtatttta ctcaaagaaa    1020
tttatataat cacaaaatcc tagtatactc aatgattttc ttaaaaaact attataacca    1080
gaaatgacaa tatgagacaa atataattat tttaataaaa atatctaaat tagaattatt    1140
tgaaaatgta aaactatatt attttttgta gttttccaaa ctttattaag catcgtttaa    1200
ttgcacacaa aatttactcc aattttttttt agtctctgaa agttgctttt tggtccatgt    1260
tttagttttg gtaattataa ttaagtttgt tcatattaat tagttctaat gtgtgtacta    1320
tatagatcat actaattttg ttcccaaact catcttagtt aggatctttg tatctactat    1380
aagattaatc cttgtgccga tataagaata tttgtcatgt tatcaactat cacaatattg    1440
tattggtgag atcatataag atttgatgtc aacatcttcg taaaggtgtc agattcgatt    1500
ctccccggta tcaatttaag tgagctaatt tagcttctta aaaaataaaa tcaaacaact    1560
tttacataaa ctcagtgaaa acttggatat aaagtatcct tatactactc tttagtcttg    1620
attagtctct gcaaagatat ttatatgtac tttgtattat cataagaaca ttcattgaca    1680
ttttaagtta atgaattact aacatgtcaa ctcttattct agccaacagt tactttgttc    1740
cctccacatt ctctttgaaa tagtcaaacg tatccaatca tgcatgtctg ttctgatcat    1800
aacagcaaaa gcatgtgtat agaaaattga tagttgaatt agagtcattt tccataaaaa    1860
```

```
aatattcaat aagtgtgaca ttattttttcg tatgaattaa tccattttttt gctgatttga    1920 gattctttct ttctttgctt cttgctttcc ttcatcagcc attttttttg ttttctcttt    1980
ctctctctct tcttgattca                                                 2000
```

<210> SEQ ID NO 263
<211> LENGTH: 1135
<212> TYPE: DNA
<213> ORGANISM: Artificial Sequence
<220> FEATURE:
<223> OTHER INFORMATION: Synthetic Construct

<400> SEQUENCE: 263

```
cgatccttcg ttgtattcac ttggtcaagt gcaagaaatc atctttacac aatcatataa      60
tgaatggacc tttggttgat gtgttgagag ctacattcag tcctctgctg acttctgcaa     120 cttgaggggga atctaatgat tgtcttattg caattaacaa ttcctttttaa tttttttgaca   180 gaaagagttg gttacaaaat ctcatctaac atattgttga gttcctcttt tttttttttt     240
tttttttttt tgataaaagg gtacatctgt tcgcagctct gaagattaat ccctcgaata     300
gggttggata acatgaacga caaatttgtt tcttaagagt tttaacactg tcatattctt      360
atggcagaat tcgaactcga acccactggt taagctagta gtaagaagtg acccatgcca      420
tctcattcaa tcgttcttgg cttgtttttcg gtttagatga atatgaagta caaaaagcta     480
cgctcaagca aaggagagca ggtaagaagg gcatcttatt tttttaatat attagatgtc      540
aagcttacgt ggcgatgtaa acactgtttc tatccgaatt agctatgtac tagaaatagg      600
gaacaaataa tataaatggt gagtttgtca aggtgtttta atatattgaa accaatgtaa      660
ctggaagtgt caacattgaa agctgttcat tgcctgtatt atattataat tgcatatata     720
taatggcatt agcctttgtt aaacgttaaa ccatatcttt tgctagtttg ccccttaaaa     780
atttggtaaa ggcatcaagt tagatggtct ttaggtacca gccagctagt tgacatcgtg      840
tatggacacc aaattgggtt ataataccat attattctta ccatctttat tatattctgc      900
gcatgatttc atacttgttt gggatttgcc aacagtgtct aagatttgaa aaagaaaaat      960
agtagaacta atgacagaga catcagcata tattttttaat atcaaaccaa aagatatttg    1020
atgtccaaag aagagataaa tataaagtta gaagtatgac aataagtctt ggttgttatt    1080
tgccataaga aactctcttt tctcttcccc tcataatttg catttcctca caaca         1135
```

<210> SEQ ID NO 264
<211> LENGTH: 2496
<212> TYPE: DNA
<213> ORGANISM: Artificial Sequence
<220> FEATURE:
<223> OTHER INFORMATION: Synthetic Construct

<400> SEQUENCE: 264

```
tcgactatat aagggggttcc tccataccta ataagacatg tttgtttcat gtcgatctac      60
ttactctatt ttatggtttt ctcgtgagca atttacatat aaaatacaca ttaaattgca     120
cccaataact aactagttac aagattagag cacataaatc atggaatgaa acaatagcct     180
atgacttggg tattcggtcc acaacatctc tagaagttcg tacaacaacg atcaaagaga     240
aagtactgac tagtgatatg agaaatttgg tcaggaacaa tgggctggac acattacgaa      300
cttgagcctg aatagtagca gcatatgtct gccttcgcaa tgacgaagaa ggttggacgg     360
agctaaagtt aaagctggaa gggtgtgtcg tggcatttga aatttagggt tcaactgtag      420
ctttgtttgt ctaactaccc ttctagcttt aataaaaaaa cgtaaatcaa ttaattaaag     480
```

```
agaaatcacg ccaacctgtc tcaaacccgc tctaacttgt tggttaaggt tatgtgttgt      540
atttcaattt gcttgttgct tcaacttgac tccttacctc ctttcatgtt ttttcttgaa      600
aattgtgtaa actcagtttt ttttttttga gaatgtatga gaatgtgata caaattaaaa      660
tacaaacata cattgaatga gcggggctaa aatgactcaa ggtacatatg agttaagttt      720
ttaccaaccc atctctttga tgagttgggt ttaattgggt tagctcacgt gttaactatt      780
tcgacaattc taactttttg gaataatgcc atccaaccct aggtaaaact caacatgact      840
tctcttaaag aaatgaagag tgaaagtcta cataaatctt aaacacttaa aacactacaa      900
cttggtagat cattaaaata tgctccagaa ataccataat acttgaaaat aaataattta      960
taaatgtaaa atataaattt gttgctgcac ccaagtctga gtgaggaatg aataaagata     1020
aataaaatat atatatgcgt tgatactaac atatgatatg atgtgataga tgtcatatat     1080
aatgaacaga atgatagaaa ttgttgagcg catggaagct tcttgttcaa taattcaaga     1140
gctgcttgtg gagggctgct gcagggttgt tatggatgca attatcaaat atcttgctgg     1200
aaattgatcc aaaagttgac tattacctta tcaatgtccg gtgtccttca agccaccatt     1260
caattagtca ataacctttt gttttgttt tttataatt ttggtgccaa ataattttaa       1320
ccatttattt ttatcatata tattatataa gatggcaagt ctataatcat ttaaaattaa     1380
attagtctaa atttttctaa tatgctgtat aaatttatta tatataagaa taaataaat      1440 taaaaatatt gtttaattgc taccagttca atcattaatt aactattgac tgaaaagaaa     1500
aatgtctaac aaattttgtt acattctgtt tgttttgaga aaaaaaaat tgtttttcat      1560 tttctgaaaa tatttatttt taaatttatt aaatttagaa attatgtttg tttttacgct     1620
ttgttttcat cttcaccgtc accaccatcg ctaccactgt cgtcactatt actatatacc     1680
actaccatcg ttgttgccgt tgtcattgtc aacaccattg ctgtcgtcgt tgttattatc     1740
gccccacaac cactatcatc atcactgcta tcgtcatagc taccacgaac accaccatca     1800
cttttcattg aaaatgaaaa atgtttattt atttattttg attatatttt aaaaaatatt     1860
tttaatcaac caaatttctt tttaactttt tttttcttat gaaaaaaaat aatatgaaaa     1920
gaacaaacca aacagatcct tatattcttg tttccattct ttatcaccca tgagagtagc     1980
tgtagcgcgt taactttcta atagaggcgg gaatttaccg ttaaccgttg ggtcatcact     2040
cagcttactg agtcatcttc ttcctactgt aggcggaacc cacacgccac tgcctctcta     2100
ttattacatc aaattctatt tttttttacat catcatcaag ataaataaat tgcattattc    2160
agaaattaat tcctgaatct ccctatctta actcaggtgt ctctagctat taccacttaa     2220
gctattatta gaagtctacg tcaaattcta taataaacac atattcttat tcttattatt     2280
atactaatac aaaccttgat ttgaagccaa aaatgataaa acaattgcag actcgttcaa     2340
acaacagaca acatgtacca ttaaattcca ccccaaattc tcaaagcaaa ttctgaattc     2400
tccaactagt ttccattctc ctagtcaact caactcaaaa cccagatgag aatgagataa    2460
ttccaacttt aacaaacaca cacaattcat cattca                              2496
```

<210> SEQ ID NO 265
<211> LENGTH: 629
<212> TYPE: PRT
<213> ORGANISM: Artificial Sequence
<220> FEATURE:
<223> OTHER INFORMATION: Synthetic Construct

<400> SEQUENCE: 265

-continued

```
Met Glu Ala Pro Leu His Ser Leu Leu Leu Leu Leu Leu Ala Ala
1               5                   10                  15

Ala Ala Gly Pro Lys Thr Ala Ala Ala Val Gly Asp Gly Cys Ser Arg
            20                  25                  30

Gly Cys Asp Leu Ala Leu Ala Ser Tyr Tyr Ile Ala Pro Gly Val Phe
            35                  40                  45

Ile Leu Gln Asn Ile Thr Thr Phe Ala Ser Leu Phe Gly Phe Ser Glu
    50                  55                  60

Tyr Arg Val Leu Gly Gln Tyr Asn Pro Gly Leu Asn Asp Ile Asn Ile
65                  70                  75                  80

Gln Ser Phe Asp Arg Leu Asn Val Ser Leu Thr Cys Lys Cys Leu Ala
                85                  90                  95

Ser Leu Ser Ala Pro Ala Ser Thr Phe Leu Ala Ala Ser Ile Pro Tyr
            100                 105                 110

Lys Val Ala Thr Gly Glu Thr Tyr Leu Arg Ile Ala Asp Asn Tyr Asn
            115                 120                 125

Asn Leu Thr Thr Ala Asp Trp Leu Val Ala Thr Asn Thr Tyr Pro Ala
    130                 135                 140

Asn Asn Ile Pro Asp Val Ala Thr Val Asn Ala Thr Val Asn Cys Ser
145                 150                 155                 160

Cys Gly Asp Ala Gly Ile Ser Thr Asp Tyr Gly Leu Phe Leu Thr Tyr
                165                 170                 175

Pro Leu Arg Asp Arg Glu Thr Leu Ala Ser Val Ala Ala Asn His Gly
                180                 185                 190

Phe Ser Ser Pro Glu Lys Met Asp Leu Leu Lys Lys Tyr Asn Pro Gly
                195                 200                 205

Met Asp Gly Val Thr Gly Ser Gly Ile Val Tyr Ile Pro Ala Lys Tyr
    210                 215                 220

Lys Asn Gly Val Tyr Val Pro Leu Tyr His Arg Thr Lys Lys Ser Ser
225                 230                 235                 240

Ala Gly Ala Ile Ala Gly Gly Val Val Ala Gly Val Val Ala Leu Val
                245                 250                 255

Leu Gly Val Val Leu Phe Leu Phe Tyr Arg Arg Arg Lys Ala Lys Lys
                260                 265                 270

Asp Ala Leu Leu Pro Ser Ser Glu Glu Ser Thr Arg Leu Ala Ser Ala
                275                 280                 285

Ile Ser Met Gln Lys Val Thr Pro Ser Thr Ser Gln Ala Asp Gly Ala
    290                 295                 300

Ser Pro Ala Ala Gly Ile Thr Val Asp Lys Ser Val Glu Phe Ser Tyr
305                 310                 315                 320

Glu Glu Leu Phe Asn Ala Thr Glu Gly Phe Asn Ile Ile His Lys Ile
                325                 330                 335

Gly Gln Gly Gly Phe Gly Ala Val Tyr Tyr Ala Glu Leu Arg Gly Glu
                340                 345                 350

Lys Ala Ala Ile Lys Lys Met Asp Met Gln Ala Thr Gln Glu Phe Leu
                355                 360                 365

Ala Glu Leu Lys Val Leu Thr His Val His His Leu Asn Leu Val Arg
    370                 375                 380

Leu Ile Gly Tyr Cys Thr Glu Ser Ser Leu Phe Leu Val Tyr Glu Phe
385                 390                 395                 400

Ile Glu Asn Gly Asn Leu Ser Gln His Leu Arg Gly Thr Gly Tyr Glu
                405                 410                 415

Pro Leu Ser Trp Val Glu Arg Val Gln Ile Ala Leu Asp Ser Ala Arg
```

-continued

```
                420             425             430
Gly Leu Glu Tyr Ile His Glu His Thr Val Pro Val Tyr Ile His Arg
            435             440             445

Asp Ile Lys Ser Ala Asn Ile Leu Ile Asp Lys Asn Thr Arg Ala Lys
        450             455             460

Val Ala Asp Phe Gly Leu Thr Lys Leu Thr Glu Val Gly Gly Gly Thr
465             470             475             480

Ser Leu Gln Thr Arg Val Val Gly Thr Phe Gly Tyr Met Pro Pro Glu
                485             490             495

Tyr Ala Arg Tyr Gly Asp Val Ser Pro Lys Val Asp Val Tyr Ala Phe
            500             505             510

Gly Val Val Leu Tyr Glu Leu Ile Ser Ala Lys Asp Ala Ile Val Arg
            515             520             525

Ser Ala Glu Ser Thr Ser Asp Ser Lys Gly Leu Val Tyr Leu Phe Glu
        530             535             540

Glu Ala Leu Ser Ala Pro Asp Pro Lys Glu Gly Ile Arg Arg Leu Met
545             550             555             560

Asp Pro Lys Leu Gly Asp Asp Tyr Pro Ile Asp Ala Ile Leu Lys Met
            565             570             575

Thr His Leu Ala Asn Ala Cys Thr Gln Glu Asp Pro Lys Leu Arg Pro
            580             585             590

Thr Met Arg Ser Val Val Val Ala Leu Met Thr Leu Ser Ser Thr Ser
            595             600             605

Glu Phe Trp Asp Met Asn Ala Leu Tyr Glu Asn Pro Gly Leu Val Asn
        610             615             620

Leu Met Ser Gly Arg
625
```

<210> SEQ ID NO 266
<211> LENGTH: 631
<212> TYPE: PRT
<213> ORGANISM: Artificial Sequence
<220> FEATURE:
<223> OTHER INFORMATION: Synthetic Construct

<400> SEQUENCE: 266

```
Met Glu Ala Pro Leu His Ser Leu Leu Leu Leu Leu Leu Ala Ala
1               5               10              15

Ala Ala Gly Pro Lys Thr Ala Ala Ala Val Gly Asp Gly Cys Leu Lys
            20              25              30

Gly Cys Asp Leu Ala Leu Ala Ser Tyr Tyr Ile Leu Pro Gly Val Phe
            35              40              45

Ile Leu Gln Asn Ile Thr Thr Phe Met Gln Ser Glu Ile Val Ser Ser
        50              55              60

Asn Asp Ala Ile Thr Ser Tyr Asn Lys Asp Lys Ile Leu Asn Asp Ile
65              70              75              80

Asn Ile Gln Ser Phe Gln Arg Leu Asn Ile Pro Phe Pro Cys Lys Cys
                85              90              95

Leu Ala Ser Leu Ser Ala Pro Ala Ser Thr Phe Leu Ala Ala Ser Ile
            100             105             110

Pro Tyr Lys Val Ala Thr Gly Glu Thr Tyr Leu Arg Ile Ala Asp Asn
            115             120             125

Tyr Asn Asn Leu Thr Thr Ala Asp Trp Leu Val Ala Thr Asn Thr Tyr
        130             135             140

Pro Ala Asn Asn Ile Pro Asp Val Ala Thr Val Asn Ala Thr Val Asn
```

-continued

```
145                    150                    155                    160

Cys Ser Cys Gly Asp Ala Gly Ile Ser Thr Asp Tyr Gly Leu Phe Leu
                165                    170                    175

Thr Tyr Pro Leu Arg Asp Arg Glu Thr Leu Ala Ser Val Ala Ala Asn
                180                    185                    190

His Gly Phe Ser Ser Pro Glu Lys Met Asp Leu Leu Lys Lys Tyr Asn
                195                    200                    205

Pro Gly Met Asp Gly Val Thr Gly Ser Gly Ile Val Tyr Ile Pro Ala
                210                    215                    220

Lys Tyr Lys Asn Gly Val Tyr Val Pro Leu Tyr His Arg Thr Lys Lys
225                    230                    235                    240

Ser Ser Ala Gly Ala Ile Ala Gly Gly Val Val Ala Gly Val Val Ala
                245                    250                    255

Leu Val Leu Gly Val Val Leu Phe Leu Phe Tyr Arg Arg Arg Lys Ala
                260                    265                    270

Lys Lys Asp Ala Leu Leu Pro Ser Ser Glu Glu Ser Thr Arg Leu Ala
                275                    280                    285

Ser Ala Ile Ser Met Gln Lys Val Thr Pro Ser Thr Ser Gln Ala Asp
                290                    295                    300

Gly Ala Ser Pro Ala Ala Gly Ile Thr Val Asp Lys Ser Val Glu Phe
305                    310                    315                    320

Ser Tyr Glu Glu Leu Phe Asn Ala Thr Glu Gly Phe Asn Ile Ile His
                325                    330                    335

Lys Ile Gly Gln Gly Gly Phe Gly Ala Val Tyr Tyr Ala Glu Leu Arg
                340                    345                    350

Gly Glu Lys Ala Ala Ile Lys Lys Met Asp Met Gln Ala Thr Gln Glu
                355                    360                    365

Phe Leu Ala Glu Leu Lys Val Leu Thr His Val His His Leu Asn Leu
                370                    375                    380

Val Arg Leu Ile Gly Tyr Cys Thr Glu Ser Ser Leu Phe Leu Val Tyr
385                    390                    395                    400

Glu Phe Ile Glu Asn Gly Asn Leu Ser Gln His Leu Arg Gly Thr Gly
                405                    410                    415

Tyr Glu Pro Leu Ser Trp Val Glu Arg Val Gln Ile Ala Leu Asp Ser
                420                    425                    430

Ala Arg Gly Leu Glu Tyr Ile His Glu His Thr Val Pro Val Tyr Ile
                435                    440                    445

His Arg Asp Ile Lys Ser Ala Asn Ile Leu Ile Asp Lys Asn Thr Arg
                450                    455                    460

Ala Lys Val Ala Asp Phe Gly Leu Thr Lys Leu Thr Glu Val Gly Gly
465                    470                    475                    480

Gly Thr Ser Leu Gln Thr Arg Val Val Gly Thr Phe Gly Tyr Met Pro
                485                    490                    495

Pro Glu Tyr Ala Arg Tyr Gly Asp Val Ser Pro Lys Val Asp Val Tyr
                500                    505                    510

Ala Phe Gly Val Val Leu Tyr Glu Leu Ile Ser Ala Lys Asp Ala Ile
                515                    520                    525

Val Arg Ser Ala Glu Ser Thr Ser Asp Ser Lys Gly Leu Val Tyr Leu
                530                    535                    540

Phe Glu Glu Ala Leu Ser Ala Pro Asp Pro Lys Glu Gly Ile Arg Arg
545                    550                    555                    560

Leu Met Asp Pro Lys Leu Gly Asp Asp Tyr Pro Ile Asp Ala Ile Leu
                565                    570                    575
```

-continued

```
Lys Met Thr His Leu Ala Asn Ala Cys Thr Gln Glu Asp Pro Lys Leu
            580                 585                 590

Arg Pro Thr Met Arg Ser Val Val Val Ala Leu Met Thr Leu Ser Ser
            595                 600                 605

Thr Ser Glu Phe Trp Asp Met Asn Ala Leu Tyr Glu Asn Pro Gly Leu
            610                 615                 620

Val Asn Leu Met Ser Gly Arg
625                 630

<210> SEQ ID NO 267
<211> LENGTH: 665
<212> TYPE: PRT
<213> ORGANISM: Marchantia polymorpha

<400> SEQUENCE: 267

Met Ile Ala Thr Gly Val Ile Thr Arg Arg Ser Pro Trp Val Ser Ser
1               5                   10                  15

Val Met Val Val Leu Val Leu Ala Ala Ala Ser Ala Trp Ile Pro Thr
            20                  25                  30

Ser Glu Gly Asp Cys Leu Pro Arg Leu Gly Cys Ser Arg Ala Leu Ala
            35                  40                  45

Tyr Tyr Lys Leu Val Asn Asp Asp Thr Leu Leu Ala Leu Ala Asp Arg
        50                  55                  60

Phe Met Thr Asn Val Ala Glu Leu Gln Lys Tyr Asn Asp Ile Pro Asn
65                  70                  75                  80

Pro Asp Ser Val Glu Ala Gly Thr Val Leu Phe Phe Pro Tyr Thr Cys
                85                  90                  95

Glu Cys Ile Asp Asp Arg Leu Gly His Glu Phe Leu Tyr Gln Val Ala
            100                 105                 110

Leu Asp Asp Thr Val Ala Gln Ile Ala Gln Ile Lys Tyr Gln Phe Leu
            115                 120                 125

Ser Arg Glu Ala Trp Ile Thr Gln Ala Ser Lys Leu Ser Ser Val Gly
        130                 135                 140

Thr Ile Tyr Pro Gly Leu Thr Val Thr Val Pro Val Asn Cys Ser Cys
145                 150                 155                 160

Gly Asp Pro Ser Val Ser Pro Asp Tyr Gly Leu Phe Leu Thr Tyr Pro
                165                 170                 175

Ile Arg Ser Gly Asp Asn Phe Thr Gly Ile Ala Gln Gln Phe Gln Ala
            180                 185                 190

Asn Glu Thr Leu Leu Gln Gln Tyr Asn Pro Ser Ile Asn Trp Ser Asn
            195                 200                 205

Leu Ser Pro Ser Thr Asp Ile Ile Phe Ile Pro Gln Arg Val Phe Ala
        210                 215                 220

Thr Gly Ala Tyr Pro Ala Phe Asn Phe Ser Ala Asp Val Ser Glu Gly
225                 230                 235                 240

Gly Ser Lys Thr Asn Ala Gly Leu Ile Ala Gly Val Ser Val Gly Gly
                245                 250                 255

Ala Leu Ala Leu Val Leu Ala Val Val Leu Phe Phe Leu Phe Cys Val
            260                 265                 270

Tyr Trp Pro Arg Gln Arg His Ser Asp Pro Ser Asn Lys Ala Ala Met
            275                 280                 285

Glu Ser Leu Arg Leu Asp Gly Ser Gln Ser Gly Asp Arg Arg Ser Ala
            290                 295                 300

Leu Leu Lys Phe Ser Gln Glu Gly Ala Gly His Ser Arg Ser Ser Thr
```

-continued

```
305                310                315                320

Gly Ser Gly Ile Pro Val Gly Pro Ile Pro Leu Thr Asp Phe Thr Val
                325                330                335

Asp Lys Ser Val Glu Phe Ser Phe Glu Glu Leu Glu Ala Ala Thr Asn
                340                345                350

Lys Phe Ser Ala Ala Asn Lys Ile Gly Glu Gly Gly Tyr Gly Ala Val
                355                360                365

Tyr Phe Ala Asn Leu Arg Gly Met Lys Leu Ala Val Lys Arg Met Asn
    370                375                380

Leu Gln Ala Thr Arg Glu Phe Leu Ala Glu Leu Gln Val Leu Thr His
385                390                395                400

Val His His Thr Asn Leu Val Gln Leu Ile Gly Tyr Cys Thr Val Asp
                405                410                415

Ser Leu Phe Leu Ile Tyr Glu Tyr Val Asp Asn Gly Thr Leu Asp Arg
                420                425                430

His Leu His Gly Lys Asn Asp Leu Ala Pro Leu Ser Trp Ser Ser Arg
                435                440                445

Val Gln Ile Ala Leu Asp Ala Ala Arg Gly Leu Glu Tyr Ile His Glu
    450                455                460

His Thr Lys Pro Thr Tyr Ile His Arg Asp Val Lys Ser Ser Asn Ile
465                470                475                480

Leu Ile Asp Lys Gln Phe His Ala Lys Val Ala Asp Phe Gly Leu Thr
                485                490                495

Lys Leu Thr Glu Ser Gly Val Gly Ser Phe Ser Leu Thr Val Pro Thr
                500                505                510

Arg Leu Val Gly Thr Phe Gly Tyr Met Ser Pro Glu Tyr Ala Arg Phe
                515                520                525

Gly Asp Val Ser Pro Lys Val Asp Val Tyr Ser Phe Gly Val Val Leu
    530                535                540

Phe Glu Ile Ile Ser Ala Lys Glu Ala Ile Val Arg Ile Ser Gly Thr
545                550                555                560

Ser Ala Asp Gly Ala Gly Gln His Lys Glu Glu Gln Arg Gly Leu Val
                565                570                575

Thr Leu Phe Asp Glu Ile Val Ser Asp Pro Asp Gly Lys Glu Lys Leu
                580                585                590

Arg Arg Leu Val Asp Pro Ala Leu Gly Asp Asn Tyr Pro Leu Glu Ser
    595                600                605

Ala Trp Lys Met Ala Gln Leu Ala Gly Ala Cys Thr Lys Glu Asn Pro
    610                615                620

Glu Leu Arg Pro Ser Met Arg Thr Ala Val Val Ala Leu Met Thr Leu
625                630                635                640

Ser Ser Thr Thr Gln Asp Trp Glu Met His Ala Tyr Gly Ser Glu Arg
                645                650                655

Ile Thr Pro Gly Leu Ile Ser Gly Arg
                660                665

<210> SEQ ID NO 268
<211> LENGTH: 663
<212> TYPE: PRT
<213> ORGANISM: Artificial Sequence
<220> FEATURE:
<223> OTHER INFORMATION: Synthetic Construct

<400> SEQUENCE: 268

Met Ile Ala Thr Gly Val Ile Thr Arg Arg Ser Pro Trp Val Ser Ser
```

-continued

```
1                5                    10                   15
Val Met Val Val Leu Val Leu Ala Ala Ala Ser Ala Trp Ile Pro Thr
                20                   25                   30

Ser Glu Gly Asp Cys Leu Pro Arg Leu Gly Cys Ser Arg Ala Leu Ala
                35                   40                   45

Tyr Tyr Lys Leu Val Pro Gly Val Phe Ile Leu Gln Asn Ile Thr Thr
                50                   55                   60

Phe Phe Met Thr Asn Val Ala Glu Leu Gln Lys Leu Asn Asp Ile Asn
65                   70                   75                   80

Ile Gln Ser Phe Gly Thr Val Leu Phe Phe Pro Tyr Thr Cys Glu Cys
                85                   90                   95

Ile Asp Asp Arg Leu Gly His Glu Phe Leu Tyr Gln Val Ala Leu Asp
                100                  105                  110

Asp Thr Val Ala Gln Ile Ala Gln Ile Lys Tyr Gln Phe Leu Ser Arg
                115                  120                  125

Glu Ala Trp Ile Thr Gln Ala Ser Lys Leu Ser Ser Val Gly Thr Ile
                130                  135                  140

Tyr Pro Gly Leu Thr Val Thr Val Pro Val Asn Cys Ser Cys Gly Asp
145                  150                  155                  160

Pro Ser Val Ser Pro Asp Tyr Gly Leu Phe Leu Thr Tyr Pro Ile Arg
                165                  170                  175

Ser Gly Asp Asn Phe Thr Gly Ile Ala Gln Gln Phe Gln Ala Asn Glu
                180                  185                  190

Thr Leu Leu Gln Gln Tyr Asn Pro Ser Ile Asn Trp Ser Asn Leu Ser
                195                  200                  205

Pro Ser Thr Asp Ile Ile Phe Ile Pro Gln Arg Val Phe Ala Thr Gly
                210                  215                  220

Ala Tyr Pro Ala Phe Asn Phe Ser Ala Asp Val Ser Glu Gly Gly Ser
225                  230                  235                  240

Lys Thr Asn Ala Gly Leu Ile Ala Gly Val Ser Val Gly Gly Ala Leu
                245                  250                  255

Ala Leu Val Leu Ala Val Val Leu Phe Phe Leu Phe Cys Val Tyr Trp
                260                  265                  270

Pro Arg Gln Arg His Ser Asp Pro Ser Asn Lys Ala Ala Met Glu Ser
                275                  280                  285

Leu Arg Leu Asp Gly Ser Gln Ser Gly Asp Arg Arg Ser Ala Leu Leu
                290                  295                  300

Lys Phe Ser Gln Glu Gly Ala Gly His Ser Arg Ser Ser Thr Gly Ser
305                  310                  315                  320

Gly Ile Pro Val Gly Pro Ile Pro Leu Thr Asp Phe Thr Val Asp Lys
                325                  330                  335

Ser Val Glu Phe Ser Phe Glu Glu Leu Glu Ala Ala Thr Asn Lys Phe
                340                  345                  350

Ser Ala Ala Asn Lys Ile Gly Glu Gly Gly Tyr Gly Ala Val Tyr Phe
                355                  360                  365

Ala Asn Leu Arg Gly Met Lys Leu Ala Val Lys Arg Met Asn Leu Gln
                370                  375                  380

Ala Thr Arg Glu Phe Leu Ala Glu Leu Gln Val Leu Thr His Val His
385                  390                  395                  400

His Thr Asn Leu Val Gln Leu Ile Gly Tyr Cys Thr Val Asp Ser Leu
                405                  410                  415

Phe Leu Ile Tyr Glu Tyr Val Asp Asn Gly Thr Leu Asp Arg His Leu
                420                  425                  430
```

-continued

```
His Gly Lys Asn Asp Leu Ala Pro Leu Ser Trp Ser Ser Arg Val Gln
        435                 440                 445

Ile Ala Leu Asp Ala Ala Arg Gly Leu Glu Tyr Ile His Glu His Thr
        450                 455                 460

Lys Pro Thr Tyr Ile His Arg Asp Val Lys Ser Ser Asn Ile Leu Ile
465                 470                 475                 480

Asp Lys Gln Phe His Ala Lys Val Ala Asp Phe Gly Leu Thr Lys Leu
                485                 490                 495

Thr Glu Ser Gly Val Gly Ser Phe Ser Leu Thr Val Pro Thr Arg Leu
                500                 505                 510

Val Gly Thr Phe Gly Tyr Met Ser Pro Glu Tyr Ala Arg Phe Gly Asp
        515                 520                 525

Val Ser Pro Lys Val Asp Val Tyr Ser Phe Gly Val Val Leu Phe Glu
        530                 535                 540

Ile Ile Ser Ala Lys Glu Ala Ile Val Arg Ile Ser Gly Thr Ser Ala
545                 550                 555                 560

Asp Gly Ala Gly Gln His Lys Glu Glu Gln Arg Gly Leu Val Thr Leu
                565                 570                 575

Phe Asp Glu Ile Val Ser Asp Pro Asp Gly Lys Glu Lys Leu Arg Arg
                580                 585                 590

Leu Val Asp Pro Ala Leu Gly Asp Asn Tyr Pro Leu Glu Ser Ala Trp
        595                 600                 605

Lys Met Ala Gln Leu Ala Gly Ala Cys Thr Lys Glu Asn Pro Glu Leu
        610                 615                 620

Arg Pro Ser Met Arg Thr Ala Val Val Ala Leu Met Thr Leu Ser Ser
625                 630                 635                 640

Thr Thr Gln Asp Trp Glu Met His Ala Tyr Gly Ser Glu Arg Ile Thr
                645                 650                 655

Pro Gly Leu Ile Ser Gly Arg
                660
```

```
<210> SEQ ID NO 269
<211> LENGTH: 670
<212> TYPE: PRT
<213> ORGANISM: Artificial Sequence
<220> FEATURE:
<223> OTHER INFORMATION: Synthetic Construct

<400> SEQUENCE: 269
```

```
Met Ile Ala Thr Gly Val Ile Thr Arg Arg Ser Pro Trp Val Ser Ser
1               5                   10                  15

Val Met Val Val Leu Val Leu Ala Ala Ala Ser Ala Trp Ile Pro Thr
                20                  25                  30

Ser Glu Gly Asp Cys Leu Lys Gly Cys Asp Leu Ala Leu Ala Ser Tyr
        35                  40                  45

Tyr Ile Leu Pro Gly Val Phe Ile Leu Gln Asn Ile Thr Thr Phe Met
        50                  55                  60

Gln Ser Glu Ile Val Ser Ser Asn Asp Ala Ile Thr Ser Tyr Asn Lys
65                  70                  75                  80

Asp Lys Ile Leu Asn Asp Ile Asn Ile Gln Ser Phe Gln Arg Leu Asn
                85                  90                  95

Ile Pro Phe Pro Cys Glu Cys Ile Asp Asp Arg Leu Gly His Glu Phe
                100                 105                 110

Leu Tyr Gln Val Ala Leu Asp Asp Thr Val Ala Gln Ile Ala Gln Ile
        115                 120                 125
```

```
Lys Tyr Gln Phe Leu Ser Arg Glu Ala Trp Ile Thr Gln Ala Ser Lys
    130                 135                 140

Leu Ser Ser Val Gly Thr Ile Tyr Pro Gly Leu Thr Val Thr Val Pro
145                 150                 155                 160

Val Asn Cys Ser Cys Gly Asp Pro Ser Val Ser Pro Asp Tyr Gly Leu
                165                 170                 175

Phe Leu Thr Tyr Pro Ile Arg Ser Gly Asp Asn Phe Thr Gly Ile Ala
                180                 185                 190

Gln Gln Phe Gln Ala Asn Glu Thr Leu Leu Gln Gln Tyr Asn Pro Ser
                195                 200                 205

Ile Asn Trp Ser Asn Leu Ser Pro Ser Thr Asp Ile Ile Phe Ile Pro
    210                 215                 220

Gln Arg Val Phe Ala Thr Gly Ala Tyr Pro Ala Phe Asn Phe Ser Ala
225                 230                 235                 240

Asp Val Ser Glu Gly Gly Ser Lys Thr Asn Ala Gly Leu Ile Ala Gly
                245                 250                 255

Val Ser Val Gly Gly Ala Leu Ala Leu Val Leu Ala Val Val Leu Phe
                260                 265                 270

Phe Leu Phe Cys Val Tyr Trp Pro Arg Gln Arg His Ser Asp Pro Ser
    275                 280                 285

Asn Lys Ala Ala Met Glu Ser Leu Arg Leu Asp Gly Ser Gln Ser Gly
    290                 295                 300

Asp Arg Arg Ser Ala Leu Leu Lys Phe Ser Gln Glu Gly Ala Gly His
305                 310                 315                 320

Ser Arg Ser Ser Thr Gly Ser Gly Ile Pro Val Gly Pro Ile Pro Leu
                325                 330                 335

Thr Asp Phe Thr Val Asp Lys Ser Val Glu Phe Ser Phe Glu Glu Leu
                340                 345                 350

Glu Ala Ala Thr Asn Lys Phe Ser Ala Ala Asn Lys Ile Gly Glu Gly
    355                 360                 365

Gly Tyr Gly Ala Val Tyr Phe Ala Asn Leu Arg Gly Met Lys Leu Ala
    370                 375                 380

Val Lys Arg Met Asn Leu Gln Ala Thr Arg Glu Phe Leu Ala Glu Leu
385                 390                 395                 400

Gln Val Leu Thr His Val His His Thr Asn Leu Val Gln Leu Ile Gly
                405                 410                 415

Tyr Cys Thr Val Asp Ser Leu Phe Leu Ile Tyr Glu Tyr Val Asp Asn
                420                 425                 430

Gly Thr Leu Asp Arg His Leu His Gly Lys Asn Asp Leu Ala Pro Leu
    435                 440                 445

Ser Trp Ser Ser Arg Val Gln Ile Ala Leu Asp Ala Ala Arg Gly Leu
    450                 455                 460

Glu Tyr Ile His Glu His Thr Lys Pro Thr Tyr Ile His Arg Asp Val
465                 470                 475                 480

Lys Ser Ser Asn Ile Leu Ile Asp Lys Gln Phe His Ala Lys Val Ala
                485                 490                 495

Asp Phe Gly Leu Thr Lys Leu Thr Glu Ser Gly Val Gly Ser Phe Ser
                500                 505                 510

Leu Thr Val Pro Thr Arg Leu Val Gly Thr Phe Gly Tyr Met Ser Pro
                515                 520                 525

Glu Tyr Ala Arg Phe Gly Asp Val Ser Pro Lys Val Asp Val Tyr Ser
    530                 535                 540
```

-continued

```
Phe Gly Val Val Leu Phe Glu Ile Ile Ser Ala Lys Glu Ala Ile Val
545                 550                 555                 560

Arg Ile Ser Gly Thr Ser Ala Asp Gly Ala Gly Gln His Lys Glu Glu
                565                 570                 575

Gln Arg Gly Leu Val Thr Leu Phe Asp Glu Ile Val Ser Asp Pro Asp
                580                 585                 590

Gly Lys Glu Lys Leu Arg Arg Leu Val Asp Pro Ala Leu Gly Asp Asn
                595                 600                 605

Tyr Pro Leu Glu Ser Ala Trp Lys Met Ala Gln Leu Ala Gly Ala Cys
        610                 615                 620

Thr Lys Glu Asn Pro Glu Leu Arg Pro Ser Met Arg Thr Ala Val Val
625                 630                 635                 640

Ala Leu Met Thr Leu Ser Ser Thr Thr Gln Asp Trp Glu Met His Ala
                645                 650                 655

Tyr Gly Ser Glu Arg Ile Thr Pro Gly Leu Ile Ser Gly Arg
                660                 665                 670
```

<210> SEQ ID NO 270
<211> LENGTH: 621
<212> TYPE: PRT
<213> ORGANISM: Artificial Sequence
<220> FEATURE:
<223> OTHER INFORMATION: Synthetic Construct

<400> SEQUENCE: 270

```
Met Glu His Gln Pro Arg Phe Thr Ser Phe Ile Ser Leu Pro Leu Phe
1                   5                   10                  15

Ser Ile Phe Leu Ala Ser Ile Pro Phe Ile Thr Glu Ser Lys Cys Thr
                20                  25                  30

His Gly Cys Ala Leu Ala Gln Ala Ser Tyr Tyr Leu Leu Asn Gly Ser
            35                  40                  45

Asn Leu Thr Tyr Ile Ser Glu Ile Met Gln Ser Ser Leu Leu Thr Lys
        50                  55                  60

Pro Glu Asp Ile Val Ser Tyr Asn Gln Asp Thr Ile Ala Ser Lys Asp
65                  70                  75                  80

Ser Val Gln Ala Gly Gln Arg Ile Asn Val Pro Phe Pro Cys Asp Cys
                85                  90                  95

Ile Asp Gly Gln Phe Leu Gly His Lys Phe Ser Tyr Asp Val Glu Thr
                100                 105                 110

Gly Asp Thr Tyr Glu Thr Val Ala Thr Asn Asn Tyr Ala Asn Leu Thr
            115                 120                 125

Asn Val Glu Trp Leu Arg Arg Phe Asn Thr Tyr Pro Pro Asn Asp Ile
        130                 135                 140

Pro Asp Thr Gly Thr Leu Asn Val Thr Val Asn Cys Ser Cys Gly Asp
145                 150                 155                 160

Ala Asp Val Gly Asn Tyr Ala Leu Phe Val Thr Tyr Pro Leu Arg Pro
                165                 170                 175

Gly Glu Thr Leu Val Ser Val Ala Asn Ser Ser Lys Val Asp Ser Ser
            180                 185                 190

Leu Leu Gln Arg Tyr Asn Pro Gly Val Asn Phe Asn Gln Gly Ser Gly
        195                 200                 205

Ile Val Phe Val Pro Gly Lys Asp Gln Asn Gly Ser Phe Val Phe Leu
        210                 215                 220

Gly Ser Ser Ser Gly Leu Gly Gly Gly Ala Ile Gly Gly Ile Ala Val
225                 230                 235                 240
```

```
Gly Ile Val Val Val Leu Leu Leu Val Ala Ala Ala Ile Tyr Phe Gly
                245                 250                 255

Tyr Phe Arg Lys Lys Lys Ile Gln Lys Glu Glu Leu Phe Ser Arg Asp
            260                 265                 270

Ser Thr Ala Leu Phe Ser Gln Asp Gly Lys Asp Glu Asn Ser His Gly
            275                 280                 285

Ala Ala Asn Val Thr Gln Arg Pro Gly Val Met Thr Gly Ile Thr Val
        290                 295                 300

Asp Lys Ser Val Glu Phe Ser Tyr Asp Glu Leu Ala Ala Ala Ser Asp
305                 310                 315                 320

Asn Phe Ser Met Ala Asn Lys Ile Gly Gln Gly Gly Phe Gly Ser Val
                325                 330                 335

Tyr Tyr Ala Glu Leu Arg Gly Glu Lys Ala Ala Ile Lys Lys Met Asp
                340                 345                 350

Met Gln Ala Thr Lys Glu Phe Leu Ala Glu Leu Lys Val Leu Thr Arg
                355                 360                 365

Val His His Leu Asn Leu Val Arg Leu Ile Gly Tyr Ser Ile Glu Gly
        370                 375                 380

Ser Leu Phe Leu Val Tyr Glu Tyr Ile Glu Asn Gly Asn Leu Ser Gln
385                 390                 395                 400

His Leu Arg Gly Ser Gly Arg Asp Pro Leu Pro Trp Ala Thr Arg Val
                405                 410                 415

Gln Ile Ala Leu Asp Ser Ala Arg Gly Leu Glu Tyr Ile His Glu His
                420                 425                 430

Thr Val Pro Val Tyr Ile His Arg Asp Ile Lys Pro Ala Asn Ile Leu
                435                 440                 445

Ile Asp Lys Asn Phe Arg Gly Lys Val Ala Asp Phe Gly Leu Thr Lys
        450                 455                 460

Leu Thr Glu Val Gly Ser Ser Ser Leu Pro Thr Gly Arg Leu Val Gly
465                 470                 475                 480

Thr Phe Gly Tyr Met Pro Pro Glu Tyr Ala Gln Tyr Gly Asp Val Ser
                485                 490                 495

Pro Lys Val Asp Val Tyr Ala Phe Gly Val Val Leu Tyr Glu Leu Ile
                500                 505                 510

Ser Ala Lys Glu Ala Ile Val Lys Ser Ser Glu Ser Val Ala Asp Ser
            515                 520                 525

Lys Gly Leu Val Gly Leu Phe Glu Gly Val Leu Ser Gln Pro Asp Pro
        530                 535                 540

Thr Glu Asp Leu Arg Lys Ile Val Asp Pro Arg Leu Gly Asp Asn Tyr
545                 550                 555                 560

Pro Ala Asp Ser Val Arg Lys Met Ala Gln Leu Ala Lys Ala Cys Thr
                565                 570                 575

Gln Glu Asn Pro Gln Leu Arg Pro Ser Met Arg Ser Ile Val Val Ala
                580                 585                 590

Leu Met Thr Leu Ser Ser Thr Thr Asp Asp Trp Asp Val Gly Ser Phe
                595                 600                 605

Tyr Glu Asn Gln Asn Leu Val Asn Leu Met Ser Gly Arg
    610                 615                 620
```

<210> SEQ ID NO 271
<211> LENGTH: 134
<212> TYPE: PRT
<213> ORGANISM: Medicago truncatula

<400> SEQUENCE: 271

-continued

```
Ser Glu Thr Asn Phe Thr Cys Pro Val Asp Ser Pro Pro Ser Cys Glu
1               5                   10                  15

Thr Tyr Val Ala Tyr Arg Ala Gln Ser Pro Asn Phe Leu Ser Leu Ser
            20                  25                  30

Asn Ile Ser Asp Ile Phe Asn Leu Ser Pro Leu Arg Ile Ala Lys Ala
        35                  40                  45

Ser Asn Ile Glu Ala Glu Asp Lys Lys Leu Ile Pro Asp Gln Leu Leu
    50                  55                  60

Leu Val Pro Val Thr Cys Gly Cys Thr Lys Asn His Ser Phe Ala Asn
65                  70                  75                  80

Ile Thr Tyr Ser Ile Lys Gln Gly Asp Asn Phe Phe Ile Leu Ser Ile
                85                  90                  95

Thr Ser Tyr Gln Asn Leu Thr Asn Tyr Leu Glu Phe Lys Asn Phe Asn
            100                 105                 110

Pro Asn Leu Ser Pro Thr Leu Leu Pro Leu Asp Thr Lys Val Ser Val
        115                 120                 125

Pro Leu Phe Cys Lys Cys
    130
```

<210> SEQ ID NO 272
<211> LENGTH: 134
<212> TYPE: PRT
<213> ORGANISM: Lotus japonicus

<400> SEQUENCE: 272

```
Ser Gly Pro Asp Phe Ser Cys Pro Val Asp Ser Pro Pro Ser Cys Glu
1               5                   10                  15

Thr Tyr Val Thr Tyr Thr Ala Gln Ser Pro Asn Leu Leu Ser Leu Thr
            20                  25                  30

Asn Ile Ser Asp Ile Phe Asp Ile Ser Pro Leu Ser Ile Ala Arg Ala
        35                  40                  45

Ser Asn Ile Asp Ala Gly Lys Asp Lys Leu Val Pro Gly Gln Val Leu
    50                  55                  60

Leu Val Pro Val Thr Cys Gly Cys Ala Gly Asn His Ser Ser Ala Asn
65                  70                  75                  80

Thr Ser Tyr Gln Ile Gln Leu Gly Asp Ser Tyr Asp Phe Val Ala Thr
            85                  90                  95

Thr Leu Tyr Glu Asn Leu Thr Asn Trp Asn Ile Val Gln Ala Ser Asn
            100                 105                 110

Pro Gly Val Asn Pro Tyr Leu Leu Pro Glu Arg Val Lys Val Val Phe
        115                 120                 125

Pro Leu Phe Cys Arg Cys
    130
```

<210> SEQ ID NO 273
<211> LENGTH: 134
<212> TYPE: PRT
<213> ORGANISM: Pisum sativum

<400> SEQUENCE: 273

```
Ser Gly Thr Asn Phe Ser Cys Pro Val Asp Ser Pro Pro Ser Cys Glu
1               5                   10                  15

Thr Tyr Val Thr Tyr Phe Ala Arg Ser Pro Asn Phe Leu Ser Leu Thr
            20                  25                  30

Asn Ile Ser Asp Ile Phe Asp Met Ser Pro Leu Ser Ile Ala Lys Ala
        35                  40                  45
```

Ser Asn Ile Glu Asp Glu Asp Lys Lys Leu Val Glu Gly Gln Val Leu
    50                  55                  60

Leu Ile Pro Val Thr Cys Gly Cys Thr Arg Asn Arg Tyr Phe Ala Asn
65                  70                  75                  80

Phe Thr Tyr Thr Ile Lys Leu Gly Asp Asn Tyr Phe Ile Val Ser Thr
                85                  90                  95

Thr Ser Tyr Gln Asn Leu Thr Asn Tyr Val Glu Met Glu Asn Phe Asn
                100                 105                 110

Pro Asn Leu Ser Pro Asn Leu Leu Pro Pro Glu Ile Lys Val Val Val
        115                 120                 125

Pro Leu Phe Cys Lys Cys
    130

<210> SEQ ID NO 274
<211> LENGTH: 138
<212> TYPE: PRT
<213> ORGANISM: Glycine max

<400> SEQUENCE: 274

Ser Gln Gln Asp Asn Arg Thr Asn Phe Ser Cys Pro Ser Asp Ser Pro
1                   5                   10                  15

Pro Ser Cys Glu Thr Tyr Val Thr Tyr Ile Ala Gln Ser Pro Asn Phe
                20                  25                  30

Leu Ser Leu Thr Asn Ile Ser Asn Ile Phe Asp Thr Ser Pro Leu Ser
        35                  40                  45

Ile Ala Arg Ala Ser Asn Leu Glu Pro Met Asp Lys Leu Val Lys
    50                  55                  60

Asp Gln Val Leu Leu Val Pro Val Thr Cys Gly Cys Thr Gly Asn Arg
65                  70                  75                  80

Ser Phe Ala Asn Ile Ser Tyr Glu Ile Asn Gln Gly Asp Ser Phe Tyr
                85                  90                  95

Phe Val Ala Thr Thr Ser Tyr Glu Asn Leu Thr Asn Trp Arg Ala Val
                100                 105                 110

Met Asp Leu Asn Pro Val Leu Ser Pro Asn Lys Leu Pro Ile Gly Ile
        115                 120                 125

Gln Val Val Phe Pro Leu Phe Cys Lys Cys
    130                 135

<210> SEQ ID NO 275
<211> LENGTH: 65
<212> TYPE: PRT
<213> ORGANISM: Arachis hypogaea subsp. hypogaea

<400> SEQUENCE: 275

Cys Gly Cys Thr Gln Asn Gln Ser Phe Ala Asn Ile Thr Tyr Glu Leu
1                   5                   10                  15

Arg Gln Gly Asp Val Tyr Asp Ile Val Ser Lys Thr Thr Tyr Glu Asn
                20                  25                  30

Leu Thr Asn Trp Arg Ala Val Asn Asn Ser Asn Pro Asp Leu Asn Pro
        35                  40                  45

Val Leu Leu Pro Ile Gly Val Lys Val Leu Phe Pro Leu Phe Cys Arg
    50                  55                  60

Cys
65

<210> SEQ ID NO 276

<211> LENGTH: 65
<212> TYPE: PRT
<213> ORGANISM: Parasponia andersonii

<400> SEQUENCE: 276

Cys Ser Cys Asn Gly Ser His Tyr Phe Ser Asn Val Thr Tyr Asn Ile
1               5                   10                  15

Thr Met Gly Asp Ser Tyr Tyr Leu Val Ser Ile His Ser Phe Glu Asn
            20                  25                  30

Leu Thr Asn Trp Pro Leu Val Arg Asp Thr Asn Pro Thr Leu Asn Pro
        35                  40                  45

Asn Leu Leu Gln Ile Gly Thr Lys Val Ile Phe Pro Leu Tyr Cys Gly
    50                  55                  60

Cys
65

<210> SEQ ID NO 277
<211> LENGTH: 65
<212> TYPE: PRT
<213> ORGANISM: Parasponia andersonii

<400> SEQUENCE: 277

Cys Thr Cys Thr Gly Asn His Tyr Phe Ala Asn Ile Thr Tyr Gln Val
1               5                   10                  15

Glu Pro Gly Asp Thr Tyr His Tyr Leu Ser Thr Leu Leu Phe Glu Asn
            20                  25                  30

Leu Thr Asn Ser Gln Val Met Lys Lys Met Asn Pro Glu Ile Ser Pro
        35                  40                  45

Glu Tyr Val Leu Pro Tyr Ile Asp Ile Ile Ile Pro Val Phe Cys Arg
    50                  55                  60

Cys
65

<210> SEQ ID NO 278
<211> LENGTH: 62
<212> TYPE: PRT
<213> ORGANISM: Lotus japonicus

<400> SEQUENCE: 278

Asp Cys Ile Glu Gly Glu Phe Leu Gly His Thr Phe Gln Tyr Asp Val
1               5                   10                  15

Gln Lys Gly Asp Arg Tyr Asp Thr Ile Ala Gly Thr Asn Tyr Ala Asn
            20                  25                  30

Leu Thr Thr Val Glu Trp Leu Arg Arg Phe Asn Ser Tyr Pro Pro Asp
        35                  40                  45

Asn Ile Pro Asp Thr Gly Thr Leu Asn Val Thr Val Asn Cys
    50                  55                  60

<210> SEQ ID NO 279
<211> LENGTH: 62
<212> TYPE: PRT
<213> ORGANISM: Phaseolus vulgaris

<400> SEQUENCE: 279

Asp Cys Ile Asp Gly Gln Phe Leu Ala His Thr Phe Lys Tyr Asp Val
1               5                   10                  15

Gln Ser Gln Asp Ser Tyr Glu Tyr Val Ala Arg Thr Val Tyr Ser Asn
            20                  25                  30

Leu Thr Asp Val Ala Trp Leu Arg Asn Phe Asn Ser Tyr Glu Pro Asp

```
           35                40                45

Asn Ile Pro Asp Thr Ala Thr Leu Asn Val Thr Val Asn Cys
   50                55                60

<210> SEQ ID NO 280
<211> LENGTH: 62
<212> TYPE: PRT
<213> ORGANISM: Arachis ipaensis

<400> SEQUENCE: 280

Asp Cys Ile Asn Gly Glu Phe Leu Gly His Thr Phe Lys Tyr Asp Ile
1               5                10                15

Gln Ser Gly Asp Thr Tyr Glu His Val Ala Thr Asn Asn Tyr Ala Asn
           20                25                30

Leu Thr Asn Val Asn Trp Leu Arg Lys Phe Asn Thr Tyr Pro Pro Asn
       35                40                45

Asn Ile Pro Asn Thr Gly Thr Leu Asn Val Thr Val Asn Cys
   50                55                60

<210> SEQ ID NO 281
<211> LENGTH: 62
<212> TYPE: PRT
<213> ORGANISM: Arachis duranensis

<400> SEQUENCE: 281

Asp Cys Ile Asn Gly Glu Phe Leu Gly His Thr Phe Gln Tyr Asp Ile
1               5                10                15

Gln Ser Gly Asp Thr Tyr Glu His Val Ala Thr Asn Asn Tyr Ala Asn
           20                25                30

Leu Thr Asn Val Asn Trp Leu Arg Lys Phe Asn Ser Tyr Pro Pro Asn
       35                40                45

Asn Ile Pro Asp Thr Gly Thr Leu Asn Val Thr Val Asn Cys
   50                55                60

<210> SEQ ID NO 282
<211> LENGTH: 62
<212> TYPE: PRT
<213> ORGANISM: Cajanus cajan

<400> SEQUENCE: 282

Asp Cys Val Asp Gln Gln Phe Leu Ala His Thr Phe Gln Tyr Asp Val
1               5                10                15

Gln Ser Gln Asp Thr Tyr Asp Tyr Val Ala Arg Thr Val Phe Ala Asn
           20                25                30

Leu Thr Asp Val Ala Trp Leu Arg Arg Phe Asn Ser Tyr Ala Pro Asp
       35                40                45

Asn Ile Pro Asp Thr Gly Thr Leu Asn Val Thr Val Asn Cys
   50                55                60

<210> SEQ ID NO 283
<211> LENGTH: 62
<212> TYPE: PRT
<213> ORGANISM: Cicer arietinum

<400> SEQUENCE: 283

Asp Cys Ile Ala Gly Glu Phe Leu Ala His Thr Phe Ser Tyr Asp Val
1               5                10                15

Gln Thr Gly Asp Thr Tyr Glu Thr Val Ala Thr Asn Asn Tyr Ala Asn
           20                25                30
```

-continued

```
Leu Thr Asn Val Gln Trp Leu Gln Arg Phe Asn Ser Tyr Pro Ala Asn
        35              40              45

Asn Ile Pro Asp Thr Gly Thr Leu Asn Val Thr Val Asn Cys
    50              55              60

<210> SEQ ID NO 284
<211> LENGTH: 62
<212> TYPE: PRT
<213> ORGANISM: Abrus precatorius

<400> SEQUENCE: 284

Asp Cys Ile Asn Gly Glu Phe Leu Gly Tyr Thr Phe Lys Tyr Asp Val
1               5              10              15

Gln Thr Gly Asp Thr Tyr Glu Thr Val Ala Gly Thr Asn Tyr Ala Asn
            20              25              30

Leu Thr Asn Val Ala Trp Leu Arg Arg Phe Asn Ser Tyr Pro Pro Asn
        35              40              45

Asn Ile Pro Asp Thr Gly Thr Leu Asn Val Thr Val Asn Cys
    50              55              60

<210> SEQ ID NO 285
<211> LENGTH: 62
<212> TYPE: PRT
<213> ORGANISM: Medicago truncatula

<400> SEQUENCE: 285

Asp Cys Ile Asp Gly Gln Phe Leu Gly His Lys Phe Ser Tyr Asp Val
1               5              10              15

Glu Thr Gly Asp Thr Tyr Glu Thr Val Ala Thr Asn Asn Tyr Ala Asn
            20              25              30

Leu Thr Asn Val Glu Trp Leu Arg Arg Phe Asn Thr Tyr Pro Pro Asn
        35              40              45

Asp Ile Pro Asp Thr Gly Thr Leu Asn Val Thr Val Asn Cys
    50              55              60

<210> SEQ ID NO 286
<211> LENGTH: 62
<212> TYPE: PRT
<213> ORGANISM: Glycine max

<400> SEQUENCE: 286

Asp Cys Ile Asp Gly Gln Phe Leu Gly His Thr Phe Arg Tyr Asp Val
1               5              10              15

Gln Ser Gln Asp Thr Tyr Glu Thr Val Ala Arg Ser Trp Phe Ala Asn
            20              25              30

Leu Thr Asp Val Ala Trp Leu Arg Arg Phe Asn Thr Tyr Pro Pro Asp
        35              40              45

Asn Ile Pro Asp Thr Gly Thr Leu Asn Val Thr Val Asn Cys
    50              55              60

<210> SEQ ID NO 287
<211> LENGTH: 62
<212> TYPE: PRT
<213> ORGANISM: Glycine max

<400> SEQUENCE: 287

Asp Cys Ile Asp Glu Glu Phe Leu Gly His Thr Phe Gln Tyr Asn Leu
1               5              10              15

Thr Thr Gly Asp Thr Tyr Leu Ser Ile Ala Thr Gln Asn Tyr Ser Asn
            20              25              30
```

-continued

```
Leu Thr Thr Ala Glu Trp Leu Arg Ser Phe Asn Arg Tyr Leu Pro Ala
        35                  40                  45

Asn Ile Pro Asp Ser Gly Thr Leu Asn Val Thr Ile Asn Cys
    50                  55                  60

<210> SEQ ID NO 288
<211> LENGTH: 62
<212> TYPE: PRT
<213> ORGANISM: Lupinus angustifolius

<400> SEQUENCE: 288

Asp Cys Ile Asp Gly Glu Phe Leu Gly His Met Phe Gln Tyr Asp Val
1               5                   10                  15

Lys Thr Gly Asp Thr Tyr Gln Leu Val Ala Glu Thr Glu Tyr Ala Asn
            20                  25                  30

Leu Thr Asn Ile Asp Trp Leu Met Lys Phe Asn Ser Tyr Pro Ala Asn
        35                  40                  45

Asn Ile Pro Asp Thr Gly Thr Leu Asn Val Thr Val Asn Cys
    50                  55                  60

<210> SEQ ID NO 289
<211> LENGTH: 62
<212> TYPE: PRT
<213> ORGANISM: Lupinus angustifolius

<400> SEQUENCE: 289

Asp Cys Ile Lys Gly Glu Phe Leu Gly His Met Phe Gln Tyr Val Val
1               5                   10                  15

Gln Thr Gly Asp Thr Tyr Glu Thr Val Ala Gly Thr Asn Tyr Ala Asn
            20                  25                  30

Leu Thr Asn Val Glu Trp Leu Arg Arg Phe Asn Thr Tyr Leu Pro Asp
        35                  40                  45

Asn Ile Ser Ser Thr Gly Met Leu Asn Val Thr Val Asn Cys
    50                  55                  60

<210> SEQ ID NO 290
<211> LENGTH: 62
<212> TYPE: PRT
<213> ORGANISM: Vigna angularis

<400> SEQUENCE: 290

Asp Cys Ile Asp Gly Gln Phe Leu Gly His Thr Phe His Tyr Asp Val
1               5                   10                  15

Gln Thr Gln Asp Thr Tyr Glu Gln Val Ala Arg Thr Val Phe Ser Asn
            20                  25                  30

Leu Thr Asp Val Thr Trp Leu Arg Arg Phe Asn Ser Tyr Glu Pro Asp
        35                  40                  45

Asn Ile Pro Asp Thr Gly Thr Leu Asn Val Thr Val Asn Cys
    50                  55                  60

<210> SEQ ID NO 291
<211> LENGTH: 62
<212> TYPE: PRT
<213> ORGANISM: Vigna radiata

<400> SEQUENCE: 291

Asp Cys Ile Asp Gly Gln Phe Leu Ala His Thr Phe Gln Tyr Asp Val
1               5                   10                  15

Gln Thr Gln Asp Thr Tyr Glu Gln Val Ala Arg Val Val Phe Ser Asn
```

```
                20              25              30

Leu Thr Asp Val Thr Trp Leu Arg Arg Phe Asn Thr Tyr Glu Pro Asp
        35              40              45

Asn Ile Pro Asp Thr Gly Thr Leu Asn Val Thr Val Asn Cys
    50              55              60

<210> SEQ ID NO 292
<211> LENGTH: 62
<212> TYPE: PRT
<213> ORGANISM: Vigna unguiculata

<400> SEQUENCE: 292

Asp Cys Ile Asp Gly Gln Phe Leu Ala His Thr Phe Gln Tyr Asp Val
1               5               10              15

Gln Thr Gln Asp Thr Tyr Glu Tyr Val Ala Arg Thr Val Phe Ser Asn
                20              25              30

Leu Thr Asp Val Thr Trp Leu Arg Arg Phe Asn Ser Tyr Glu Pro Asn
        35              40              45

Asn Ile Pro Asp Thr Gly Thr Leu Asn Val Thr Val Asn Cys
    50              55              60

<210> SEQ ID NO 293
<211> LENGTH: 62
<212> TYPE: PRT
<213> ORGANISM: Arachis hypogaea

<400> SEQUENCE: 293

Asp Cys Ile Asn Gly Glu Phe Leu Gly His Thr Phe Gln Tyr Asp Ile
1               5               10              15

Gln Ser Gly Asp Thr Tyr Glu His Val Ala Thr Asn Asn Tyr Ala Asn
                20              25              30

Leu Thr Asn Val Asn Trp Leu Arg Lys Phe Asn Ser Tyr Pro Pro Asn
        35              40              45

Asn Ile Pro Asp Thr Gly Thr Leu Asn Val Thr Val Asn Cys
    50              55              60

<210> SEQ ID NO 294
<211> LENGTH: 62
<212> TYPE: PRT
<213> ORGANISM: Mimosa pudica

<400> SEQUENCE: 294

Asp Cys Ile Asn Gly Gln Phe Leu Gly His Met Phe Gln Tyr Asp Val
1               5               10              15

Ala Thr Gly Asp Thr Tyr Asp Lys Ile Ala Ser Thr Asp Phe Ala Asn
                20              25              30

Leu Thr Thr Val Glu Trp Leu Gln Lys Phe Asn Ser Tyr Ala Ala Asp
        35              40              45

Asn Ile Pro Asp Thr Ala Thr Leu Asn Val Thr Val Asn Cys
    50              55              60

<210> SEQ ID NO 295
<211> LENGTH: 62
<212> TYPE: PRT
<213> ORGANISM: Chamaecrista fasciculata

<400> SEQUENCE: 295

Asp Cys Ile Glu Asp Glu Phe Leu Gly Tyr Asn Phe Leu Tyr Asp Val
1               5               10              15
```

-continued

```
Gln Thr Gly Asp Thr Tyr Glu Arg Ile Ala Arg Thr Asn Phe Ala Asn
        20                  25                  30

Leu Thr Thr Val Asp Trp Leu Gln Lys Phe Asn Ser Tyr Pro Pro Asn
        35                  40                  45

Asn Ile Pro Asp Thr Gly Thr Leu Asn Val Thr Ile Asn Cys
    50                  55                  60
```

<210> SEQ ID NO 296
<211> LENGTH: 62
<212> TYPE: PRT
<213> ORGANISM: Lupinus albus

<400> SEQUENCE: 296

```
Asp Cys Ile Asn Gly Glu Phe Leu Gly His Met Phe Arg Tyr Asp Val
1               5                   10                  15

Lys Thr Asn Asp Thr Tyr Thr Ser Val Ala Glu Thr Glu Tyr Ala Asn
        20                  25                  30

Leu Thr Asn Val Asn Trp Leu Met Lys Phe Asn Asn Tyr Pro Ala Ser
        35                  40                  45

Asn Ile Pro Asp Thr Gly Thr Leu Asn Val Thr Val Asn Cys
    50                  55                  60
```

<210> SEQ ID NO 297
<211> LENGTH: 62
<212> TYPE: PRT
<213> ORGANISM: Pisum sativum

<400> SEQUENCE: 297

```
Asp Cys Ile Asn Gly Asp Phe Leu Ala His Asn Phe Ser Tyr Asp Val
1               5                   10                  15

Gln Thr Gly Asp Thr Tyr Ala Ser Val Ala Gly Ser Asn Tyr Ala Asn
        20                  25                  30

Leu Thr Asn Val Gln Trp Leu Arg Asn Phe Asn Thr Tyr Pro Pro Asn
        35                  40                  45

Ser Ile Pro Asp Thr Gly Thr Leu Asn Val Met Ile Asn Cys
    50                  55                  60
```

<210> SEQ ID NO 298
<211> LENGTH: 62
<212> TYPE: PRT
<213> ORGANISM: Arachis hypogaea

<400> SEQUENCE: 298

```
Asp Cys Ile Asn Gly Glu Phe Leu Gly His Thr Phe Lys Tyr Asp Ile
1               5                   10                  15

Gln Ser Gly Asp Thr Tyr Glu His Val Ala Thr Asn Asn Tyr Ala Asn
        20                  25                  30

Leu Thr Asn Val Asn Trp Leu Arg Lys Phe Asn Thr Tyr Pro Pro Asn
        35                  40                  45

Asn Ile Pro Asn Thr Gly Thr Leu Asn Val Thr Val Asn Cys
    50                  55                  60
```

<210> SEQ ID NO 299
<211> LENGTH: 62
<212> TYPE: PRT
<213> ORGANISM: Spatholobus suberectus

<400> SEQUENCE: 299

```
Asp Cys Leu Asn Gly Val Phe Leu Gly His Thr Phe Ser Phe Ala Thr
1               5                   10                  15
```

-continued

Gln His Gly Asp Thr Tyr Lys Val Ile Ala Glu Val Gly Phe Ser Asn
        20                  25                  30

Leu Thr Thr Glu Asp Trp Val Ser Arg Val Asn Arg Tyr Pro Pro Asn
        35                  40                  45

Gln Ile Pro Asp Asn Val Asn Ile Asn Val Thr Val Asn Cys
        50                  55                  60

<210> SEQ ID NO 300
<211> LENGTH: 62
<212> TYPE: PRT
<213> ORGANISM: Prosopis alba

<400> SEQUENCE: 300

Lys Cys Ile Asn Gly Glu Phe Leu Gly His Thr Phe Gln Tyr Val Val
1               5                   10                  15

Glu Thr Gly Asp Thr Tyr Glu Lys Val Ala Val Thr Asn Tyr Ala Asn
        20                  25                  30

Leu Thr Thr Val Asp Trp Leu Arg Lys Phe Asn Ser Tyr Pro Pro Asp
        35                  40                  45

Asn Ile Pro Asp Thr Gly Thr Leu Asn Val Thr Val Asn Cys
        50                  55                  60

<210> SEQ ID NO 301
<211> LENGTH: 599
<212> TYPE: PRT
<213> ORGANISM: Phaseolus vulgaris

<400> SEQUENCE: 301

Met Glu Leu Lys Lys Gly Leu Leu Leu Leu Phe Leu Leu Leu Glu Tyr
1               5                   10                  15

Val Cys Cys Asn Val Glu Ala Lys Cys Leu Lys Gly Cys Gly Ala Ala
        20                  25                  30

Leu Ala Ser Tyr Tyr Val Ser Pro Gly Ile Ser Thr Leu Asp Asp Ile
        35                  40                  45

Thr His Leu Met Lys Ser Ser Val Val Ser Asn Ser Asp Asp Ile Val
        50                  55                  60

Ser Tyr Asn Lys Asp Arg Ile Phe Asn Lys Asn Val Leu Phe Phe Tyr
65                  70                  75                  80

Arg Ile Asn Ile Pro Phe Pro Cys Glu Cys Ile Arg Asp Glu Phe Leu
                85                  90                  95

Gly His Val Phe Glu Tyr Ser Ala Ala Ala Gly Asp Thr Tyr Asp Ser
            100                 105                 110

Ile Ala Lys Val Thr Tyr Ala Asn Leu Thr Thr Val Glu Leu Leu Arg
        115                 120                 125

Arg Phe Asn Ser Tyr Gly Gln Asn Asp Ile Pro Thr Asn Ala Lys Val
        130                 135                 140

Asn Val Thr Val Asn Cys Ser Cys Gly Asn Ser Gln Val Ser Gln Asp
145                 150                 155                 160

Tyr Gly Leu Phe Ile Thr Tyr Pro Leu Arg Pro Gly Asn Asn Leu His
                165                 170                 175

Asp Ile Ala Asn Glu Thr Gln Leu Asp Ala Gln Leu Leu Gln Asn Tyr
            180                 185                 190

Asn Pro Gly Val Asn Phe Ser Gln Glu Ser Gly Ile Val Phe Ile Pro
        195                 200                 205

Gly Arg Gly Leu Ser Arg Gly Ala Ala Ala Gly Ile Ser Ile Ala Gly
        210                 215                 220

-continued

```
Ile Cys Gly Leu Leu Leu Leu Val Ile Cys Ile Tyr Ala Lys Phe Phe
225                 230                 235                 240

Gln Lys Lys Glu Gly Glu Lys Ser Lys Leu Pro Thr Met Val Phe Ser
                245                 250                 255

Thr Gln Tyr Ala Ser Gly Ser Ala Glu Tyr Glu Thr Ser Gly Ser Ser
                260                 265                 270

Gly Thr Ala Thr Ala Thr Gly Leu Thr Gly Ile Met Val Ala Lys Ser
            275                 280                 285

Met Glu Phe Thr Tyr Gln Glu Leu Ala Lys Ala Thr Asn Asn Phe Ser
        290                 295                 300

Leu Glu Asn Lys Ile Gly Gln Gly Gly Phe Gly Ala Val Tyr Tyr Ala
305                 310                 315                 320

Glu Leu Arg Gly Glu Lys Thr Ala Ile Lys Lys Met Asp Val Gln Ala
            325                 330                 335

Ser Thr Glu Phe Leu Cys Glu Leu Lys Val Leu Thr His Val His His
            340                 345                 350

Leu Asn Leu Val Arg Leu Ile Gly Tyr Cys Val Glu Gly Ser Leu Phe
            355                 360                 365

Leu Val Tyr Glu Tyr Ile Asp Asn Gly Asn Leu Gly Gln Tyr Leu His
        370                 375                 380

Gly Ile Gly Lys Asp Pro Leu Pro Trp Ser Ser Arg Val Gln Ile Ala
385                 390                 395                 400

Leu Asp Ser Ala Arg Gly Leu Glu Tyr Ile His Glu His Thr Val Pro
                405                 410                 415

Val Tyr Ile His Arg Asp Val Lys Ser Ala Asn Ile Leu Ile Asp Lys
            420                 425                 430

Asn Phe Arg Gly Lys Val Ala Asp Phe Gly Leu Thr Lys Leu Ile Glu
            435                 440                 445

Val Gly Gly Ser Thr Leu His Thr Arg Leu Val Gly Thr Phe Gly Tyr
        450                 455                 460

Met Pro Pro Glu Tyr Ala Gln Tyr Gly Asp Val Ser Pro Lys Val Asp
465                 470                 475                 480

Val Tyr Ala Phe Gly Val Val Leu Tyr Glu Leu Ile Ser Ala Lys Asn
                485                 490                 495

Ala Val Leu Lys Thr Gly Glu Tyr Val Ala Glu Ser Lys Gly Leu Val
            500                 505                 510

Ala Leu Phe Glu Glu Ala Leu Asn Gln Ser Asn Pro Ser Glu Val Ile
            515                 520                 525

Arg Lys Leu Val Asp Pro Arg Leu Gly Glu Asn Tyr Pro Ile Asp Ser
        530                 535                 540

Val Leu Lys Ile Ala Gln Leu Gly Arg Ala Cys Thr Arg Asp Asn Pro
545                 550                 555                 560

Leu Leu Arg Pro Ser Met Arg Ser Ile Val Val Ala Leu Met Thr Leu
                565                 570                 575

Ser Ser Pro Thr Glu Asp Leu Asp Asp Ser Tyr Glu Asn Gln Thr Leu
                580                 585                 590

Ile Asn Leu Leu Ser Val Arg
            595
```

```
<210> SEQ ID NO 302
<211> LENGTH: 633
<212> TYPE: PRT
<213> ORGANISM: Arachis hypogaea
```

<400> SEQUENCE: 302

```
Met Lys Leu Lys Lys Ser Phe Leu Leu Phe Phe Leu Leu Leu Glu Cys
1               5                   10                  15

Ser Cys Phe Ile Asn Leu Glu Ser Lys Cys Leu Lys Gly Cys Asp Leu
            20                  25                  30

Ala Ile Ala Ser Tyr Phe Val Tyr Pro Lys Val Met Leu Gly Ser Ile
            35                  40                  45

Ala Ser Phe Met His Ser Asn Val Val Pro Asn Ser Asn Val Ile Ile
        50                  55                  60

Ser Tyr Asn Lys Asp Lys Met Pro Asn Asn Leu Pro Val Ser Phe Thr
65                  70                  75                  80

Arg Ile Asn Ile Pro Phe Pro Cys Asp Cys Ile Asn Gly Glu Phe Leu
                85                  90                  95

Gly His Val Phe Glu Tyr Ser Ala Ile Glu Gly Asp Thr Tyr Asp Leu
            100                 105                 110

Ile Ala Asn Met Arg Tyr Ser Asp Leu Thr Thr Val Glu Ile Leu Gln
            115                 120                 125

Arg Phe Asn Asn Tyr Asp Pro Asn His Val Pro Val Asn Ala Lys Val
        130                 135                 140

Asn Val Thr Val Asn Cys Ser Cys Gly Asn Ser Asn Val Ser Lys Asp
145                 150                 155                 160

Tyr Gly Leu Phe Val Thr Phe Pro Leu Ser Glu Gly Asn Thr Leu Leu
                165                 170                 175

Gln Ile Ala Asn Gln Thr Lys Leu Asp Pro Lys Leu Leu Gln Gly Tyr
            180                 185                 190

Asn Pro Gly Val Asn Phe Asn Gln Thr Arg Gly Ile Val Phe Ile Pro
            195                 200                 205

Gly Arg Asp Gln Asn Gly Val Tyr Val Pro Leu Tyr Pro Arg Leu Ala
        210                 215                 220

Gly Leu Ala Lys Gly Val Ala Val Gly Ile Ser Ile Ala Gly Thr Ser
225                 230                 235                 240

Gly Val Leu Leu Leu Leu Ile Cys Ala Cys Val Arg Tyr Phe Gln Lys
                245                 250                 255

Lys Glu Glu Glu Lys Ile Lys Leu Pro Thr Glu Asp Phe Ile Ser Ser
            260                 265                 270

Ser Thr Gln Val Gly Asn Ala Ser Ser Ser Gly Glu Tyr Glu Thr Ser
            275                 280                 285

Gly Ser Thr Ala Ala Ser Ala Ser Gly Leu Pro Ala Ile Met Ala Ala
        290                 295                 300

Lys Ser Met Glu Phe Ser Tyr Gln Glu Leu Ala Lys Ala Thr Asn Asn
305                 310                 315                 320

Phe Ser Ser Asp Asn Lys Ile Gly Gln Gly Gly Phe Gly Ala Val Tyr
                325                 330                 335

Phe Ala Glu Leu Arg Gly Gln Lys Ala Ala Ile Lys Lys Met Asp Val
            340                 345                 350

Gln Ala Ser Thr Glu Phe Leu Ser Glu Leu Lys Val Leu Thr His Val
            355                 360                 365

His His Leu Asn Leu Val Arg Leu Ile Gly Tyr Cys Val Glu Gly Ser
        370                 375                 380

Leu Phe Leu Val Tyr Glu Tyr Ile Glu Asn Gly Asn Leu Gly Gln Tyr
385                 390                 395                 400

Leu His Gly Thr Glu Arg Glu Pro Leu Ala Trp Ser Thr Arg Val Gln
                405                 410                 415
```

-continued

```
Ile Ala Leu Asp Ser Ala Arg Gly Leu Glu Tyr Ile His Glu His Thr
            420                 425                 430

Val Pro Val Tyr Ile His Arg Asp Val Lys Pro Ala Asn Ile Leu Ile
            435                 440                 445

Asp Lys Asp Phe Arg Gly Lys Val Ala Asp Phe Gly Leu Thr Lys Leu
            450                 455                 460

Arg Glu Val Gly Ser Ser Leu Ser Leu His Thr Arg Leu Val Gly Thr
465                 470                 475                 480

Phe Gly Tyr Met Pro Pro Glu Tyr Ala Gln Tyr Gly Asp Val Ser Pro
                    485                 490                 495

Lys Val Asp Val Tyr Ala Phe Gly Val Val Leu Tyr Glu Leu Ile Ser
                    500                 505                 510

Ala Lys Asn Ala Val Leu Lys Thr Gly Glu Thr Val Ala Glu Ser Ser
            515                 520                 525

Lys Gly Leu Val Thr Leu Phe Glu Glu Ala Leu Asn Lys Ser Asp Pro
        530                 535                 540

Ser Lys Ala Ile Arg Lys Leu Val Asp Pro Arg Leu Gly Glu Asn Tyr
545                 550                 555                 560

Pro Ile Asp Ser Val Leu Lys Val Ala Glu Leu Gly Arg Ala Cys Thr
                565                 570                 575

Arg Asp Asn Pro Leu Leu Arg Pro Ser Met Arg Ser Val Val Val Ala
            580                 585                 590

Leu Met Thr Leu Leu Ala Ser Ser Thr Ser Ile Glu Asp Cys Asp Asp
        595                 600                 605

Asn Asp Asp Asp Asp Asp Asp Asp Asp Asn Ser Tyr Glu Asn Arg
        610                 615                 620

Thr Leu Ile Asp Gln Leu Ser Val Arg
625                 630
```

<210> SEQ ID NO 303
<211> LENGTH: 631
<212> TYPE: PRT
<213> ORGANISM: Arachis hypogaea

<400> SEQUENCE: 303

```
Met Lys Leu Lys Lys Ser Phe Leu Leu Phe Phe Leu Leu Leu Glu Cys
1               5                   10                  15

Ser Cys Phe Ile Asn Leu Glu Ser Lys Cys Leu Lys Gly Cys Asp Leu
            20                  25                  30

Ala Ile Ala Ser Tyr Phe Val Tyr Pro Arg Val Lys Leu Gly Ser Ile
            35                  40                  45

Ala Ser Phe Met His Ser Asn Val Val Pro Asn Ser Asn Val Ile Ile
        50                  55                  60

Ser Tyr Asn Lys Asp Lys Met Pro Asn Asn Leu Pro Val Ser Phe Thr
65                  70                  75                  80

Thr Ile Asn Ile Pro Phe Pro Cys Asp Cys Ile Asn Gly Glu Phe Leu
                85                  90                  95

Gly His Val Phe Glu Tyr Ser Ala Ile Glu Gly Asp Thr Tyr Tyr Leu
            100                 105                 110

Ile Ala Asn Met Arg Tyr Ser Asp Leu Thr Thr Val Glu Ile Leu Gln
        115                 120                 125

Arg Phe Asn Asn Tyr Asp Pro Asn His Val Pro Val Asn Ala Lys Val
        130                 135                 140

Asn Val Thr Val Asn Cys Ser Cys Gly Asn Ser His Val Ser Lys Asp
```

```
145              150              155              160

Tyr Gly Leu Phe Val Thr Phe Pro Leu Ser Glu Gly Asn Thr Leu Leu
             165              170              175

Gln Ile Ala Asn Gln Thr Lys Leu Asp Pro Lys Leu Leu Gln Ser Tyr
             180              185              190

Asn Pro Gly Val Asn Phe Asn Gln Thr Arg Gly Ile Val Phe Ile Pro
             195              200              205

Gly Arg Asp Gln Asn Gly Val Tyr Val Pro Leu Tyr Pro Arg Leu Ala
        210              215              220

Gly Leu Ala Lys Asp Val Ala Val Gly Ile Ser Ile Ala Gly Thr Ser
225              230              235              240

Gly Val Leu Leu Leu Leu Ile Cys Val Cys Val Arg Tyr Phe Gln Lys
             245              250              255

Lys Glu Glu Glu Lys Ile Lys Leu Pro Thr Glu Asp Phe Ile Ser Ser
             260              265              270

Ser Thr Gln Asp Gly Asn Ala Ser Ser Ser Gly Glu Tyr Glu Thr Ser
             275              280              285

Gly Ser Thr Ala Ala Ser Ala Ser Gly Leu Pro Ala Ile Met Ala Ala
        290              295              300

Lys Ser Met Glu Phe Ser Tyr Gln Glu Leu Ala Lys Ala Thr Asn Asn
305              310              315              320

Phe Ser Ser Asp Asn Lys Ile Gly Gln Gly Gly Phe Gly Ala Val Tyr
             325              330              335

Phe Ala Glu Leu Arg Gly Gln Lys Ala Ala Ile Lys Lys Met Asp Val
             340              345              350

Gln Ala Ser Thr Glu Phe Leu Ser Glu Leu Lys Val Leu Thr His Val
             355              360              365

His His Leu Asn Leu Val Arg Leu Ile Gly Tyr Cys Val Glu Gly Ser
        370              375              380

Leu Phe Leu Val Tyr Glu Tyr Ile Glu Asn Gly Asn Leu Gly Gln Tyr
385              390              395              400

Leu His Gly Thr Gly Arg Glu Pro Leu Ala Trp Leu Thr Arg Val Gln
             405              410              415

Ile Ala Leu Asp Ser Ala Arg Gly Leu Glu Tyr Ile His Glu His Thr
             420              425              430

Val Pro Val Tyr Ile His Arg Asp Val Lys Pro Ala Asn Ile Leu Ile
             435              440              445

Asp Lys Asp Phe Arg Gly Lys Val Ala Asp Phe Gly Leu Thr Lys Leu
        450              455              460

Arg Glu Val Gly Ser Ser Leu Ser Leu His Thr Arg Leu Val Gly Thr
465              470              475              480

Phe Gly Tyr Met Pro Pro Glu Tyr Ala Gln Tyr Gly Asp Val Ser Pro
             485              490              495

Lys Val Asp Val Tyr Ala Phe Gly Val Val Leu Tyr Glu Leu Ile Ser
             500              505              510

Ala Lys Asn Ala Val Leu Lys Thr Gly Glu Thr Val Ala Glu Ser Ser
             515              520              525

Lys Gly Leu Val Thr Leu Phe Glu Glu Ala Leu Asn Lys Asn Asp Pro
        530              535              540

Ser Lys Ala Ile Arg Lys Leu Val Asp Pro Arg Leu Gly Glu Asn Tyr
545              550              555              560

Pro Ile Asp Ser Val Leu Lys Val Ala Glu Leu Gly Arg Ala Cys Thr
             565              570              575
```

```
Arg Asp Asn Pro Leu Leu Arg Pro Ser Met Arg Ser Val Val Val Ala
            580                 585             590

Leu Met Thr Leu Leu Ala Ser Ser Thr Ser Ile Glu Asp Cys Asp Asp
            595                 600             605

Asn Asp Asp Asp Asp Asp Asp Asn Ser Tyr Glu Asn Arg Thr Leu
    610                 615             620

Ile Asp Gln Leu Ser Val Arg
625                 630

<210> SEQ ID NO 304
<211> LENGTH: 632
<212> TYPE: PRT
<213> ORGANISM: Cajanus cajan

<400> SEQUENCE: 304

Met Phe Leu Ser Tyr Pro Met Glu Leu Lys Lys Gly Leu Leu Phe Leu
1               5                   10                  15

Leu Leu Leu Glu Cys Val Phe Cys Asp Val Glu Ser Met Cys Val Lys
            20                  25                  30

Glu Cys Asp Val Ala Leu Ala Ser Tyr Tyr Ile Leu Pro Gly Tyr Leu
            35                  40                  45

Thr Val Glu Asn Val Thr Gly Trp Leu Glu Ser Ser Val Leu Ser Asn
    50                  55                  60

Ser Asp Val Ile Lys Ser Tyr Asn Lys Asp Lys Ile Ile Lys Asp Asn
65                  70                  75                  80

Leu Pro Ser Phe Asp Arg Ile Asn Val Pro Phe Pro Cys Asp Cys Ile
                85                  90                  95

His Glu Glu Phe Leu Gly His Val Phe Glu Tyr Ser Ala Ala Ala Gly
            100                 105                 110

Asp Thr Tyr Asp Ser Ile Ala Lys Val Thr Tyr Ala Asn Leu Thr Thr
            115                 120                 125

Val Glu Leu Leu Thr Arg Phe Asn Ser Tyr Gly His Asp Ile Pro Gln
    130                 135                 140

Asn Ala Lys Ile Asn Val Thr Val Lys Cys Ser Cys Gly Asn Ser Gln
145                 150                 155                 160

Val Ser Lys Asp Tyr Gly Leu Phe Ile Thr Tyr Pro Leu Arg Pro Gly
                165                 170                 175

Asn Asn Leu His Asp Ile Ala Asn Glu Val His Leu Asp Ala Gln Leu
            180                 185                 190

Leu Glu Lys Tyr Asn Pro Gly Val Asn Phe Ser Lys Asp Ser Gly Ile
            195                 200                 205

Val Phe Ile Pro Gly Arg Asp Gln Asn Gly Asp Tyr Val Pro Leu Tyr
    210                 215                 220

Pro Arg Lys Ala Gly Gly Ile Lys Lys Lys Ile Ser Ala Lys Asp Ala
225                 230                 235                 240

Ala Val Gly Val Ser Ile Ala Gly Ile Cys Gly Leu Leu Leu Leu Val
                245                 250                 255

Val Cys Ile Tyr Val Lys Tyr Leu Gln Lys Lys Glu Gly Glu Glu Val
                260                 265                 270

Lys Leu Pro Thr Glu Ser Ser Met Ala Phe Ser Thr Gln Asp Gly Thr
            275                 280                 285

Ala Ser Gly Ser Ser Glu Tyr Glu Thr Ser Gly Ser Ser Gly Pro Thr
    290                 295                 300

Thr Ala Ser Ala Thr Gly Leu Thr Gly Ile Met Val Ala Lys Ser Met
```

```
305                 310                 315                 320

Glu Phe Ser Tyr Gln Glu Leu Ala Lys Ala Thr Asn Asn Phe Ser Leu
                325                 330                 335

Glu Asn Lys Ile Gly Gln Gly Gly Phe Gly Ala Val Tyr Tyr Ala Glu
                340                 345                 350

Leu Arg Gly Glu Lys Thr Ala Ile Lys Lys Met Asp Val Gln Ala Ser
                355                 360                 365

Thr Glu Phe Leu Cys Glu Leu Lys Val Leu Thr His Val His His Leu
                370                 375                 380

Asn Leu Val Arg Leu Ile Gly Tyr Cys Val Glu Gly Ser Leu Phe Leu
385                 390                 395                 400

Val Tyr Glu Tyr Ile Asp Asn Gly Asn Leu Gly Gln Tyr Leu His Gly
                    405                 410                 415

Thr Gly Lys Asp Pro Leu Pro Trp Ser Ser Arg Val Gln Ile Ala Leu
                420                 425                 430

Asp Ser Ala Arg Gly Leu Glu Tyr Ile His Glu His Thr Val Pro Val
                435                 440                 445

Tyr Ile His Arg Asp Val Lys Ser Ala Asn Ile Leu Ile Asp Lys Asn
    450                 455                 460

Phe Arg Gly Lys Val Ala Asp Phe Gly Leu Thr Lys Leu Ile Glu Val
465                 470                 475                 480

Gly Gly Ser Thr Leu His Thr Arg Leu Val Gly Thr Phe Gly Tyr Met
                485                 490                 495

Pro Pro Glu Tyr Ala Gln Tyr Gly Asp Val Ser Pro Lys Val Asp Val
                500                 505                 510

Tyr Ala Phe Gly Val Val Leu Tyr Glu Leu Ile Ser Ala Lys Asn Ala
                515                 520                 525

Ile Leu Arg Thr Gly Glu Ser Val Ala Glu Thr Lys Gly Leu Val Ala
    530                 535                 540

Leu Phe Glu Glu Ala Leu Asn Gln Ser Asn Pro Gly Glu Gly Ile Arg
545                 550                 555                 560

Lys Leu Val Asp Pro Arg Leu Gly Glu Asn Tyr Pro Ile Asp Ser Val
                565                 570                 575

Leu Lys Ile Ala Gln Leu Gly Arg Ala Cys Thr Arg Asp Asn Pro Leu
                580                 585                 590

Leu Arg Pro Ser Met Arg Ser Ile Val Val Ala Leu Met Thr Leu Ser
                595                 600                 605

Ser Pro Thr Glu Asp Cys Glu Asp Gly Ala Ser Tyr Glu Asn Gln Thr
    610                 615                 620

Leu Ile Asn Leu Leu Ser Val Arg
625                 630
```

<210> SEQ ID NO 305
<211> LENGTH: 616
<212> TYPE: PRT
<213> ORGANISM: Cicer arietinum

<400> SEQUENCE: 305

```
Met Lys Leu Lys Asn Ile Phe Leu Phe Phe Phe Met Phe Leu Glu
1               5                   10                  15

Cys Val Phe Phe Lys Val Glu Ser Lys Cys Val Lys Gly Cys Asp Leu
                20                  25                  30

Ala Leu Ala Ser Tyr Tyr Ile Lys Pro Pro Phe Glu Phe Thr Asn Ile
        35                  40                  45
```

```
Thr Asn Phe Met Gln Ser Asn Ser Asp Ile Ile Ile Ser Tyr Asn Lys
    50              55              60

Gln Leu Val Ser Asn Asn Gly Lys Leu Phe Ser Phe Ser Arg Ile Asn
65              70              75              80

Ile Pro Phe Gln Cys Glu Cys Ile Gln Gly Glu Phe Leu Gly His Met
            85              90              95

Phe Glu Tyr Thr Thr Asn Glu Gly Asp Thr Tyr Asp Leu Ile Ala Asn
            100             105             110

Ser Tyr Tyr Ala Ser Leu Thr Thr Ile Asp Leu Leu Gln Lys Phe Asn
        115             120             125

Lys Tyr Asp His Asn Gln Thr Leu Pro Ser Lys Val Lys Val Asn Val
    130             135             140

Thr Val Asn Cys Ser Cys Gly Asn Ser Gln Ile Ser Lys Glu Tyr Gly
145             150             155             160

Leu Phe Leu Thr Tyr Pro Leu Arg Ser Ser Asp Thr Leu Gln Ile Ile
            165             170             175

Ala Ile Glu Ser Lys Val Asp Glu Val Leu Ile Gln Asn Tyr Asn Pro
        180             185             190

Asn Val Asn Phe Ser Arg Gly Ser Gly Ile Val Phe Ile Pro Gly Arg
        195             200             205

Asp Lys Asn Gly Asp Tyr Val Pro Leu Tyr Pro Arg Thr Gly Leu Ala
    210             215             220

Lys Gly Ala Ala Val Gly Ile Ser Met Ala Gly Ile Phe Gly Phe Leu
225             230             235             240

Leu Phe Val Ile Cys Ile Tyr Val Lys Tyr Phe Gln Lys Asn Glu Glu
            245             250             255

Gln Asn Thr Lys Leu Leu Glu Thr Ser Ile Ala Leu Ser Thr Gln Ser
            260             265             270

Ala Ser Gly Ser Gly Glu Tyr Glu Thr Ser Gly Ser Ser Gly His Gly
        275             280             285

Thr Ser Ser Ala Ala Gly Leu Thr Gly Ile Met Val Ala Lys Ser Thr
    290             295             300

Glu Phe Ser Tyr Gln Glu Leu Ala Lys Ala Thr Asn Asn Phe Ser Leu
305             310             315             320

Asp Asn Lys Ile Gly Gln Gly Gly Phe Gly Ala Val Tyr Tyr Ala Glu
            325             330             335

Leu Arg Gly Glu Lys Thr Ala Ile Lys Lys Met Asp Val Gln Ala Ser
            340             345             350

Thr Glu Phe Leu Cys Glu Leu Lys Val Leu Thr His Val His His Leu
        355             360             365

Asn Leu Val Arg Leu Ile Gly Tyr Cys Val Glu Gly Ser Leu Phe Leu
    370             375             380

Val Tyr Glu His Ile Asp Asn Gly Asn Leu Gly Gln Tyr Leu His Gly
385             390             395             400

Ile Gly Thr Glu Pro Leu Pro Trp Ser Ser Arg Val Gln Ile Ala Leu
            405             410             415

Asp Ser Ala Arg Gly Leu Glu Tyr Ile His Glu His Thr Val Pro Val
            420             425             430

Tyr Ile His Arg Asp Val Lys Ser Ala Asn Ile Leu Ile Asp Lys Asn
        435             440             445

Leu Arg Gly Lys Val Ala Asp Phe Gly Leu Thr Lys Leu Ile Glu Val
    450             455             460

Gly Asn Ser Thr Leu His Thr Arg Leu Val Gly Thr Phe Gly Tyr Met
```

-continued

```
465                470                475                480
Pro Pro Glu Tyr Ala Gln Tyr Gly Asp Val Ser Pro Lys Ile Asp Val
            485                490                495

Tyr Ala Phe Gly Val Val Ile Tyr Glu Leu Ile Ser Ala Lys Asn Ala
            500                505                510

Val Leu Lys Thr Gly Glu Ser Val Ala Glu Ser Lys Gly Leu Val Ala
            515                520                525

Leu Phe Glu Glu Ala Leu Asn Lys Ser Asp Pro Cys Glu Gly Leu Arg
            530                535                540

Lys Leu Val Asp Pro Arg Leu Gly Glu Asn Tyr Pro Ile Asp Ser Val
545                550                555                560

Leu Lys Met Ala Gln Leu Gly Arg Ala Cys Thr Arg Asp Asn Pro Leu
            565                570                575

Leu Arg Pro Ser Met Arg Ser Ile Val Val Ala Leu Met Thr Leu Ser
            580                585                590

Ser Pro Thr Glu Asp Cys Asp Asp Asp Thr Ser Tyr Glu Asn Gln Thr
            595                600                605

Leu Ile Asn Leu Leu Ser Val Arg
    610                615

<210> SEQ ID NO 306
<211> LENGTH: 620
<212> TYPE: PRT
<213> ORGANISM: Abrus precatorius

<400> SEQUENCE: 306

Met Lys Pro Ala Asn Gly Phe Leu Leu Phe Leu Leu Leu Leu Glu Tyr
1                5                10                15

Val Cys Cys Asn Val Glu Ser Lys Cys Met Lys Gly Cys His Val Ala
            20                25                30

Leu Ala Ser Tyr Tyr Val Arg Pro Lys Phe Leu Ser Leu Asp Asn Ile
            35                40                45

Met Arg Leu Met Gln Ser Lys Ile Leu Ser Thr Ser Asp Val Ile Arg
    50                55                60

Ser Tyr Asn Lys Asp Lys Ile Leu Asn Asp Asn Val Pro Ser Phe Ser
65                70                75                80

Arg Val Asn Ile Pro Phe Pro Cys Asp Cys Ile Gly Asp Glu Phe Leu
            85                90                95

Gly His Val Phe Glu Tyr Ser Thr Ala Ala Gly Asp Thr Tyr Asp Leu
            100                105                110

Ile Ala Lys Val Lys Tyr Ala Asn Leu Thr Thr Val Glu Leu Leu Gln
            115                120                125

Arg Phe Asn Ser Tyr Asp Gln Asp Asp Ile Pro Ala Asn Ser Lys Leu
            130                135                140

Asn Val Thr Val Asn Cys Tyr Cys Gly Asn Ser Gln Ile Ser Lys Asp
145                150                155                160

Tyr Gly Met Phe Ile Thr Tyr Pro Leu Arg Pro Gly Asn Thr Leu Gln
            165                170                175

Asp Ile Ser Asn Glu Thr Asn Leu Asp Ala His Leu Leu Gln Ser Tyr
            180                185                190

Asn Pro Gly Val Asn Phe Ser Ser Glu Ser Gly Ile Val Phe Ile Pro
            195                200                205

Gly Arg Asp Gln Asn Gly Asp Tyr Val Pro Leu Tyr Pro Arg Ser Gly
    210                215                220
```

```
Leu Ala Thr Gly Ala Ala Val Gly Ile Thr Ile Ala Ala Ile Cys Gly
225                 230                 235                 240

Leu Ile Leu Leu Val Ile Phe Met Tyr Val Lys Tyr Phe Gln Lys Lys
                245                 250                 255

Glu Gly Glu Lys Ala Lys Leu Pro Ser Glu Ser Ser Val Ala Phe Ser
                260                 265                 270

Thr Gln Asp Ala Ser Gly Ser Gly Glu Tyr Glu Thr Ser Gly Ser Thr
            275                 280                 285

Gly Pro Ala Asn Ala Ser Ala Ala Gly Leu Thr Gly Ile Met Val Ala
        290                 295                 300

Lys Ser Thr Glu Phe Ser Tyr Gln Glu Leu Ala Lys Ala Thr Asn Asn
305                 310                 315                 320

Phe Ser Leu Asp Asn Lys Ile Gly Gln Gly Gly Phe Gly Ala Val Tyr
                325                 330                 335

Tyr Ala Glu Leu Arg Gly Glu Lys Thr Ala Ile Lys Lys Met Asp Val
                340                 345                 350

Gln Ala Ser Thr Glu Phe Leu Cys Glu Leu Lys Val Leu Thr His Val
            355                 360                 365

His His Leu Asn Leu Val Arg Leu Ile Gly Tyr Cys Val Glu Gly Ser
        370                 375                 380

Leu Phe Leu Val Tyr Glu Tyr Ile Asp Asn Gly Asn Leu Gly Gln Tyr
385                 390                 395                 400

Leu His Gly Thr Gly Lys Asp Pro Leu Pro Trp Ser Ser Arg Val Gln
                405                 410                 415

Ile Ala Leu Asp Ser Ala Arg Gly Leu Glu Tyr Ile His Glu His Thr
                420                 425                 430

Val Pro Val Tyr Ile His Arg Asp Val Lys Ser Ala Asn Ile Leu Ile
                435                 440                 445

Asp Lys His Phe Arg Gly Lys Val Ala Asp Phe Gly Leu Thr Lys Leu
        450                 455                 460

Ile Glu Val Gly Ser Ser Thr Leu His Thr Arg Leu Val Gly Thr Phe
465                 470                 475                 480

Gly Tyr Met Pro Pro Glu Tyr Ala Gln Tyr Gly Asp Val Ser Pro Lys
                485                 490                 495

Ile Asp Val Tyr Ala Phe Gly Val Val Leu Tyr Glu Leu Ile Ser Ala
                500                 505                 510

Lys Asn Ala Val Leu Lys Thr Gly Glu Ser Val Ala Glu Ser Lys Gly
            515                 520                 525

Leu Val Ala Leu Phe Glu Glu Ala Leu Asn Gln Ser Asn Pro Leu Glu
        530                 535                 540

Gly Ile His Lys Leu Val Asp Pro Arg Leu Gly Glu Asn Tyr Pro Ile
545                 550                 555                 560

Asp Ser Val Leu Lys Ile Ala Gln Leu Gly Arg Ala Cys Thr Arg Asp
                565                 570                 575

Asn Pro Leu Leu Arg Pro Ser Met Arg Ser Ile Val Val Ala Leu Met
                580                 585                 590

Thr Leu Ala Ser Pro Thr Glu Asp Cys Asp Asp Thr Ile Ser Tyr
            595                 600                 605

Glu Asn Gln Thr Leu Ile Asn Leu Leu Ser Val Arg
        610                 615                 620
```

<210> SEQ ID NO 307
<211> LENGTH: 611
<212> TYPE: PRT

-continued

```
<213> ORGANISM: Glycine max

<400> SEQUENCE: 307

Met Glu Leu Lys Lys Gly Leu Leu Val Phe Phe Leu Leu Leu Glu Cys
1               5                   10                  15

Val Cys Tyr Asn Val Glu Ser Lys Cys Val Lys Gly Cys Asp Val Ala
                20                  25                  30

Phe Ala Ser Tyr Tyr Val Ser Pro Asp Leu Ser Leu Glu Asn Ile Ala
            35                  40                  45

Arg Leu Met Glu Ser Ser Ile Glu Val Ile Ile Ser Phe Asn Glu Asp
        50                  55                  60

Asn Ile Ser Asn Gly Tyr Pro Leu Ser Phe Tyr Arg Leu Asn Ile Pro
65                  70                  75                  80

Phe Pro Cys Asp Cys Ile Gly Gly Glu Phe Leu Gly His Val Phe Glu
                85                  90                  95

Tyr Ser Ala Ser Ala Gly Asp Thr Tyr Asp Ser Ile Ala Lys Val Thr
            100                 105                 110

Tyr Ala Asn Leu Thr Thr Val Glu Leu Leu Arg Arg Phe Asn Gly Tyr
        115                 120                 125

Asp Gln Asn Gly Ile Pro Ala Asn Ala Arg Val Asn Val Thr Val Asn
        130                 135                 140

Cys Ser Cys Gly Asn Ser Gln Val Ser Lys Asp Tyr Gly Met Phe Ile
145                 150                 155                 160

Thr Tyr Pro Leu Arg Pro Gly Asn Asn Leu His Asp Ile Ala Asn Glu
                165                 170                 175

Ala Arg Leu Asp Ala Gln Leu Leu Gln Arg Tyr Asn Pro Gly Val Asn
            180                 185                 190

Phe Ser Lys Glu Ser Gly Thr Val Phe Ile Pro Gly Arg Asp Gln His
            195                 200                 205

Gly Asp Tyr Val Pro Leu Tyr Pro Arg Lys Thr Gly Leu Ala Arg Gly
        210                 215                 220

Ala Ala Val Gly Ile Ser Ile Ala Gly Ile Cys Ser Phe Leu Leu Leu
225                 230                 235                 240

Val Ile Cys Leu Tyr Gly Lys Tyr Phe Gln Lys Lys Glu Gly Glu Lys
                245                 250                 255

Thr Lys Leu Pro Thr Glu Asn Ser Met Ala Phe Ser Thr Gln Asp Val
                260                 265                 270

Ser Gly Ser Ala Glu Tyr Glu Thr Ser Gly Ser Ser Gly Thr Ala Ser
        275                 280                 285

Ala Thr Gly Leu Thr Gly Ile Met Val Ala Lys Ser Met Glu Phe Ser
        290                 295                 300

Tyr Gln Glu Leu Ala Lys Ala Thr Asn Asn Phe Ser Leu Glu Asn Lys
305                 310                 315                 320

Ile Gly Gln Gly Gly Phe Gly Ala Val Tyr Tyr Ala Glu Leu Arg Gly
                325                 330                 335

Glu Lys Thr Ala Ile Lys Lys Met Asp Val Gln Ala Ser Thr Glu Phe
            340                 345                 350

Leu Cys Glu Leu Lys Val Leu Thr His Val His His Phe Asn Leu Val
            355                 360                 365

Arg Leu Ile Gly Tyr Cys Val Glu Gly Ser Leu Phe Leu Val Tyr Glu
        370                 375                 380

Tyr Ile Asp Asn Gly Asn Leu Gly Gln Tyr Leu His Gly Thr Gly Lys
385                 390                 395                 400
```

```
Asp Pro Leu Pro Trp Ser Gly Arg Val Gln Ile Ala Leu Asp Ser Ala
            405             410             415

Arg Gly Leu Glu Tyr Ile His Glu His Thr Val Pro Val Tyr Ile His
            420             425             430

Arg Asp Val Lys Ser Ala Asn Ile Leu Ile Asp Lys Asn Ile Arg Gly
            435             440             445

Lys Val Ala Asp Phe Gly Leu Thr Lys Leu Ile Glu Val Gly Gly Ser
        450             455             460

Thr Leu His Thr Arg Leu Val Gly Thr Phe Gly Tyr Met Pro Pro Glu
465             470             475             480

Tyr Ala Gln Tyr Gly Asp Ile Ser Pro Lys Val Asp Val Tyr Ala Phe
                485             490             495

Gly Val Val Leu Tyr Glu Leu Ile Ser Ala Lys Asn Ala Val Leu Lys
            500             505             510

Thr Gly Glu Ser Val Ala Glu Ser Lys Gly Leu Val Ala Leu Phe Glu
            515             520             525

Glu Ala Leu Asn Gln Ser Asn Pro Ser Glu Ser Ile Arg Lys Leu Val
        530             535             540

Asp Pro Arg Leu Gly Glu Asn Tyr Pro Ile Asp Ser Val Leu Lys Ile
545             550             555             560

Ala Gln Leu Gly Arg Ala Cys Thr Arg Asp Asn Pro Leu Leu Arg Pro
                565             570             575

Ser Met Arg Ser Ile Val Val Ala Leu Met Thr Leu Ser Ser Pro Thr
            580             585             590

Glu Asp Cys Asp Thr Ser Tyr Glu Asn Gln Thr Leu Ile Asn Leu Leu
            595             600             605

Ser Val Arg
        610

<210> SEQ ID NO 308
<211> LENGTH: 618
<212> TYPE: PRT
<213> ORGANISM: Glycine max

<400> SEQUENCE: 308

Met Glu Leu Lys Lys Trp Leu Leu Phe Phe Leu Leu Leu Glu Tyr Val
1               5               10              15

Cys Cys Asn Ala Glu Ser Lys Cys Val Lys Gly Cys Asp Val Ala Leu
            20              25              30

Ala Ser Tyr Tyr Val Ser Pro Gly Tyr Leu Leu Leu Glu Asn Ile Thr
            35              40              45

Arg Leu Met Glu Ser Ile Val Leu Ser Asn Ser Asp Val Ile Ile Tyr
        50              55              60

Asn Lys Asp Lys Ile Phe Asn Glu Asn Val Leu Ala Phe Ser Arg Leu
65              70              75              80

Asn Ile Pro Phe Pro Cys Gly Cys Ile Asp Gly Glu Phe Leu Gly His
                85              90              95

Val Phe Glu Tyr Ser Ala Ser Ala Gly Asp Thr Tyr Asp Ser Ile Ala
            100             105             110

Lys Val Thr Tyr Ala Asn Leu Thr Thr Val Glu Leu Leu Arg Arg Phe
            115             120             125

Asn Ser Tyr Asp Gln Asn Gly Ile Pro Ala Asn Ala Thr Val Asn Val
        130             135             140

Thr Val Asn Cys Ser Cys Gly Asn Ser Gln Val Ser Lys Asp Tyr Gly
145             150             155             160
```

```
Leu Phe Ile Thr Tyr Leu Leu Arg Pro Gly Asn Asn Leu His Asp Ile
                165                 170                 175

Ala Asn Glu Ala Arg Leu Asp Ala Gln Leu Leu Gln Ser Tyr Asn Pro
                180                 185                 190

Gly Val Asn Phe Ser Lys Glu Ser Gly Asp Ile Val Phe Ile Pro Gly
                195                 200                 205

Lys Asp Gln His Gly Asp Tyr Val Pro Leu Tyr Pro Arg Lys Thr Gly
        210                 215                 220

Leu Ala Thr Ser Ala Ser Val Gly Ile Pro Ile Ala Gly Ile Cys Val
225                 230                 235                 240

Leu Leu Leu Val Ile Cys Ile Tyr Val Lys Tyr Phe Gln Lys Lys Glu
                245                 250                 255

Gly Glu Lys Ala Lys Leu Ala Thr Glu Asn Ser Met Ala Phe Ser Thr
                260                 265                 270

Gln Asp Val Ser Gly Ser Ala Glu Tyr Glu Thr Ser Gly Ser Ser Gly
        275                 280                 285

Thr Ala Ser Thr Ser Ala Thr Gly Leu Thr Gly Ile Met Val Ala Lys
        290                 295                 300

Ser Met Glu Phe Ser Tyr Gln Glu Leu Ala Lys Ala Thr Asn Asn Phe
305                 310                 315                 320

Ser Leu Glu Asn Lys Ile Gly Gln Gly Gly Phe Gly Ile Val Tyr Tyr
                325                 330                 335

Ala Glu Leu Arg Gly Glu Lys Thr Ala Ile Lys Lys Met Asp Val Gln
                340                 345                 350

Ala Ser Thr Glu Phe Leu Cys Glu Leu Lys Val Leu Thr His Val His
        355                 360                 365

His Leu Asn Leu Val Arg Leu Ile Gly Tyr Cys Val Glu Gly Ser Leu
        370                 375                 380

Phe Leu Val Tyr Glu Tyr Ile Asp Asn Gly Asn Leu Gly Gln Tyr Leu
385                 390                 395                 400

His Gly Thr Gly Lys Asp Pro Phe Leu Trp Ser Ser Arg Val Gln Ile
                405                 410                 415

Ala Leu Asp Ser Ala Arg Gly Leu Glu Tyr Ile His Glu His Thr Val
        420                 425                 430

Pro Val Tyr Ile His Arg Asp Val Lys Ser Ala Asn Ile Leu Ile Asp
        435                 440                 445

Lys Asn Phe Arg Gly Lys Val Ala Asp Phe Gly Leu Thr Lys Leu Ile
        450                 455                 460

Glu Val Gly Gly Ser Thr Leu Gln Thr Arg Leu Val Gly Thr Phe Gly
465                 470                 475                 480

Tyr Met Pro Pro Glu Tyr Ala Gln Tyr Gly Asp Ile Ser Pro Lys Val
                485                 490                 495

Asp Val Tyr Ala Phe Gly Val Val Leu Tyr Glu Leu Ile Ser Ala Lys
                500                 505                 510

Asn Ala Val Leu Lys Thr Val Glu Ser Val Ala Glu Ser Lys Gly Leu
        515                 520                 525

Val Ala Leu Phe Glu Glu Ala Leu Asn Gln Ser Asn Pro Ser Glu Ser
        530                 535                 540

Ile Arg Lys Leu Val Asp Pro Arg Leu Gly Glu Asn Tyr Pro Ile Asp
545                 550                 555                 560

Ser Val Leu Lys Ile Ala Gln Leu Gly Arg Ala Cys Thr Arg Asp Asn
                565                 570                 575
```

```
Pro Leu Leu Arg Pro Ser Met Arg Ser Ile Val Val Ala Leu Leu Thr
            580             585                 590

Leu Ser Ser Pro Thr Glu Asp Cys Tyr Asp Asp Thr Ser Tyr Glu Asn
        595             600                 605

Gln Thr Leu Ile Asn Leu Leu Ser Val Arg
    610             615

<210> SEQ ID NO 309
<211> LENGTH: 621
<212> TYPE: PRT
<213> ORGANISM: Lupinus angustifolius

<400> SEQUENCE: 309

Met Lys Leu Lys Leu Val Phe Leu Leu Leu Leu Lys Tyr Val Cys Phe
1               5                   10                  15

Ile Val Glu Ser Lys Cys Ile Lys Gly Cys Asp Leu Ala Leu Ala Ser
            20                  25                  30

Tyr Tyr Val Pro Val Trp Pro Ile Val Ser Leu Gly Asn Ile Thr Ser
        35                  40                  45

Phe Met His Ser Asn Val Leu Thr Asn Pro Asn Val Val Thr Ser Tyr
    50                  55                  60

Asn Lys Asp Lys Val Phe Asn Gly Asp Val Met Leu Ala Leu Tyr Arg
65                  70                  75                  80

Thr Asn Val Pro Phe Pro Cys Asp Cys Ile Gly Gly Glu Phe Leu Gly
                85                  90                  95

His Val Phe Glu Tyr Ser Ala Val Glu Gly Asp Thr Tyr Gly Leu Ile
            100                 105                 110

Ala Met Lys Arg Tyr Ser Asn Leu Thr Thr Val Glu Ile Leu Lys Arg
        115                 120                 125

Phe Asn Ser Tyr Asp Pro Asn His Ile Pro Val Asn Ala Lys Val Asn
    130                 135                 140

Val Thr Val Lys Cys Ser Cys Gly Asn Ser Gln Ile Ser Lys Asp Tyr
145                 150                 155                 160

Gly Leu Phe Ile Thr Tyr Pro Leu Arg Pro Gly Asn Asn Leu Gln Glu
                165                 170                 175

Leu Ser Lys Glu Thr Lys Ile Asp Ala Lys Leu Leu Gln Ser Tyr Asn
            180                 185                 190

Pro Gly Val Asn Phe Ser Gln Glu Asn Gly Ile Val Phe Ile Pro Gly
        195                 200                 205

Lys Asp Gln Asn Gly Val Tyr Val Pro Leu Tyr Pro Arg Thr Gly Gly
    210                 215                 220

Val Ala Lys Gly Val Ala Val Gly Ile Ser Ile Ala Ala Thr Cys Gly
225                 230                 235                 240

Leu Val Leu Leu Val Ile Cys Ile Tyr Asp Arg Tyr Phe Lys Lys Lys
                245                 250                 255

Glu Gly Glu Lys Ala Lys Leu Ser Ile Glu Asn Ser Ile Gly Phe Ser
            260                 265                 270

Thr Gln Asp Ala Tyr Gly Ser Gly Glu Tyr Glu Thr Ser Gly Ser Ser
        275                 280                 285

Val His Ala Ser Ala Leu Thr Gly Ile Met Val Ala Lys Ser Leu Glu
    290                 295                 300

Phe Ser Tyr Gln Glu Leu Ala Lys Ala Thr Asn Asn Phe Ser Leu Asp
305                 310                 315                 320

Asn Lys Ile Gly Gln Gly Gly Phe Gly Ala Val Tyr Tyr Ala Glu Leu
                325                 330                 335
```

```
Arg Gly Glu Lys Thr Ala Ile Lys Lys Met Asp Val Gln Ala Ser Ser
        340                 345                 350

Glu Phe Leu Ala Glu Leu Lys Val Leu Thr His Val His His Leu Asn
        355                 360                 365

Leu Val Arg Leu Ile Gly Tyr Cys Val Glu Gly Ser Leu Phe Leu Val
        370                 375                 380

Tyr Glu Tyr Ile Asp Asn Gly Asn Leu Gly Gln Tyr Leu His Gly Lys
385                 390                 395                 400

Gly Lys Asp Pro Leu Pro Trp Ser Thr Arg Leu Gln Ile Ala Leu Asp
                405                 410                 415

Ser Ala Arg Gly Leu Glu Tyr Ile His Glu His Thr Val Pro Leu Tyr
                420                 425                 430

Ile His Arg Asp Val Lys Ser Ala Asn Ile Leu Ile Asp Lys Asn Leu
        435                 440                 445

Arg Gly Lys Val Ala Asp Phe Gly Leu Thr Lys Leu Ile Glu Val Gly
        450                 455                 460

Thr Ser Ser Leu His Thr Arg Leu Val Gly Thr Phe Gly Tyr Met Pro
465                 470                 475                 480

Pro Glu Tyr Ala Gln Tyr Gly Asp Ile Ser Pro Lys Ile Asp Val Tyr
                485                 490                 495

Ala Phe Gly Val Val Leu Tyr Glu Leu Ile Ser Ala Lys Asn Ala Val
                500                 505                 510

Leu Lys Thr Gly Glu Thr Val Ala Glu Ser Lys Gly Leu Val Asn Leu
        515                 520                 525

Phe Glu Glu Ala Leu Asn Gln Ile Asn Pro Leu Glu Pro Leu Thr Thr
        530                 535                 540

Leu Val Asp Pro Arg Leu Gly Asp Asn Tyr Pro Ile Gln Ser Leu Leu
545                 550                 555                 560

Lys Ile Ala Glu Leu Gly Arg Ala Cys Thr Arg Asp Asn Pro Leu Leu
                565                 570                 575

Arg Pro Asn Met Lys Ser Ile Val Val Ala Leu Met Thr Leu Ser Ser
                580                 585                 590

Ser Asn Glu Asp Asn Thr Thr Ser Ser Tyr Asp Asn Gln Thr Leu Ile
        595                 600                 605

Asn Leu Leu Leu Asp Glu Gly Phe Arg Gly Ile Thr Phe
        610                 615                 620

<210> SEQ ID NO 310
<211> LENGTH: 624
<212> TYPE: PRT
<213> ORGANISM: Lupinus angustifolius

<400> SEQUENCE: 310

Met Lys Leu Lys Phe Val Phe Phe Leu Leu Leu Glu Cys Val Cys Phe
1               5                   10                  15

Ile Val Glu Ser Lys Cys Ile Lys Gly Cys Asp Leu Ala Leu Ala Ser
                20                  25                  30

Tyr Tyr Val Ser Val Trp Pro Ser Ile Ser Leu Gly Asn Ile Thr Asn
        35                  40                  45

Phe Met His Ser Asn Val Leu Thr Asn Ser Asp Val Ile Ile Ser Tyr
        50                  55                  60

Asn Lys Gly Lys Ile Phe Asn Gly Asp Val Leu Leu Ser Leu Thr Arg
65                  70                  75                  80

Thr Asn Val Pro Phe Pro Cys Asp Cys Ile Gly Gly Glu Phe Leu Gly
```

-continued

```
                  85                    90                    95
His Val Phe Gln Tyr Ser Ser Val Ala Gly Asp Thr Tyr Asp Thr Ile
                 100                   105                   110

Ala Met Lys Ser Tyr Ser Asn Leu Thr Thr Val Glu Phe Leu Lys Arg
             115                   120                   125

Phe Asn Ser Tyr Asp Pro Asn His Ile Pro Val Asn Ser Lys Val Asn
         130                   135                   140

Val Thr Ile Asn Cys Ser Cys Gly Asn Ser Leu Ile Ser Lys Asp Tyr
145                   150                   155                   160

Gly Leu Phe Thr Thr Tyr Pro Leu Arg Pro Gly Asn Asn Leu Gln Glu
                 165                   170                   175

Leu Ser Lys Glu Thr Asn Ile Asp Ala Lys Leu Leu Gln Ser Tyr Asn
             180                   185                   190

Pro Gly Ala Asn Phe Ser Gln Glu Ser Arg Ile Val Phe Ile Pro Gly
         195                   200                   205

Arg Asp Gln Asn Gly Val Tyr Val Pro Leu Tyr Pro Arg Ile Gly Gly
     210                   215                   220

Leu Ala Arg Gly Ala Ala Val Gly Ile Ser Ile Ala Ala Thr Cys Gly
225                   230                   235                   240

Leu Val Leu Leu Ile Ile Cys Ile Tyr Asp Arg Tyr Phe Lys Lys Lys
                 245                   250                   255

Glu Gly Glu Lys Thr Lys Leu Ser Thr Glu Asp Ser Ile Gly Leu Ser
             260                   265                   270

Thr Glu Asp Gly Thr Gly Ser Gly Ser Gly Glu Tyr Glu Ala Ser Gly
         275                   280                   285

Ser Ser Gly His Ala Val Gly Leu Thr Ser Ile Met Val Ala Lys Ser
     290                   295                   300

Leu Glu Phe Ser Tyr Gln Glu Leu Ala Lys Ala Thr Asn Asn Phe Ser
305                   310                   315                   320

Leu Asp Asn Lys Ile Gly Gln Gly Gly Phe Gly Ala Val Tyr Tyr Ala
                 325                   330                   335

Glu Leu Arg Gly Glu Lys Thr Ala Ile Lys Lys Met Asp Val Gln Ala
             340                   345                   350

Ser Ser Glu Phe Leu Ala Glu Leu Lys Val Leu Thr His Ile His His
         355                   360                   365

Ser Asn Leu Val Arg Leu Ile Gly Tyr Cys Val Glu Gly Ser Leu Phe
     370                   375                   380

Leu Val Tyr Glu Tyr Ile Asp Asn Gly Asn Leu Gly Gln Tyr Leu His
385                   390                   395                   400

Gly Lys Gly Arg Asp Pro Leu Pro Trp Ser Thr Arg Leu Gln Ile Ala
                 405                   410                   415

Leu Asp Ser Ala Arg Gly Leu Glu Tyr Ile His Glu His Thr Val Pro
             420                   425                   430

Leu Tyr Ile His Arg Asp Val Lys Ser Ala Asn Ile Leu Ile Asp Lys
         435                   440                   445

Asn Leu Arg Gly Lys Val Ala Asp Phe Gly Leu Thr Lys Leu Ile Glu
     450                   455                   460

Val Gly Thr Ser Ser Phe His Thr Arg Leu Val Gly Thr Phe Gly Tyr
465                   470                   475                   480

Met Pro Pro Glu Tyr Ala Gln Tyr Gly Asp Ile Ser Ser Lys Ile Asp
                 485                   490                   495

Val Tyr Ala Phe Gly Val Val Leu Tyr Glu Leu Ile Ser Ala Lys Ser
                 500                   505                   510
```

```
Ala Ile Leu Lys Thr Gly Glu Thr Val Ser Glu Ser Lys Gly Leu Val
        515                 520                 525

Thr Leu Phe Glu Gly Ala Leu Asn Gln Ile Asn Pro Leu Glu Ala Leu
    530                 535                 540

Pro Lys Leu Val Asp Pro Arg Ile Gly Asp Asn Tyr Pro Ile Glu Ser
545                 550                 555                 560

Val Leu Lys Ile Ala Gln Leu Gly Arg Ala Cys Thr Arg Asp Asn Pro
                565                 570                 575

Leu Leu Arg Pro Asn Met Lys Ser Ile Val Val Ala Leu Met Thr Leu
                580                 585                 590

Ser Ser Ser Ala Glu His Ser Thr Ser Tyr Asp Asn Gln Thr Leu Ile
        595                 600                 605

Asn Leu Leu Leu Asp Glu Gly Phe Arg Glu Ile Ile Thr Pro Thr Ser
        610                 615                 620
```

<210> SEQ ID NO 311
<211> LENGTH: 617
<212> TYPE: PRT
<213> ORGANISM: Pisum sativum

<400> SEQUENCE: 311

```
Met Lys Leu Lys Asn Gly Leu Leu Leu Phe Phe Met Phe Leu Asp Cys
1               5                   10                  15

Ile Phe Phe Lys Val Glu Ser Lys Cys Val Ile Gly Cys Asp Ile Ala
                20                  25                  30

Leu Ala Ser Tyr Tyr Val Met Pro Leu Val Glu Leu Leu Asn Ile Thr
            35                  40                  45

Thr Phe Met Gln Ser Lys Leu Val Thr Asn Ser Ser Glu Val Ile Val
        50                  55                  60

Arg Tyr Asn Arg Asp Ile Val Phe Ser Asn Asp Asn Leu Phe Ser Tyr
65                  70                  75                  80

Phe Arg Ile Asn Ile Pro Phe Pro Cys Glu Cys Ile Gly Gly Glu Phe
                85                  90                  95

Leu Gly His Val Phe Glu Tyr Thr Ala Asn Glu Gly Asp Thr Tyr Asp
            100                 105                 110

Leu Ile Ala Asn Thr Tyr Tyr Ala Ser Leu Thr Thr Val Glu Val Leu
        115                 120                 125

Lys Lys Phe Asn Ser Tyr Asp Pro Asn His Ile Pro Ala Lys Ala Lys
        130                 135                 140

Val Asn Val Thr Val Asn Cys Ser Cys Gly Asn Ser Gln Ile Ser Lys
145                 150                 155                 160

Asp Tyr Gly Leu Phe Ile Thr Tyr Pro Leu Arg Pro Arg Asp Thr Leu
                165                 170                 175

Glu Lys Ile Ala Ser His Ser Lys Leu Asp Glu Gly Val Ile Gln Ser
            180                 185                 190

Tyr Asn Leu Gly Val Asn Phe Ser Lys Gly Ser Gly Ile Val Phe Phe
            195                 200                 205

Pro Gly Arg Asp Lys Asn Gly Glu Tyr Val Pro Leu Tyr Pro Arg Ala
    210                 215                 220

Gly Leu Gly Lys Gly Ala Ala Ala Gly Ile Ser Ile Ala Gly Ile Phe
225                 230                 235                 240

Ala Leu Leu Leu Phe Val Ile Cys Ile Tyr Ile Lys Tyr Phe Gln Lys
                245                 250                 255

Lys Glu Glu Glu Lys Thr Lys Leu Pro Gln Ile Ser Thr Ala Leu Ser
```

-continued

```
                 260               265               270
Ala Gln Asp Ala Ser Gly Ser Gly Glu Tyr Glu Thr Ser Gly Ser Ser
             275               280               285

Gly His Gly Thr Gly Ser Thr Ala Gly Leu Thr Gly Ile Met Val Ala
         290               295               300

Lys Ser Thr Glu Phe Ser Tyr Gln Glu Leu Ala Lys Ala Thr Asn Asn
305               310               315               320

Phe Ser Leu Asp Asn Lys Ile Gly Gln Gly Gly Phe Gly Ala Val Tyr
             325               330               335

Tyr Ala Val Leu Arg Gly Glu Lys Thr Ala Ile Lys Lys Met Asp Val
             340               345               350

Gln Ala Ser Thr Glu Phe Leu Cys Glu Leu Gln Val Leu Thr His Val
             355               360               365

His His Leu Asn Leu Val Arg Leu Ile Gly Tyr Cys Val Glu Gly Ser
         370               375               380

Leu Phe Leu Val Tyr Glu His Ile Asp Asn Gly Asn Leu Gly Gln Tyr
385               390               395               400

Leu His Gly Ile Asp Lys Ala Pro Leu Pro Trp Pro Ser Arg Val Gln
             405               410               415

Ile Ala Leu Asp Ser Ala Arg Gly Leu Glu Tyr Ile His Glu His Thr
             420               425               430

Val Pro Val Tyr Ile His Arg Asp Val Lys Ser Ala Asn Ile Leu Ile
             435               440               445

Asp Lys Asn Leu His Gly Lys Val Ala Asp Phe Gly Leu Thr Lys Leu
         450               455               460

Ile Glu Val Gly Asn Ser Thr Leu His Thr Arg Leu Val Gly Thr Phe
465               470               475               480

Gly Tyr Met Pro Pro Glu Tyr Ala Gln Tyr Gly Asp Val Ser Pro Lys
             485               490               495

Ile Asp Val Tyr Ala Phe Gly Val Val Leu Tyr Glu Leu Ile Ser Ala
             500               505               510

Lys Asn Ala Ile Leu Lys Thr Gly Glu Ser Ala Val Glu Ser Lys Gly
         515               520               525

Leu Val Ala Leu Phe Glu Glu Ala Leu Asn Gln Ile Asp Pro Leu Glu
         530               535               540

Ala Leu Arg Ile Leu Val Asp Pro Arg Leu Lys Glu Asn Tyr Pro Ile
545               550               555               560

Asp Ser Val Leu Lys Met Ala Gln Leu Gly Arg Ala Cys Thr Arg Asp
             565               570               575

Asn Pro Leu Leu Arg Pro Ser Met Arg Ser Leu Val Val Ala Leu Met
             580               585               590

Thr Leu Leu Ser His Thr Asp Asp Asp Thr Phe Tyr Glu Asn Gln
         595               600               605

Ser Leu Thr Asn Leu Leu Ser Val Arg
    610               615
```

<210> SEQ ID NO 312
<211> LENGTH: 618
<212> TYPE: PRT
<213> ORGANISM: Vigna angularis

<400> SEQUENCE: 312

```
Met Glu Leu Arg Lys Gly Leu Leu Leu Leu Phe Leu Leu Leu Glu Tyr
1               5               10               15
```

-continued

```
Val Cys Cys Asn Val Glu Ala Lys Cys Leu Lys Gly Cys Asp Leu Ala
            20                  25                  30

Leu Ala Ser Tyr Tyr Val Ser Ser Gly Leu Thr Leu Asp Asp Ile Thr
            35                  40                  45

His Leu Met Lys Ser Ser Val Val Ser Asn Ser Asp Asp Ile Ile Ser
        50                  55                  60

Tyr Asn Lys Asp Lys Thr Phe Asn Lys Asn Ile Phe Leu Phe Asp Arg
65                  70                  75                  80

Ile Asn Val Pro Phe Pro Cys Asp Cys Ile His Asp Glu Phe Leu Gly
                85                  90                  95

His Val Phe Glu Tyr Ser Ala Ala Glu Gly Asp Thr Tyr Asp Ser Ile
            100                 105                 110

Ala Lys Val Glu Tyr Ala Asp Leu Thr Thr Val Glu Leu Leu Arg Arg
            115                 120                 125

Phe Asn Ser Tyr Gly Gln Asn Gly Ile Pro Lys Asn Ala Lys Val Asn
        130                 135                 140

Val Thr Val Asn Cys Ser Cys Gly Asn Ser Gln Val Ser Gln Glu Tyr
145                 150                 155                 160

Gly Leu Phe Ile Thr Tyr Pro Leu Arg Pro Asp Asn Asn Leu His Asp
                165                 170                 175

Ile Ala Asn Glu Ala His Leu Asp Ala Gln Leu Leu Gln Asn Tyr Asn
            180                 185                 190

Pro Gly Val Asn Phe Ser Lys Glu Ser Gly Ile Val Phe Ile Pro Gly
            195                 200                 205

Arg Asp Gln Phe Gly Asp Tyr Val Pro Leu His Pro Arg Lys Thr Gly
        210                 215                 220

Leu Ala Thr Gly Ala Val Ala Gly Ile Ser Ile Ala Gly Ile Cys Gly
225                 230                 235                 240

Leu Leu Leu Phe Ile Ile Cys Thr Tyr Val Lys Phe Phe Lys Lys Met
                245                 250                 255

Glu Gly Glu Lys Pro Lys Leu Pro Thr Glu Lys Ser Thr Ala Phe Ser
            260                 265                 270

Ile Gln Asp Ala Ser Gly Ser Ala Asp Tyr Glu Thr Ser Gly Ser Ser
            275                 280                 285

Gly Thr Ala Thr Ala Thr Gly Leu Thr Gly Ile Met Val Ala Lys Ser
        290                 295                 300

Met Glu Phe Thr Tyr Gln Glu Leu Ala Lys Ala Thr Asn Asn Phe Ser
305                 310                 315                 320

Leu Glu Asn Lys Ile Gly Gln Gly Gly Phe Gly Ala Val Tyr Tyr Ala
                325                 330                 335

Glu Leu Arg Gly Glu Lys Thr Ala Ile Lys Lys Met Asp Val Gln Ala
            340                 345                 350

Ser Thr Glu Phe Leu Cys Glu Leu Lys Val Leu Thr His Val His His
            355                 360                 365

Leu Asn Leu Val Arg Leu Ile Gly Tyr Cys Val Glu Gly Ser Leu Phe
        370                 375                 380

Leu Val Tyr Glu His Ile Asp Asn Gly Asn Leu Gly Gln Tyr Leu His
385                 390                 395                 400

Gly Thr Gly Lys Asp Pro Leu Thr Trp Ser Ser Arg Val Gln Ile Ala
                405                 410                 415

Leu Asp Ser Ala Arg Gly Leu Glu Tyr Ile His Glu His Thr Val Pro
            420                 425                 430

Val Tyr Ile His Arg Asp Val Lys Ser Ala Asn Ile Leu Ile Asp Lys
```

```
              435                 440                 445
Asn Phe Arg Gly Lys Val Ala Asp Phe Gly Leu Thr Lys Leu Ile Glu
    450                 455                 460

Val Gly Ser Ser Thr Leu His Thr Arg Leu Val Gly Thr Phe Gly Tyr
465                 470                 475                 480

Met Pro Pro Glu Tyr Ala Gln Tyr Gly Asp Val Ser Pro Lys Val Asp
                485                 490                 495

Val Tyr Ala Phe Gly Val Val Leu Tyr Glu Leu Ile Ser Ala Lys Asn
                500                 505                 510

Ala Val Leu Lys Thr Gly Glu Tyr Val Ala Glu Ser Lys Gly Leu Val
                515                 520                 525

Ala Leu Phe Glu Glu Ala Leu Asn Gln Ser Asn Pro Ser Glu Ala Ile
    530                 535                 540

Arg Lys Leu Val Asp Pro Arg Leu Gly Glu Asn Tyr Pro Ile Asp Ser
545                 550                 555                 560

Val Leu Lys Ile Ala Gln Leu Gly Arg Ala Cys Thr Arg Asp Asn Pro
                565                 570                 575

Leu Leu Arg Pro Ser Met Arg Ser Ile Val Val Ala Leu Met Thr Leu
                580                 585                 590

Ser Ser Pro Thr Glu Asp Phe Asp Asp Glu Thr Ala Ser Tyr Glu Asn
                595                 600                 605

Gln Thr Leu Ile Asn Leu Leu Ser Val Arg
    610                 615

<210> SEQ ID NO 313
<211> LENGTH: 618
<212> TYPE: PRT
<213> ORGANISM: Vigna radiata var. radiata

<400> SEQUENCE: 313

Met Glu Leu Arg Lys Gly Leu Leu Leu Leu Phe Leu Leu Leu Glu Tyr
1               5                   10                  15

Val Cys Cys Asn Val Glu Ala Lys Cys Leu Lys Gly Cys Asp Leu Ala
                20                  25                  30

Leu Ala Ser Tyr Tyr Val Asn Arg Gly Leu Ser Leu Asp Asn Ile Thr
        35                  40                  45

His Leu Met Lys Ser Ser Val Val Ser Asn Ser Asp Asp Ile Ile Ser
    50                  55                  60

Tyr Asn Lys Asn Lys Ile Phe Asn Lys Asn Val Phe Met Phe Asn Arg
65                  70                  75                  80

Tyr Asn Val Pro Phe Pro Cys Asp Cys Ile Arg Asp Glu Phe Leu Gly
                85                  90                  95

His Val Phe Glu Tyr Ser Ala Ala Glu Gly Asp Thr Tyr Asp Ser Ile
                100                 105                 110

Ala Lys Val Glu Tyr Ala Asp Leu Thr Thr Val Glu Leu Leu Arg Arg
        115                 120                 125

Phe Asn Ser Tyr Gly Gln Asn Gly Ile Pro Lys Asn Ala Lys Val Asn
    130                 135                 140

Val Thr Val Asn Cys Ser Cys Gly Asn Ser Gln Val Ser Gln Glu Tyr
145                 150                 155                 160

Gly Leu Phe Ile Thr Tyr Pro Leu Arg Pro Asp Asn Asn Leu His Asp
                165                 170                 175

Ile Ala Asn Glu Ala His Leu Asp Ala Gln Leu Leu Gln Asn Tyr Asn
                180                 185                 190
```

-continued

```
Pro Gly Val Asn Phe Ser Lys Glu Ser Gly Ile Val Phe Ile Pro Gly
        195             200             205

Arg Asp Gln Phe Gly Asp Tyr Val Pro Leu His Pro Arg Lys Thr Gly
        210             215             220

Leu Ala Thr Gly Ala Val Ala Gly Ile Ser Ile Ala Gly Ile Cys Gly
225             230             235             240

Leu Leu Leu Leu Val Ile Cys Ile Tyr Val Lys Phe Phe Lys Lys Met
            245             250             255

Glu Gly Glu Lys Pro Lys Leu Pro Thr Glu Lys Ser Thr Ala Ser Ser
            260             265             270

Ile Gln Asp Ala Ser Gly Ser Ala Glu Tyr Glu Thr Ser Gly Ser Ser
        275             280             285

Gly Thr Ala Thr Ala Thr Gly Leu Thr Gly Ile Met Val Ala Lys Ser
    290             295             300

Met Glu Phe Thr Tyr Gln Glu Leu Ala Lys Ala Thr Asn Asn Phe Ser
305             310             315             320

Leu Glu Asn Lys Ile Gly Gln Gly Gly Phe Gly Ala Val Tyr Tyr Ala
            325             330             335

Glu Leu Arg Gly Glu Lys Thr Ala Ile Lys Lys Met Asp Val Gln Ala
            340             345             350

Ser Thr Glu Phe Leu Cys Glu Leu Lys Val Leu Thr His Val His His
        355             360             365

Leu Asn Leu Val Arg Leu Ile Gly Tyr Cys Val Glu Gly Ser Leu Phe
    370             375             380

Leu Val Tyr Glu His Ile Asp Asn Gly Asn Leu Gly Gln Tyr Leu His
385             390             395             400

Gly Thr Gly Lys Asp Pro Leu Thr Trp Ser Ser Arg Val Gln Ile Ala
            405             410             415

Leu Asp Ser Ala Arg Gly Leu Glu Tyr Ile His Glu His Thr Val Pro
            420             425             430

Val Tyr Ile His Arg Asp Val Lys Ser Ala Asn Ile Leu Ile Asp Lys
        435             440             445

Asn Phe Arg Gly Lys Val Ala Asp Phe Gly Leu Thr Lys Leu Ile Glu
    450             455             460

Val Gly Ser Ser Thr Leu His Thr Arg Leu Val Gly Thr Phe Gly Tyr
465             470             475             480

Met Pro Pro Glu Tyr Ala Gln Tyr Gly Asp Val Ser Pro Lys Val Asp
            485             490             495

Val Tyr Ala Phe Gly Val Val Leu Tyr Glu Leu Ile Ser Ala Lys Asn
            500             505             510

Ala Val Leu Lys Thr Gly Glu Phe Val Ala Glu Ser Lys Gly Leu Val
            515             520             525

Ala Leu Phe Glu Glu Ala Leu Asn Gln Ser Asn Pro Ser Glu Ala Ile
    530             535             540

Arg Lys Leu Val Asp Pro Arg Leu Gly Glu Asn Tyr Pro Ile Asp Ser
545             550             555             560

Val Leu Lys Ile Ala Gln Leu Gly Arg Ala Cys Thr Arg Asp Asn Pro
            565             570             575

Leu Leu Arg Pro Ser Met Arg Ser Ile Val Val Ala Leu Met Thr Leu
            580             585             590

Ser Ser Pro Thr Glu Asp Phe Asp Asp Glu Thr Ala Ser Tyr Glu Asn
            595             600             605

Gln Thr Leu Ile Asn Leu Leu Ser Val Arg
```

-continued

```
     610               615

<210> SEQ ID NO 314
<211> LENGTH: 618
<212> TYPE: PRT
<213> ORGANISM: Vigna unguiculata

<400> SEQUENCE: 314

Met Glu Leu Arg Lys Gly Leu Leu Leu Phe Leu Leu Leu Glu Tyr
1               5                   10                  15

Val Cys Cys Asn Val Glu Ala Lys Cys Leu Lys Gly Cys Asn Val Ala
                20                  25                  30

Leu Gly Ser Tyr Tyr Val Asn Thr Gly Met Ser Leu Asp Val Ile Thr
            35                  40                  45

Pro Leu Met Lys Ser Ser Val Val Ser Asn Ser Asp Asp Ile Ile Ser
        50                  55                  60

Tyr Asn Lys Asp Lys Ile Phe Asn Lys Asn Val Phe Tyr Phe Asp Arg
65                  70                  75                  80

Ile Asn Val Pro Phe Pro Cys Asp Cys Ile Ser Asp Glu Phe Leu Gly
                85                  90                  95

His Val Phe Glu Tyr Ser Ala Ala Glu Gly Asp Thr Tyr Asp Ser Ile
            100                 105                 110

Ala Lys Val Glu Tyr Ala Asp Leu Thr Thr Val Glu Leu Leu Arg Arg
        115                 120                 125

Phe Asn Ser Tyr Gly Gln Asn Gly Ile Pro Lys Asn Ala Lys Val Asn
        130                 135                 140

Val Thr Val Asn Cys Ser Cys Gly Asn Ser Gln Val Ser Gln Asp Tyr
145                 150                 155                 160

Gly Leu Phe Ile Thr Tyr Pro Leu Arg Pro Gly Asn Asn Leu His Asp
                165                 170                 175

Ile Ala Asn Glu Ala His Leu Asp Ala Gln Leu Leu Gln Asn Tyr Asn
            180                 185                 190

Pro Gly Val Asn Phe Ser Lys Glu Ser Gly Ile Val Phe Ile Pro Gly
        195                 200                 205

Arg Asp Gln Phe Gly Glu Tyr Val Pro Leu His Pro Arg Asn Thr Gly
        210                 215                 220

Leu Ala Lys Gly Asp Val Ala Gly Ile Ser Ile Ala Gly Ile Cys Gly
225                 230                 235                 240

Leu Leu Leu Leu Val Ile Cys Ile Tyr Val Lys Phe Phe Lys Lys Lys
                245                 250                 255

Glu Gly Glu Lys Pro Lys Leu Pro Thr Glu Asn Ser Thr Ala Phe Ser
            260                 265                 270

Thr Gln Asp Ala Ser Gly Ser Ala Glu Tyr Glu Ile Ser Gly Ser Ser
        275                 280                 285

Gly Thr Thr Thr Ala Ala Gly Leu Thr Gly Ile Met Val Ala Lys Ser
        290                 295                 300

Met Glu Phe Thr Tyr Gln Glu Leu Ala Lys Ala Thr Asn Asn Phe Ser
305                 310                 315                 320

Leu Glu Asn Lys Ile Gly Gln Gly Gly Phe Gly Ala Val Tyr Tyr Ala
                325                 330                 335

Glu Leu Arg Gly Glu Lys Thr Ala Ile Lys Lys Met Asp Val Gln Ala
            340                 345                 350

Ser Thr Glu Phe Leu Cys Glu Leu Lys Val Leu Thr His Val His His
        355                 360                 365
```

-continued

```
Leu Asn Leu Val Arg Leu Ile Gly Tyr Cys Val Glu Gly Ser Leu Phe
    370             375             380

Leu Val Tyr Glu His Ile Asp Asn Gly Asn Leu Gly Gln Tyr Leu His
385             390             395             400

Gly Thr Gly Lys Asp Pro Leu Pro Trp Ser Ser Arg Val Gln Ile Ala
            405             410             415

Leu Asp Ser Ala Arg Gly Leu Glu Tyr Ile His Glu His Thr Val Pro
            420             425             430

Val Tyr Ile His Arg Asp Val Lys Ser Ala Asn Ile Leu Ile Asp Lys
            435             440             445

Asn Phe Arg Gly Lys Val Ala Asp Phe Gly Leu Thr Lys Leu Ile Glu
    450             455             460

Val Gly Gly Ser Thr Leu His Thr Arg Leu Val Gly Thr Phe Gly Tyr
465             470             475             480

Met Pro Pro Glu Tyr Ala Gln Tyr Gly Asp Val Ser Pro Lys Val Asp
            485             490             495

Val Tyr Ala Phe Gly Val Val Leu Tyr Glu Leu Ile Ser Ala Lys Asn
            500             505             510

Ala Val Leu Lys Thr Gly Glu Phe Val Ala Glu Ser Lys Gly Leu Val
            515             520             525

Ala Leu Phe Glu Glu Ala Leu Asn Gln Ser Asn Pro Ser Glu Ala Ile
    530             535             540

Arg Lys Leu Val Asp Pro Arg Leu Gly Glu Asn Tyr Pro Ile Asp Ser
545             550             555             560

Val Leu Lys Ile Ala Gln Leu Gly Arg Ala Cys Thr Arg Asp Asn Pro
            565             570             575

Leu Leu Arg Pro Ser Met Arg Ser Ile Val Val Ala Leu Met Thr Leu
            580             585             590

Ser Ser Pro Thr Glu Asp Phe Glu Asp Glu Thr Ala Ser Tyr Glu Asn
            595             600             605

Gln Thr Leu Ile Asn Leu Leu Ser Val Arg
    610             615
```

```
<210> SEQ ID NO 315
<211> LENGTH: 629
<212> TYPE: PRT
<213> ORGANISM: Arachis duranensis

<400> SEQUENCE: 315
```

```
Met Lys Leu Lys Arg Ser Phe Leu Leu Phe Phe Leu Leu Leu Glu Cys
1               5               10              15

Ser Cys Phe Ile Asn Leu Glu Ser Lys Cys Leu Lys Gly Cys Asp Leu
            20              25              30

Ala Ile Ala Ser Tyr Phe Val Tyr Pro Gly Val Met Leu Gly Ser Ile
            35              40              45

Ala Ser Phe Met His Ser Asn Val Val Pro Asn Ser Asn Val Ile Ile
    50              55              60

Ser Tyr Asn Lys Asp Lys Met Pro Asn Asn Leu Pro Val Ser Phe Ser
65              70              75              80

Arg Ile Asn Ile Pro Phe Pro Cys Asp Cys Ile Asn Gly Glu Phe Leu
            85              90              95

Gly His Val Phe Glu Tyr Ser Ala Ile Glu Gly Asp Thr Tyr Asp Leu
            100             105             110

Ile Ala Asn Leu Arg Tyr Ser Asp Leu Thr Thr Val Glu Ile Leu Gln
            115             120             125
```

-continued

```
Arg Phe Asn Asn Tyr Asp Pro Asn His Val Pro Val Asn Ala Lys Val
    130             135             140

Asn Val Thr Val Asn Cys Ser Cys Gly Asn Ser Asn Val Ser Lys Asp
145             150             155             160

Tyr Gly Leu Phe Val Thr Phe Pro Leu Ser Glu Gly Asn Thr Leu Leu
            165             170             175

Gln Ile Ala Asn Gln Thr Lys Leu Asp Pro Lys Leu Leu Gln Ser Tyr
            180             185             190

Asn Pro Gly Val Asn Phe Asn Gln Thr Arg Gly Ile Val Phe Ile Pro
        195             200             205

Ala Arg Asp Gln Asn Gly Val Tyr Val Pro Leu Tyr Pro Arg Thr Gly
    210             215             220

Leu Ala Lys Gly Val Ala Val Gly Ile Ser Ile Ala Gly Thr Ser Gly
225             230             235             240

Val Leu Leu Leu Leu Ile Cys Ala Cys Val Arg Tyr Phe Gln Lys Lys
            245             250             255

Glu Glu Glu Lys Ile Lys Leu Pro Thr Glu Asp Phe Ile Ser Ser Ser
            260             265             270

Thr Gln Asp Ala Ser Ser Ser Gly Glu Tyr Glu Thr Ser Gly Ser Thr
    275             280             285

Ala Ala Ser Ala Ser Gly Leu Pro Ala Ile Met Ala Ala Lys Ser Met
    290             295             300

Glu Phe Ser Tyr Gln Glu Leu Ser Lys Ala Thr Asn Asn Phe Ser Ser
305             310             315             320

Asp Asn Lys Ile Gly Gln Gly Gly Phe Gly Ala Val Tyr Phe Ala Glu
            325             330             335

Leu Arg Gly Gln Lys Ala Ala Ile Lys Lys Met Asp Val Gln Ala Ser
            340             345             350

Thr Glu Phe Leu Ser Glu Leu Lys Val Leu Thr His Val His His Leu
    355             360             365

Asn Leu Val Arg Leu Ile Gly Tyr Cys Val Glu Gly Ser Leu Phe Leu
    370             375             380

Val Tyr Glu Tyr Ile Glu Asn Gly Asn Leu Gly Gln Tyr Leu His Gly
385             390             395             400

Thr Gly Arg Glu Pro Leu Ala Trp Leu Thr Arg Val Gln Ile Ala Leu
            405             410             415

Asp Ser Ala Arg Gly Leu Glu Tyr Ile His Glu His Thr Val Pro Val
            420             425             430

Tyr Ile His Arg Asp Val Lys Pro Ala Asn Ile Leu Ile Asp Lys Asp
        435             440             445

Phe Arg Gly Lys Val Ala Asp Phe Gly Leu Thr Lys Leu Arg Glu Val
    450             455             460

Gly Ser Ser Leu Ser Leu His Thr Arg Leu Val Gly Thr Phe Gly Tyr
465             470             475             480

Met Pro Pro Glu Tyr Ala Gln Tyr Gly Asp Val Ser Pro Lys Val Asp
            485             490             495

Val Tyr Ala Phe Gly Val Val Leu Tyr Glu Leu Ile Ser Ala Lys Asn
            500             505             510

Ala Val Leu Lys Thr Gly Glu Thr Val Ala Glu Ser Ser Lys Gly Leu
    515             520             525

Val Thr Leu Phe Glu Glu Ala Leu Asp Lys Ser Asp Pro Ser Lys Ala
    530             535             540
```

```
Ile Arg Lys Leu Val Asp Pro Arg Leu Gly Glu Asn Tyr Ser Ile Asp
545                 550                 555                 560

Ser Val Leu Lys Val Ala Glu Leu Gly Arg Ala Cys Thr Arg Asp Asn
                565                 570                 575

Pro Leu Leu Arg Pro Ser Met Arg Ser Val Val Val Ala Leu Met Thr
                580                 585                 590

Leu Leu Ala Ser Ser Thr Ser Ile Glu Asn Cys Asp Asp Asp Asp
                595                 600                 605

Asp Asp Asp Asp Asp Asp Asn Ser Tyr Glu Asn Arg Thr Leu Ile Asp
        610                 615                 620

Gln Leu Ser Val Arg
625

<210> SEQ ID NO 316
<211> LENGTH: 630
<212> TYPE: PRT
<213> ORGANISM: Arachis ipaensis

<400> SEQUENCE: 316

Met Lys Leu Lys Lys Ser Phe Leu Leu Phe Phe Leu Leu Leu Glu Cys
1               5                   10                  15

Ser Cys Phe Ile Asn Leu Glu Ser Lys Cys Leu Lys Gly Cys Asp Leu
                20                  25                  30

Ala Ile Ala Ser Tyr Phe Val Tyr Pro Lys Val Met Leu Gly Ser Ile
            35                  40                  45

Ala Ser Phe Met His Ser Asn Val Val Pro Asn Ser Asn Val Ile Ile
        50                  55                  60

Ser Tyr Asn Lys Asp Lys Met Pro Asn Asn Leu Pro Val Ser Phe Thr
65                  70                  75                  80

Arg Ile Asn Ile Pro Phe Pro Cys Asp Cys Ile Asn Gly Glu Phe Leu
                85                  90                  95

Gly His Val Phe Glu Tyr Ser Ala Ile Glu Gly Asp Thr Tyr Asp Leu
                100                 105                 110

Ile Ala Asn Met Arg Tyr Ser Asp Leu Thr Thr Val Glu Ile Leu Gln
            115                 120                 125

Arg Phe Asn Asn Tyr Asp Pro Asn His Val Pro Val Asn Ala Lys Val
        130                 135                 140

Asn Val Thr Val Asn Cys Ser Cys Gly Asn Ser Asn Val Ser Lys Asp
145                 150                 155                 160

Tyr Gly Leu Phe Val Thr Phe Pro Leu Ser Glu Gly Asn Thr Leu Leu
                165                 170                 175

Gln Ile Ala Asn Gln Thr Lys Leu Asp Pro Lys Leu Leu Gln Gly Tyr
            180                 185                 190

Asn Pro Gly Val Asn Phe Asn Gln Thr Arg Gly Ile Val Phe Ile Pro
        195                 200                 205

Gly Arg Asp Gln Asn Gly Val Tyr Val Pro Leu Tyr Pro Arg Thr Gly
        210                 215                 220

Leu Ala Lys Gly Val Ala Val Gly Ile Ser Ile Ala Gly Thr Ser Gly
225                 230                 235                 240

Val Leu Leu Leu Leu Ile Cys Ala Cys Val Arg Tyr Phe Gln Lys Lys
                245                 250                 255

Glu Glu Glu Lys Ile Lys Leu Pro Thr Glu Asp Phe Ile Ser Ser Ser
            260                 265                 270

Thr Gln Val Ala Ser Ser Ser Gly Glu Tyr Glu Thr Ser Gly Ser Thr
            275                 280                 285
```

-continued

```
Ala Ala Ser Ala Ser Gly Leu Pro Ala Ile Met Ala Ala Lys Ser Met
    290                 295                 300

Glu Phe Ser Tyr Gln Glu Leu Ala Lys Ala Thr Asn Asn Phe Ser Ser
305                 310                 315                 320

Asp Asn Lys Ile Gly Gln Gly Gly Phe Gly Ala Val Tyr Phe Ala Glu
                325                 330                 335

Leu Arg Gly Gln Lys Ala Ala Ile Lys Lys Met Asp Val Gln Ala Ser
                340                 345                 350

Thr Glu Phe Leu Ser Glu Leu Lys Val Leu Thr His Val His His Leu
                355                 360                 365

Asn Leu Val Arg Leu Ile Gly Tyr Cys Val Glu Gly Ser Leu Phe Leu
    370                 375                 380

Val Tyr Glu Tyr Ile Glu Asn Gly Asn Leu Gly Gln Tyr Leu His Gly
385                 390                 395                 400

Thr Glu Arg Glu Pro Leu Ala Trp Ser Thr Arg Val Gln Ile Ala Leu
                405                 410                 415

Asp Ser Ala Arg Gly Leu Glu Tyr Ile His Glu His Thr Val Pro Val
                420                 425                 430

Tyr Ile His Arg Asp Val Lys Pro Ala Asn Ile Leu Ile Asp Lys Asp
                435                 440                 445

Phe Arg Gly Lys Val Ala Asp Phe Gly Leu Thr Lys Leu Arg Glu Val
    450                 455                 460

Gly Ser Ser Leu Ser Leu His Thr Arg Leu Val Gly Thr Phe Gly Tyr
465                 470                 475                 480

Met Pro Pro Glu Tyr Ala Gln Tyr Gly Asp Val Ser Pro Lys Val Asp
                485                 490                 495

Val Tyr Ala Phe Gly Val Val Leu Tyr Glu Leu Ile Ser Ala Lys Asn
                500                 505                 510

Ala Val Leu Lys Thr Gly Glu Thr Val Ala Glu Ser Ser Lys Gly Leu
                515                 520                 525

Val Thr Leu Phe Glu Glu Ala Leu Asn Lys Ser Asp Pro Ser Lys Ala
    530                 535                 540

Ile Arg Lys Leu Val Asp Pro Arg Leu Gly Glu Asn Tyr Pro Ile Asp
545                 550                 555                 560

Ser Val Leu Lys Val Ala Glu Leu Gly Arg Ala Cys Thr Arg Asp Asn
                565                 570                 575

Pro Leu Leu Arg Pro Ser Met Arg Ser Val Val Val Ala Leu Met Thr
                580                 585                 590

Leu Leu Ala Ser Ser Thr Ser Ile Glu Asp Cys Asp Asp Asn Asp Asp
                595                 600                 605

Asp Asp Asp Asp Asp Asp Asn Ser Tyr Glu Asn Arg Thr Leu Ile
    610                 615                 620

Asp Gln Leu Ser Val Arg
625                 630

<210> SEQ ID NO 317
<211> LENGTH: 550
<212> TYPE: PRT
<213> ORGANISM: Chamaecrista fasciculata

<400> SEQUENCE: 317

Met Lys Pro Leu Leu Ala Leu Ala Leu Leu Phe Leu Leu Leu Glu Thr
1               5                   10                  15

Ala Phe Leu Asn Val Glu Ser Met Cys Ile Lys Gly Cys Asp Leu Ala
```

-continued

```
                    20                25                30
Leu Ala Ser Tyr Tyr Ile Pro Leu Phe Phe Thr Leu Gln Asn Leu Thr
            35                40                45
Ile Leu Leu Gln Ser Lys Val Leu Ser Asp Tyr Gln Val Ile Ala Ser
        50                55                60
Phe Asn Lys Asp Ser Ile Phe Asn Gly Val Asn Ile Lys Ser Tyr Gln
65                70                75                80
Ser Ile Asn Val Pro Phe Pro Cys Asp Cys Ile Asp Gly Asp Phe Leu
                85                90                95
Gly His Val Phe Glu Tyr Thr Ile Ala Asn Gly Asp Thr Tyr Glu Arg
            100               105               110
Ile Ala Ser Arg Lys Tyr Ala Met Leu Thr Ser Val Glu Leu Leu Lys
            115               120               125
Lys Tyr Asn Asn Tyr Ser Asp Pro Asn His Leu Pro Ile Asn Gly Lys
        130               135               140
Leu Asn Val Thr Val Asn Cys Tyr Cys Gly Asp Arg Gln Ile Ser Lys
145               150               155               160
Asp Tyr Gly Leu Phe Val Thr Tyr Pro Leu Arg Asp Gly Asp Ser Leu
                165               170               175
Gln Thr Ile Ala Glu Lys Thr Asn Leu Asp Leu Gly Leu Leu Glu Arg
            180               185               190
Tyr Asn Gln Gly Met Asn Phe Ser Gln Gly Ser Gly Leu Val Phe Tyr
            195               200               205
Pro Gly Lys Gly Leu Arg Gly Ser Ala Ile Thr Gly Met Ser Ile Gly
        210               215               220
Gly Met Leu Gly Ser Leu Leu Val Ala Ile Tyr Ile Tyr Leu Arg Tyr
225               230               235               240
Tyr Arg Lys Lys Ala Val Lys Val Ala Leu Thr Thr Glu Asp Ser Thr
            245               250               255
Asp Leu Ser Thr Gln Asp Ala Ser Gly Ser Ala Gly Tyr Asp Thr Ser
            260               265               270
Gly Ser Gly Asn Ser Ala Ala Gly Leu Lys Gly Ile Val Val Ser Lys
        275               280               285
Ser Val Glu Phe Ser Tyr Gln Glu Ile Ala Lys Ala Thr Asn Asn Phe
    290               295               300
Ser Phe Asp Asn Lys Ile Gly Gln Gly Gly Phe Gly Ala Val Tyr Tyr
305               310               315               320
Ala Glu Leu Arg Gly Glu Lys Thr Ala Ile Lys Lys Met Asp Ile Glu
            325               330               335
Ala Ser Gln Glu Phe Leu Ala Glu Leu Lys Val Leu Thr His Val His
            340               345               350
His Leu Asn Leu Val Ser His Leu Ser Met Lys Gly Glu Arg Gln Cys
        355               360               365
His Gly Leu Arg Gly Cys Lys Leu Leu Trp Ile Gln Gln Glu Val Ala
    370               375               380
Asp Phe Gly Leu Ser Lys Leu Ile Glu Val Gly Asn Ala Ser Leu Asn
385               390               395               400
Thr Arg Leu Val Gly Thr Phe Gly Tyr Met Ser Pro Glu Tyr Ala Gln
            405               410               415
Tyr Gly Ile Thr Ser Pro Lys Ile Asp Val Tyr Ala Phe Gly Val Val
            420               425               430
Leu Tyr Glu Leu Ile Ser Ala Lys Asn Ala Val Leu Lys Thr Gly Glu
        435               440               445
```

```
Cys Val Gly Val Ala Glu Ser Lys Gly Leu Val Thr Leu Phe Glu Glu
    450             455             460

Ala Leu Arg Trp Pro Asp Pro Ile Glu Gly Leu Arg Lys Leu Val Asp
465             470             475             480

Pro Lys Leu Gly Glu Asn Tyr Pro Ile Asp Ser Ile Tyr Lys Met Ala
                485             490             495

Gln Leu Ala Arg Ala Cys Thr Gln Glu Asp Pro Gln Leu Arg Pro Ser
            500             505             510

Met Arg Ser Ile Val Val Ala Leu Met Thr Leu Ser Ser Tyr Gly Glu
            515             520             525

Asp Cys Asp His Val Asp Ser Asn Leu Tyr Asp Asn Gln Thr Leu Ile
            530             535             540

Asn Met Leu Ser Glu Arg
545             550

<210> SEQ ID NO 318
<211> LENGTH: 594
<212> TYPE: PRT
<213> ORGANISM: Mimosa pudica

<400> SEQUENCE: 318

Met Gln Pro Lys Ser His Asn Ala Leu Val Leu Ala Val Phe Phe Gln
1               5               10              15

Ile Leu Leu Leu Glu Thr Thr Phe Leu Ile Asn Asn Val Glu Ser Lys
            20              25              30

Cys His Lys Gly Cys Pro Leu Ala Leu Ala Ser Tyr Leu Cys His Gln
            35              40              45

Asn Ile Thr Leu Ser Asn Ile Thr His Leu Leu Lys Ser Asn Leu Val
    50              55              60

Ser Leu Asp Phe Gln Ile Ile Ser Ser Tyr Asn Lys Glu Gly Ile Val
65              70              75              80

Pro Asn Asn Ile Gln Phe Phe Thr Arg Ile Asn Ile Pro Phe Pro Cys
                85              90              95

Glu Cys Ile Asn Asn Asp Asp Phe Leu Gly His Val Phe Glu Tyr Thr
            100             105             110

Ile Ser Lys Gly Asp Thr Tyr His Ser Ile Ala Thr Gln Thr Tyr Ser
            115             120             125

Ser Leu Thr Ser Val Asp Leu Leu Arg Arg Phe Asn Asn Tyr Ser Asp
    130             135             140

Pro Asn Gln Leu Pro Pro Asn Gly Lys Leu Asn Val Thr Val Lys Cys
145             150             155             160

Ser Cys Gly Asn Arg Gln Ile Ser Lys Asp Tyr Gly Leu Phe Ile Thr
                165             170             175

Tyr Pro Leu Gly Phe Glu Asp Ser Leu Glu Ser Ile Val Asn Gln Thr
                180             185             190

Gly Ile Asp Ala Leu Leu Leu Gln Ser Tyr Asn Pro Gly Ala Asn Phe
            195             200             205

Ser Gln Gln Ser Gly Val Val Phe Ile Pro Gly Arg Ala Asp Gln Thr
    210             215             220

Gly Asn Tyr Met Pro Leu Asp Tyr Ile Arg Ser Gly Arg Leu Arg Gly
225             230             235             240

Thr Ala Ile Ala Gly Ile Ser Val Ala Ala Thr Phe Val Phe Leu Leu
                245             250             255

Leu Ala Ala Tyr Val Phe Val Arg Tyr Phe Arg Lys Lys Glu Asn Ala
```

```
                260             265             270
Lys Leu Ala Leu Phe Ser Glu Asn Ser Ala Glu Leu Ser Ser Gln Glu
            275             280             285

Gly Ser Ser Gly Val Ala Ser Thr Thr Asp Leu Arg Gly Ile Met Glu
        290             295             300

Glu Lys Ser Met Glu Phe Ser Tyr Gln Glu Ile Ala Lys Ala Thr Asn
305             310             315             320

Asn Phe Ser Ser Asp Asn Arg Ile Gly Gln Gly Gly Phe Gly Thr Val
            325             330             335

Tyr Tyr Ala Glu Leu Arg Gly Gln Lys Thr Ala Ile Lys Lys Met Asp
            340             345             350

Ile Lys Ala Ser Gln Gly Phe Leu Ser Glu Leu Lys Val Leu Thr His
            355             360             365

Val His His Leu Asn Leu Cys Phe Phe His Tyr Ile Asn Val Asn Ile
            370             375             380

Tyr Asn Asp Phe Asp Gln Glu Lys Ile Tyr Asn Lys Ile Tyr Cys Leu
385             390             395             400

Asn Val Leu Pro Trp Ser Thr Arg Val Gln Ile Ala Leu Asp Ser Ala
            405             410             415

Arg Gly Leu Glu Tyr Ile His Glu His Thr Val Pro Thr Tyr Ile His
            420             425             430

Arg Asp Val Lys Ser Leu Asn Ile Leu Ile Asp Lys Thr Tyr His Ala
            435             440             445

Lys Val Val Ala Asp Phe Gly Leu Ser Lys Leu Ile Glu Val Gly Asn
            450             455             460

Ala Ser Leu Asn Thr Arg Arg Leu Val Gly Thr Phe Gly Tyr Met Ser
465             470             475             480

Pro Glu Tyr Ala Gln Tyr Gly Ile Gln Ser Pro Lys Ile Asp Val Tyr
            485             490             495

Ala Phe Gly Val Val Leu Tyr Glu Leu Ile Ser Ala Lys Asn Ala Val
            500             505             510

Leu Lys Ile Thr Asn Glu Phe Val Ala Glu Ser Lys Gly Leu Val Ala
            515             520             525

Leu Phe Glu Lys Cys Leu Arg Arg Pro Asp Ala Val Glu Asp Leu Arg
        530             535             540

Asn Leu Val Asp Pro Arg Leu Gly Gln Asn Tyr Pro Ile Glu Ser Val
545             550             555             560

Tyr Lys Val Gln Lys Leu Phe Glu Tyr Glu Ser Gly Leu Asp Ser Leu
            565             570             575

Asn Phe Glu Ile Leu Lys Phe Phe Ile Lys Asn Ser Lys Arg Lys Val
            580             585             590

Val Thr
```

```
<210> SEQ ID NO 319
<211> LENGTH: 626
<212> TYPE: PRT
<213> ORGANISM: Lupinus albus

<400> SEQUENCE: 319

Met Lys Leu Lys Phe Val Phe Leu Leu Leu Leu Glu Tyr Val Cys Phe
1               5               10              15

Thr Val Glu Ser Lys Cys Ile Lys Gly Cys Asp Ile Ala Leu Ala Ser
            20              25              30

Tyr Tyr Val Pro Val Trp Pro Thr Val Ser Leu Gly Asn Ile Thr Asn
```

-continued

```
              35                  40                  45

Tyr Met Tyr Ser Asn Val Leu Thr Lys Ser Asn Val Ile Ile Ser Tyr
    50                  55                  60

Asn Lys Asp Lys Val Phe Asn Gly Asp Val Met Leu Ala Leu Tyr Arg
65                  70                  75                  80

Thr Asn Ile Pro Ile Pro Cys Asp Cys Ile Gly Gly Glu Phe Leu Gly
                85                  90                  95

His Val Phe Glu Tyr Thr Ala Val Ala Gly Asp Thr Tyr Asp Leu Ile
            100                 105                 110

Ala Met Lys Arg Tyr Ser Asn Leu Thr Thr Val Glu Phe Leu Lys Arg
            115                 120                 125

Phe Asn Ser Tyr Asp Pro Asn His Ile Pro Val Asn Ala Lys Val Asn
    130                 135                 140

Val Thr Val Asn Cys Ser Cys Gly Asn Ser Leu Ile Ser Lys Asp Tyr
145                 150                 155                 160

Gly Leu Phe Ile Thr Tyr Pro Leu Arg Pro Gly Asn Asn Leu Gln Glu
                165                 170                 175

Leu Ser Lys Glu Thr Asn Ile Asp Ala Lys Leu Leu Gln Ser Tyr Asn
            180                 185                 190

Pro Ser Val Asn Phe Ser Gln Glu Asn Gly Ile Val Phe Ile Pro Gly
            195                 200                 205

Arg Asp Gln Asn Gly Val Tyr Val Pro Leu Tyr Pro Arg Thr Glu Gly
    210                 215                 220

Leu Ala Arg Gly Val Ala Val Gly Ile Ser Ile Ala Ala Ser Cys Gly
225                 230                 235                 240

Leu Val Leu Leu Val Ile Cys Ile Tyr Asp Arg Tyr Phe Lys Lys Lys
                245                 250                 255

Glu Gly Glu Lys Ala Lys Leu Ser Ile Glu Asn Ser Leu Val Leu Ser
            260                 265                 270

Thr Gln Asp Ala Ser Gly Ser Ser Glu Tyr Glu Thr Ser Gly Ser Ser
            275                 280                 285

Val His Ala Ser Gly Leu Thr Gly Ile Met Val Ala Lys Ser Leu Glu
    290                 295                 300

Phe Ser Tyr Gln Glu Leu Ala Lys Ala Thr Asn Asn Phe Ser Leu Asp
305                 310                 315                 320

Asn Lys Ile Gly Gln Gly Gly Phe Gly Ala Val Tyr Tyr Ala Glu Leu
            325                 330                 335

Arg Gly Glu Lys Thr Ala Ile Lys Lys Met Asp Val Gln Ala Ser Ser
            340                 345                 350

Glu Phe Leu Ala Glu Leu Lys Val Leu Thr His Val His His Leu Asn
    355                 360                 365

Leu Val Arg Leu Ile Gly Tyr Cys Val Glu Gly Ser Leu Phe Leu Val
    370                 375                 380

Tyr Glu His Ile Asp Asn Gly Asn Leu Gly Gln Tyr Leu His Gly Lys
385                 390                 395                 400

Gly Lys Asp Pro Leu Pro Trp Ser Thr Arg Leu Gln Ile Ala Leu Asp
                405                 410                 415

Ser Ala Arg Gly Leu Glu Tyr Ile His Glu His Thr Val Pro Leu Tyr
            420                 425                 430

Ile His Arg Asp Val Lys Ser Ala Asn Ile Leu Ile Asp Lys Asn Leu
    435                 440                 445

Arg Gly Lys Val Ala Asp Phe Gly Leu Thr Lys Leu Ile Glu Val Gly
    450                 455                 460
```

-continued

```
Thr Ser Ser Leu His Thr Arg Leu Val Gly Thr Phe Gly Tyr Met Pro
465                 470                 475                 480

Pro Glu Tyr Ala Gln Tyr Gly Asp Ile Ser Pro Lys Ile Asp Val Tyr
                485                 490                 495

Ala Phe Gly Val Val Leu Tyr Glu Leu Ile Ser Ala Lys Asn Ala Val
                500                 505                 510

Leu Lys Thr Gly Glu Thr Val Ala Glu Ser Lys Gly Leu Val Ser Leu
            515                 520                 525

Phe Glu Gly Ala Leu Asn His Ile Asn Pro Leu Glu Ala Leu Ser Thr
            530                 535                 540

Leu Val Asp Pro Arg Leu Gly Asp Asn Tyr Pro Ile Glu Ser Val Leu
545                 550                 555                 560

Lys Ile Ala Gln Val Gly Arg Ala Cys Thr Arg Asp Asn Pro Ile Leu
                565                 570                 575

Arg Pro Asn Met Lys Ser Ile Val Val Ala Leu Met Thr Leu Ser Ser
                580                 585                 590

Ser Thr His Gln Asp His Thr Ser Ser Ser Tyr Asp His Gln Thr
            595                 600                 605

Leu Ile Asn Leu Leu Leu Asp Glu Gly Phe Arg Gly Ile Ile Thr Pro
    610                 615                 620

Thr Phe
625

<210> SEQ ID NO 320
<211> LENGTH: 644
<212> TYPE: PRT
<213> ORGANISM: Spatholobus suberectus

<400> SEQUENCE: 320

Met Phe Leu Leu Phe Gly Leu Arg Asp Pro Met Lys Leu Lys Lys Gly
1               5                   10                  15

Leu Leu Phe Phe Leu Leu Leu Glu Tyr Val Cys Arg Ser Val Glu Ser
            20                  25                  30

Lys Cys Val Lys Gly Cys Asp Val Ala Leu Ala Ser Tyr Tyr Val Ser
            35                  40                  45

Pro Gly Tyr Phe Pro Leu Glu Asn Ile Thr Arg Leu Met Glu Ser Ser
    50                  55                  60

Val Leu Ser Asn Ser Asp Val Val Thr Ser Tyr Asn Lys Asp Lys Ile
65                  70                  75                  80

Phe Asn Asp Met Val Gln Ser Phe Val Arg Leu Asn Ile Pro Phe Ser
                85                  90                  95

Cys Gly Cys Ile Gly Gly Glu Phe Leu Gly His Val Phe Glu Tyr Ser
                100                 105                 110

Ala Ala Ala Gly Asp Thr Tyr Asp Ser Ile Ala Lys Val Thr Tyr Ala
            115                 120                 125

Asn Leu Thr Thr Val Glu Leu Leu Arg Arg Phe Asn Ser Tyr Asp Gln
    130                 135                 140

Asn Asp Ile Pro Ala Asn Ala Lys Leu Asn Val Thr Val Asn Cys Ser
145                 150                 155                 160

Cys Gly Asn Ser Gln Val Ser Lys Asp Tyr Gly Leu Phe Ile Thr Tyr
                165                 170                 175

Pro Leu Arg Pro Gly Asn Asn Leu His Asp Ile Ala Asn Glu Thr Gln
            180                 185                 190

Leu Asp Ala Gln Leu Leu Gln Ser Tyr Asn Pro Gly Val Asn Phe Ser
```

-continued

```
              195                 200                 205

Gln Glu Ser Gly Ile Val Phe Ile Pro Gly Arg Gly Ile Leu Ser Phe
    210                 215                 220

Ser His His Val His Leu Val His Ser Ser Leu Tyr Phe Asp Gln Asn
225                 230                 235                 240

Gly Asp Tyr Val Pro Leu Tyr Pro Arg Lys Thr Gly Leu Ala Arg Gly
                245                 250                 255

Ala Ala Val Gly Ile Ser Ile Ala Gly Ile Cys Gly Leu Leu Leu Leu
                260                 265                 270

Val Ile Phe Val Tyr Val Arg Tyr Phe Gln Asn Lys Glu Gly Lys Lys
                275                 280                 285

Asp Lys Leu Pro Thr Glu Asn Ser Met Val Phe Ser Thr Gln Asp Gly
    290                 295                 300

Thr Glu Tyr Glu Thr Ser Gly Ser Ser Gly Leu Ala Thr Ala Ser Ala
305                 310                 315                 320

Ala Gly Leu Thr Gly Ile Met Val Ala Lys Ser Met Glu Phe Ser Tyr
                325                 330                 335

Gln Glu Leu Ala Lys Ala Thr Asn Asn Phe Ser Leu Glu Asn Lys Ile
                340                 345                 350

Gly Gln Gly Gly Phe Gly Ala Val Tyr Tyr Ala Glu Leu Gly Gly Glu
                355                 360                 365

Lys Thr Ala Ile Lys Lys Met Asp Val Gln Ala Ser Thr Glu Phe Leu
    370                 375                 380

Cys Glu Leu Lys Val Leu Thr His Val His His Leu Asn Leu Val Arg
385                 390                 395                 400

Leu Ile Gly Tyr Cys Val Glu Gly Ser Leu Phe Leu Val Tyr Glu Tyr
                405                 410                 415

Ile Asp Asn Gly Asn Leu Gly Gln Tyr Leu His Gly Thr Gly Lys Asp
                420                 425                 430

Pro Leu Pro Trp Ser Ser Arg Val Gln Ile Ala Leu Asp Ser Ala Arg
                435                 440                 445

Gly Leu Glu Tyr Ile His Glu His Thr Val Pro Val Tyr Ile His Arg
    450                 455                 460

Asp Val Lys Ser Ala Asn Ile Leu Ile Asp Lys Asn Leu Arg Gly Lys
465                 470                 475                 480

Val Ala Asp Phe Gly Leu Thr Lys Leu Ile Glu Val Gly Gly Ser Thr
                485                 490                 495

Leu His Thr Arg Leu Val Gly Thr Phe Gly Tyr Met Pro Pro Glu Tyr
                500                 505                 510

Ala Gln Tyr Gly Asp Ile Ser Pro Lys Val Asp Val Tyr Ala Phe Gly
                515                 520                 525

Val Val Leu Tyr Glu Leu Ile Ser Ala Lys Asn Ala Val Leu Lys Thr
    530                 535                 540

Gly Glu Ser Val Ala Glu Thr Lys Gly Leu Val Ala Leu Phe Glu Glu
545                 550                 555                 560

Ala Leu Ser Gln Ser Asn Pro Ser Glu Gly Ile Arg Lys Leu Val Asp
                565                 570                 575

Pro Arg Leu Gly Glu Asn Tyr Pro Val Asp Ser Val Leu Lys Ile Ala
                580                 585                 590

Gln Leu Gly Arg Ala Cys Thr Arg Asp Asn Pro Leu Leu Arg Pro Ser
                595                 600                 605

Met Arg Ser Ile Val Val Ala Leu Met Thr Leu Ser Ser Pro Thr Glu
    610                 615                 620
```

```
Asp Cys Asp Asp Asp Ala Ser Tyr Glu Asn Gln Thr Leu Ile Asn Leu
625                 630                 635                 640

Leu Ser Val Arg

<210> SEQ ID NO 321
<211> LENGTH: 629
<212> TYPE: PRT
<213> ORGANISM: Prosopis alba

<400> SEQUENCE: 321

Met Gln Pro Lys Ser Asn Ser Leu Val Leu Val Phe Phe Leu Leu Leu
1               5                   10                  15

Leu Glu Thr Ser Leu Leu Asn Asn Val Glu Ser Lys Cys Leu Gln Gly
                20                  25                  30

Cys Pro Leu Ala Leu Ala Ser Tyr Tyr Ala Tyr Lys Asn Asn Leu Gly
            35                  40                  45

Asn Ile Thr Lys Phe Leu Arg Ser Asp Leu Val Ser Asp Phe Gly Val
        50                  55                  60

Val Ser Ser Tyr Asn Glu Gly Lys Val Ser Asn Asn Gly Met Tyr Val
65                  70                  75                  80

Gln Ser Leu Thr Arg Ile Asn Ile Pro Phe Pro Cys Asp Cys Ile Asn
                85                  90                  95

Asn Gly Asp Phe Leu Gly His Val Phe Glu Tyr Thr Ile Ala Glu Gly
            100                 105                 110

Asp Thr Tyr Asp Ser Ile Ala Thr Gln Thr Tyr Ser Ser Leu Thr Thr
        115                 120                 125

Val Asp Leu Leu Arg Arg Phe Asn Ser Tyr Lys Asp Pro Asn Gln Leu
    130                 135                 140

Pro Leu Asn Gly Lys Leu Asn Val Thr Val Asn Cys Ser Cys Gly Asp
145                 150                 155                 160

Arg Gln Ile Ser Lys Asp Tyr Gly Leu Phe Leu Thr Tyr Pro Leu Arg
                165                 170                 175

Phe Gly Asp Ser Leu Glu Ser Ile Val Asp Gln Thr Gly Ile Asp Ala
            180                 185                 190

Thr Leu Leu Gln Lys Tyr Asn Leu Arg Val Asn Phe Ser Gln Glu Ser
        195                 200                 205

Gly Val Val Phe Ile Pro Gly Arg Asp Gln Asn Gly Asn Tyr Val Pro
    210                 215                 220

Leu Asp Pro Arg Ser Arg Gly Leu Ser Glu Val Ala Ile Ala Gly Ile
225                 230                 235                 240

Cys Val Gly Ala Thr Phe Val Phe Leu Leu Leu Ser Ala Tyr Val Phe
                245                 250                 255

Val Lys His Phe Arg Arg Lys Thr Ala Lys Val Ala Leu Ile Thr Glu
                260                 265                 270

Asn Ser Thr Asp Leu Ser Ser Asn Gln Asp Gly Met Ile Ile Thr Ser
        275                 280                 285

Thr Asn Tyr Glu Thr Ser Gly Ser Ser Gly Ser Ala Ser Ala Thr Gly
    290                 295                 300

Leu Arg Gly Ile Met Val Gly Lys Ser Met Glu Phe Ser Tyr Gln Glu
305                 310                 315                 320

Ile Ala Lys Ala Thr Asn Asn Phe Ser Ser Asp Asn Lys Ile Gly Gln
            325                 330                 335

Gly Gly Phe Gly Ala Val Tyr Tyr Ala Glu Leu Arg Gly Glu Lys Thr
        340                 345                 350
```

```
Ala Ile Lys Lys Met Asp Ile Glu Ala Ser Gln Glu Phe Leu Ala Glu
        355                 360                 365

Leu Lys Val Leu Thr His Val His His Leu Asn Leu Val Arg Leu Ile
        370                 375                 380

Gly Tyr Cys Val Glu Gly Ser Leu Phe Leu Val Tyr Glu Tyr Ile Asn
385                 390                 395                 400

Asn Gly Asn Leu Ser Gln His Leu Arg Ser Ser Glu Leu Asp Ala Leu
                405                 410                 415

Pro Trp Cys Thr Arg Val Gln Ile Ala Leu Asp Ser Ala Arg Gly Leu
                420                 425                 430

Glu Tyr Ile His Glu His Thr Val Pro Val Tyr Ile His Arg Asp Val
        435                 440                 445

Lys Ser Leu Asn Ile Leu Ile Asp Glu Ser Phe His Ala Lys Val Ala
        450                 455                 460

Asp Phe Gly Leu Ser Lys Leu Ile Glu Val Gly Asn Ala Ser Leu Asn
465                 470                 475                 480

Thr Arg Leu Val Gly Thr Phe Gly Tyr Met Ser Pro Glu Tyr Ala Gln
                485                 490                 495

Tyr Gly Ile Thr Ser Pro Lys Ile Asp Val Tyr Ala Phe Gly Val Val
                500                 505                 510

Leu Tyr Glu Leu Ile Ser Ala Lys Asn Ala Val Leu Lys Thr Gly Glu
        515                 520                 525

Phe Val Ala Glu Ser Lys Gly Leu Val Ala Leu Phe Glu Lys Ser Leu
        530                 535                 540

Gly Arg Pro Asp Ala Val Glu Asp Leu Arg Lys Leu Val Asp Pro Arg
545                 550                 555                 560

Leu Gly Gln Asn Tyr Pro Ile Asp Ser Val Phe Lys Met Ala Gln Leu
                565                 570                 575

Ala Arg Ala Cys Thr Gln Asp Asp Pro Gln Leu Arg Pro Thr Met Arg
                580                 585                 590

Ser Ile Val Val Ala Leu Met Thr Leu Ser Ser Asn Ala Asp Asp Glu
        595                 600                 605

Asp Cys Asp Val Gly Ser Ala Phe Ser Asp Asn His Thr Ile Ile Asn
        610                 615                 620

Leu Leu Ser Gly Arg
625
```

```
<210> SEQ ID NO 322
<211> LENGTH: 618
<212> TYPE: PRT
<213> ORGANISM: Phaseolus vulgaris

<400> SEQUENCE: 322

Met Glu Gly Gly Leu Gly Cys Val Leu Leu Pro Leu Leu Leu Phe Cys
1               5                   10                  15

Val Val Leu Thr Ala Glu Ser Ala Cys Lys Glu Gly Cys Pro Leu Ala
        20                  25                  30

Leu Gly Ser Tyr Tyr Met Trp Gln Asn Ser Asn Leu Thr Tyr Ile Ser
        35                  40                  45

Gln Ile Met Ala Ser Ser Leu Leu Thr Thr Ala Asp Asp Ile Val Leu
        50                  55                  60

Tyr Asn Lys Asp Thr Ile Pro Asn Lys Asp Ser Val Gln Ala Phe Ile
65                  70                  75                  80

Arg Val Asn Val Pro Phe Pro Cys Asp Cys Ile Asp Gly Gln Phe Leu
```

-continued

```
                85               90               95

Ala His Thr Phe Lys Tyr Asp Val Gln Ser Gln Asp Ser Tyr Glu Tyr
            100             105             110

Val Ala Arg Thr Val Tyr Ser Asn Leu Thr Asp Val Ala Trp Leu Arg
            115             120             125

Asn Phe Asn Ser Tyr Glu Pro Asp Asn Ile Pro Asp Thr Ala Thr Leu
    130             135             140

Asn Val Thr Val Asn Cys Ser Cys Gly Asn Ser Asp Val Ala Asp Tyr
145             150             155             160

Gly Leu Phe Ile Thr Tyr Pro Leu Arg Thr Gly Glu Thr Leu Gly Ser
            165             170             175

Val Ala Ala Ala Val Ser Leu Asp Ser Gly Leu Leu Gln Arg Tyr Asn
            180             185             190

Pro Gly Val Asn Phe Asn Gln Gly Ser Gly Leu Val Tyr Ile Pro Gly
            195             200             205

Lys Asp Gln Asn Gly Ser Tyr Val Phe Leu Ala Ser Ser Ser Gly Gly
    210             215             220

Leu Ala Val Gly Ala Ile Ala Gly Ile Val Val Gly Val Val Ala Val
225             230             235             240

Leu Leu Leu Leu Gly Val Phe Ile Tyr Phe Arg Arg Phe Arg Lys Lys
            245             250             255

Ile Gln Lys Asp Glu Leu Pro Arg Asp Ser Ser Ala Leu Phe Ala Gln
            260             265             270

His Gly Lys Asp Glu Ala Ser Arg Ser Ser Ala Asn Glu Thr Leu Gly
            275             280             285

Pro Gly Gly Pro Ala Ala Ile Thr Gly Ile Lys Val Asp Lys Ser Val
    290             295             300

Lys Phe Thr Tyr Glu Glu Leu Ala Thr Ala Thr Asp Asn Phe Ser Leu
305             310             315             320

Ala Asn Lys Ile Gly Gln Gly Gly Phe Gly Ser Val Tyr Tyr Ala Glu
            325             330             335

Leu Arg Gly Glu Lys Ala Ala Ile Lys Lys Met Asp Met Gln Ala Thr
            340             345             350

Lys Glu Phe His Ala Glu Leu Asn Val Leu Thr Arg Val His His Leu
            355             360             365

Asn Leu Val Arg Leu Ile Gly Tyr Ser Met Glu Gly Ser Leu Phe Leu
    370             375             380

Val Tyr Glu Tyr Ile Glu Asn Gly Asn Leu Ser Gln His Leu Arg Gly
385             390             395             400

Ser Gly Ser Arg Glu Pro Leu Pro Trp Ala Thr Arg Val Gln Ile Ala
            405             410             415

Leu Asp Ser Ala Arg Gly Leu Glu Tyr Ile His Glu His Thr Val Pro
            420             425             430

Leu Tyr Ile His Arg Asp Ile Lys Ser Ala Asn Ile Leu Ile Asp Lys
            435             440             445

Asn Phe Arg Gly Lys Val Ala Asp Phe Gly Leu Thr Lys Leu Thr Glu
    450             455             460

Val Gly Ser Ser Ser Leu Pro Thr Gly Arg Leu Val Gly Thr Phe Gly
465             470             475             480

Tyr Met Pro Pro Glu Tyr Ala Gln Tyr Gly Asp Val Ser Pro Lys Val
            485             490             495

Asp Val Tyr Ala Phe Gly Val Val Leu Tyr Glu Leu Ile Ser Ala Lys
            500             505             510
```

-continued

```
Glu Ala Ile Val Lys Thr Asn Asp Ser Ala Val Asp Ser Lys Gly Leu
        515                 520                 525

Val Ala Leu Phe Asp Gly Val Phe Gly Gln Pro Asp Pro Thr Glu Asp
    530                 535                 540

Leu Cys Lys Leu Val Asp Pro Arg Leu Gly Asp Asn Tyr Pro Ile Asp
545                 550                 555                 560

Ser Val Arg Lys Met Ala Gln Leu Ala Lys Ala Cys Thr Gln Asp Asn
                565                 570                 575

Pro Gln Leu Arg Pro Ser Met Arg Ser Ile Val Val Ala Leu Met Thr
            580                 585                 590

Leu Ser Ser Thr Thr Asp Glu Trp Asp Val Gly Ser Phe Tyr Glu Asn
        595                 600                 605

Gln Asn Leu Val Asn Leu Met Ser Gly Arg
    610                 615
```

<210> SEQ ID NO 323
<211> LENGTH: 622
<212> TYPE: PRT
<213> ORGANISM: Arachis ipaensis

<400> SEQUENCE: 323

```
Met Glu Pro Arg Tyr Gly Phe Ala Ser Val Leu Leu Gln Leu Leu Leu
1               5                   10                  15

Leu Gly Cys Val Leu Tyr Gly Ala Glu Ser Gln Cys Ser Lys Gly Cys
            20                  25                  30

Pro Leu Ala Leu Ala Ser Tyr Tyr Met Trp Thr Gly Ser Asn Leu Thr
        35                  40                  45

Tyr Val Ser Gln Ile Met Lys Ser Asn Val Leu Ser Asp Pro Asn Gly
    50                  55                  60

Ile Val Asn Tyr Asn Lys Asp Thr Ile Pro Asn Lys Asp Ser Val Gln
65                  70                  75                  80

Ala Phe Ile Arg Val Asn Val Pro Phe Pro Cys Asp Cys Ile Asn Gly
                85                  90                  95

Glu Phe Leu Gly His Thr Phe Lys Tyr Asp Ile Gln Ser Gly Asp Thr
            100                 105                 110

Tyr Glu His Val Ala Thr Asn Asn Tyr Ala Asn Leu Thr Asn Val Asn
        115                 120                 125

Trp Leu Arg Lys Phe Asn Thr Tyr Pro Pro Asn Asn Ile Pro Asn Thr
    130                 135                 140

Gly Thr Leu Asn Val Thr Val Asn Cys Ser Cys Gly Asn Arg Gln Val
145                 150                 155                 160

Ala Asn Tyr Gly Leu Phe Ile Thr Tyr Pro Leu Arg Pro Gly Asp Thr
                165                 170                 175

Leu Gln Ala Val Ala Lys Asn Gln Ser Val Asp Ala Phe Leu Leu Gln
            180                 185                 190

Lys Tyr Asn Pro Ser Val Asn Phe Asn Gln Gly Ser Gly Leu Val Tyr
        195                 200                 205

Ile Pro Gly Lys Asp Gln Asn Gly Ser Phe Val Phe Leu Ser Ser Ser
    210                 215                 220

Ser Gly Gly Leu Ala Ala Gly Ala Ile Ala Gly Ile Val Val Gly Ile
225                 230                 235                 240

Val Ala Gly Leu Leu Leu Val Ala Val Gly Ile Tyr Phe Gly Tyr Phe
                245                 250                 255

Arg Lys Lys Lys Met Gln Arg Glu Glu Leu Leu Ser Gln Asp Ser Lys
```

-continued

```
                260              265                 270
Pro Met Phe Arg Gln Asp Gly Lys Asp Glu Thr Ser Arg Ser Ala Ala
        275              280                 285

Tyr Glu Ala Ala Gly Pro Ala Gly Pro Gly Thr Ile Thr Gly Ile Thr
    290              295                 300

Val Asp Lys Ser Val Glu Phe Ser Tyr Glu Glu Leu Ala Thr Ala Thr
305              310                 315                 320

Asn Asn Phe Asn Leu Ala Asn Lys Ile Gly Gln Gly Gly Phe Gly Ala
            325              330                 335

Val Tyr Tyr Ala Glu Leu Arg Gly Glu Lys Ala Ala Ile Lys Lys Met
            340              345                 350

Asp Met Gln Ala Ser Lys Glu Phe Leu Ala Glu Leu Lys Val Leu Thr
        355              360                 365

Arg Val His His Leu Asn Leu Val Arg Leu Ile Gly Tyr Ser Ile Glu
    370              375                 380

Gly Ser Leu Phe Leu Val Tyr Glu Tyr Ile Glu Asn Gly Asn Leu Ser
385              390                 395                 400

Gln His Leu Arg Gly Ser Gly Arg Glu Pro Leu Pro Trp Ala Thr Arg
            405              410                 415

Val Gln Ile Ala Leu Asp Ser Ala Arg Gly Leu Glu Tyr Ile His Glu
            420              425                 430

His Thr Val Pro Val Tyr Ile His Arg Asp Ile Lys Ser Ala Asn Ile
            435              440                 445

Leu Ile Asp Lys Asn Tyr Arg Gly Lys Val Ala Asp Phe Gly Leu Thr
    450              455                 460

Lys Leu Thr Glu Val Gly Ser Ser Ser Leu Pro Thr Gly Arg Leu Val
465              470                 475                 480

Gly Thr Phe Gly Tyr Met Pro Pro Glu Tyr Ala Gln Tyr Gly Asp Val
            485              490                 495

Ser Pro Lys Val Asp Val Tyr Ala Phe Gly Val Val Leu Phe Glu Leu
            500              505                 510

Ile Ser Ala Lys Glu Ala Ile Val Lys Thr Ser Glu Ser Val Ala Asp
            515              520                 525

Ser Lys Gly Leu Val Ala Leu Phe Glu Gly Val Leu Ser Gln Pro Asp
    530              535                 540

Pro Thr Glu Asp Leu Cys Lys Leu Val Asp Pro Arg Leu Gly Glu Asn
545              550                 555                 560

Tyr Pro Ile Asp Ser Val Arg Lys Met Ala His Leu Ala Lys Ala Cys
            565              570                 575

Thr Gln Asp Asn Pro Gln Leu Arg Pro Ser Met Arg Ser Ile Val Val
            580              585                 590

Ala Leu Met Thr Leu Ser Ser Thr Thr Asp Asp Trp Asp Val Gly Ser
            595              600                 605

Phe Tyr Glu Asn Gln Asn Leu Val Asn Leu Met Ser Gly Arg
    610              615                 620
```

```
<210> SEQ ID NO 324
<211> LENGTH: 622
<212> TYPE: PRT
<213> ORGANISM: Arachis duranensis

<400> SEQUENCE: 324

Met Glu Pro Arg His Arg Phe Val Ser Val Leu Leu Gln Leu Leu Leu
1               5                   10                  15
```

```
Leu Gly Cys Val Leu Tyr Gly Ala Glu Ser Gln Cys Ser Lys Gly Cys
        20              25              30

Pro Leu Ala Leu Ala Ser Tyr Tyr Met Trp Thr Gly Ser Asn Leu Thr
        35              40              45

Tyr Val Ser Glu Ile Met Lys Ser Asn Val Leu Ser Asp Pro Asn Asp
        50              55              60

Ile Val Asn Tyr Asn Lys Asp Thr Ile Pro Asn Lys Asp Ser Val Gln
65              70              75              80

Ala Ser Ile Arg Val Asn Val Pro Phe Pro Cys Asp Cys Ile Asn Gly
        85              90              95

Glu Phe Leu Gly His Thr Phe Gln Tyr Asp Ile Gln Ser Gly Asp Thr
        100             105             110

Tyr Glu His Val Ala Thr Asn Asn Tyr Ala Asn Leu Thr Asn Val Asn
        115             120             125

Trp Leu Arg Lys Phe Asn Ser Tyr Pro Pro Asn Asn Ile Pro Asp Thr
        130             135             140

Gly Thr Leu Asn Val Thr Val Asn Cys Ser Cys Gly Asn Arg Gln Val
145             150             155             160

Ala Asn Tyr Gly Leu Phe Ile Thr Tyr Pro Leu Arg Pro Gly Asp Thr
        165             170             175

Leu Gln Ala Val Ala Lys Asn Gln Ser Val Asp Ala Phe Leu Leu Gln
        180             185             190

Lys Tyr Asn Pro Ser Val Asn Phe Asn Gln Gly Ser Gly Leu Val Tyr
        195             200             205

Ile Pro Gly Lys Asp Gln Asn Gly Ser Phe Val Phe Leu Ser Ser Ser
        210             215             220

Ser Gly Gly Leu Ala Ala Gly Ala Ile Ala Gly Ile Ala Ile Gly Ile
225             230             235             240

Val Ala Gly Leu Leu Leu Val Ala Val Gly Ile Tyr Phe Gly Tyr Phe
        245             250             255

Arg Lys Lys Lys Met Gln Arg Glu Glu Leu Leu Ser Gln Asp Ser Lys
        260             265             270

Pro Met Phe Arg Gln Asp Gly Lys Asp Glu Thr Ser Arg Ser Ala Ala
        275             280             285

Tyr Glu Ala Ala Gly Pro Ala Gly Pro Gly Thr Ile Thr Gly Ile Thr
        290             295             300

Val Asp Lys Ser Val Glu Phe Ser Tyr Glu Glu Leu Ala Thr Ala Thr
305             310             315             320

Asn Asn Phe Asn Leu Ala Asn Lys Ile Gly Gln Gly Gly Phe Gly Ala
        325             330             335

Val Tyr Tyr Ala Glu Leu Arg Gly Glu Lys Ala Ala Ile Lys Lys Met
        340             345             350

Asp Met Gln Ala Ser Lys Glu Phe Leu Ala Glu Leu Lys Val Leu Thr
        355             360             365

Arg Val His His Leu Asn Leu Val Arg Leu Ile Gly Tyr Ser Ile Glu
        370             375             380

Gly Ser Leu Phe Leu Val Tyr Glu Tyr Ile Glu Asn Gly Asn Leu Ser
385             390             395             400

Gln His Leu Arg Gly Ser Gly Arg Glu Pro Leu Pro Trp Ala Thr Arg
        405             410             415

Val Gln Ile Ala Leu Asp Ser Ala Arg Gly Leu Glu Tyr Ile His Glu
        420             425             430

His Thr Val Pro Val Tyr Ile His Arg Asp Ile Lys Ser Ala Asn Ile
```

-continued
_____

```
              435                440                445
Leu Ile Asp Lys Asn Tyr Arg Gly Lys Val Ala Asp Phe Gly Leu Thr
    450                455                460
Lys Leu Thr Glu Val Gly Ser Ser Ser Leu Pro Thr Gly Arg Leu Val
465                470                475                480
Gly Thr Phe Gly Tyr Met Pro Pro Glu Tyr Ala Gln Tyr Gly Asp Val
                485                490                495
Ser Pro Lys Val Asp Val Tyr Ala Phe Gly Val Val Leu Phe Glu Leu
                500                505                510
Ile Ser Ala Lys Glu Ala Ile Val Lys Thr Ser Glu Ser Val Ala Asp
                515                520                525
Ser Lys Gly Leu Val Ala Leu Phe Glu Gly Val Leu Ser Gln Pro Asp
    530                535                540
Pro Thr Glu Asp Leu Cys Lys Leu Val Asp Pro Arg Leu Gly Glu Asn
545                550                555                560
Tyr Pro Ile Asp Ser Val Arg Lys Met Ala His Leu Ala Lys Ala Cys
                565                570                575
Thr Gln Asp Asn Pro Gln Leu Arg Pro Ser Met Arg Ser Ile Val Val
                580                585                590
Ala Leu Met Thr Leu Ser Ser Thr Thr Asp Asp Trp Asp Val Gly Ser
                595                600                605
Phe Tyr Glu Asn Gln Asn Leu Val Asn Leu Met Ser Gly Arg
    610                615                620

<210> SEQ ID NO 325
<211> LENGTH: 624
<212> TYPE: PRT
<213> ORGANISM: Cajanus cajan

<400> SEQUENCE: 325

Met Glu Pro Arg Phe Arg Phe Leu Leu Ile Leu Val Leu Leu Val Leu
1                5                10                15
Val Leu Val Ile Val Pro Leu Glu Val Glu Ser Ala Cys Lys Gln Gly
                20                25                30
Cys Pro Val Ala Leu Gly Ser Tyr Tyr Met Trp Ser Gly Ser Lys Leu
                35                40                45
Thr Tyr Ile Ser Gln Ile Met Pro Ser Ala Leu Leu Thr Lys Pro Glu
    50                55                60
Asp Ile Val Ala Tyr Asn Lys Asp Thr Val Pro Asn Lys Asp Ser Val
65                70                75                80
Gln Ala Phe Ile Arg Val Asn Val Pro Phe Pro Cys Asp Cys Val Asp
                85                90                95
Gln Gln Phe Leu Ala His Thr Phe Gln Tyr Asp Val Gln Ser Gln Asp
                100                105                110
Thr Tyr Asp Tyr Val Ala Arg Thr Val Phe Ala Asn Leu Thr Asp Val
                115                120                125
Ala Trp Leu Arg Arg Phe Asn Ser Tyr Ala Pro Asp Asn Ile Pro Asp
    130                135                140
Thr Gly Thr Leu Asn Val Thr Val Asn Cys Ser Cys Gly Asn Ser Asp
145                150                155                160
Val Gly Gly Tyr Gly Leu Phe Val Thr Tyr Pro Leu Arg Pro Gly Asp
                165                170                175
Thr Leu Gly Ser Val Ala Ser Ser Val Gly Leu Asp Ser Gly Leu Leu
                180                185                190
```

```
Gln Arg Tyr Asn Pro Gly Val Asn Phe Asn Gln Gly Thr Gly Leu Val
        195                 200                 205

Tyr Ile Pro Gly Lys Asp Gln Asn Gly Ser Tyr Val Phe Leu Ser Ser
        210                 215                 220

Ser Ser Gly Ala Gly Leu Pro Gly Gly Ala Ile Ala Gly Ile Ala Val
225                 230                 235                 240

Gly Val Val Ala Gly Leu Leu Leu Gly Val Cys Leu Tyr Val Gly
                245                 250                 255

Tyr Phe Arg Lys Lys Lys Ile Arg Lys Val Glu Leu Pro Leu Asp Ser
                260                 265                 270

Ser Ala Leu Phe Ala Gln Asp Gly Lys Asp Glu Thr Ser Arg Ser Ser
        275                 280                 285

Ala Asn Glu Thr Ser Gly Pro Gly Gly Pro Ala Ala Ile Thr Gly Ile
        290                 295                 300

Thr Val Asp Lys Ser Val Glu Phe Thr Tyr Glu Glu Leu Ala Thr Ala
305                 310                 315                 320

Thr Asp Asn Phe Ser Leu Ala Asn Lys Ile Gly Gln Gly Gly Phe Gly
                325                 330                 335

Ser Val Tyr Tyr Ala Glu Leu Arg Gly Glu Lys Ala Ala Ile Lys Lys
                340                 345                 350

Met Asp Met Gln Ala Ser Lys Glu Phe Leu Ala Glu Leu Lys Val Leu
                355                 360                 365

Thr Arg Val His His Leu Asn Leu Val Arg Leu Ile Gly Tyr Ser Ile
        370                 375                 380

Glu Gly Ser Leu Phe Leu Val Tyr Glu Tyr Ile Glu Asn Gly Asn Leu
385                 390                 395                 400

Ser Gln His Leu Arg Gly Ala Gly Ser Arg Glu Pro Leu Pro Trp Ala
                405                 410                 415

Thr Arg Val Gln Ile Ala Leu Asp Ser Ala Arg Gly Leu Glu Tyr Ile
                420                 425                 430

His Glu Tyr Thr Val Pro Val Tyr Ile His Arg Asp Ile Lys Ser Ala
                435                 440                 445

Asn Ile Leu Ile Asp Lys Asn Phe Arg Gly Lys Val Ala Asp Phe Gly
        450                 455                 460

Leu Thr Lys Leu Thr Glu Val Gly Ser Ser Ser Leu Pro Thr Gly Arg
465                 470                 475                 480

Leu Val Gly Thr Phe Gly Tyr Met Pro Pro Glu Tyr Ala Gln Tyr Gly
                485                 490                 495

Asp Val Ser Pro Lys Val Asp Val Tyr Ala Phe Gly Val Val Leu Tyr
                500                 505                 510

Glu Leu Ile Ser Ala Lys Glu Ala Ile Val Lys Thr Ser Glu Ser Glu
                515                 520                 525

Ala Asp Ser Lys Gly Leu Val Ala Leu Phe Asp Gly Val Leu Ser Gln
        530                 535                 540

Pro Asp Pro Thr Glu Asp Leu Cys Lys Leu Val Asp Pro Arg Leu Gly
545                 550                 555                 560

Asp Asn Tyr Pro Ile Asp Ser Val Arg Lys Met Ala Gln Leu Gly Lys
                565                 570                 575

Ala Cys Thr Gln Asp Asn Pro Gln Leu Arg Pro Ser Met Arg Ser Ile
                580                 585                 590

Val Val Ala Leu Met Thr Leu Ser Ser Thr Thr Asp Asp Trp Asp Val
                595                 600                 605

Gly Ser Phe Tyr Glu Asn Gln Asn Leu Val Asn Leu Met Ser Gly Arg
```

-continued

```
      610                615                620

<210> SEQ ID NO 326
<211> LENGTH: 622
<212> TYPE: PRT
<213> ORGANISM: Cicer arietinum

<400> SEQUENCE: 326

Met Glu Gln Leu Arg Phe Thr Ser Phe Leu Phe Phe Ser Ser Leu Leu
1               5                   10                  15

Phe Ser Ile Pro Phe Ile Ser Glu Ser Lys Cys Thr Lys Gly Cys Ser
                20                  25                  30

Pro Ala Leu Ala Ser Tyr Tyr Leu Asn Ser Gly Ala Asn Leu Thr His
            35                  40                  45

Ile Ser Gly Ile Phe Ser Ser Ser Ile Leu Thr Lys Pro Glu Asp Ile
        50                  55                  60

Val Asp Tyr Asn Gln Asp Thr Ile Ala Asn Lys Asp Thr Ile Ile Ala
65                  70                  75                  80

Gly Lys Arg Ile Asn Ile Pro Phe Pro Cys Asp Cys Ile Ala Gly Glu
                85                  90                  95

Phe Leu Ala His Thr Phe Ser Tyr Asp Val Gln Thr Gly Asp Thr Tyr
            100                 105                 110

Glu Thr Val Ala Thr Asn Asn Tyr Ala Asn Leu Thr Asn Val Gln Trp
            115                 120                 125

Leu Gln Arg Phe Asn Ser Tyr Pro Ala Asn Asn Ile Pro Asp Thr Gly
        130                 135                 140

Thr Leu Asn Val Thr Val Asn Cys Ser Cys Gly Asn Ser Asp Val Ala
145                 150                 155                 160

Asn Tyr Gly Leu Phe Leu Thr Tyr Pro Leu Arg Pro Gly Glu Thr Leu
                165                 170                 175

Gly Ser Val Ala Asn Ser Ser Asn Ile Asp Ser Ser Leu Leu Arg Ser
            180                 185                 190

Tyr Asn Pro Gly Val Asn Phe Asn Gln Gly Ser Gly Leu Val Phe Ile
        195                 200                 205

Pro Gly Lys Asp Gln Lys Gly Asn Phe Val Phe Leu Ser Ser Ser Ser
        210                 215                 220

Gly Gly Leu Gly Ser Gly Val Ile Ala Gly Ile Ala Val Gly Ile Val
225                 230                 235                 240

Val Val Leu Leu Ser Leu Ala Val Ala Ile Tyr Phe Gly Ile Phe Arg
                245                 250                 255

Lys Lys Lys Ile Gln Lys Glu Glu Leu Leu Ser Arg Asp Ser Thr Ala
            260                 265                 270

Leu Phe Ser Arg Gly Arg Met Asp Glu Asn Ser His Gly Ala Ala Asn
        275                 280                 285

Val Thr Thr Arg His Gly Val Pro Ala Ala Ile Thr Gly Ile Thr Val
    290                 295                 300

Asp Lys Ser Val Glu Phe Ser Tyr Asp Glu Leu Ala Ala Ala Ser Asp
305                 310                 315                 320

Asn Phe Ser Leu Ala Asn Lys Ile Gly Gln Gly Gly Phe Gly Ser Val
            325                 330                 335

Tyr Tyr Ala Glu Leu Arg Gly Glu Lys Ala Ala Ile Lys Lys Met Asp
            340                 345                 350

Met Gln Ala Ser Lys Glu Phe Leu Ala Glu Leu Lys Val Leu Thr Arg
        355                 360                 365
```

-continued

```
Val His His Leu Asn Leu Val Arg Leu Ile Gly Tyr Ser Ile Glu Gly
    370             375             380

Ser Leu Phe Leu Val Tyr Glu Phe Ile Glu Asn Gly Asn Leu Ser Gln
385             390             395             400

His Leu Arg Gly Ser Gly Arg Asp Pro Leu Pro Trp Ala Thr Arg Val
            405             410             415

Gln Ile Ala Leu Asp Ser Ala Arg Gly Leu Glu Tyr Ile His Glu His
            420             425             430

Thr Val Pro Val Tyr Ile His Arg Asp Ile Lys Pro Ala Asn Ile Leu
            435             440             445

Ile Asp Lys Asn Phe Arg Gly Lys Val Ala Asp Phe Gly Leu Thr Lys
    450             455             460

Leu Thr Glu Val Gly Ser Ser Ser Leu Pro Thr Gly Arg Leu Val Gly
465             470             475             480

Thr Phe Gly Tyr Met Pro Pro Glu Tyr Ala Gln Tyr Gly Asp Val Ser
            485             490             495

Pro Lys Val Asp Val Tyr Ala Phe Gly Val Val Leu Tyr Glu Leu Ile
            500             505             510

Ser Ala Lys Glu Ala Ile Val Lys Thr Asn Glu Ser Val Ala Ala Asp
            515             520             525

Ser Lys Gly Leu Val Ala Leu Phe Glu Gly Val Leu Ser Gln Pro Asp
    530             535             540

Pro Thr Glu Asp Leu His Lys Leu Val Asp Pro Arg Leu Gly Asp Thr
545             550             555             560

Tyr Pro Val Asp Ser Val Arg Lys Met Ala Gln Leu Ala Lys Ala Cys
            565             570             575

Thr Gln Glu Asn Pro Gln Leu Arg Pro Ser Met Arg Ser Ile Val Val
            580             585             590

Ala Leu Met Thr Leu Ser Ser Ser Thr Asp Asp Trp Asp Val Gly Ser
    595             600             605

Phe Tyr Glu Asn Gln Asn Leu Val Asn Leu Met Ser Gly Arg
    610             615             620
```

```
<210> SEQ ID NO 327
<211> LENGTH: 615
<212> TYPE: PRT
<213> ORGANISM: Abrus precatorius

<400> SEQUENCE: 327

Met Phe Phe Phe Ile Met Leu Leu Leu Phe Phe Ser Leu Pro Phe Thr
1               5               10              15

Val Glu Ser Lys Cys Thr Glu Gly Cys Pro Leu Ala Leu Ala Ser Tyr
            20              25              30

Phe Leu Trp Arg Gly Ser Asn Leu Thr Tyr Val Ser Gln Ile Met Ala
            35              40              45

Ser Asn Val Leu Thr Arg Pro Glu Asp Ile Val Ser Tyr Asn Lys Asp
    50              55              60

Thr Val Pro Asn Lys Asp Ser Ile Gln Ala Leu Ser Arg Val Asn Val
65              70              75              80

Pro Phe Pro Cys Asp Cys Ile Asn Gly Glu Phe Leu Gly Tyr Thr Phe
            85              90              95

Lys Tyr Asp Val Gln Thr Gly Asp Thr Tyr Glu Thr Val Ala Gly Thr
            100             105             110

Asn Tyr Ala Asn Leu Thr Asn Val Ala Trp Leu Arg Arg Phe Asn Ser
    115             120             125
```

-continued

```
Tyr Pro Pro Asn Asn Ile Pro Asp Thr Gly Thr Leu Asn Val Thr Val
    130             135             140

Asn Cys Ser Cys Gly Met Ser Glu Val Ser Asn Tyr Gly Leu Phe Ile
145             150             155             160

Thr Tyr Pro Leu Arg Pro Gly Glu Thr Leu Gly Thr Val Ala Ser Ser
            165             170             175

Val Gly Leu Asp Ser Ala Leu Leu Gln Ser Tyr Asn Pro Ser Val Asn
            180             185             190

Phe Asn Gln Gly Ser Gly Leu Val Phe Ile Pro Gly Lys Asp Gln Asn
        195             200             205

Gly Ser Tyr Val Phe Leu Ser Ser Ser Ser Gly Gly Leu Ala Gly Gly
    210             215             220

Ala Val Ala Gly Ile Ala Val Gly Val Val Gly Leu Leu Phe Leu
225             230             235             240

Gly Val Cys Ile Tyr Val Gly Tyr Phe Arg Lys Lys Lys Ile Gln Lys
            245             250             255

Glu Glu Leu Leu Pro Gln Glu Ser Ser Ala Leu Phe Ala Gln Asn Gly
            260             265             270

Lys Asp Glu Thr Ser Arg Ser Ser Gly Asn Glu Thr Ala Gly Ala Gly
        275             280             285

Gly Pro Ala Ala Met Thr Gly Ile Ala Val Glu Lys Ser Leu Glu Phe
    290             295             300

Ser Tyr Glu Glu Leu Ala Thr Ala Thr Asn Asn Phe Asn Met Ala Asn
305             310             315             320

Lys Ile Gly Gln Gly Gly Phe Gly Ala Val Tyr Tyr Ala Glu Leu Arg
            325             330             335

Gly Glu Lys Ala Ala Ile Lys Lys Met Asp Met Gln Ala Ser Lys Glu
            340             345             350

Phe Leu Ala Glu Leu Lys Val Leu Thr Arg Val His His Leu Asn Leu
        355             360             365

Val Arg Leu Ile Gly Tyr Ser Ile Glu Gly Ser Leu Phe Leu Val Tyr
    370             375             380

Glu Tyr Ile Glu Asn Gly Asn Leu Ser Gln His Leu Arg Gly Ser Gly
385             390             395             400

Arg Asp Pro Leu Pro Trp Ala Thr Arg Val Gln Ile Ala Leu Asp Ser
            405             410             415

Ala Arg Gly Leu Glu Tyr Ile His Glu His Thr Val Pro Val Tyr Ile
            420             425             430

His Arg Asp Ile Lys Ser Ala Asn Ile Leu Ile Asp Arg Asn Phe Arg
        435             440             445

Gly Lys Val Ala Asp Phe Gly Leu Thr Lys Leu Thr Glu Val Gly Ser
    450             455             460

Ser Ser Leu Pro Thr Gly Arg Leu Val Gly Thr Phe Gly Tyr Met Pro
465             470             475             480

Pro Glu Tyr Ala Gln Tyr Gly Asp Val Ser Pro Lys Val Asp Val Tyr
            485             490             495

Ala Phe Gly Val Val Leu Tyr Glu Leu Ile Ser Ala Lys Glu Ala Ile
            500             505             510

Val Lys Thr Ser Glu Ser Asp Ala Asp Ser Lys Gly Leu Val Ala Leu
        515             520             525

Phe Glu Gly Val Leu Ser Gln Pro Asp Pro Thr Glu Gly Leu Cys Lys
    530             535             540
```

-continued

```
Leu Val Asp Pro Arg Leu Gly Asp Asn Tyr Pro Ile Asp Ser Val Arg
545                 550                 555                 560

Lys Met Ala Gln Leu Ala Lys Ala Cys Thr Gln Asp Asn Pro Gln Leu
                565                 570                 575

Arg Pro Ser Met Arg Ser Ile Val Val Ala Leu Met Thr Leu Ser Ser
                580                 585                 590

Thr Thr Asp Asp Trp Asp Val Gly Ser Phe Tyr Glu Asn Gln Asn Leu
                595                 600                 605

Val Asn Leu Met Ser Gly Arg
        610                 615

<210> SEQ ID NO 328
<211> LENGTH: 618
<212> TYPE: PRT
<213> ORGANISM: Glycine max

<400> SEQUENCE: 328

Met Glu Ala Leu Arg Leu Ala Tyr Leu Leu Leu Pro Trp Trp Leu Val
1               5                   10                  15

Phe Ser Thr Ala Glu Ser Ala Cys Lys Glu Gly Cys Gly Val Ala Leu
                20                  25                  30

Gly Ser Tyr Tyr Leu Trp Arg Gly Ser Asn Leu Thr Tyr Ile Ser Ser
            35                  40                  45

Ile Met Ala Ser Ser Leu Leu Thr Thr Pro Asp Asp Ile Val Asn Tyr
        50                  55                  60

Asn Lys Asp Thr Val Pro Ser Lys Asp Ile Ile Ile Ala Asp Gln Arg
65                  70                  75                  80

Val Asn Val Pro Phe Pro Cys Asp Cys Ile Asp Gly Gln Phe Leu Gly
                85                  90                  95

His Thr Phe Arg Tyr Asp Val Gln Ser Gln Asp Thr Tyr Glu Thr Val
                100                 105                 110

Ala Arg Ser Trp Phe Ala Asn Leu Thr Asp Val Ala Trp Leu Arg Arg
                115                 120                 125

Phe Asn Thr Tyr Pro Pro Asp Asn Ile Pro Asp Thr Gly Thr Leu Asn
        130                 135                 140

Val Thr Val Asn Cys Ser Cys Gly Asn Thr Asp Val Ala Asn Tyr Gly
145                 150                 155                 160

Leu Phe Val Thr Tyr Pro Leu Arg Ile Gly Asp Thr Leu Gly Ser Val
                165                 170                 175

Ala Ala Asn Leu Ser Leu Asp Ser Ala Leu Leu Gln Arg Tyr Asn Pro
                180                 185                 190

Asp Val Asn Phe Asn Gln Gly Thr Gly Leu Val Tyr Val Pro Gly Lys
                195                 200                 205

Asp Gln Asn Gly Ser Phe Val Arg Leu Pro Ser Ser Ser Gly Gly Leu
        210                 215                 220

Thr Gly Arg Ala Ile Ala Gly Ile Ala Val Gly Ile Val Ala Ala Leu
225                 230                 235                 240

Leu Leu Leu Gly Val Cys Ile Tyr Val Gly Tyr Phe Arg Lys Lys Ile
                245                 250                 255

Gln Lys Asp Glu Phe Leu Pro Arg Asp Ser Thr Ala Leu Phe Ala Gln
                260                 265                 270

Asp Gly Lys Asp Glu Thr Ser Arg Ser Ser Ala Asn Glu Thr Ser Gly
                275                 280                 285

Pro Gly Gly Pro Ala Ile Ile Thr Asp Ile Thr Val Asn Lys Ser Val
        290                 295                 300
```

```
Glu Phe Ser Tyr Glu Glu Leu Ala Thr Ala Thr Asp Asn Phe Ser Leu
305                 310                 315                 320

Ala Asn Lys Ile Gly Gln Gly Gly Phe Gly Ser Val Tyr Tyr Ala Glu
                325                 330                 335

Leu Arg Gly Glu Lys Ala Ala Ile Lys Lys Met Asp Met Gln Ala Ser
            340                 345                 350

Lys Glu Phe Leu Ala Glu Leu Asn Val Leu Thr Arg Val His His Leu
        355                 360                 365

Asn Leu Val Arg Leu Ile Gly Tyr Ser Ile Glu Gly Ser Leu Phe Leu
    370                 375                 380

Val Tyr Glu Tyr Ile Glu Asn Gly Asn Leu Ser Gln His Leu Arg Gly
385                 390                 395                 400

Ser Gly Ser Arg Glu Pro Leu Pro Trp Ala Thr Arg Val Gln Ile Ala
            405                 410                 415

Leu Asp Ser Ala Arg Gly Leu Glu Tyr Ile His Glu His Thr Val Pro
            420                 425                 430

Val Tyr Ile His Arg Asp Ile Lys Ser Ala Asn Ile Leu Ile Asp Lys
        435                 440                 445

Asn Phe Arg Gly Lys Val Ala Asp Phe Gly Leu Thr Lys Leu Thr Glu
    450                 455                 460

Val Gly Ser Ser Ser Leu Pro Thr Gly Arg Leu Val Gly Thr Phe Gly
465                 470                 475                 480

Tyr Met Pro Pro Glu Tyr Ala Gln Tyr Gly Asp Val Ser Pro Lys Val
            485                 490                 495

Asp Val Tyr Ala Phe Gly Val Val Leu Tyr Glu Leu Ile Ser Ala Lys
            500                 505                 510

Glu Ala Ile Val Lys Thr Asn Asp Ser Val Ala Asp Ser Lys Gly Leu
        515                 520                 525

Val Ala Leu Phe Asp Gly Val Leu Ser Gln Pro Asp Pro Thr Glu Glu
    530                 535                 540

Leu Cys Lys Leu Val Asp Pro Arg Leu Gly Asp Asn Tyr Pro Ile Asp
545                 550                 555                 560

Ser Val Arg Lys Met Ala Gln Leu Ala Lys Ala Cys Thr Gln Asp Asn
                565                 570                 575

Pro Gln Leu Arg Pro Ser Met Arg Ser Ile Val Val Ala Leu Met Thr
            580                 585                 590

Leu Ser Ser Thr Thr Asp Asp Trp Asp Val Gly Ser Phe Tyr Glu Asn
        595                 600                 605

Gln Asn Leu Val Asn Leu Met Ser Gly Arg
    610                 615
```

```
<210> SEQ ID NO 329
<211> LENGTH: 613
<212> TYPE: PRT
<213> ORGANISM: Glycine max

<400> SEQUENCE: 329

Met Glu His Ser Phe Arg Leu Pro Val Phe Phe Leu Leu Cys Ala Ser
1               5                   10                  15

Ile Ala Phe Ser Ala Glu Ser Lys Cys Ser Arg Gly Cys Asp Leu Ala
                20                  25                  30

Leu Ala Ser Tyr Tyr Leu Ser Gln Gly Asp Leu Thr Tyr Val Ser Lys
        35                  40                  45

Leu Met Glu Ser Glu Val Val Ser Lys Pro Glu Asp Ile Leu Ser Tyr
```

-continued

```
                50                55                60

Asn Thr Asp Thr Ile Thr Asn Lys Asp Leu Leu Pro Ala Ser Ile Arg
65                  70                75                80

Val Asn Val Pro Phe Pro Cys Asp Cys Ile Asp Glu Glu Phe Leu Gly
                85                90                95

His Thr Phe Gln Tyr Asn Leu Thr Thr Gly Asp Thr Tyr Leu Ser Ile
                100               105               110

Ala Thr Gln Asn Tyr Ser Asn Leu Thr Thr Ala Glu Trp Leu Arg Ser
            115               120               125

Phe Asn Arg Tyr Leu Pro Ala Asn Ile Pro Asp Ser Gly Thr Leu Asn
            130               135               140

Val Thr Ile Asn Cys Ser Cys Gly Asn Ser Glu Val Ser Lys Asp Tyr
145               150               155               160

Gly Leu Phe Ile Thr Tyr Pro Leu Arg Pro Glu Asp Ser Leu Gln Ser
                165               170               175

Ile Ala Asn Glu Thr Gly Val Asp Arg Asp Leu Leu Val Lys Tyr Asn
                180               185               190

Pro Gly Val Asn Phe Ser Gln Gly Ser Gly Leu Val Tyr Ile Pro Gly
            195               200               205

Lys Asp Gln Asn Ala Ile Tyr Val Pro Leu His Leu Ser Ser Gly Gly
        210               215               220

Leu Ala Gly Gly Val Ile Ala Gly Ile Ser Ile Gly Val Val Thr Gly
225               230               235               240

Leu Leu Leu Leu Ala Phe Cys Val Tyr Val Thr Tyr Tyr Arg Arg Lys
                245               250               255

Lys Val Trp Lys Lys Asp Leu Leu Ser Glu Glu Ser Arg Lys Asn Ser
                260               265               270

Ala Arg Val Lys Asn Asp Glu Ala Ser Gly Asp Ser Ala Ala Glu Gly
            275               280               285

Gly Thr Asn Thr Ile Gly Ile Arg Val Asn Lys Ser Ala Glu Phe Ser
        290               295               300

Tyr Glu Glu Leu Ala Asn Ala Thr Asn Asn Phe Ser Leu Ala Asn Lys
305               310               315               320

Ile Gly Gln Gly Gly Phe Gly Val Val Tyr Tyr Ala Glu Leu Asn Gly
                325               330               335

Glu Lys Ala Ala Ile Lys Lys Met Asp Ile Gln Ala Thr Arg Glu Phe
            340               345               350

Leu Ala Glu Leu Lys Val Leu Thr His Val His His Leu Asn Leu Val
            355               360               365

Arg Leu Ile Gly Tyr Cys Val Glu Gly Ser Leu Phe Leu Val Tyr Glu
        370               375               380

Tyr Ile Glu Asn Gly Asn Leu Gly Gln His Leu Arg Lys Ser Gly Phe
385               390               395               400

Asn Pro Leu Pro Trp Ser Thr Arg Val Gln Ile Ala Leu Asp Ser Ala
                405               410               415

Arg Gly Leu Gln Tyr Ile His Glu His Thr Val Pro Val Tyr Ile His
            420               425               430

Arg Asp Ile Lys Ser Glu Asn Ile Leu Ile Asp Lys Asn Phe Gly Ala
        435               440               445

Lys Val Ala Asp Phe Gly Leu Thr Lys Leu Ile Asp Val Gly Ser Ser
    450               455               460

Ser Leu Pro Thr Val Asn Met Lys Gly Thr Phe Gly Tyr Met Pro Pro
465               470               475               480
```

-continued

Glu Tyr Ala Tyr Gly Asn Val Ser Pro Lys Ile Asp Val Tyr Ala Phe
                485                     490                     495

Gly Val Val Leu Tyr Glu Leu Ile Ser Gly Lys Glu Ala Leu Ser Arg
                500                     505                     510

Gly Gly Val Ser Gly Ala Glu Leu Lys Gly Leu Val Ser Leu Phe Asp
                515                     520                     525

Glu Val Phe Asp Gln Gln Asp Thr Thr Glu Gly Leu Lys Lys Leu Val
        530                     535                     540

Asp Pro Arg Leu Gly Asp Asn Tyr Pro Ile Asp Ser Val Cys Lys Met
545                     550                     555                     560

Ala Gln Leu Ala Arg Ala Cys Thr Glu Ser Asp Pro Gln Gln Arg Pro
                565                     570                     575

Asn Met Ser Ser Val Val Val Thr Leu Thr Ala Leu Thr Ser Thr Thr
                580                     585                     590

Glu Asp Trp Asp Ile Ala Ser Ile Ile Glu Asn Pro Thr Leu Ala Asn
                595                     600                     605

Leu Met Ser Gly Lys
        610

<210> SEQ ID NO 330
<211> LENGTH: 608
<212> TYPE: PRT
<213> ORGANISM: Lupinus angustifolius

<400> SEQUENCE: 330

Met Lys Pro Ile Leu Met Phe Leu Ile Met Phe Leu Leu Trp Leu Leu
1                       5                       10                      15

Leu Leu Ser Ser Ala Glu Ser Lys Cys Thr Gln Gly Cys Ser Leu Ala
                20                      25                      30

Leu Ala Ser Tyr Tyr Met Tyr Ser Gly Ser Thr Leu Thr Ser Ile Ser
                35                      40                      45

Gln Val Met Ser Ser Gln Leu Leu Gln Ile Pro Glu Asp Ile Val Thr
        50                      55                      60

Tyr Asn Lys Asp Thr Ile Pro Asn Lys Asp Ser Val Gln Ala Phe Ile
65                      70                      75                      80

Arg Val Asn Val Pro Phe Pro Cys Asp Cys Ile Asp Gly Glu Phe Leu
                85                      90                      95

Gly His Met Phe Gln Tyr Asp Val Lys Thr Gly Asp Thr Tyr Gln Leu
                100                     105                     110

Val Ala Glu Thr Glu Tyr Ala Asn Leu Thr Asn Ile Asp Trp Leu Met
                115                     120                     125

Lys Phe Asn Ser Tyr Pro Ala Asn Asn Ile Pro Asp Thr Gly Thr Leu
        130                     135                     140

Asn Val Thr Val Asn Cys Ser Cys Gly Glu Lys Asn Val Ser Asn Tyr
145                     150                     155                     160

Gly Leu Phe Ile Thr Tyr Pro Leu Arg Pro Gly Asp Thr Leu Asp Ser
                165                     170                     175

Val Ser Lys Ser Val Asp Leu Asp Ser Gly Leu Leu Gln Arg Tyr Asn
                180                     185                     190

Pro Gly Val Asn Phe Asn Gln Gly Ser Gly Leu Val Tyr Ile Pro Gly
                195                     200                     205

Lys Asp Gln Asn Gly Ser Tyr Val Phe Leu Asn Ser Ser Ser Glu Gly
        210                     215                     220

Leu Ala Gly Gly Val Ile Ala Gly Ile Val Ile Gly Val Leu Ala Gly

-continued

```
225                 230                 235                 240

Ile Leu Leu Leu Val Ala Gly Ile Tyr Val Gly Tyr Phe Arg Lys Lys
                245                 250                 255

Lys Ile Gln Lys Glu Glu Leu Leu Glu Gln Asp Ser Lys Ser Leu Phe
                260                 265                 270

Val Gln Asn Gly Met Asp Glu Thr Ala Arg Thr Ala Ala Thr Thr Gly
                275                 280                 285

Ile Ser Val Asp Lys Ser Val Glu Phe Ser Tyr Glu Glu Leu Ala Ser
                290                 295                 300

Ala Thr Asp Asn Phe Ser Met Ala Asn Lys Ile Gly Gln Gly Gly Phe
305                 310                 315                 320

Gly Val Val Tyr Tyr Ala Glu Leu Arg Gly Glu Lys Ala Ala Ile Lys
                325                 330                 335

Lys Met Asp Met Gln Ala Ser Lys Glu Phe Leu Ala Glu Leu Lys Val
                340                 345                 350

Leu Thr His Val His His Leu Asn Leu Val Arg Leu Ile Gly Tyr Ser
                355                 360                 365

Ile Glu Gly Ser Leu Phe Leu Val Tyr Glu Phe Ile Glu Asn Gly Asn
                370                 375                 380

Leu Ser Gln His Leu Arg Gly Ser Gly Arg Asp Pro Leu Pro Trp Pro
385                 390                 395                 400

Ala Arg Val Gln Ile Ala Leu Asp Ser Ala Arg Gly Leu Glu Tyr Ile
                405                 410                 415

His Glu His Thr Val Pro Val Tyr Ile His Arg Asp Ile Lys Ser Ala
                420                 425                 430

Asn Ile Leu Ile Asp Lys Asn Phe Arg Gly Lys Val Ala Asp Phe Gly
                435                 440                 445

Leu Thr Lys Leu Thr Glu Val Gly Ser Ser Ser Leu Pro Thr Gly Arg
                450                 455                 460

Leu Val Gly Thr Phe Gly Tyr Met Pro Pro Glu Tyr Ala Gln Tyr Gly
465                 470                 475                 480

Asp Val Ser Pro Lys Val Asp Val Tyr Ala Phe Gly Val Val Leu Tyr
                485                 490                 495

Glu Leu Ile Ser Ala Lys Glu Ala Ile Ile Gln Ala Asn Glu Ser Ile
                500                 505                 510

Ala Asp Ser Lys Gly Leu Val Ala Leu Phe Glu Gly Val Leu Asn Gln
                515                 520                 525

Pro Asp Ser Thr Glu Asp Leu Cys Lys Val Val Asp Pro Arg Leu Gly
                530                 535                 540

Asp Asn Tyr Pro Ile Asp Ser Val Arg Lys Leu Ala Gln Leu Ala Lys
545                 550                 555                 560

Ala Cys Thr Gln Asp Asn Pro Gln Leu Arg Pro Ser Met Arg Ser Ile
                565                 570                 575

Val Val Ala Leu Met Thr Leu Ser Ser Thr Thr Asp Asp Trp Asp Val
                580                 585                 590

Gly Ser Phe Tyr Glu Asn Gln Asn Leu Val Asn Leu Met Ser Gly Arg
                595                 600                 605
```

<210> SEQ ID NO 331
<211> LENGTH: 610
<212> TYPE: PRT
<213> ORGANISM: Lupinus angustifolius

<400> SEQUENCE: 331

```
Met Glu Pro Ile Phe Trp Phe Leu Ile Lys Leu Ser Pro Leu Phe Phe
1               5                   10                  15

Leu Cys Ser Asn Ala Glu Ser Lys Cys Thr Gln Gly Cys Pro Ile Ala
            20                  25                  30

Leu Ala Ser Tyr Tyr Met Leu Ser Gly Ser Asn Leu Thr Tyr Ile Ser
        35                  40                  45

Gln Ile Met Ser Ser His Val Leu His Ser Pro Glu Asp Ile Val Ser
    50                  55                  60

Tyr Asn Lys Asp Lys Val Gln Pro Phe Thr Arg Val Asn Val Pro Phe
65                  70                  75                  80

Pro Cys Asp Cys Ile Lys Gly Glu Phe Leu Gly His Met Phe Gln Tyr
                85                  90                  95

Val Val Gln Thr Gly Asp Thr Tyr Glu Thr Val Ala Gly Thr Asn Tyr
            100                 105                 110

Ala Asn Leu Thr Asn Val Glu Trp Leu Arg Arg Phe Asn Thr Tyr Leu
        115                 120                 125

Pro Asp Asn Ile Ser Ser Thr Gly Met Leu Asn Val Thr Val Asn Cys
    130                 135                 140

Ser Cys Gly Asn Ser Asp Val Ser Asp Tyr Glu Leu Phe Ile Thr Tyr
145                 150                 155                 160

Pro Leu Arg Pro Gly Glu Thr Leu Gly Ser Val Ala Lys Ser Val Lys
                165                 170                 175

Leu Asp Ser Gly Leu Leu Gln Arg Tyr Asn Pro Ser Val Asn Phe Asn
            180                 185                 190

Gln Gly Ser Gly Leu Val Tyr Ile Pro Gly Lys Asp Gln Asn Gly Ser
        195                 200                 205

Tyr Val Phe Leu Ser Ser Ser Ser Gly Gly Leu Ala Gly Gly Ala Ile
    210                 215                 220

Ala Gly Ile Ala Val Gly Val Val Ala Gly Ile Leu Leu Leu Val Val
225                 230                 235                 240

Cys Ile Tyr Val Gly Cys Phe Arg Lys Lys Ile Gln Lys Glu Glu
                245                 250                 255

Val Val Arg Pro Asp Ser Lys Ser His Ser Val Pro Asp Gly Met Asp
                260                 265                 270

Glu Ile Ser Leu Val Ala Ala Tyr Glu Thr Ser Arg Pro Arg Gly Ser
    275                 280                 285

Ala Ala Ile Ala Gly Ile Ser Met Asp Lys Ser Val Glu Phe Ser Tyr
    290                 295                 300

Glu Glu Leu Ala Ser Ala Thr Asn Asn Phe Ser Val Ala Asn Lys Ile
305                 310                 315                 320

Gly Gln Gly Gly Phe Ala Val Val Tyr Tyr Ala Glu Leu Arg Gly Glu
                325                 330                 335

Lys Ala Ala Ile Lys Lys Met Asp Met Gln Ala Ser Lys Glu Phe Leu
            340                 345                 350

Ala Glu Leu Asn Val Leu Thr His Val His His Leu Asn Leu Val Arg
        355                 360                 365

Leu Ile Gly Tyr Ser Ile Lys Gly Ser Leu Cys Leu Val Tyr Glu Phe
    370                 375                 380

Ile Glu Asn Gly Asn Leu Ser Gln His Leu His Gly Ser Gly Arg Glu
385                 390                 395                 400

Pro Leu Pro Trp Thr Ile Arg Val Gln Ile Ala Leu Asp Ser Ala Arg
                405                 410                 415

Gly Leu Glu Tyr Ile His Glu His Thr Met Pro Ile Tyr Ile His Arg
```

-continued

```
              420              425              430

Asp Ile Lys Ser Ala Asn Ile Leu Ile Asp Lys Asn Phe Arg Gly Lys
        435              440              445

Val Ala Asp Phe Gly Leu Ala Lys Leu Ala Glu Val Gly Ser Ser Leu
        450              455              460

Arg Pro Thr Val Arg Leu Val Gly Thr Phe Gly Tyr Met Pro Pro Glu
465              470              475              480

Tyr Ala Gln Tyr Gly Asp Val Ser Pro Lys Val Asp Val Tyr Ala Phe
                485              490              495

Gly Val Val Leu Tyr Glu Leu Ile Ser Ala Lys Glu Ala Ile Ile Gln
                500              505              510

Ser Ile Val Asp Ser Lys Gly Leu Val His Trp Phe Lys Glu Val Leu
                515              520              525

Ser Gln Pro His Ser Thr Glu Asp Leu Cys Lys Leu Val Asp Pro Lys
                530              535              540

Leu Gly Asp Asn Tyr Pro Ile Asp Ser Val Leu Lys Leu Ala Gln Leu
545              550              555              560

Ala Lys Ala Cys Thr Gln His Asn Pro Gln Leu Arg Pro Ser Met Arg
                565              570              575

Ser Ile Val Val Ala Leu Met Thr Leu Ser Ser Thr Thr Asp Asp Trp
                580              585              590

Asp Val Gly Ser Phe Tyr Glu Asn Gln Asn Leu Val Asn Leu Met Ser
        595              600              605

Gly Lys
    610

<210> SEQ ID NO 332
<211> LENGTH: 619
<212> TYPE: PRT
<213> ORGANISM: Vigna angularis

<400> SEQUENCE: 332

Met Glu Pro Arg Leu Gly Val Leu Leu Leu Pro Leu Val Leu Phe Ser
1               5               10              15

Leu Val Leu Ala Ala Glu Ser Ala Cys Lys Lys Gly Cys Ser Leu Ala
                20              25              30

Leu Gly Ser Tyr Tyr Met Trp Ser Gly Ser Asn Leu Thr Tyr Ile Ser
                35              40              45

Glu Val Met Ser Ser Ser Leu Leu Thr Thr Pro Asp Asp Ile Val Leu
        50              55              60

Tyr Asn Lys Asp Thr Ile Pro Asn Lys Asp Ser Val Gln Ala Phe Ile
65              70              75              80

Arg Val Asn Val Pro Phe Pro Cys Asp Cys Ile Asp Gly Gln Phe Leu
                85              90              95

Gly His Thr Phe His Tyr Asp Val Gln Thr Gln Asp Thr Tyr Glu Gln
                100             105             110

Val Ala Arg Thr Val Phe Ser Asn Leu Thr Asp Val Thr Trp Leu Arg
                115             120             125

Arg Phe Asn Ser Tyr Glu Pro Asp Asn Ile Pro Asp Thr Gly Thr Leu
        130             135             140

Asn Val Thr Val Asn Cys Ser Cys Gly Asn Thr Asp Val Ala Asp Tyr
145             150             155             160

Gly Leu Phe Val Thr Tyr Pro Leu Arg Thr Gly Glu Thr Leu Gly Ser
                165             170             175
```

-continued

```
Val Ala Ser Asp Val Ser Leu Asp Ser Gly Leu Leu Gln Arg Tyr Asn
            180                 185                 190

Pro Asp Val Asn Phe Asn Gln Gly Ser Gly Leu Val Tyr Ile Pro Gly
            195                 200                 205

Lys Asp Gln Asn Gly Ser Tyr Val Val Leu Pro Ser Ser Ser Gly Ala
            210                 215                 220

Gly Leu Ala Gly Gly Ala Ile Ala Gly Ile Ala Val Gly Val Val Ala
225                 230                 235                 240

Val Leu Leu Val Ile Gly Val Val Ile Tyr Phe Arg Ile Phe Arg Lys
                245                 250                 255

Lys Ile Lys Lys Glu Glu Leu Ser Arg Asp Ser Ser Ala Leu Phe Ala
            260                 265                 270

Gln Asp Gly Lys Asp Glu Ala Ser Arg Ser Ser Ala His Glu Thr Leu
            275                 280                 285

Arg Pro Gly Gly Pro Thr Ala Ile Thr Gly Ile Lys Val Asp Lys Ser
    290                 295                 300

Val Glu Phe Thr Tyr Glu Glu Leu Ala Thr Ala Thr Asp Asn Phe Ser
305                 310                 315                 320

Leu Ala Asn Lys Ile Gly Gln Gly Gly Phe Gly Ser Val Tyr Tyr Ala
                325                 330                 335

Lys Leu Arg Gly Glu Lys Ala Ala Ile Lys Lys Met Asp Met Gln Ala
                340                 345                 350

Ser Lys Glu Phe Leu Ala Glu Leu Lys Val Leu Thr Arg Val His His
            355                 360                 365

Leu Asn Leu Val Arg Leu Ile Gly Tyr Ser Ile Glu Gly Ser Leu Phe
    370                 375                 380

Leu Val Tyr Glu Tyr Ile Glu Asn Gly Asn Leu Ser Gln His Leu Arg
385                 390                 395                 400

Gly Ser Gly Ser Arg Glu Pro Leu Pro Trp Ala Thr Arg Val Gln Ile
                405                 410                 415

Ala Leu Asp Ser Ala Arg Gly Leu Glu Tyr Ile His Glu His Thr Val
            420                 425                 430

Pro Val Tyr Ile His Arg Asp Ile Lys Ser Ala Asn Ile Leu Ile Asp
            435                 440                 445

Lys Asn Phe Arg Gly Lys Val Ala Asp Phe Gly Leu Thr Lys Leu Thr
    450                 455                 460

Glu Val Gly Ser Ser Ser Leu Pro Thr Gly Arg Leu Val Gly Thr Phe
465                 470                 475                 480

Gly Tyr Met Pro Pro Glu Tyr Ala Gln Tyr Gly Asp Val Ser Pro Lys
                485                 490                 495

Val Asp Val Tyr Ala Phe Gly Val Val Leu Tyr Glu Leu Ile Ser Ala
            500                 505                 510

Lys Glu Ala Ile Val Lys Thr Asn Asp Ser Val Thr Asp Ser Lys Gly
            515                 520                 525

Leu Val Ala Leu Phe Glu Gly Val Leu Gly Gln Pro Asp Asn Thr Glu
    530                 535                 540

Asp Leu Cys Lys Leu Val Asp Pro Arg Leu Gly Asp Asn Tyr Pro Val
545                 550                 555                 560

Asp Ser Val Arg Lys Met Ala Gln Leu Ala Lys Ala Cys Thr Gln Asp
                565                 570                 575

Asn Pro Gln Leu Arg Pro Ser Met Arg Ser Ile Val Val Ala Leu Met
            580                 585                 590

Thr Leu Ser Ser Thr Thr Asp Glu Trp Asp Val Gly Ser Phe Tyr Glu
```

-continued

```
          595              600              605
Asn Gln Asn Leu Val Asn Leu Met Ser Gly Arg
    610              615

<210> SEQ ID NO 333
<211> LENGTH: 618
<212> TYPE: PRT
<213> ORGANISM: Vigna radiata

<400> SEQUENCE: 333

Met Glu Pro Arg Leu Gly Phe Leu Leu Leu Pro Leu Val Leu Phe Ser
1               5                   10                  15

Leu Val Leu Ala Ala Glu Ser Ala Cys Lys Gln Gly Cys Pro Leu Ala
            20                  25                  30

Leu Gly Ser Tyr Tyr Met Trp Ser Gly Ser Asn Leu Thr Tyr Ile Ser
            35                  40                  45

Glu Val Met Ser Ser Ser Leu Leu Thr Thr Pro Asp Asp Ile Val Leu
        50                  55                  60

Tyr Asn Lys Asp Thr Ile Pro Asn Lys Asp Ser Val Gln Ala Phe Ile
65                  70                  75                  80

Arg Val Asn Val Pro Phe Pro Cys Asp Cys Ile Asp Gly Gln Phe Leu
                85                  90                  95

Ala His Thr Phe Gln Tyr Asp Val Gln Thr Gln Asp Thr Tyr Glu Gln
            100                 105                 110

Val Ala Arg Val Val Phe Ser Asn Leu Thr Asp Val Thr Trp Leu Arg
            115                 120                 125

Arg Phe Asn Thr Tyr Glu Pro Asp Asn Ile Pro Asp Thr Gly Thr Leu
        130                 135                 140

Asn Val Thr Val Asn Cys Ser Cys Gly Asn Thr Asp Val Ala Asp Tyr
145                 150                 155                 160

Gly Leu Phe Ile Thr Tyr Pro Leu Arg Thr Gly Glu Thr Leu Gly Ser
                165                 170                 175

Val Ala Ser Asp Val Ser Leu Asp Ser Gly Leu Leu Gln Arg Tyr Asn
            180                 185                 190

Pro Asp Val Asn Phe Asn Gln Gly Ser Gly Leu Val Tyr Ile Pro Gly
            195                 200                 205

Lys Asp Gln Asn Gly Ser Tyr Val Phe Leu Pro Ser Ser Ser Gly Gly
        210                 215                 220

Leu Ala Gly Gly Ala Ile Ala Gly Ile Ala Val Gly Val Val Ala Val
225                 230                 235                 240

Leu Leu Val Leu Gly Val Val Ile Tyr Phe Arg Ile Phe Arg Lys Lys
                245                 250                 255

Ile Lys Lys Glu Glu Leu Ser Arg Asp Ser Ser Ala Leu Phe Ala Gln
            260                 265                 270

Asp Gly Lys Asp Glu Ala Ser Arg Ser Ser Ala His Glu Thr Leu Gly
            275                 280                 285

Pro Gly Gly Pro Thr Ala Ile Thr Gly Ile Lys Val Asp Lys Ser Val
        290                 295                 300

Glu Phe Thr Tyr Glu Glu Leu Ala Thr Ala Thr Asp Asn Phe Ser Leu
305                 310                 315                 320

Ala Asn Lys Ile Gly Gln Gly Gly Phe Gly Ser Val Tyr Tyr Ala Glu
                325                 330                 335

Leu Arg Gly Glu Lys Ala Ala Ile Lys Lys Met Asp Met Gln Ala Ser
            340                 345                 350
```

-continued

```
Lys Glu Phe Leu Ala Glu Leu Lys Val Leu Thr Arg Val His His Leu
        355                 360                 365

Asn Leu Val Arg Leu Ile Gly Tyr Ser Ile Glu Gly Ser Leu Phe Leu
        370                 375                 380

Val Tyr Glu Tyr Ile Glu Asn Gly Asn Leu Ser Gln His Leu Arg Gly
385                 390                 395                 400

Ser Gly Ser Arg Glu Pro Leu Pro Trp Ala Thr Arg Val Gln Ile Ala
                405                 410                 415

Leu Asp Ser Ala Arg Gly Leu Glu Tyr Ile His Glu His Thr Val Pro
                420                 425                 430

Val Tyr Ile His Arg Asp Ile Lys Ser Ala Asn Ile Leu Ile Asp Lys
        435                 440                 445

Asn Phe Arg Gly Lys Val Ala Asp Phe Gly Leu Thr Lys Leu Thr Glu
        450                 455                 460

Val Gly Ser Ser Ser Leu Pro Thr Gly Arg Leu Val Gly Thr Phe Gly
465                 470                 475                 480

Tyr Met Pro Pro Glu Tyr Ala Gln Tyr Gly Asp Val Ser Pro Lys Val
                485                 490                 495

Asp Val Tyr Ala Phe Gly Val Val Leu Tyr Glu Leu Ile Ser Ala Lys
                500                 505                 510

Glu Ala Ile Val Lys Thr Asn Asp Ser Ala Thr Asp Ser Lys Gly Leu
        515                 520                 525

Val Ala Leu Phe Asp Gly Val Leu Gly Gln Pro Asp Asn Thr Glu Asp
        530                 535                 540

Leu Ile Lys Leu Val Asp Pro Arg Leu Gly Asp Asn Tyr Pro Val Asp
545                 550                 555                 560

Ser Val Arg Lys Met Ala Gln Leu Ala Lys Ala Cys Thr Gln Asp Asn
                565                 570                 575

Pro Gln Leu Arg Pro Ser Met Arg Ser Ile Val Val Ala Leu Met Thr
                580                 585                 590

Leu Ser Ser Thr Thr Asp Glu Trp Asp Val Gly Ser Phe Tyr Glu Asn
        595                 600                 605

Gln Asn Leu Val Asn Leu Met Ser Gly Arg
    610                 615
```

```
<210> SEQ ID NO 334
<211> LENGTH: 618
<212> TYPE: PRT
<213> ORGANISM: Vigna unguiculata

<400> SEQUENCE: 334
```

```
Met Glu Ala Arg Leu Gly Phe Val Val Val Pro Leu Val Leu Phe Cys
1               5                   10                  15

Leu Val Leu Ala Ala Glu Ser Ala Cys Arg Gln Gly Cys Ser Leu Ala
        20                  25                  30

Leu Gly Ser Tyr Tyr Met Trp Ser Gly Ser Asn Leu Thr Tyr Ile Ser
        35                  40                  45

Glu Val Met Ser Ser Pro Leu Leu Thr Thr Pro Asp Asp Ile Val Leu
    50                  55                  60

Tyr Asn Lys Asp Thr Ile Pro Asn Lys Asp Ser Val Gln Ala Phe Ile
65                  70                  75                  80

Arg Val Asn Val Pro Phe Pro Cys Asp Cys Ile Asp Gly Gln Phe Leu
                85                  90                  95

Ala His Thr Phe Gln Tyr Asp Val Gln Thr Gln Asp Thr Tyr Glu Tyr
        100                 105                 110
```

```
Val Ala Arg Thr Val Phe Ser Asn Leu Thr Asp Val Thr Trp Leu Arg
        115             120             125

Arg Phe Asn Ser Tyr Glu Pro Asn Asn Ile Pro Asp Thr Gly Thr Leu
    130             135             140

Asn Val Thr Val Asn Cys Ser Cys Gly Asn Thr Asp Val Ala Asp Tyr
145             150             155             160

Gly Leu Phe Ile Thr Tyr Pro Leu Arg Thr Gly Glu Thr Leu Gly Ser
            165             170             175

Val Ala Ala Asp Val Ser Leu Asp Ser Gly Leu Leu Gln Arg Tyr Asn
            180             185             190

Pro Asp Val Asn Phe Asn Gln Gly Ser Gly Leu Val Tyr Ile Pro Gly
        195             200             205

Lys Asp Gln Asn Gly Ser Tyr Val Phe Leu Pro Ser Ser Ser Gly Gly
    210             215             220

Leu Ala Gly Gly Ala Ile Ala Gly Ile Ala Val Gly Val Val Ala Val
225             230             235             240

Leu Leu Val Leu Gly Val Val Ile Tyr Phe Arg Ile Phe Arg Met Lys
            245             250             255

Ile Gln Lys Glu Glu Leu Ser Arg Asp Ser Ser Ala Leu Phe Ala Gln
        260             265             270

Asp Gly Lys Asp Glu Ala Ser Arg Ser Ser Ala His Glu Thr Leu Gly
        275             280             285

Pro Gly Gly Pro Ala Ala Ile Thr Gly Ile Lys Val Asp Lys Ser Val
    290             295             300

Glu Phe Thr Tyr Glu Glu Leu Ala Thr Ala Thr Asp Asn Phe Ser Leu
305             310             315             320

Ala Asn Lys Ile Gly Gln Gly Gly Phe Gly Ser Val Tyr Tyr Ala Glu
            325             330             335

Leu Arg Gly Glu Lys Ala Ala Ile Lys Lys Met Asp Met Gln Ala Ser
        340             345             350

Lys Glu Phe Leu Ala Glu Leu Lys Val Leu Thr Arg Val His His Leu
        355             360             365

Asn Leu Val Arg Leu Ile Gly Tyr Ser Ile Glu Gly Ser Leu Phe Leu
    370             375             380

Val Tyr Glu Tyr Ile Glu Asn Gly Asn Leu Ser Gln His Leu Arg Gly
385             390             395             400

Ser Gly Ser Arg Glu Pro Leu Pro Trp Ala Thr Arg Val Gln Ile Ala
            405             410             415

Leu Asp Ser Ala Arg Gly Leu Glu Tyr Ile His Glu His Thr Val Pro
            420             425             430

Val Tyr Ile His Arg Asp Ile Lys Ser Ala Asn Ile Leu Ile Asp Lys
            435             440             445

Asn Phe Arg Gly Lys Val Ala Asp Phe Gly Leu Thr Lys Leu Thr Glu
    450             455             460

Val Gly Ser Ser Ser Leu Pro Thr Gly Arg Leu Val Gly Thr Phe Gly
465             470             475             480

Tyr Met Pro Pro Glu Tyr Ala Gln Tyr Gly Asp Val Ser Pro Lys Val
            485             490             495

Asp Val Tyr Ala Phe Gly Val Val Leu Tyr Glu Leu Ile Ser Ala Lys
            500             505             510

Glu Ala Ile Val Lys Thr Asn Asp Ser Val Thr Asp Ser Lys Gly Leu
        515             520             525
```

Val Ala Leu Phe Asp Gly Val Leu Gly Gln Pro Asp Pro Thr Glu Asp
    530             535             540

Leu Cys Lys Leu Val Asp Pro Arg Leu Gly Asp Asn Tyr Pro Ile Asp
545             550             555             560

Ser Val Arg Lys Met Ala Gln Leu Ala Lys Ala Cys Thr Gln Asp Asn
            565             570             575

Pro Gln Leu Arg Pro Ser Met Arg Ser Ile Val Val Ala Leu Met Thr
            580             585             590

Leu Ser Ser Thr Thr Asp Glu Trp Asp Val Gly Ser Phe Tyr Glu Asn
            595             600             605

Gln Asn Leu Val Asn Leu Met Ser Gly Arg
    610             615

<210> SEQ ID NO 335
<211> LENGTH: 627
<212> TYPE: PRT
<213> ORGANISM: Mimosa pudica
<220> FEATURE:
<221> NAME/KEY: VARIANT
<222> LOCATION: 222, 223, 224
<223> OTHER INFORMATION: Xaa = Any Amino Acid

<400> SEQUENCE: 335

Met Glu Pro Arg Phe Gly Phe Leu Leu Phe Met Leu Ala Ser Ile Phe
1               5               10              15

Val Ser Ser Lys Ser Gln Cys Ser Glu Ser Cys Asp Thr Ala Leu Ala
            20              25              30

Ser Tyr Tyr Val Lys Asn Gly Thr Asn Leu Thr Phe Ile Ser Lys Leu
            35              40              45

Met Thr Ser Lys Leu Val Ser Thr Pro Asp Asp Ile Val Ser Tyr Asn
    50              55              60

Lys Asp Lys Ile Pro Asn Lys Asp Ser Leu Ser Ala Ser Ile Arg Ile
65              70              75              80

Asn Ile Pro Phe Pro Cys Asp Cys Ile Asn Gly Gln Phe Leu Gly His
            85              90              95

Met Phe Gln Tyr Asp Val Ala Thr Gly Asp Thr Tyr Asp Lys Ile Ala
            100             105             110

Ser Thr Asp Phe Ala Asn Leu Thr Thr Val Glu Trp Leu Gln Lys Phe
            115             120             125

Asn Ser Tyr Ala Ala Asp Asn Ile Pro Asp Thr Ala Thr Leu Asn Val
    130             135             140

Thr Val Asn Cys Ser Cys Gly Asn Arg Asp Val Ser Asp Asp Tyr Gly
145             150             155             160

Leu Phe Ile Thr Tyr Pro Leu Leu Pro Gly Glu Thr Leu Gln Ser Val
            165             170             175

Ala Ser Glu Val Gly Phe Asn Asp Thr Gly Leu Leu Gln Arg Tyr Asn
            180             185             190

Pro Ser Val Asn Phe Asn Gln Gly Ser Gly Leu Val Phe Leu Pro Gly
            195             200             205

Lys Asp Gln Asn Gly Thr Tyr Val Pro Leu His Ile Arg Xaa Xaa Xaa
    210             215             220

Gly Leu Ser Thr Gly Ala Ile Val Gly Ile Cys Ile Gly Val Val Ala
225             230             235             240

Gly Leu Leu Leu Leu Ala Val Gly Ile Tyr Phe Gly Tyr Phe Lys Lys
            245             250             255

Lys Lys Thr Ser Lys Val Lys Val Leu Ser Gln Gly Leu Thr Ser Gln

-continued

```
                260             265             270

Asp Arg Arg Gly Lys Ala Ser Asp Thr Thr Thr Gly Asn Asp Glu Tyr
        275             280             285

Gly Thr Ser Val Ser Gly Gly Pro Val Ser Ser Ile Ala Gly Met Thr
    290             295             300

Asn Ile Thr Val Asp Lys Ser Val Glu Phe Ser Tyr Glu Glu Leu Ala
305             310             315             320

Thr Ala Thr Asn Asn Phe Asn Met Ala Asn Met Ile Gly Gln Gly Gly
            325             330             335

Phe Gly Ala Val Tyr Tyr Ala Glu Leu Arg Gly Glu Lys Ala Ala Ile
            340             345             350

Lys Lys Met Asp Met Gln Ala Thr Lys Glu Phe Leu Ala Glu Leu Lys
        355             360             365

Val Leu Thr Asn Val His His Leu Asn Leu Val Arg Leu Ile Gly Tyr
    370             375             380

Cys Val Glu Asp Ser Leu Phe Leu Val Tyr Glu Tyr Ile Glu Asn Gly
385             390             395             400

Asn Leu Ser Gln His Leu Arg Gly Ser Gly Pro Gly Arg Asp Pro Leu
            405             410             415

Pro Trp Ser Thr Arg Val Gln Ile Ala Leu Asp Ser Ala Arg Gly Leu
            420             425             430

Glu Tyr Ile His Glu His Thr Val Pro Val Tyr Ile His Arg Asp Ile
            435             440             445

Lys Pro Ala Asn Ile Leu Ile Asp Lys Asn Phe Arg Gly Lys Val Ala
    450             455             460

Asp Phe Gly Leu Ala Lys Leu Thr Glu Val Gly Ser Gly Thr Leu Pro
465             470             475             480

Thr Gly Arg Leu Val Gly Thr Phe Gly Tyr Met Pro Pro Glu Tyr Ala
            485             490             495

Gln Tyr Gly Asp Val Ser Pro Lys Ile Asp Val Tyr Ala Phe Gly Val
            500             505             510

Val Leu Tyr Glu Leu Ile Ser Ala Lys Glu Ala Ile Ile Lys Ile Asn
        515             520             525

Glu Ser Ile Thr Asp Ser Lys Gly Leu Val Ser Met Val Asn Gly Val
        530             535             540

Leu Asn Gln Pro Asn Pro Met Glu Asp Leu Arg Lys Leu Val Asp Pro
545             550             555             560

Arg Leu Gly Asp Asp Tyr Ser Met Asp Ser Val Phe Lys Val Ala Gln
            565             570             575

Leu Ala Lys Ala Cys Thr Gln Asp Asn Pro Gln Leu Arg Pro Ser Met
            580             585             590

Arg Ser Ile Val Val Ala Leu Met Thr Leu Ser Ser Ala Thr Glu Asp
        595             600             605

Trp Asp Val Gly Ser Phe Tyr Gln Asn Pro Ala Leu Met Asn Leu Met
    610             615             620

Ser Gly Arg
625
```

<210> SEQ ID NO 336
<211> LENGTH: 618
<212> TYPE: PRT
<213> ORGANISM: Chamaecrista fasciculata
<220> FEATURE:
<221> NAME/KEY: VARIANT
<222> LOCATION: 215, 216, 217

-continued

<223> OTHER INFORMATION: Xaa = Any Amino Acid

<400> SEQUENCE: 336

```
Met Glu Pro Arg Phe Gly Phe Pro Val Phe Phe Phe Phe Phe Phe
1               5                   10                  15

Ser Leu Thr Ser Ile Phe Leu Gly Ala Glu Ser Lys Cys Ser Glu Thr
            20                  25                  30

Cys Asn Leu Ala Leu Ala Ser Tyr Tyr Ile Gln Asp Gly Ser Asn Leu
        35                  40                  45

Thr Tyr Ile Ser Thr Ile Leu Lys Ser Gln Leu Val Ser Ser Pro Asp
    50                  55                  60

Asp Ile Val Ser Tyr Asn Lys Asp Lys Ile Pro Asn Lys Asp Ser Val
65                  70                  75                  80

Pro Ser Asp Ile Arg Leu Asn Val Pro Phe Pro Cys Asp Cys Ile Glu
                85                  90                  95

Asp Glu Phe Leu Gly Tyr Asn Phe Leu Tyr Asp Val Gln Thr Gly Asp
                100                 105                 110

Thr Tyr Glu Arg Ile Ala Arg Thr Asn Phe Ala Asn Leu Thr Thr Val
            115                 120                 125

Asp Trp Leu Gln Lys Phe Asn Ser Tyr Pro Pro Asn Asn Ile Pro Asp
    130                 135                 140

Thr Gly Thr Leu Asn Val Thr Ile Asn Cys Ser Cys Gly Asn Arg Asp
145                 150                 155                 160

Val Ser Lys Asp Tyr Gly Leu Phe Ile Thr Tyr Pro Leu Met Pro Gly
                165                 170                 175

Gln Thr Leu Gln Ser Val Ala Gln Glu Val Asn Leu Asp Thr Gly Leu
            180                 185                 190

Leu Gln Arg Tyr Asn Pro Ser Val Asn Phe Asn Gln Gly Ser Gly Leu
        195                 200                 205

Val Tyr Ile Pro Gly Lys Xaa Xaa Xaa Gly Leu Gly Val Gly Ala Ile
    210                 215                 220

Val Gly Ile Ser Ile Gly Val Val Ala Gly Val Leu Leu Leu Ala Gly
225                 230                 235                 240

Tyr Ile Tyr Ile Arg Tyr Phe Gln Lys Lys Lys Glu Glu Val Gln
                245                 250                 255

Leu Leu Ser Ile Tyr Pro Asn Gly His Ser Ser Gln Pro Arg Arg Asp
            260                 265                 270

Ala Thr Ser Gly Asn Ala Glu Tyr Gly Thr Ser Gly Ser Val Ser Pro
        275                 280                 285

Ala Val Gly Gly Val Ala Gly Ile Thr Gly Ile Thr Val Asp Lys Ser
    290                 295                 300

Val Glu Phe Ser Tyr Glu Glu Leu Ala Thr Ala Thr Asn Asn Phe Asn
305                 310                 315                 320

Ile Ala Asn Lys Ile Gly Gln Gly Gly Phe Gly Ala Val Tyr Tyr Ala
                325                 330                 335

Glu Leu Arg Gly Glu Lys Ala Ala Ile Lys Lys Met Asp Met Gln Ala
            340                 345                 350

Thr Arg Glu Phe Leu Ala Glu Leu Lys Val Leu Thr His Val His His
        355                 360                 365

Leu Asn Leu Val Arg Leu Ile Gly Tyr Cys Val Glu Ser Ser Leu Phe
    370                 375                 380

Leu Val Tyr Glu Tyr Ile Glu Asn Gly Asn Leu Ser Gln His Leu Arg
385                 390                 395                 400
```

-continued

```
Ser Ala Gly Arg Asp Pro Leu Pro Trp Ser Asn Arg Val Gln Ile Ala
            405             410             415

Leu Asp Ser Ala Arg Gly Leu Glu Tyr Ile His Glu His Thr Val Pro
        420             425             430

Val Tyr Ile His Arg Asp Ile Lys Ser Ala Asn Ile Leu Ile Asp Lys
        435             440             445

Asn Phe His Gly Lys Val Ala Asp Phe Gly Leu Thr Lys Leu Thr Glu
    450             455             460

Val Gly Ser Ser Thr Asn Pro Thr Gly Arg Leu Val Gly Thr Phe Gly
465             470             475             480

Tyr Met Pro Pro Glu Tyr Ala Gln Tyr Gly Glu Val Ser Pro Lys Val
            485             490             495

Asp Val Tyr Ala Phe Gly Val Val Leu Tyr Glu Leu Ile Ser Ala Lys
            500             505             510

Glu Ala Ile Ile Lys Thr Ala Glu Ser Ile Thr Asp Ser Lys Gly Leu
        515             520             525

Val Ala Leu Phe Glu Gly Val Leu Asn Leu Pro Asp Pro Thr Glu Asp
        530             535             540

Leu Arg Lys Leu Val Asp Pro Arg Leu Gly Asp Asp Tyr Pro Ile Asp
545             550             555             560

Ser Val Arg Lys Met Ala Ile Leu Ala Lys Ala Cys Thr Gln Asp Asn
            565             570             575

Pro Gln Leu Arg Pro Thr Met Arg Ser Ile Val Val Ala Leu Met Thr
            580             585             590

Leu Ser Ser Thr Thr Glu Asp Trp Asp Val Gly Ser Phe Tyr Glu Asn
        595             600             605

Pro Ala Leu Leu Asn Leu Met Ser Gly Arg
    610             615
```

```
<210> SEQ ID NO 337
<211> LENGTH: 614
<212> TYPE: PRT
<213> ORGANISM: Lupinus albus

<400> SEQUENCE: 337

Met Lys Pro Ile Leu Met Phe Leu Ile Ile Phe Phe Leu Leu Leu Leu
1               5               10              15

Leu Leu Ser Ser Ala Glu Ser Lys Cys Lys Gln Gly Cys Ser Leu Ala
            20              25              30

Leu Ala Ser Tyr Tyr Met Tyr Ser Gly Ser Thr Leu Thr Ser Ile Ser
        35              40              45

Gln Val Met Ser Ser Gln Leu Leu Thr Val Pro Glu Asp Ile Val Thr
    50              55              60

Tyr Asn Lys Asp Thr Ile Pro Asn Lys Asp Ser Val Gln Ala Phe Ile
65              70              75              80

Arg Val Asn Val Pro Phe Pro Cys Asp Cys Ile Asn Gly Glu Phe Leu
            85              90              95

Gly His Met Phe Arg Tyr Asp Val Lys Thr Asn Asp Thr Tyr Thr Ser
            100             105             110

Val Ala Glu Thr Glu Tyr Ala Asn Leu Thr Asn Val Asn Trp Leu Met
        115             120             125

Lys Phe Asn Asn Tyr Pro Ala Ser Asn Ile Pro Asp Thr Gly Thr Leu
    130             135             140

Asn Val Thr Val Asn Cys Ser Cys Gly Glu Ser Ser Val Ser Asn Tyr
145             150             155             160
```

```
Gly Leu Phe Ile Thr Tyr Pro Leu Arg Pro Gly Asp Thr Leu Asp Ser
            165             170             175

Val Ser Lys Ser Val Asn Leu Asp Ser Gly Leu Leu Gln Ser Tyr Asn
        180             185             190

Pro Gly Val Asn Phe Asn Gln Gly Ser Gly Leu Val Tyr Ile Pro Gly
        195             200             205

Lys Asp Gln Asn Gly Ser Tyr Val Phe Leu Asn Pro Ser Ser Gly Gly
    210             215             220

Leu Ala Gly Gly Ala Ile Ala Gly Ile Val Ile Gly Val Leu Ala Gly
225             230             235             240

Ile Leu Leu Leu Val Val Cys Ile Tyr Val Gly Tyr Phe Arg Lys Lys
            245             250             255

Lys Ile Gln Lys Asp Glu Leu Leu Gly Gln Asp Ser Lys Ser Leu Phe
        260             265             270

Ala Gln Asp Gly Met Asp Glu Thr Thr Arg Thr Ala Ala Pro Gly Gly
        275             280             285

Pro Ala Ala Ile Thr Gly Ile Ser Val Asp Lys Ser Val Glu Phe Ser
    290             295             300

Tyr Glu Glu Leu Ala Ser Ala Thr Asn Asn Phe Ser Met Ala Asn Lys
305             310             315             320

Ile Gly Gln Gly Gly Phe Gly Val Val Tyr Tyr Ala Glu Leu Arg Gly
            325             330             335

Glu Lys Ala Ala Ile Lys Lys Met Asp Met Gln Ala Ser Lys Glu Phe
        340             345             350

Leu Ala Glu Leu Lys Val Leu Thr His Val His His Leu Asn Leu Val
        355             360             365

Arg Leu Ile Gly Tyr Ser Ile Glu Gly Ser Leu Phe Leu Val Tyr Glu
    370             375             380

Phe Ile Glu Asn Gly Asn Leu Ser Glu His Leu Arg Gly Ser Ala Arg
385             390             395             400

Asp Pro Leu Pro Trp Pro Thr Arg Val Gln Ile Ala Leu Asp Ser Ala
            405             410             415

Arg Gly Leu Glu Tyr Ile His Glu His Thr Val Pro Val Tyr Ile His
        420             425             430

Arg Asp Ile Lys Ser Ala Asn Ile Leu Ile Asp Lys Asn Phe Arg Gly
        435             440             445

Lys Val Ala Asp Phe Gly Leu Thr Lys Leu Thr Glu Val Gly Ser Ser
    450             455             460

Ser Leu Pro Thr Gly Arg Leu Val Gly Thr Phe Gly Tyr Met Pro Pro
465             470             475             480

Glu Tyr Ala Gln Tyr Gly Asp Val Ser Pro Lys Val Asp Val Tyr Ala
            485             490             495

Phe Gly Val Val Leu Tyr Glu Leu Ile Ser Ala Lys Glu Ala Ile Ile
            500             505             510

Gln Ala Ser Glu Ser Ile Ala Asp Ser Lys Gly Leu Val Ala Leu Phe
        515             520             525

Glu Gly Val Leu Asn Gln Pro Asp Ser Thr Glu Asp Leu Cys Lys Leu
    530             535             540

Val Asp Ser Arg Leu Gly Asp Asn Tyr Pro Ile Asp Ser Val Arg Lys
545             550             555             560

Leu Ala Gln Leu Gly Lys Ala Cys Thr Gln Asp Asn Pro Gln Leu Arg
            565             570             575
```

-continued

Pro Ser Met Arg Ser Ile Val Val Ala Leu Met Thr Leu Ser Ser Thr
                580                     585                 590

Thr Asp Glu Trp Asp Val Ala Ser Phe Tyr Glu Asn Gln Asn Leu Val
        595                 600                 605

Asn Leu Met Ser Gly Arg
    610

<210> SEQ ID NO 338
<211> LENGTH: 614
<212> TYPE: PRT
<213> ORGANISM: Pisum sativum

<400> SEQUENCE: 338

Met Lys Gln Gln His Arg Phe Thr Phe Phe Ile Ser Leu Pro Leu Phe
1               5                   10                  15

Ile Ser Leu Leu Ala Ser Ile Pro Thr Thr Thr Gln Ser Lys Cys Thr
                20                  25                  30

Lys Gly Cys Ser Leu Ala Leu Ala Asn Phe Tyr Leu Ala Ser Gly Thr
            35                  40                  45

Asn Leu Thr Tyr Val Ala Gly Ile Leu Lys Ser Pro Ile Leu Thr Lys
    50                  55                  60

Pro Glu Asp Ile Val Asp Tyr Asn Arg Asp Thr Val Pro Asn Lys Asp
65                  70                  75                  80

Ile Ile Leu Gly Gly Glu Arg Val Asn Ile Pro Phe Pro Cys Asp Cys
                85                  90                  95

Ile Asn Gly Asp Phe Leu Ala His Asn Phe Ser Tyr Asp Val Gln Thr
            100                 105                 110

Gly Asp Thr Tyr Ala Ser Val Ala Gly Ser Asn Tyr Ala Asn Leu Thr
        115                 120                 125

Asn Val Gln Trp Leu Arg Asn Phe Asn Thr Tyr Pro Pro Asn Ser Ile
    130                 135                 140

Pro Asp Thr Gly Thr Leu Asn Val Met Ile Asn Cys Ser Cys Gly Asp
145                 150                 155                 160

Arg Glu Ile Ala Asp Tyr Gly Leu Phe Val Thr Tyr Pro Leu Arg Pro
            165                 170                 175

Gly Glu Thr Leu Gly Ser Val Ala Asn Ser Thr Lys Leu Asp Ser Ala
        180                 185                 190

Leu Leu Gln Arg Tyr Asn Pro Gly Val Asn Phe Asn Gln Gly Ser Gly
        195                 200                 205

Leu Val Phe Ile Pro Gly Lys Asp Lys Asn Gly Ser Tyr Val Phe Leu
    210                 215                 220

Asp Thr Ser Ser Gly Gly Leu Ala Gly Gly Ala Ile Ala Gly Ile Ala
225                 230                 235                 240

Val Gly Ile Val Val Leu Leu Leu Leu Ala Ala Gly Val Tyr Phe Gly
            245                 250                 255

Tyr Phe Arg Lys Lys Lys Ile Gln Lys Glu Asn Ser Leu Ser Arg Asp
            260                 265                 270

Ser Thr Ser Leu Phe Pro Gln Asp Gly Lys Asp Glu Thr Ser Arg Asn
        275                 280                 285

Ala Val Ile Thr Gly Ile Thr Val Asp Lys Ser Val Glu Phe Ser Tyr
    290                 295                 300

Asp Glu Leu Ala Ala Ala Ser Asp Asn Phe Ser Met Ala Asn Lys Ile
305                 310                 315                 320

Gly Gln Gly Gly Phe Gly Ser Val Tyr Tyr Ala Glu Leu Arg Gly Glu
            325                 330                 335

```
Lys Ala Ala Ile Lys Lys Met Asp Met Gln Ala Thr Lys Glu Phe Leu
        340             345             350

Ala Glu Leu Asn Val Leu Thr Arg Val His His Leu Asn Leu Val Arg
        355             360             365

Leu Ile Gly Tyr Ser Ile Glu Gly Ser Leu Phe Leu Val Tyr Glu Tyr
        370             375             380

Ile Glu Asn Gly Asn Leu Ser Gln His Leu Arg Gly Ser Gly Arg Asp
385             390             395             400

Pro Leu Pro Trp Ala Thr Arg Val Gln Ile Ala Leu Asp Ser Ala Arg
                405             410             415

Gly Leu Glu Tyr Ile His Glu His Thr Val Pro Val Tyr Ile His Arg
            420             425             430

Asp Ile Lys Pro Ala Asn Ile Leu Ile Asp Lys Asn Phe Arg Gly Lys
        435             440             445

Val Ala Asp Phe Gly Leu Thr Lys Leu Thr Glu Val Gly Ser Ser Ser
    450             455             460

Leu Pro Thr Gly Arg Leu Val Gly Thr Phe Gly Tyr Met Pro Pro Glu
465             470             475             480

Tyr Ala Gln Tyr Gly Asp Val Ser Pro Lys Val Asp Val Tyr Ala Phe
                485             490             495

Gly Val Val Leu Tyr Glu Ile Ile Ser Ala Lys Glu Ala Ile Val Lys
            500             505             510

Thr Ser Glu Ser Val Ala Ala Asp Ser Lys Gly Leu Val Ser Met Phe
        515             520             525

Glu Gly Val Leu Ser Gln Pro Asp Pro Ser Glu Asp Leu Arg Lys Ile
        530             535             540

Val Asp Pro Arg Leu Gly Asp Asn Tyr Pro Val Asp Ser Val Arg Lys
545             550             555             560

Met Ala Gln Leu Ala Lys Ala Cys Thr Gln Glu Asn Pro Gln Leu Arg
                565             570             575

Pro Ser Met Arg Ser Ile Val Val Ala Leu Met Thr Leu Ser Ser Thr
            580             585             590

Thr Asp Asp Trp Asp Ile Gly Ser Phe Tyr Glu Asn Gln Asn Leu Val
            595             600             605

Asn Leu Met Ser Gly Arg
        610

<210> SEQ ID NO 339
<211> LENGTH: 622
<212> TYPE: PRT
<213> ORGANISM: Spatholobus suberectus

<400> SEQUENCE: 339

Met Thr Thr Asn Pro Asn Arg Lys Ala Lys Thr Ala His Val Phe Leu
1               5               10              15

Leu Phe Leu Leu Leu Ile Ile Thr Arg Val Arg Gly Ser Cys Phe Thr
            20              25              30

Gly Cys Asn Leu Ala Leu Ala Ser Tyr Tyr Ile Trp Asn Gly Thr Asn
            35              40              45

Leu Thr Tyr Ile Ser Asn Leu Phe Gly Arg Pro Thr Ser Glu Ile Leu
        50              55              60

Lys Tyr Asn Pro Ser Val Glu Asn Pro Asp Val Ile Gln Ser Gln Thr
65              70              75              80

Arg Ile Asn Val Pro Phe Thr Cys Asp Cys Leu Asn Gly Val Phe Leu
```

-continued

```
                     85              90              95

Gly His Thr Phe Ser Phe Ala Thr Gln His Gly Asp Thr Tyr Lys Val
            100             105             110

Ile Ala Glu Val Gly Phe Ser Asn Leu Thr Thr Glu Asp Trp Val Ser
        115             120             125

Arg Val Asn Arg Tyr Pro Pro Asn Gln Ile Pro Asp Asn Val Asn Ile
        130             135             140

Asn Val Thr Val Asn Cys Ser Cys Gly Asp Arg His Val Ser Lys Asp
145             150             155             160

Tyr Gly Leu Phe Ala Thr Tyr Pro Leu Arg Val Gly Asp Asn Leu His
            165             170             175

Arg Ile Ala Ala Glu Ser Gly Val Pro Ala Glu Leu Leu Leu Arg Tyr
            180             185             190

Asn Pro Thr Ser Asp Phe Ser Ala Gly Asn Gly Leu Val Phe Val Pro
            195             200             205

Ala Lys Asp Glu His Gly Asn Phe Pro Pro Met Gln Arg Gly Ser Gly
        210             215             220

Ile Ser Ser Gly Ala Ile Ala Gly Ile Ala Val Gly Gly Ala Val Gly
225             230             235             240

Ile Leu Leu Leu Ala Leu Ile Leu Tyr Val Gly Leu Tyr Arg Arg Lys
            245             250             255

Lys Val Ala Glu Val Ser Leu Leu Pro Val Pro Glu Ala Ser Glu Asp
            260             265             270

Gln Cys Ser Pro Leu Arg His Gly Ile Gly Cys Gly Ser Ser Leu Asp
            275             280             285

Lys Ala Ser Glu Ser Ser Val Val Ser Ser Pro Arg Leu Thr Gly Ile
        290             295             300

Thr Val Asp Lys Ser Val Glu Phe Ser Tyr Gln Glu Leu Ala Lys Ala
305             310             315             320

Thr Asp Asp Phe Ser Val Ala Asn Ile Ile Gly Lys Gly Gly Phe Gly
            325             330             335

Ser Val Tyr Tyr Ala Glu Leu Arg Asn Glu Lys Ala Ala Ile Lys Lys
            340             345             350

Met Asp Met Gln Ala Ser Asn Glu Phe Leu Ala Glu Leu Lys Val Leu
            355             360             365

Thr His Val His His Leu Asn Leu Val Arg Leu Ile Gly Tyr Cys Val
            370             375             380

Glu Gly Ser Leu Phe Leu Val Tyr Glu Tyr Ile Glu Asn Gly Asn Leu
385             390             395             400

Ser Gln His Leu Arg Gly Ser Gly Arg Asp Pro Leu Thr Trp Ala Ala
            405             410             415

Arg Val Gln Ile Ala Leu Asp Ala Ala Arg Gly Leu Glu Tyr Ile His
            420             425             430

Glu His Thr Val Pro Val Tyr Ile His Arg Asp Ile Lys Ser Ala Asn
            435             440             445

Ile Leu Ile Asp Lys Asn Phe Arg Gly Lys Val Ala Asp Phe Gly Leu
        450             455             460

Thr Lys Leu Thr Glu Tyr Gly Ser Ser Ser Leu Gln Thr Arg Leu Val
465             470             475             480

Gly Thr Phe Gly Tyr Met Pro Pro Glu Tyr Ala Gln Tyr Gly Glu Val
            485             490             495

Ser Leu Lys Ile Asp Val Tyr Ala Phe Gly Val Val Leu Tyr Glu Leu
            500             505             510
```

```
Ile Ser Gly Lys Ala Ala Ile Val Lys Thr Asn Glu Pro Glu Asn Glu
        515                 520                 525

Ser Lys Gly Leu Val Gly Leu Phe Glu Glu Ala Leu Gly Leu Ser Glu
        530                 535                 540

Pro Lys Glu Asp Leu Arg Gln Leu Val Asp Pro Lys Leu Gly Asp Ser
545                 550                 555                 560

Tyr Pro Leu Asp Ser Val Phe Lys Val Ser Gln Leu Ala Lys Ala Cys
                565                 570                 575

Thr His Glu Asn Pro Gln Leu Arg Pro Ser Met Arg Ser Ile Val Val
                580                 585                 590

Ala Leu Met Thr Leu Ser Ser Ala Thr Glu Asp Trp Asp Val Gly Ser
                595                 600                 605

Phe Tyr Glu Asn Gln Ala Leu Val His Leu Met Ser Gly Arg
        610                 615                 620
```

<210> SEQ ID NO 340
<211> LENGTH: 627
<212> TYPE: PRT
<213> ORGANISM: Prosopis alba

<400> SEQUENCE: 340

```
Met Glu Leu Arg Phe Glu Phe Leu Val Leu Phe Phe Phe Ser Ser Leu
1                   5                   10                  15

Ala Ser Ile Phe Val Ile Ala Lys Ala Gln Cys Ser Glu Thr Cys Asp
                20                  25                  30

Phe Ala Leu Gly Ser Tyr Tyr Val Arg Asn Gly Ser Asn Leu Thr Tyr
        35                  40                  45

Val Ser Lys Val Met Lys Ser Gln Leu Leu Ser Thr Pro Asp Asp Ile
        50                  55                  60

Val Asn Tyr Asn Lys Asp Lys Ile Pro Asn Lys Asp Ser Val Pro Ala
65                  70                  75                  80

Leu Thr Arg Val Asn Val Pro Phe Pro Cys Lys Cys Ile Asn Gly Glu
                85                  90                  95

Phe Leu Gly His Thr Phe Gln Tyr Val Val Glu Thr Gly Asp Thr Tyr
                100                 105                 110

Glu Lys Val Ala Val Thr Asn Tyr Ala Asn Leu Thr Thr Val Asp Trp
        115                 120                 125

Leu Arg Lys Phe Asn Ser Tyr Pro Pro Asp Asn Ile Pro Asp Thr Gly
        130                 135                 140

Thr Leu Asn Val Thr Val Asn Cys Ser Cys Gly Asn Ser Asp Val Ser
145                 150                 155                 160

Lys Asp Tyr Gly Leu Phe Ile Thr Tyr Pro Leu Arg Pro Gly Gln Thr
                165                 170                 175

Leu Gln Ser Val Ala Gly Glu Ala Gly Leu Asp Thr Gly Leu Leu Gln
                180                 185                 190

Arg Tyr Asn Pro Ser Val Asn Phe Asn Gln Gly Ser Gly Leu Val Tyr
        195                 200                 205

Ile Pro Gly Lys Asp Gln Asn Gly Thr Phe Val Pro Leu Leu Ser Arg
        210                 215                 220

Lys Ala Gly Gly Leu Ala Thr Gly Ala Ile Val Gly Ile Ser Ile Gly
225                 230                 235                 240

Val Val Ala Gly Leu Leu Leu Leu Ala Val Gly Ile Tyr Ile Gly Tyr
                245                 250                 255

Ser Arg Lys Lys Lys Ala His Lys Val Lys Leu Leu Ser Gln Glu Ser
```

-continued

```
             260              265              270

Lys Gly Leu Thr Ser Gln Asp Arg Arg Asp Thr Thr Ser Gly Asn Gly
         275              280              285

Gly Asn Gly Thr Ser Gly Ser Gly Gly Pro Val Ala Pro Ile Ala Gly
         290              295              300

Ile Ala Gly Ile Thr Val Asp Lys Ser Val Glu Phe Ser Tyr Glu Glu
305              310              315              320

Leu Ala Thr Ala Thr Asn Asn Phe Asn Met Ala Asn Met Ile Gly Gln
             325              330              335

Gly Gly Phe Gly Ala Val Tyr Tyr Ala Glu Leu Gly Gly Glu Lys Ala
             340              345              350

Ala Ile Lys Lys Met Asp Met Gln Ala Thr Arg Glu Phe Leu Ala Glu
             355              360              365

Leu Lys Val Leu Thr Asn Val His His Leu Asn Leu Val Arg Leu Ile
         370              375              380

Gly Tyr Cys Val Glu Asp Ser Leu Phe Leu Val Tyr Glu Tyr Ile Glu
385              390              395              400

Asn Gly Asn Leu Ser Gln His Leu Arg Ser Ser Gly Arg Asp Pro Leu
             405              410              415

Pro Trp Ser Thr Arg Val Gln Ile Ala Leu Asp Ser Ala Arg Gly Leu
             420              425              430

Glu Tyr Ile His Glu His Thr Val Pro Val Tyr Ile His Arg Asp Ile
             435              440              445

Lys Ser Ala Asn Ile Leu Ile Asp Lys Asn Phe Arg Gly Lys Val Ala
         450              455              460

Asp Phe Gly Leu Ala Lys Leu Thr Glu Val Gly Ser Ser Thr Leu Pro
465              470              475              480

Thr Gly Arg Leu Val Gly Thr Phe Gly Tyr Met Pro Pro Glu Tyr Ala
             485              490              495

Gln Tyr Gly Asp Val Ser Pro Lys Ile Asp Val Tyr Ala Phe Gly Val
             500              505              510

Val Ile Tyr Glu Leu Ile Ser Ala Lys Glu Ala Ile Ile Lys Ile Asn
         515              520              525

Glu Ser Ile Thr Asp Ser Lys Gly Ile Val Ser Leu Phe Asp Gly Val
         530              535              540

Leu Asn Gln Pro Asn Pro Thr Glu Asp Leu Arg Lys Leu Val Asp Pro
545              550              555              560

Arg Leu Gly Asp Asp Tyr Pro Ile Asp Ser Val His Lys Met Ala Gln
             565              570              575

Leu Ala Lys Ala Cys Thr Gln Asp Asn Pro Gln Leu Arg Pro Ser Met
             580              585              590

Arg Ser Ile Val Val Ala Leu Met Thr Leu Ser Ser Ala Thr Glu Asp
             595              600              605

Trp Asp Val Gly Ser Phe Tyr Glu Asn Pro Ala Leu Met Lys Leu Met
         610              615              620

Ser Gly Arg
625
```

-continued

```
<210> SEQ ID NO 341
<211> LENGTH: 6
<212> TYPE: PRT
<213> ORGANISM: Solanum lycopersicum

<400> SEQUENCE: 341

Arg Gly Ser Asn Leu Thr
1               5
```